(12) United States Patent
Banister et al.

(10) Patent No.: US 12,428,380 B2
(45) Date of Patent: Sep. 30, 2025

(54) COMPOUNDS

(71) Applicant: PSYLO PTY LTD, Sydney (AU)

(72) Inventors: Samuel Banister, Sydney (AU); William Jorgensen, Sydney (AU); Jinlong Tan, Sydney (AU); Lachlan Whish, Sydney (AU)

(73) Assignee: PSYLO PTY LTD, Sydney (AU)

( * ) Notice: Subject to any disclaimer, the term of this patent is extended or adjusted under 35 U.S.C. 154(b) by 0 days.

(21) Appl. No.: 19/002,491

(22) Filed: Dec. 26, 2024

(65) Prior Publication Data

US 2025/0214943 A1 Jul. 3, 2025

Related U.S. Application Data

(63) Continuation of application No. PCT/AU2024/050708, filed on Jun. 28, 2024.

(30) Foreign Application Priority Data

Jun. 28, 2023 (AU) ................................ 2023902054

(51) Int. Cl.
*C07D 231/56* (2006.01)
*C07D 403/06* (2006.01)

(52) U.S. Cl.
CPC ......... *C07D 231/56* (2013.01); *C07D 403/06* (2013.01)

(58) Field of Classification Search
CPC ............................ C07D 231/56; C07D 403/06
See application file for complete search history.

(56) References Cited

U.S. PATENT DOCUMENTS

| | | | |
|---|---|---|---|
| 5,364,866 A | 11/1994 | Strupczewski et al. | |
| 7,332,149 B1 | 2/2008 | Rajopadhye et al. | |
| 11,000,534 B1 | 5/2021 | Sippy | |
| 2010/0029629 A1 | 2/2010 | Conticello et al. | |

FOREIGN PATENT DOCUMENTS

| | | |
|---|---|---|
| CN | 111825702 A | 10/2020 |
| EP | 0494774 A1 | 7/1992 |
| WO | WO 2000/012482 A2 | 3/2000 |
| WO | WO 2001/070701 A1 | 9/2001 |
| WO | WO 2001/083472 A1 | 11/2001 |
| WO | 2008004117 A1 | 1/2008 |
| WO | 2009102805 A1 | 8/2009 |
| WO | 2010011546 A1 | 1/2010 |
| WO | WO 2011/008572 A2 | 1/2011 |
| WO | 2013063492 A1 | 5/2013 |
| WO | WO 2015/129926 A1 | 9/2015 |
| WO | WO 2016/057834 A1 | 4/2016 |
| WO | WO 2021/007477 A1 | 1/2021 |
| WO | 2021076572 A1 | 4/2021 |
| WO | 2021155468 A1 | 8/2021 |
| WO | 2021155470 A1 | 8/2021 |
| WO | 2021168082 A1 | 8/2021 |
| WO | 2021179091 A1 | 9/2021 |
| WO | 2021226416 A1 | 11/2021 |
| WO | 2023018864 A1 | 2/2023 |
| WO | WO 2023/115165 A1 | 6/2023 |

OTHER PUBLICATIONS

C. Ainsworth; "The Indazole Analog of Serotonin"; Journal of the American Chemical Society; vol. 79; Oct. 1957; p. 5245-5247.
C. Ainsworth; "Substituted ß-Aminoethylindazoles"; Journal of the American Chemical Society; vol. 80; Feb. 1958; p. 965-967.
Tjin et al.; "Synthesis and Biological Evaluation of an Indazole-Based Selective Protein Arginine Deiminase 4 (PAD4) Inhibitor"; ACS Medicinal Chemistry Letters; vol. 9; 2018; p. 1013-1018.
Berge et al.; "Pharmaceuticals Salts"; Journal of Pharmaceutical Sciences; vol. 66 No. 1; Jan. 1977; 19 pages.
Bertaccini et al., The relative potency of 5-hydroxytryptamine like substances, Arch Int Pharmacodyn Ther., 133:138-56, 1961.
Communication pursuant to Rule 114(2) EPC, Third Party Observations Regarding European Application No. 22908927.1, mailed Mar. 21, 2025, 27 pages.
Klein et al., Toward selective drug development for the human 5-hydroxytryptamine 1E receptor: a comparison of 5-hydroxytryptamine 1E and 1F receptor structure-affinity relationships, Journal of Pharmacology and Experimental Therapeutics, 337(3), 860-867, 2011.
Pigini et al., Analogs with a 1,2-benzisoxazole nucleus of biologically active indole derivatives. IV. 5-Hydroxytryptamine isosteres, Eur J Med Chem, 10:33-6, 1975.
Rao et al., Synthesis and radioprotective activity of beta-(3-indazolyl)-ethylamine derivatives , Yao Xue Xue Bao 22(6): 426-432, 1987.

*Primary Examiner* — Rebecca L Anderson
(74) *Attorney, Agent, or Firm* — BakerHostetler

(57) ABSTRACT

The present disclosure relates generally to compounds, their methods of synthesis, and their use in the treatment of mental illness or central nervous system disorders.

1 Claim, 6 Drawing Sheets

COMPOUNDS

CROSS REFERENCE TO RELATED APPLICATION

This application is a continuation of PCT/AU2024/050708 filed 28 Jun. 2024, which claims priority to Australian provisional application no. 2023902054 (filed on 28 Jun. 2023), the entire contents of which are incorporated herein by reference.

FIELD OF THE INVENTION

The present disclosure relates generally to novel compounds, their methods of synthesis, and their use in the treatment of mental illness or central nervous system disorders.

BACKGROUND OF THE INVENTION

Mental illness covers many neuropsychiatric disorders which cause enormous burden to the lives of their sufferers. Diagnoses such as treatment resistant depression, major depressive disorder, eating disorders, substance abuse disorders, post-traumatic stress disorder, obsessive compulsive disorder, attention deficit disorders, schizophrenia, and others can cause such devastating symptoms that many sufferers lose the capability of leading a normal life.

A variety of serotonergic drugs such as antidepressants, serotonin reuptake inhibitors, monoamine oxidase inhibitors, selective serotonin reuptake inhibitors, and others are commercially available to treat mental illnesses. Unfortunately, in many indications, these therapeutics provide limited benefit when compared to a placebo. Additionally, these therapeutics can result in a wide range of side effects including loss of libido, insomnia, fatigue, weight gain, and others. In spite of their limited efficacy, these drugs continue to be used to treat neuropsychiatric conditions as well as a broad range of auxiliary medical indications. There have been limited advances in new treatment options since many of these drugs were released, and the pharmaceutical industry has come under increased financial pressure to de-emphasise neuroscience programmes entirely. The unmet need for more efficacious mental health treatment is on the rise, and the global COVID-19 pandemic is likely to increase disease burden around the world.

In the 1950s and 1960s, the use of psychedelic drugs to treat various mental illnesses was extensively explored, and these substances showed promise as treatments for many diseases of the central nervous system (CNS). Following decades of prohibition, scientific research into the application of psychedelics as treatments for mental illnesses has been gaining momentum. The serotonergic psychedelic agent psilocybin has been designated a Breakthrough Therapy by the FDA for the treatment of major depressive disorder (2019) and treatment-resistant depression (2018). Psilocybin is the prodrug compound produced by many species of mushrooms known collectively as psilocybin mushrooms or "magic mushrooms". Psilocybin is rapidly metabolized to the bioactive compound psilocin, which produces a state of altered consciousness including changes in perception, visual hallucinations, and distorted sense of space, time, and self. Many patients report spiritual or "mystical" experiences which have profound and lasting impact on the patients' mood and behaviour. Psilocybin has shown promise in more than 50 clinical trials for neuropsychiatric indications, including numerous anxiety disorders, obsessive-compulsive disorder, anorexia nervosa, alcohol dependence, and tobacco addiction. Psilocybin and other psychedelic compounds such as N,N-dimethyltryptamine (DMT) and 5-methoxy-N,N-dimethyltryptamine (5-MeO-DMT) have both immediate and persistent effects on mental state, with the latter extending far beyond the duration of action, possibly as a result of their ability to incite increased neuroplasticity, promote neural outgrowth, and increase spine density of the synaptic neurons in the brain.

To date, psilocybin remains classified as a controlled substance and/or drug of abuse in most countries under national drug laws. However, clinical investigations have recently led to increased awareness of the potential for psychedelic drugs as breakthrough therapies to treat CNS diseases of enormous unmet medical need.

Despite its therapeutic potential, psilocybin and other psychedelics remain scheduled drugs of abuse in most countries and the commercial path to market for these drugs as medicines is uncertain. As an adjunct to psychotherapy, the long duration of action of psilocybin and LSD make treatment sessions costly and impractical for broad implementation. In spite of a long history of safe human use, several adverse events have been reported in clinical trials, and it is possible that these may be attributed to signalling bias at $5\text{-HT}_{2A}$ (the primary target) or off-target activity at, for example, $5\text{-HT}_{2B}$ receptors (a cardiac liability antitarget) or 5-HT1A (an anxiolytic target) or 5-HT2C receptors (a disease-relevant target for obesity and some genetic epilepsies, for example). Naturally-occurring psychedelics provide important lead structures for a new generation of neurotherapeutic agents with novel mechanisms of action and/or superior clinical efficacy to currently available neuropsychiatric medications.

In view of the foregoing there is an ongoing need to develop new compounds which may be useful in the treatment of mental illness or central nervous system disorders.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect the present disclosure provides a compound of formula (I):

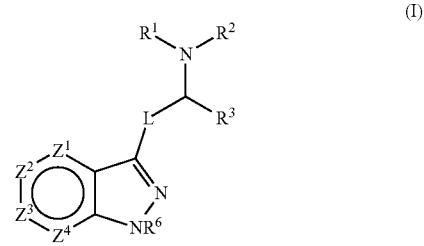

or a pharmaceutically acceptable salt, solvate, tautomer, N-oxide, stereoisomer, metabolite, polymorph or prodrug thereof,
wherein
$R^1$ and $R^2$ are each independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with a substituent independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ together with the nitrogen atom to which they are attached form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ together the atoms to which they are attached to form a $C_{3-12}$ heterocycloalkyl, said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

L is selected from $C_{1-4}$ alkylene, $C_2$-$C_4$ alkenylene and $C_2$-$C_4$ alkynylene;

$Z^1$ is $CR^8$ or N;

$Z^2$ is $CR^9$ or N;

$Z^3$ is $CR^{10}$ or N;

$Z^4$ is $CR^{11}$ or N;

$R^6$ is selected from hydrogen, $C_{1-6}$ alkyl, $C_{2-6}$ alkenyl, $C_{2-6}$ alkynyl, $C_{1-6}$ alkyleneP(O)(OR$^{12}$)$_2$, $C(O)R^{12}$, $CO_2R^{12}$, $C(O)N(R^{12})_2$, $S(O)R^{12}$ and $SO_2R^{12}$, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^{12}$, $C(O)N(R^{12})_2$, $OR^{12}$, $N(R^{12})_2$, $NO_2$, $SR^{12}$ and $SO_2R^{12}$, said $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{12}$;

each $R^{12}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)

NHCH₃, OH, NH₂, N(CH₃)₂, NHCH₃, NO₂, SH, SCH₃, SO₂CH₃, SOCH₃, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO₂, N, NH and NCH₃;

$R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, NO₂, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$alkylsulfonyl, $CO_2R^{13}$, $C(O)N(R^{13})_2$, $OR^{13}$, $N(R^{13})_2$, NO₂, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), SO₂, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, NH₂, N(CH₃)₂, NHCH₃, NO₂, SH, SCH₃, SO₂CH₃, SOCH₃, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO₂, N, NH and NCH₃;

alternatively, when $Z^1$ is $CR^8$ and $Z^2$ is $CR^9$, or when $Z^2$ is $CR^9$ and $Z^3$ is $CR^{10}$, or when $Z^3$ is $CR^{10}$ and $Z^4$ is $CR^{11}$, then $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, NO₂, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), SO₂ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl;

said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-11}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, NH₂, N(CH₃)₂, NO₂, NHCH₃, SH, SCH₃, SO₂CH₃, SOCH₃, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO₂, N, NH and NCH₃; and wherein the compound of formula (I) is not one of the following:

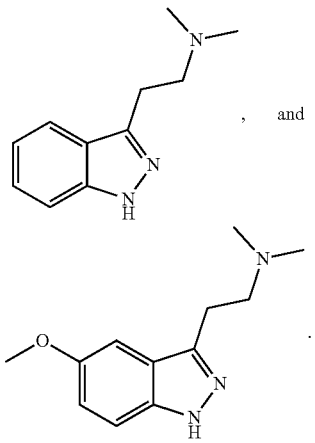

, and

In some embodiments, $R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, NO₂, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$ haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$ haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ together with the nitrogen atom to which they are attached form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

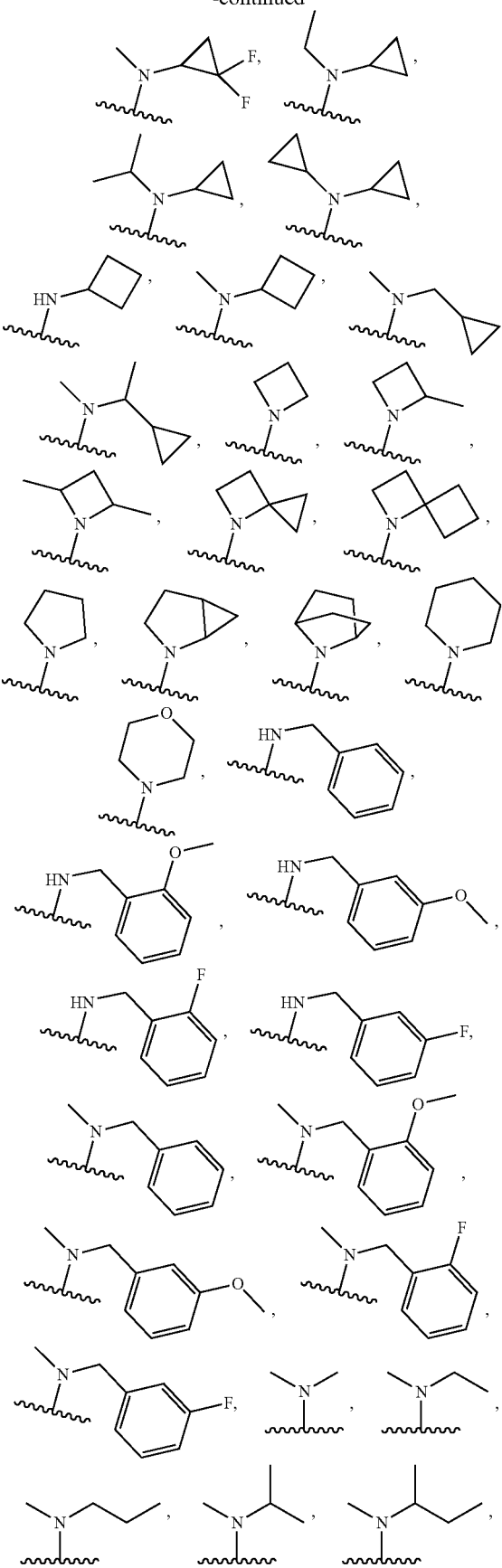

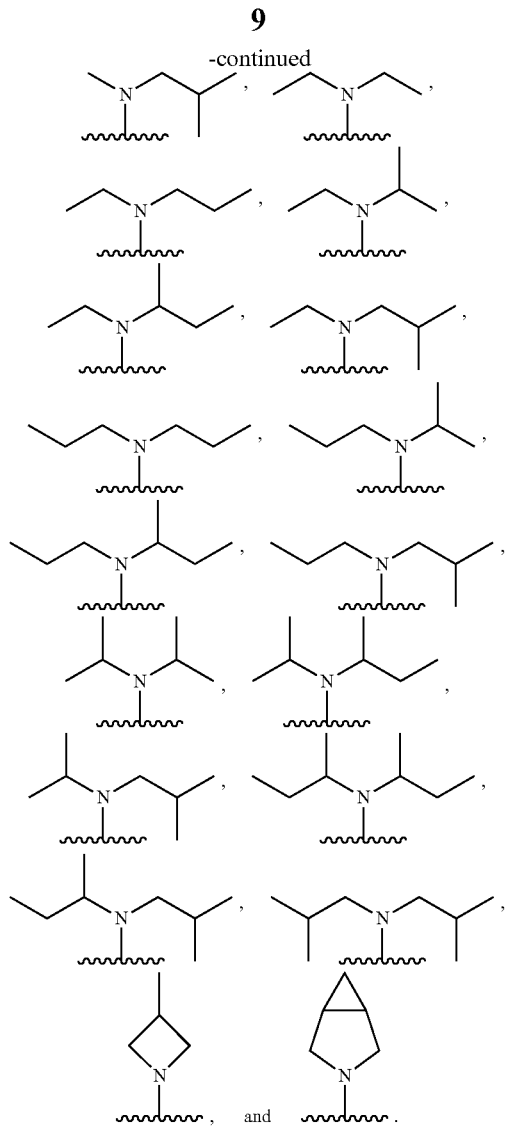
In some embodiments, $R^1$ and $R^2$, together with the nitrogen to which they are attached, form any one of the following:
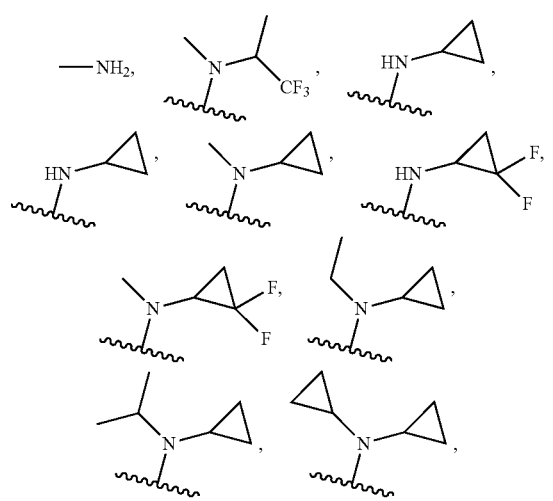
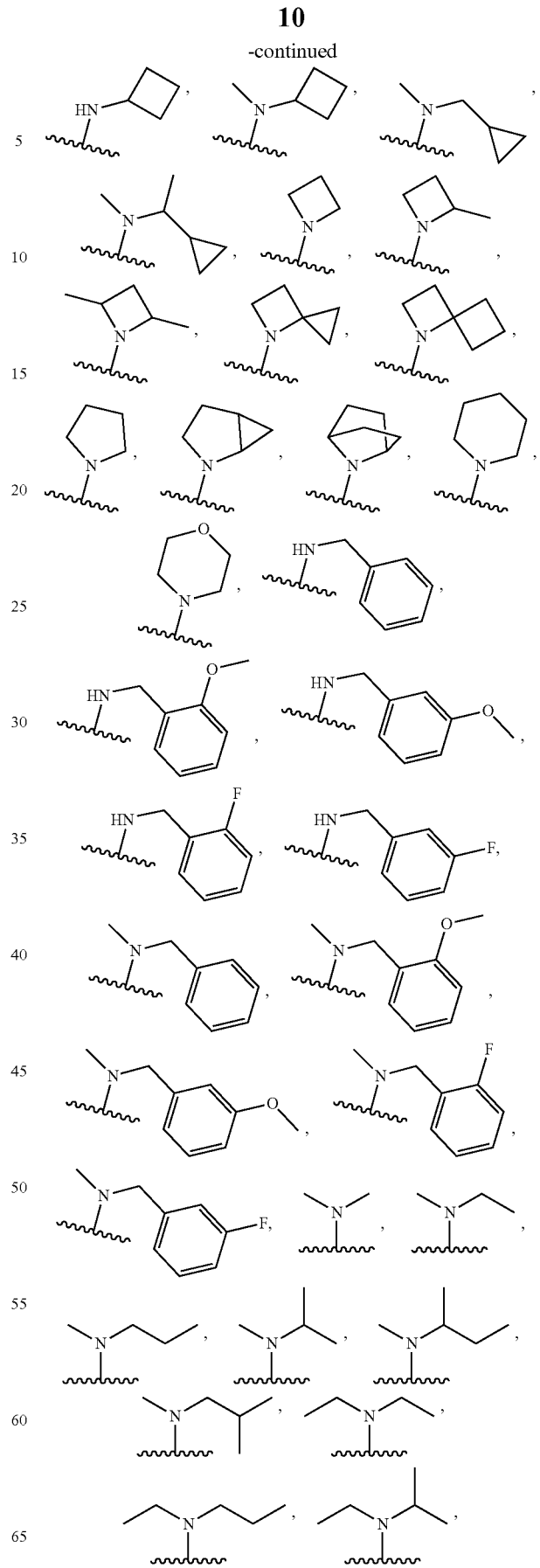

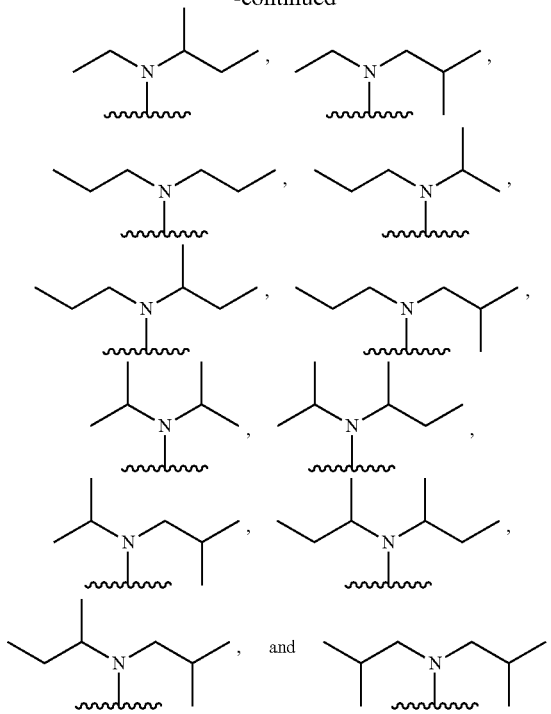
In some embodiments, $R^1$ and $R^2$, together with the nitrogen to which they are attached, form any one of the following:
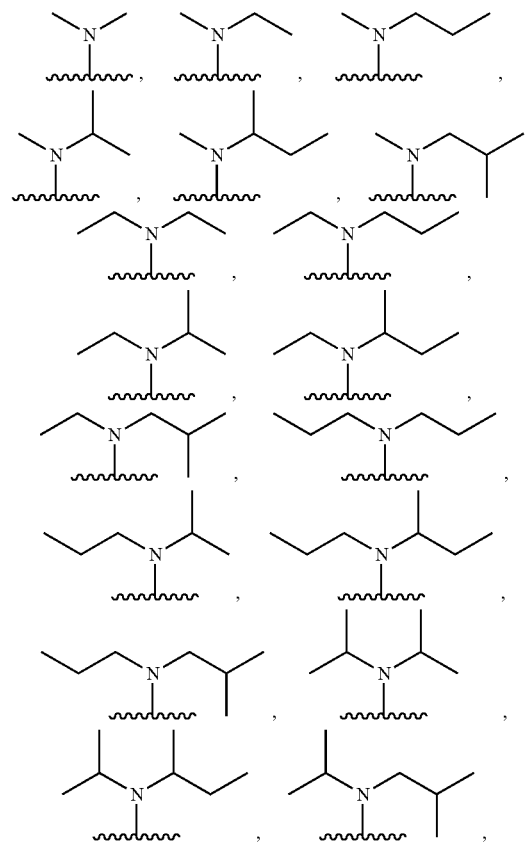
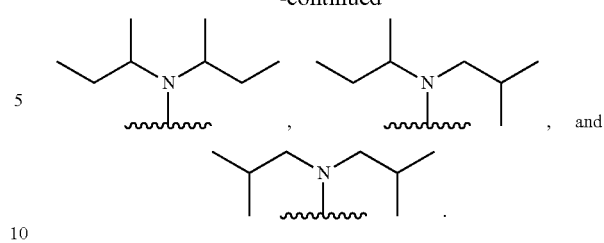
In some embodiments, $R^1$ and $R^2$, together with the nitrogen to which they are attached, form any one of the following:
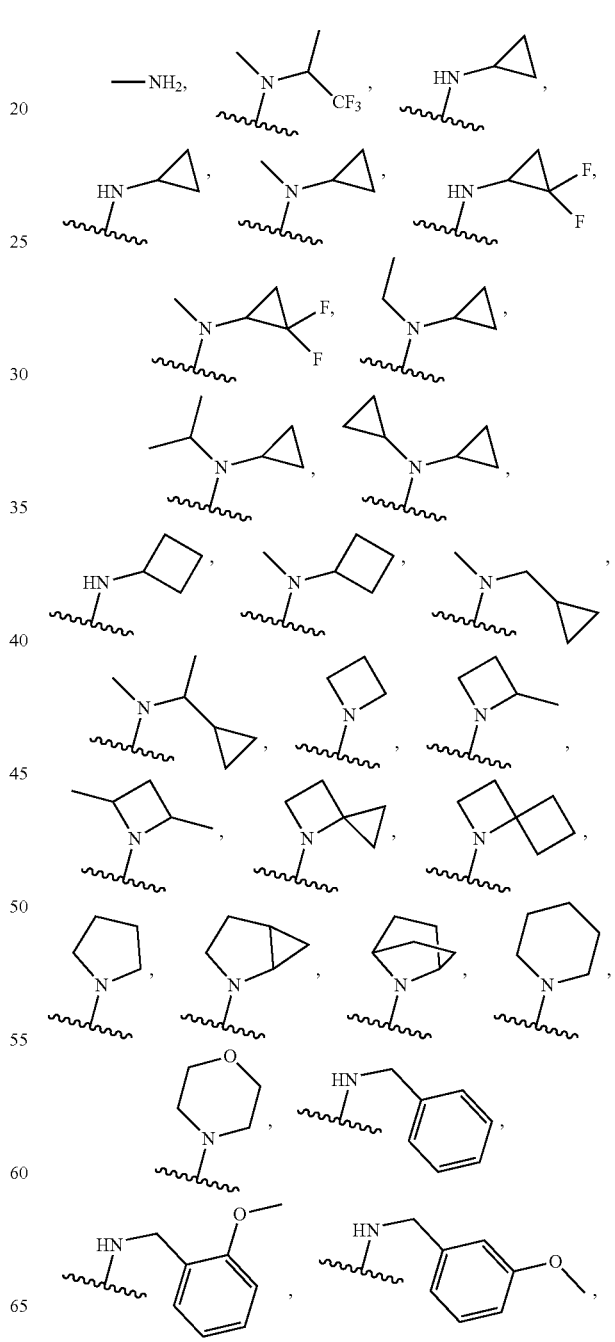

-continued

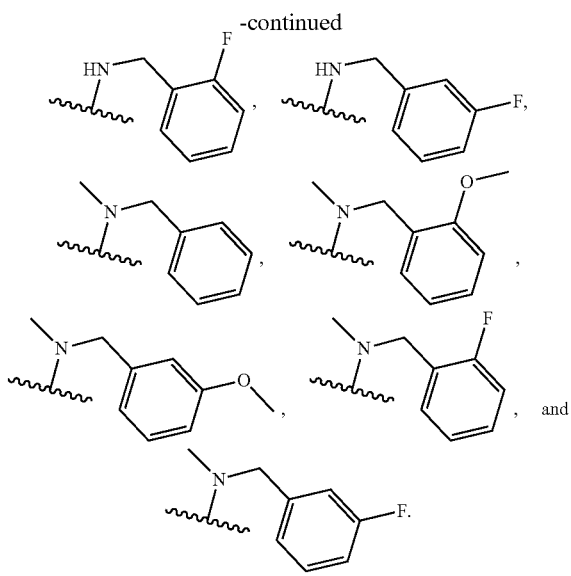

In some embodiments, $R^1$ and $R^2$ are combined with the atoms to which they are attached to form an optionally substituted $C_{3-6}$ heterocycloalkyl.

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined as herein.

In embodiments, $R^1$ and $R^2$ together with the nitrogen atom to which they are attached form a $C_{4-8}$ heterocycloalkyl that does not include additional ring heteromoieties.

In embodiments, $R^1$ and $R^2$ together with the nitrogen atom to which they are attached form a $C_{4-8}$ heterocycloalkyl that is monocyclic or fused bicyclic.

In embodiments, $R^1$ and $R^2$ together with the nitrogen atom to which they are attached form a monocyclic $C_{6-8}$ heterocycloalkyl.

In embodiments, $R^1$ and $R^2$ together with the nitrogen atom to which they are attached form a bicyclic $C_{6-8}$ heterocycloalkyl.

In embodiments, $R^1$ and $R^2$ together with the nitrogen atom to which they are attached form a $C_{4-8}$ heterocycloalkyl that is fused.

In embodiments, $R^1$ and $R^2$ together with the nitrogen atom to which they are attached form a $C_{4-8}$ heterocycloalkyl that is unsubstituted.

In embodiments, $R^1$ and $R^2$ together with the nitrogen atom to which they are attached form a $C_{4-8}$ heterocycloalkyl that is unsubstituted and moncyclic or fused bicyclic.

In embodiments, $R^1$ and $R^2$ together with the nitrogen atom to which they are attached form a $C_{4-8}$ heterocycloalkyl that is unsubstituted and moncyclic.

In embodiments, $R^1$ and $R^2$ together with the nitrogen atom to which they are attached form a $C_{4-8}$ heterocycloalkyl that is unsubstituted and fused bicyclic.

In any one of the herein disclosed embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined as herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$; wherein $R^{13}$ is as defined herein.

In some embodiments, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined as herein.

In some embodiments, 1 or 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments, 1 or 2 of $R^8$ and $R^9$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ (if present) are each hydrogen.

In some embodiments, 1 or 2 of $R^9$ and $R^{10}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ (if present) are each hydrogen.

In some embodiments, 1 or 2 of $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ (if present) are each hydrogen.

In some embodiments, 1 or 2 of $R^8$ and $R^{10}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ (if present) are each hydrogen.

In some embodiments, 1 or 2 of $R^8$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ (if present) are each hydrogen.

In some embodiments, 1 or 2 of $R^9$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ (if present) are each hydrogen.

In some embodiments, 1 or 2 of $R^8$, $R^9$, $R^{10}$ and $R^{11}$ (if present) are independently hydrogen, and the remaining $R^8$ $R^9$, $R^{10}$ and $R^{11}$ (if present) are as defined in any embodiment described herein.

In some embodiments, 1 or 2 of $R^8$ and $R^9$ when present are each independently hydrogen.

In some embodiments, 1 or 2 of $R^9$ and $R^{10}$ when present are each independently hydrogen.

In some embodiments, 1 or 2 of $R^{10}$ and $R^{11}$ when present are each independently hydrogen.

In some embodiments, 1 or 2 of $R^8$ and $R^{10}$ when present are each independently hydrogen.

In some embodiments, 1 or 2 of $R^8$ and $R^{11}$ when present are each independently hydrogen.

In some embodiments, 1 or 2 of $R^9$ and $R^{11}$ when present are each independently hydrogen.

In some embodiments, $R^8$ (if present) is independently selected from hydrogen, halogen, CN, $OR^{13}$, $N(R^{13})_2$, $SR^{13}$, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ is $C_{1-6}$alkyl and $Z^2$ is $CR^9$.

In some embodiments, $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ and $R^9$ are combined to form a $C_{5-8}$ heterocycloalkyl or $C_{5-10}$ heteroaryl selected from the following:

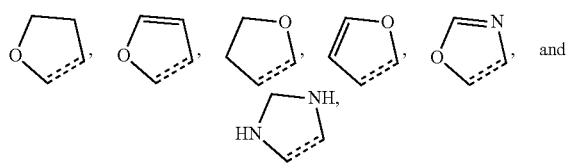

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments, $R^8$ and $R^9$ are combined to form a $C_{5-8}$ heterocycloalkyl or $C_{5-10}$ heteroaryl selected from the following:

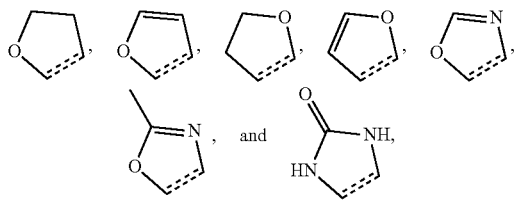

wherein the dashed bond denotes the bond shared with the aromatic ring to which $R^8$ and $R^9$ are attached.

In some embodiments, L is $C_{1-4}$ alkylene.

In some embodiments, L is methylene.

In any one of the herein disclosed embodiments, $R^6$ is selected from hydrogen and $C_{1-6}$ alkyl.

In any one of the herein disclosed embodiments, $R^6$ is hydrogen.

In any one of the herein disclosed embodiments, $R^6$ is $C_{1-6}$ alkyl.

In any one of the herein disclosed embodiments, $R^6$ is methyl.

In some embodiments, $R^6$ is $C_{1-6}$alkyl (preferably methyl), and one or more of the following further conditions is met:

$R^8$ is H;

$R^{11}$ is H $R^1$ and $R^2$ are combined with the atoms to which they are attached to form a $C_{3-8}$ heterocycloalkyl including 0, 1 or 2 additional ring heteromoieties selected from O, S, S(O), $SO_2$, N and $NR^4$, wherein the $C_{3-8}$ heterocycloalkyl moiety is optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$ $R^3$ is H In some embodiments, $R^6$ is H and L is methylene. In these embodiments, the compound of formula (I) has the formula (II):

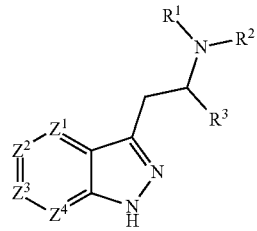

wherein $R^1$, $R^2$, $R^3$, $Z^1$, $Z^2$, $Z^3$ and $Z^4$ are as defined herein.

In some embodiments, the compound of formula (I) has the formula (IIa):

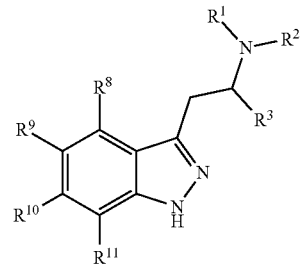

wherein $R^1$, $R^2$, $R^3$, $R^8$, $R^9$, $R^{10}$ and $R^{11}$ are as defined herein.

In some embodiments, the compound of formula (I) has the formula (III):

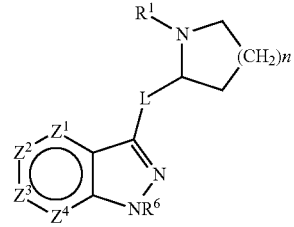

wherein n=0, 1 or 2; and
L, $R^1$, $R^6$, $Z^1$, $Z^2$, $Z^3$ and $Z^4$ are as defined herein.

In some embodiments, the compound of formula (I) is selected from any one of the following:

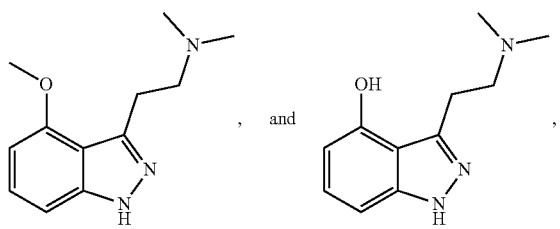

or a pharmaceutically acceptable salt, solvate, tautomer, N-oxide, stereoisomer, metabolite, polymorph or prodrug thereof.

In another aspect the present disclosure provides a medicament comprising a compound according to any one of the herein disclosed embodiments, or a pharmaceutically acceptable salt, solvate, tautomer, N-oxide, stereoisomer, metabolite, polymorph or prodrug thereof.

In another aspect the present disclosure provides a pharmaceutical composition comprising a compound according to any one of the herein disclosed embodiments, or a pharmaceutically acceptable salt, solvate, tautomer, N-oxide, stereoisomer, metabolite, polymorph or prodrug thereof, and a pharmaceutically acceptable excipient.

In another aspect the present disclosure provides a pharmaceutical composition comprising a compound according to any one of the herein disclosed embodiments, or a pharmaceutically acceptable salt, solvate, tautomer, N-oxide, stereoisomer, metabolite, polymorph or prodrug thereof, an additional therapeutic agent, and a pharmaceutically acceptable excipient.

In another aspect the present disclosure provides a method of treating a disease, disorder or condition by activation of a serotonin receptor, the method comprising administering to a subject in need thereof a compound of formula (I):

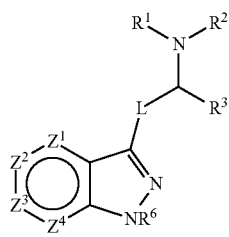

or a pharmaceutically acceptable salt, solvate, tautomer, N-oxide, stereoisomer, metabolite, polymorph or prodrug thereof,
wherein
$R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $SR^4$ and $SO_2R^4$, said $C_{3-8}$ cycloalkyl, $C_{4-14}$ alkylenecycloalkyl, $C_4$-$C_{14}$ alkyleneheterocycloalkyl, $C_3$-$C_8$ heterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ are combined with the atoms to which they are attached to form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO$_2$, N and NR$^5$;

each R$^5$ is independently selected from hydrogen, C$_{1-6}$ alkyl, C$_{2-6}$ alkenyl, C$_{2-6}$ alkynyl, C$_{1-6}$ haloalkyl, C$_{3-8}$ cycloalkyl, C$_{5-11}$ heterocycloalkyl, C$_{6-12}$ aryl and C$_{5-11}$ heteroaryl, said C$_{1-6}$ alkyl, C$_{2-6}$ alkenyl, C$_{2-6}$ alkynyl, C$_{1-6}$ haloalkyl, C$_{3-8}$ cycloalkyl, C$_{5-10}$ heterocycloalkyl, C$_{6-12}$ aryl and C$_{5-11}$ heteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NHCH$_3$, NO$_2$, SH, SCH$_3$, SO$_2$CH$_3$, SOCH$_3$, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, S(O), SO$_2$, N, NH and NCH$_3$;

L is selected from C$_{1-4}$ alkylene, C$_2$-C$_4$ alkenylene and C$_2$-C$_4$ alkynylene;

Z$^1$ is CR$^8$ or N;

Z$^2$ is CR$^9$ or N;

Z$^3$ is CR$^{10}$ or N;

Z$^4$ is CR$^{11}$ or N;

R$^6$ is selected from hydrogen, C$_{1-6}$ alkyl, C$_{2-6}$ alkenyl, C$_{2-6}$ alkynyl, C$_{1-6}$ alkyleneP(O)(OR$^{12}$)$_2$, C(O)R$^{12}$, CO$_2$R$^{12}$, C(O)N(R$^{12}$)$_2$, S(O)R$^{12}$ and SO$_2$R$^{12}$, C$_{3-6}$ cycloalkyl, C$_{6-9}$ alkylenecycloalkyl, C$_{3-6}$ heterocyclyl, C$_{6-9}$ alkyleneheterocycloalkyl, C$_{4-7}$ heterocyclyl, C$_{7-10}$ alkyneneheterocycloalkyl, C$_{6-12}$ aryl, C$_{7-18}$ alkylenearyl, C$_{5-10}$ heteroaryl, and C$_{6-16}$ alkyleneheteroaryl, said C$_{1-6}$ alkyl, C$_{2-6}$ alkenyl, C$_{2-6}$ alkynyl, C$_{3-6}$ cycloalkyl, C$_{6-9}$ alkylenecycloalkyl, C$_{3-6}$ heterocyclyl, C$_{6-9}$ alkyleneheterocycloalkyl, C$_{4-7}$ heterocyclyl, C$_{7-10}$ alkyneneheterocycloalkyl, C$_{6-12}$ aryl, C$_{7-18}$ alkylenearyl, C$_{5-10}$ heteroaryl, and C$_{6-16}$ alkyleneheteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$R$^{12}$, C(O)N(R$^{12}$)$_2$, OR$^{12}$, N(R$^{12}$)$_2$, NO$_2$, SR$^{12}$ and SO$_2$R$^{12}$, said C$_{3-6}$ cycloalkyl, C$_{6-9}$ alkylenecycloalkyl, C$_{3-6}$ heterocyclyl, C$_{6-s}$ alkyleneheterocycloalkyl, C$_{4-7}$ heterocyclyl, C$_{7-10}$ alkyneneheterocycloalkyl, C$_{6-12}$ aryl, C$_{7-18}$ alkylenearyl, C$_{5-10}$ heteroaryl, and C$_{6-16}$ alkyleneheteroaryl each being further optionally substituted with one or more substituents independently selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, N, S(O), SO$_2$ and NR$^{12}$;

each R$^{12}$ is independently selected from hydrogen, C$_{1-6}$ alkyl, C$_{2-6}$ alkenyl, C$_{2-6}$ alkynyl, C$_{1-6}$ haloalkyl, C$_{3-8}$ cycloalkyl, C$_{4-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-11}$ heteroaryl, and C$_{6-16}$ alkyleneheteroaryl, said C$_{1-6}$ alkyl, C$_{2-6}$ alkenyl, C$_{2-6}$ alkynyl, C$_{1-6}$ haloalkyl, C$_{3-8}$ cycloalkyl, C$_{4-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NHCH$_3$, NO$_2$, SH, SCH$_3$, SO$_2$CH$_3$, SOCH$_3$, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, S(O), SO$_2$, N, NH and NCH$_3$;

R$^8$, R$^9$, R$^{10}$ and R$^{11}$ are each independently selected from hydrogen, halogen, CN, OR$^{13}$, N(R$^{13}$)$_2$, SR$^{13}$, C$_{1-6}$ alkyl, C$_{1-6}$ haloalkyl, C$_{2-6}$ alkenyl, C$_2$-C$_6$ haloalkenyl, C$_{2-6}$ alkynyl, C$_{2-6}$ haloalkynyl, C$_{1-6}$ alkylamine, C$_{1-6}$ alkoxy, C$_{1-6}$ haloalkoxy, CO$_2$R$^{13}$, C(O)R$^{13}$, C(O)N(R$^{13}$)$_2$, C(O)C(O)N(R$^{13}$)$_2$, OC(O)R$^{13}$, OC(O)OR$^{13}$, OC(O)N(R$^{13}$)$_2$, OS(O)R$^{13}$, OS(O)N(R$^{13}$)$_2$, OSO$_2$R$^{13}$, OP(O)(OR$^{13}$)$_2$, OC$_{1-6}$alkyleneP(O)(OR$^{13}$)$_2$, S(O)R$^{13}$, S(O)N(R$^{13}$)$_2$, SO$_2$R$^{13}$, N(R$^{13}$)$_2$, N(R$^{13}$)C(O)R$^{13}$, N(R$^{13}$)C(O)OR$^{13}$, N(R$^{13}$)C(O)N(R$^{13}$)$_2$, NO$_2$, C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, C$_{4-16}$ alkyleneheteroaryl, said C$_{1-6}$ alkyl, C$_{1-6}$ haloalkyl, C$_{2-6}$ alkenyl, C$_2$-C$_6$ haloalkenyl, C$_{2-6}$ alkynyl, C$_{2-6}$ haloalkynyl, C$_{1-6}$ alkylamine, C$_{1-6}$ alkoxy, C$_{1-6}$ haloalkoxy, C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{4-16}$ alkyleneheteroaryl being optionally substituted with one or more substituents independently selected from halogen, CN, C$_{1-8}$ alkoxy, C$_{1-8}$ alkylamino, C$_{1-8}$ alkylsulfonyl, CO$_2$R$^{13}$, C(O)N(R$^{13}$)$_2$, OR$^{13}$, NO$_2$, N(R$^{13}$)$_2$, SR$^{13}$ and SO$_2$R$^{13}$, said C$_{3-8}$ cycloalkyl, C$_{3-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-11}$ heteroaryl, and C$_{4-16}$ alkyleneheteroaryl each being further optionally substituted with one or more substituents independently selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$cycloalkyl and C$_{3-6}$ heterocycloalkyl including 1 or 2 ring heteromoieties selected from O, S, S(O), SO$_2$, N, and NR$^{13}$;

each R$^{13}$ is independently selected from hydrogen, C$_{1-6}$ alkyl, C$_{2-6}$ alkenyl, C$_{2-6}$ alkynyl, C$_{1-6}$ haloalkyl, C$_{3-8}$ cycloalkyl, C$_{4-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{6-16}$ alkyleneheteroaryl, said C$_{1-6}$ alkyl, C$_{2-6}$ alkenyl, C$_{2-6}$ alkynyl, C$_{1-6}$ haloalkyl, C$_{3-8}$ cycloalkyl, C$_{4-14}$ alkylenecycloalkyl, C$_{3-10}$ heterocycloalkyl, C$_{4-16}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NHCH$_3$, NO$_2$, SH, SCH$_3$, SO$_2$CH$_3$, SOCH$_3$, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, S(O), SO$_2$, N, NH and NCH$_3$;

alternatively, when Z$^1$ is CR$^8$ and Z$^2$ is CR$^9$, or when Z$^2$ is CR$^9$ and Z$^3$ is CR$^{10}$, or when Z$^3$ is CR$^{10}$ and Z$^4$ is CR$^{11}$, then R$^8$ and R$^9$, or R$^9$ and R$^{10}$, or R$^{10}$ and R$^{11}$ are combined with the atoms to which they are each attached to form a C$_{4-8}$ cycloalkyl, C$_{5-8}$ heterocycloalkyl, C$_{6-12}$ aryl, or C$_{5-10}$ heteroaryl, said C$_{4-8}$ cycloalkyl, C$_{5-8}$ heterocycloalkyl, C$_{6-12}$ aryl, and C$_{5-11}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$cycloalkyl, $C_{3-10}$ heterocycloalkyl, $C_{6-12}$ aryl and $C_{5-10}$ heteroaryl; and said $C_{1-6}$ alkyl, $C_2$-$C_6$ alkenyl, $C_2$-$C_6$ alkynyl, $C_1$-$C_6$ haloalkyl, $C_3$-$C_7$cycloalkyl, $C_{3-10}$ heterocycloalkyl, $C_{6-12}$ aryl and $C_{5-11}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments of the method, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments of the method, $R^1$ and $R^2$ are each independently selected from $C_{1-4}$ alkyl.

In some embodiments of the method, $R^1$ and $R^2$, together with the nitrogen to which they are attached, form any one of the following:

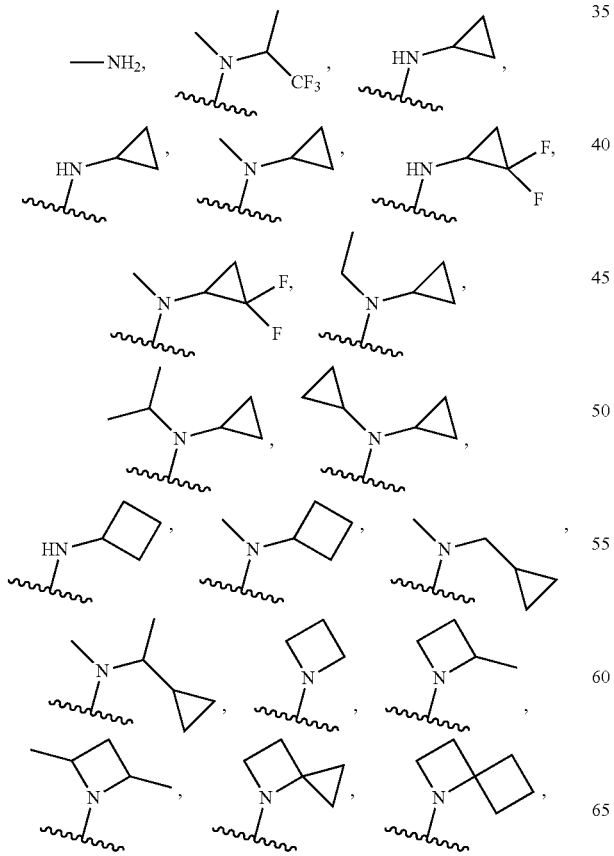

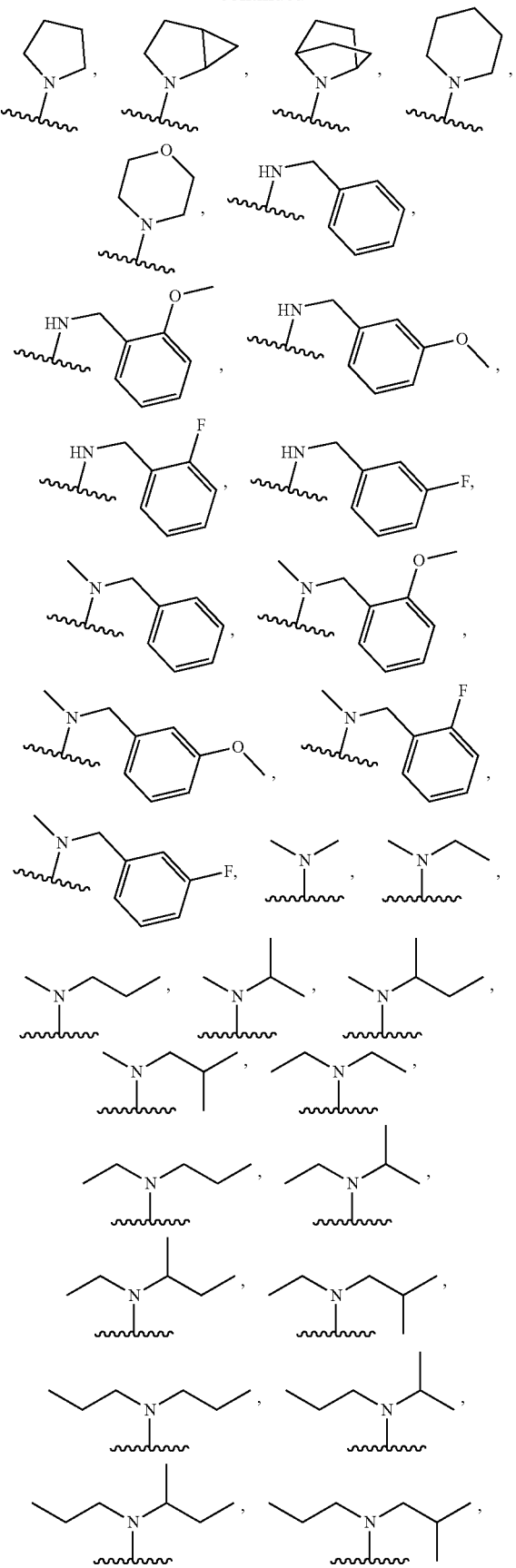

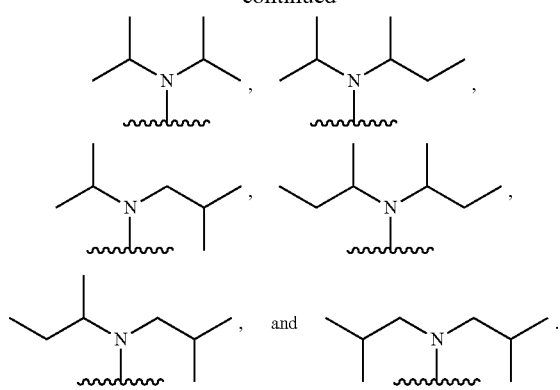
In some embodiments of the method, $R^1$ and $R^2$, together with the nitrogen to which they are attached, form any one of the following:
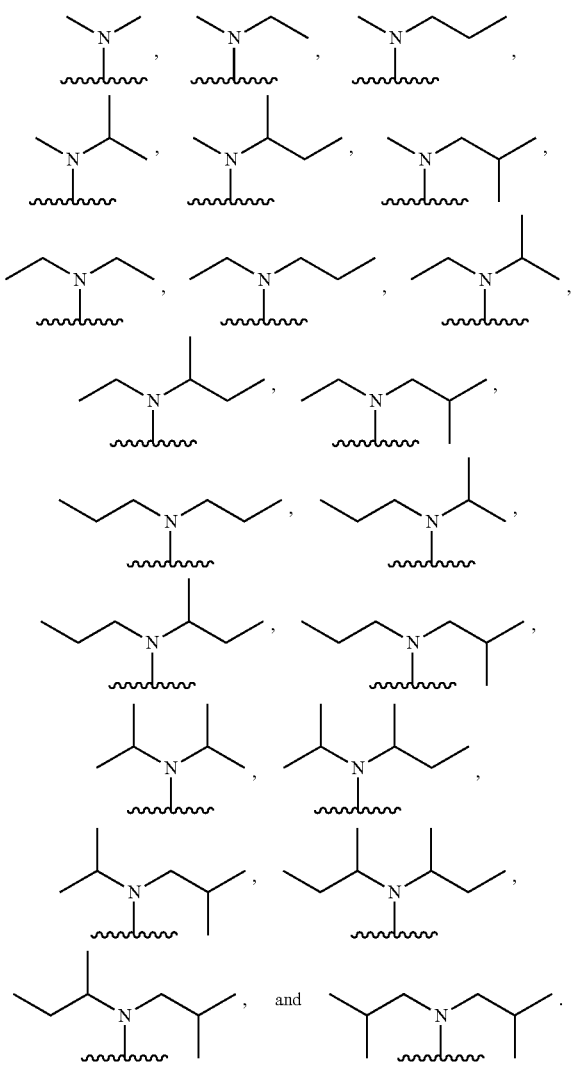
In some embodiments of the method, $R^1$ and $R^2$, together with the nitrogen to which they are attached, form any one of the following:
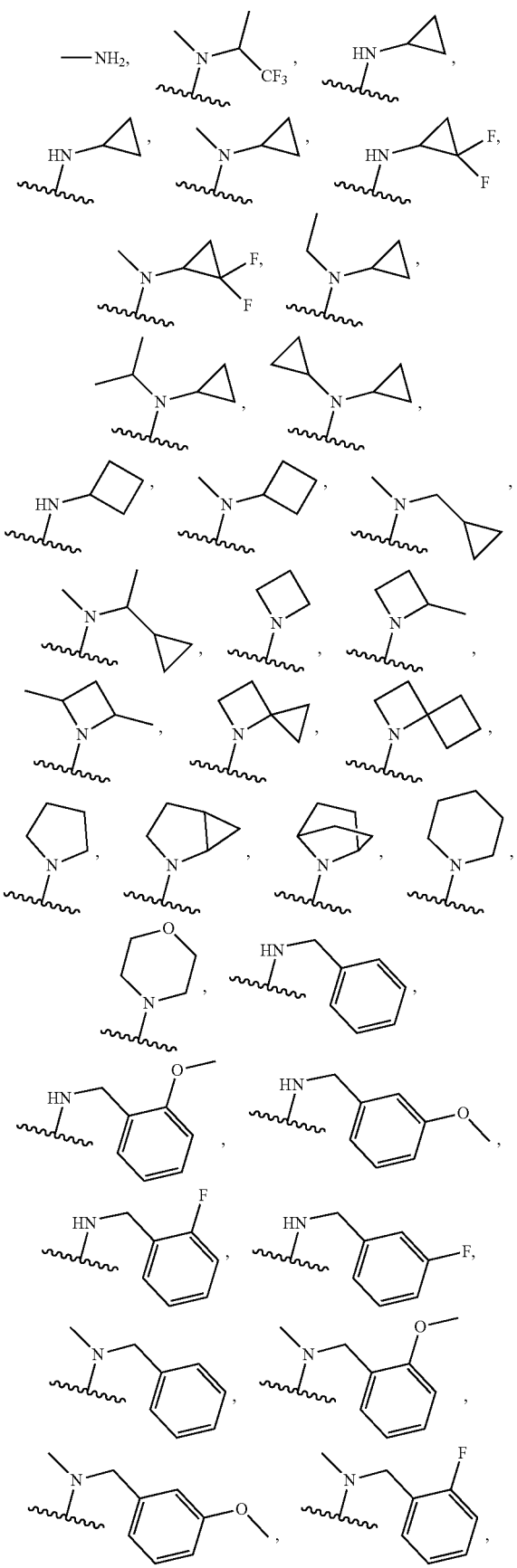

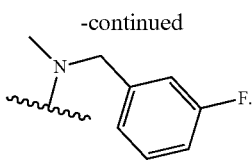

In some embodiments of the method, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined as herein.

In some embodiments of the method, $R^3$ is hydrogen.

In some embodiments of the method, $R^3$ and one of $R^1$ and $R^2$ are combined with the atoms to which they are attached to form a $C_{3-8}$ heterocycloalkyl, said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $SR^4$, $NO_2$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined as herein.

In some embodiments of the method, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR$^{13}$)$_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments of the method, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$ alkyleneP(O)(OR$^{13}$)$_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments of the method, 1 or 2 of $R^8$ $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen. In some embodiments of the method, $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments of the method, $R^8$ and $R^9$ are combined to form a $C_{5-8}$ heterocycloalkyl or $C_{5-10}$ heteroaryl selected from the following:

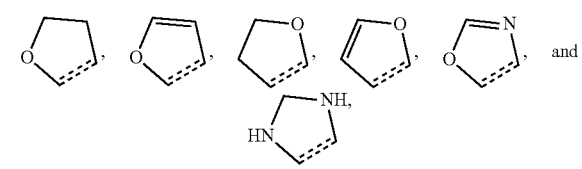

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments of the method, $R^8$ and $R^9$ are combined to form a $C_{5-8}$ heterocycloalkyl or $C_{5-10}$ heteroaryl selected from the following:

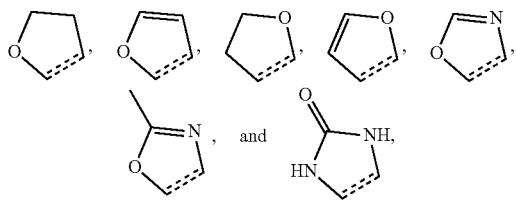

wherein the dashed bond denotes the bond shared with the aromatic ring to which $R^8$ and $R^9$ are attached.

In some embodiments of the method, L is $C_{1-4}$ alkylene.

In some embodiments of the method, L is methylene.

In some embodiments of the method, $R^6$ is selected from hydrogen and $C_{1-6}$ alkyl.

In some embodiments of the method, $R^6$ is hydrogen.

In some embodiments of the method, the compound of formula (I) has the formula (II):

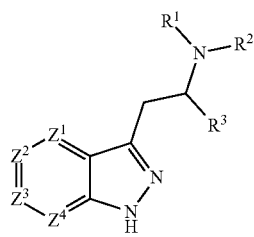

wherein $R^1$, $R^2$, $R^3$, $Z^1$, $Z^2$, $Z^3$ and $Z^4$ are as defined herein.

In some embodiments of the method, the compound of formula (I) has the formula (IIa):

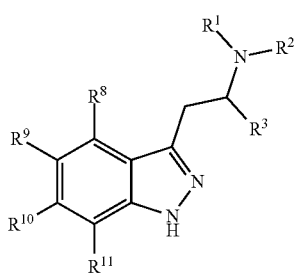

wherein $R^1$, $R^2$, $R^3$, $R^8$, $R^9$, $R^{10}$ and $R^{11}$ are as defined herein.

In some embodiments of the method, the compound of formula (I) has the formula (III):

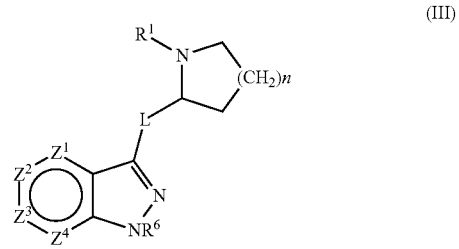

wherein n=0, 1 or 2; and
L, $R^1$, $R^6$, $Z^1$, $Z^2$, $Z^3$ and $Z^4$ are as defined herein.

In some embodiments of the method, the compound of formula (I) is selected from any one of the following:

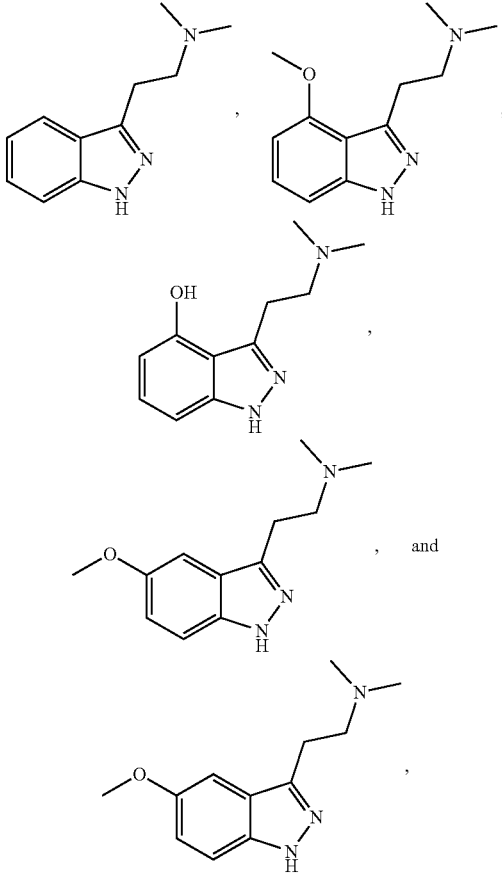

or a pharmaceutically acceptable salt, solvate, tautomer, N-oxide, stereoisomer, metabolite, polymorph or prodrug thereof.

In another aspect the present disclosure provides a method of treating a disease, disorder or condition by activation of a serotonin receptor, the method comprising administering to a subject in need thereof a compound of formula (I) as defined in any one of the herein disclosed embodiments, or a pharmaceutically acceptable salt, solvate, tautomer, N-oxide, stereoisomer, metabolite, polymorph or prodrug thereof, in combination with another known agent useful for treatment of a disease, disorder or condition by activation of a serotonin receptor.

In another aspect the present disclosure provides a method of treating a mental illness, the method comprising administering to a subject in need thereof a compound of formula (I) as defined in any one of the herein disclosed embodiments, or a pharmaceutically acceptable salt, solvate, tautomer, N-oxide, stereoisomer, metabolite, polymorph or prodrug thereof.

In some embodiments, the mental illness is selected from anxiety disorders; depression; mood disorders; psychotic disorders; impulse control and addiction disorders; drug addiction; obsessive-compulsive disorder (OCD); post-traumatic stress disorder (PTSD); stress response syndromes; dissociative disorders; depersonalization disorder; factitious disorders; sexual and gender disorders; somatic symptom disorders; hallucinations; delusions; psychosis; and combinations thereof.

In another aspect the present disclosure provides a method for treating a central nervous system (CNS) disease, disorder or condition and/or a neurological disease, disorder or condition, the method comprising administering to a subject in need thereof a compound of formula (I) as defined in any one of the herein disclosed embodiments, or a pharmaceutically acceptable salt, solvate, tautomer, N-oxide, stereoisomer, metabolite, polymorph or prodrug thereof.

In some embodiments, the CNS disease, disorder or condition and/or neurological disease, disorder or condition is selected from neurological diseases including neurodevelopmental diseases and neurodegenerative diseases such as Alzheimer's disease; presenile dementia; senile dementia; vascular dementia; Lewy body dementia; cognitive impairment, Parkinson's disease and Parkinsonian related disorders such as Parkinson dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neuro-otological and eye movement disorders; neurodegenerative diseases of the retina amyotrophic lateral sclerosis; tardive dyskinesias; hyperkinetic disorders; attention deficit hyperactivity disorder and attention deficit disorders; restless leg syndrome; Tourette's syndrome; schizophrenia; autism spectrum disorders; tuberous sclerosis; Rett syndrome; cerebral palsy; disorders of the reward system including eating disorders such as anorexia nervosa and bulimia nervosa; binge eating disorder, trichotillomania, dermotillomania, nail biting; migraine; fibromyalgia; and peripheral neuropathy of any etiology, and combinations thereof.

In another aspect the present disclosure provides a method for increasing neuronal plasticity and/or increasing dendritic spine density, the method comprising contacting a neuronal cell with a compound of formula (I) as defined in any one of the herein disclosed embodiments, or a pharmaceutically acceptable salt, solvate, tautomer, N-oxide, stereoisomer, metabolite, polymorph or prodrug thereof, in an amount sufficient to increase neuronal plasticity and/or increase dendritic spine density of the neuronal cell.

In another aspect the present disclosure provides methods of treating weight, comprising administering an effective amount of a compound of the invention to a subject in need thereof. Treatment of weight may include treating weight gain; weight loss; metabolic disorder; weight gain associated with pharmaceutical intervention; weight gain associated with a mental illness (including those described herein); eating disorders such as anorexia, bulimia, cachexia, etc.; eating behaviour; obesity; diabetes; insulin resistance; pre-diabetes; glucose intolerance; hyperlipidemia; and cardiovascular disease.

In another aspect the present disclosure provides a method for activating a serotonin receptor in a cell, either in a biological sample or in a patient, comprising administering a compound of formula (I) as defined in any one of the herein disclosed embodiments to the cell.

Any embodiment herein shall be taken to apply mutatis mutandis to any other embodiment unless specifically stated otherwise.

The present disclosure is not to be limited in scope by the specific embodiments described herein, which are intended for the purpose of exemplification only. Functionally-equivalent products, compositions and methods are clearly within the scope of the invention, as described herein.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 1: Plasma concentrations of a subset of exemplar compounds P-8, P-5, P-3, and P-1 in male C57BL/6 mice following IP administration at 10 mg/kg described in Example 49a.

FIG. 2: Time binned and mean±SD (n=3) HTR counts of a subset of exemplar compounds P-4, P-3, and P-1 in male C57BL/6 mice following SC administration over several doses as described in Example 50a.

FIG. 3: Temperature results displayed as mean±SD (n=3) of a subset of exemplar compounds P-4, P-3, and P-1 in male C57BL/6 mice following SC administration over several doses as described in Example 50a.

FIG. 4: Locomotor results (total distance) displayed as mean±SD (n=3) HTR counts of a subset of exemplar compounds P-4, P-3, and P-1 in male C57BL/6 mice following SC administration over several doses as described in Example 50a.

FIG. 5: Locomotor results (distance/time) displayed as mean±SD (n=3) HTR counts of a subset of exemplar compounds P-4, P-3, and P-1 in male C57BL/6 mice following SC administration over several doses as described in Example 50a.

DETAILED DESCRIPTION OF THE EMBODIMENTS

Figure 1:
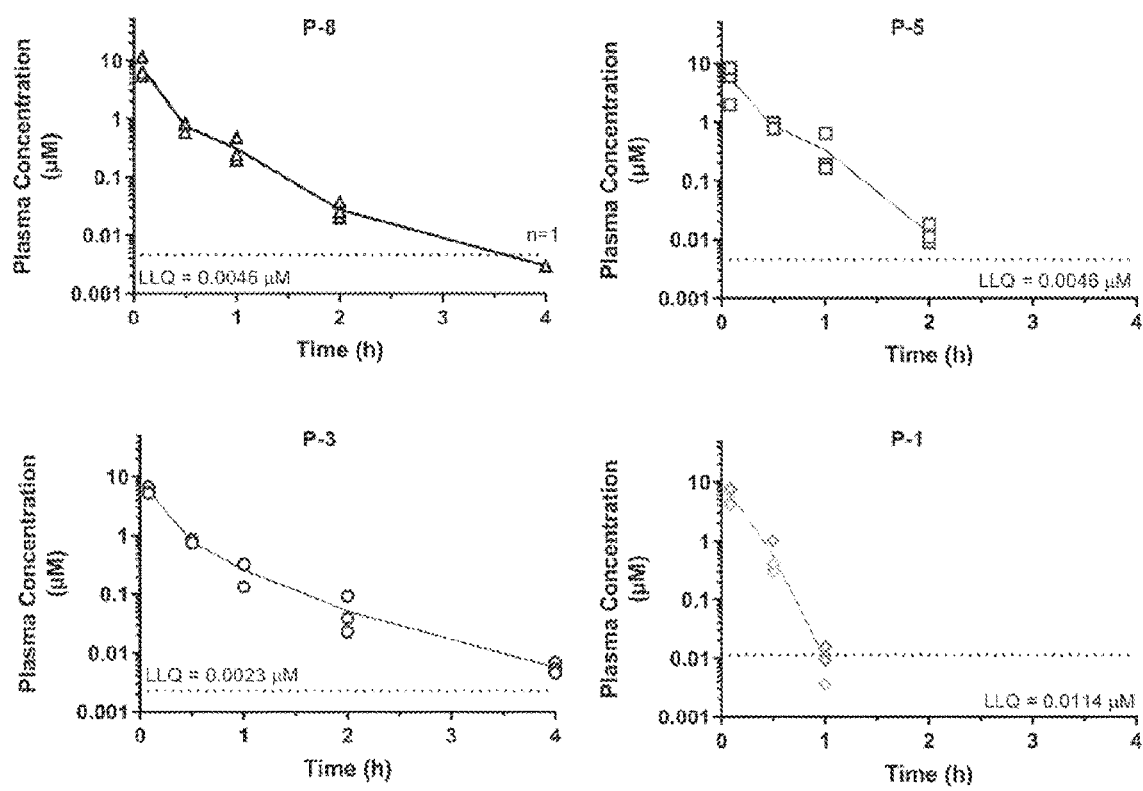
Figure 2:
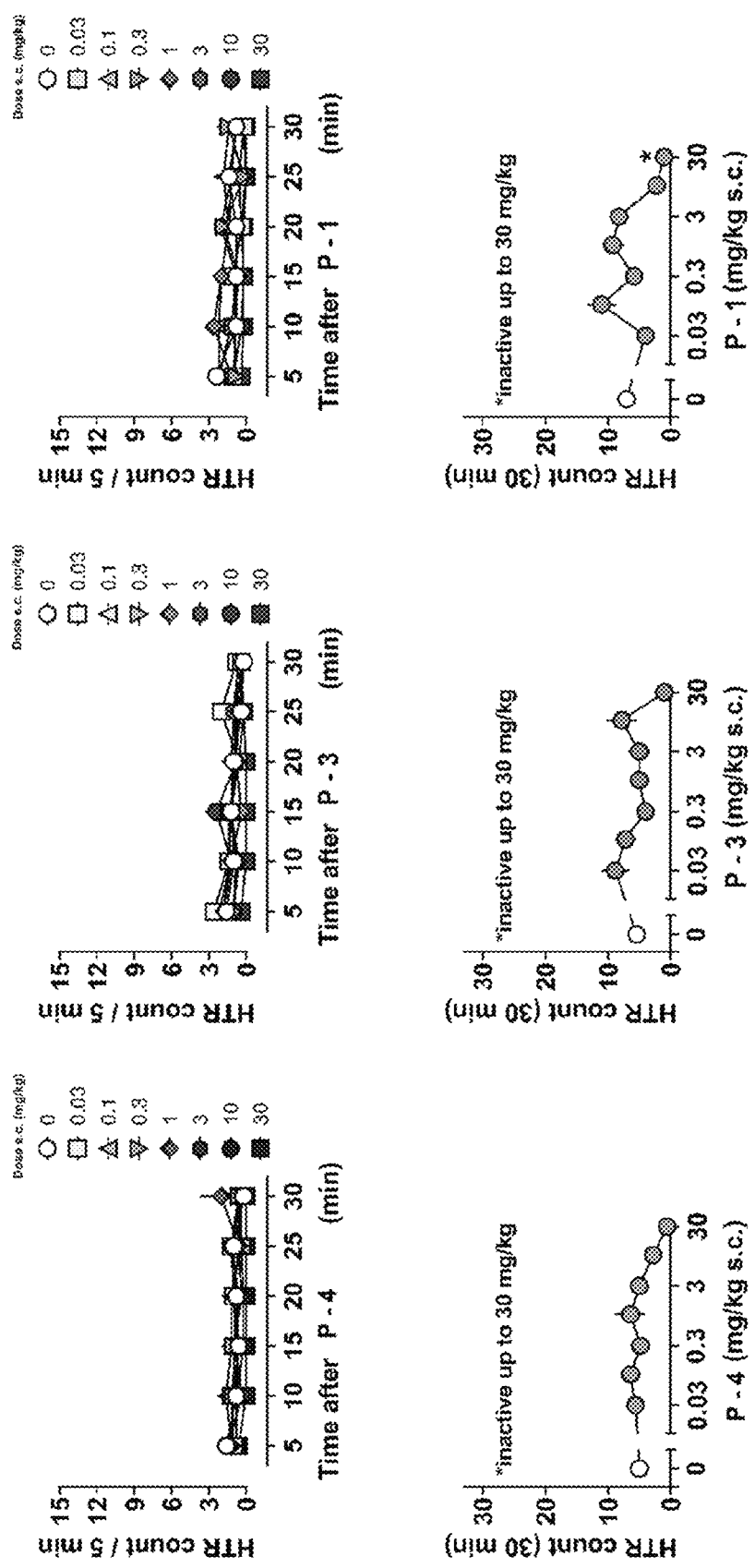
Figure 3:
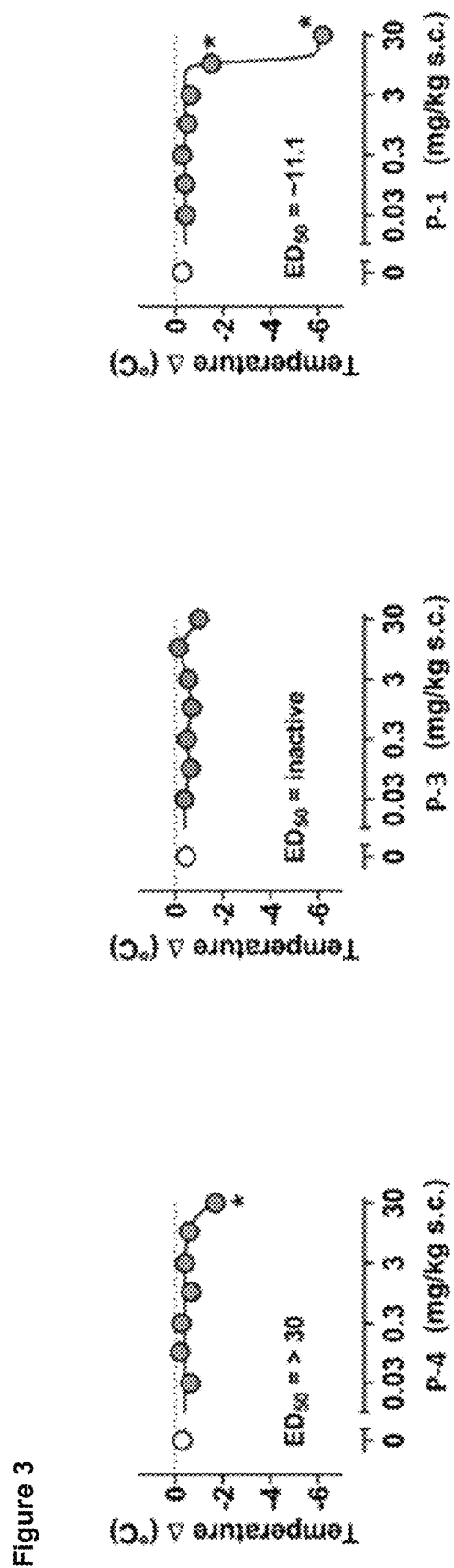
Figure 4:
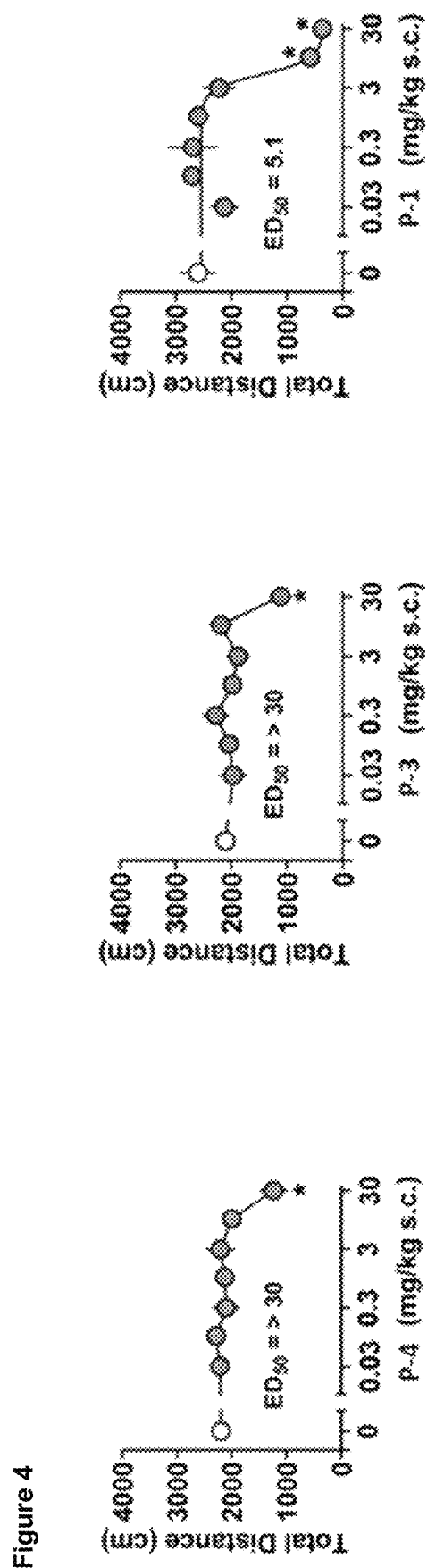
Figure 5:
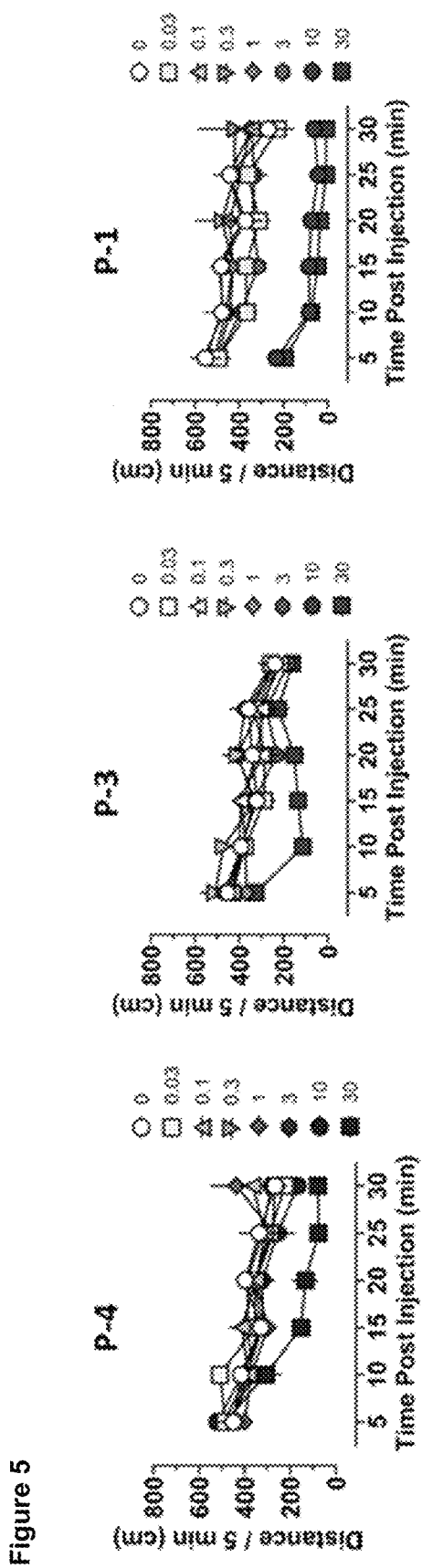

It will be understood that the invention disclosed and defined in this specification extends to all alternative combinations of two or more of the individual features mentioned or evident from the text or drawings. All of these different combinations constitute various alternative aspects of the invention.

Definitions

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps.

The terms "treatment" or "treating" of a subject includes delaying, slowing, stabilizing, curing, healing, alleviating, relieving, altering, remedying, less worsening, ameliorating, improving, or affecting the disease or condition, the sign or symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of signs or symptoms or making the injury, pathology or condition more tolerable to the individual; slowing in the rate of degeneration or decline; making the final point of degeneration less debilitating.

In particularly preferred embodiments, the methods of the present invention can be to prevent or reduce the severity, or inhibit or minimise progression, of a sign or symptom of a disease or condition as described herein. As such, the methods of the present invention have utility as treatments as well as prophylaxes.

As used herein, "preventing" or "prevention" is intended to refer to at least the reduction of likelihood of the risk of (or susceptibility to) acquiring a disease or disorder (i.e., causing at least one of the clinical signs or symptoms of the disease not to develop in an individual that may be exposed to or predisposed to the disease but does not yet experience or display signs or symptoms of the disease). Biological and physiological parameters for identifying such patients are provided herein and are also well known by physicians.

Herein, the term "subject" or "patient" can be used interchangeably with each other. The term "individual" or "patient" refers to an animal that is treatable by the compound and/or method, respectively, including but not limited to, for example, dogs, cats, horses, sheep, pigs, cows, and the like, as well as human, non-human primates. Unless otherwise specified, the "subject" or "patient" may include both male and female genders. Further, it also includes a subject or patient, preferably a human, suitable for receiving treatment with a pharmaceutical composition and/or method of the present invention.

The term "selective" means a greater activity against a first target (e.g., a 5-HT receptor subtype) relative to a second target (e.g., a second 5-HT receptor subtype). In some embodiments a compound has a selectivity of at least 1.25-fold, at least 1.5 fold, at least 2-fold, at least 3-fold, at least 4-fold, at least 5-fold, at least 6-fold, at least 10-fold or at least 100-fold greater towards a first target relative to a second target. In some embodiments, a compound described herein is selective towards the $5\text{-HT}_{2A}$ receptor relative to one or more other 5-HT receptor subtypes such as $5\text{-HT}_{2B}$ and/or $5\text{-HT}_{2C}$, preferably $5\text{-HT}_{2B}$. In some embodiments, a compound described herein is selective towards the $5\text{-HT}_{2C}$ receptor relative to one or more other 5-HT receptor subtypes such as $5\text{-HT}_{2A}$ and/or $5\text{-HT}_{2B}$, preferably $5\text{-HT}_{2B}$.

"About" as used herein when referring to a measurable value such as an amount, a temporal duration, and the like, is meant to encompass variations of ±20% or ±10%, in some instances±5%, in some instances 1%, and in some instances ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein the term "alkyl" refers to a straight or branched chain hydrocarbon radical having from one to twelve carbon atoms, or any range between, i.e. it contains 1, 2, 3, 4, 5, 6, 7, 8, 9, 10, 11 or 12 carbon atoms. The alkyl group is optionally substituted with substituents. Examples of "alkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_2$ alkyl", "$C_1$-$C_3$ alkyl" and "$C_1$-$C_6$ alkyl" refer to an alkyl group, as defined herein, containing at least 1, and at most 2, 3 or 6 carbon atoms respectively, or any range in between (eg alkyl groups containing 2-5 carbon atoms are also within the range of $C_1$-$C_6$).

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

The term "alkenyl" whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "$C_{n1\text{-}n2}$". For example, the term $C_{2\text{-}6}$ alkylene means an alkylene group having 2, 3, 4, 5 or 6 carbon atoms. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "$C_{n1\text{-}n2}$". For example, the term $C_{2\text{-}6}$ alkynyl means an alkynyl group having 2, 3, 4, 5 or 6 carbon atoms. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

The term "cycloalkyl" is intended to include mono-, bi- or tricyclic alkyl groups. The number of carbon atoms that are possible in the referenced cycloalkyl group are indicated by the prefix "$C_{n1\text{-}n2}$". For example, the term $C_{3\text{-}8}$ cycloalkyl means an cycloalkyl group having 3, 4, 5, 6, 7 or 8 carbon atoms. In some embodiments, cycloalkyl groups have from 3 to 12, from 3 to 10, from 3 to 8, from 3 to 6, from 3 to 5 carbon atoms in the ring(s). In some embodiments, cycloalkyl groups have 5 or 6 ring carbon atoms. Examples of monocyclic cycloalkyl groups include, but are not limited to, cyclopropyl, cyclobutyl, cyclopentyl, cyclohexyl, cycloheptyl, and cyclooctyl. In some embodiments, the cycloalkyl group has from 3 to 8, from 3 to 7, from 3 to 6, from 4 to 6, from 3 to 5, or from 4 to 5 ring carbon atoms. Bi- and tricyclic ring systems include bridged, spiro, and fused cycloalkyl ring systems. Examples of bi- and tricyclic ring cycloalkyl systems include, but are not limited to, bicyclo[3.1.0]hexanyl, bicyclo[2.1.1]hexanyl, bicyclo[2.2.1]heptanyl, adamantyl, and decalinyl.

The term "alkylenecycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined herein. The numerical range from x to y in "$C_{x-y}$ alkylenecycloalkyl" relates to the total number of alkyl carbons and cycloalkyl ring atoms. Exemplary alkylenecycloalkyl groups include, but are not limited to, methylenecyclopropyl, methylenecyclobutyl, methylenecyclopentyl and methylenecyclohexyl.

The term "aryl" refers to an aromatic ring system having any suitable number of ring atoms and any suitable number of rings. The number of carbon atoms that are possible in the referenced aryl group are indicated by the prefix "$C_{n1-n2}$". For example, the term $C_{6-12}$ aryl means an aryl group having 6, 7, 8, 9, 10, 11 or 12 carbon atoms. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

The term "alkylenearyl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{1-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. The numerical range from x to y in "$C_{x-y}$ alkylenearyl" relates to the total number of alkyl carbons and aryl ring atoms. Examples of alkylenearyl groups include, but are not limited to, benzyl and ethylenephenyl.

As used herein, the term "alkoxy" refers to an alkyl group as defined herein covalently bound via an O linkage. The alkoxy group is optionally substituted with substituents. Examples of "alkoxy" as used herein include, but are not limited to methoxy, ethoxy, propoxy, isoproxy, butoxy, isobutoxy, tert-butoxy and pentoxy.

As used herein, the terms "$C_1$-$C_2$ alkoxy", "$C_1$-$C_3$ alkoxy" and "$C_1$-$C_6$ alkoxy" refer to an alkoxy group, as defined herein, containing at least 1, and at most 2, 3 or 6 carbon atoms respectively, or any range in between (eg alkoxy groups containing 2-5 carbon atoms are also within the range of $C_1$-$C_6$).

As used herein, the term "alkylamine" refers to an alkyl group as defined herein having one or more amino groups. The amino groups can be primary, secondary or tertiary. The alkyl amine can be further substituted with a hydroxy group to form an amino-hydroxy group. Examples of alkylamines include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the terms "$C_1$-$C_2$ alkylamine", "$C_1$-$C_3$ alkylamine" and "$C_1$-$C_6$ alkylamine" refer to an alkylamine group, as defined herein, containing at least 1, and at most 2, 3 or 6 carbon atoms respectively, or any range in between (e.g., alkylamine groups containing 2-5 carbon atoms are also within the range of $C_1$-$C_6$).

As used herein, the term "alkylsulfonyl" refers to an alkyl group as defined herein having one or more sulfonyl groups. The sulfonyl group can link the alkylsulfonyl to the point of attachment with the rest of the compound, be at the omega position of the alkyl group, or link together at least two carbon atoms of the alkyl group.

As used herein, the terms "$C_1$-$C_2$ alkylsulfonyl", "$C_1$-$C_3$ alkylsulfonyl" and "$C_1$-$C_6$ alkylsulfonyl" refer to an alkylsulfonyl group, as defined herein, containing at least 1, and at most 2, 3 or 6 carbon atoms respectively, or any range in between (e.g., alkylsulfonyl groups containing 2-5 carbon atoms are also within the range of $C_1$-$C_6$).

The term "heteroatom" as used herein means an atom of any element other than carbon or hydrogen. Examples of heteroatoms include nitrogen, oxygen, sulfur and phosphorus. Preferred heteroatoms include N, O and S, preferably N and O.

The term "heteromoiety" as used herein means a chemical group comprising a heteroatom. Examples of heteromoieties include O, S, S(O), $SO_2$, N and NH.

A "substituent" as used herein, refers to a molecular moiety that is covalently bonded to an atom within a molecule of interest. Reference to "a substituent" may include a single substituent or to one or more substituents from the specified list. In some embodiments, a substituted moiety may include 1, 2, 3, 4, 5 or 6 substituents, preferably 1, 2, 3 or 4, more preferably 1, 2 or 3, 1 or 2 or only 1 substituent. For example, a "ring substituent" may be a moiety such as a halogen, alkyl group, or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, ie, a compound that can be isolated, characterized and tested for biological activity.

The terms "optionally substituted" or "may be substituted" and the like, as used throughout the specification, denotes that the group may or may not be further substituted or fused (so as to form a polycyclic system), with one or more non-hydrogen substituent groups. Suitable chemically viable substituents for a particular functional group will be apparent to those skilled in the art.

Examples of substituents include but are not limited to $C_1$-$C_6$ alkyl, $C_1$-$C_6$ haloalkyl, $C_1$-$C_6$ haloalkoxy, $C_1$-$C_6$ hydroxyalkyl, $C_3$-$C_7$ heterocyclyl, $C_3$-$C_7$ cycloalkyl, $C_1$-$C_6$ alkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, halo, ureido, $C_1$-$C_6$ perfluoroalkyl. Preferably the substituents include amino, halo, $C_1$-$C_6$ alkyl, amido, hydroxyl.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I). Preferably, 'halo' is fluoro or chloro.

As used herein, the term "haloalkyl" refers to an alkyl group as defined herein in which one or more (up to all) of the available hydrogen atoms have been replaced with a halogen. In some instances, the term"perfluoro" can be used to define a compound or radical where all the hydrogens are replaced with fluorine. For example, perfluoromethyl refers to 1,1,1-trifluoromethyl.

As used herein, the terms "$C_1$-$C_2$ haloalkyl", "$C_1$-$C_3$ haloalkyl" and "$C_1$-$C_6$ haloalkyl" refer to a haloalkyl group, as defined herein, containing at least 1, and at most 2, 3 or 6 carbon atoms respectively, or any range in between (e.g. haloalkyl groups containing 2-carbon atoms are also within the range of $C_1$-$C_6$).

For example a $C_1$ haloalkyl group could be, but is not limited to, fluoromethyl, or difluoromethyl, or trifluoromethyl.

As used herein, the term "haloalkenyl" refers to an alkenyl group as defined above in which one or more of the available hydrogen atoms have been replaced with a halogen.

Thus, for example, "$C_{1-6}$ haloalkenyl" (or "$C_1$-$C_6$ haloalkenyl") refers to a $C_1$ to $C_6$ linear or branched alkenyl group as defined above with one or more halogen substituents.

As used herein, the term "haloalkynyl" refers to an alkynyl group as defined above in which one or more of the available hydrogen atoms have been replaced with a halogen. Thus, for example, "$C_{1-6}$ haloalkynyl" (or "$C_1$-$C_6$ haloalkynyl") refers to a $C_1$ to $C_6$ linear or branched alkynyl group as defined above with one or more halogen substituents.

As used herein the term haloalkoxy refers to an alkoxy group as defined herein substituted with at least one halogen.

The term "amino" or "amine" refers to the group —$NH_2$.

The term "substituted amino" or "secondary amino" refers to an amino group having a hydrogen replaced with, for example a $C_1$-$C_6$ alkyl group ("$C_1$-$C_6$ alkylamino"), an aryl or aralkyl group ("arylamino", "aralkylamino") and so on. $C_1$-$C_3$ alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a $C_1$-$C_6$alkyl group, which may be the same or different ("dialkylamino"), an aryl and alkyl group ("aryl(alkyl)amino") and so on. Di($C_1$-$C_3$alkyl)amino groups are preferred, such as for example, dimethylamino (NMe$_2$), diethylamino (NEt$_2$), dipropylamino (NPr$_2$) and variations thereof (eg N(Me)(Et) and so on).

The term "nitro" refers to the group —$NO_2$.

The term "cyano" and "nitrile" refer to the group —CN.

The term "amido" or "amide" refers to the group —C(O)NH$_2$.

The term "substituted amido" or "substituted amide" refers to an amido group having a hydrogen replaced with, for example a $C_1$-$C_6$ alkyl group ("$C_1$-$C_6$ alkylamido" or "$C_1$-$C_6$ alkylamide"), an aryl ("arylamido"), aralkyl group ("aralkylamido") and so on. $C_1$-$C_3$ alkylamide groups are preferred, such as for example, methylamide (—C(O)NHMe), ethylamide (—C(O)NHEt) and propylamide (—C(O)NHPr) and includes reverse amides thereof (eg NHMeC(O)—, —NHEtC(O)— and —NHPrC(O)—).

The term "disubstituted amido" or "disubstituted amide" refers to an amido group having the two hydrogens replaced with, for example a $C_1$-$C_6$alkyl group ("di($C_1$-$C_6$ alkyl)amido" or "di($C_1$-$C_6$ alkyl)amide"), an aralkyl and alkyl group ("alkyl(aralkyl)amido") and so on. Di($C_1$-$C_3$ alkyl) amide groups are preferred, such as for example, dimethylamide (—C(O)NMe$_2$), diethylamide (—C(O)NEt$_2$) and dipropylamide ((—C(O)NPr$_2$) and variations thereof (eg C(O)N(Me)Et and so on) and includes reverse amides thereof.

The term "sulfonyl" refers to the group —SO$_2$H.

The term "substituted sulfonyl" refers to a sulfonyl group having the hydrogen replaced with, for example a $C_1$-$C_6$ alkyl group ("sulfonyl$C_1$-$C_6$ alkyl"), an aryl ("arylsulfonyl"), an aralkyl ("aralkylsulfonyl") and so on. Sulfonyl $C_1$-$C_3$ alkyl groups are preferred, such as for example, —SO$_2$Me, —SO$_2$Et and —SO$_2$Pr.

The term "sulfonylamido" or "sulfonamide" refers to the group —SO$_2$NH$_2$.

The term "substituted sulfonamido" or "substituted sulphonamide" refers to an sulfonylamido group having a hydrogen replaced with, for example a $C_1$-$C_6$ alkyl group ("sulfonylamido$C_1$-$C_6$ alkyl"), an aryl ("arylsulfonamide"), aralkyl ("aralkylsulfonamide") and so on. Sulfonylamido$C_1$-$C_3$ alkyl groups are preferred, such as for example, SO$_2$NHMe, SO$_2$NHEt and —SO$_2$NHPr and includes reverse sulfonamides thereof (e.g. —NHSO$_2$Me, NHSO$_2$Et and —NHSO$_2$Pr).

The term "disubstituted sufonamido" or "disubstituted sulphonamide" refers to an sulfonylamido group having the two hydrogens replaced with, for example a $C_1$-$C_6$ alkyl group, which may be the same or different ("sulfonylamidodi($C_1$-$C_6$ alkyl)"), an aralkyl and alkyl group ("sulfonamido(aralkyl)alkyl") and so on. Sulfonylamidodi($C_1$-$C_3$ alkyl) groups are preferred, such as for example, —SO$_2$NMe$_2$, —SO$_2$NEt$_2$ and —SO$_2$NPr$_2$ and variations thereof (eg SO$_2$N(Me)Et and so on) and includes reserve sulfonamides thereof (eg —N(Me)SO$_2$Me and so on).

The term "sulfate" refers to the group OS(O)$_2$OH and includes groups having the hydrogen replaced with, for example a $C_1$-$C_6$ alkyl group ("alkylsulfates"), an aryl ("arylsulfate"), an aralkyl ("aralkylsulfate") and so on. $C_1$-$C_3$ alkylsulfates are preferred, such as for example, OS(O)$_2$OMe, OS(O)$_2$OEt and OS(O)$_2$OPr.

The term "sulfonate" refers to the group SO$_3$H and includes groups having the hydrogen replaced with, for example a $C_1$-$C_6$ alkyl group ("alkylsulfonate"), an aryl ("arylsulfonate"), an aralkyl ("aralkylsulfonate") and so on. $C_1$-$C_3$ alkylsulfonates are preferred, such as for example, SO$_3$Me, SO$_3$Et and SO$_3$Pr.

The term "amino acid" as herein defined refers to a moiety containing an amino group and a carboxyl group linked by at least one carbon. An amino acid may refer a natural or non-natural amino acid, preferably a natural amino acid such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, preferably the amino acid is arginine, lysine or histidine, most preferably lysine.

The term "carboxylate" or "carboxyl" refers to the group —COO— or —COOH.

The term "carbamate" or "carbomyl" refers to the group —OC(O)NH$_2$. The carbamate may be substituted, or may be disubstituted, for example with an alkyl group such as but not limited to $C_1$-$C_6$ alkyl.

The term "carbonate" refers to the group —OC(O)O— or —OC(O)OH.

The term "alkylcarbonate" as herein defined refers to a carbonate group having the hydrogen replaced with, for example a $C_1$-$C_6$ alkyl group, an aryl or aralkyl group ("arylcarbonate" or "aralkylcarbonate") and so on. $CO_3C_1$-$C_3$alkyl groups are preferred, such as for example, methylcarbonate ($CO_3Me$), ethylcarbonate ($CO_3Et$) and propylcarbonate ($CO_3Pr$).

The term "ester" refers to a carboxyl group having the hydrogen replaced with, for example a $C_1$-$C_6$ alkyl group ("carboxyl$C_1$-$C_6$ alkyl" or "alkylester"), an aryl or aralkyl group ("arylester" or "aralkylester") and so on. $CO_2C_1$-$C_3$ alkyl groups are preferred, such as for example, methylester ($CO_2Me$), ethylester ($CO_2Et$) and propylester ($CO_2Pr$) and includes reverse esters thereof (eg —OC(O)Me, —OC(O)Et and —OC(O)Pr).

The term "heterocyclyl" refers to a moiety obtained by removing a hydrogen atom from a ring atom of a heterocyclic compound which moiety has from 3 to 12 ring atoms (unless otherwise specified), of which 1, 2, 3, 4 or more are ring heteroatoms, for example independently selected from O, S and N, or ring heteromoieties, for example independently selected from O, S, S(O), SO$_2$, N and NH. When a heterocyclyl group contains the prefix $C_{n1-n2}$ or "n1 to n2" this prefix indicates the number of carbon atoms in the corresponding carbocyclic group, in which one or more, suitably 1, 2, 3, 4 or more, of the ring atoms is replaced with a heteroatom or heteromoiety.

In this context, the prefixes 3-, 4-, 5-, 6-, 7-, 8-, 9- and 10-membered denote the number of ring atoms, or range of ring atoms, whether carbon atoms or heteroatoms. For example, the term "$C_{3-10}$ heterocyclyl" or "3-10 membered heterocylyl", as used herein, pertains to a heterocyclyl group having 3, 4, 5, 6, 7, 8, 9 or 10 ring atoms. Examples of heterocylyl groups include 5-6-membered monocyclic heterocyclyls and 6-10 membered bicyclic heterocyclyls (including fused, bridged and spirocyclic ring systems).

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (eg 3-pyrroline, 2,5-dihydropyrrole), 2Hpyrrole or 3H-pyrrole (isopyrrole, isoazole) or pyrrolidinone (5-membered rings), piperidine, dihydropyridine, tetrahydropyridine (6-membered rings), and azepine (7 membered ring); those containing two nitrogen atoms such as imidazoline, pyrazolidine (diazolidine), imidazoline, pyrazoline (dihydropyrazole) (5-membered rings), piperazine (6 membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7 membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass heteroaryl (aromatic heterocyclyls) and heterocycloalkyl (non-aromatic heterocyclyls). Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O. The aromatic heterocyclyl groups may comprise 1, 2, 3, 4 or more ring heteroatoms. When a heteroaryl group contains the prefix $C_{n1-n2}$ or "n1 to n2" this prefix indicates the number of carbon atoms in the corresponding aryl group, in which one or more, suitably 1, 2, 3, 4 or more, of the ring atoms is replaced with a heteroatom. In the case of fused aromatic heterocyclyl groups, only one of the rings may contain a heteroatom and not all rings must be aromatic.

"Heteroaryl" is used herein to denote a heterocyclic group having aromatic character and embraces aromatic monocyclic ring systems and polycyclic (eg bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulphur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, napthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6 membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoiine, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "heterocycloalkyl" or "non-aromatic heterocyclyl" encompasses optionally substituted saturated and unsaturated rings which contain at least one heteroatom such as N, S and O, or a heteromoiety such as O, S, S(O), $SO_2$, N and NH. The ring may contain 1, 2, 3, 4 or more heteroatoms or heteromoieties. When a heterocycloalkyl group contains the prefix $C_{n1-n2}$ or "n1 to n2" this prefix indicates the number of carbon atoms in the corresponding carbocyclic group, in which one or more, suitably 1, 2, 3, 4 or more, of the ring atoms is replaced with a heteroatom or heteromoiety. The ring may be a monocyclic ring or part of a polycyclic ring system. Polycyclic ring systems include fused and/or bridged rings and spirocycles. Not every ring in a non-aromatic heterocyclic polycyclic ring system must contain a heteroatom, provided at least one ring contains one or more heteroatoms.

Non-aromatic heterocyclyls may be 3-8 membered monocyclic rings.

Examples of 5-membered non-aromatic heterocyclyl rings include 2H-pyrrolyl, 1pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5triozalanyl, 1,3,5-trithianyl, 1,4-morpholinyl, thiomorpholinyl, 1,4-oxathianyl, triazinyl, 1,4thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7 membered heterocyclyls fused to carbocyclic aromatic rings include indolinyl, benzodiazepinyl, benzazepinyl, dihydrobenzofuranyl and the like.

The term "alkyleneheteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heteroaryl component is as defined herein. The numerical range from x to y in "$C_{x-y}$ alkylenecycloalkyl" relates to the total number of alkyl carbons and heteroaryl ring atoms (carbon and heteroatoms together).

The term "alkyleneheterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heterocycloalkyl component is as defined herein. The numerical range from x to y in "$C_{x-y}$ alkyleneheterocycloalkyl" relates to the total number of alkyl carbons and heterocycloalkyl ring atoms (carbon and heteroatoms together).

As used herein, the term solvate refers to a complex of the compound and either stoichiometric or non-stoichiometric amounts of a solvent. Solvates are often formed during the process of crystallization with pharmaceutically acceptable solvents such as water, ethanol, and the like. Hydrates are formed when the solvent is water, or alcoholates are formed when the solvent is alcohol.

As used herein, the term polymorph refers to the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

As used herein, the term "metabolite" refers to a derivative of a compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. Metabolites of the compounds disclosed herein are optionally identified either by administration of compounds to a host and analysis of tissue samples from the host, or by incubation of compounds with hepatic cells in vitro and analysis of the resulting compounds.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. The term "stereoisomers" refers to compounds which have identical chemical constitution, but differ with regard to the arrangement of the atoms or groups in space. As used herein, the term "stereoisomer" includes but is not limited to diastereomers, enantiomers and atropisomers, as well as mixtures thereof such as racemic mixtures.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Compounds

The present disclosure provides compounds of formula (I):

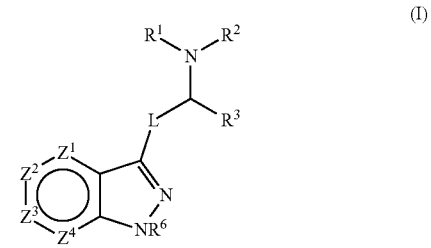

or a pharmaceutically acceptable salt, solvate, tautomer, N-oxide, stereoisomer, metabolite, polymorph or prodrug thereof, wherein $R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$ haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$ haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ are combined with the atoms to which they are attached to form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

L is selected from $C_{1-4}$ alkylene, $C_2$-$C_4$ alkenylene and $C_2$-$C_4$ alkynylene;

$Z^1$ is $CR^8$ or N;

$Z^2$ is $CR^9$ or N;

$Z^3$ is $CR^{10}$ or N;

$Z^4$ is $CR^{11}$ or N;

$R^6$ is selected from hydrogen, $C_{1-6}$ alkyl, $C_{2-6}$ alkenyl, $C_{2-6}$ alkynyl, $C_{1-6}$ alkyleneP(O)(OR$^{12}$)$_2$, $C(O)R^{12}$, $CO_2R^{12}$, $C(O)N(R^{12})_2$, $S(O)R^{12}$ and $SO_2R^{12}$, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-11}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^{12}$, $C(O)N(R^{12})_2$, $OR^{12}$, $N(R^{12})_2$, $NO_2$, $SR^{12}$ and $SO_2R^{12}$, said $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{12}$;

each $R^{12}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

$R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR$^{13}$)$_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively, when $Z^1$ is $CR^8$ and $Z^2$ is $CR^9$, or when $Z^2$ is $CR^9$ and $Z^3$ is $CR^{10}$, or when $Z^3$ is $CR^{10}$ and $Z^4$ is $CR^{11}$, then $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl; and said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, the compound of formula (I) is not one of the following:

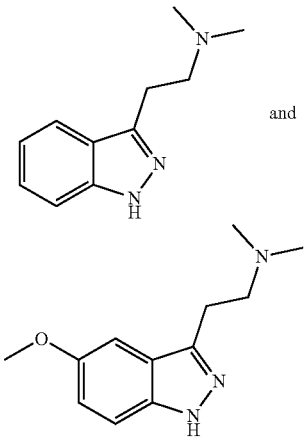

and $R^6$

In some embodiments, $R^6$ is H.

In some embodiments, $R^6$ is $C_{1-6}$alkyl, preferably $C_{1-4}$alkyl, more preferably $C_1$alkyl.

$Z^1$ & $Z^2$, $R^8$ & $R^9$

In some embodiments, $Z^1$ is N. In some embodiments, $Z^2$ is N.

In some embodiments, one of $R^8$ and $R^9$ (if present) is selected from halogen, $OR^{13}$, $N(R^{13})_2$, $SR^{13}$, $C_{1-6}$ alkyl and $C_{1-6}$ haloalkyl, the other (if present) being hydrogen.

In some embodiments, $R^8$ (if present) is selected from halogen, $OR^{13}$, $N(R^{13})_2$, $SR^{13}$, $C_{1-6}$ alkyl and $C_{1-6}$ haloalkyl, and $R^9$ (if present) is hydrogen.

In some embodiments, $R^9$ (if present) is selected from halogen, $OR^{13}$, $N(R^{13})_2$, $SR^{13}$, $C_{1-6}$ alkyl and $C_{1-6}$ haloalkyl, and $R^8$ (if present) is hydrogen.

In some embodiments, $R^8$ (if present) is selected from halogen, $OR^{13}$ and $C_{1-6}$ alkyl, and $R^9$ (if present) is hydrogen.

In some embodiments, $R^9$ (if present) is selected from halogen, $OR^{13}$ and $C_{1-6}$ alkyl, and $R^8$ (if present) is hydrogen.

In some embodiments, $Z^1$ is $CR^8$.

In some embodiments, $Z^1$ is $CR^8$ and at least one of $R^9$, $R^{10}$, $R^{11}$ (if present) is other than H. In some embodiments, $Z^1$ is $CR^8$ and at least one of $R^9$, $R^{10}$, $R^{11}$ (if present) is selected from halogen, $OR^{13}$, $N(R^{13})_2$, $SR^{13}$, $C_{1-6}$ alkyl and $C_{1-6}$ haloalkyl.

In some embodiments, $Z^2$ is $CR^9$.

In some embodiments, $Z^1$ is $CR^8$ and $R^8$ is selected from halogen, $OR^{13}$, $N(R^{13})_2$, $SR^{13}$, $C_{1-6}$ alkyl and $C_{1-6}$ haloalkyl.

In some embodiments, $Z^2$ is $CR^9$ and $R^9$ is selected from halogen, $OR^{13}$, $N(R^{13})_2$, $SR^{13}$, $C_{1-6}$ alkyl and $C_{1-6}$ haloalkyl.

In some embodiments, $Z^1$ is $CR^8$ and $R^8$ is selected from halogen, $OR^{13}$, $N(R^{13})_2$, $SR^{13}$, $C_{1-6}$ alkyl and $C_{1-6}$ haloalkyl, and $Z^2$ is N or CH.

In some embodiments, $Z^2$ is $CR^9$ and $R^9$ is selected from halogen, $OR^{13}$, $N(R^{13})_2$, $SR^{13}$, $C_{1-6}$ alkyl and $C_{1-6}$ haloalkyl, and $Z^1$ is N or CH.

In some embodiments, $Z^3$ is $CR^{10}$, and preferably $R^{10}$ is H.

In some embodiments, one of $R^8$ and $R^9$ is $OR^{13}$.

In some embodiments, one or both of $Z^1$ is $CR^8$ and/or $Z^2$ is $CR^9$.

In some embodiments, each $R^{13}$ (if present) is independently selected from hydrogen and $C_{1-6}$ alkyl.

In some embodiments, each $R^{13}$ (if present) is H.

In some embodiments, each $R^{13}$ (if present) is $C_{1-6}$alkyl, preferably $C_{1-4}$alkyl, more preferably methyl.

In some embodiments, $Z^1$ is $CR^8$.

In some embodiments, $R^8$ (if present) is hydrogen.

In some embodiments, $Z^2$ is $CR^9$.

In some embodiments, $R^9$ (if present) is hydrogen.

In some embodiments, $R^8$ and $R^9$ (if present) are each hydrogen.

In some embodiments, $R^8$ (if present) is selected from the group consisting of hydrogen, $OR^{13}$ (wherein preferably $R^{13}$ is selected from hydrogen, $C_{1-3}$ alkyl [more preferably $C_1$alkyl]), and halogen (preferably fluoro).

In some embodiments, $R^9$ (if present) is selected from the group consisting of hydrogen, $OR^{13}$ (wherein preferably $R^{13}$ is selected from hydrogen, $C_{1-3}$ alkyl [more preferably $C_1$alkyl]), and halogen (preferably fluoro).

In some embodiments, $R^8$ and $R^9$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some of these embodiments, $R^{10}$ and $R^{11}$ are preferably hydrogen.

$Z^3$ & $Z^4$, $R^{10}$ & $R^{11}$

In some embodiments, $Z^3$ is N. In some embodiments, $Z^4$ is N.

In some embodiments, $Z^3$ is $CR^{10}$.

In some embodiments, $R^{10}$ (if present) is hydrogen.

In some embodiments, $Z^4$ is $CR^{11}$.

In some embodiments, $R^{11}$ (if present) is hydrogen.

In some embodiments, $R^{10}$ and $R^{11}$ (if present) are each hydrogen.

In some embodiments, $R^{10}$ (if present) is selected from the group consisting of hydrogen, $OR^{13}$ (wherein preferably $R^{13}$ is selected from hydrogen, $C_{1-3}$ alkyl [more preferably $C_1$alkyl]), and halogen (preferably fluoro).

In some embodiments, $R^{11}$ (if present) is selected from the group consisting of hydrogen, $OR^{13}$ (wherein preferably $R^{13}$ is selected from hydrogen, $C_{1-3}$ alkyl [more preferably $C_1$alkyl]), and halogen (preferably fluoro).

In some embodiments, $R^{10}$ and $R^{11}$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some of these embodiments, $R^8$ and $R^9$ are preferably hydrogen.

$R^6$, $R^{10}$ & $R^{11}$

In some embodiments, $R^6$, $R^{10}$ and $R^{11}$ (if present) are each hydrogen.

In some embodiments, at least one of $R^6$, $R^{10}$ and $R^{11}$ is present and is other than hydrogen. In some embodiments, at least two of $R^6$, $R^{10}$ and $R^{11}$ are present and are other than hydrogen.

$R^6$, $R^8$, $R^9$, $R^{10}$ & $R^{11}$

In some embodiments, only one of $R^8$, $R^9$, $R^{10}$ and $R^{11}$ (if present) is other than hydrogen. In some embodiments, only $R^8$ of $R^8$, $R^9$, $R^{10}$ and $R^{11}$ (if present) is other than hydrogen. In some embodiments, only $R^9$ of $R^8$, $R^9$, $R^{10}$ and $R^{11}$ (if present) is other than hydrogen. In some embodiments, only $R^{10}$ of $R^8$, $R^9$, $R^{10}$ and $R^{11}$ (if present) is other than hydrogen. In some embodiments, only $R^{11}$ of $R^8$, $R^9$, $R^{10}$ and $R^{11}$ (if present) is other than hydrogen.

In some embodiments, only one of $R^6$, $R^8$, $R^9$, $R^{10}$ and $R^{11}$ (if present) is other than hydrogen. In some embodiments, only $R^6$ of $R^6$, $R^8$, $R^9$, $R^{10}$ and $R^{11}$ (if present) is other than hydrogen. In some embodiments, only $R^8$ of $R^6$, $R^8$, $R^9$, $R^{10}$ and $R^{11}$ (if present) is other than hydrogen. In some embodiments, only $R^9$ of $R^6$, $R^8$, $R^9$, $R^{10}$ and $R^{11}$ (if present) is other than hydrogen. In some embodiments, only $R^{10}$ of $R^6$, $R^8$, $R^9$, $R^{10}$ and $R^{11}$ (if present) is other than hydrogen. In some embodiments, only $R^{11}$ of $R^6$, $R^8$, $R^9$, $R^{10}$ and $R^{11}$ (if present) is other than hydrogen.

In some embodiments, $R^8$ and $R^9$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some of these embodiments, $R^{10}$ and $R^{11}$ are preferably hydrogen.

In some embodiments, $R^8$ and $R^9$ are both other than hydrogen. In some embodiments, $R^8$ is $OR^{13}$ (wherein preferably $R^{13}$ is selected from hydrogen, $C_{1-3}$ alkyl [more preferably $C_1$alkyl]), and $R^9$ is halogen (preferably fluoro). In some of these embodiments, $R^{10}$ and $R^{11}$ are preferably hydrogen.

In some embodiments, $R^8$ and $R^{10}$ are both other than hydrogen. In some embodiments, $R^8$ is $OR^{13}$ (wherein preferably $R^{13}$ is selected from hydrogen, $C_{1-3}$ alkyl [more preferably $C_1$alkyl]), and $R^{10}$ is halogen (preferably fluoro). In some embodiments, $R^8$ is $OR^{13}$ (wherein preferably $R^{13}$ is selected from hydrogen, $C_{1-3}$ alkyl [more preferably $C_1$alkyl]), and $R^{11}$ is halogen (preferably fluoro). In some of these embodiments, $R^9$ and $R^{11}$ are preferably hydrogen.

In some embodiments, $R^9$ and $R^{10}$ are both other than hydrogen. In some embodiments, $R^9$ is $OR^{13}$ (wherein preferably $R^{13}$ is selected from hydrogen, $C_{1-3}$ alkyl [more preferably $C_1$alkyl]), and $R^{10}$ is halogen (preferably fluoro). In some of these embodiments, $R^8$ and $R^{11}$ are preferably hydrogen.

In some embodiments, $R^8$ and $R^{10}$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some of these embodiments, $R^9$ and $R^{11}$ are preferably hydrogen.

In some embodiments, $R^8$ and $R^{11}$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some of these embodiments, $R^9$ and $R^{10}$ are preferably hydrogen.

In some embodiments, $R^9$ and $R^{10}$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some of these embodiments, $R^8$ and $R^{11}$ are preferably hydrogen.

In some embodiments, $R^9$ and $R^{11}$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some of these embodiments, $R^8$ and $R^{10}$ are preferably hydrogen.

In some embodiments, one or more of $R^8$, $R^9$, $R^{10}$ and $R^{11}$ (if present) are other than hydrogen. In some embodiments, two or more (preferably two) of $R^8$, $R^9$, $R^{10}$ and $R^{11}$ (if present) are other than hydrogen. In some embodiments, two or more (preferably two) of $R^8$, $R^9$, $R^{10}$ and $R^{11}$ are selected from the group consisting of $OR^{13}$ (wherein preferably $R^{13}$ is selected from hydrogen, $C_{1-3}$ alkyl [more preferably $C_1$alkyl]), and halogen (preferably fluoro). In some embodiments, two or more (preferably two) of $R^8$, $R^9$, $R^{10}$ and $R^{11}$ are selected from the group consisting of methoxy and fluoro.

$R^1$ & $R^2$

In some embodiments, at least one of $R^1$ and $R^2$ is not methyl. In some embodiments, both of $R^1$ and $R^2$ are not methyl.

In some embodiments, at least one of $R^1$ and $R^2$ is not isopropyl. In some embodiments, both of $R^1$ and $R^2$ are not isopropyl.

In some embodiments, at least one of $R^1$ and $R^2$ is $C_{7-18}$ alkylenearyl. In some embodiments, at least one of $R^1$ and $R^2$ is $C_{7-18}$ alkylenearyl that is $C_{1-4}$alkoxy substituted, preferably $C_{1-4}$alkoxy substituted at the 2-position (ortho relative to the core Markush structure).

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

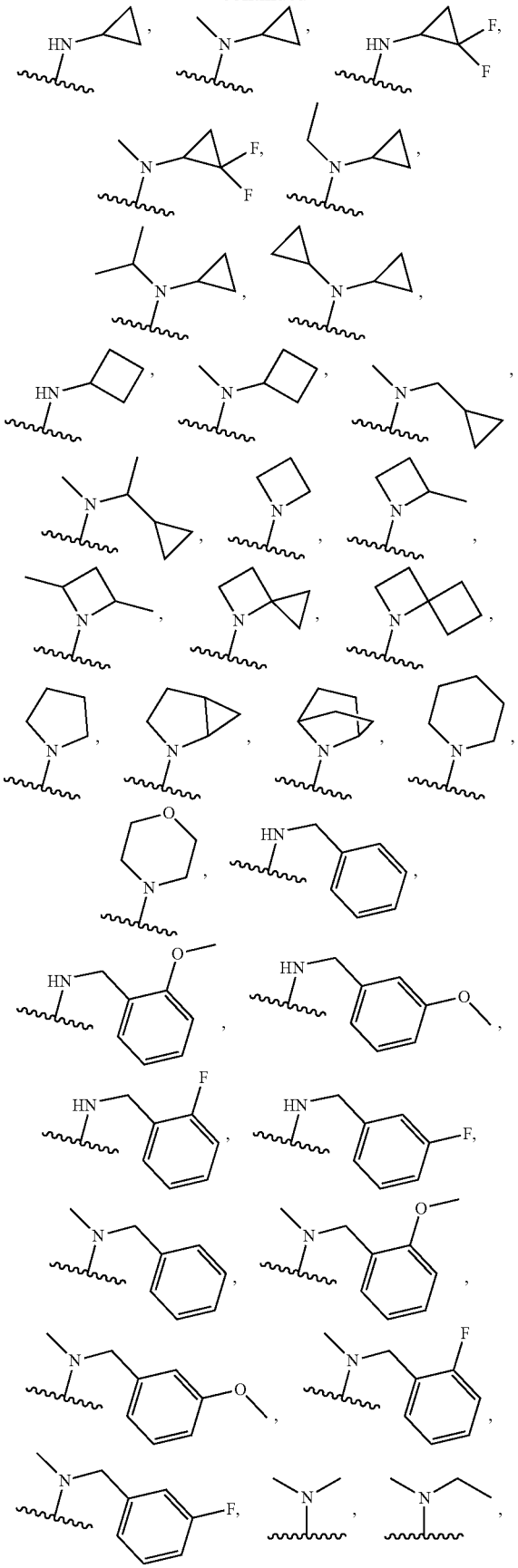

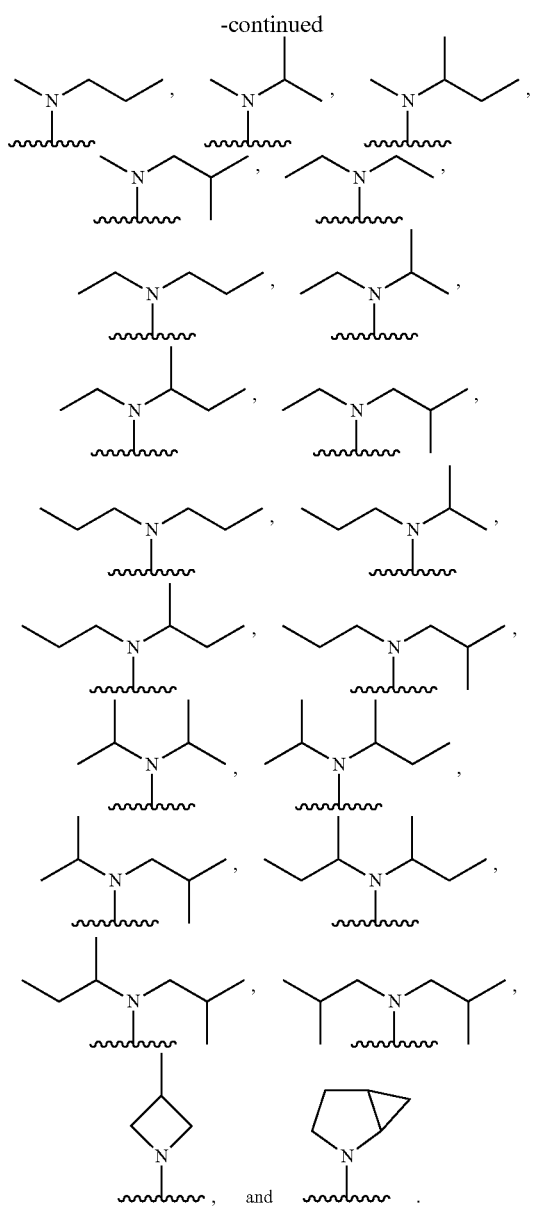

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^1$ and $R^2$ are combined with the atoms to which they are attached to form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$.

In some embodiments, $R^1$ and $R^2$ together with the nitrogen atom to which they are attached form a $C_{4-8}$ heterocycloalkyl that does not include additional ring heteromoieties.

In some embodiments, $R^1$ and $R^2$ together with the nitrogen atom to which they are attached form a $C_{4-8}$ heterocycloalkyl that is monocyclic or fused.

In some embodiments, $R^1$ and $R^2$ together with the nitrogen atom to which they are attached form a $C_{4-8}$ heterocycloalkyl that is monocyclic.

In some embodiments, $R^1$ and $R^2$ together with the nitrogen atom to which they are attached form a $C_{4-8}$ heterocycloalkyl that is fused.

In some embodiments, $R^1$ and $R^2$ together with the nitrogen atom to which they are attached form a $C_{4-8}$ heterocycloalkyl that is unsubstituted and moncyclic or fused.

In some embodiments, $R^1$ and $R^2$ together with the nitrogen atom to which they are attached form a $C_{4-8}$ heterocycloalkyl that is unsubstituted and moncyclic.

In some embodiments, $R^1$ and $R^2$ together with the nitrogen atom to which they are attached form a $C_{4-8}$ heterocycloalkyl that is unsubstituted and fused.

$R^3$, $R^1$ & $R^2$

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined as herein.

$R^8$ $R^9$, $R^{10}$ & $R^{11}$

In some embodiments, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkylene$P(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

$R^8$ and $R^9$

In some embodiments, $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ and $R^9$ are combined to form a $C_{5-8}$ heterocycloalkyl or $C_{5-10}$ heteroaryl selected from the following:

and

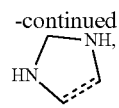

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments, $R^8$ and $R^9$ are combined to form a $C_{5-8}$ heterocycloalkyl or $C_{5-10}$ heteroaryl selected from the following:

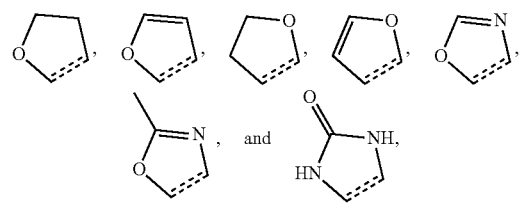

wherein the dashed bond denotes the bond shared with the aromatic ring to which $R^8$ and $R^9$ are attached.

$R^1$, $R^2$, $R^8$ $R^9$, $R^{10}$ & $R^{11}$

In some embodiments, $R^1$ and $R^2$ are each independently selected from $C_{1-6}$ alkyl; and only one of $R^8$ $R^9$, $R^{10}$ and $R^{11}$ is other than hydrogen. In preferred embodiments, the only one of $R^8$ $R^9$, $R^{10}$ and $R^{11}$ other than hydrogen is selected from the group consisting of group consisting of $OR^{13}$ (wherein preferably $R^{13}$ is selected from hydrogen, $C_{1-3}$ alkyl [more preferably $C_1$alkyl]), and halogen (preferably fluoro).

In some embodiments, $R^1$ and $R^2$ are each independently selected from $C_{1-6}$ alkyl (preferably $C_{2-6}$ alkyl, more preferably $C_{3-6}$ alkyl); and $R^9$ is selected from the group consisting of group consisting of $OR^{13}$ (wherein preferably $R^{13}$ is selected from hydrogen, $C_{1-3}$ alkyl [more preferably $C_1$alkyl]), and halogen (preferably fluoro).

In some embodiments, $R^9$ is $OR^{13}$ (wherein preferably $R^{13}$ is selected from hydrogen, $C_{1-3}$ alkyl [more preferably $C_1$alkyl]), and $R^{10}$ is halogen (preferably fluoro); and $R^1$ and $R^2$ are each independently selected from $C_{1-6}$ alkyl (preferably $C_{1-3}$ alkyl, more preferably $C_{1-2}$ alkyl).

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

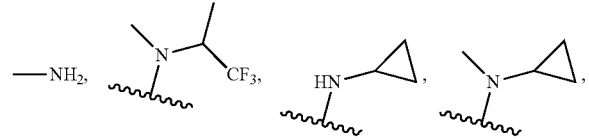

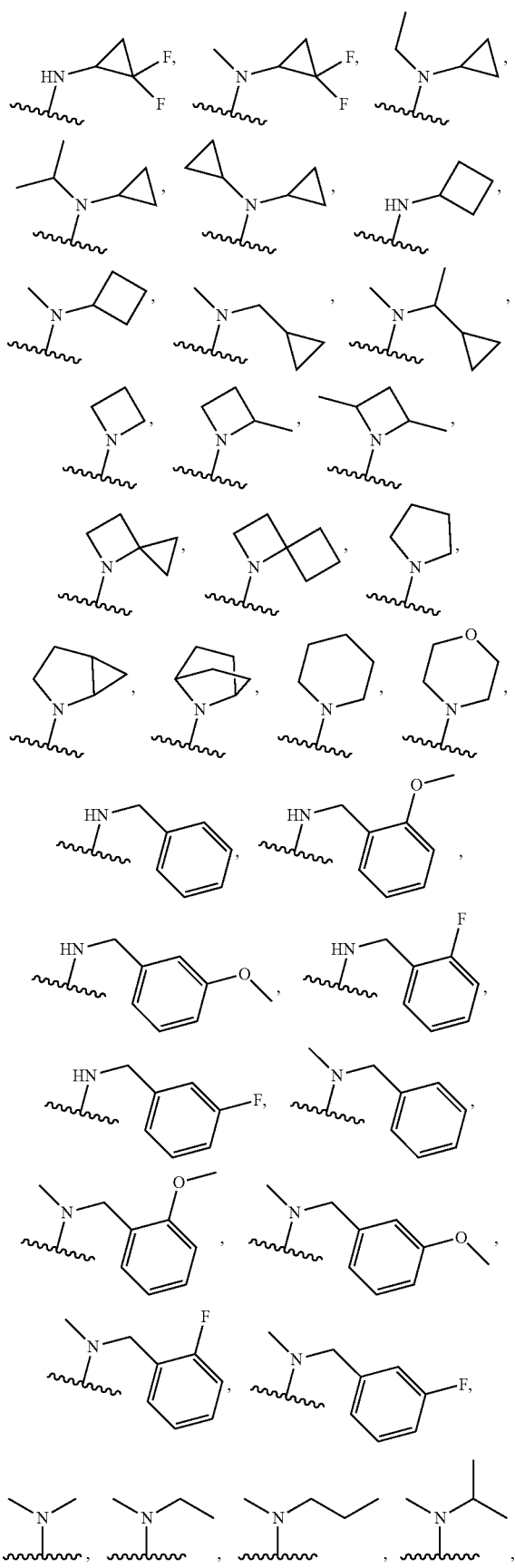
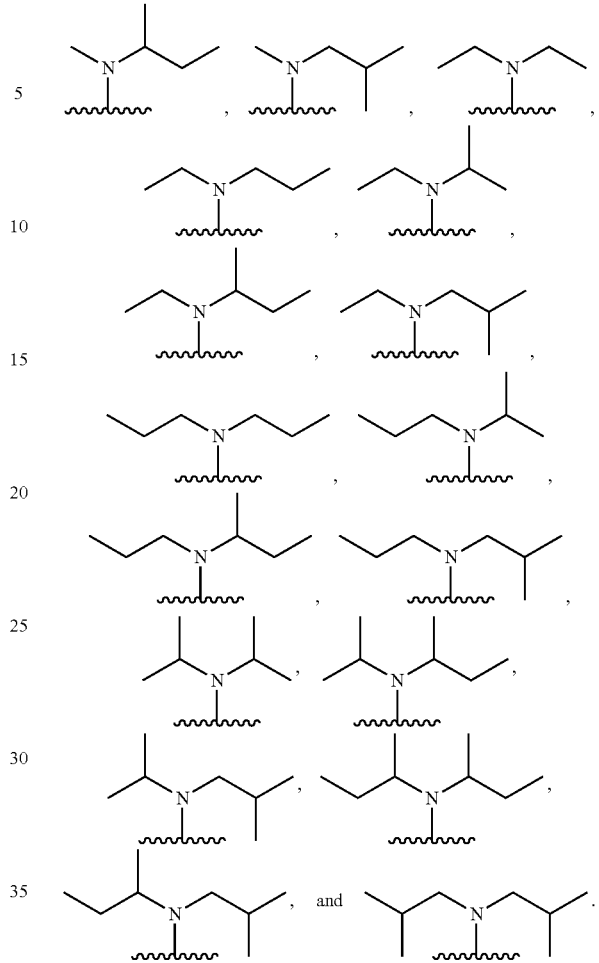

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, C(O)

$N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR$^{13}$)$_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR$^{13}$)$_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined as herein.

In some embodiments, 1 or 2 of $R^9$, $R^{10}$ and $R^{11}$ are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^9$, $R^{10}$ and $R^{11}$ are each hydrogen.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

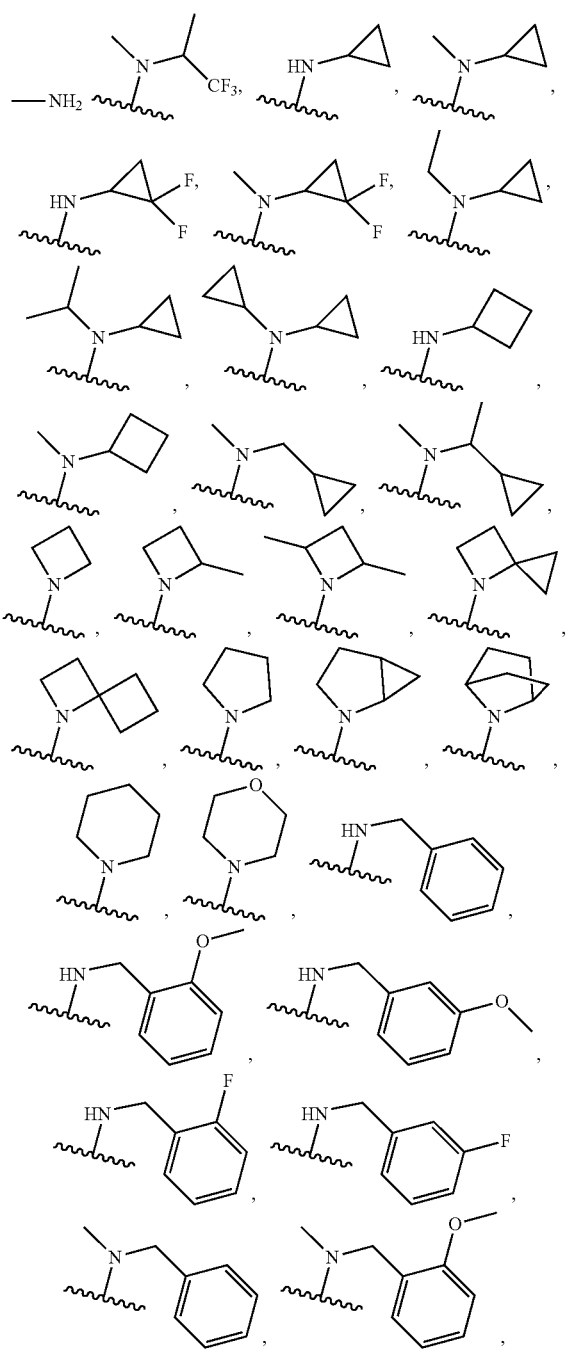

-continued

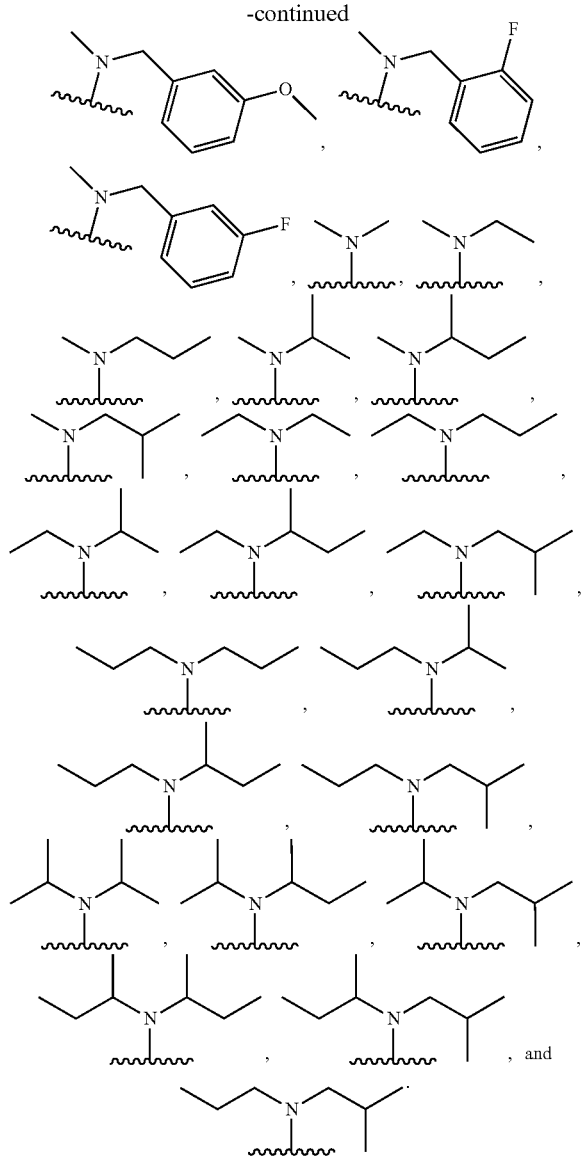

, and

.

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^{10}$ and $R^{11}$ are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$, $R^{10}$ and $R^{11}$ are each hydrogen.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

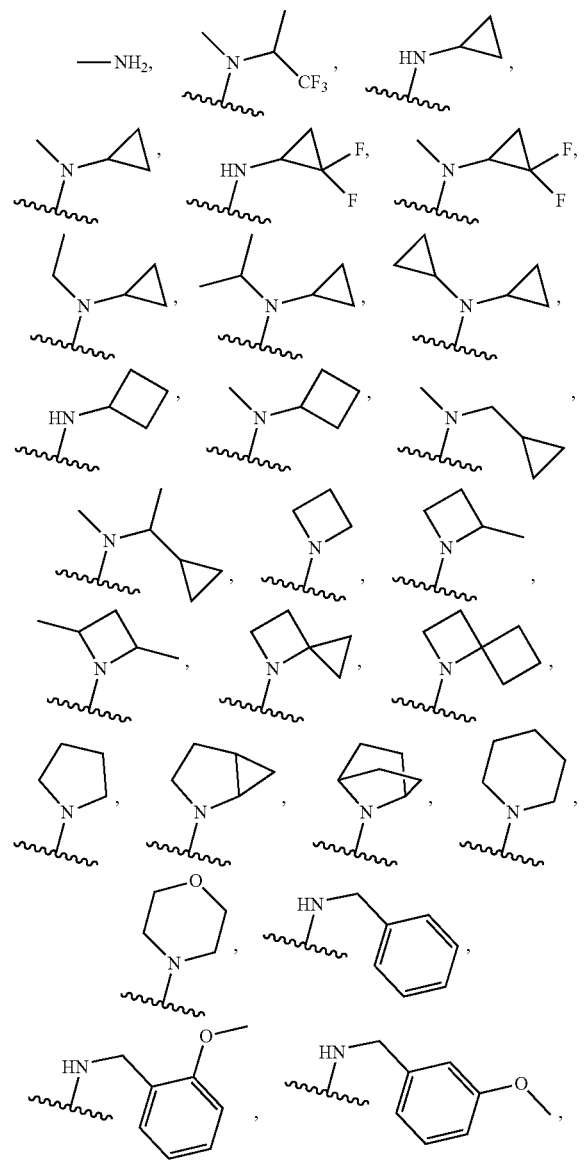

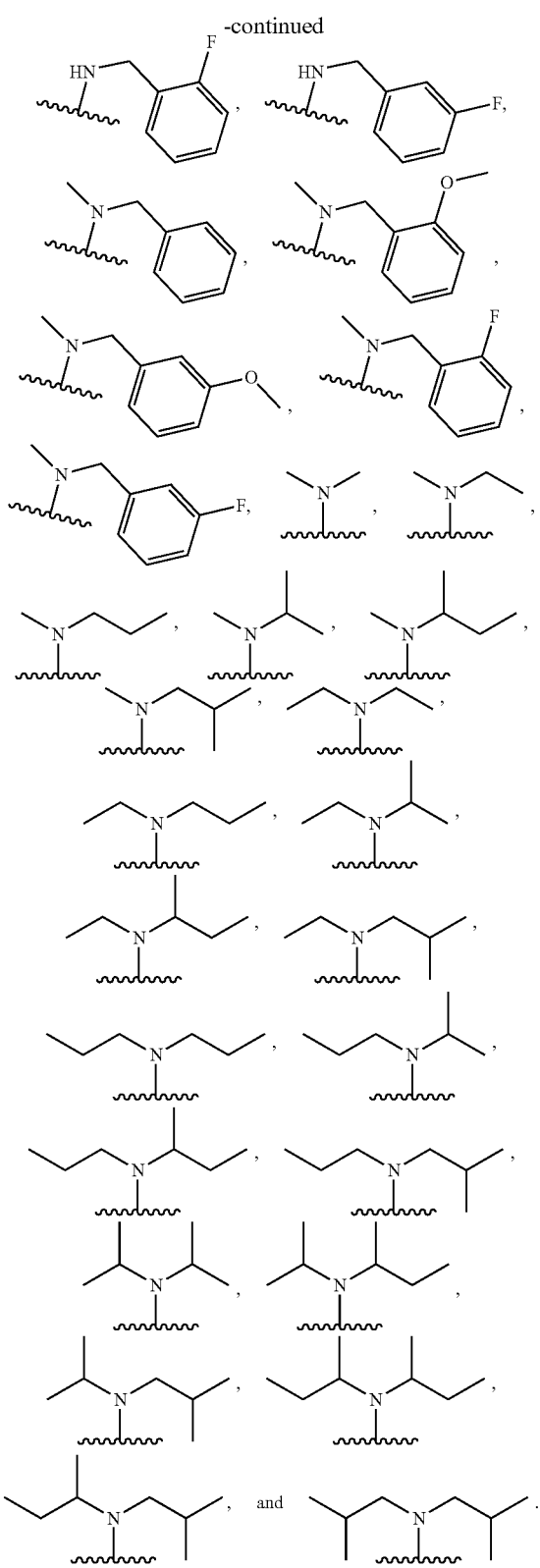

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)$(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$, $R^9$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)$(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$ and $R^{11}$ are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$, $R^9$ and $R^{11}$ are each hydrogen.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

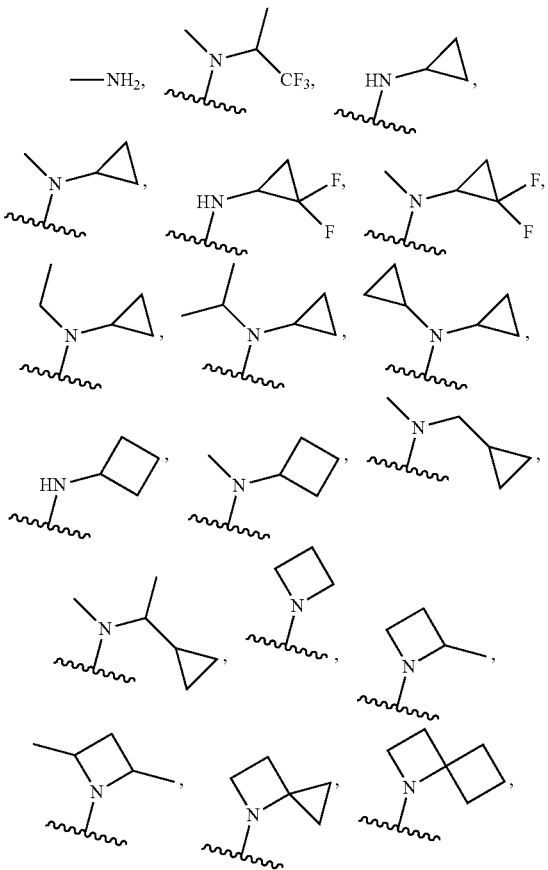

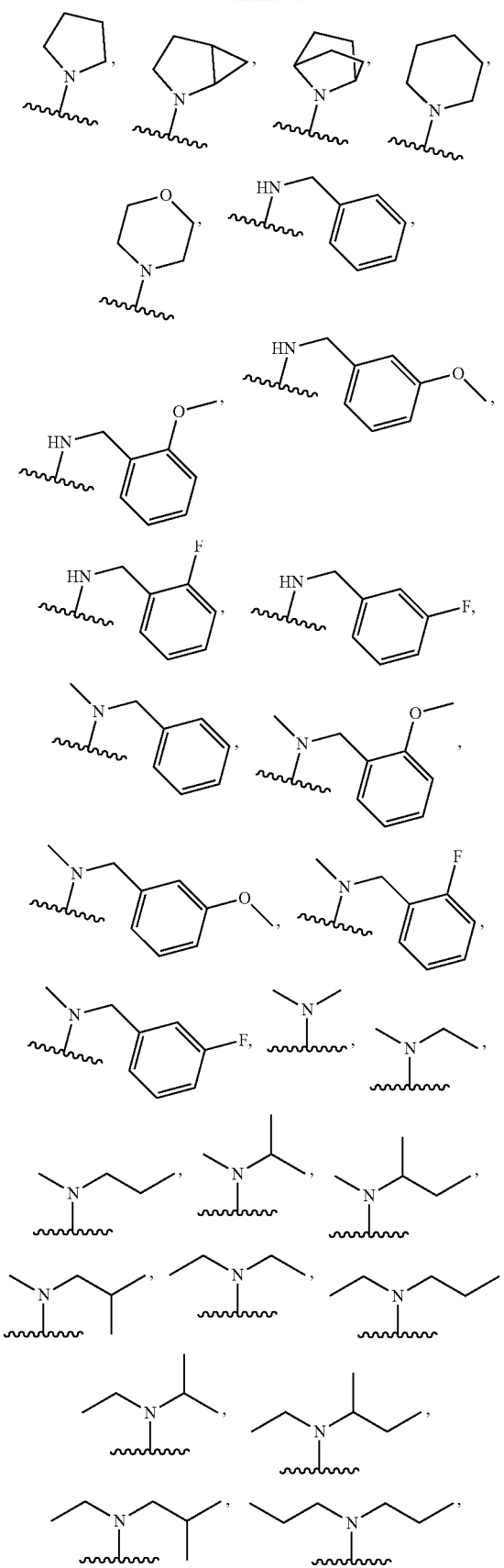
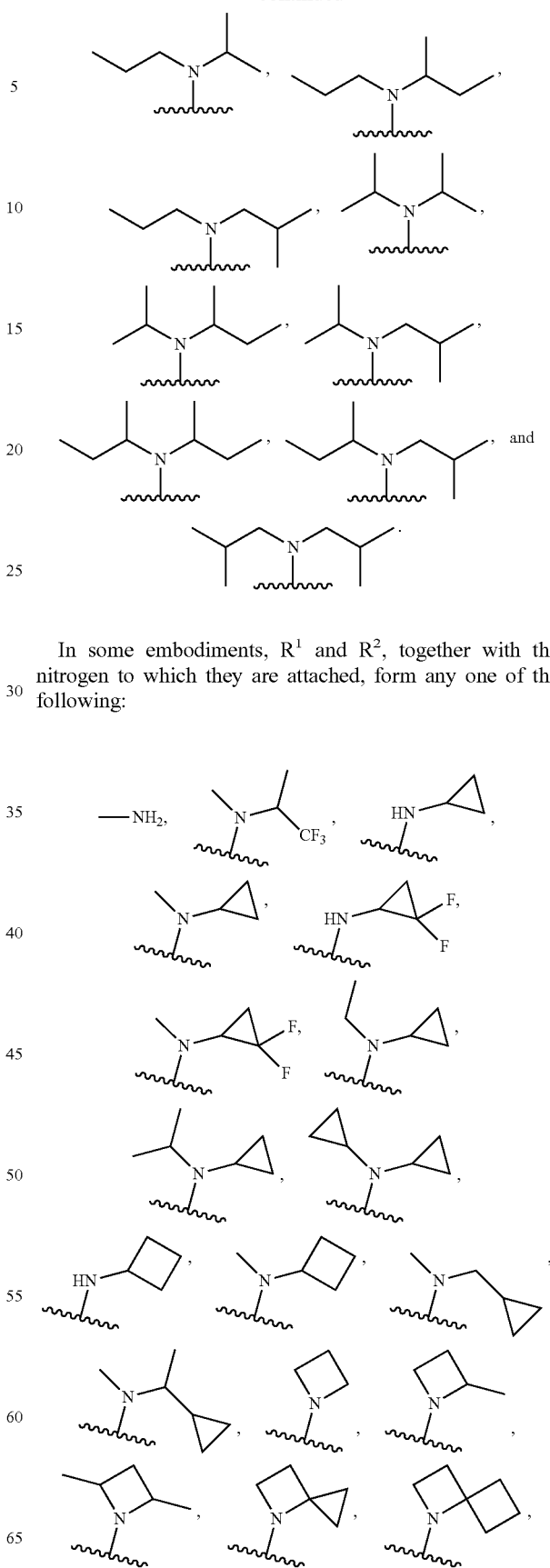
In some embodiments, $R^1$ and $R^2$, together with the nitrogen to which they are attached, form any one of the following:

-continued
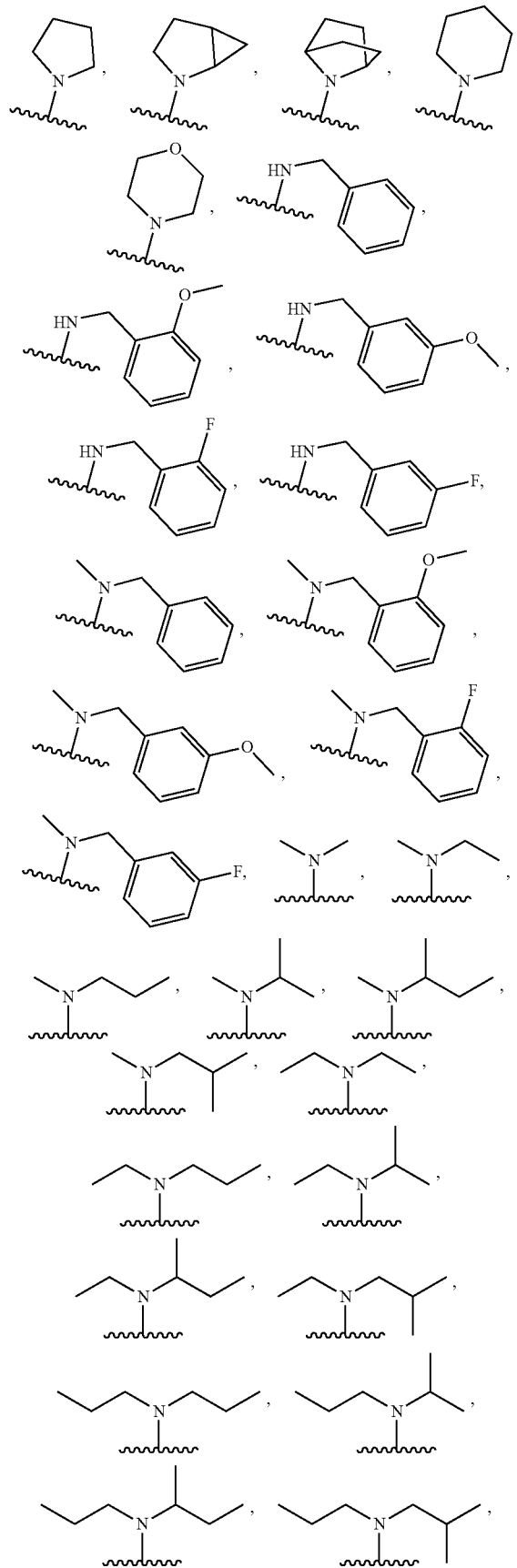
-continued
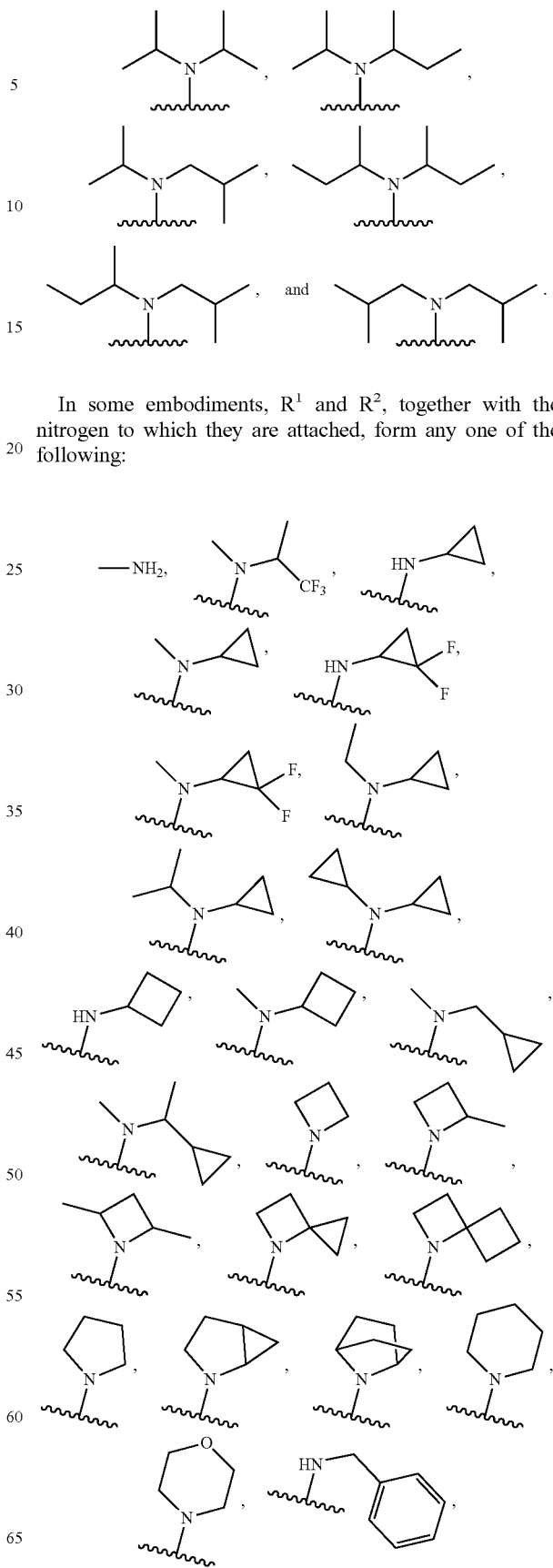
In some embodiments, $R^1$ and $R^2$, together with the nitrogen to which they are attached, form any one of the following:

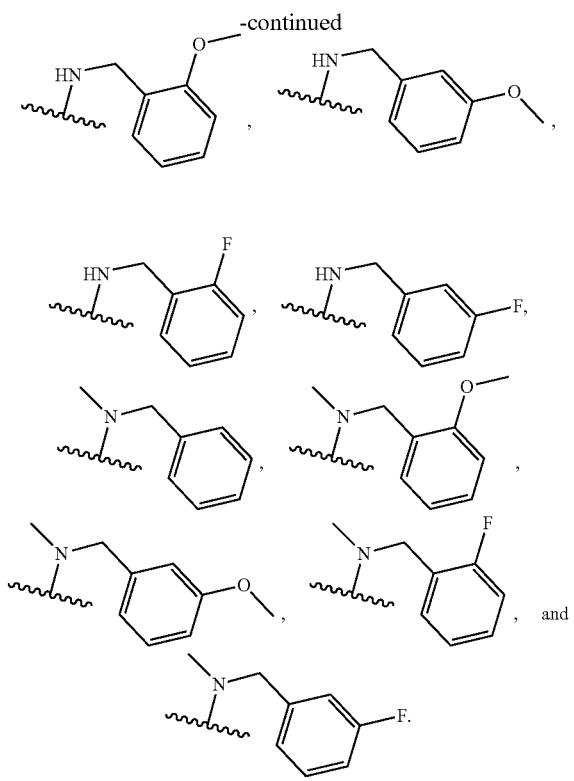

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$ and $R^{10}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$, $R^9$ and $R^{10}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$ and $R^{10}$ are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$, $R^9$ and $R^{10}$ are each hydrogen.

In some embodiments, the compound of formula (I) has the formula (II):

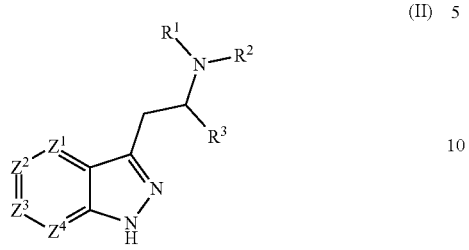

(II)

wherein
R$^1$ is independently selected from hydrogen, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl,
said C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-11}$ heteroaryl, and C$_{6-16}$ alkyleneheteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$R$^4$, C(O)N(R$^4$)$_2$, OR$^4$, N(R$^4$)$_2$, NO$_2$, SR$^4$ and SO$_2$R$^4$,
said C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being further optionally substituted with one or more substituents independently selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, N, S(O), SO$_2$ and NR$^4$;
R$^2$ is independently selected from hydrogen, C$_{1-6}$haloalkyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl,
said C$_{1-6}$haloalkyl, C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$R$^4$, C(O)N(R$^4$)$_2$, OR$^4$, N(R$^4$)$_2$, NO$_2$, SR$^4$ and SO$_2$R$^4$,
said C$_{3-8}$ cycloalkyl, C$_{4-14}$ alkylenecycloalkyl, C$_3$-C$_8$ heterocycloalkyl, C$_4$-C$_{14}$ alkyleneheterocycloalkyl, C$_{6-12}$ aryl, C$_{7-18}$ alkylenearyl, C$_{5-10}$ heteroaryl, and C$_{6-16}$ alkyleneheteroaryl each being further optionally substituted with one or more substituents independently selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, N, S(O), SO$_2$ and NR$^4$;
alternatively R$^1$ and R$^2$ are combined with the atoms to which they are attached to form a C$_{3-8}$ heterocycloalkyl including 0, 1 or 2 additional ring heteromoieties selected from O, S, S(O), SO$_2$, N and NR$^4$,
said C$_{3-8}$ heterocycloalkyl being further optionally substituted with one or more substituents independently selected from halogen, (O), CN, C$_{1-8}$ alkoxy, C$_{1-8}$ alkylamino, C$_{1-8}$ alkylsulfonyl, CO$_2$R$^4$, C(O)N(R$^4$)$_2$, OR$^4$, N(R$^4$)$_2$, NO$_2$, SR$^4$, SO$_2$R$^4$, C$_{1-6}$ alkyl, C$_{1-6}$ haloalkyl, C$_{2-6}$alkenyl, C$_{2-6}$ haloalkenyl, C$_{2-6}$ alkynyl, C$_{2-6}$ haloalkynyl, C$_{1-8}$ alkylamino, C$_{1-8}$ alkylsulfonyl, C$_{3-6}$ cycloalkyl and C$_{3-6}$ heterocycloalkyl including 1 or 2 ring heteromoieties selected from O, S, N, S(O), SO$_2$ and NR$^4$;
R$^3$ is selected from hydrogen, C$_{1-6}$ alkyl, C$_{3-8}$ cycloalkyl, or C$_{4-14}$ alkylenecycloalkyl;
alternatively R$^3$ and one of R$^1$ and R$^2$ are combined with the atoms to which they are attached to form a C$_{3-12}$ heterocycloalkyl,
said C$_{3-12}$ heterocycloalkyl being further optionally substituted with one or more substituents independently selected from halogen, (O), CN, C$_{1-8}$ alkoxy, C$_{1-8}$ alkylamino, C$_{1-8}$ alkylsulfonyl, CO$_2$R$^4$, C(O)N(R$^4$)$_2$, OR$^4$, N(R$^4$)$_2$, NO$_2$, SR$^4$, SO$_2$R$^4$, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, N, S(O), SO$_2$ and NR$^4$;
each R$^4$ is independently selected from hydrogen, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-7}$ cycloalkyl, and C$_{3-7}$ heterocycloalkyl including 1 or 2 ring heteromoieties selected from O, S, S(O), SO$_2$, N and NR$^5$,
said C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-7}$ cycloalkyl and C$_{3-7}$ heterocycloalkyl each being optionally substituted with one or more substituents independently selected from halogen, CN, C$_{1-8}$ alkoxy, C$_{1-8}$ alkylamino, C$_{1-8}$alkylsulfonyl, CO$_2$R$^5$, C(O)N(R$^5$)$_2$, OR$^5$, N(R$^5$)$_2$, NO$_2$, SR$^5$ and SO$_2$R$^5$,
said C$_3$-C$_7$ cycloalkyl and C$_{3-7}$ heterocycloalkyl each being further optionally substituted with one or more substituents independently selected from (O), C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, S(O), SO$_2$, N and NR$^5$;
each R$^5$ is independently selected from hydrogen, C$_{1-6}$ alkyl, C$_{2-6}$ alkenyl, C$_{2-6}$ alkynyl, C$_{1-6}$ haloalkyl, C$_{3-8}$ cycloalkyl, C$_{5-11}$ heterocycloalkyl, C$_{6-12}$ aryl and C$_{5-10}$ heteroaryl,
said C$_{1-6}$ alkyl, C$_{2-6}$ alkenyl, C$_{2-6}$ alkynyl, C$_{1-6}$ haloalkyl, C$_{3-8}$ cycloalkyl, C$_{5-10}$ heterocycloalkyl, C$_{6-12}$ aryl and C$_{5-11}$ heteroaryl each being optionally substituted with one or more substituents independently selected from halogen, CN, C$_{1-8}$ alkoxy, C$_{1-8}$ alkylamino, C$_{1-8}$ alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NHCH$_3$, NO$_2$, SH, SCH$_3$, SO$_2$CH$_3$, SOCH$_3$, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, S(O), SO$_2$, N, NH and NCH$_3$;
Z$^1$ is CR$^8$ or N;
Z$^2$ is CR$^9$ or N;
Z$^3$ is CR$^{10}$ or N;
Z$^4$ is CR$^{11}$ or N;
R$^8$, R$^9$, R$^{10}$ and R$^{11}$ are each independently selected from hydrogen, halogen, CN, OR$^{13}$, N(R$^{13}$)$_2$, SR$^{13}$, C$_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively, when $Z^1$ is $CR^8$ and $Z^2$ is $CR^9$, or when $Z^2$ is $CR^9$ and $Z^3$ is $CR^{10}$, or when $Z^3$ is $CR^{10}$ and $Z^4$ is $CR^{11}$, then $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-11}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl; and said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-11}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, one or more of $Z^1$, $Z^2$, $Z^3$ and $Z^4$ is N.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

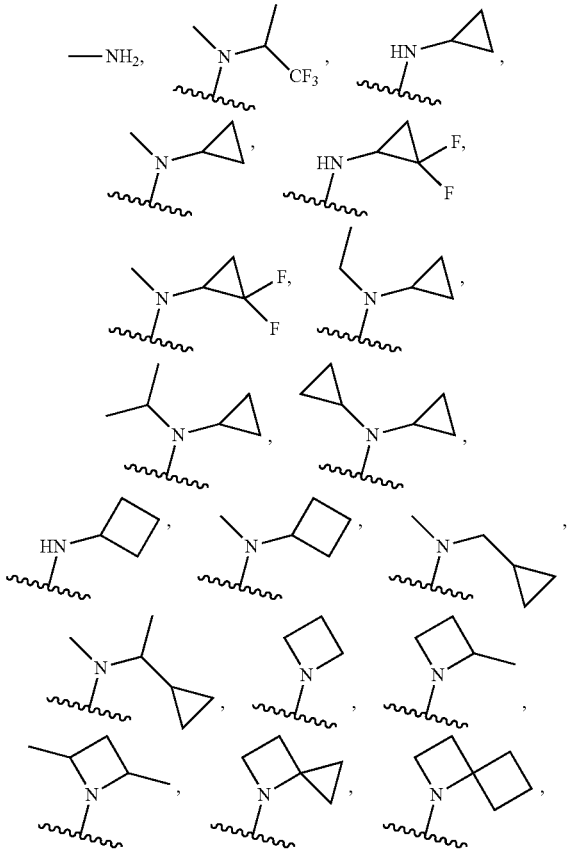

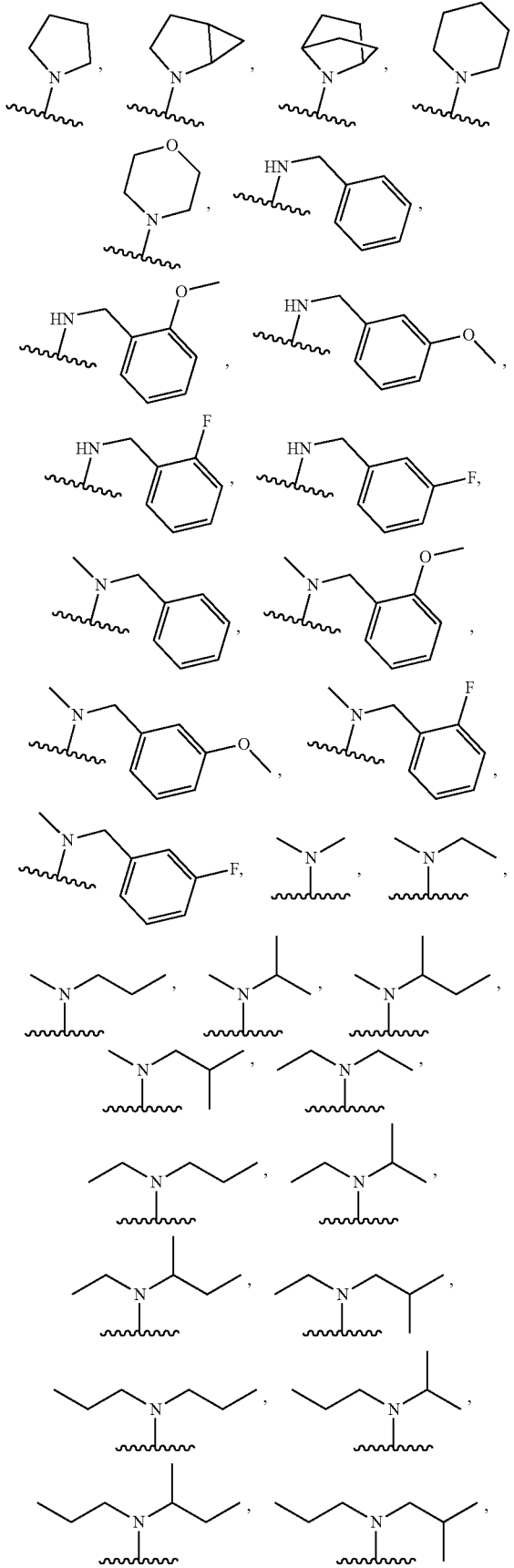
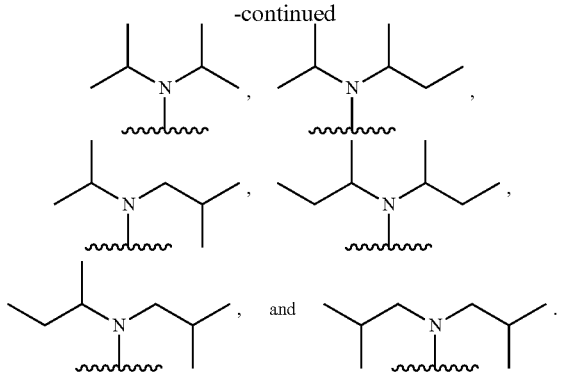

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2-C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2-C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$;

said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments. 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments, $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ and $R^9$ are combined to form a $C_{5-8}$ heterocycloalkyl or $C_{5-10}$ heteroaryl selected from the following:

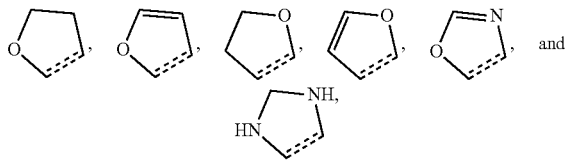

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments, $R^8$ and $R^9$ are combined to form a $C_{5-8}$ heterocycloalkyl or $C_{5-10}$ heteroaryl selected from the following:

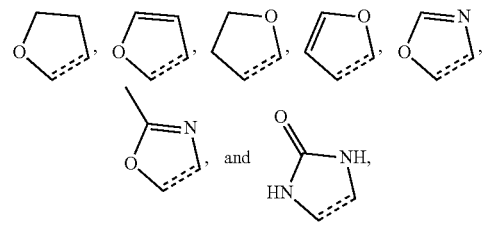

wherein the dashed bond denotes the bond shared with the aromatic ring to which $R^8$ and $R^9$ are attached.

In some embodiments, the compound of formula (I) has the formula (IIa):

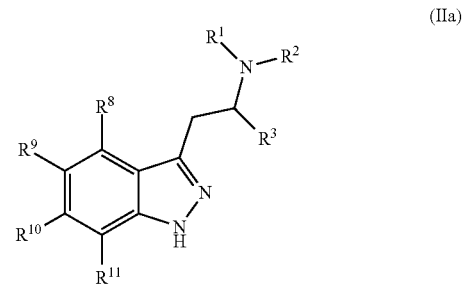

(IIa)

wherein $R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3-C_8$ heterocycloalkyl, $C_4-C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3-C_8$ heterocycloalkyl, $C_4-C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ are combined with the atoms to which they are attached to form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-11}$ heterocycloalkyl, $C_{6-12}$ aryl and $C_{5-11}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-11}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

$R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively, $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl; and said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, one or more of $Z^1$, $Z^2$, $Z^3$ and $Z^4$ is N.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

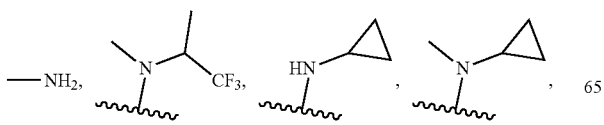

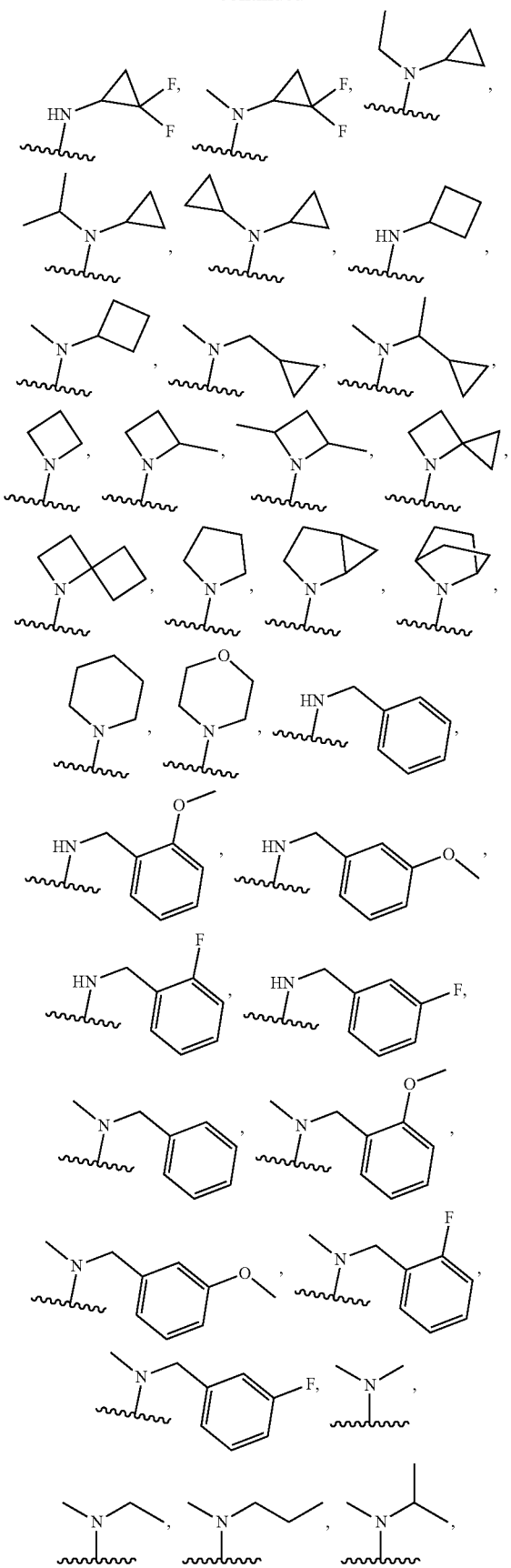

-continued

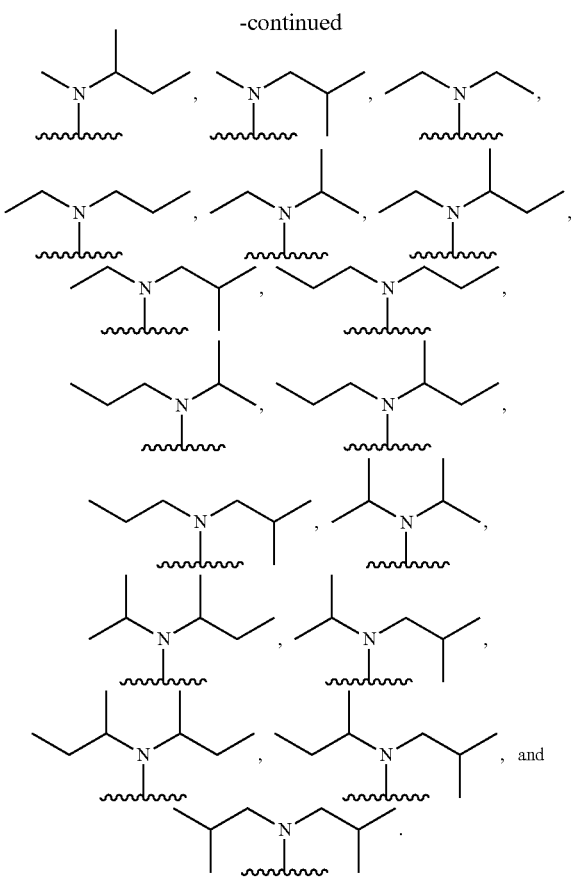

, and

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)$ $OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl,
said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$,
said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;
wherein $R^{13}$ is as defined herein.

In some embodiments, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl,
said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)$ $NHCH_3$, OH, $NH_2$, $N(CH_3)_2$, $NO_2$, $NHCH_3$, SH, $SCH_3$, $SO_2CH_3$, and $SOCH_3$,
said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;
wherein $R^{13}$ is as defined herein.

In some embodiments, 1 or 2 of $R^8$, $R^9$, $R^{10}$ and $R^{11}$ are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments, $R^8$ and $R^9$ are combined with the atoms to which they are each attached to form a $C_{5-8}$ heterocycloalkyl or $C_{5-10}$ heteroaryl, said $C_{5-8}$ heterocycloalkyl and $C_{5-11}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ and $R^9$ are combined to form a $C_{5-8}$ heterocycloalkyl or $C_{5-10}$ heteroaryl selected from the following:

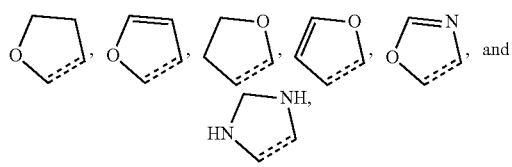

wherein the dashed bond denotes the bond shared with the aromatic ring to which $R^8$ and $R^9$ are attached;
said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments, $R^8$ and $R^9$ are combined to form a $C_{5-8}$ heterocycloalkyl or $C_{5-10}$ heteroaryl selected from the following:

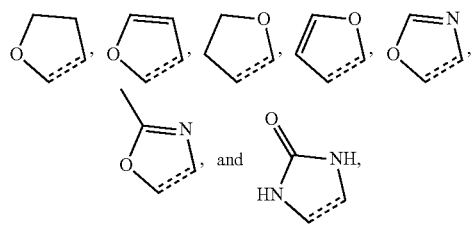

wherein the dashed bond denotes the bond shared with the aromatic ring to which $R^8$ and $R^9$ are attached.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

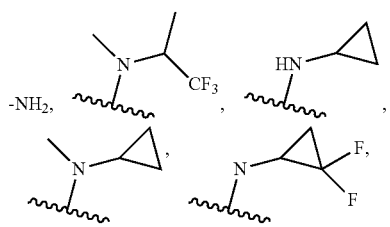

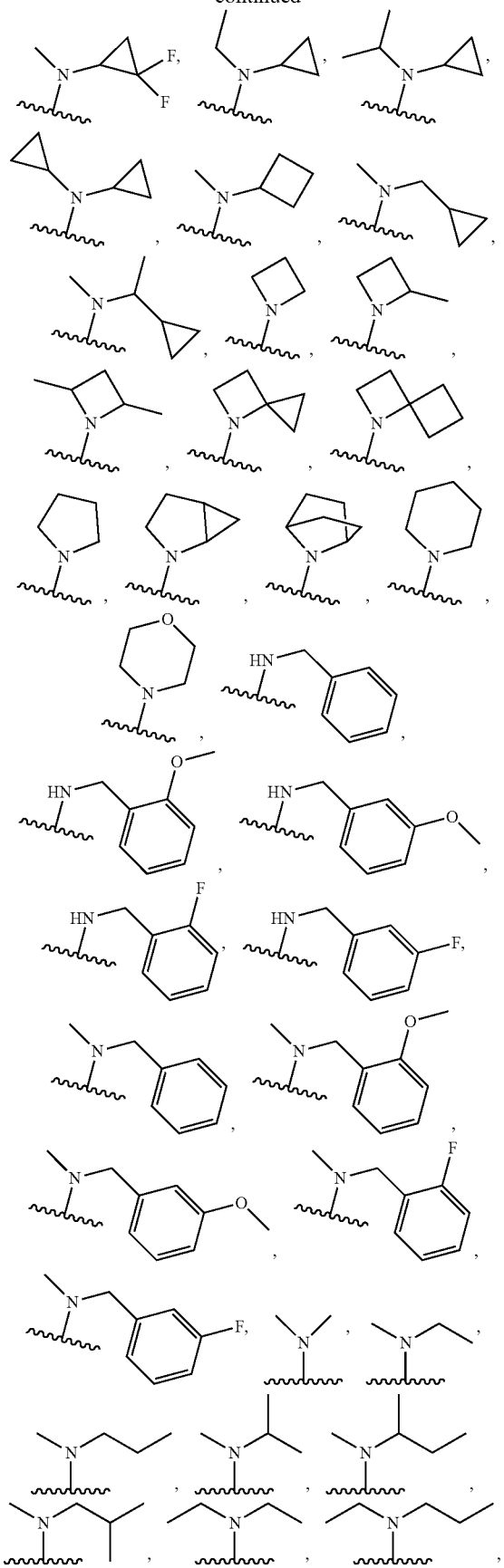

-continued

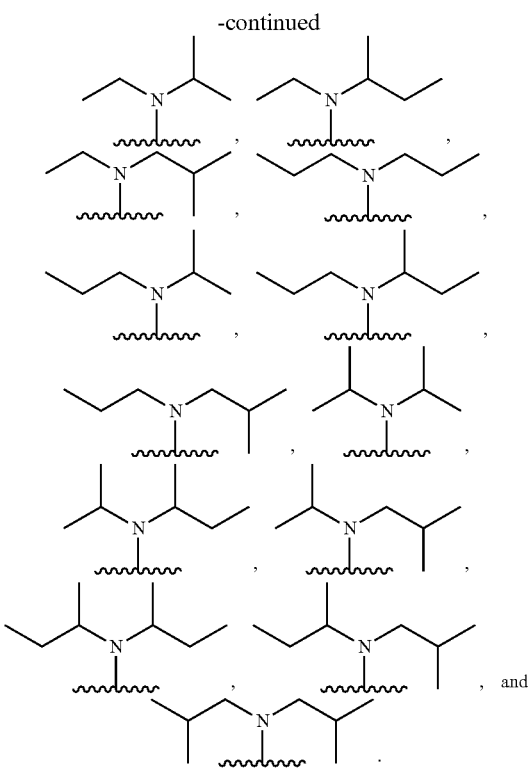

, and

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments, $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, C(O)N(CH₃)₂, C(O)NHCH₃, OH, NH₂, N(CH₃)₂, NHCH₃, NO₂, SH, SCH₃, SO₂CH₃, SOCH₃, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl and C$_{3-6}$ heterocycloalkyl including 1 or 2 ring heteromoieties selected from O, S, S(O), SO₂, N, NH and NCH₃.

In some embodiments, R⁸ and R⁹ are combined to form a C$_{5-8}$ heterocycloalkyl or C$_{5-10}$ heteroaryl selected from the following:

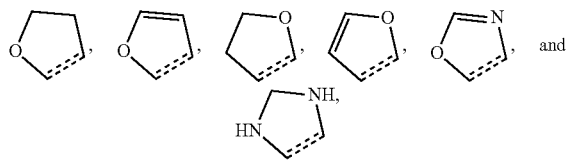

and wherein the dashed bond denotes the bond shared with the aromatic ring to which R⁸ and R⁹ are attached;
said C$_{5-8}$ heterocycloalkyl and C$_{5-10}$ heteroaryl each being further optionally substituted with one or more substituents independently selected from halogen, (O), CN, CO₂H, CO₂CH₃, C(O)NH₂, C(O)N(CH₃)₂, C(O)NHCH₃, OH, NH₂, N(CH₃)₂, NHCH₃, NO₂, SH, SCH₃, SO₂CH₃, SOCH₃, C$_{1-6}$ alkyl and C$_{1-6}$ haloalkyl.

In some embodiments, R⁸ and R⁹ are combined to form a C$_{5-8}$ heterocycloalkyl or C$_{5-10}$ heteroaryl selected from the following:

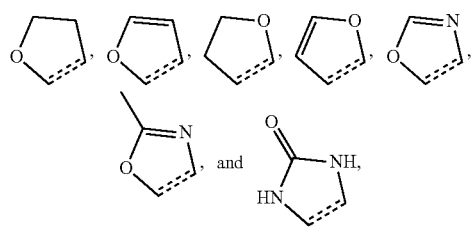

wherein the dashed bond denotes the bond shared with the aromatic ring to which R⁸ and R⁹ are attached.

In some embodiments, R¹ and R² are each independently selected from C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, C$_{3-8}$ cycloalkyl and C$_{4-14}$ alkylenecycloalkyl.

In some embodiments, R¹ and R² are each independently selected from C$_{1-4}$ alkyl.

In some embodiments, R¹ and R², together with the nitrogen to which they are attached, form any one of the following:

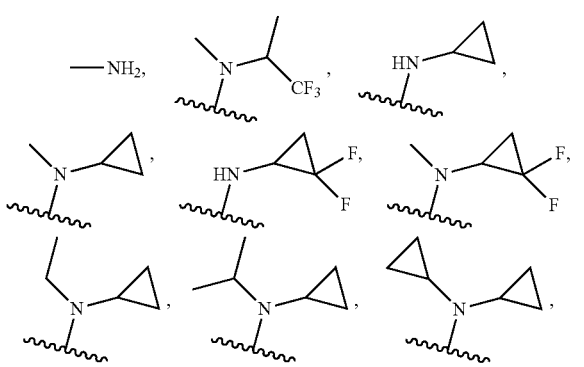

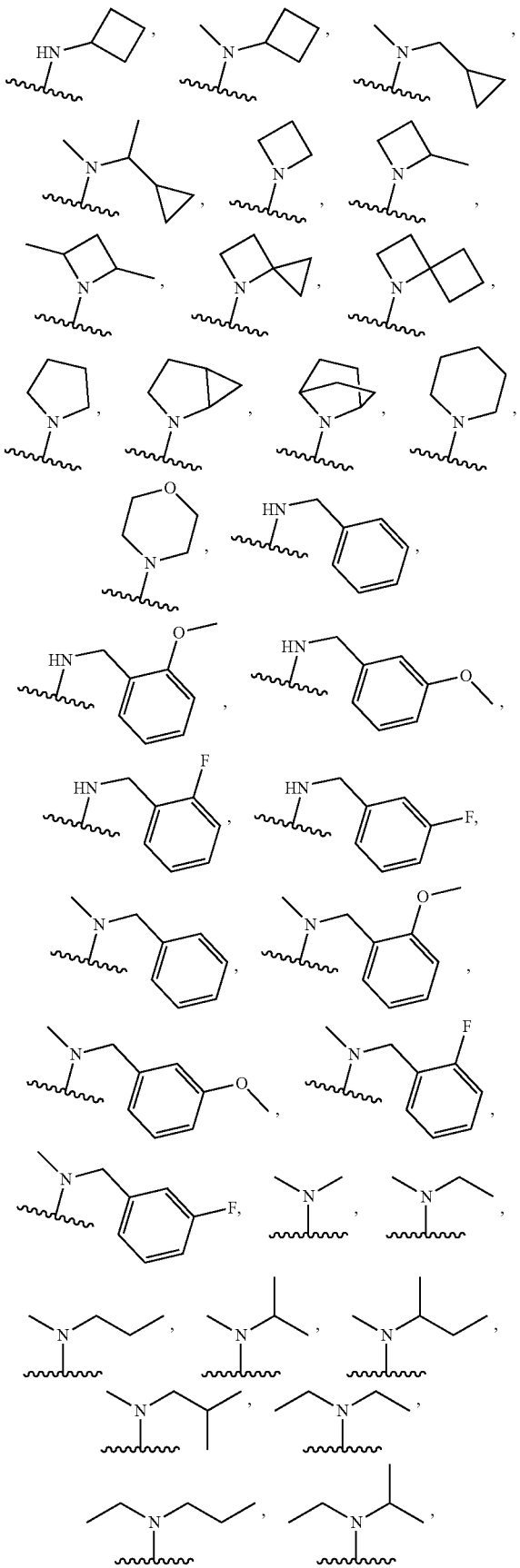

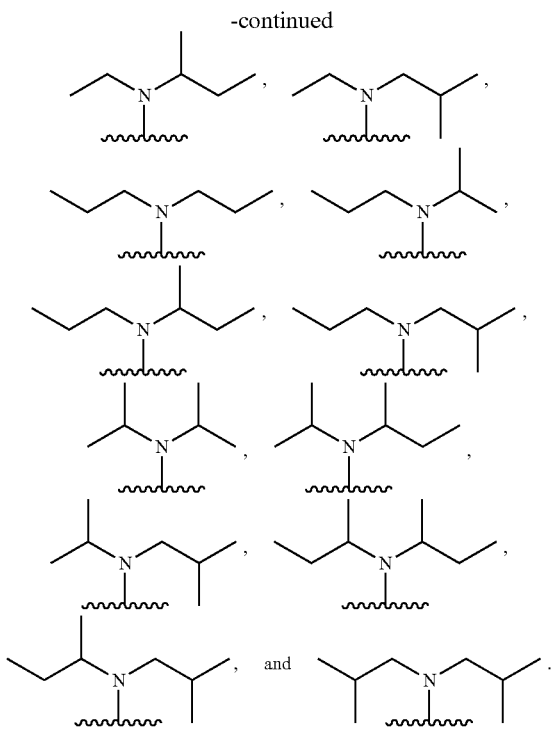

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$, $R^{10}$ and $R^{11}$ are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments, $R^8$ and $R^9$ are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ and $R^9$ are combined to form a $C_{5-8}$ heterocycloalkyl or $C_{5-10}$ heteroaryl selected from the following:

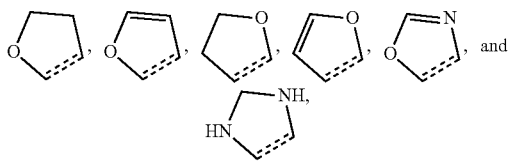

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments, $R^8$ and $R^9$ are combined to form a $C_{5-8}$ heterocycloalkyl or $C_{5-10}$ heteroaryl selected from the following:

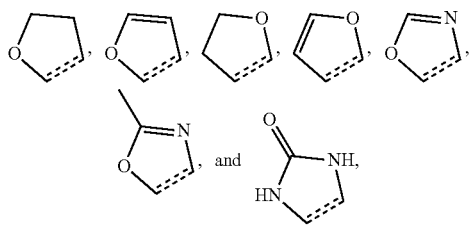

wherein the dashed bond denotes the bond shared with the aromatic ring to which Ra and $R^9$ are attached.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

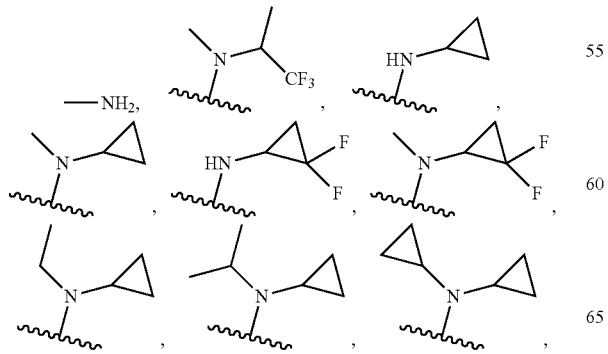

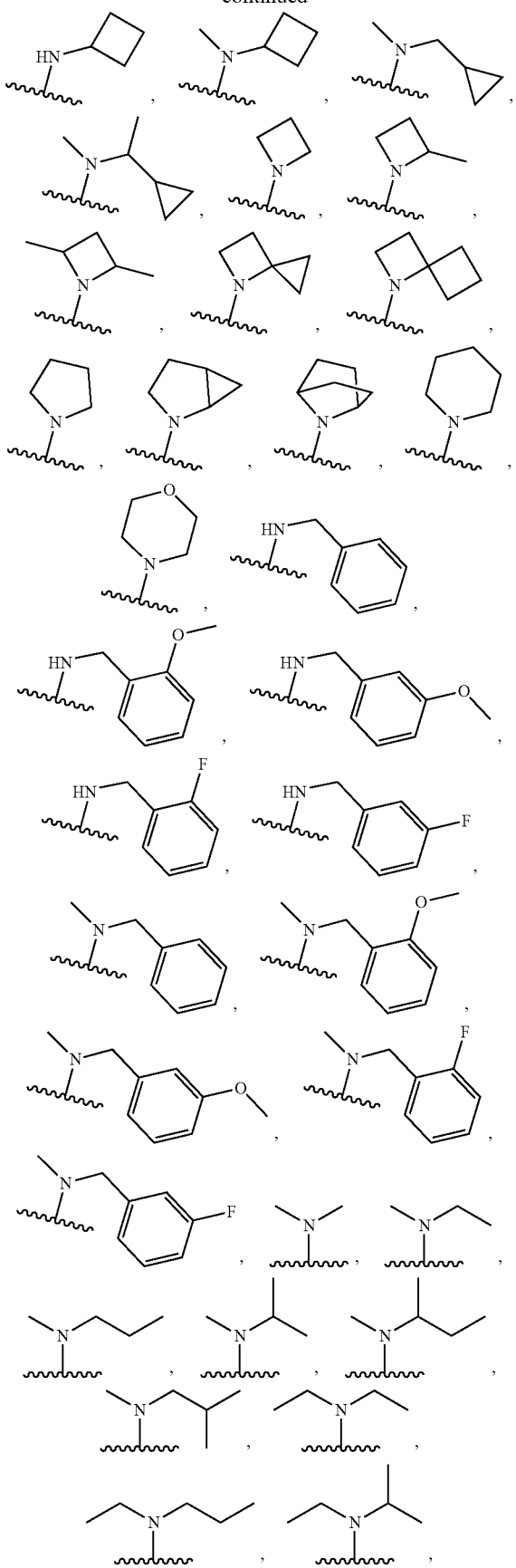

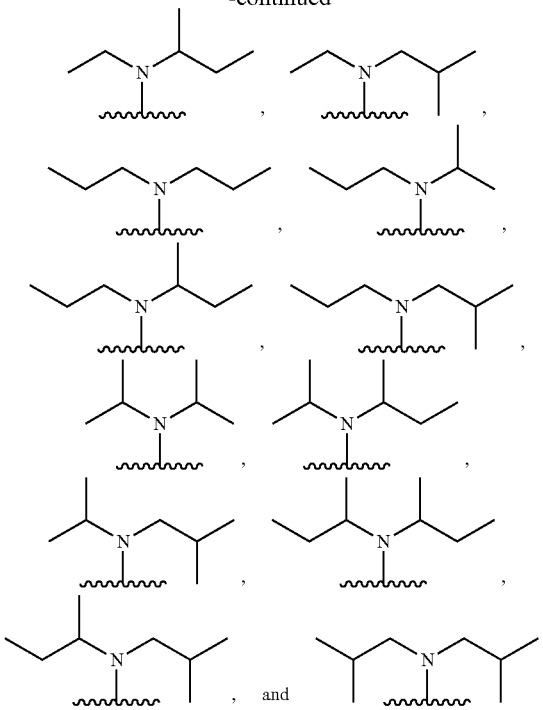

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)$ $N(R^{13})_2$, $SO_2R^{13}$, $N(R^{13})_2$, $N(R^{13})C(O)R^{13}$, $N(R^{13})C(O)$ $OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N$ $(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)$ $NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments, $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ and $R^9$ are combined to form a $C_{5-8}$ heterocycloalkyl or $C_{5-10}$ heteroaryl selected from the following:

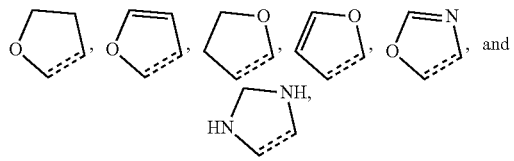

and wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments, $R^8$ and $R^9$ are combined to form a $C_{5-8}$ heterocycloalkyl or $C_{5-10}$ heteroaryl selected from the following:

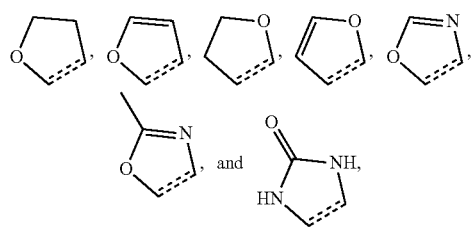

wherein the dashed bond denotes the bond shared with the aromatic ring to which $R^8$ and $R^9$ are attached.

In some embodiments, $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

In some embodiments, $R^1$ and $R^2$ are each independently selected from $C_{1-4}$ alkyl.

In some embodiments, $R^1$ and $R^2$, together with the nitrogen to which they are attached, form any one of the following:

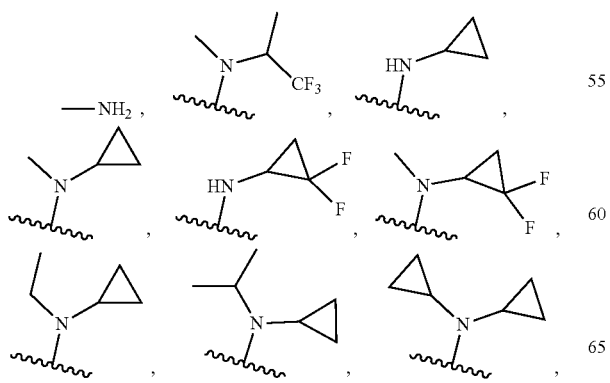

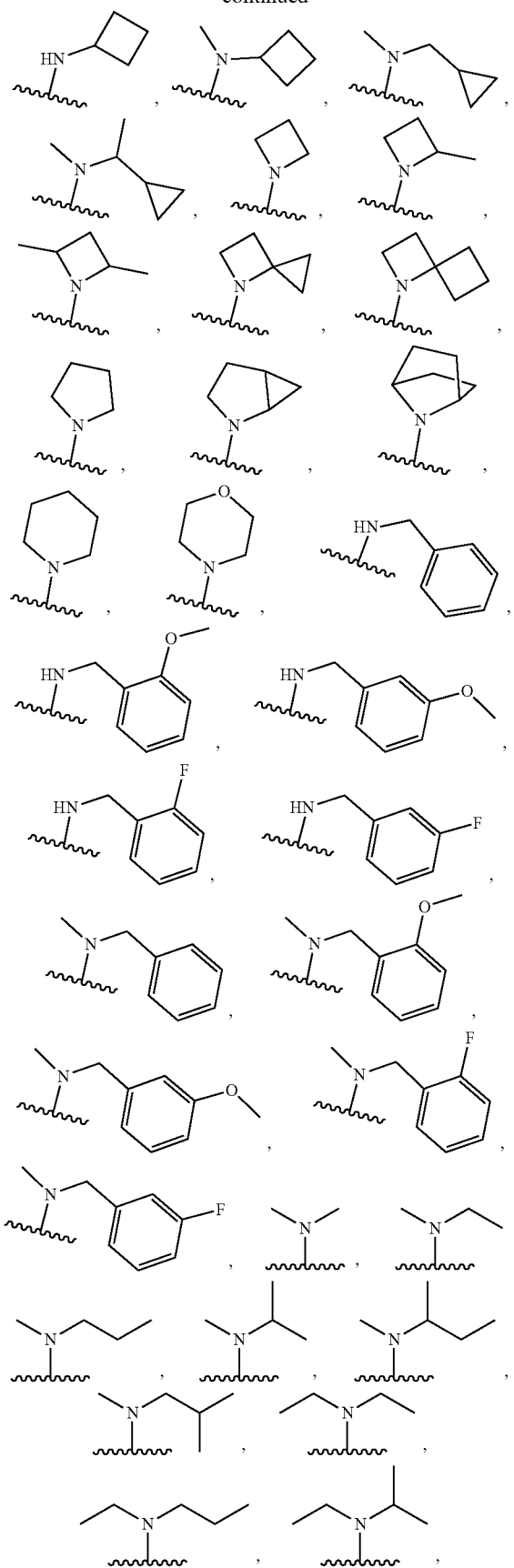

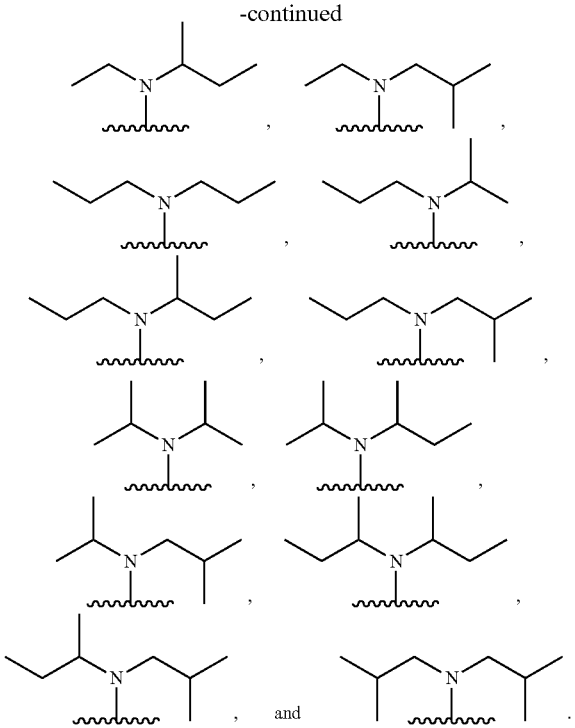

In some embodiments, $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments $R^3$ is hydrogen.

In some embodiments, $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is defined herein.

In some embodiments, $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR$^{13}$)$_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined herein.

In some embodiments, $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N$ $(R^{13})_2$, $OC(O)R^{13}$, $OSO_2R^{13}$, $OP(O)(OR^{13})_2$, $OC_{1-6}$alkyleneP(O)(OR$^{13}$)$_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined herein.

In some embodiments, 1 or 2 of $R^8$, $R^9$, $R^{10}$ and $R^{11}$ are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

In some embodiments, $R^8$ and $R^9$ are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

In some embodiments, $R^8$ and $R^9$ are combined to form a $C_{5-8}$ heterocycloalkyl or $C_{5-10}$ heteroaryl selected from the following:

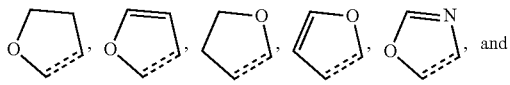

, and

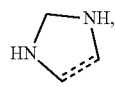

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

In some embodiments, $R^8$ and $R^9$ are combined to form a $C_{5-8}$ heterocycloalkyl or $C_{5-10}$ heteroaryl selected from the following:

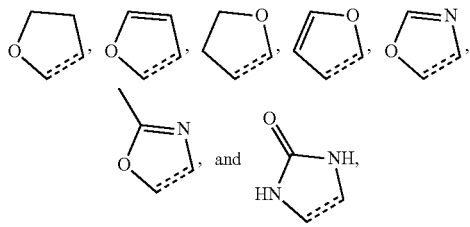

wherein the dashed bond denotes the bond shared with the aromatic ring to which $R^8$ and $R^9$ are attached.

In some embodiments, the compound of formula (I) is a compound of formula (IIb)

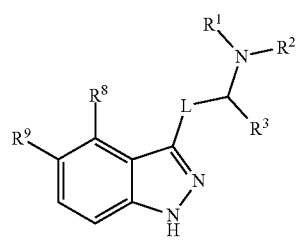

(IIb)

wherein L, $R^1$, $R^2$, $R^3$, $R^8$ and $R^9$ are as defined herein.

In some embodiments, the compound of formula (I) is a compound of formula (IIc)

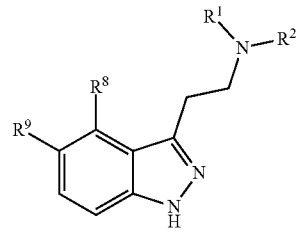

(IIc)

wherein $R^1$, $R^2$, $R^8$ and $R^9$ are as defined herein.

In some embodiments of any one of formulae (II), (IIa), (IIb), and (IIc), the compound is not one of the following:

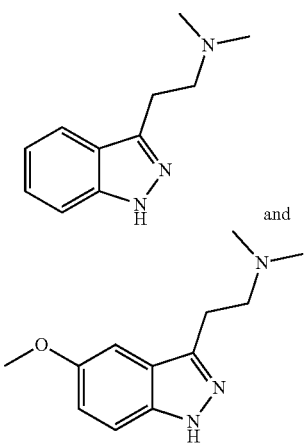

and

In some embodiments, the compound of any of formulae (I), (II), (IIa), (IIb), and (IIc) may be selected from compounds P-6 to P-8, P-42 to P-45, P-48, P-49, P-51, P-52, P-55 and P-56.

In some embodiments, the compound of any of formulae (I), (II), (IIa), (IIb), and (IIc) may be selected from Table A.

TABLE A

| Compound | Structure |
|---|---|
| A-1 | 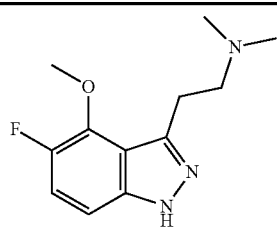 |
| A-2 | 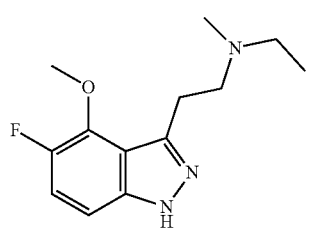 [SMILES: CCN(C)CCc1n[nH]c2ccc(F)c(OC)c12] |

TABLE A-continued
| Compound | Structure |
|---|---|
| A-3 | 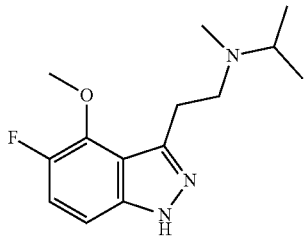 [SMILES: COc1c(F)ccc2[nH]nc(CCN(C)C(C)C)c12] |
| A-4 | 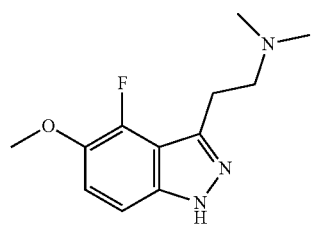 |
| A-5 | 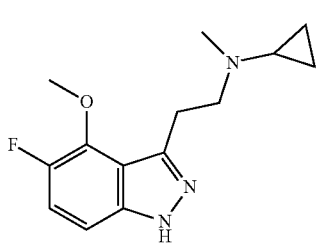 [SMILES: COc1c(F)ccc2[nH]nc(CCN(C)C3CC3)c12] |
| A-6 | 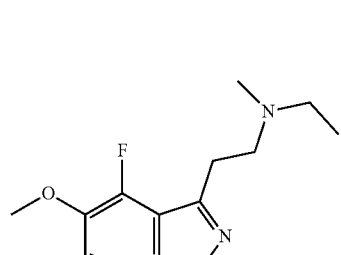 |
| A-7 | 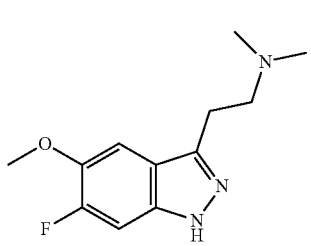 |
| A-8 | 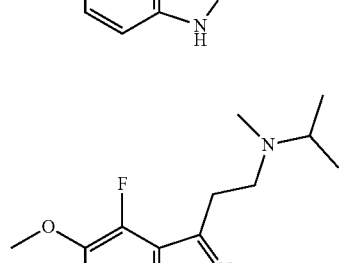 |
| A-9 | 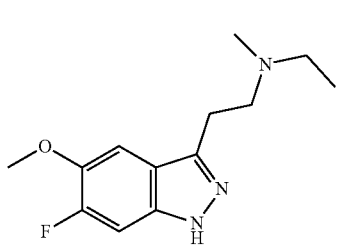 [SMILES: CCN(C)CCc1n[nH]c2cc(F)c(OC)cc12] |
| A-10 | 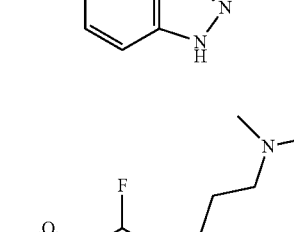 |
| A-11 | 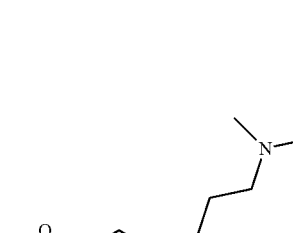 |
| A-12 | 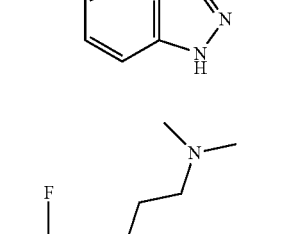 |
| A-13 | 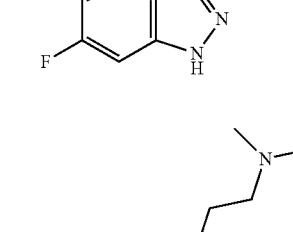 |
| A-14 | 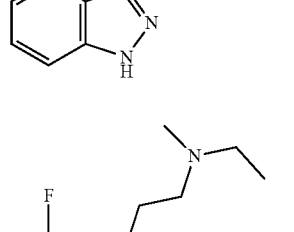 |

TABLE A-continued
| Compound | Structure |
|---|---|
| A-15 | 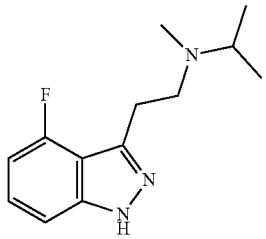 [SMILES: CC(C)N(C)CCc1n[nH]c2cccc(F)c12] |
| A-16 | 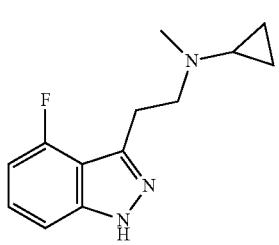 [SMILES: CN(CCc1n[nH]c2cccc(F)c12)C1CC1] |
| A-17 | 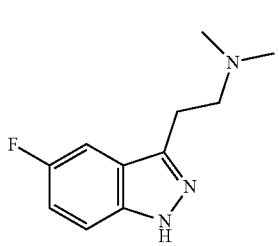 |
| A-18 | 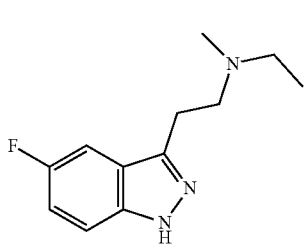 [SMILES: CCN(C)CCc1n[nH]c2ccc(F)cc12] |
| A-19 | 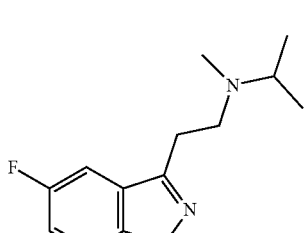 |
| A-20 | 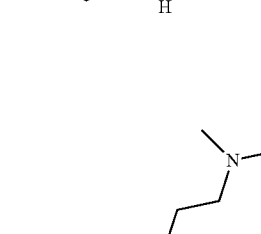 |
| A-21 | 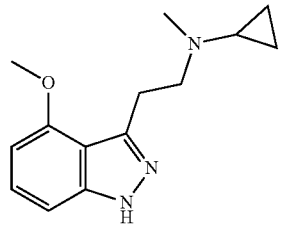 [SMILES: COc1cccc2[nH]nc(CCN(C)C3CC3)c12] |
| A-22 | 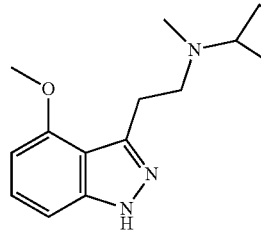 |
| A-23 | 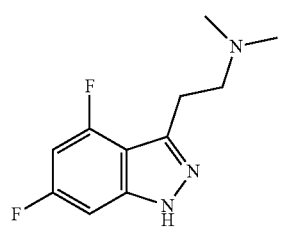 |
| A-24 | 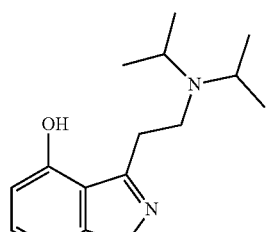 |
| A-25 | 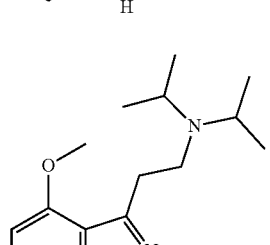 |
| A-26 | 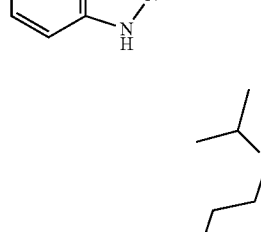 |

TABLE A-continued
| Compound | Structure |
|---|---|
| A-27 | 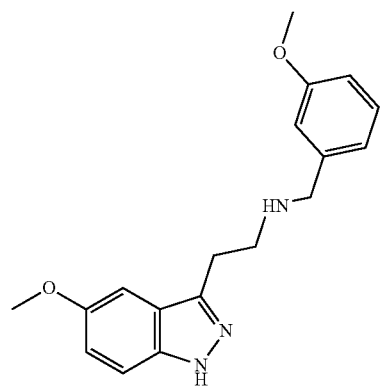 [SMILES: COc1cccc(CNCCc2n[nH]c3ccc(OC)cc23)c1] |
| A-28 | 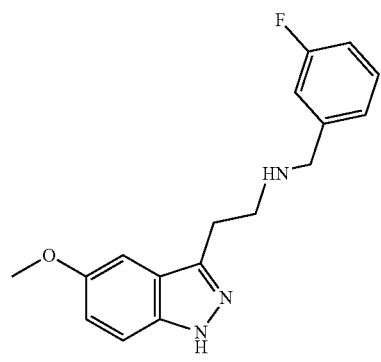 [SMILES: COc1ccc2[nH]nc(CCNCc3cccc(F)c3)c2c1] |
| A-29 | 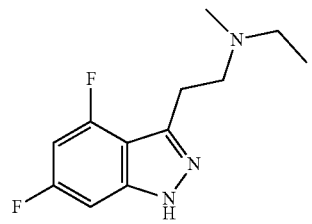 [SMILES: CCN(C)CCc1n[nH]c2cc(F)cc(F)c12] |
| A-30 | 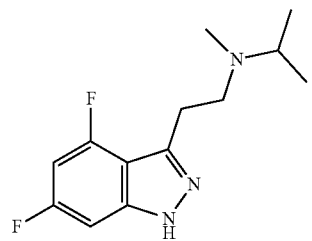 [SMILES: CC(C)N(C)CCc1n[nH]c2cc(F)cc(F)c12] |
| A-31 | 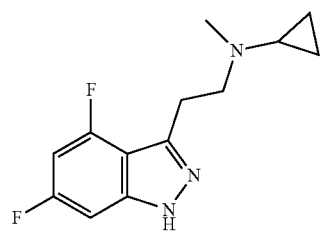 [SMILES: CN(CCc1n[nH]c2cc(F)cc(F)c12)C1CC1] |
TABLE A-continued
| Compound | Structure |
|---|---|
| A-32 | 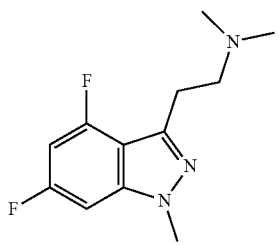 [SMILES: CN(C)CCc1nn(C)c2cc(F)cc(F)c12] |
| A-33 | 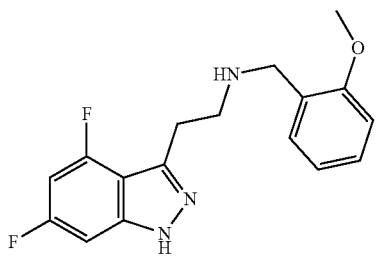 [SMILES: COc1ccccc1CNCCc1n[nH]c2cc(F)cc(F)c12] |
| A-34 | 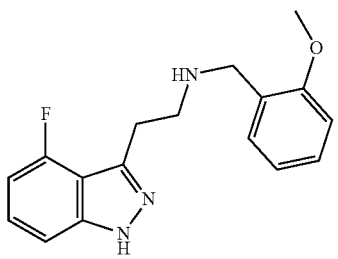 [SMILES: COc1ccccc1CNCCc1n[nH]c2cccc(F)c12] |
| A-35 | 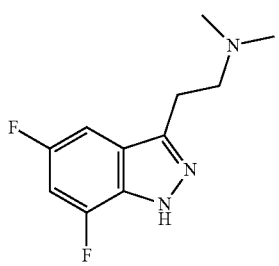 [SMILES: CN(C)CCc1n[nH]c2c(F)cc(F)cc12] |
| A-36 | 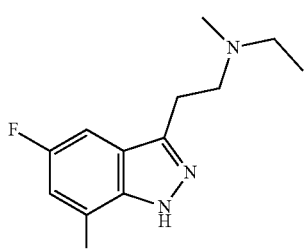 |
| A-37 | 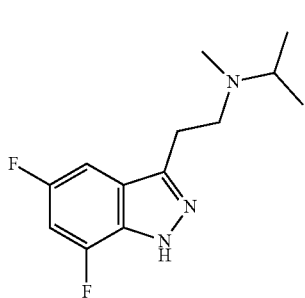 [SMILES: CC(C)N(C)CCc1n[nH]c2c(F)cc(F)cc12] |

TABLE A-continued
| Compound | Structure |
|---|---|
| A-38 | 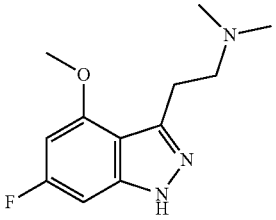 [SMILES: COc1cc(F)cc2[nH]nc(CCN(C)C)c12] |
| A-39 | 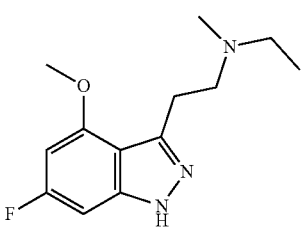 [SMILES: CCN(C)CCc1n[nH]c2cc(F)cc(OC)c12] |
| A-40 | 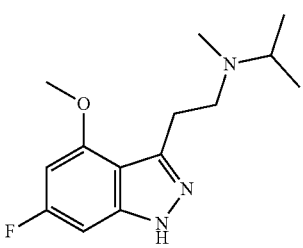 [SMILES: COc1cc(F)cc2[nH]nc(CCN(C)C(C)C)c12] |
| A-41 | 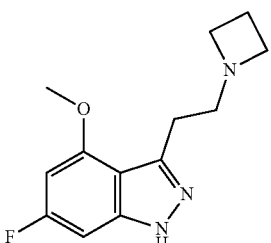 |
| A-42 | 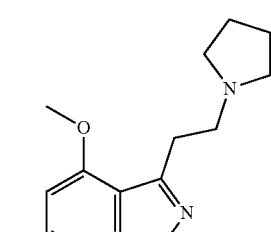 |
| A-43 | 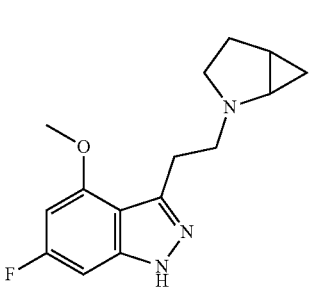 [SMILES: COc1cc(F)cc2[nH]nc(CCN3CCC4CC43)c12] |
| A-44 | 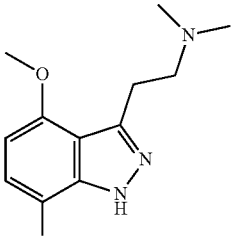 |
| A-45 | 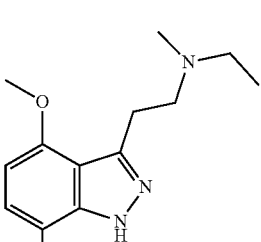 |
| A-46 | 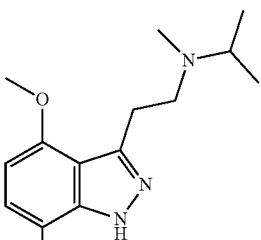 |
| A-47 | 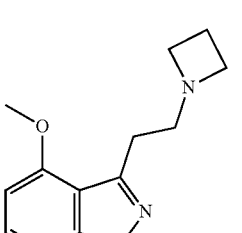 |
| A-48 | 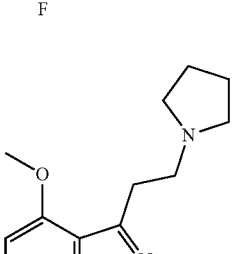 |

TABLE A-continued
| Compound | Structure |
|---|---|
| A-49 | 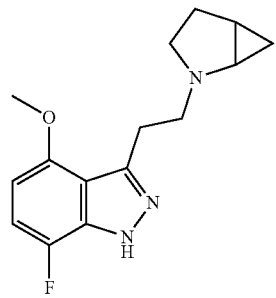 [SMILES: COc1ccc(F)c2[nH]nc(CCN3CCC4CC43)c12] |
| A-50 | 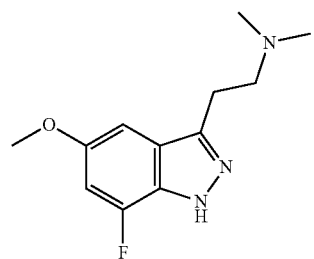 |
| A-51 | 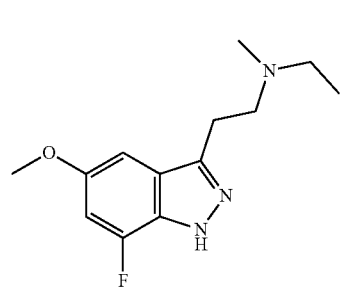 [SMILES: CCN(C)CCc1n[nH]c2c(F)cc(OC)cc12] |
| A-52 | 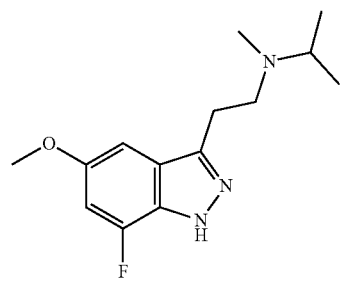 [SMILES: COc1cc(F)c2[nH]nc(CCN(C)C(C)C)c2c1] |
| A-53 | 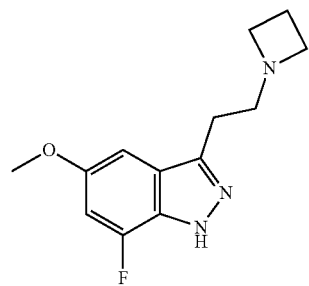 [SMILES: COc1cc(F)c2[nH]nc(CCN3CCC3)c2c1] |
TABLE A-continued
| Compound | Structure |
|---|---|
| A-54 | 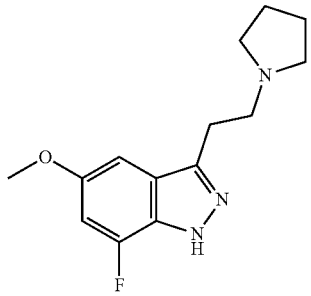 [SMILES: COc1cc(F)c2[nH]nc(CCN3CCCC3)c2c1] |
| A-55 | 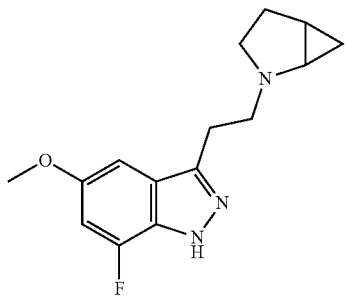 [SMILES: COc1cc(F)c2[nH]nc(CCN3CCC4CC43)c2c1] |
| A-56 | 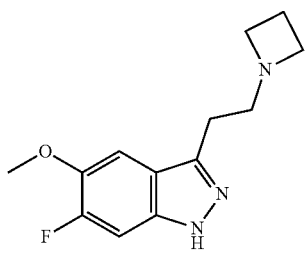 [SMILES: COc1cc2c(CCN3CCC3)n[nH]c2cc1F] |
| A-57 | 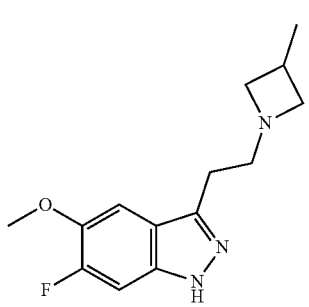 [SMILES: COc1cc2c(CCN3CC(C)C3)n[nH]c2cc1F] |
| A-58 | 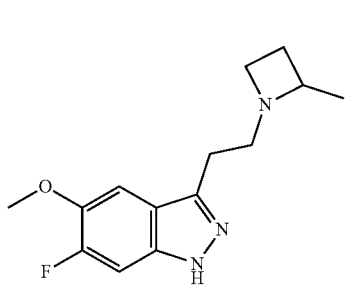 |

TABLE A-continued

| Compound | Structure |
|---|---|
| A-59 | |
| A-60 | |
| A-61 | |
| A-62 | |
| A-63 | |
| A-64 | 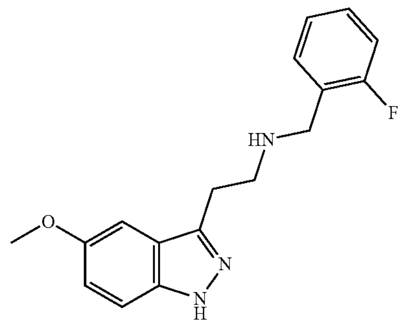 [SMILES: COc1ccc2[nH]nc(CCNCc3ccccc3F)c2c1] |
| A-65 | 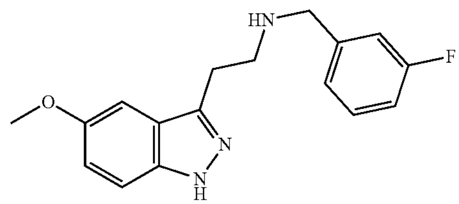 [SMILES: COc1ccc2[nH]nc(CCNCc3cccc(F)c3)c2c1] |
| A-66 | 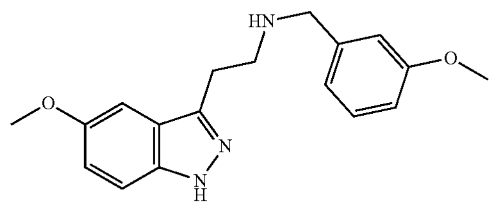 |
| A-67 | 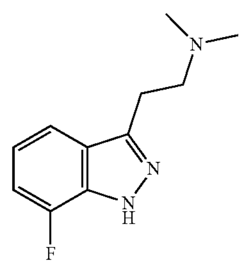 |
| A-68 | 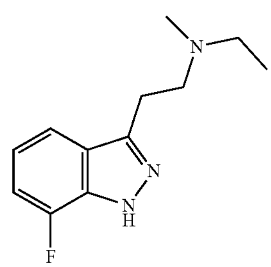 [SMILES: CCN(C)CCc1n[nH]c2c(F)cccc12] |
| A-69 | 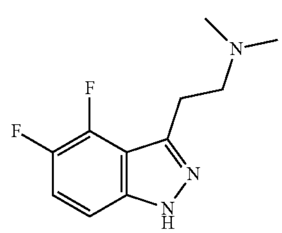 [SMILES: CN(C)CCc1n[nH]c2ccc(F)c(F)c12] |

TABLE A-continued
| Compound | Structure |
|---|---|
| A-70 | 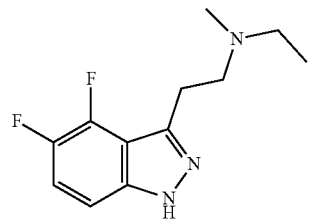 [SMILES: CCN(C)CCc1n[nH]c2ccc(F)c(F)c12] |
| A-71 | 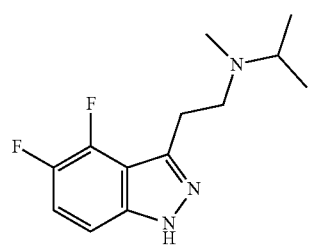 [SMILES: CC(C)N(C)CCc1n[nH]c2ccc(F)c(F)c12] |
| A-72 | 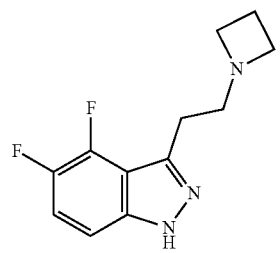 |
| A-73 | 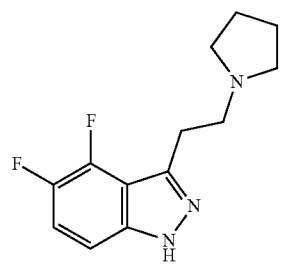 [SMILES: Fc1ccc2[nH]nc(CCN3CCCC3)c2c1F] |
| A-74 | 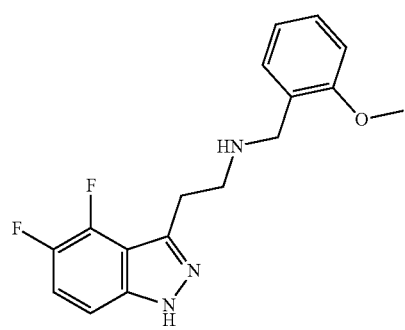 [SMILES: COc1ccccc1CNCCc1n[nH]c2ccc(F)c(F)c12] |
TABLE A-continued
| Compound | Structure |
|---|---|
| A-75 | 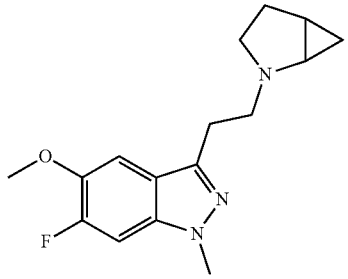 [SMILES: COc1cc2c(CCN3CCC4CC43)nn(C)c2cc1F] |
In some embodiments, the compound may be any of those included in the following Table A1:
TABLE A1
| Code | Structure |
|---|---|
| P-6 | 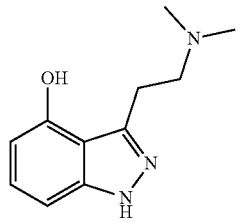 |
| P-7 | 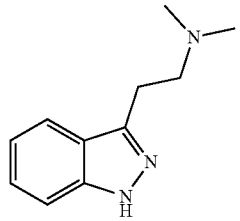 |
| P-8 | 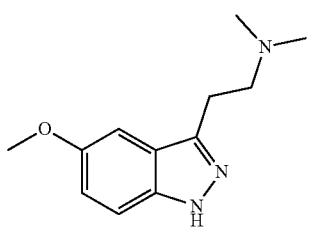 |
| P-42 | 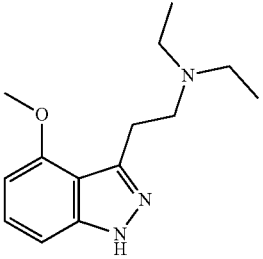 [SMILES: CCN(CC)CCc1n[nH]c2cccc(OC)c12] |

TABLE A1-continued

| Code | Structure |
|---|---|
| P-43 | 4-hydroxy-3-[2-(diethylamino)ethyl]-1H-indazole |
| P-44 | 4-methoxy-3-[2-(dipropylamino)ethyl]-1H-indazole |
| P-45 | 4-hydroxy-3-[2-(dipropylamino)ethyl]-1H-indazole |
| P-48 | 5-methoxy-3-[2-(diethylamino)ethyl]-1H-indazole |
| P-49 | 5-methoxy-3-[2-(dipropylamino)ethyl]-1H-indazole |
| P-51 | 5-methoxy-3-[2-(N-methyl-N-ethylamino)ethyl]-1H-indazole |
| P-52 | 5-methoxy-3-[2-(N-methyl-N-isopropylamino)ethyl]-1H-indazole |
| P-55 | 4-methoxy-3-[2-(dimethylamino)ethyl]-1H-indazole |
| P-56 | 4-hydroxy-3-[2-(dimethylamino)ethyl]-1H-indazole |
| A-1 | 5-fluoro-4-methoxy-3-[2-(dimethylamino)ethyl]-1H-indazole |
| A-2 | 5-fluoro-4-methoxy-3-[2-(N-methyl-N-ethylamino)ethyl]-1H-indazole |

TABLE A1-continued
| Code | Structure |
|---|---|
| A-3 | 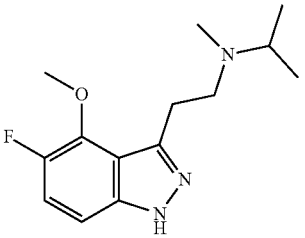 |
| A-4 | 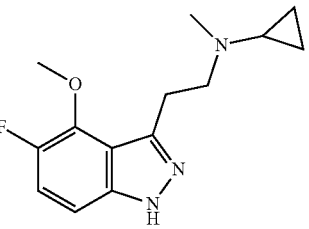 |
| A-5 | 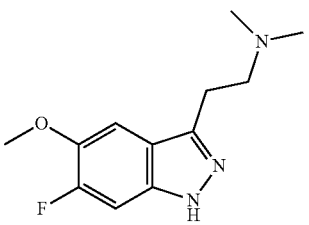 |
| A-6 | 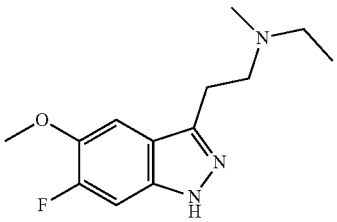 [SMILES: CCN(C)CCc1n[nH]c2cc(F)c(OC)cc12] |
| A-7 | 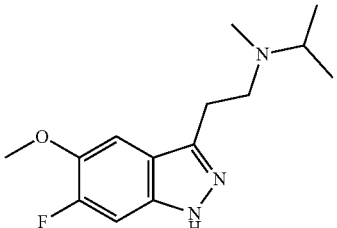 |
| A-8 | 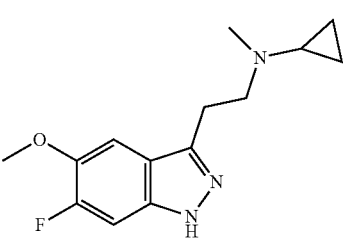 [SMILES: COc1cc2c(CCN(C)C3CC3)n[nH]c2cc1F] |
| A-9 | 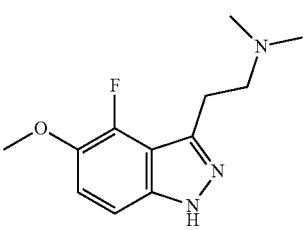 |
| A-10 | 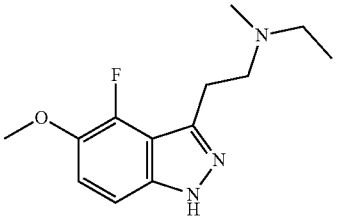 [SMILES: CCN(C)CCc1n[nH]c2ccc(OC)c(F)c12] |
| A-11 | 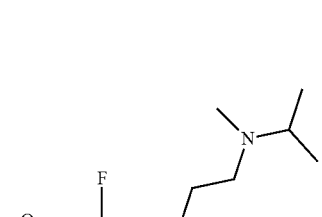 |
| A-12 | 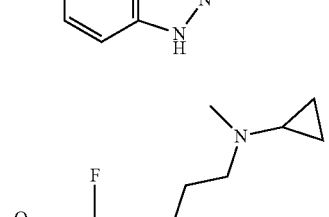 |
| A-13 | 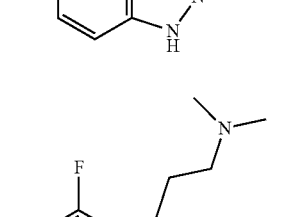 |
| A-14 | 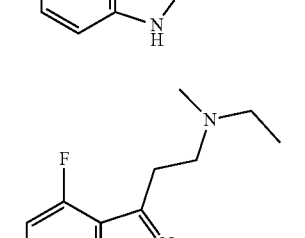 |

TABLE A1-continued
| Code | Structure |
|---|---|
| A-15 | 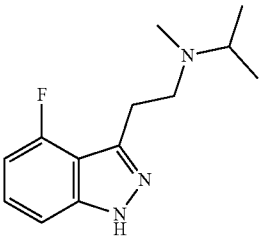 [SMILES: CC(C)N(C)CCc1n[nH]c2cccc(F)c12] |
| A-16 | 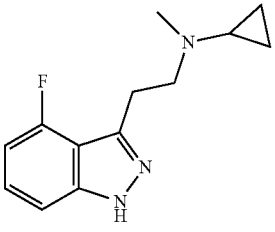 [SMILES: CN(CCc1n[nH]c2cccc(F)c12)C1CC1] |
| A-17 | 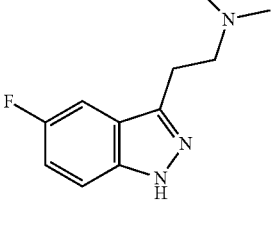 |
| A-18 | 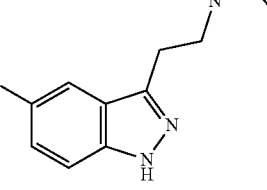 |
| A-19 | 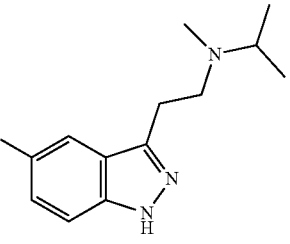 |
| A-20 | 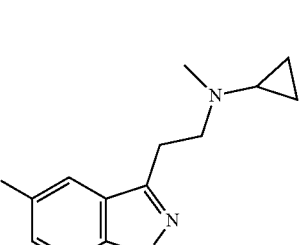 |
| A-21 | 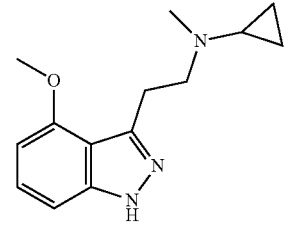 [SMILES: COc1cccc2[nH]nc(CCN(C)C3CC3)c12] |
| A-22 | 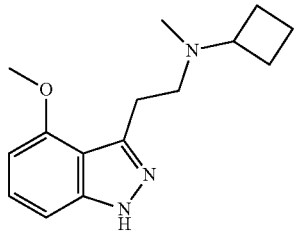 [SMILES: COc1cccc2[nH]nc(CCN(C)C3CCC3)c12] |
| A-23 | 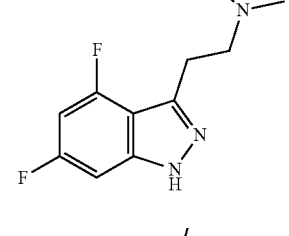 |
| A-24 | 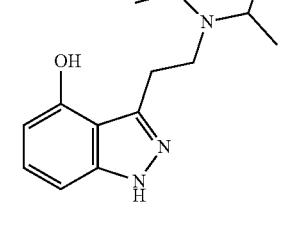 |
| A-25 | 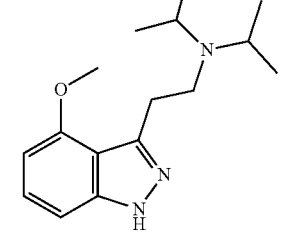 |
| A-26 | 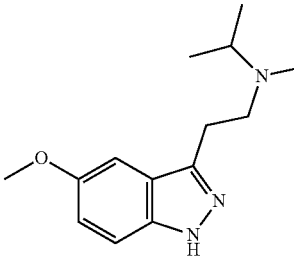 |

TABLE A1-continued

| Code | Structure |
|---|---|
| A-27 | 3-(2-((3-methoxybenzyl)amino)ethyl)-5-methoxy-1H-indazole |
| A-28 | 3-(2-((3-fluorobenzyl)amino)ethyl)-5-methoxy-1H-indazole |
| A-29 | 2-(4,6-difluoro-1H-indazol-3-yl)-N-ethyl-N-methylethan-1-amine |
| A-30 | 2-(4,6-difluoro-1H-indazol-3-yl)-N-isopropyl-N-methylethan-1-amine |
| A-31 | 2-(4,6-difluoro-1H-indazol-3-yl)-N-cyclopropyl-N-methylethan-1-amine |
| A-32 | 2-(4,6-difluoro-1-methyl-1H-indazol-3-yl)-N,N-dimethylethan-1-amine |
| A-32 | 2-(4,6-difluoro-1-methyl-1H-indazol-3-yl)-N,N-dimethylethan-1-amine |
| A-33 | 3-(2-((2-methoxybenzyl)amino)ethyl)-4,6-difluoro-1H-indazole |
| A-34 | 3-(2-((2-methoxybenzyl)amino)ethyl)-4-fluoro-1H-indazole |
| A-35 | 2-(5,7-difluoro-1H-indazol-3-yl)-N,N-dimethylethan-1-amine |
| A-36 | 2-(5,7-difluoro-1H-indazol-3-yl)-N-ethyl-N-methylethan-1-amine |

TABLE A1-continued

| Code | Structure |
|---|---|
| A-37 | 5,7-difluoro-3-(2-(N-methyl-N-isopropylamino)ethyl)-1H-indazole |
| A-38 | 6-fluoro-4-methoxy-3-(2-(N,N-dimethylamino)ethyl)-1H-indazole |
| A-39 | 6-fluoro-4-methoxy-3-(2-(N-methyl-N-ethylamino)ethyl)-1H-indazole |
| A-40 | 6-fluoro-4-methoxy-3-(2-(N-methyl-N-isopropylamino)ethyl)-1H-indazole |
| A-41 | 6-fluoro-4-methoxy-3-(2-(azetidin-1-yl)ethyl)-1H-indazole |
| A-42 | 6-fluoro-4-methoxy-3-(2-(pyrrolidin-1-yl)ethyl)-1H-indazole |
| A-43 | 6-fluoro-4-methoxy-3-(2-(3-azabicyclo[3.1.0]hexan-3-yl)ethyl)-1H-indazole |
| A-44 | 7-fluoro-4-methoxy-3-(2-(N,N-dimethylamino)ethyl)-1H-indazole |
| A-45 | 7-fluoro-4-methoxy-3-(2-(N-methyl-N-ethylamino)ethyl)-1H-indazole |
| A-46 | 7-fluoro-4-methoxy-3-(2-(N-methyl-N-isopropylamino)ethyl)-1H-indazole |
| A-47 | 7-fluoro-4-methoxy-3-(2-(azetidin-1-yl)ethyl)-1H-indazole |

TABLE A1-continued

| Code | Structure |
|---|---|
| A-48 | (4-methoxy-7-fluoro-1H-indazol-3-yl)ethyl-pyrrolidine |
| A-49 | (4-methoxy-7-fluoro-1H-indazol-3-yl)ethyl-3-azabicyclo[3.1.0]hexane |
| A-50 | (5-methoxy-7-fluoro-1H-indazol-3-yl)ethyl-N,N-dimethylamine |
| A-51 | (5-methoxy-7-fluoro-1H-indazol-3-yl)ethyl-N-ethyl-N-methylamine |
| A-52 | (5-methoxy-7-fluoro-1H-indazol-3-yl)ethyl-N-isopropyl-N-methylamine |

TABLE A1-continued

| Code | Structure |
|---|---|
| A-53 | (5-methoxy-7-fluoro-1H-indazol-3-yl)ethyl-azetidine |
| A-54 | (5-methoxy-7-fluoro-1H-indazol-3-yl)ethyl-pyrrolidine |
| A-55 | (5-methoxy-7-fluoro-1H-indazol-3-yl)ethyl-3-azabicyclo[3.1.0]hexane |
| A-56 | (5-methoxy-6-fluoro-1H-indazol-3-yl)ethyl-azetidine |
| A-57 | (5-methoxy-6-fluoro-1H-indazol-3-yl)ethyl-3-methylazetidine |

TABLE A1-continued
| Code | Structure |
|---|---|
| A-58 | 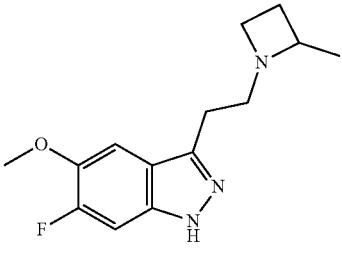 |
| A-59 | 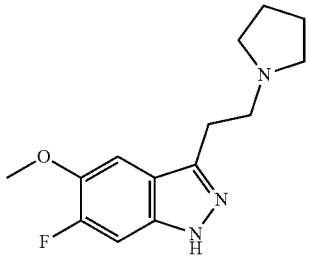 [SMILES: COc1cc2c(CCN3CCCC3)n[nH]c2cc1F] |
| A-60 | 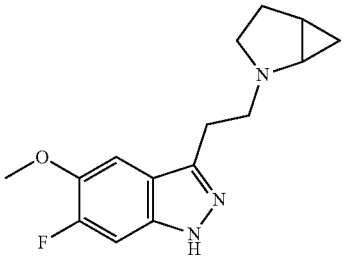 [SMILES: COc1cc2c(CCN3CCC4CC43)n[nH]c2cc1F] |
| A-61 | 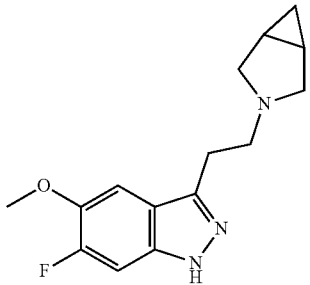 [SMILES: COc1cc2c(CCN3CC4CC4C3)n[nH]c2cc1F] |
| A-62 | 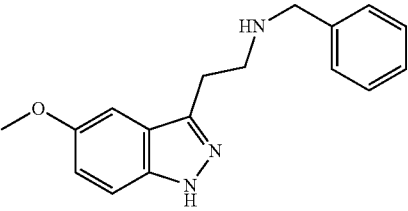 [SMILES: COc1ccc2[nH]nc(CCNCc3ccccc3)c2c1] |
| A-63 | 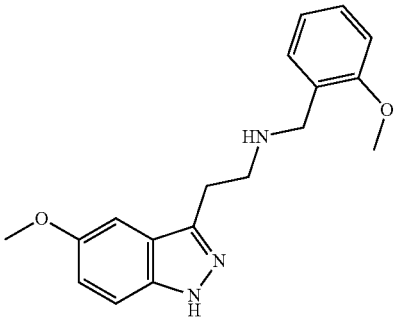 [SMILES: COc1ccc2[nH]nc(CCNCc3ccccc3OC)c2c1] |
| A-64 | 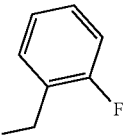 |
| A-65 | 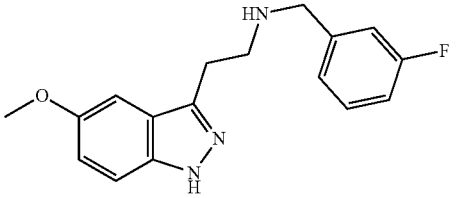 [SMILES: COc1ccc2[nH]nc(CCNCc3cccc(F)c3)c2c1] |
| A-66 | 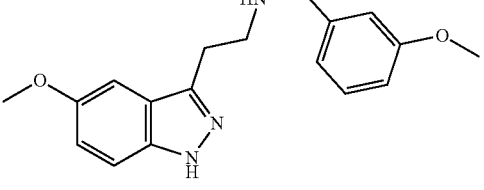 |
| A-67 | 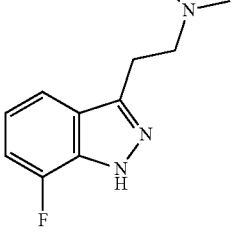 |
| A-68 | 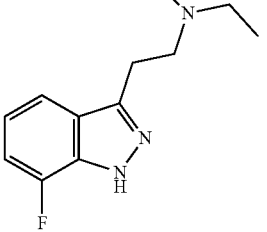 |

TABLE A1-continued

| Code | Structure |
|---|---|
| A-69 | 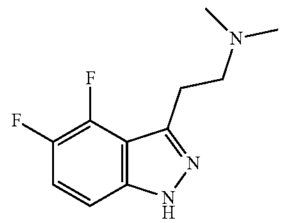 [SMILES: CN(C)CCc1n[nH]c2ccc(F)c(F)c12] |
| A-70 | 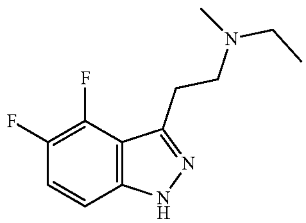 [SMILES: CCN(C)CCc1n[nH]c2ccc(F)c(F)c12] |
| A-71 | 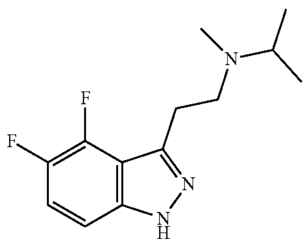 [SMILES: CC(C)N(C)CCc1n[nH]c2ccc(F)c(F)c12] |
| A-72 | 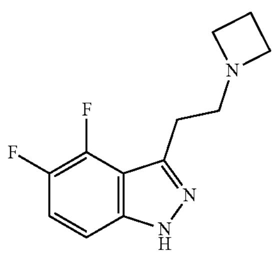 [SMILES: Fc1ccc2[nH]nc(CCN3CCC3)c2c1F] |
| A-73 | 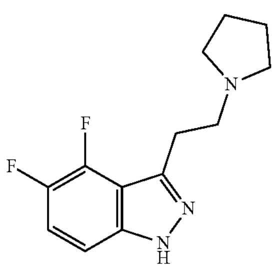 [SMILES: Fc1ccc2[nH]nc(CCN3CCCC3)c2c1F] |
| A-74 | |
| A-75 | |

In some embodiments, the compound of formula (I) has the formula (IIa):

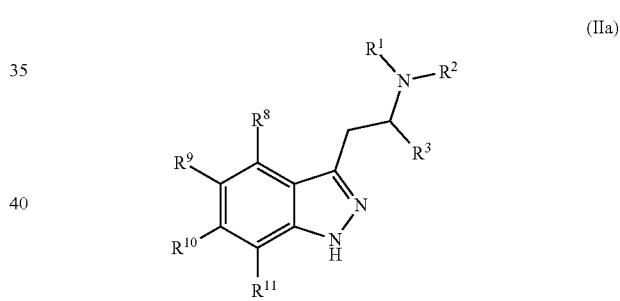

(IIa)

wherein $R^3$ is hydrogen and $R^1$, $R^2$, $R^8$, $R^9$, $R^{10}$ and $R^{11}$ are as defined in Table B. In entries of Table B where $R^1$ and $R^2$ form a heterocyclyl together with the nitrogen to which they are attached, the nitrogen atom to which they are attached is depicted in Table B.

In some embodiments, the compound of any of formulae (I) and (IIa) may be selected from Table B. Compounds of Table B may be prepared by similar techniques to those described herein for structurally related compounds.

TABLE B

| $R^1$ | $R^2$ | $R^6$ | $R^8$ | $R^9$ | $R^{10}$ | $R^{11}$ |
|---|---|---|---|---|---|---|
| —CH₃ | —CH₃ | H | OH | H | H | H |
| —CH₃ | —CH₂CH₃ | H | OH | H | H | H |

TABLE B-continued
| R¹ | R² | R⁶ | R⁸ | R⁹ | R¹⁰ | R¹¹ |
|---|---|---|---|---|---|---|
|  |  | H | OH | H | H | H |
|  | 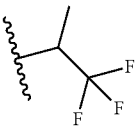 [SMILES: *C(C)C(F)(F)F] | H | OH | H | H | H |
|  |  | H | OH | H | H | H |
|  | 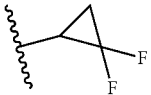 | H | OH | H | H | H |
|  |  | H | OH | H | H | H |
|  |  | H | OH | H | H | H |
|  |  | H | OH | H | H | H |
|  |  | H | OH | H | H | H |
|  |  | H | OH | H | H | H |
|  |  | H | OH | H | H | H |
| |  | H | OH | H | H | H |
| |  | H | OH | H | H | H |
| |  | H | OH | H | H | H |
| |  | H | OH | H | H | H |

TABLE B-continued
| R¹ | R² | R⁶ | R⁸ | R⁹ | R¹⁰ | R¹¹ |
|---|---|---|---|---|---|---|
|  |  | H | OH | H | H | H |
|  |  | H | OH | H | H | H |
|  |  | H | OH | H | H | H |
| H | 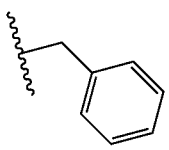 [SMILES: *Cc1ccccc1] | H | OH | H | H | H |
| H | 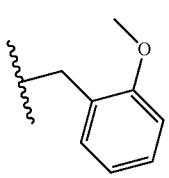 [SMILES: *Cc1ccccc1OC] | H | OH | H | H | H |
| H | 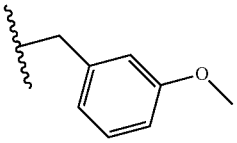 [SMILES: *Cc1cccc(OC)c1] | H | OH | H | H | H |
| H | 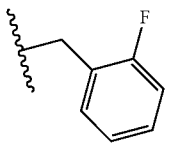 [SMILES: *Cc1ccccc1F] | H | OH | H | H | H |
| H | 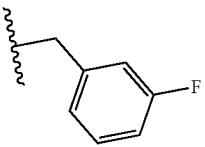 [SMILES: *Cc1cccc(F)c1] | H | OH | H | H | H |
| CH₃ | CH₃ | CH₃ | OH | H | H | H |
| CH₃ | CH₃ |  | H | OMe | H | H | H |
| CH₃ |  |  | H | OMe | H | H | H |
| 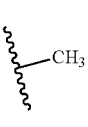CH₃ | 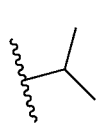 |  | H | OMe | H | H | H |

TABLE B-continued
| R¹ | R² | R⁶ | R⁸ | R⁹ | R¹⁰ | R¹¹ |
|---|---|---|---|---|---|---|
|  | 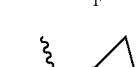 | H | OMe | H | H | H |
|  |  | H | OMe | H | H | H |
|  | 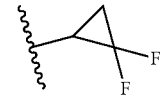 [SMILES: *C1CC1(F)F] | H | OMe | H | H | H |
|  |  | H | OMe | H | H | H |
|  | 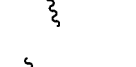 | H | OMe | H | H | H |
|  |  | H | OMe | H | H | H |
|  |  | H | OMe | H | H | H |
|  | 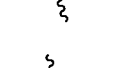 | H | OMe | H | H | H |
|  |  | H | OMe | H | H | H |
| |  | H | OMe | H | H | H |
| |  | H | OMe | H | H | H |
| | 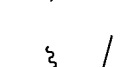 | H | OMe | H | H | H |
| |  | H | OMe | H | H | H |
| |  | H | OMe | H | H | H |

TABLE B-continued

| R¹ | R² | R⁶ | R⁸ | R⁹ | R¹⁰ | R¹¹ |
|---|---|---|---|---|---|---|
| | pyrrolidine | H | OMe | H | H | H |
| | 2-azabicyclo[3.1.0]hexane | H | OMe | H | H | H |
| H | benzyl | H | OMe | H | H | H |
| H | 2-methoxybenzyl | H | OMe | H | H | H |
| H | 3-methoxybenzyl | H | OMe | H | H | H |
| H | 2-fluorobenzyl | H | OMe | H | H | H |
| H | 3-fluorobenzyl | H | OMe | H | H | H |
| CH₃ | CH₃ | CH₃ | OMe | H | H | H |
| CH₃ | CH₃ | H | H | OMe | H | H |
| CH₃ | CH₂CH₃ | H | H | OMe | H | H |
| CH₃ | CH(CH₃)₂ | H | H | OMe | H | H |
| CH₃ | CH(CH₃)CF₃ | H | H | OMe | H | H |

TABLE B-continued
| R¹ | R² | R⁶ | R⁸ | R⁹ | R¹⁰ | R¹¹ |
|---|---|---|---|---|---|---|
|  | 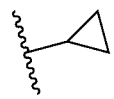 [SMILES: *C1CC1] | H | H | OMe | H | H |
|  |  | H | H | OMe | H | H |
|  | 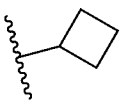 | H | H | OMe | H | H |
|  |  | H | H | OMe | H | H |
|  | 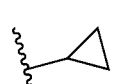 | H | H | OMe | H | H |
|  |  | H | H | OMe | H | H |
|  |  | H | H | OMe | H | H |
|  | 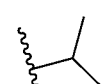 | H | H | OMe | H | H |
| |  | H | H | OMe | H | H |
| |  | H | H | OMe | H | H |
| | 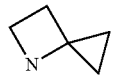 | H | H | OMe | H | H |
| |  | H | H | OMe | H | H |
| | 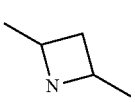 | H | H | OMe | H | H |
| | 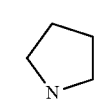 | H | H | OMe | H | H |
| |  | H | H | OMe | H | H |

TABLE B-continued

| R¹ | R² | R⁶ | R⁸ | R⁹ | R¹⁰ | R¹¹ |
|---|---|---|---|---|---|---|
| H | benzyl | H | H | OMe | H | H |
| H | 2-methoxybenzyl | H | H | OMe | H | H |
| H | 3-methoxybenzyl | H | H | OMe | H | H |
| H | 2-fluorobenzyl | H | H | OMe | H | H |
| H | 3-fluorobenzyl | H | H | OMe | H | H |
| CH₃ | CH₃ | CH₃ | H | OMe | H | H |
| CH₃ | CH₃ | | H | F | H | H | H |
| CH₃ | CH₂CH₃ | | H | F | H | H | H |
| CH₃ | isopropyl | | H | F | H | H | H |
| CH₃ | CH(CH₃)CF₃ | | H | F | H | H | H |
| CH₃ | cyclopropyl | | H | F | H | H | H |

TABLE B-continued
| R¹ | R² | R⁶ | R⁸ | R⁹ | R¹⁰ | R¹¹ |
|---|---|---|---|---|---|---|
|  |  | H | F | H | H | H |
|  |  | H | F | H | H | H |
|  |  | H | F | H | H | H |
|  | 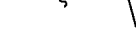 | H | F | H | H | H |
|  |  | H | F | H | H | H |
|  | 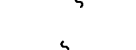 | H | F | H | H | H |
|  |  | H | F | H | H | H |
| |  | H | F | H | H | H |
| |  | H | F | H | H | H |
| |  | H | F | H | H | H |
| |  | H | F | H | H | H |
| |  | H | F | H | H | H |
| |  | H | F | H | H | H |
| |  | H | F | H | H | H |

TABLE B-continued
| R¹ | R² | R⁶ | R⁸ | R⁹ | R¹⁰ | R¹¹ |
|---|---|---|---|---|---|---|
| H | 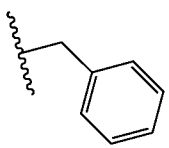 [SMILES: *Cc1ccccc1] | H | F | H | H | H |
| H | 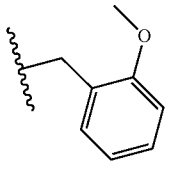 [SMILES: *Cc1ccccc1OC] | H | F | H | H | H |
| H | 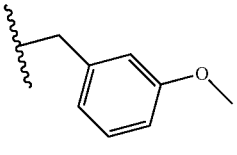 [SMILES: *Cc1cccc(OC)c1] | H | F | H | H | H |
| H | 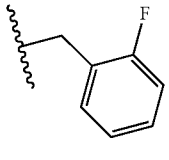 [SMILES: *Cc1ccccc1F] | H | F | H | H | H |
| H | 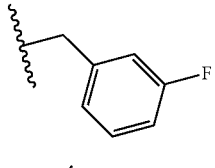 | H | F | H | H | H |
|  |  |  | F | H | H | H |
|  |  | H | H | F | H | H |
|  | 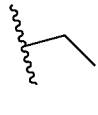 | H | H | F | H | H |
|  | 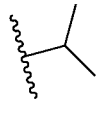 | H | H | F | H | H |
|  | 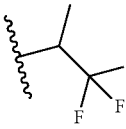 | H | H | F | H | H |
|  | 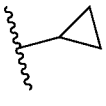 | H | H | F | H | H |
|  | 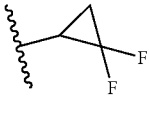 [SMILES: *C1CC1(F)F] | H | H | F | H | H |

TABLE B-continued
| R¹ | R² | R⁶ | R⁸ | R⁹ | R¹⁰ | R¹¹ |
|---|---|---|---|---|---|---|
| 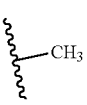 | 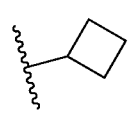 | H | H | F | H | H |
| 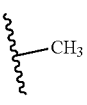 |  | H | H | F | H | H |
|  | 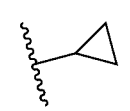 | H | H | F | H | H |
|  | 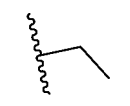 | H | H | F | H | H |
| 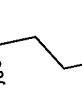 | 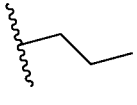 [SMILES: *CCC] | H | H | F | H | H |
| 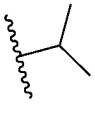 | 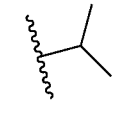 | H | H | F | H | H |
| |  | H | H | F | H | H |
| |  | H | H | F | H | H |
| |  | H | H | F | H | H |
| |  | H | H | F | H | H |
| |  | H | H | F | H | H |
| |  | H | H | F | H | H |
| |  | H | H | F | H | H |
| H | 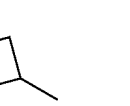 | H | H | F | H | H |

TABLE B-continued
| R¹ | R² | R⁶ | R⁸ | R⁹ | R¹⁰ | R¹¹ |
|---|---|---|---|---|---|---|
| H | 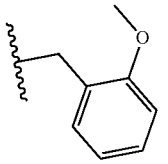 [SMILES: *Cc1ccccc1OC] | H | H | F | H | H |
| H | 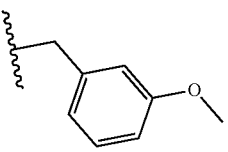 [SMILES: *Cc1cccc(OC)c1] | H | H | F | H | H |
| H | 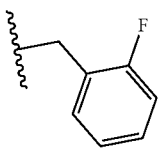 [SMILES: *Cc1ccccc1F] | H | H | F | H | H |
| H | 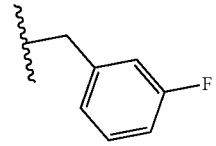 [SMILES: *Cc1cccc(F)c1] | H | H | F | H | H |
|  —CH₃ |  —CH₃ |  —CH₃ | H | F | H | H |
|  —CH₃ |  —CH₃ | H | H | H | F | H |
|  —CH₃ |  | H | H | H | F | H |
|  —CH₃ |  | H | H | H | F | H |
|  —CH₃ | 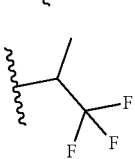 | H | H | H | F | H |
|  —CH₃ |  | H | H | H | F | H |
|  —CH₃ | 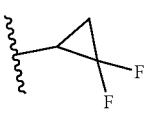 [SMILES: *C1CC1(F)F] | H | H | H | F | H |
|  —CH₃ | 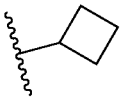 | H | H | H | F | H |

TABLE B-continued
| R¹ | R² | R⁶ | R⁸ | R⁹ | R¹⁰ | R¹¹ |
|---|---|---|---|---|---|---|
|  | 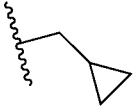 | H | H | H | F | H |
|  | 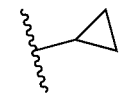 | H | H | H | F | H |
|  |  | H | H | H | F | H |
|  |  | H | H | H | F | H |
|  | 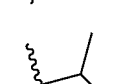 | H | H | H | F | H |
|  | | H | H | H | F | H |
|  | | H | H | H | F | H |
|  | | H | H | H | F | H |
|  | | H | H | H | F | H |
| 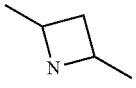 | | H | H | H | F | H |
|  | | H | H | H | F | H |
|  | | H | H | H | F | H |
| H | 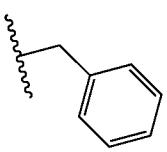 [SMILES: *Cc1ccccc1] | H | H | H | F | H |
| H | 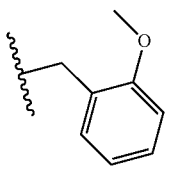 [SMILES: *Cc1ccccc1OC] | H | H | H | F | H |

TABLE B-continued
| R¹ | R² | R⁶ | R⁸ | R⁹ | R¹⁰ | R¹¹ |
|---|---|---|---|---|---|---|
| H | 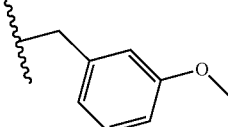 | H | H | H | F | H |
| H | 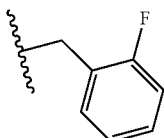 | H | H | H | F | H |
| H | 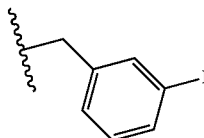 | H | H | H | F | H |
|  —CH₃ |  —CH₃ |  —CH₃ | H | H | F | H |
|  —CH₃ |  —CH₃ | H | H | H | H | F |
|  —CH₃ |  | H | H | H | H | F |
|  —CH₃ |  | H | H | H | H | F |
|  —CH₃ | 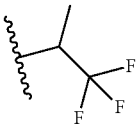 [SMILES: *C(C)C(F)(F)F] | H | H | H | H | F |
|  —CH₃ |  | H | H | H | H | F |
|  —CH₃ | 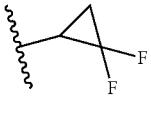 [SMILES: *C1CC1(F)F] | H | H | H | H | F |
|  —CH₃ |  | H | H | H | H | F |
|  —CH₃ | 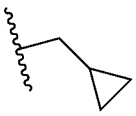 [SMILES: *CC1CC1] | H | H | H | H | F |

TABLE B-continued
| R¹ | R² | R⁶ | R⁸ | R⁹ | R¹⁰ | R¹¹ |
|---|---|---|---|---|---|---|
|  | 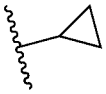 | H | H | H | H | F |
|  | 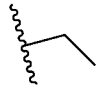 | H | H | H | H | F |
| 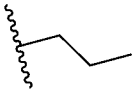 [SMILES: *CCC] | 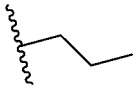 [SMILES: *CCC] | H | H | H | H | F |
|  | 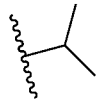 | H | H | H | H | F |
| |  | H | H | H | H | F |
| |  | H | H | H | H | F |
| |  | H | H | H | H | F |
| | 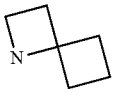 | H | H | H | H | F |
| | 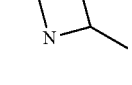 | H | H | H | H | F |
| |  | H | H | H | H | F |
| | 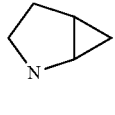 | H | H | H | H | F |
| H | 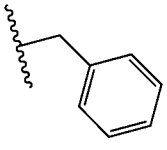 [SMILES: *Cc1ccccc1] | H | H | H | H | F |
| H | 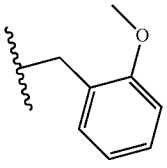 [SMILES: *Cc1ccccc1OC] | H | H | H | H | F |

TABLE B-continued
| R¹ | R² | R⁶ | R⁸ | R⁹ | R¹⁰ | R¹¹ |
|---|---|---|---|---|---|---|
| H | 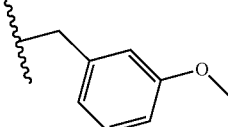 | H | H | H | H | F |
| H | 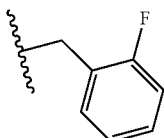 | H | H | H | H | F |
| H | 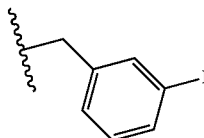 | H | H | H | H | F |
|  |  |  | H | H | H | F |
|  |  | H | OMe | F | H | H |
|  |  | H | OMe | F | H | H |
|  |  | H | OMe | F | H | H |
|  |  | H | OMe | F | H | H |
|  |  | H | OMe | F | H | H |
|  |  | H | OMe | F | H | H |
|  |  | H | OMe | F | H | H |
|  |  | H | OMe | F | H | H |

TABLE B-continued
| R¹ | R² | R⁶ | R⁸ | R⁹ | R¹⁰ | R¹¹ |
|---|---|---|---|---|---|---|
|  |  | H | OMe | F | H | H |
|  |  | H | OMe | F | H | H |
| 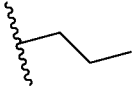 [SMILES: *CCC] | 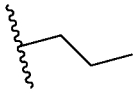 | H | OMe | F | H | H |
|  |  | H | OMe | F | H | H |
| |  | H | OMe | F | H | H |
| |  | H | OMe | F | H | H |
| |  | H | OMe | F | H | H |
| |  | H | OMe | F | H | H |
| |  | H | OMe | F | H | H |
| | 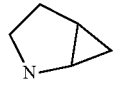 | H | OMe | F | H | H |
| | 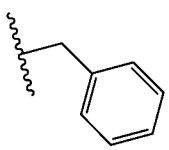 [SMILES: *Cc1ccccc1] | H | OMe | F | H | H |
| H | 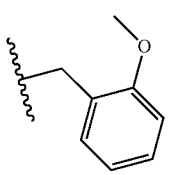 [SMILES: *Cc1ccccc1OC] | H | OMe | F | H | H |
| H |  | H | OMe | F | H | H |

TABLE B-continued

| R¹ | R² | R⁶ | R⁸ | R⁹ | R¹⁰ | R¹¹ |
|---|---|---|---|---|---|---|
| H | 3-methoxybenzyl | H | OMe | F | H | H |
| H | 2-fluorobenzyl | H | OMe | F | H | H |
| H | 3-fluorobenzyl | H | OMe | F | H | H |
| —CH₃ | —CH₃ | —CH₃ | OMe | F | H | H |
| —CH₃ | —CH₃ | H | H | OMe | F | H |
| —CH₃ | —CH₂CH₃ | H | H | OMe | F | H |
| —CH₃ | —CH(CH₃)₂ | H | H | OMe | F | H |
| —CH₃ | —CH(CH₃)CF₃ | H | H | OMe | F | H |
| —CH₃ | cyclopropyl | H | H | OMe | F | H |
| —CH₃ | 2,2-difluorocyclopropyl | H | H | OMe | F | H |
| —CH₃ | cyclobutyl | H | H | OMe | F | H |
| —CH₃ | cyclopropylmethyl | H | H | OMe | F | H |

TABLE B-continued
| R¹ | R² | R⁶ | R⁸ | R⁹ | R¹⁰ | R¹¹ |
|---|---|---|---|---|---|---|
|  |  | H | H | OMe | F | H |
|  |  | H | H | OMe | F | H |
| 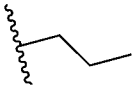 [SMILES: *CCC] |  | H | H | OMe | F | H |
|  |  | H | H | OMe | F | H |
| |  | H | H | OMe | F | H |
| |  | H | H | OMe | F | H |
| |  | H | H | OMe | F | H |
| |  | H | H | OMe | F | H |
| | 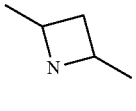 | H | H | OMe | F | H |
| |  | H | H | OMe | F | H |
| | 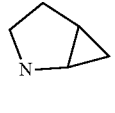 | H | H | OMe | F | H |
| H | 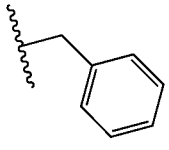 [SMILES: *Cc1ccccc1] | H | H | OMe | F | H |
| H | 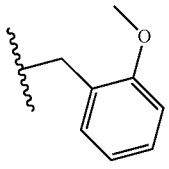 [SMILES: *Cc1ccccc1OC] | H | H | OMe | F | H |

TABLE B-continued

| R¹ | R² | R⁶ | R⁸ | R⁹ | R¹⁰ | R¹¹ |
|---|---|---|---|---|---|---|
| H | 3-methoxybenzyl | H | H | OMe | F | H |
| H | 2-fluorobenzyl | H | H | OMe | F | H |
| H | 2-fluorobenzyl | H | H | OMe | F | H |
| 3-fluorobenzyl | CH₃ | CH₃ | H | OMe | F | H |
| CH₃ | CH₃ | H | F | OMe | H | H |
| CH₃ | ethyl | H | F | OMe | H | H |
| CH₃ | isopropyl | H | F | OMe | H | H |
| CH₃ | 1,1,1-trifluoroisopropyl | H | F | OMe | H | H |
| CH₃ | cyclopropyl | H | F | OMe | H | H |
| CH₃ | 2,2-difluorocyclopropyl | H | F | OMe | H | H |
| CH₃ | cyclobutyl | H | F | OMe | H | H |
| CH₃ | cyclopropylmethyl | H | F | OMe | H | H |

TABLE B-continued

| R¹ | R² | R⁶ | R⁸ | R⁹ | R¹⁰ | R¹¹ |
|---|---|---|---|---|---|---|
| ethyl | cyclopropyl | H | F | OMe | H | H |
| ethyl | ethyl | H | F | OMe | H | H |
| propyl | propyl | H | F | OMe | H | H |
| isopropyl | isopropyl | H | F | OMe | H | H |
|  | azetidinyl | H | F | OMe | H | H |
|  | 2-methylazetidinyl | H | F | OMe | H | H |
|  | 1-azaspiro[2.3]hexyl | H | F | OMe | H | H |
|  | 2-azaspiro[3.3]heptyl | H | F | OMe | H | H |
|  | 2,4-dimethylazetidinyl | H | F | OMe | H | H |
|  | pyrrolidinyl | H | F | OMe | H | H |
|  | CH₃ | H | F | OMe | H | H |
| H | benzyl | H | F | OMe | H | H |
| H | 2-methoxybenzyl | H | F | OMe | H | H |
| H | 3-methoxybenzyl | H | F | OMe | H | H |

TABLE B-continued
| R¹ | R² | R⁶ | R⁸ | R⁹ | R¹⁰ | R¹¹ |
|---|---|---|---|---|---|---|
| H |  | H | F | OMe | H | H |
| H | 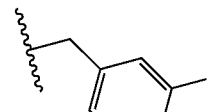 | H | F | OMe | H | H |
|  |  |  | F | OMe | H | H |
|  |  | H | F | OMe | H | H |
|  |  | H | H | OMe | H | F |
|  |  | H | H | OMe | H | F |
|  | 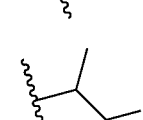 | H | H | OMe | H | F |
|  |  | H | H | OMe | H | F |
|  |  | H | H | OMe | H | F |
|  |  | H | H | OMe | H | F |
|  |  | H | H | OMe | H | F |
|  |  | H | H | OMe | H | F |
|  |  | H | H | OMe | H | F |

TABLE B-continued

| R¹ | R² | R⁶ | R⁸ | R⁹ | R¹⁰ | R¹¹ |
|---|---|---|---|---|---|---|
| *propyl* | *propyl* | H | H | OMe | H | F |
| *isopropyl* | *isopropyl* | H | H | OMe | H | F |
| | *azetidine* | H | H | OMe | H | F |
| | *2-methylazetidine* | H | H | OMe | H | F |
| | *1-azaspiro[3.2]* | H | H | OMe | H | F |
| | *2-azaspiro[3.3]heptane* | H | H | OMe | H | F |
| | *2,4-dimethylazetidine* | H | H | OMe | H | F |
| | *pyrrolidine* | H | H | OMe | H | F |
| | *azabicyclo[3.1.0]hexane* | H | H | OMe | H | F |
| H | *benzyl* | H | H | OMe | H | F |
| H | *2-methoxybenzyl* | H | H | OMe | H | F |
| H | *3-methoxybenzyl* | H | H | OMe | H | F |
| H | *2-fluorobenzyl* | H | H | OMe | H | F |

TABLE B-continued
| R¹ | R² | R⁶ | R⁸ | R⁹ | R¹⁰ | R¹¹ |
|---|---|---|---|---|---|---|
| H | 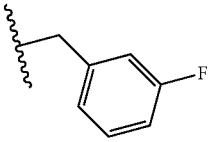 [SMILES: *Cc1cccc(F)c1] | H | H | OMe | H | F |
| —CH₃ | —CH₃ | —CH₃ | H | OMe | H | F |
| —CH₃ | —CH₃ | H | H | OMe | H | F |
| —CH₃ |  | H | OMe | H | F | H |
| —CH₃ |  | H | OMe | H | F | H |
| —CH₃ | 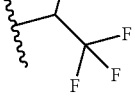 | H | OMe | H | F | H |
| —CH₃ |  | H | OMe | H | F | H |
| —CH₃ | —CH₃ | H | OMe | H | F | H |
| —CH₃ | 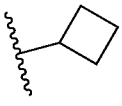 [SMILES: *C1CCC1] | H | OMe | H | F | H |
| —CH₃ |  | H | OMe | H | F | H |
|  |  | H | OMe | H | F | H |
|  |  | H | OMe | H | F | H |
| 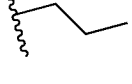 | 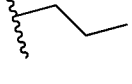 | H | OMe | H | F | H |

TABLE B-continued

| R¹ | R² | R⁶ | R⁸ | R⁹ | R¹⁰ | R¹¹ |
|---|---|---|---|---|---|---|
| isopropyl | isopropyl | H | OMe | H | F | H |
|  | azetidine | H | OMe | H | F | H |
|  | 2-methylazetidine | H | OMe | H | F | H |
|  | 1-azaspiro[2.3]hexane | H | OMe | H | F | H |
|  | 2-azaspiro[3.3]heptane | H | OMe | H | F | H |
|  | 2,4-dimethylazetidine | H | OMe | H | F | H |
|  | pyrrolidine | H | OMe | H | F | H |
|  | 3-azabicyclo[3.1.0]hexane | H | OMe | H | F | H |
| H | benzyl-CH₂ | H | OMe | H | LL | H |
| H | 2-methoxybenzyl-CH₂ | H | OMe | H | F | H |
| H | 3-methoxybenzyl-CH₂ | H | OMe | H | F | H |
| H | 2-fluorobenzyl-CH₂ | H | OMe | H | F | H |
| H | 3-fluorobenzyl-CH₂ |  | OMe | H | F | H |

TABLE B-continued

| R¹ | R² | R⁶ | R⁸ | R⁹ | R¹⁰ | R¹¹ |
|---|---|---|---|---|---|---|
| -CH₃ | -CH₃ | -CH₃ | OMe | H | F | H |
| -CH₃ | -CH₃ | H | OMe | H | F | H |
| -CH₃ | -CH₂CH₃ | H | OMe | H | H | F |
| -CH₃ | -CH(CH₃)₂ | H | OMe | H | H | F |
| -CH₃ | -CH(CH₃)CF₃ | H | OMe | H | H | F |
| -CH₃ | cyclopropyl | H | OMe | H | H | F |
| -CH₃ | 2,2-difluorocyclopropyl | H | OMe | H | H | F |
| -CH₃ | cyclobutyl | H | OMe | H | H | F |
| -CH₃ | -CH₂-cyclopropyl | H | OMe | H | H | F |
| -CH₂CH₃ | cyclopropyl | H | OMe | H | H | F |
| -CH₂CH₃ | -CH₂CH₃ | H | OMe | H | H | F |
| -CH₂CH₂CH₃ | -CH₂CH₂CH₃ | H | OMe | H | H | F |
| -CH(CH₃)₂ | -CH(CH₃)₂ | H | OMe | H | H | F |
|  | azetidinyl | H | OMe | H | H | F |

TABLE B-continued

| R¹ | R² | R⁶ | R⁸ | R⁹ | R¹⁰ | R¹¹ |
|---|---|---|---|---|---|---|
| | 2-methylazetidinyl | H | OMe | H | H | F |
| | 1-azaspiro[3.2]hexyl | H | OMe | H | H | F |
| | 2-azaspiro[3.3]heptyl | H | OMe | H | H | F |
| | 2,4-dimethylazetidinyl | H | OMe | H | H | F |
| | pyrrolidinyl | H | OMe | H | H | F |
| | 3-azabicyclo[3.1.0]hexyl | H | OMe | H | H | F |
| H | benzyl | H | OMe | H | H | F |
| H | 2-methoxybenzyl | H | OMe | H | H | F |
| H | 3-methoxybenzyl | H | OMe | H | H | F |
| H | 2-fluorobenzyl | H | OMe | H | H | F |
| H | 3-fluorobenzyl | H | OMe | H | H | F |
| —CH₃ | —CH₃ | —CH₃ | OMe | H | H | F |

TABLE B-continued

| R¹ | R² | R⁶ | R⁸ | R⁹ | R¹⁰ | R¹¹ |
|---|---|---|---|---|---|---|
| —CH₃ | —CH₃ | H | OMe | H | H | F |
| —CH₃ | —CH₂CH₃ (ethyl) | H | F | F | H | H |
| —CH₃ | —CH(CH₃)₂ (isopropyl) | H | F | F | H | H |
| —CH₃ | —CH(CH₃)CF₃ | H | F | F | H | H |
| —CH₃ | —cyclopropyl | H | F | F | H | H |
| —CH₃ | —(2,2-difluorocyclopropyl) | H | F | F | H | H |
| —CH₃ | —cyclobutyl | H | F | F | H | H |
| —CH₃ | —CH₂-cyclopropyl | H | F | F | H | H |
| —CH₂CH₃ | —cyclopropyl | H | F | F | H | H |
| —CH₂CH₃ | —CH₂CH₃ | H | F | F | H | H |
| —CH₂CH₂CH₃ | —CH₂CH₂CH₃ | H | F | F | H | H |
| —CH(CH₃)₂ | —CH(CH₃)₂ | H | F | F | H | H |
| azetidine | | H | F | F | H | H |
| 2-methyl azetidine | | H | F | F | H | H |

TABLE B-continued

| R¹ | R² | R⁶ | R⁸ | R⁹ | R¹⁰ | R¹¹ |
|---|---|---|---|---|---|---|
| | ![azaspiro] | H | F | F | H | H |
| | ![azaspiro] | H | F | F | H | H |
| | ![2,4-dimethylazetidine] | H | F | F | H | H |
| | ![pyrrolidine] | H | F | F | H | H |
| | ![azabicyclic] | H | F | F | H | H |
| H | ![benzyl] | H | F | F | H | H |
| H | ![2-methoxybenzyl] | H | F | F | H | H |
| H | ![3-methoxybenzyl] | H | F | F | H | H |
| H | ![2-fluorobenzyl] | H | F | F | H | H |
| H | ![3-fluorobenzyl] | H | F | F | H | H |
| —CH₃ | —CH₃ | —CH₃ | F | F | H | H |
| —CH₃ | —CH₃ | H | F | F | H | H |

TABLE B-continued
| R$^1$ | R$^2$ | R$^6$ | R$^8$ | R$^9$ | R$^{10}$ | R$^{11}$ |
|---|---|---|---|---|---|---|
|  |  | H | F | F | H | H |
|  |  | H | F | H | F | H |
|  | 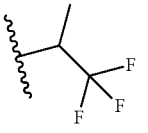 | H | F | H | F | H |
|  |  | H | F | H | F | H |
|  | 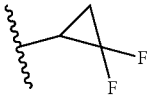 [SMILES: *C1CC1(F)F] | H | F | H | F | H |
|  | 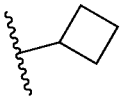 [SMILES: *C1CCC1] | H | F | H | F | H |
|  |  | H | F | H | F | H |
|  |  | H | F | H | F | H |
|  |  | H | F | H | F | H |
|  | 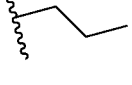 | H | F | H | F | H |
|  |  | H | F | H | F | H |
| |  | H | F | H | F | H |
| |  | H | F | H | F | H |
| |  | H | F | H | F | H |

TABLE B-continued
| R¹ | R² | R⁶ | R⁸ | R⁹ | R¹⁰ | R¹¹ |
|---|---|---|---|---|---|---|
|  | 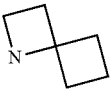 | H | F | H | F | H |
|  | 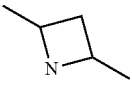 | H | F | H | F | H |
|  |  | H | F | H | F | H |
|  | 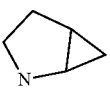 | H | F | H | F | H |
| H | 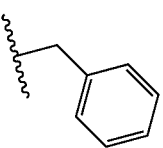 [SMILES: *Cc1ccccc1] | H | F | H | F | H |
| H | 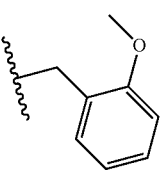 [SMILES: *Cc1ccccc1OC] | H | F | H | F | H |
| H | 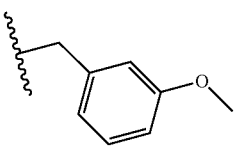 [SMILES: *Cc1cccc(OC)c1] | H | F | H | F | H |
| H | 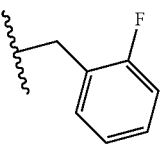 [SMILES: *Cc1ccccc1F] | H | F | H | F | H |
| H | 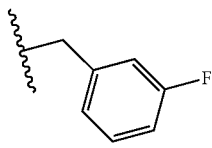 [SMILES: *Cc1cccc(F)c1] | H | F | H | F | H |
|  |  |  | F | H | F | H |
|  |  | H | F | H | H | F |
|  |  | H | F | H | H | F |

TABLE B-continued
| R¹ | R² | R⁶ | R⁸ | R⁹ | R¹⁰ | R¹¹ |
|---|---|---|---|---|---|---|
|  | 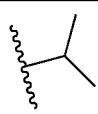 | H | F | H | H | F |
| 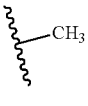 | 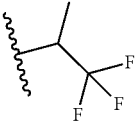 [SMILES: *C(C)C(F)(F)F] | H | F | H | H | F |
| 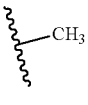 |  | H | F | H | H | F |
| 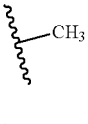 | 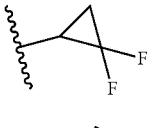 | H | F | H | H | F |
| 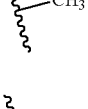 | 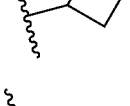 | H | F | H | H | F |
| 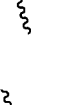 |  | H | F | H | H | F |
|  |  | H | F | H | H | F |
|  |  | H | F | H | H | F |
| 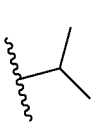 [SMILES: *C(C)C] | 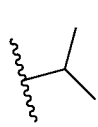 | H | F | H | H | F |
|  |  | H | F | H | H | F |
| |  | H | F | H | H | F |
| |  | H | F | H | H | F |
| |  | H | F | H | H | F |
| |  | H | F | H | H | F |

TABLE B-continued

| R¹ | R² | R⁶ | R⁸ | R⁹ | R¹⁰ | R¹¹ |
|---|---|---|---|---|---|---|
| | 2,4-dimethylazetidinyl | H | F | H | H | F |
| | pyrrolidinyl | H | F | H | H | F |
| | 3-azabicyclo[3.1.0] | H | F | H | H | F |
| H | benzyl-CH₂- | H | F | H | H | F |
| H | 2-methoxybenzyl-CH₂- | H | F | H | H | F |
| H | 3-methoxybenzyl-CH₂- | H | F | H | H | F |
| H | 2-fluorobenzyl-CH₂- | H | F | H | H | F |
| H | 3-fluorobenzyl-CH₂- | H | F | H | H | F |
| —CH₃ | —CH₃ | —CH₃ | F | H | H | F |
| —CH₃ | —CH₃ | H | H | F | F | H |
| —CH₃ | —CH₂CH₃ | H | H | F | F | H |
| —CH₃ | —CH(CH₃)₂ | H | H | F | F | H |

TABLE B-continued
| R¹ | R² | R⁶ | R⁸ | R⁹ | R¹⁰ | R¹¹ |
|---|---|---|---|---|---|---|
|  | 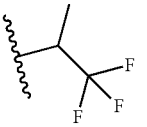 [SMILES: *C(C)C(F)(F)F] | H | H | F | F | H |
|  |  | H | H | F | F | H |
|  | 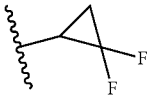 [SMILES: *C1CC1(F)F] | H | H | F | F | H |
|  |  | H | H | F | F | H |
|  | 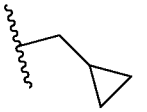 [SMILES: *CC1CC1] | H | H | F | F | H |
|  |  | H | H | F | F | H |
|  |  | H | H | F | F | H |
|  | 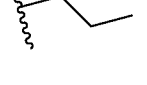 | H | H | F | F | H |
|  |  | H | H | F | F | H |
| |  | H | H | F | F | H |
| |  | H | H | F | F | H |
| |  | H | H | F | F | H |
| |  | H | H | F | F | H |
| | 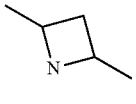 | H | H | F | F | H |

TABLE B-continued

| R¹ | R² | R⁶ | R⁸ | R⁹ | R¹⁰ | R¹¹ |
|---|---|---|---|---|---|---|
|  | pyrrolidine | H | H | F | F | H |
|  | 3-azabicyclo[3.1.0]hexane | H | H | F | F | H |
| H | benzyl | H | H | F | F | H |
| H | 2-methoxybenzyl | H | H | F | F | H |
| H | 3-methoxybenzyl | H | H | F | F | H |
| H | 2-fluorobenzyl | H | H | F | F | H |
| H | 3-fluorobenzyl | H | H | F | F | H |
| CH₃ | CH₃ | CH₃ | H | F | F | H |
| CH₃ | CH₃ | H | H | F | H | F |
| CH₃ | CH₂CH₃ | H | H | F | H | F |
| CH₃ | CH(CH₃)₂ | H | H | F | H | F |
| CH₃ | CH(CH₃)CF₃ | H | H | F | H | F |

TABLE B-continued

| R¹ | R² | R⁶ | R⁸ | R⁹ | R¹⁰ | R¹¹ |
|---|---|---|---|---|---|---|
| —CH₃ | cyclopropyl | H | H | F | H | F |
| —CH₃ | 2,2-difluorocyclopropyl | H | H | F | H | F |
| —CH₃ | cyclobutyl | H | H | F | H | F |
| —CH₃ | cyclopropylmethyl | H | H | F | H | F |
| ethyl | cyclopropyl | H | H | F | H | F |
| ethyl | ethyl | H | H | F | H | F |
| n-propyl | n-propyl | H | H | F | H | F |
| isopropyl | isopropyl | H | H | F | H | F |
| H | benzyl | H | H | F | H | F |
| H | 2-methoxybenzyl | H | H | F | H | F |
| H | 3-methoxybenzyl | H | H | F | H | F |
| H | 2-fluorobenzyl | H | H | F | H | F |

TABLE B-continued
| R¹ | R² | R⁶ | R⁸ | R⁹ | R¹⁰ | R¹¹ |
|---|---|---|---|---|---|---|
| H | 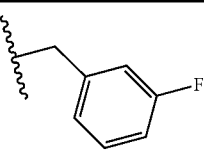 | H | H | F | H | F |
|  CH₃ |  CH₃ |  CH₃ | H | F | H | F |
|  CH₃ |  CH₃ | H | H | H | F | F |
|  CH₃ |  | H | H | H | F | F |
|  CH₃ |  | H | H | H | F | F |
|  CH₃ | 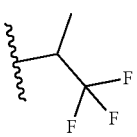 [SMILES: *C(C)C(F)(F)F] | H | H | H | F | F |
|  CH₃ |  | H | H | H | F | F |
|  CH₃ | 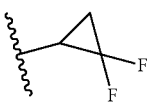 [SMILES: *C1CC1(F)F] | H | H | H | F | F |
|  CH₃ | 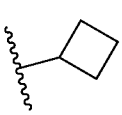 | H | H | H | F | F |
|  CH₃ |  | H | H | H | F | F |
|  |  | H | H | H | F | F |
|  |  | H | H | H | F | F |
|  | 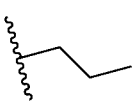 | H | H | H | F | F |

TABLE B-continued

| R¹ | R² | R⁶ | R⁸ | R⁹ | R¹⁰ | R¹¹ |
|---|---|---|---|---|---|---|
| isopropyl | isopropyl | H | H | H | F | F |
|  | azetidinyl | H | H | H | F | F |
|  | 2-methylazetidinyl | H | H | H | F | F |
|  | 1-azaspiro[3.2]hexyl | H | H | H | F | F |
|  | 2-azaspiro[3.3]heptyl | H | H | H | F | F |
|  | 2,4-dimethylazetidinyl | H | H | H | F | F |
|  | pyrrolidinyl | H | H | H | F | F |
|  | 3-azabicyclo[3.1.0]hexyl | H | H | H | F | F |
| H | benzyl | H | H | H | F | F |
| H | 2-methoxybenzyl | H | H | H | F | F |
| H | 3-methoxybenzyl | H | H | H | F | F |
| H | 2-fluorobenzyl | H | H | H | F | F |
| H | 3-fluorobenzyl | H | H | H | F | F |

TABLE B-continued

| R¹ | R² | R⁶ | R⁸ | R⁹ | R¹⁰ | R¹¹ |
|---|---|---|---|---|---|---|
| ⁓―CH₃ | ⁓―CH₃ | ⁓―CH₃ | H | H | F | F |

In some embodiments, the compound of any of formulae (I), (II), (IIa), (IIb), and (IIc) may be selected from compounds P-6 to P-8, P-42 to P-45, P-48, P-49, P-51, P-52, P-55 and P-56, and Table A, or a pharmaceutically acceptable salt, solvate, tautomer, N-oxide, stereoisomer, metabolite, polymorph or prodrug thereof.

In some embodiments, the compound of any of formulae (I), (II), (IIa), (IIb), and (IIc) may be selected from compounds P-6 to P-8, P-42 to P-45, P-48, P-49, P-51, P-52, P-55 and P-56, Table A and Table B, or a pharmaceutically acceptable salt, solvate, tautomer, N-oxide, stereoisomer, metabolite, polymorph or prodrug thereof.

In some embodiments, the compound of any of formulae (I), (II), (IIa), (IIb), and (IIc) may be selected from compounds of Table A and Table B, or a pharmaceutically acceptable salt, solvate, tautomer, N-oxide, stereoisomer, metabolite, polymorph or prodrug thereof.

In some embodiments, the compound of any of formulae (I), (II), (IIa), (IIb), and (IIc) may be selected from A-1 to A-75, or a pharmaceutically acceptable salt, solvate, tautomer, N-oxide, stereoisomer, metabolite, polymorph or prodrug thereof.

In some embodiments, the compound of any of formulae (I), (II), (IIa), (IIb), and (IIc) may be selected from A-1 to A11, A-13, A-17 to A-20, A-24 to A-31, A-33 to A-66, and A-75 or a pharmaceutically acceptable salt, solvate, tautomer, N-oxide, stereoisomer, metabolite, polymorph or prodrug thereof.

In some embodiments, the compound of any of formulae (I), (II), (IIa), (IIb), and (IIc) may be selected from A-1 to A-32, or a pharmaceutically acceptable salt, solvate, tautomer, N-oxide, stereoisomer, metabolite, polymorph or prodrug thereof.

Forms of the Compound

In the case of compounds that are solids, it will be understood by those skilled in the art that the inventive compounds, agents and salts may exist in different crystalline or polymorphic forms, all of which are intended to be within the scope of the present invention and specified formulae.

The invention includes all crystalline forms of a compound of Formula (I) including anhydrous crystalline forms, hydrates, solvates and mixed solvates. If any of these crystalline forms demonstrates polymorphism, all polymorphs are within the scope of this invention.

Formula (I) is intended to cover, where applicable, solvated as well as unsolvated forms of the compounds. Thus, Formula (I) includes compounds having the indicated structures, including the hydrated or solvated forms, as well as the non-hydrated and non-solvated forms.

The compounds of Formula (I) or salts, tautomers, N-oxides, polymorphs or prodrugs thereof may be provided in the form of solvates. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF), acetic acid, and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the invention.

Basic nitrogen-containing groups may be quaternised with such agents as $C_{1-6}$alkyl halide, such as methyl, ethyl, propyl, and butyl chlorides, bromides and iodides; dialkyl sulfates like dimethyl and diethyl sulfate; and others.

Nitrogen containing groups may also be oxidised to form an N-oxide.

The compound of Formula (I) or salts, tautomers, N-oxides, solvates and/or prodrugs thereof that form crystalline solids may demonstrate polymorphism. All polymorphic forms of the compounds, salts, tautomers, N-oxides, solvates and/or prodrugs are within the scope of the invention.

The compound of Formula (I) may demonstrate tautomerism. Tautomers are two interchangeable forms of a molecule that typically exist within an equilibrium. Any tautomers of the compounds of Formula (I) are to be understood as being within the scope of the invention.

The compound of Formula (I) may contain one or more stereocentres. All stereoisomers of the compounds of formula (I) are within the scope of the invention. Stereoisomers include enantiomers, diastereomers, geometric isomers (E and Z olephinic forms and cis and trans substitution patterns) and atropisomers. In some embodiments, the compound is a stereoisomerically enriched form of the compound of formula (I) at any stereocentre. The compound may be enriched in one stereoisomer over another by at least about 60, 70, 80, 90, 95, 98 or 99%.

The compound of Formula (I) or its salts, tautomers, solvates, N-oxides, and/or stereoisomers, may be isotopically enriched with one or more of the isotopes of the atoms present in the compound. For example, the compound may be enriched with one or more of the following minor isotopes: $^2H$, $^3H$, $^{13}C$, $^{14}C$ $^{15}N$, $^{17}O$, and/or $^{18}F$, preferably $^2H$. An isotope may be considered enriched when its abundance is greater than its natural abundance.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

Prodrugs include compounds wherein an amino acid residue, or a polypeptide chain of two or more (eg, two, three or four) amino acid residues which are covalently joined to free amino, and amido groups of compounds of Formula (I). The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of Formula (I) through the carbonyl carbon prodrug sidechain.

Compositions, Formulations and Modes of Administration

The compounds of formula (I) can be administered alone or in the form of a pharmaceutical composition. In practice, the compounds of formula (I) are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, there is provided a pharmaceutical composition comprising a compound of formula (I) or a pharmaceutically acceptable salt, stereoisomer, solvate, metabolite, or polymorph thereof, and at least one pharmaceutically acceptable excipient.

Pharmaceutical compositions of the disclosure typically include a therapeutically effective amount of one or more active ingredients in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial perilymph, possibly supplemented with other materials common in compositions for parenteral administration. Neutral buffered saline or saline mixed with serum albumin are further exemplary vehicles.

Pharmaceutical compositions of the present disclosure additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminium hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as colouring agents, releasing agents, coating agents, sweetening, flavouring and perfuming agents, preservatives and antioxidants can also be present in the composition, according to the judgment of the formulator.

Various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

A compound of formula (I) may be administered in any form and route which makes the compound bioavailable.

Compositions described herein may be administered systemically or directly to the site of condition or disease.

Compositions described herein may be formulated from compounds according to Formula (I) for any appropriate route of administration including, for example, oral, rectal, nasal, vaginal, topical (including transdermal, buccal, ocular and sublingual), parenteral (including subcutaneous, intraperitoneal, intradermal, intravascular (for example, intravenous), intramuscular, spinal, intracranial, intrathecal, intraocular, periocular, intraorbital, intrasynovial and intraperitoneal injection, intracisternal injection as well as any other similar injection or infusion techniques), inhalation, insufflation, infusion or implantation techniques (e.g., as sterile injectable aqueous or non-aqueous solutions or suspensions). In some embodiments, compositions described herein may be administered orally, nasally, intravenously, intramuscularly, topically, subcutaneously, rectally, vaginally or by urethral application.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or *arachis* oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such Formulations may also comprise one or more demulcents, preservatives, flavouring agents and/or colouring agents.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical Formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

A pharmaceutical composition may be formulated as inhaled formulations, including sprays, mists, or aerosols. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable Formulations, wherein the carrier is a liquid, for administration, as for example, a nasal spray or as nasal drops, include aqueous or oily solutions of the active ingredient.

Compositions suitable for rectal administration are preferably presented as unit dose suppositories. These may be prepared by at least partially dispersing the active in one or more lipophilic bases and then shaping the mixture.

Pharmaceutical compositions may be formulated as sustained release formulations such as a capsule that creates a slow release of active following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of active release. The amount of active contained within a sustained release formulation depends upon, for example, the site of implantation, the rate and expected duration of release and the nature of the condition to be treated.

One skilled in the art can readily select the proper form and route of administration depending on the particular characteristics of the compound selected, the disease or condition to be treated, the stage of the disease or condition, and other relevant circumstances.

It will be understood, that the specific dose level for any particular patient will depend upon a variety of factors including the activity of the specific compound employed, the age, body weight, general health, sex, diet, time of administration, route of administration, number of doses, and rate of excretion, drug combination (i.e. other drugs being used to treat the patient), and the severity of the particular disorder undergoing therapy.

The phrase "therapeutically effective amount" generally refers to an amount of one or more active ingredients of the invention that (i) treats the particular disease, condition, or disorder, (ii) attenuates, ameliorates, or eliminates one or more sign or symptoms of the particular disease, condition, or disorder, or (iii) delays the onset of one or more sign or symptoms of the particular disease, condition, or disorder described herein.

Typically, a therapeutically effective dosage is formulated to contain a concentration (by weight) of at least about 0.1% up to about 50% or more, and all combinations and subcombinations of ranges therein. The compositions can be formulated to contain one or more actives described herein in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30%. Exemplary compositions may contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 16, 15, 14, 13, 12, 11 or 10%. The compositions can contain from greater than about 1% for example, about 2%, to less than about 10%, for example about 9 or 8%, including concentrations of greater than about 2%, for example, about 3 or 4%, to less than about 8%, for example, about 7 or 6%. The active agent can, for example, be present in a concentration of about 5%. In all cases, amounts may be adjusted to compensate for differences in amounts of active ingredients actually delivered to the treated cells or tissue.

The frequency of administration may be once daily, 2, 3 or 4 times daily. The treatment period may be for the duration of the detectable disease.

In some embodiments, the pharmaceutical composition comprises a compound according to any one of the herein disclosed embodiments, or a pharmaceutically acceptable salt, solvate, tautomer, N-oxide, stereoisomer, metabolite, polymorph or prodrug thereof, an additional therapeutic agent, and a pharmaceutically acceptable excipient.

The additional agent may be any suitable agent described herein. In some embodiments, the additional agent is a psychoactive drug, including those described herein. In some embodiments, the additional agent is useful for treatment of a disease, disorder or condition by activation of a serotonin receptor, including those described herein. In some embodiments, the additional agent is selected from any one of the following, including those described herein: an agent for a mental illness and/or a neuropsychiatric condition; an agent for psychosis and/or psychotic symptoms; an agent for attention deficit hyperactivity disorder and/or attention deficit disorder; an agent for dementia and/or Alzheimer's disease; and an agent for an addiction disorder.

Applications

The present disclosure provides methods of using the compounds of formula (I) and compositions as described herein. The present disclosure also provides methods of delivering to a subject in need thereof a compound of formula (I) or a composition (e.g., an effective amount of the compound or composition) of the present disclosure.

In another aspect, the present disclosure provides methods of treating a disease in a subject in need thereof comprising administering to the subject in need thereof an effective amount (e.g., therapeutically effective amount) of a compound or composition (e.g., pharmaceutical composition) of the present disclosure.

In another aspect, the present disclosure provides methods of preventing a disease in a subject in need thereof comprising administering to the subject in need thereof an effective amount (e.g., therapeutically effective amount) of a compound of formula (I) or composition (e.g., pharmaceutical composition) of the present disclosure.

In another aspect, provided herein are uses of the compounds of formula (I) or compositions of the present disclosure in the manufacture of a medicament for use in a method (e.g., method of delivering an active agent to a subject in need thereof, method of treating a disease in a subject in need thereof, method of preventing a disease in a subject in need thereof) of the present disclosure.

In another aspect, provided herein are uses of the compounds of formula (I) or compositions of the present disclosure in a method (e.g., method of delivering an active agent to a subject in need thereof, method of treating a disease in a subject in need thereof, method of preventing a disease in a subject in need thereof) of the present disclosure.

In certain embodiments, the effective amount is effective in treating the disease. In certain embodiments, the effective amount is effective in preventing the disease.

In another aspect, the present disclosure provides a method of treating a disease, disorder or condition by activation of a serotonin receptor, the method comprising administering to a subject in need thereof a compound of formula (I) or a pharmaceutical composition as described herein.

In another aspect, the present disclosure provides a method of preventing a disease, disorder or condition by activation of a serotonin receptor, the method comprising administering to a subject in need thereof a compound of formula (I) or a pharmaceutical composition as described herein.

In another aspect, the present disclosure provides method of treating a disease, disorder or condition by activation of a serotonin receptor, the method comprising administering to a subject in need thereof a compound of formula (I) or a pharmaceutical composition as described herein, in combination with another known agent useful for treatment of a disease, disorder or condition by activation of a serotonin receptor. The other known agents useful for treatment of a disease, disorder or condition by activation of a serotonin receptor may be any suitable agents known in the art, including those described herein.

In another aspect, the present disclosure provides method of preventing a disease, disorder or condition by activation of a serotonin receptor, the method comprising administering to a subject in need thereof a compound of formula (I) or a pharmaceutical composition as described herein, in combination with another known agent useful for prevention of a disease, disorder or condition by activation of a serotonin receptor.

In certain embodiments, the serotonin receptor is $5\text{-}HT_{2A}$.

In certain embodiments, the serotonin receptor is one or both of $5\text{-}HT_{2A}$ and $5\text{-}HT_{2C}$. Additionally, or alternatively, in some embodiments, the serotonin receptor is not $5\text{-}HT_{2B}$.

In some embodiments, the compound of formula (I) of the present disclosure is selective towards the $5\text{-}HT_{2A}$ receptor over one or both of the $5\text{-}HT_{2C}$ receptor and the $5\text{-}HT_{2B}$ receptor, preferably over the $5\text{-}HT_{2B}$ receptor. In some embodiments, the compound of formula (I) is selective towards the $5\text{-}HT_{2C}$ receptor over one or both of the $5\text{-}HT_{2A}$ receptor and the $5\text{-}HT_{2B}$ receptor, preferably over the $5\text{-}HT_{2B}$ receptor. In some embodiments, the compound of formula (I) is selective toward the $5\text{-}HT_{2A}$ receptor and $5\text{-}HT_{2C}$ receptor over the $5\text{-}HT_{2B}$ receptor.

In certain embodiments, the serotonin receptor is $5\text{-}HT_{1A}$.

In certain embodiments, the serotonin receptor is one or more of $5\text{-}HT_{1A}$, $5\text{-}HT_{2A}$ and $5\text{-}HT_{2C}$. Additionally, or alternatively, in some embodiments, the serotonin receptor is not $5\text{-}HT_{2B}$.

In some embodiments, the compound of formula (I) of the present disclosure exhibits an $EC_{50}$ value for the $5\text{-}HT_{2A}$ receptor of less than about 1 mM, less than about 100 μM, less than about 10 μM, less than about 1 μM, or less than about 100 nM, or less than about 10 nM, as determined by an assay described herein, for example an assay of calcium flux activity such as measuring changes in intracellular calcium. In some embodiments, the compound of formula (I) exhibits an $EC_{50}$ for the $5\text{-}HT_{2A}$ receptor of less than about 1 mM, less than about 900 μM, less than about 800 μM, less than about 700 μM, less than about 600 μM, less than about 500 μM, less than about 400 μM, less than about 300 μM, less than about 200 μM, less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 9 μM, less than about 8 μM, less than about 7 μM, less than about 6 μM, less than about 5 μM, less than about 4 μM, less than about 3 μM, less than about 2 μM, less than about 1 μM, less than about 900 nM, less than about 800 nM, less than about 700 nM, less than about 600 nM, less than about 500 nM, less than about 400 nM, less than about 300 nM, less than about 200 nM, or less than about 100 nM, or any equivalent unit of measure (e.g., mol/L), as determined by an assay of calcium flux activity.

In some embodiments, the compound of formula (I) of the present disclosure exhibits an $EC_{50}$ value for the $5\text{-}HT_{2C}$ receptor of less than about 1 mM, less than about 100 μM, less than about 10 μM, less than about 1 μM, or less than about 100 nM, or less than about 10 nM, as determined by an assay described herein, for example an assay of calcium flux activity such as measuring changes in intracellular calcium. In some embodiments, the compound of formula (I) exhibits an $EC_{50}$ for the $5\text{-}HT_{2C}$ receptor of less than about 1 mM, less than about 900 μM, less than about 800 μM, less than about 700 μM, less than about 600 μM, less than about 500 μM, less than about 400 μM, less than about 300 μM, less than about 200 μM, less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 9 μM, less than about 8 μM, less than about 7 μM, less than about 6 μM, less than about 5 μM, less than about 4 μM, less than about 3 μM, less than about 2 μM, less than about 1 μM, less than about 900 nM, less than about 800 nM, less than about 700 nM, less than about 600 nM, less than about 500 nM, less than about 400 nM, less than about 300 nM, less than about 200 nM, or less than about 100 nM, or any equivalent unit of measure (e.g., mol/L), as determined by an assay of calcium flux activity.

In some embodiments, the compound of formula (I) of the present disclosure exhibits an $EC_{50}$ value for the $5\text{-}HT_{2B}$ receptor of greater than about 1 μM, greater than about 10 μM, or greater than about 100 μM, as determined by an assay described herein, for example an assay of calcium flux activity such as measuring changes in intracellular calcium.

In some embodiments, the disease, disorder or condition that is treated by activation of a serotonin receptor is a mental illness or a neuropsychiatric condition. Accordingly, the present application also includes a method of treating a mental illness or a neuropsychiatric condition comprising administering to a subject in need thereof a compound of formula (I) or a composition as described herein. The present application also includes a use of a compound of formula (I) of the present disclosure for treatment of a mental illness or a neuropsychiatric condition, as well as a use of a compound of formula (I) of the present disclosure for the preparation of a medicament for treatment of a mental illness or a neuropsychiatric condition. The application further includes a compound of formula (I) of the present disclosure for use in treating a mental illness or a neuropsychiatric condition.

In some embodiments, the disease, disorder or condition that is treated by activation of a serotonin receptor is a mental illness or a neuropsychiatric condition and compound of formula (I) of the present disclosure is administered in combination with one or more additional agents for a mental illness or a neuropsychiatric condition. The one or more additional agents for a mental illness or a neuropsychiatric condition may be any suitable agents known in the art, including those described herein. In some embodiments, the additional agents for a mental illness or a neuropsychiatric condition is selected from antipsychotics, including typical antipsychotics and atypical antipsychotics; antidepressants including selective serotonin reuptake inhibitors (SSRIs) and selective norepinephrine reuptake inhibitors (SNRIs), tricyclic antidepressants and monoamine oxidase inhibitors (MAOIs) (e.g. bupropion); anti-anxiety medication including benzodiazepines such as alprazolam; agents for an addiction disorder such as alcohol addiction (e.g., disulfiram), nicotine dependence (e.g., varenicline) and opioid use disorder (e.g., methadone, buprenorphine, buprenorphine-naloxone and buprenorphine long-acting injection); mood stabilizers such as lithium and anticonvulsants such carbamazepine, divalproex (valproic acid), lamotrigine, gabapentin and topiramate.

In some embodiments, the disease, disorder or condition that is treated by activation of a serotonin receptor is neurodegeneration. Accordingly, the present application also includes a method of treating neurodegeneration comprising administering to a subject in need thereof a compound of formula (I) or a composition as described herein. The present application also includes a use of a compound of formula (I) of the present disclosure for treatment of neurodegeneration, as well as a use of a compound of formula (I) of the present disclosure for the preparation of a medicament for treatment neurodegeneration. The application further includes a compound of formula (I) of the present disclosure for use in treating neurodegeneration. In some embodiments, the disease, disorder or condition that is treated by activation of a serotonin receptor is reduced brain-derived neurotrophic factor (BDNF), mammalian target of rapamycin (mTOR) activation and/or inflammation.

In some embodiments, the disease, disorder or condition that is treated by activation of a serotonin receptor comprises cognitive impairment; ischemia including stroke; neurodegeneration; refractory substance use disorders; sleep disorders; pain, such as social pain, acute pain, cancer pain, chronic pain, breakthrough pain, bone pain, soft tissue pain, nerve pain, referred pain, phantom pain, neuropathic pain, cluster headaches and migraine; obesity and eating disorders; epilepsies and seizure disorders; neuronal cell death; excitotoxic cell death; or a combination thereof.

In some embodiments, the disease, disorder or condition that is treated by activation of a serotonin receptor is psychosis or psychotic symptoms. Accordingly, the present application also includes a method of treating psychosis or psychotic symptoms comprising administering to a subject in need thereof a compound of formula (I) or a composition as described herein. The present application also includes a use of a compound of formula (I) of the present disclosure for treatment of psychosis or psychotic symptoms, as well as a use of a compound of formula (I) of the present disclosure for the preparation of a medicament for treatment of psychosis or psychotic symptoms. The application further includes a compound of formula (I) of the present disclosure for use in treating psychosis or psychotic symptoms.

In some embodiments, the disease, disorder or condition that is treated by activation of a serotonin receptor is psychosis or psychotic symptoms and the compound of formula (I) of the present disclosure is administered in combination with one or more additional agents for psychosis or psychotic symptoms. The one or more additional agents for psychosis or psychotic symptoms may be any suitable agents known in the art, including those described herein. In some embodiments, the additional agents for psychosis or psychotic symptoms are selected typical antipsychotics and atypical antipsychotics. The typical antipsychotics may be selected from acepromazine, acetophenazine, benperidol, bromperidol, butaperazine, carfenazine, chlorproethazine, chlorpromazine, chlorprothixene, clopenthixol, cyamemazine, dixyrazine, droperidol, fluanisone, flupentixol, fluphenazine, fluspirilene, haloperidol, levomepromazine, lenperone, loxapine, mesoridazine, metitepine, molindone, moperone, oxypertine, oxypro- tepine, penfluridol, perazine, periciazine, perphenazine, pimozide, pipamperone, piperacetazine, pipotiazine, prochlorperazine, promazine, prothipendyl, spiperone, sulforidazine, thiopropazate, thioproperazine, thioridazine, thiothixene, timiperone, trifluoperazine, trifluperidol, triflupromazine and zuclopenthixol and combinations thereof. The atypical antipsychotics may be selected from amoxapine, amisulpride, aripiprazole, asenapine, blonanserin, brexpiprazole, cariprazine, carpipramine, clocapramine, clorotepine, clotiapine, clozapine, iloperidone, levosulpiride, lurasidone, melperone, mosapramine, nemonapride, olanzapine, paliperidone, perospirone, quetiapine, remoxipride, reserpine, risperidone, sertindole, sulpiride, sultopride, tiapride, veralipride, ziprasidone and zotepine, and combinations thereof.

In some embodiments, administering to said subject in need thereof a therapeutically effective amount of the compound of formula (I) of the present disclosure does not result in a worsening of psychosis or psychotic symptoms such as, but not limited to, hallucinations and delusions. In some embodiments, administering to said subject in need thereof a therapeutically effective amount of the compound of formula (I) results in an improvement of psychosis or psychotic symptoms such as, but not limited to, hallucinations and delusions. In some embodiments, administering to said subject in need thereof a therapeutically effective amount of the compounds of formula (I) results in an improvement of psychosis or psychotic symptoms.

In some embodiments, the disease, disorder or condition that is treated by activation of a serotonin receptor is a central nervous system (CNS) disease, disorder or condition and/or a neurological disease, disorder or condition. Accordingly, the present application also includes a method of treating a CNS disease, disorder or condition and/or a neurological disease, disorder or condition comprising administering a therapeutically effective amount of compound of formula (I) or a composition of the present disclosure to a subject in need thereof. The present application also includes a use of compound of formula (I) of the present disclosure for treatment a CNS disease, disorder or condition and/or a neurological disease, disorder or condition, as well as a use of compound of formula (I) of the present disclosure for the preparation of a medicament for treatment of a CNS disease, disorder or condition and/or a neurological disease, disorder or condition. The application further includes a compound of formula (I) of the present disclosure of the application for use in treating a CNS disease, disorder or condition and/or a neurological disease, disorder or condition.

In some embodiments, the disease, disorder or condition that is treated by activation of a serotonin receptor is a central nervous system (CNS) disease, disorder or condition and/or a neurological disease, disorder or condition and the compound of formula (I) of the present disclosure is administered in combination with one or more additional agents for a central nervous system (CNS) disease, disorder or condition and/or a neurological disease, disorder or condition. The one or more additional agents for a central nervous system (CNS) disease, disorder or condition and/or a neurological disease, disorder or condition may be any suitable agents known in the art, including those described herein. In some embodiments, the additional agents for a central nervous system (CNS) disease, disorder or condition and/or a neurological disease, disorder or condition are selected from lithium, olanzapine, quetiapine, risperidone, aripiprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Non limiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline.

In some embodiments, the disease, disorder or condition that is treated by activation of a serotonin receptor is selected from attention deficit hyperactivity disorder and attention deficit disorder and a combination thereof. Accordingly, the present application also includes a method of treating attention deficit hyperactivity disorder and/or attention deficit disorder comprising administering to a subject in need thereof a compound of formula (I) or a composition as described herein. The present application also includes a use of a compound of formula (I) of the present disclosure for treatment of attention deficit hyperactivity disorder and/or attention deficit disorder, as well as a use of a compound of formula (I) of the present disclosure for the preparation of a medicament for treatment of attention deficit hyperactivity disorder and/or attention deficit disorder. The application further includes a compound of formula (I) of the present disclosure for use in treating attention deficit hyperactivity disorder and/or attention deficit disorder.

In some embodiments, the disease, disorder or condition that is treated by activation of a serotonin receptor is attention deficit hyperactivity disorder and/or attention deficit disorder and a combination thereof and the compound of formula (I) of the present disclosure is administered in combination with one or more additional agents for attention deficit hyperactivity disorder and/or attention deficit disorder and a combination thereof. The one or more additional agents for attention deficit hyperactivity disorder and/or attention deficit disorder may be any suitable agents known in the art, including those described herein. In some embodiments, the additional agents for attention deficit hyperactivity disorder and/or attention deficit disorder and a combination thereof are selected from methylphenidate, dexamphetamine, lisdexamfetine, atomoxetine and amphetamine and a combination thereof.

In some embodiments, the disease, disorder or condition that is treated by activation of a serotonin receptor is selected from dementia and Alzheimer's disease and a combination thereof. Accordingly, the present application also includes a method of treating dementia and/or Alzheimer's disease comprising administering to a subject in need thereof a compound of formula (I) or a composition as described herein. The present application also includes a use of a compound of formula (I) of the present disclosure for treatment of dementia and/or Alzheimer's disease, as well as a use of a compound of formula (I) of the present disclosure for the preparation of a medicament for treatment of dementia and/or Alzheimer's disease. The application further includes a compound of formula (I) of the present disclosure for use in treating dementia and/or Alzheimer's disease.

In some embodiments, the disease, disorder or condition that is treated by activation of a serotonin receptor is dementia or Alzheimer's disease and the compound of formula (I) of the present disclosure is administered in combination with one or more additional agents for dementia or Alzheimer's disease. The one or more additional agents for dementia or Alzheimer's disease may be any suitable agents known in the art, including those described herein. In some embodiments, the additional agents for dementia and Alzheimer's disease are selected from acetylcholinesterase inhibitors, NMDA antagonists and nicotinic agonists. The acetylcholinesterase inhibitors may be selected from donepezil, galantamine, rivastigmine, and phenserine, and combinations thereof. The NMDA antagonists may be selected from MK-801, ketamine, phencyclidine, and memantine, and combinations thereof. The nicotinic agonists may be selected from nicotine, nicotinic acid, nicotinic alpha7 agonists, or alpha2 beta4 agonists or a combination thereof.

In another aspect, the present disclosure provides a method of treating a mental illness, the method comprising administering to a subject in need thereof a compound of formula (I) or a pharmaceutical composition as described herein. In another aspect, the present disclosure provides a method of preventing a mental illness, the method comprising administering to a subject in need thereof a compound of formula (I) or a pharmaceutical composition as described herein. The mental illness may be a neuropsychiatric condition.

In certain embodiments, the mental illness is selected from anxiety disorders such as generalized anxiety disorder, panic disorder, social anxiety disorder and specific phobias; depression such as, hopelessness, loss of pleasure, fatigue and suicidal thoughts; mood disorders, such as depression, bipolar disorder, cancer-related depression, anxiety and cyclothymic disorder; psychotic disorders, such as hallucinations, delusions, mania, schizophrenia, schizoaffective disorder, schizophreniform Disorder; impulse control and addiction disorders, such as pyromania (starting fires), kleptomania (stealing) and compulsive gambling; alcohol addiction; drug addiction, such as opioid addiction/dependence, nicotine dependence, cocaine dependence, marijuana abuse and so on; smoking cessation; personality disorders, such as antisocial personality disorder, aggression, obsessive-compulsive personality disorder and paranoid personality disorder; obsessive-compulsive disorder (OCD), such as thoughts or fears that cause a subject to perform certain rituals or routines; post-traumatic stress disorder (PTSD); stress response syndromes (formerly called adjustment disorders); dissociative disorders, formerly called multiple personality disorder, or "split personality," and depersonalization disorder; factitious disorders; sexual and gender disorders, such as sexual dysfunction, gender identity disorder and the paraphilias; somatic symptom disorders, formerly known as a psychosomatic disorder or somatoform disorder.

In certain embodiments, the mental illness is selected from hallucinations and delusions and a combination thereof. In these embodiments, the hallucinations may be selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations and chronoceptive hallucinations, and a combination thereof.

In another aspect, the present disclosure provides a method for treating a central nervous system (CNS) disease, disorder or condition and/or a neurological disease, disorder or condition, the method comprising administering to a subject in need thereof a compound of formula (I) or a pharmaceutical composition as described herein.

In another aspect, the present disclosure provides a method for preventing a central nervous system (CNS) disease, disorder or condition and/or a neurological disease, disorder or condition, the method comprising administering to a subject in need thereof a compound of formula (I) or a pharmaceutical composition as described herein.

In some embodiments, the CNS disease, disorder or condition and/or neurological disease, disorder or condition is selected from neurological diseases including neurodevelopmental diseases and neurodegenerative diseases such as Alzheimer's disease; presenile dementia; senile dementia; vascular dementia; Lewy body dementia; cognitive impairment, Parkinson's disease and Parkinsonian related disorders such as Parkinson dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neuro-otological and eye movement disorders; neurodegenerative diseases of the retina amyotrophic lateral sclerosis; tardive dyskinesias; hyperkinetic disorders; attention deficit hyperactivity disorder and attention deficit disorders; restless leg syndrome; Tourette's syndrome; Tic disorder; schizophrenia; autism spectrum disorders; tuberous sclerosis; Rett syndrome; cerebral palsy; disorders of the reward system including eating disorders such as anorexia nervosa and bulimia nervosa; binge eating disorder, trichotillomania, dermotillomania, nail biting; migraine; fibromyalgia; and peripheral neuropathy of any etiology, and combinations thereof.

In another aspect, the present disclosure provides a method for increasing neuronal plasticity, the method comprising contacting a neuronal cell with a compound of formula (I) or a pharmaceutical composition as described herein, in an amount sufficient to increase neuronal plasticity of the neuronal cell. "Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In another aspect the present disclosure provides methods of treating weight, comprising administering an effective amount of a compound of the invention to a subject in need thereof. Treatment of weight may include treating weight gain; weight loss; metabolic disorder; weight gain associated with pharmaceutical intervention; weight gain associated with a mental illness (including those described herein); eating disorders such as anorexia, bulimia, cachexia, etc.; eating behaviour; obesity; diabetes; insulin resistance; pre-diabetes; glucose intolerance; hyperlipidemia; and cardiovascular disease.

In another aspect, the present disclosure provides a method for increasing dendritic spine density, the method comprising contacting a neuronal cell with a compound of formula (I) or a pharmaceutical composition as described herein, in an amount sufficient to increase dendritic spine density of the neuronal cell.

In certain embodiments, the compound of formula (I) produces a maximum number of dendritic crossings with an increase of greater than 1.0 fold by a Sholl Analysis.

In another aspect the present disclosure provides a method for activating a serotonin receptor in a cell, either in a biological sample or in a patient, comprising administering a compound of formula (I) as defined in any one of the herein disclosed embodiments to the cell. The serotonin receptor may be a 5-HT receptor subtype, preferably one or both of 5-HT$_{2A}$ and 5-HT$_{2C}$.

In some embodiments, effective amounts vary according to factors such as the disease state, age, sex and/or weight of the subject or species. In some embodiments, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated and the like, but can nevertheless be routinely determined by one skilled in the art.

In some embodiments, the compounds of formula (I) of the present disclosure are administered one, two, three or four times a year. In some embodiments, the compounds of the present disclosure are administered at least once a week. However, in another embodiment, the compounds are administered to the subject from about one time per two weeks, three weeks or one month. In another embodiment, the compounds are administered about one time per week to about once daily. In another embodiment, the compounds are administered 1, 2, 3, 4, 5 or 6 times daily. The length of the treatment period depends on a variety of factors, such as the severity of the disease, disorder or condition, the age of the subject, the concentration and/or the activity of the compounds of the application and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

In some embodiments, the compounds of the application are administered at doses that are hallucinogenic or psychotomimetic and taken in conjunction with psychotherapy or therapy and may occur once, twice, three, or four times a year. However, in some embodiments, the compounds are administered to the subject once daily, once every two days, once every 3 days, once a week, once every two weeks, once a month, once every two months, or once every three months at doses that are not hallucinogenic or psychotomimetic.

A compound of formula (I) of the present disclosure may be either used alone or in combination with other known agents useful for treating diseases, disorders or conditions by activation of a serotonin receptor, such as the compounds of the present disclosure. When used in combination with other known agents useful in treating diseases, disorders by activation of a serotonin receptor, it is an embodiment that a compound of formula (I) is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In some embodiments, a compound of formula (I) of the present disclosure is administered with another therapeutic agent simultaneously or sequentially in separate unit dosage forms or together in a single unit dosage form. Accordingly, the present application provides a single unit dosage form comprising one or more compounds of formula (I) as described herein, an additional therapeutic agent and a pharmaceutically acceptable carrier.

In some embodiments, the compounds of the application are used or administered in an effective amount which comprises administration of doses or dosage regimens that are devoid of clinically meaningful psychedelic/psychotomimetic actions. In some embodiments, the compounds of the application are used or administered in an effective amount which comprises administration of doses or dosage regimens that provide clinical effects similar to those exhibited by a human plasma psilocin Cmax of 4 ng/mL or less and/or human $5\text{-}HT_{2A}$ human CNS receptor occupancy of 40% or less or those exhibited by a human plasma psilocin Cmax of 1 ng/mL or less and/or human $5\text{-}HT_{2A}$ human CNS receptor occupancy of 30% or less. In some embodiments, the compounds of the application are used or administered in an effective amount which comprises administration of doses or dosage regimens that provide clinical effects similar to those exhibited by a human plasma psilocin Tmax in excess of 60 minutes, in excess of 120 minutes or in excess of 180 minutes.

Kit

In another embodiment there is provided a kit or article of manufacture including one or more compounds, pharmaceutically acceptable salt, stereoisomer, solvate, metabolite, or polymorph, and/or pharmaceutical compositions as described above.

In other embodiments there is provided a kit for use in a therapeutic application mentioned above, the kit including:
 a container holding one or more compounds, pharmaceutically acceptable salt, stereoisomer, solvate, metabolite, or polymorph and/or pharmaceutical compositions as described herein;
 a label or package insert with instructions for use.

It will be understood that the invention disclosed and defined in this specification extends to all alternative combinations of two or more of the individual features mentioned or evident from the text or drawings. All of these different combinations constitute various alternative aspects of the invention.

EXAMPLES

General

In the examples below, unless otherwise stated, temperatures are given in degrees Celsius (° C.); operations were carried out at room or ambient temperature, "rt," or "RT," (typically a range of from about 18-25° C.; evaporation of solvent was carried out using a rotary evaporator under reduced pressure (typically, 4.5-30 mm Hg) with a bath temperature of up to 60° C.; the course of reactions was typically followed by thin layer chromatography (TLC); melting points are uncorrected; products exhibited satisfactory $^{1}H$ NMR and/or microanalytical data; and the following conventional abbreviations are also used: L (litres), mL (millilitres), mmol (millimoles), g (grams), mg (milligrams), m (minutes), and h (hours).

Unless otherwise specified, all solvents and reagents were purchased from suppliers and used without further purification. Reactions were conducted under a blanket of nitrogen unless otherwise stated. Compounds were visualized under UV lamp (254 nm). $^{1}H$ NMR spectra were recorded on a 300 MHz, 400 MHz, or 600 MHz NMR instrument as indicated. Column and flash chromatography was performed using $SiO_2$ as the stationary phase and "MeOH/$NH_3$" refers to a 9 (1 solution of methanol to 15 M aqueous ammonia. LCMS was carried out under the following conditions.

| Condition | Instrument | Column | Mobile Phase (A/B) | Time Program |
|---|---|---|---|---|
| A | Shimadzu LC-20AD XR, 8030 triple quadrupole mass spectrometer | Waters XSelect C18 (3.5 μm, 1.6 × 150 mm) [25° C.] | 0.1% FA in $H_2O$/0.1% FA in MeCN | 5-100% B over 7 minutes (1 mL/min) |
| B | Agilent 1260 HPLC, 6120 single quadrupole mass spectrometer | Phenomenex Kinetex C18 (5 μm, 2.1 × 50 mm) [40° C.] | 0.4% TFA in $H_2O$/0.2% TFA in MeCN | 5-95% B over 3 minutes (1 mL/min) |
| C | Waters AQUITY UPLC with QDa mass spectrometer | Waters XBridge BEH C18 (2.5 μm, 2.1 × 50 mm) [35° C.] | 2 mM NH4OAc in 0.1% FA in $H_2O$/0.1% FA in MeCN | 5-100% B over 2.1 minutes (0.55 mL/min) |
| D | Agilent 1260 HPLC, 6125B single quadrupole mass spectrometer | Phenomenex Luna C18 (5 μm, 2.0 × 50 mm) [40° C.] | 0.4% TFA in $H_2O$/0.2% TFA in MeCN | 5-95% B over 3 minutes (1 mL/min) |

Appropriately substituted 1H-indazole building blocks can be synthesised following the steps outlined in schemes 1-6 or similar as one in the art may consider.

Scheme 1: Appropriately substituted 1H-indazole building blocks can be synthesised via a one-pot condensation and annulation reaction of an appropriately substituted 2-fluoro or 2-bromo benzaldehyde with hydrazine.

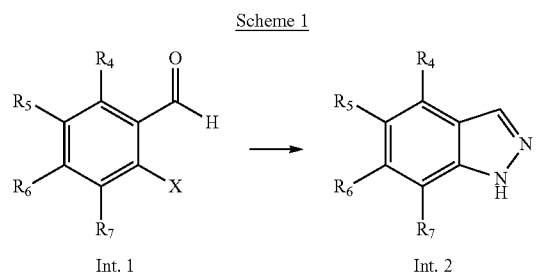

Scheme 2: Alternatively, substituted 1H-indazoles can be synthesised by condensation of an appropriately substituted 2-bromo benzaldehyde with 4-methylbenzenesulfonohydrazide (Int. 4) followed by copper catalysed annulation to yield Int. 5. Detosylsation allows access to 1H-indazole building blocks for further derivatisation.

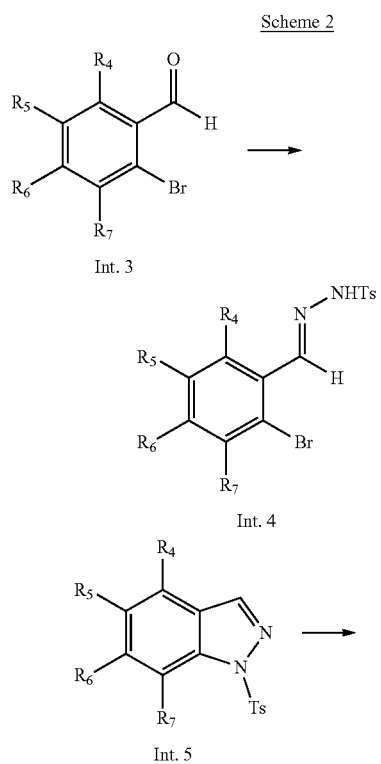

Scheme 3: Access to 1H-indazoles can also be achieved by reaction of appropriately substituted 2-fluorobenzonitrile compounds (Int. 6) with hydrazine to produce Int. 7. Subsequent diazotisation and nucleophilic substitution with an iodide source allows access to Int. 8 which can be further derivatised to compounds of general formula (I).

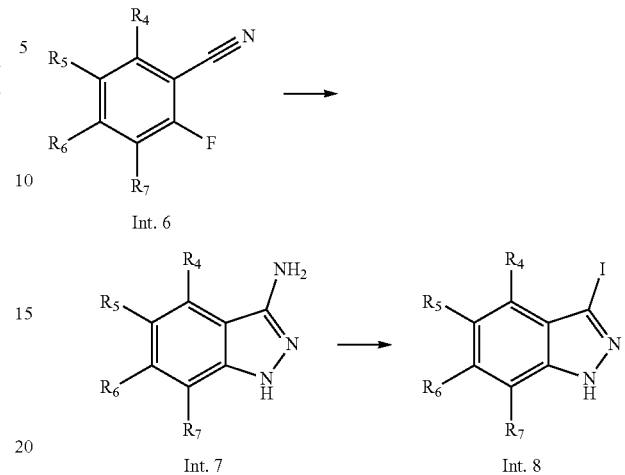

Scheme 4: Nucleophilic aromatic substitution of an appropriately substituted 2-bromo-6-fluorobenzaldehyde (Int. 9) or 2,6-difluorobenzonitrile (Int. 11) with MeOH under basic conditions allows access to Int. 10 and Int. 12 which can be further derivatised to 4-methoxy-1H-indazole compounds. Alternatively, substituted 4-fluoro-1H-indazoles (Int. 13) with a protecting group at the one position can also undergo nucleophilic aromatic substitution with MeOH under basic conditions to yield Int. 14 which can be further derivatised to compounds of general formula (I).

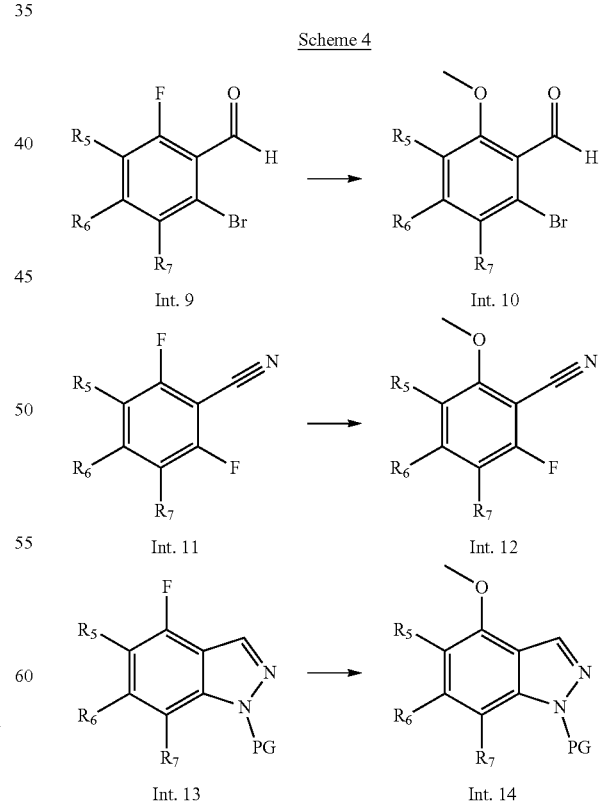

Scheme 5: Compounds of general formula (I) can be accessed by the synthetic steps outlined in scheme 4 or similar as one skilled in the art may consider. Electrophilic halogenation at the three position of an appropriately substituted 1H-indazole (Int. 2) allows access to Int. 15, which can then undergo palladium catalysed cross coupling with 4,4,5,5-tetramethyl-2-vinyl-1,3,2-dioxaborolane to access Int. 12. Installation of an appropriate N-protecting group such as tetrahydro-2H-pyran (THP) or (trimethylsilyl) ethoxymethyl (SEM) permits alkene hydroboration to access Int. 18. The alcohol functional group can be converted to the mesylate (Int. 19) which can then be reacted with a desired amine under basic conditions to access Int. 21. Alternatively, the alcohol can be oxidised to the aldehyde (Int. 20) which can undergo reductive amination with a desired amine and appropriate reducing agent to access Int. 21. Deprotection of Int. 21 allows access to compounds of general formula (I).

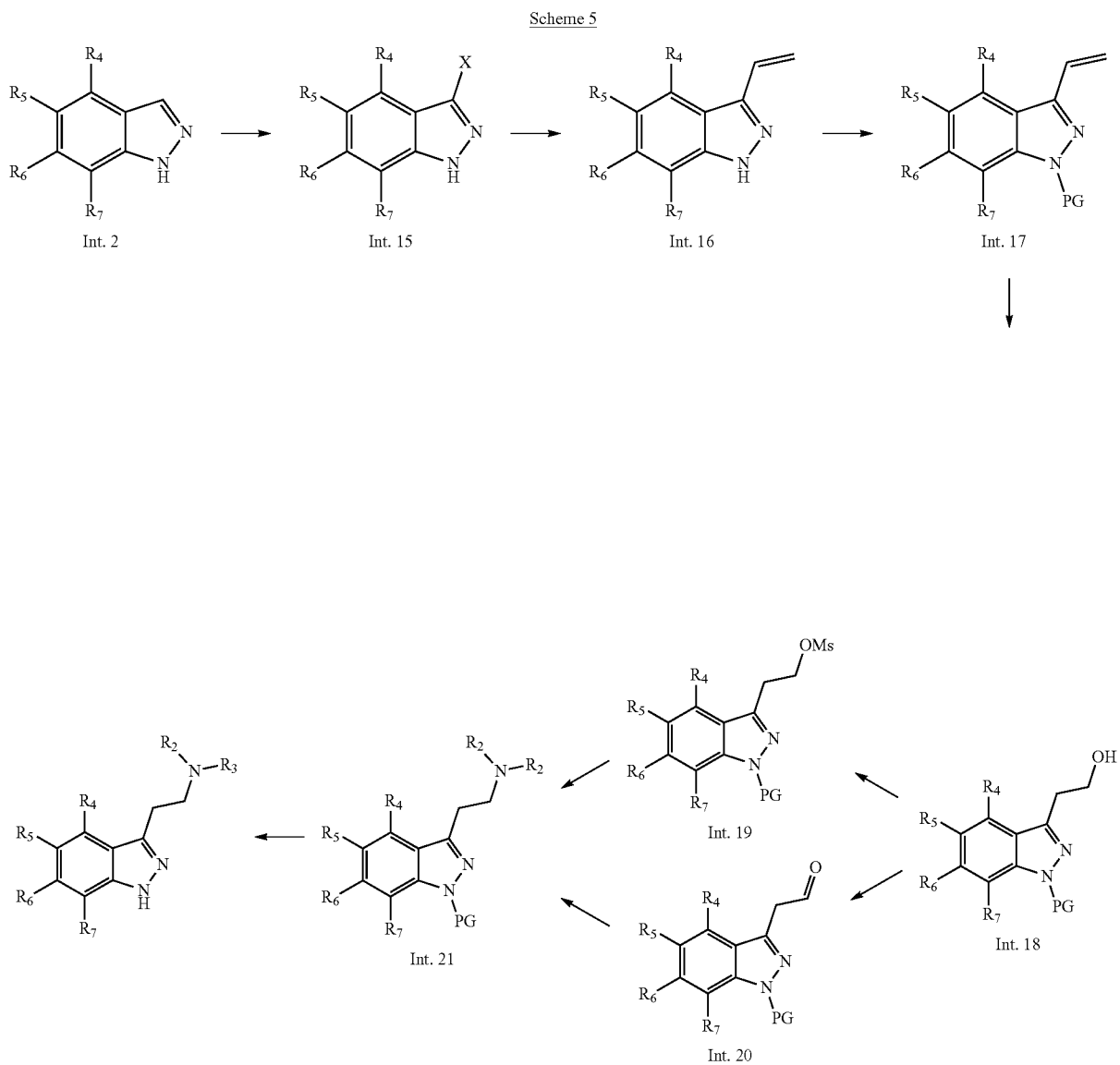

Scheme 5

Scheme 6: Compounds of general formula (I) can be synthesised following the steps outlined in scheme 6 or similar as one skilled in the art may consider. Reaction of an appropriately substituted 1H-indole (Int. 22) with NaNO₂ and HCl allows access to Int. 23 which can undergo a Henry reaction to yield Int. 24. Reduction to the primary amine (Int. 25) permits sequential reductive alkylations to furnish compounds of general formula (I).

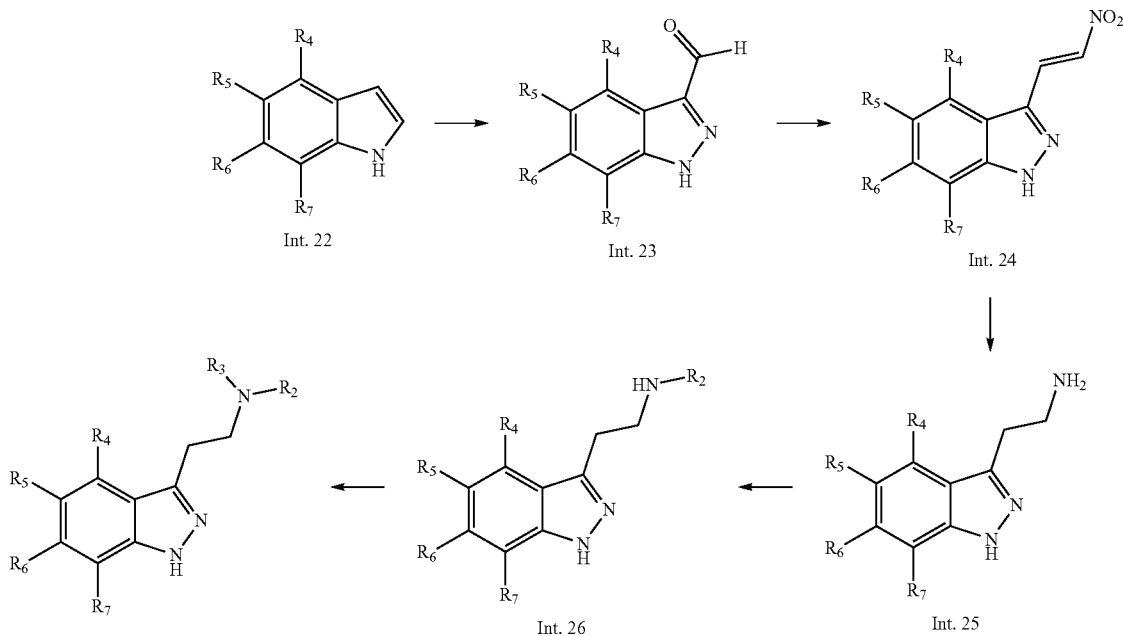

Scheme 6

General Procedure A: Synthesis of OMs Intermediates

To a solution of substituted 2-(1-SEM)-1H-indazol-3-yl)ethan-1-ol or 2-(1-THP)-1H-indazol-3-yl)ethan-1-ol in CH₂Cl₂ (10 mL per 1.0 g) at 0° C. was added Et₃N (1.2-17 eq.) followed by methanesulfonyl chloride (1.2-10 eq.) and the mixture was stirred at RT until TLC indicated complete consumption of starting material. The reaction was poured into cold H₂O or saturated aq. NaHCO₃ and extracted with CH₂Cl₂. The organic extracts were washed with brine, dried over MgSO₄ or Na₂SO₄, filtered, and the filtrate concentrated under reduced pressure. The product was purified by column chromatography or used in the next reaction without further purification.

General Procedure B: Nucleophilic Amination of OMs Intermediates

To a solution of substituted 2-(1-SEM)-1H-indazol-3-yl)ethyl methanesulfonate or 2-(1-THP)-1H-indazol-3-yl)ethyl methanesulfonate in MeCN or DMF (10-30 mL per 1.0 g) was added K₂CO₃ (10 eq.) and amine (5-10 eq.) and the mixture was stirred at 80° C. until TLC indicated complete consumption of starting material. The reaction mixture was diluted with H₂O (10-20 V) and extracted with EtOAc or CH₂Cl₂. The organic extracts were washed with brine, dried over MgSO₄ or Na₂SO₄, filtered, and the filtrate concentrated under reduced pressure. The product was purified by column chromatography or used in the next reaction without further purification.

General Procedure C: 2-(Trimethylsilyl)Ethoxymethyl (SEM) Protecting Group Removal Starting N-(2-(trimethylsilyl)ethoxymethyl) protected indazole was dissolved in CH₂Cl₂ (1 mL per 0.1 mmol), cooled in an ice-bath, and treated dropwise with 4 M HCl in 1,4-dioxane (1.5 mL per 0.1 mmol). The reaction was then stirred at RT until TLC indicated consumption of the starting material. The reaction was then quenched with ten times the reaction volume with 4 M aq. NaOH before being extracted with CH₂Cl₂ three times. The combined organic layer was dried over anhydrous Na₂SO₄, filtered, and the filtrate concentrated. The residue was purified by reverse phase column chromatography to afford the product compound.

General Procedure D: Tetrahydro-2H-Pyran Protecting Group Removal

Starting N-(tetrahydro-2H-pyran-2-yl) indazole was dissolved in MeOH (1 mL per 100 mg), cooled in an ice-bath, and treated dropwise with 6 M aq. HCl (1 mL per 100 mg). The reaction was then stirred at RT until TLC indicated consumption of the starting material. The reaction was diluted with twice the reaction volume with H₂O and then washed with CH₂Cl₂ three times. The CH₂Cl₂ layers were discarded and the aqueous layer was neutralised with saturated aq. Na₂CO₃ before the pH was adjusted to 12-13 with 15% aq. NaOH. The aqueous layer was then extracted with iPrOH:CHCl₃ (1:3) three times and the combined organic layer was dried over anhydrous Na₂SO₄, filtered, and the filtrate concentrated. The residue was purified by flash chromatography (1% to 10% MeOH/NH₃ in CH₂Cl₂) to afford the product compound.

General Procedure E: Formulation of Hydrochloride Salts from Amines

Starting freebase amine was dissolved in a minimal amount of solvent (MeOH, iPrOH or mixture thereof) and acidified to pH 1 by dropwise addition of concentrated HCl (37%). Precipitation was initiated by addition of $Et_2O$ and the mixture was left to stand at 0° C. The product was collected by vacuum filtration and washed with $Et_2O$.

General Procedure F: Formulation of Fumaric Acid and Maleic Acid Salts from Amines A solution of freebase amine in a minimal amount of solvent (acetone or iPrOH) was added to a hot solution of fumaric acid or maleic acid in either acetone or iPrOH (1-3 eq., 0.02-0.2 M) and the mixture was heated to between 40-60° C. The mixture was cooled and precipitation was initiated by addition of $Et_2O$ or hexane and then left to stand at 0° C. The product was collected by vacuum filtration and washed with $Et_2O$.

Scheme 10: Compounds of general formula (I) can be synthesised from the appropriately substituted indazole following the outlined sequence of steps in Scheme 10 or similar as one skilled in the art may consider. Addition of SEM protecting group to indazole starting material 17 allows access to intermediate 77 which can be formylated at the 3 position with n-BuLi and DMF to provide intermediate 78. Reaction of intermediate 78 with nitromethane allows access to nitrostyrene intermediate 79 which can be subsequently deprotected at the 1 position with TFA providing intermediate 80. Chemoselective reduction of intermediate 80 with $LiAlH_4$ allows access to intermediate 81. Reductive alkylation and subsequent demethylation provides compounds of general formula (I) (exemplified by P-55 and P-56). One skilled in the art will recognise that utilising different aldehydes during the reductive alkylation step would allow access to alternative compounds of general formula (I) disclosed herein.

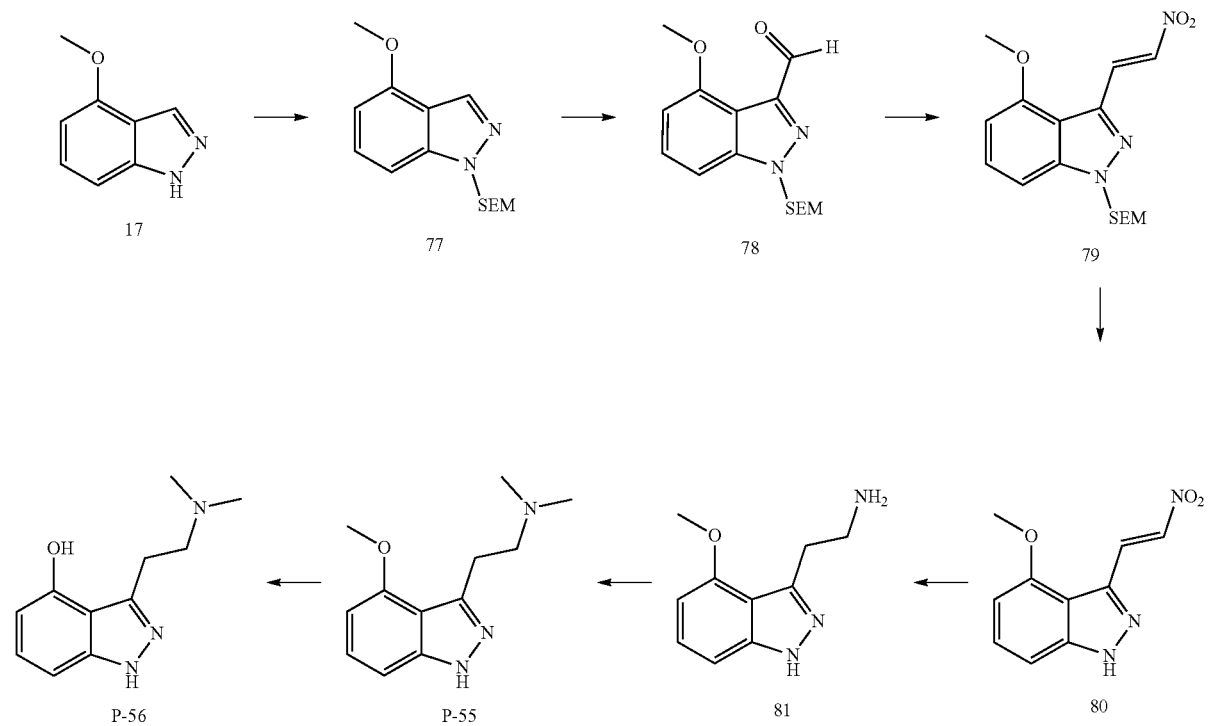

Example 1: Synthesis of 2-(5-fluoro-4-methoxy-1H-indazol-3-yl)-N,N-dimethylethan-1-amine (A1)

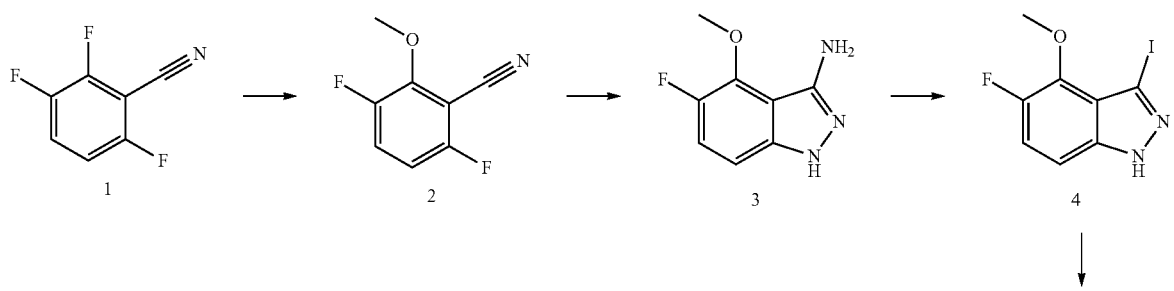

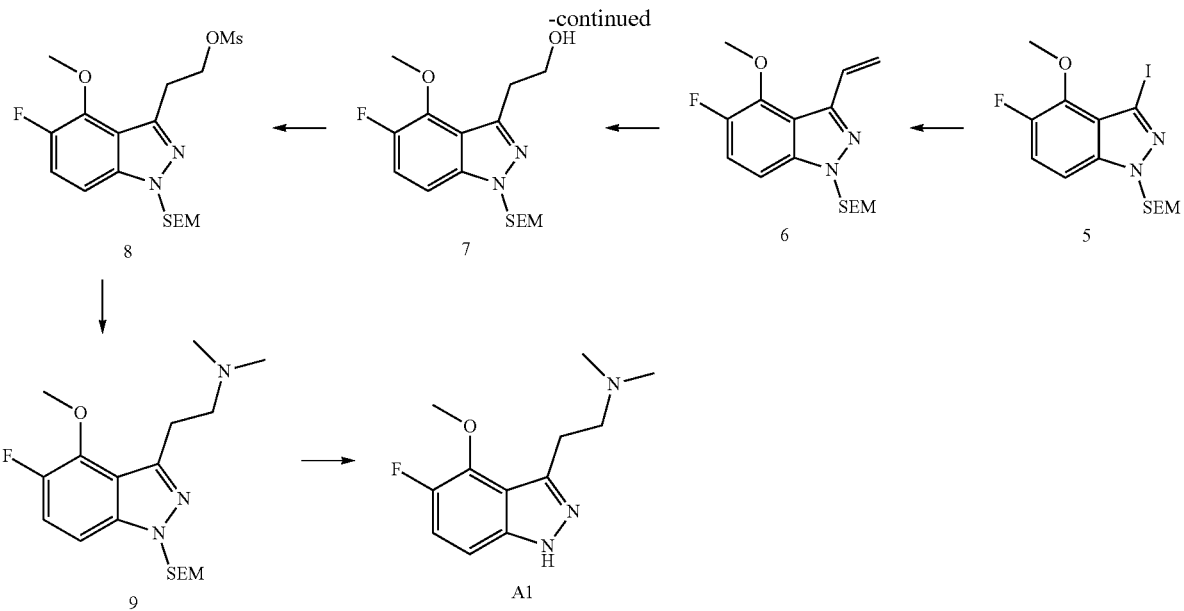

Step 1: 3,6-difluoro-2-methoxybenzonitrile (2)

To an ice-cold solution of 2,3,6-trifluorobenzonitrile (50 g, 318 mmol) in MeOH (350 mL), was added NaOMe (30% w/w, 60.1 g, 333 mmol) at a rate that maintained the internal temperature below 5° C. The reaction mixture was then stirred at RT for 16 h. The reaction was filtered, and the filtrate was concentrated in vacuo. The residue was purified by column chromatography (1% to 9% EtOAc in petroleum ether) to afford the title compound as white solid (45.0 g, 84%). $^1$H NMR (400 MHz, CDCl$_3$): δ 7.30-7.26 (m, 1H), 6.83-6.81 (m, 1H), 4.19 (d, J=3.6 Hz, 3H).

Step 2: 5-fluoro-4-methoxy-1H-indazol-3-amine (3)

To a solution of 3,6-difluoro-2-methoxybenzonitrile (35 g, 207 mmol) in EtOH (245 mL) was added dropwise NH$_2$NH$_2$·H$_2$O (41.4 g, 827 mmol) and the reaction was stirred at 70° C. for 6 h. At which point the mixture was concentrated in vacuo and the residue was partitioned between EtOAc (30 mL) and H$_2$O (50 mL). The layers were separated and the aqueous layer was further extracted with EtOAc (3×50 mL). The combined organic layer was dried over anhydrous Na$_2$SO$_4$ and concentrated in vacuo. The residue was purified by column chromatography (3% EtOAc in Petroleum ether to 100% EtOAc) to afford the title compound as a purple solid (10 g, 27%). $^1$H NMR (400 MHz, MeOD-d$_4$): δ 7.13-7.07 (m, 1H), 6.88-6.85 (m, 1H), 4.11 (d, J=3.2 Hz, 3H).

Step 3: 5-fluoro-3-iodo-4-methoxy-1H-indazole (4)

To an ice-cold solution of 5-fluoro-4-methoxy-1H-indazol-3-amine (7.0 g, 38.6 mmol) in 6 M aq. H$_2$SO$_4$ (70 mL) was added NaNO$_2$ (3.2 g, 46.3 mmol) at a rate that maintained the temperature below 5° C. The reaction was then stirred at 0° C. for 1 h, before being added slowly to mixture of KI (64.1 g, 386 mmol) and CuI (7.36 g, 38.6 mmol) in H$_2$O (100 mL). The resulting mixture was stirred at 50° C. for 16 h. The mixture was then poured into an aqueous solution of Na$_2$SO$_3$ (50 mL), then extracted with EtOAc (3×20 mL). The combined organic layer was dried over anhydrous Na$_2$SO$_4$ and concentrated in vacuo. The residue was purified by column chromatography (3% to 15% EtOAc in petroleum ether) to afford the title compound as an off-white solid (3.10 g, 27%). $^1$H NMR (400 MHz, CDCl$_3$): δ 7.25-7.20 (m, 1H), 7.16-7.14 (m, 1H), 4.14 (d, J=2.4 Hz, 3H).

Step 4: 5-fluoro-3-iodo-4-methoxy-1-((2-(trimethylsilyl)ethoxy)methyl)-1H-indazole (5)

To an ice-cold solution of 5-fluoro-3-iodo-4-methoxy-1H-indazole (3.1 g, 10.6 mmol) in THF (30 mL) was added NaH (60% w/w dispersion in mineral oil, 509 mg, 12.7 mmol) under nitrogen atmosphere. The reaction was stirred at 0° C. for 30 min and then 2-(trimethylsilyl)ethoxymethyl chloride (2.12 g, 12.7 mmol) was added and the reaction was stirred at RT for 2 h. The reaction mixture was poured into an aqueous solution of NH$_4$Cl (30 mL) and then extracted with EtOAc (3×10 mL). The combined organic layer was dried over anhydrous Na$_2$SO$_4$ and concentrated in vacuo. The residue was purified by column chromatography (1% to 2% EtOAc in petroleum ether) to afford the title compound as a yellow oil (3.80 g, 85%). $^1$H NMR (400 MHz, CDCl$_3$): δ 7.26-7.24 (m, 1H), 7.21-7.17 (m, 1H), 5.66 (s, 2H), 4.13 (d, J=2.4 Hz, 3H), 3.58-3.53 (m, 2H), 0.90-0.86 (m, 2H), 0.05 (s, 9H).

Step 5: 5-fluoro-4-methoxy-1-((2-(trimethylsilyl)ethoxy)methyl)-3-vinyl-1H-indazole (6)

A solution of 5-fluoro-3-iodo-4-methoxy-1-((2-(trimethylsilyl)ethoxy)methyl)-1H-indazole (3.8 g, 9.0 mmol), 4,4,5,5-tetramethyl-2-vinyl-1,3,2-dioxaborolane (1.39 g, 9.0 mmol), and K$_2$CO$_3$ (3.73 g, 27.0 mmol) in THF (30 mL) and H$_2$O (6 mL) was sparged with nitrogen gas for 5 min before Pd(dppf)Cl$_2$ (329 mg, 0.45 mmol) was added under nitrogen atmosphere. The mixture was stirred at 90° C. for 16 h under nitrogen atmosphere and then the cooled reaction mixture was concentrated in vacuo. The residue was partitioned between EtOAc (10 mL) and H$_2$O (20 mL) and the layers were separated. The aqueous layer was further extracted with EtOAc (3×10 mL) and the combined organics were washed with brine (20 mL), dried over anhydrous $Na_2SO_4$ and concentrated in vacuo. The residue was purified by column chromatography (1% to 2% EtOAc in petroleum ether) to afford the title compound as a yellow oil (2.30 g, 79%). $^1$H NMR (400 MHz, $CDCl_3$): δ 7.29-7.23 (m, 2H), 7.21-7.15 (m, 1H), 6.28-6.23 (m, 1H), 5.69 (s, 2H), 5.47-5.44 (m, 1H), 4.13 (d, J=2.8 Hz, 3H), 3.62-3.57 (m, 2H), 0.94-0.90 (m, 2H), 0.03 (s, 9H).

Step 6: 2-(5-fluoro-4-methoxy-1-((2-(trimethylsilyl)ethoxy)methyl)-1H-indazol-3-yl)ethan-1-ol (7)

To an ice-cold solution of 5-fluoro-4-methoxy-1-((2-(trimethylsilyl)ethoxy)methyl)-3-vinyl-1H-indazole (2.3 g, 7.13 mmol) in THF (23 mL) was added 9-borabicyclo[3.3.1]nonane (0.5 M in THF, 85.6 mL, 42.8 mmol) and the reaction was then stirred at RT for 2 h. The reaction was cooled in an ice bath and treated dropwise with $H_2O_2$ (30% w/w in $H_2O$, 4.4 mL, 42.8 mmol) and 4 M aq. NaOH (14.3 mL) before being stirred at RT for 3 h. The reaction was poured into an aqueous solution of $Na_2SO_3$ (30 mL) and then extracted with EtOAc (3×10 mL). The combined organic layer was washed with brine (20 mL), dried over anhydrous $Na_2SO_4$ and concentrated in vacuo. The residue was purified by column chromatography (3% to 50% EtOAc in petroleum ether) to afford the title compound as a red oil (1.80 g, 74%). $^1$H NMR (400 MHz, $CDCl_3$): δ 7.22-7.16 (m, 1H), 7.10-7.08 (m, 1H), 5.62 (s, 2H), 4.14 (d, J=3.2 Hz, 3H), 4.07-4.04 (m, 2H), 3.57-3.53 (m, 2H), 3.33-3.30 (m, 2H), 0.91-0.87 (m, 2H), 0.05 (s, 9H).

Step 7: 2-(5-fluoro-4-methoxy-1-((2-(trimethylsilyl)ethoxy)methyl)-1H-indazol-3-yl)ethyl methanesulfonate (8)

To an ice-cold solution of 2-(5-fluoro-4-methoxy-1-((2-(trimethylsilyl)ethoxy)methyl)-1H-indazol-3-yl)ethan-1-ol (1.8 g, 5.29 mmol), $Et_3N$ (1.1 mL, 7.93 mmol) in $CH_2Cl_2$ (20 mL), was added dropwise methanesulfonyl chloride (0.92 mL, 11.9 mmol) and then the reaction was stirred at RT for 3 h. The reaction was poured into saturated aq. $NaHCO_3$ (20 mL) and then extracted with $CH_2Cl_2$ (3×10 mL). The combined organic layer was washed with brine (20 mL), dried over anhydrous $Na_2SO_4$ and concentrated in vacuo. The residue was purified by column chromatography (1% to 16% EtOAc in petroleum ether) to afford the title compound as a red oil (1.80 g, 81%). $^1$H NMR (400 MHz, $CDCl_3$): δ 7.22-7.16 (m, 1H), 7.09-7.07 (m, 1H), 5.60 (s, 2H), 4.65 (t, J=7.2 Hz, 2H), 4.17 (d, J=3.6 Hz, 3H), 3.55-3.49 (m, 4H), 2.98 (s, 3H), 0.91-0.87 (m, 2H), 0.05 (s, 9H).

Step 8: 2-(5-fluoro-4-methoxy-1-((2-(trimethylsilyl)ethoxy)methyl)-1H-indazol-3-yl)-N,N-dimethylethan-1-amine (9)

2-(5-fluoro-4-methoxy-1-((2-(trimethylsilyl)ethoxy)methyl)-1H-indazol-3-yl)-N,N-dimethylethan-1-amine was synthesised according to General Procedure B using 2-(5-fluoro-4-methoxy-1-((2-(trimethylsilyl)ethoxy)methyl)-1H-indazol-3-yl)ethyl methanesulfonate (400 mg, 0.96 mmol), $K_2CO_3$ (1.32 g, 9.56 mmol) and N,N-dimethylamine (2 M in THF, 4.78 mL, 9.56 mmol). The title compound was obtained as a yellow oil (400 mg) which was used in the next step without further purification.

Step 9: 2-(5-fluoro-4-methoxy-1H-indazol-3-yl)-N,N-dimethylethan-1-amine (A1)

To a solution of crude 2-(5-fluoro-4-methoxy-1-((2-(trimethylsilyl)ethoxy)methyl)-1H-indazol-3-yl)-N,N-dimethylethan-1-amine (400 mg) and tetrabutylammonium fluoride (1 M in THF, 5.44 mL, 5.44 mmol) in THF (4 mL) was added ethylenediamine (327 mg, 5.44 mmol). The reaction was stirred at 60° C. for 16 h and then the cooled reaction was filtered and the filtrate was concentrated in vacuo. The residue was purified by prep-HPLC (column: Phenomenex Luna C18, 100×30 mm, 3 μm; mobile phase: [$H_2O$ (0.2% formic acid)-MeCN]; gradient: 1%-30% B over 8.00 min) to afford the title compound as an off-white solid (25.9 mg, 11% over 2 steps). LCMS (Condition D): $t_R$ (1.676 min) m/z=238.1 [M+H]$^+$; $^1$H NMR (400 MHz, $CDCl_3$): δ 7.11-7.05 (m, 1H), 6.95-6.93 (m, 1H), 4.13 (d, J=3.2 Hz, 3H), 3.35-3.31 (m, 2H), 3.05-3.01 (m, 2H), 2.54 (s, 6H); $^{19}$F NMR (376 MHz, $CDCl_3$): δ −144.7.

Example 2: Synthesis of N-ethyl-2-(5-fluoro-4-methoxy-1H-indazol-3-yl)-N-methylethan-1-amine (A2)

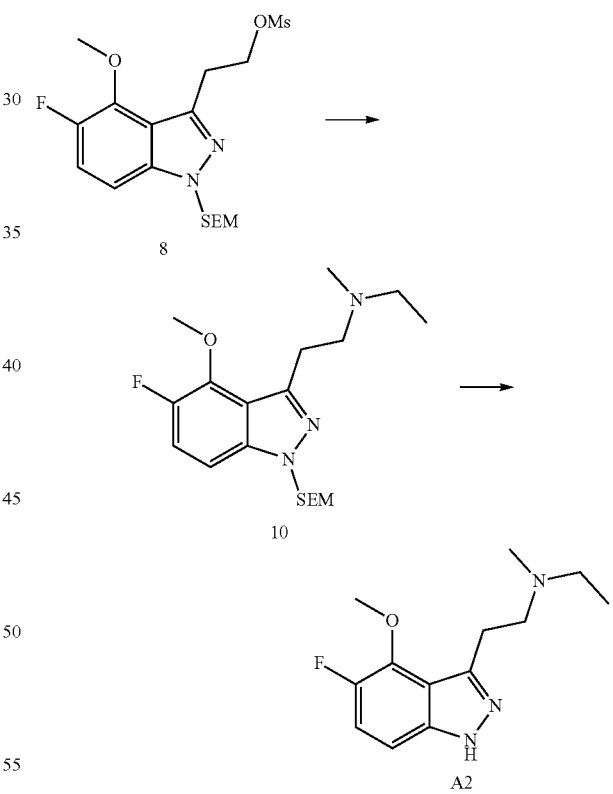

Step 1: N-ethyl-2-(5-fluoro-4-methoxy-1-((2-(trimethylsilyl)ethoxy)methyl)-1H-indazol-3-yl)-N-methylethan-1-amine (10)

N-ethyl-2-(5-fluoro-4-methoxy-1-((2-(trimethylsilyl)ethoxy)methyl)-1H-indazol-3-yl)-N-methylethan-1-amine was synthesised according to General Procedure B using 2-(5-fluoro-4-methoxy-1-((2-(trimethylsilyl)ethoxy)methyl)-1H-indazol-3-yl)ethyl methanesulfonate (300 mg, 0.72 mmol), K$_2$CO$_3$ (991 mg, 7.17 mmol) and N-methylethanamine (0.31 mL, 3.58 mmol). The title compound was obtained as a yellow oil (300 mg) which was used in the next step without further purification.

Step 2: N-ethyl-2-(5-fluoro-4-methoxy-1H-indazol-3-yl)-N-methylethan-1-amine (A2)

To a solution of crude N-ethyl-2-(5-fluoro-4-methoxy-1-((2-(trimethylsilyl)ethoxy)methyl)-1H-indazol-3-yl)-N-methylethan-1-amine (300 mg) and tetrabutylammonium fluoride (1 M in THF, 3.93 mL, 3.93 mmol) in THF (3 mL) was added ethylenediamine (236 mg, 3.93 mmol). The reaction was stirred at 60° C. for 16 h and then the cooled reaction was filtered and the filtrate was concentrated in vacuo. The residue was partially purified by prep-HPLC (column: Phenomenex Luna C18, 100×30 mm, 3 µm; mobile phase: [H$_2$O (0.2% formic acid)-MeCN]; gradient: 1%-30% B over 8.00 min) and the lyophilised crude product was taken up in EtOAc (2 mL) and washed with saturated aq. NaHCO$_3$ (5 mL). The aqueous layer was extracted with EtOAc (3×3 mL) and the combined EtOAc layers were dried over anhydrous Na$_2$SO$_4$ and concentrated in vacuo to afford the title compound as a yellow oil (26 mg, 14% over 2 steps). LCMS (Condition D): t$_R$ (1.735 min) m/z=252.1 [M+H]$^+$; $^1$H NMR (400 MHz, CDCl$_3$): δ 7.08-7.03 (m, 1H), 6.90-6.87 (m, 1H), 4.12 (d, J=3.2 Hz, 3H), 3.27-3.23 (m, 2H), 2.90-2.86 (m, 2H), 2.60 (q, J=7.2 Hz, 2H), 2.40 (s, 3H), 1.12 (t, J=7.2 Hz, 3H); $^{19}$F NMR (376 MHz, CDCl$_3$): δ −144.9.

Example 3: Synthesis of N-(2-(5-fluoro-4-methoxy-1H-indazol-3-yl)ethyl)-N-methylpropan-2-amine (A3)

Step 1: N-(2-(5-fluoro-4-methoxy-1-((2-(trimethylsilyl)ethoxy)methyl)-1H-indazol-3-yl)ethyl)-N-methylpropan-2-amine (11)

N-(2-(5-fluoro-4-methoxy-1-((2-(trimethylsilyl)ethoxy)methyl)-1H-indazol-3-yl)ethyl)-N-methylpropan-2-amine was synthesised according to General Method B with 2-(5-fluoro-4-methoxy-1-((2-(trimethylsilyl)ethoxy)methyl)-1H-indazol-3-yl)ethyl methanesulfonate (300 mg, 0.72 mmol), K$_2$CO$_3$ (991 mg, 7.17 mmol) and N-methylpropan-2-amine (0.75 mL, 7.17 mmol). The title compound was obtained as a yellow oil (300 mg) which was used in the next step without further purification.

Step 2: N-(2-(5-fluoro-4-methoxy-1H-indazol-3-yl)ethyl)-N-methylpropan-2-amine (A3)

To a solution of crude N-(2-(5-fluoro-4-methoxy-1-((2-(trimethylsilyl)ethoxy)methyl)-1H-indazol-3-yl)ethyl)-N-methylpropan-2-amine (300 mg) and tetrabutylammonium fluoride (1 M in THF, 3.79 mL, 3.79 mmol) in THF (3 mL) was added ethylenediamine (228 mg, 3.79 mmol). The reaction was stirred at 60° C. for 16 h and then the cooled reaction was filtered and the filtrate was concentrated in vacuo. The residue was partially purified by prep-HPLC (column: Phenomenex Luna C18, 100×30 mm, 3 µm; mobile phase: [H$_2$O (0.2% formic acid)-MeCN]; gradient: 1%-30% B over 8.00 min) and the lyophilised crude product was taken up in EtOAc (2 mL) and washed with saturated aq. NaHCO$_3$ (5 mL). The aqueous layer was extracted with EtOAc (3×3 mL) and the combined EtOAc layers were dried over anhydrous Na$_2$SO$_4$ and concentrated in vacuo to afford the title compound as a yellow oil (25.5 mg, 13% over 2 steps). LCMS (Condition D): t$_R$ (1.809 min) m/z=266.2 [M+H]$^+$; $^1$H NMR (400 MHz, CDCl$_3$): δ 7.14-7.08 (m, 1H), 6.99-6.96 (m, 1H), 4.13 (d, J=3.2 Hz, 3H), 3.27-3.23 (m, 2H), 2.97-2.95 (m, 1H), 2.89-2.85 (m, 2H), 2.40 (s, 3H), 1.07 (d, J=6.8 Hz, 6H); $^{19}$F NMR (376 MHz, CDCl$_3$): δ −144.7.

Example 4: Synthesis of N-(2-(5-fluoro-4-methoxy-1H-indazol-3-yl)ethyl)-N-methylcyclopropanamine (A4)

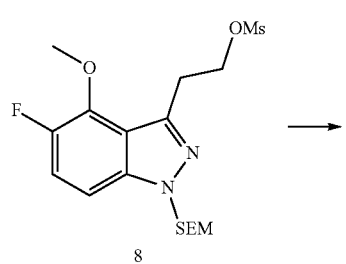

8

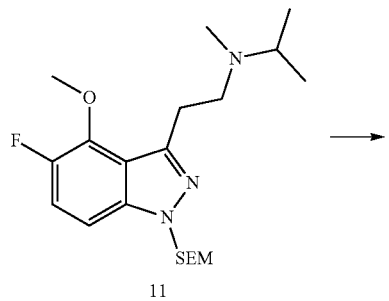

11

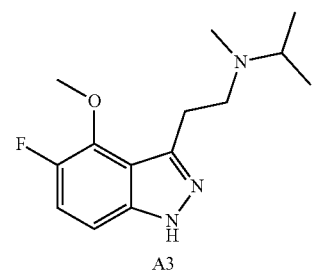

A3

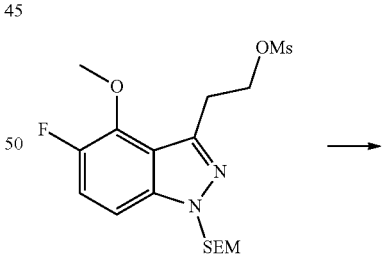

8

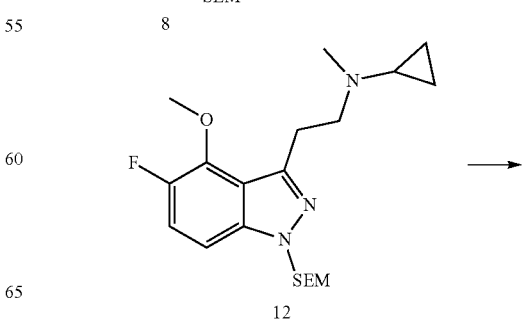

12

-continued

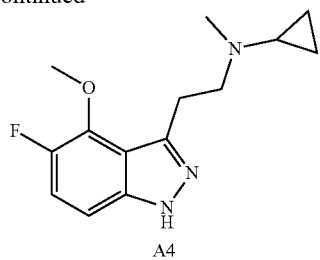

A4

Step 1: N-(2-(5-fluoro-4-methoxy-1-((2-(trimethylsilyl)ethoxy)methyl)-1H-indazol-3-yl)ethyl)-N-methylcyclopropanamine (12)

N-(2-(5-fluoro-4-methoxy-1-((2-(trimethylsilyl)ethoxy)methyl)-1H-indazol-3-yl)ethyl)-N-methylcyclopropanamine was synthesised according to General Method B with 2-(5-fluoro-4-methoxy-1-((2-(trimethylsilyl)ethoxy)methyl)-1H-indazol-3-yl)ethyl methanesulfonate (400 mg, 0.96 mmol), $K_2CO_3$ (1.32 g, 9.56 mmol) and N-methylcyclopropanamine (680 mg, 9.56 mmol). The title compound was obtained as a yellow oil (400 mg) which was used in the next step without further purification.

Step 2: N-(2-(5-fluoro-4-methoxy-1H-indazol-3-yl)ethyl)-N-methylcyclopropanamine (A4)

To a solution of crude N-(2-(5-fluoro-4-methoxy-1-((2-(trimethylsilyl)ethoxy)methyl)-1H-indazol-3-yl)ethyl)-N-methylcyclopropanamine (400 mg) and tetrabutylammonium fluoride (1 M in THF, 5.08 mL, 5.08 mmol) in THF (4 mL) was added ethylenediamine (305 mg, 5.08 mmol). The reaction was stirred at 60° C. for 16 h and then the cooled reaction was filtered and the filtrate was concentrated in vacuo. The residue was partially purified by prep-HPLC (column: Phenomenex Luna C18, 100×30 mm, 3 μm; mobile phase: [$H_2O$ (0.2% formic acid)-ACN]; gradient: 1%-30% B over 8.00 min) and the lyophilised crude product was taken up in EtOAc (2 mL) and washed with saturated aq. $NaHCO_3$ (5 mL). The aqueous layer was extracted with EtOAc (3×3 mL) and the combined EtOAc layers were dried over anhydrous $Na_2SO_4$, and concentrated in vacuo to afford the title compound as an off-white solid (25.3 mg, 10% over 2 steps). LCMS (Condition D): $t_R$ (1.779 min) m/z=264.1 [M+H]$^+$; $^1$H NMR (400 MHz, $CDCl_3$): δ 7.13-7.08 (m, 1H), 6.97-6.95 (m, 1H), 4.13 (d, J=3.2 Hz, 3H), 3.31-3.27 (m, 2H), 3.04-3.00 (m, 2H), 2.49 (s, 3H), 1.79-1.74 (m, 1H), 0.52-0.50 (m, 4H); $^{19}$F NMR (376 MHz, $CDCl_3$): δ −144.7.

Example 5: Synthesis of 2-(6-fluoro-5-methoxy-1H-indazol-3-yl)-N,N-dimethylethan-1-amine (A5)

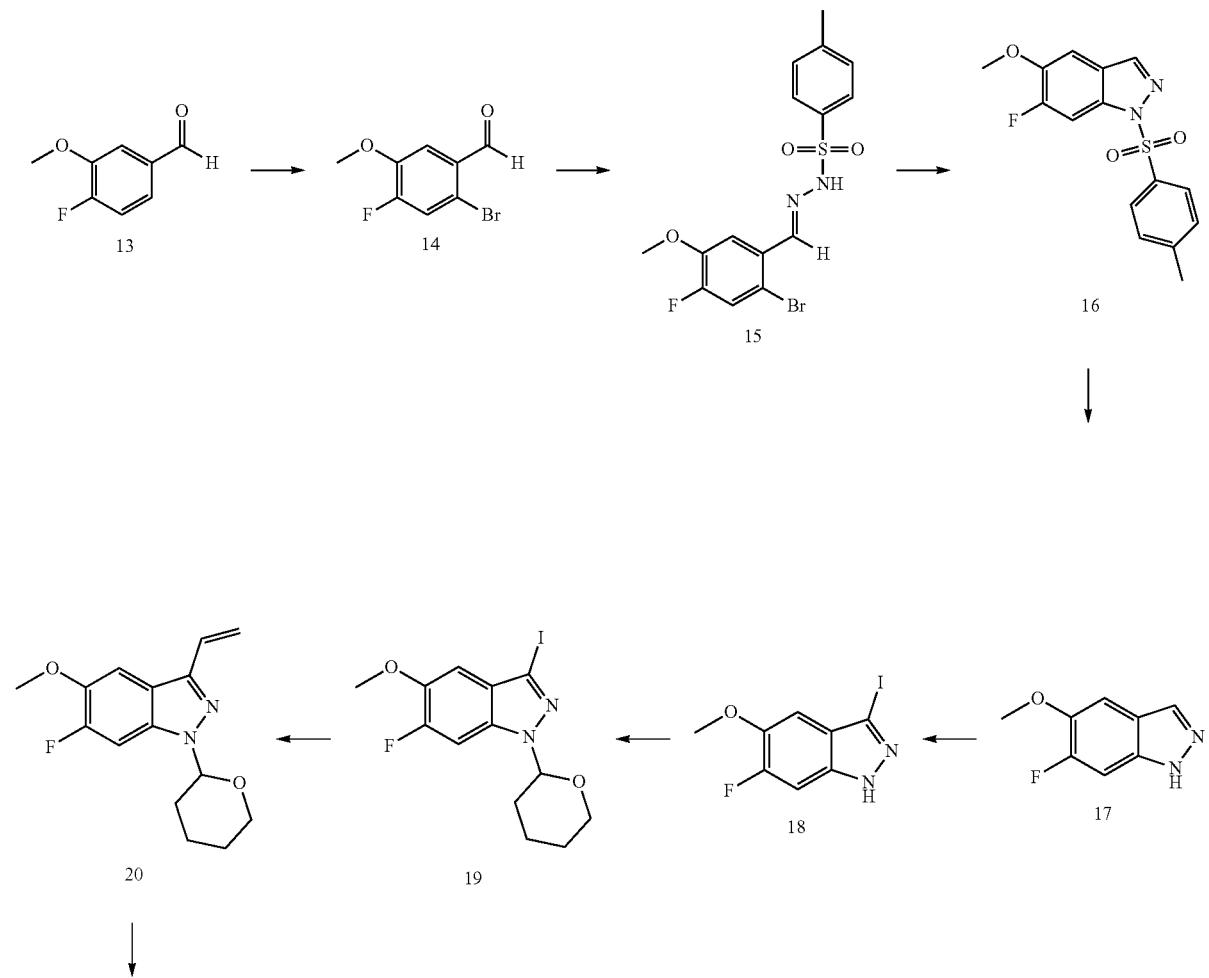

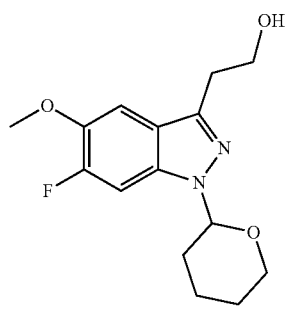

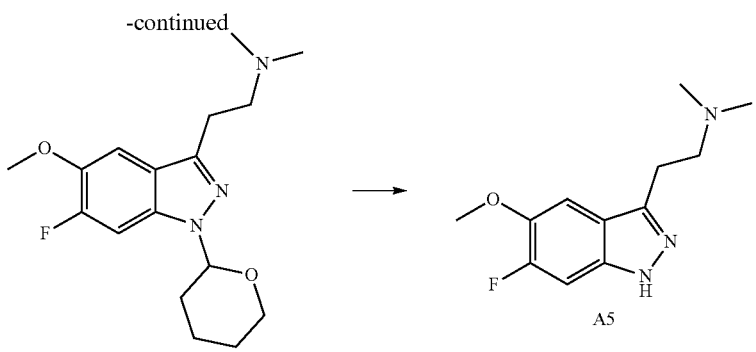

Step 1: 2-bromo-4-fluoro-5-methoxybenzaldehyde (14)

To a solution of 4-fluoro-3-anisaldehyde (40 g, 260 mmol) in H$_2$O (400 mL) was added KBr (154 g, 1.30 mol) and Br$_2$ (124 g, 778 mmol) and the reaction was stirred at RT for 16 h. TLC indicated the reaction was complete so the reaction mixture was filtered. The collected white solid was washed with plenty of water before being dried under vacuum to a constant weight and identified as the title compound (55 g, 91%). $^1$H NMR (400 MHz, CDCl$_3$): δ 10.19 (s, 1H), 7.49 (d, J=8.9 Hz, 1H), 7.33 (d, J=10.0 Hz, 1H), 3.90 (s, 3H); $^{13}$C NMR (101 MHz, CDCl$_3$): δ 190.5, 155.9 (d, J=262.2 Hz), 148.0 (d, J=10.9 Hz), 130.0 (d, J=3.5 Hz), 121.3 (d, J=21.9 Hz), 118.2 (d, J=8.8 Hz), 113.1 (d, J=3.8 Hz), 56.5.

Step 2: (E)-N-(2-bromo-4-fluoro-5-methoxybenzylidene)-4-methylbenzenesulfonohydrazide (15)

To a stirred suspension of 2-bromo-4-fluoro-5-methoxybenzaldehyde (35.7 g, 153 mmol) in methanol (1 L) was added 4-methylbenzenesulfonohydrazide (30 g, 161 mmol) at RT and the resulting mixture stirred at RT for 1 h. The suspension was allowed to settle and then the majority of the solvent was decanted. The residue was filtered under vacuum to afford the title compound as a white solid (53 g). The filtrate and decanted solvent was combined and concentrated, and additional product was crystallised from the residue with methanol for a total of 60 g (98%). $^1$H NMR (400 MHz, CDCl$_3$): δ 8.65 (s, 1H), 8.05 (s, 1H), 7.88 (d, J=8.2 Hz, 2H), 7.44 (d, J=8.9 Hz, 1H), 7.31 (d, J=8.2 Hz, 2H), 7.18 (d, J=10.2 Hz, 1H), 3.89 (s, 3H), 2.40 (s, 3H); $^{13}$C NMR (101 MHz, CDCl$_3$): δ 153.4 (d, J=256.4 Hz), 147.6 (d, J=11.0 Hz), 145.5 (d, J=2.0 Hz), 144.6, 135.3, 129.9, 128.6 (d, J=4.0 Hz), 128.1, 120.4 (d, J=21.7 Hz), 114.2 (d, J=8.2 Hz), 111.3 (d, J=2.4 Hz), 56.5, 21.7.

Step 3: 6-fluoro-5-methoxy-1-tosyl-1H-indazole (16)

In two batches: a mixture of (E)-N'-(2-bromo-4-fluoro-5-methoxybenzylidene)-4-methylbenzenesulfonohydrazide (25 g, 62.5 mmol) and Cu$_2$O (8.92 g) in isoamyl alcohol (200 mL) was stirred at reflux for 3 h under a nitrogen atmosphere. The cooled reaction mixture was poured into 1.5 L of hexane and the residue in the flask was washed in with additional hexane. The suspension was allowed to settle by standing for 1 h in the fridge and the solid was collected by vacuum filtration and washed with plenty of hexane. The collected solid from both batches were combined and stirred in CH$_2$Cl$_2$:MeOH (~4:1, 1 L) until only the inorganic material remained undissolved. The suspension was then filtered through a celite pad and washed with additional CH$_2$Cl$_2$. The combined filtrate was concentrated in vacuo and the white solid was suspended in hexane and the solid collected by filtration. The off-white solid was washed with hexane until it no longer carried the smell of isoamyl alcohol and identified as the title compound (35.2 g, 88%). $^1$H NMR (400 MHz, DMSO-d$_6$): δ 8.43 (d, J=0.8 Hz, 1H), 7.95-7.88 (m, 1H), 7.86-7.77 (m, 2H), 7.52 (d, J=8.2 Hz, 1H), 7.38 (d, J=8.0 Hz, 2H), 3.87 (s, 3H), 2.32 (s, 3H); $^{13}$C NMR (101 MHz, DMSO-d$_6$): δ 153.5 (d, J=250.8 Hz), 146.0, 146.0 (d, J=12.8 Hz), 142.3, 133.7 (d, J=11.8 Hz), 133.2, 130.3, 127.2, 121.9, 104.2 (d, J=3.2 Hz), 100.3 (d, J=25.4 Hz), 56.3, 21.1.

Step 4: 6-fluoro-5-methoxy-1H-indazole (17)

A solution of 6-fluoro-5-methoxy-1-tosyl-1H-indazole (35.2 g, 110 mmol) in THF (162 mL) and water (54 mL) was treated with cetrimonium bromide (2.0 g, 5.49 mmol) and KOH (30.8 g, 549 mmol) and the resulting mixture was stirred at reflux for 6 h. The cooled reaction mixture was then partitioned between water:EtOAc (1:2, 300 mL) and the layers separated. The aqueous layer was further extracted with EtOAc (2×100 mL) and the combined organic layer was washed with brine (100 mL), and then dried over anhydrous Na$_2$SO$_4$ and concentrated in vacuo. The residue was then triturated with Et$_2$O (200 mL), a few drops of CH$_2$Cl$_2$ and the off-white solid was collected which was identified as the title compound (18.3 g, quant.). $^1$H NMR (400 MHz, DMSO-d$_6$): δ12.99 (s, 1H), 8.03-7.90 (m, 1H), 7.42-7.33 (m, 2H), 3.84 (s, 3H); $^{13}$C NMR (101 MHz, DMSO-d$_6$): δ 152.5 (d, J=245.6 Hz), 143.5 (d, J=13.8 Hz), 134.1, 133.3, 118.6, 102.2, 96.9 (d, J=24.0 Hz), 56.2.

Step 5: 6-fluoro-3-iodo-5-methoxy-1H-indazole (18)

To a solution of 6-fluoro-5-methoxy-1H-indazole (17 g, 102 mmol) in MeOH (360 mL) and 2 M aq. NaOH (360 mL) was added 12 (39 g, 153 mmol) portionwise over a period of 20 min. The reaction mixture was stirred for 2 h until TLC indicated consumption of the starting material. 35% aq. HCl (50 mL) was added dropwise at 0° C. and the pH was then adjusted to 2-3 with 2 M aq. HCl. Saturated aq. Na$_2$S$_2$O$_3$ (~150 mL) was added until the iodine colour disappeared. The precipitate was filtered, washed with water, and then taken up in methanol (500 mL). The insoluble material was removed by filtration under vacuum and washed with additional methanol until TLC indicated no further product was being dissolved from the residue. The combined filtrate was concentrated and the aqueous suspension that remained was extracted with EtOAc (600 mL) which was then washed with brine (3×200 mL), dried over anhydrous $Na_2SO_4$, filtered, and the filtrate concentrated in vacuo. The residue was triturated in warm $CH_2Cl_2$ (50 mL) and then allowed to stand in an ice-bath for 1 h before the white solid was collected, dried under vacuum and identified as the title compound (28.5 g, 95%). $^1$H NMR (400 MHz, DMSO-$d_6$): δ 7.46 (d, J=10.9 Hz, 1H), 6.94 (d, J=8.0 Hz, 1H), 3.90 (s, 3H); $^{13}$C NMR (101 MHz, DMSO-$d_6$): δ153.3 (d, J=247.6 Hz), 144.3 (d, J=13.8 Hz), 134.3 (d, J=11.2 Hz), 122.7, 101.7, 97.3 (d, J=23.7 Hz), 92.7, 56.2.

Step 6: 6-fluoro-3-iodo-5-methoxy-1-(tetrahydro-2H-pyran-2-yl)-1H-indazole (19)

To a solution of 6-fluoro-3-iodo-5-methoxy-1H-indazole (28 g, 95.9 mmol) in $CH_2Cl_2$ (400 mL) was added 3,4-dihydro-2H-pyran (26.2 mL, 288 mmol) and p-TsOH·$H_2O$ (1.82 g, 9.59 mmol) and the resulting solution was stirred at RT for 16 h. TLC indicated complete conversion to a single spot. The reaction was diluted with $H_2O$ (200 mL) and the layers separated. The aqueous layer was further extracted with $CH_2Cl_2$ (2×100 mL) and the combined organic layer was washed with brine (200 mL). The organic layer was dried over anhydrous $Na_2SO_4$ and the mixture was passed through a silica plug and eluted with $CH_2Cl_2$ until TLC indicated all the desired product had eluted from plug. The combined filtrate was concentrated in vacuo and the resulting oil was left under a stream of nitrogen gas 16 h which produced a chalky, white solid. The solid was broken up, dried under vacuum and identified as the title compound (32 g, 89%). $^1$H NMR (400 MHz, CDCl$_3$): δ 7.32 (d, J=10.7 Hz, 1H), 6.86 (d, J=7.8 Hz, 1H), 5.58 (dd, J=9.1, 2.7 Hz, 1H), 4.07-3.97 (m, 1H), 3.96 (s, 3H), 3.78-3.60 (m, 1H), 2.62-2.39 (m, 1H), 2.19-1.99 (m, 2H), 1.84-1.60 (m, 3H); $^{13}$C NMR (101 MHz, CDCl$_3$): δ 154.4 (d, J=250.8 Hz), 145.5 (d, J=13.8 Hz), 134.1 (d, J=11.4 Hz), 124.8, 102.7 (d, J=3.2 Hz), 97.8 (d, J=24.5 Hz), 92.2, 86.3, 67.5, 56.6, 29.5, 25.1, 22.4.

Step 7: 6-fluoro-5-methoxy-1-(tetrahydro-2H-pyran-2-yl)-3-vinyl-1H-indazole (20)

A solution of Et$_3$N (36 mL, 258 mmol) in iPrOH (325 mL) and THF (65 mL) was sparged for 60 min with nitrogen gas before 6-fluoro-3-iodo-5-methoxy-1-(tetrahydro-2H-pyran-2-yl)-1H-indazole (32.4 g, 103 mmol) and potassium vinyltrifluoroborate (13.8 g, 103 mmol) and Pd(dppf)Cl$_2$ (6.3 g, 8.6 mmol) was added. The resulting mixture was stirred at 80° C. for 24 h under a nitrogen atmosphere. The cooled reaction mixture was filtered through a celite plug and washed with EtOAc (500 mL). The combined filtrate was concentrated in vacuo and the residue taken up in EtOAc (200 mL) and filtered through the celite plug again. The plug was washed with EtOAc (200 mL) and the combined filtrate was washed with water (3×100 mL) and then brine (2×200 mL), before being dried over anhydrous $Na_2SO_4$ and concentrated in vacuo. The residue was purified by column chromatography (4% to 8% EtOAc in hexane) to afford the title compound as a slightly yellow resin (21 g, 88%) which was stored at −20° C. under nitrogen. $^1$H NMR (400 MHz, CDCl$_3$): δ 7.35-7.27 (m, 2H), 6.99 (dd, J=18.0, 11.4 Hz, 1H), 6.00 (dd, J=18.0, 1.2 Hz, 1H), 5.58 (dd, J=9.4, 2.7 Hz, 1H), 5.51 (dd, J=11.5, 1.2 Hz, 1H), 4.07-3.99 (m, 1H), 3.94 (s, 3H), 3.80-3.64 (m, 1H), 2.60-2.37 (m, 1H), 2.20-1.97 (m, 2H), 1.82-1.57 (m, 3H); $^{13}$C NMR (101 MHz, CDCl$_3$): δ 153.5 (d, J=249.0 Hz), 145.0 (d, J=13.5 Hz), 142.7, 135.19 (d, J=11.0 Hz), 128.9, 118.2, 116.7, 102.6 (d, J=3.0 Hz), 97.8 (d, J=23.9 Hz), 86.1, 67.7, 56.7, 29.6, 25.2, 22.6.

Step 8: 2-(6-fluoro-5-methoxy-1-(tetrahydro-2H-pyran-2-yl)-1H-indazol-3-yl)ethan-1-ol (21)

An ice-cold solution of 6-fluoro-5-methoxy-1-(tetrahydro-2H-pyran-2-yl)-3-vinyl-1H-indazole (19.2 g, 69.5 mmol) in anhydrous THF (400 mL) was treated with 9-borabicyclo[3.3.1]nonane (0.5 M in THF, 347 mL, 174 mmol) and the mixture was stirred at RT for 16 h. TLC indicated the starting material was consumed so the reaction was cooled to 0° C. and 4 M aq. NaOH (174 mL, 695 mmol) and $H_2O_2$ (30% w/w in $H_2O$, 79 mL, 695 mmol) was added as follows. First, 20 mL of the NaOH solution was added, followed by 5 mL of $H_2O_2$ solution, then 10 mL of NaOH and 5 mL of $H_2O_2$ was added in an alternating manner at a rate that maintained a gentle effervescence and a temperature below the boiling point of THF. After the addition (over 1 h), the mixture was stirred at RT for 2 h. The reaction was quenched by addition of saturated aq. $Na_2S_2O_3$ and diluted with $H_2O$ (200 mL). The solution was then extracted with EtOAc (2×100 mL) and the combined organic layer was washed with brine (200 mL), dried over anhydrous $Na_2SO_4$ and concentrated in vacuo. The residue was purified by flash chromatography (10% to 40% EtOAc in hexane) to afford the title compound as a white solid (20 g, 98%). $^1$H NMR (400 MHz, CDCl$_3$): δ 7.28 (d, J=10.9 Hz, 1H), 7.06 (d, J=7.9 Hz, 1H), 5.53 (dd, J=9.6, 2.6 Hz, 1H), 4.19-3.97 (m, 3H), 3.92 (s, 3H), 3.81-3.66 (m, 1H), 3.13 (t, J=5.8 Hz, 2H), 2.57-2.39 (m, 1H), 2.18-1.99 (m, 2H), 1.80-1.59 (m, 3H); $^{13}$C NMR (101 MHz, CDCl$_3$): δ 153.9 (d, J=249.0 Hz), 144.6 (d, J=13.5 Hz), 143.9, 134.7 (d, J=11.3 Hz), 119.4, 101.7 (d, J=3.2 Hz), 97.7 (d, J=24.1 Hz), 85.8, 67.7, 61.4, 56.7, 29.5, 29.5, 25.2, 22.7.

Step 9: 2-(6-fluoro-5-methoxy-1-(tetrahydro-2H-pyran-2-yl)-1H-indazol-3-yl)-N,N-dimethylethan-1-amine (22)

To an ice-cold solution of 2-(6-fluoro-5-methoxy-1-(tetrahydro-2H-pyran-2-yl)-1H-indazol-3-yl)ethan-1-ol (150 mg, 0.51 mmol) in $CH_2Cl_2$ (3 mL) in a pressure tube, was added Et$_3$N (0.1 mL, 0.76 mmol) and methanesulfonyl chloride (0.05 mL, 0.62 mmol) and the mixture was stirred at RT for 1 h. TLC indicated consumption of the starting material so the reaction was concentrated under a stream of nitrogen gas. The residue was treated with dimethylamine (2 M in THF, 0.76 mL, 1.53 mmol) and the pressure tube was sealed and heated at 60° C. for 16 h. The reaction was concentrated and the residue was taken up in EtOAc (20 mL) and washed with $H_2O$ (3×10 mL), then brine (5 mL), before being dried over anhydrous $Na_2SO_4$ and concentrated in vacuo. The residue was purified by flash chromatography (0.1% to 8% MeOH/NH$_3$ in $CH_2Cl_2$) to afford the title compound as an off-white solid (120 mg, 73%). LCMS (Condition B): $t_R$ (1.529 min) m/z=238.1 [M+H]$^+$; $^1$H NMR (400 MHz, DMSO-$d_6$): δ7.58 (d, J=11.5 Hz, 1H), 7.39 (d, J=8.2 Hz, 1H), 5.66 (dd, J=9.9, 2.5 Hz, 1H), 3.88 (s, 3H), 3.87-3.82 (m, 1H), 3.77-3.63 (m, 1H), 3.06-2.94 (m, 2H), 2.69-2.56 (m, 2H), 2.42-2.27 (m, 1H), 2.23 (s, 6H), 2.08-1.95 (m, 1H), 1.94-1.83 (m, 1H), 1.79-1.45 (m, 3H); $^{13}$C NMR (101 MHz, DMSO-$d_6$): δ 152.6 (d, J=246.0 Hz), 143.5 (d, J=1.4 Hz), 143.4 (d, J=13.5 Hz), 134.4 (d, J=11.5 Hz), 118.6, 102.3 (d, J=3.0 Hz), 97.3 (d, J=23.9 Hz), 84.0, 66.5, 58.1, 56.3, 45.0, 29.0, 24.8, 24.8, 22.4.

Step 10: 2-(6-fluoro-5-methoxy-1H-indazol-3-yl)-N, N-dimethylethan-1-amine (A5-fumarate)

The title compound was synthesised according to General Procedure D utilising 2-(6-fluoro-5-methoxy-1-(tetrahydro-2H-pyran-2-yl)-1H-indazol-3-yl)-N,N-dimethylethan-1-amine (100 mg, 0.31 mmol) which upon purification generated the title compound as a colourless oil (50 mg, 65%) which was then formulated as the fumarate salt as per General Procedure F (50 mg, 54%) as a white crystalline solid. $^1$H NMR (400 MHz, DMSO-$d_6$): δ 7.43 (d, J=8.2 Hz, 1H), 7.33 (d, J=11.2 Hz, 1H), 6.56 (s, 3H), 3.88 (s, 3H), 3.30-3.08 (m, 4H), 2.61 (s, 6H); $^{13}$C NMR (101 MHz, DMSO-$d_6$): δ 167.1, 152.6 (d, J=245.6 Hz), 143.0 (d, J=13.8 Hz), 141.4, 135.0 (d, J=11.4 Hz), 134.6, 117.2, 101.7, 96.9 (d, J=23.0 Hz), 56.2, 56.0, 43.0, 22.7; $^1$H qNMR Purity: 97.0% (ERETIC).

Example 6: Synthesis of N-ethyl-2-(6-fluoro-5-methoxy-1H-indazol-3-yl)-N-methylethan-1-amine (A6)

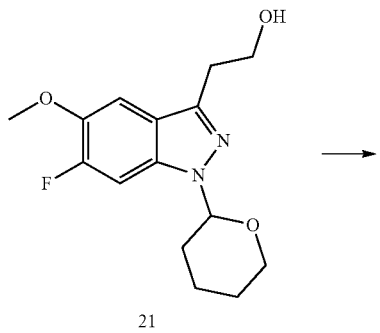

21

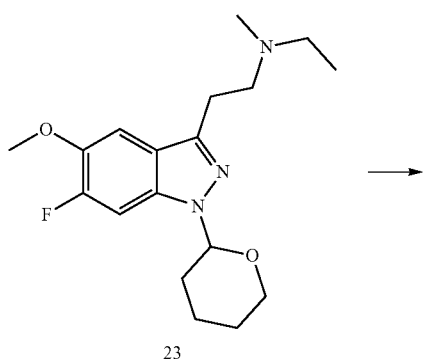

23

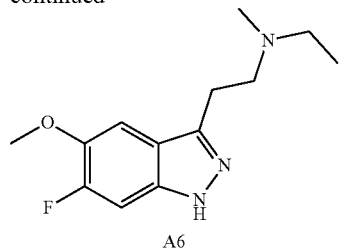

A6

Step 1: N-ethyl-2-(6-fluoro-5-methoxy-1-(tetrahydro-2H-pyran-2-yl)-1H-indazol-3-yl)-N-methylethan-1-amine (23)

To an ice-cold solution of 2-(6-fluoro-5-methoxy-1-(tetrahydro-2H-pyran-2-yl)-1H-indazol-3-yl)ethan-1-ol (1.0 g, 3.40 mmol) in CH$_2$Cl$_2$ (20 mL) in a pressure tube, was added Et$_3$N (0.85 mL, 6.12 mmol) and methanesulfonyl chloride (0.39 mL, 5.10 mmol) and the mixture was stirred at RT for 4 h. TLC indicated consumption of the starting material so the reaction was concentrated under a stream of nitrogen gas. The residue was dissolved in DMF (7 mL) and then treated with N-methylethanamine (1.46 mL, 17.0 mmol) and the pressure tube was sealed and heated at 80° C. for 1.5 h. The reaction was diluted with EtOAc (120 mL) and washed with H$_2$O (2×40 mL), then brine (40 mL), before being dried over anhydrous MgSO$_4$ and concentrated in vacuo. The residue was purified by flash chromatography (0.1% to 10% MeOH/NH$_3$ in CH$_2$Cl$_2$) to afford the title compound as a colourless resin (473 mg, 42%). $^1$H NMR (400 MHz, DMSO-$d_6$): δ7.25 (d, J=11.0 Hz, 2H), 7.15 (d, J=8.0 Hz, 1H), 5.51 (dd, J=9.8, 2.6 Hz, 1H), 4.09-4.01 (m, 1H), 3.93 (s, 3H), 3.71 (td, J=11.1, 2.9 Hz, 1H), 3.21-3.13 (m, 2H), 2.95-2.87 (m, 2H), 2.64 (q, J=7.2 Hz, 2H), 2.53-2.36 (m, 1H), 2.42 (s, 3H), 2.17-2.05 (m, 1H), 2.05-1.96 (m, 1H), 1.80-1.69 (m, 2H), 1.67-1.58 (m, 1H), 1.16 (t, J=7.2 Hz, 3H).

Step 2: N-ethyl-2-(6-fluoro-5-methoxy-1H-indazol-3-yl)-N-methylethan-1-amine (A6)

The title compound was synthesised according to General Procedure D utilising 2-(6-fluoro-5-methoxy-1-(tetrahydro-2H-pyran-2-yl)-1H-indazol-3-yl)-N,N-dimethylethan-1-amine (450 mg, 1.34 mmol) which upon purification generated the title compound as a colourless oil (257 mg, 76%). $^1$H NMR (400 MHz, DMSO-$d_6$): δ 7.34 (d, J=8.2 Hz, 1H), 7.29 (d, J=11.2 Hz, 1H), 3.86 (s, 3H), 3.05-2.96 (m, 2H), 2.75-2.68 (m, 2H), 2.45 (q, J=7.1 Hz, 2H), 2.24 (s, 3H), 0.98 (t, J=7.1 Hz, 3H).

Step 3: N-ethyl-2-(6-fluoro-5-methoxy-1H-indazol-3-yl)-N-methylethan-1-amine (A6-fumarate)

N-Ethyl-2-(6-fluoro-5-methoxy-1H-indazol-3-yl)-N-methylethan-1-amine (244 mg, 0.97 mmol) was formulated as the fumarate salt as per General Procedure F (236 mg, 57%) as a white crystalline solid. LCMS (Condition A): $t_R$ (4.086 min) m/z=252.15 [M+H]$^+$; $^1$H NMR (400 MHz, DMSO-$d_6$): δ 7.43 (d, J=8.3 Hz, 1H), 7.33 (d, J=11.1 Hz, 1H), 6.55 (s, 3H), 3.88 (s, 3H), 3.27-3.16 (m, 4H), 2.95 (q, J=7.2 Hz, 2H), 2.62 (s, 3H), 1.16 (t, J=7.2 Hz, 3H); $^{13}$C NMR (101 MHz, DMSO-$d_6$): δ 167.3, 152.6 (d, J=245.7 Hz), 143.1 (d, J=13.7 Hz), 141.4, 135.0 (d, J=11.5 Hz), 134.7, 117.2, 101.7 (d, J=3.1 Hz), 97.0 (d, J=23.0 Hz), 56.2, 53.6, 49.9, 39.0, 22.2, 9.8; $^1$H qNMR Purity: 97.5% (ERETIC).

Example 7: Synthesis of N-(2-(6-fluoro-5-methoxy-1H-indazol-3-yl)ethyl)-N-methylpropan-2-amine (A7)

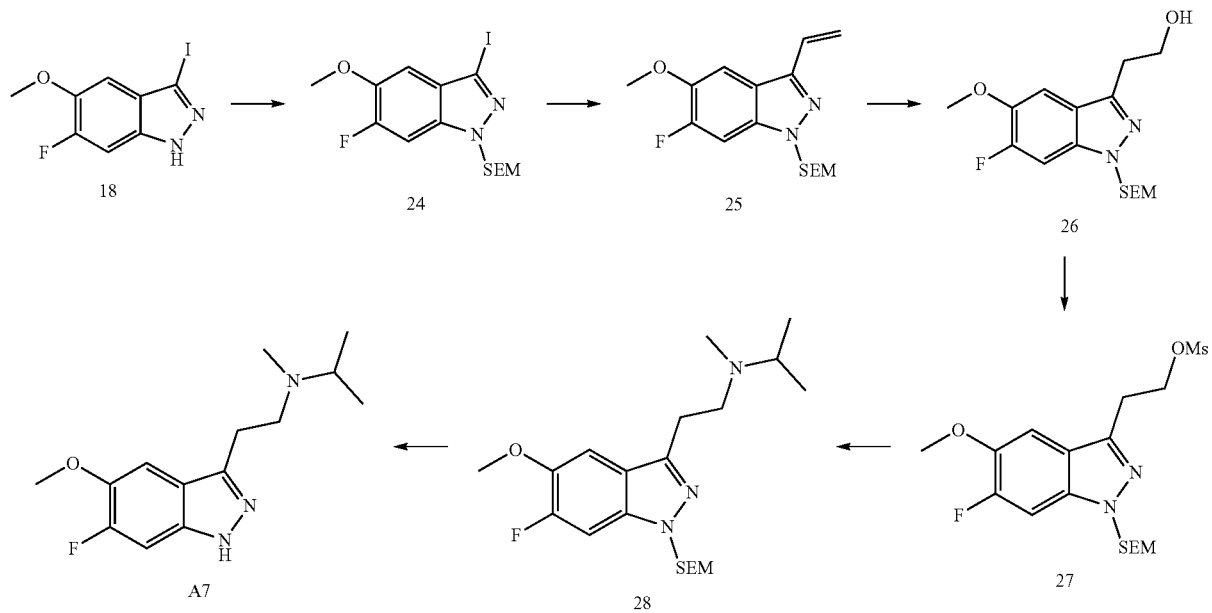

Step 1: 6-fluoro-3-iodo-5-methoxy-1-((2-(trimethylsilyl)ethoxy)methyl)-1H-indazole (24)

To an ice-cold solution of 6-fluoro-3-iodo-5-methoxy-1H-indazole (7.5 g, 25.6 mmol) in THF (75 mL) was added NaH (60% w/w dispersion in mineral oil, 1.54 g, 38.5 mmol) and then 2-(trimethylsilyl)ethoxymethyl chloride (5.14 g, 30.8 mmol) under nitrogen atmosphere. The reaction was stirred cold for 3 h and TLC indicated consumption of the starting material. The reaction mixture was quenched with H$_2$O (50 mL) and then extracted with EtOAc (3×30 mL). The combined organic layer was washed with brine (40 mL) and then dried over anhydrous Na$_2$SO$_4$ and concentrated in vacuo. The residue was purified by column chromatography (1% to 50% EtOAc in petroleum ether) to afford the title compound as a mixture of N1- and N2-protected indazole as a white solid (8.5 g, 78%). $^1$H NMR (400 MHz, DMSO-d$_6$): δ 7.77 (d, J=11.2 Hz, 1H), 6.97 (d, J=8.00 Hz, 1H), 5.60 (s, 2H), 3.92 (s, 3H), 3.55-3.47 (m, 5H), 0.87-0.83 (m, 3H), −0.004 (s, 12H)

Step 2: 6-fluoro-5-methoxy-1-((2-(trimethylsilyl)ethoxy)methyl)-3-vinyl-1H-indazole (25)

A solution of 6-fluoro-3-iodo-5-methoxy-1-((2-(trimethylsilyl)ethoxy)methyl)-1H-indazole (7.0 g, 16.5 mmol), potassium vinyltrifluoroborate (2.66 g, 19.8 mmol) in iPrOH (58 mL) and THF (12 mL) was sparged with nitrogen gas for 5 min before Et$_3$N (6.9 mL, 49.7 mmol) and Pd(dppf)Cl$_2$ (1.21 g, 1.66 mmol) was added under nitrogen atmosphere. The mixture was stirred at 100° C. for 24 h under nitrogen atmosphere and then the cooled reaction mixture was concentrated in vacuo. The residue was partitioned between EtOAc (30 mL) and H$_2$O (20 mL) and the layers were separated. The aqueous layer was further extracted with EtOAc (2×30 mL) and the combined organic layer was washed with brine (20 mL), dried over anhydrous Na$_2$SO$_4$ and concentrated in vacuo. The residue was purified by column chromatography (1% to 50% EtOAc in petroleum ether) to afford the title compound as a yellow oil (3.5 g) which was used in the next step without further purification.

Step 3: 2-(6-fluoro-5-methoxy-1-((2-(trimethylsilyl)ethoxy)methyl)-1H-indazol-3-yl)ethan-1-ol (26)

To an ice-cold solution of crude 6-fluoro-5-methoxy-1-((2-(trimethylsilyl)ethoxy)methyl)-3-vinyl-1H-indazole (3.5 g) in THF (15 mL) was added 9-borabicyclo[3.3.1]nonane (0.5 M in THF, 130 mL, 65 mmol) and the reaction was then stirred at RT for 2 h. The reaction was cooled in an ice bath and treated dropwise with H$_2$O$_2$ (30% w/w in H$_2$O, 5.3 mL, 174 mmol) and 4M aq. NaOH (13.5 mL) before being stirred at RT for 12 h. The reaction was cooled in an ice bath and quenched by dropwise addition of H$_2$O (20 mL) before being extracted with EtOAc (3×30 mL). The combined organic layer was washed with brine (30 mL), dried over anhydrous Na$_2$SO$_4$ and concentrated in vacuo. The residue was purified by column chromatography (2% to 50% EtOAc in petroleum ether) to afford the title compound as a yellow oil (3.2 g, 57% over 2 steps). $^1$H NMR (400 MHz, DMSO-d$_6$): δ 7.60 (d, J=11.2 Hz, 1H), 7.40 (d, J=8.4 Hz, 1H), 5.59 (s, 2H), 4.74-4.71 (m, 1H), 3.87 (s, 3H), 3.77-3.72 (m, 2H), 3.49-3.32 (m, 2H), 3.04-3.00 (m, 2H), 0.77 (t, J=8.0 Hz, 2H), −0.10 (s, 9H).

Step 4: 2-(6-fluoro-5-methoxy-1-((2-(trimethylsilyl)ethoxy)methyl)-1H-indazol-3-yl)ethyl methanesulfonate (27)

2-(6-fluoro-5-methoxy-1-((2-(trimethylsilyl)ethoxy)methyl)-1H-indazol-3-yl)ethyl methanesulfonate was synthesised according to General Method A with 2-(6-fluoro- 5-methoxy-1-((2-(trimethylsilyl)ethoxy)methyl)-1H-indazol-3-yl)ethan-1-ol (3.2 g, 9.40 mmol), methanesulfonyl chloride (1.5 mL, 19.2 mmol) and Et₃N (2.6 mL, 18.8 mmol). The title compound was obtained as a yellow oil (3.5 g, 89%), which was used in the next reaction without further purification. LCMS: m/z=419.1 [M+H]⁺.

Step 5: N-(2-(6-fluoro-5-methoxy-1-((2-(trimethylsilyl)ethoxy)methyl)-1H-indazol-3-yl)ethyl)-N-methylpropan-2-amine (28)

N-(2-(6-fluoro-5-methoxy-1-((2-(trimethylsilyl)ethoxy)methyl)-1H-indazol-3-yl)ethyl)-N-methylpropan-2-amine was synthesised according to General Method B with 2-(6-fluoro-5-methoxy-1-((2-(trimethylsilyl)ethoxy)methyl)-1H-indazol-3-yl)ethyl methanesulfonate (1.08 g, 2.57 mmol), K₂CO₃ (3.56 g, 25.7 mmol) and N-methylpropan-2-amine (2.7 mL, 25.8 mmol). The title compound was obtained as a yellow oil (500 mg) which was used in the next step without further purification.

Step 6: N-(2-(6-fluoro-5-methoxy-1H-indazol-3-yl)ethyl)-N-methylpropan-2-amine (A7)

To a solution of crude N-(2-(6-fluoro-5-methoxy-1-((2-(trimethylsilyl)ethoxy)methyl)-1H-indazol-3-yl)ethyl)-N-methylpropan-2-amine (500 mg) and tetrabutylammonium fluoride (1 M in THF, 6.32 mL, 6.32 mmol) in THF (5 mL) was added ethylenediamine (380 mg, 6.66 mmol). The reaction was stirred at 60° C. for 16 h and then the cooled reaction was filtered and the filtrate was concentrated in vacuo. The residue was purified by prep-HPLC (column: Phenomenex Luna C18, 100×40 mm, 3 μm; mobile phase: [H₂O (0.2% formic acid)-MeCN]; gradient: 1%-40% B over 8.00 min) to afford the title compound as a white solid (30 mg, 4% over 2 steps). LCMS (Condition B): $t_R$ (1.697 min) m/z=266.1 [M+H]⁺; ¹H NMR (400 MHz, DMSO-d₆): δ 8.22 (s, 1H), 7.37 (d, J=8.4 Hz, 1H), 7.30 (d, J=11.6 Hz, 1H), 3.87 (s, 3H), 3.06-3.02 (m, 2H), 2.99-2.90 (m, 1H), 2.85-2.81 (m, 2H), 2.31 (s, 3H), 0.98 (d, J=6.4 Hz, 6H); ¹⁹F NMR (376 MHz, CDCl₃): δ −133.3.

Example 8: Synthesis of N-(2-(6-fluoro-5-methoxy-1H-indazol-3-yl)ethyl)-N-methylcyclopropanamine (A8)

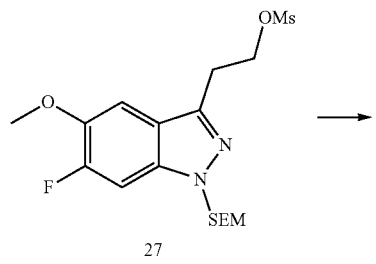

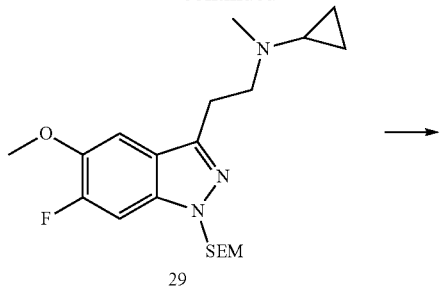

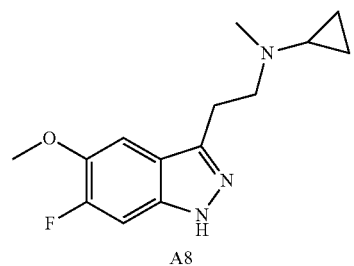

Step 1: N-(2-(6-fluoro-5-methoxy-1-((2-(trimethylsilyl)ethoxy)methyl)-1H-indazol-3-yl)ethyl)-N-methylcyclopropanamine (29)

N-(2-(6-fluoro-5-methoxy-1-((2-(trimethylsilyl)ethoxy)methyl)-1H-indazol-3-yl)ethyl)-N-methylcyclopropanamine was synthesised according to General Method B with 2-(6-fluoro-5-methoxy-1-((2-(trimethylsilyl)ethoxy)methyl)-1H-indazol-3-yl)ethyl methanesulfonate (0.65 g, 1.54 mmol), K₂CO₃ (2.13 g, 15.4 mmol) and N-methylcyclopropanamine (1.1 g, 15.4 mmol). The title compound was obtained as a yellow oil (500 mg) which was used in the next step without further purification.

Step 2: N-(2-(6-fluoro-5-methoxy-1H-indazol-3-yl)ethyl)-N-methylcyclopropanamine (A8)

To a solution of crude N-(2-(6-fluoro-5-methoxy-1-((2-(trimethylsilyl)ethoxy)methyl)-1H-indazol-3-yl)ethyl)-N-methylcyclopropanamine (500 mg) and tetrabutylammonium fluoride (1 M in THF, 6.35 mL, 6.35 mmol) in THF (5 mL) was added ethylenediamine (420 mg, 6.99 mmol). The reaction was stirred at 60° C. for 16 h and then the cooled reaction was filtered and the filtrate was concentrated in vacuo. The residue was purified by prep-HPLC (column: Phenomenex Luna C18, 100×40 mm, 3 μm; mobile phase: [H₂O (0.2% formic acid)-MeCN]; gradient: 1%-40% B over 8.00 min) to afford the title compound as a white solid (30 mg, 7% over 2 steps). LCMS (Condition B): $t_R$ (1.685 min) m/z=264.1 [M+H]⁺; ¹H NMR (400 MHz, DMSO-d₆): δ8.16 (s, 1H), 7.30-7.27 (m, 2H), 3.86 (s, 3H), 3.06-3.01 (m, 2H), 2.89-2.85 (m, 2H), 2.35 (s, 3H), 1.73-1.71 (m, 1H), 0.48-0.42 (m, 2H), 0.30-0.24 (m, 2H); ¹⁹F NMR (376 MHz, CDCl₃): δ −133.4.

Example 9: Synthesis of 2-(4-fluoro-5-methoxy-1H-indazol-3-yl)-N,N-dimethylethan-1-amine (A9)

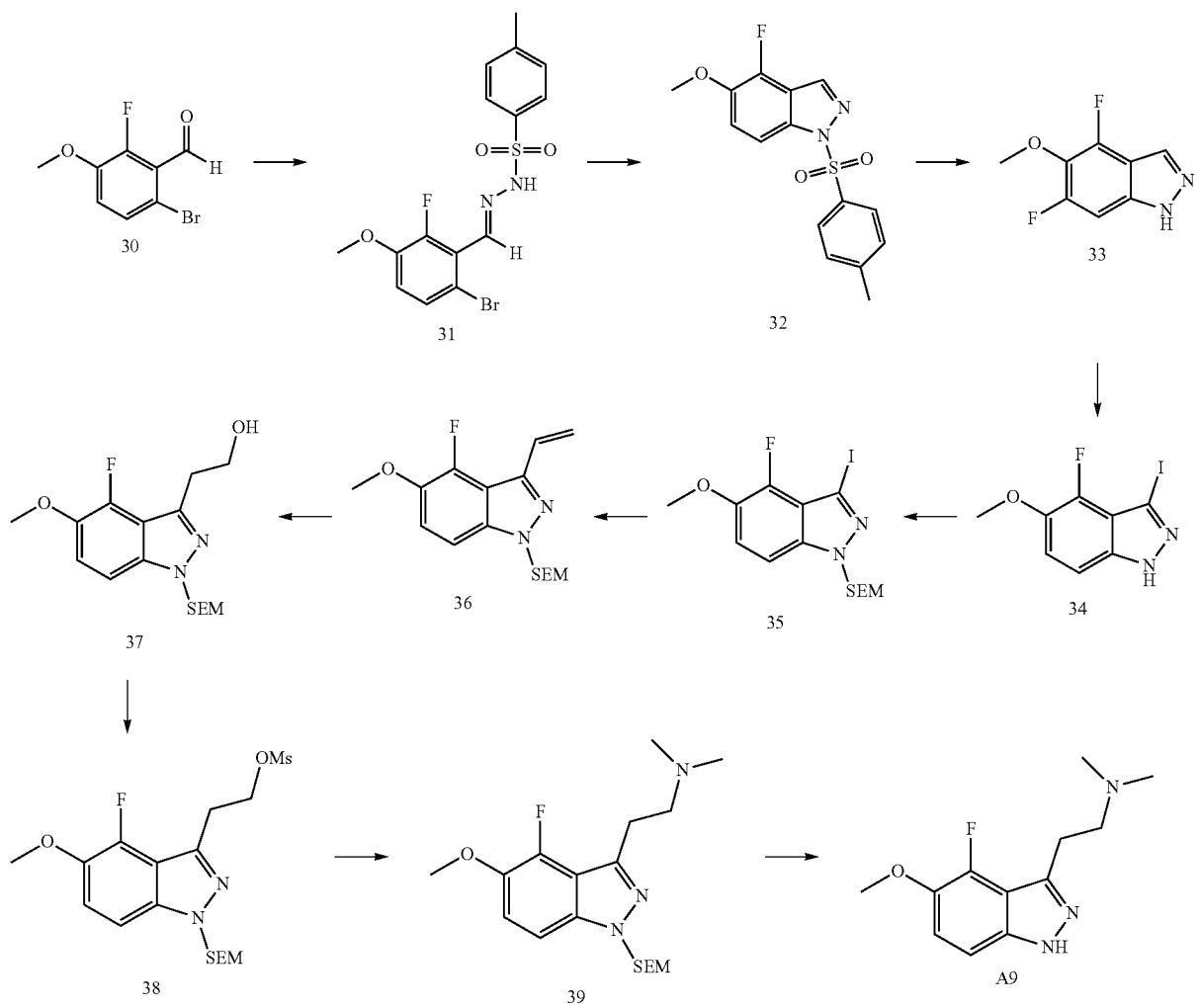

Step 1: (E)-N-(6-bromo-2-fluoro-3-methoxybenzylidene)-4-methylbenzenesulfonohydrazide (31)

In two batches: a stirred suspension of 6-bromo-2-fluoro-3-methoxybenzaldehyde (5.0 g, 21.5 mmol) in methanol (25 mL) was added 4-methylbenzenesulfonohydrazide (4.2 g, 21.5 mmol) at RT under nitrogen atmosphere and the resulting mixture was stirred at RT for 16 h. TLC indicated consumption of the starting material so the mixture was concentrated in vacuo and the two batches were combined to afford the crude title compound (8.6 g) which was used in the next step without further purification.

Step 2: 4-fluoro-5-methoxy-1-tosyl-1H-indazole (32)

A mixture of crude (E)-N-(6-bromo-2-fluoro-3-methoxybenzylidene)-4-methylbenzenesulfonohydrazide (8.6 g) and Cu$_2$O (1.53 g, 10.7 mmol) in isoamyl alcohol (25 mL) was stirred at reflux for 1 h. The cooled reaction mixture diluted with H$_2$O (200 mL) and extracted with EtOAc (3×100 mL). The combined organic layer was dried over anhydrous Na$_2$SO$_4$ and concentrated in vacuo. The residue was triturated with n-pentane to afford an off-white solid which was collected by vacuum filtration and identified as the title compound (10.0 g, 73% over 2 steps). $^1$H NMR (400 MHz, DMSO-d$_6$): δ 8.64 (s, 1H), 7.89 (d, J=9.2 Hz, 1H), 7.79 (d, J=8.4 Hz, 2H), 7.65-7.59 (m, 1H), 7.39 (d, J=8.0 Hz, 2H), 3.91 (s, 3H), 2.32 (s, 3H).

Step 3: 4-fluoro-5-methoxy-1H-indazole (33)

In five batches: a solution of 4-fluoro-5-methoxy-1-tosyl-1H-indazole (2.0 g, 6.24 mmol) in DMSO (7 mL) and water (7 mL) was treated with K$_2$CO$_3$ (2.6 g, 18.8 mmol) and the resulting mixture was stirred at 110° C. for 2 h. The cooled reaction mixture was then diluted with ice-cold H$_2$O (200 mL) and the solid was collected by vacuum filtration. The solid from five batches were combined and identified as the title compound (3.5 g, 68%). $^1$H NMR (400 MHz, DMSO-d$_6$): δ13.25 (s, 1H), 8.11 (s, 1H), 7.34-7.31 (m, 2H), 3.87 (s, 3H).

Step 4: 4-fluoro-3-iodo-5-methoxy-1H-indazole (34)

To a solution of 4-fluoro-5-methoxy-1H-indazole (3.5 g, 21.1 mmol) in DMF (20 mL) was added N-iodosuccinimide (7.1 g, 31.6 mmol). The reaction mixture was stirred at RT for 3 h until TLC indicated consumption of the starting material. The reaction was poured into ice-cold $H_2O$ (250 mL) and the grey solid was collected, dried under vacuum and identified as the title compound (6.15 g, quant.). $^1H$ NMR (400 MHz, DMSO-$d_6$): δ13.57 (s, 1H), 7.41-7.33 (m, 2H), 3.87 (s, 3H).

Step 5: 4-fluoro-3-iodo-5-methoxy-1-((2-(trimethylsilyl)ethoxy)methyl)-1H-indazole (35)

To an ice-cold solution of 4-fluoro-3-iodo-5-methoxy-1H-indazole (6.15 g, 21.1 mmol) in DMF (30 mL) was added NaH (60% w/w dispersion in mineral oil, 0.86 g, 34.0 mmol) and stirred cold for 15 min before 2-(trimethylsilyl)ethoxymethyl chloride (7.99 g, 47.9 mmol) was added under nitrogen atmosphere. The reaction was stirred at RT for 1.5 h and TLC indicated consumption of the starting material. The reaction mixture was poured into ice-cold $H_2O$ (200 mL) and then extracted with EtOAc (3×100 mL). The combined organic layer was dried over anhydrous $Na_2SO_4$ and concentrated in vacuo. The residue was purified by column chromatography (0% to 5% EtOAc in hexane) to afford the title compound as a yellow oil (2.6 g, 29%). $^1H$ NMR (400 MHz, DMSO-$d_6$): δ 7.59-7.48 (m, 1H), 7.37-7.32 (m, 1H), 5.74 (s, 2H), 3.89 (s, 3H), 3.61 (t, J=7.6 Hz, 2H), 0.84 (t, J=8.0 Hz, 2H), −0.06 (s, 9H).

Step 6: 4-fluoro-5-methoxy-1-((2-(trimethylsilyl)ethoxy)methyl)-3-vinyl-1H-indazole (36)

In two batches: a solution of 4-fluoro-3-iodo-5-methoxy-1-((2-(trimethylsilyl)ethoxy)methyl)-1H-indazole (0.5 g, 1.18 mmol) and 4,4,5,5-tetramethyl-2-vinyl-1,3,2-dioxaborolane (180 mg, 1.18 mmol) in THF (4 mL) was added $K_2CO_3$ (490 mg, 3.55 mmol), pre-dissolved in $H_2O$ (1 mL). The reaction mixture was sparged with nitrogen gas for 15 min before Pd(dppf)$Cl_2$ (40 mg, 0.05 mmol) was added under nitrogen atmosphere. The mixture was stirred at 95° C. for 16 h under nitrogen atmosphere and the cooled reaction mixture was poured into $H_2O$ (50 mL) before being extracted with EtOAc (3 50 mL). The combined organic layer was dried over anhydrous $Na_2SO_4$ and concentrated in vacuo. The residue was purified by column chromatography (0% to 8% EtOAc in hexane) and the yellow oil obtained from both batches were combined and identified as the title compound (500 mg, 66%). $^1H$ NMR (400 MHz, DMSO-$d_6$): δ 7.58-7.42 (m, 2H), 7.02-6.95 (m, 1H), 6.08 (d, J=17.6 Hz, 1H), 5.72 (s, 2H), 5.48 (d, J=11.6 Hz, 1H), 3.90 (s, 3H), 3.54-3.48 (m, 2H), 0.80 (t, J=7.6 Hz, 2H), −0.10 (s, 9H).

Step 7: 2-(4-fluoro-5-methoxy-1-((2-(trimethylsilyl)ethoxy)methyl)-1H-indazol-3-yl)ethan-1-ol (37)

To an ice-cold solution of 4-fluoro-5-methoxy-1-((2-(trimethylsilyl)ethoxy)methyl)-3-vinyl-1H-indazole (500 mg, 1.55 mmol) in THF (5 mL) was added 9-borabicyclo[3.3.1]nonane (0.5 M in THF, 25 mL, 12.5 mmol) under nitrogen atmosphere. The reaction was then stirred at RT for 6 h. The reaction was then cooled in an ice bath and treated dropwise with $H_2O_2$ (30% w/w in $H_2O$, 12 mL, 394 mmol) and 4 M aq. NaOH (2.5 mL) before being stirred at RT for 16 h. The reaction was then poured into $H_2O$ (100 mL) before being extracted with EtOAc (3 100 mL). The combined organics were dried over anhydrous $Na_2SO_4$ and concentrated in vacuo. The residue was purified by column chromatography (0% to 25% EtOAc in hexane) to afford the title compound as a yellow oil (200 mg, 38%). $^1H$ NMR (400 MHz, DMSO-$d_6$): δ 7.45-7.37 (m, 2H), 5.64 (s, 2H), 4.74 (t, J=5.6 Hz, 1H), 3.87 (s, 3H), 3.78-3.71 (m, 2H), 3.49 (t, J=8.0 Hz, 2H), 3.07 (t, J=7.2 Hz, 2H), 0.78 (t, J=8.0 Hz, 2H), −0.10 (s, 9H).

Step 8: 2-(4-fluoro-5-methoxy-1-((2-(trimethylsilyl)ethoxy)methyl)-1H-indazol-3-yl)ethyl methanesulfonate (38)

2-(4-fluoro-5-methoxy-1-((2-(trimethylsilyl)ethoxy)methyl)-1H-indazol-3-yl)ethyl methanesulfonate was synthesised according to General Method A with 2-(4-fluoro-5-methoxy-1-((2-(trimethylsilyl)ethoxy)methyl)-1H-indazol-3-yl)ethan-1-ol (140 mg, 0.42 mmol), methanesulfonyl chloride (0.3 mL, 3.84 mmol) and $Et_3N$ (1.0 mL, 7.23 mmol). After column chromatography (0% to 25% EtOAc in hexane) the title compound was obtained as a yellow oil (100 mg, 56%). $^1H$ NMR (400 MHz, DMSO-$d_6$): δ 7.51-7.41 (m, 2H), 5.68 (s, 2H), 4.57 (t, J=6.4 Hz, 2H), 3.89 (s, 3H), 3.50 (t, J=7.6 Hz, 2H), 3.38-3.34 (m, 2H), 3.14 (s, 3H), 0.80 (t, J=7.2 Hz, 2H), −0.09 (s, 9H).

Step 9: 2-(4-fluoro-5-methoxy-1-((2-(trimethylsilyl)ethoxy)methyl)-1H-indazol-3-yl)-N,N-dimethylethan-1-amine (39)

2-(4-fluoro-5-methoxy-1-((2-(trimethylsilyl)ethoxy)methyl)-1H-indazol-3-yl)-N,N-dimethylethan-1-amine was synthesised according to General Method B with 2-(4-fluoro-5-methoxy-1-((2-(trimethylsilyl)ethoxy)methyl)-1H-indazol-3-yl)ethyl methanesulfonate (230 mg, 0.54 mmol), $K_2CO_3$ (760 mg, 5.49 mmol) and N,N-dimethylamine hydrochloride (120 mg, 2.75 mmol). The title compound was obtained as a yellow oil (130 mg, 63%) which was used in the next step without further purification. $^1H$ NMR (400 MHz, DMSO-$d_6$): δ 7.45-7.39 (m, 2H), 5.64 (s, 2H), 3.87 (s, 3H), 3.48 (t, J=8.0 Hz, 2H), 3.04 (t, J=7.6 Hz, 2H), 2.60 (t, J=8.0, 2H), 2.18 (s, 6H), 0.77 (t, J=8.0 Hz, 2H), −0.10 (s, 9H).

Step 10: 2-(4-fluoro-5-methoxy-1H-indazol-3-yl)-N,N-dimethylethan-1-amine (A9)

The title compound was synthesised according to General Procedure C utilising 2-(4-fluoro-5-methoxy-1-((2-(trimethylsilyl)ethoxy)methyl)-1H-indazol-3-yl)-N,N-dimethylethan-1-amine (130 mg, 0.35 mmol) which upon reverse phase purification (product eluted at 36% MeCN in $H_2O$) generated the title compound as a white solid (30 mg, 36%). LCMS (Condition C): $t_R$ (1.031 min) m/z=237.93 [M+H]$^+$; $^1H$ NMR (400 MHz, DMSO-$d_6$): δ 12.78 (s, 1H), 7.32-7.25 (m, 1H), 7.21 (d, J=8.8 Hz, 1H), 3.87 (s, 3H), 3.05 (t, J=7.6 Hz, 2H), 2.61 (t, J=7.6 Hz, 2H), 2.20 (s, 6H).

Example 10: Synthesis of N-ethyl-2-(4-fluoro-5-methoxy-1H-indazol-3-yl)-N-methylethan-1-amine (A10)

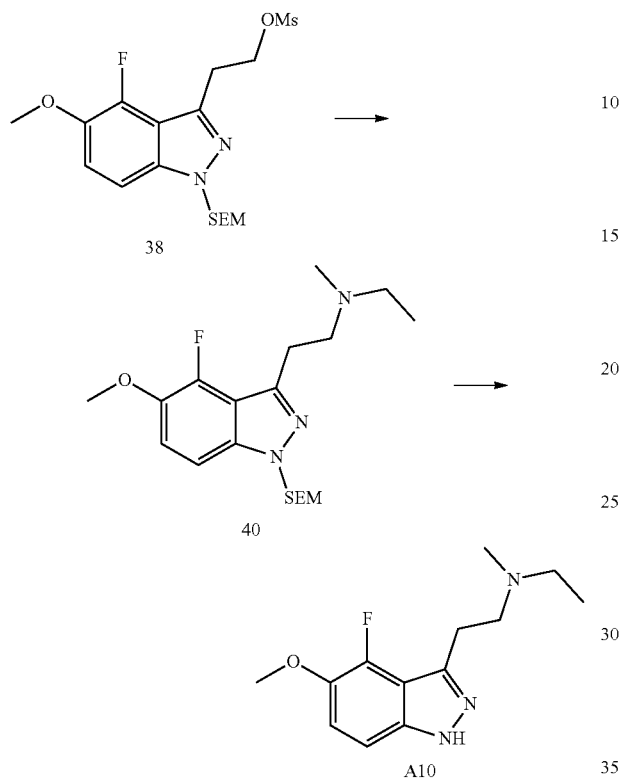

Step 1: N-ethyl-2-(4-fluoro-5-methoxy-1-((2-(trimethylsilyl)ethoxy)methyl)-1H-indazol-3-yl)-N-methylethan-1-amine (40)

N-ethyl-2-(4-fluoro-5-methoxy-1-((2-(trimethylsilyl)ethoxy)methyl)-1H-indazol-3-yl)-N-methylethan-1-amine was synthesised according to General Procedure B with 2-(4-fluoro-5-methoxy-1-((2-(trimethylsilyl)ethoxy)methyl)-1H-indazol-3-yl)ethyl methanesulfonate (400 mg, 0.95 mmol), $K_2CO_3$ (1.32 g, 95.5 mmol) and N-methylethanamine (0.40 mL, 4.77 mmol). The title compound was obtained as a yellow oil (360 mg, quant.) which was used in the next step without further purification. $^1$H NMR (400 MHz, DMSO-$d_6$): δ 7.46-7.37 (m, 2H), 5.64 (s, 2H), 3.87 (s, 3H), 3.48 (t, J=8.0 Hz, 2H), 3.05 (t, J=7.2 Hz, 2H), 2.69 (t, J=8.0 Hz, 2H), 2.51 (q, J=7.2 Hz, 2H), 2.21 (s, 3H), 0.96 (t, J=7.2 Hz, 3H), 0.77 (t, J=8.0 Hz, 2H), −0.10 (s, 9H).

Step 2: N-ethyl-2-(4-fluoro-5-methoxy-1H-indazol-3-yl)-N-methylethan-1-amine (A10)

The title compound was synthesised according to General Procedure C utilising N-ethyl-2-(4-fluoro-5-methoxy-1-((2-(trimethylsilyl)ethoxy)methyl)-1H-indazol-3-yl)-N-methylethan-1-amine (360 mg, 0.95 mmol) which upon reverse phase purification (product eluted at 35% MeCN in $H_2O$) generated the title compound as a white solid (150 mg, 63%). LCMS (Condition C): $t_R$ (1.072 min) m/z=251.73 [M+H]$^+$; $^1$H NMR (400 MHz, DMSO-$d_6$): δ 12.78 (s, 1H), 7.30-7.20 (m, 2H), 3.85 (s, 3H), 3.04 (t, J=8.0 Hz, 2H), 2.67 (t, J=8.0 Hz, 2H), 2.41 (q, J=7.2 Hz, 2H), 2.21 (s, 3H), 0.96 (t, J=7.2 Hz, 3H).

Example 11: Synthesis of N-(2-(4-fluoro-5-methoxy-1H-indazol-3-yl)ethyl)-N-methylpropan-2-amine (A11)

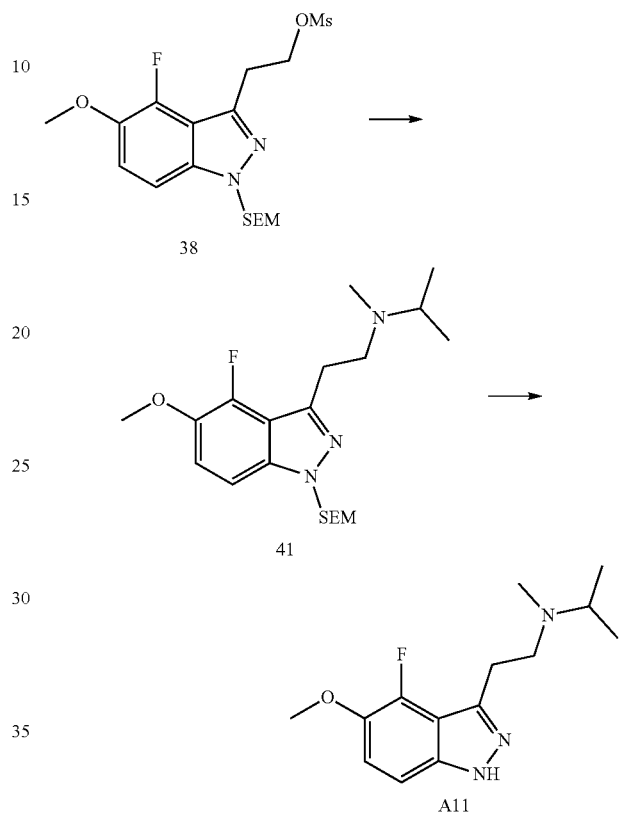

Step 1: N-(2-(4-fluoro-5-methoxy-1-((2-(trimethylsilyl)ethoxy)methyl)-1H-indazol-3-yl)ethyl)-N-methylpropan-2-amine (41)

N-(2-(4-fluoro-5-methoxy-1-((2-(trimethylsilyl)ethoxy)methyl)-1H-indazol-3-yl)ethyl)-N-methylpropan-2-amine was synthesised according to General Procedure B with 2-(4-fluoro-5-methoxy-1-((2-(trimethylsilyl)ethoxy)methyl)-1H-indazol-3-yl)ethyl methanesulfonate (400 mg, 0.95 mmol), $K_2CO_3$ (1.32 g, 95.5 mmol) and N-methylpropan-2-amine (0.48 mL, 4.77 mmol). The title compound was obtained as a yellow oil (370 mg, quant.) which was used in the next step without further purification. $^1$H NMR (400 MHz, DMSO-$d_6$): δ 7.45-7.36 (m, 2H), 5.64 (s, 2H), 3.87 (s, 3H), 3.48 (t, J=8.0 Hz, 2H), 3.01 (t, J=7.2 Hz, 2H), 2.80-2.77 (m, 1H), 2.71-2.67 (m, 2H), 2.20 (s, 3H), 0.90 (d, J=6.8 Hz, 6H), 0.77 (t, J=8.0 Hz, 2H), −0.11 (s, 9H).

Step 2: N-(2-(4-fluoro-5-methoxy-1H-indazol-3-yl)ethyl)-N-methylpropan-2-amine (A11)

The title compound was synthesised according to General Procedure C utilising N-(2-(4-fluoro-5-methoxy-1-((2-(trimethylsilyl)ethoxy)methyl)-1H-indazol-3-yl)ethyl)-N-methylpropan-2-amine (370 mg, 0.95 mmol) which upon reverse phase purification (product eluted at 35% MeCN in $H_2O$) generated the title compound as a white solid (140 mg, 56%). LCMS (Condition C): $t_R$ (1.105 min) m/z=265.73 [M+H]$^+$; $^1$H NMR (400 MHz, DMSO-d$_6$): δ 12.78 (s, 1H), 7.31-7.20 (m, 2H), 3.85 (s, 3H), 3.02 (t, J=7.2 Hz, 2H), 2.83-2.76 (m, 1H), 2.68 (t, J=7.2 Hz, 2H), 2.21 (s, 3H), 0.92 (d, J=6.4 Hz, 6H).

Example 13: Synthesis of 2-(4-fluoro-1H-indazol-3-yl)-N,N-dimethylethan-1-amine (A13)

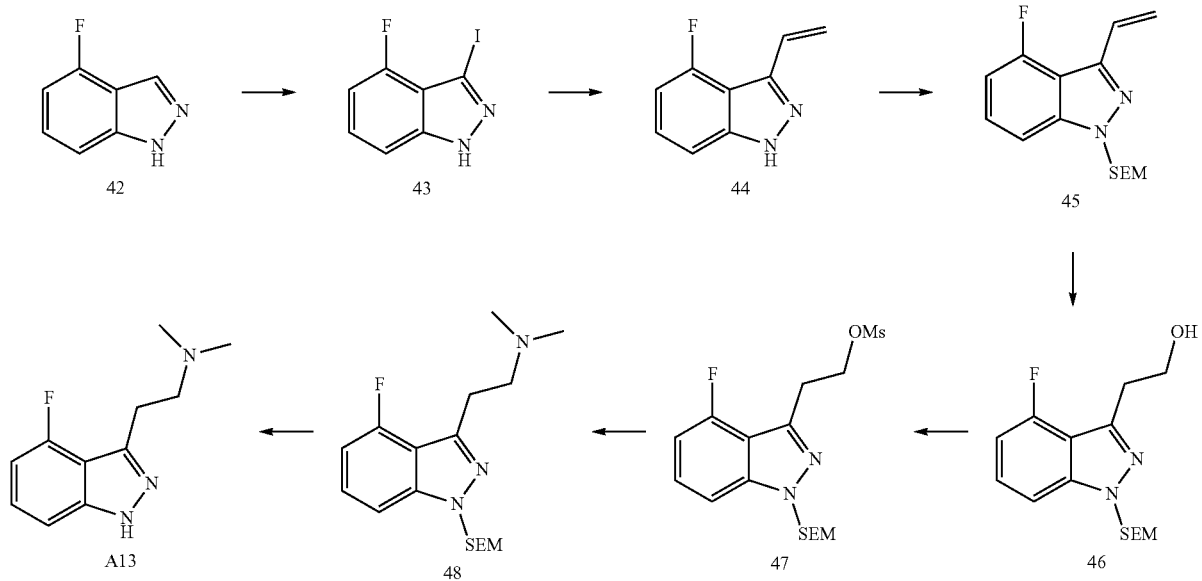

Step 1: 4-fluoro-3-iodo-1H-indazole (43)

To a solution of 4-fluoro-1H-indazole (2.5 g, 18.4 mmol) in MeOH (65 mL) and 2 M aq. NaOH (65 mL) was added 12 (6.99 g, 55.1 mmol) portionwise over a period of 20 min. The reaction mixture was stirred for 2 h until TLC indicated consumption of the starting material. 35% aq. HCl (7.5 mL) was added dropwise at 0° C. and the pH was then adjusted to 2-3 with 2M aq. HCl. Saturated aq. Na$_2$S$_2$O$_3$ (20 mL) was added until the iodine colour disappeared. The precipitate was filtered, washed with water, and then taken up in methanol (200 mL). The mixture was stirred for 5 min before the insoluble material was removed by vacuum filtration and washed with additional methanol until TLC indicated no further product was being dissolved from the residue. The combined filtrate was concentrated and the resulting aqueous suspension was extracted with CH$_2$Cl$_2$ (100 mL). The organic layer was dried over anhydrous Na$_2$SO$_4$ and concentrated in vacuo to afford the title compound as a white solid (4.8 g, quant.). $^1$H NMR (400 MHz, MeOD-d$_4$): δ 7.44-7.31 (m, 2H), 6.86-6.72 (m, 1H).

Step 2: 4-fluoro-3-vinyl-1H-indazole (44)

A solution of 4-fluoro-3-iodo-1H-indazole (6.5 g, 24.8 mmol) in 1,4-dioxane (180 mL) and H$_2$O (38 mL) was sparged with nitrogen gas for 20 min. K$_2$CO$_3$ (6.9 g, 49.6 mmol) and 4,4,5,5-tetramethyl-2-vinyl-1,3,2-dioxaborolane (5.1 mL, 29.8 mmol) was added and the mixture was further sparged with nitrogen for 5 min before Pd(dppf)Cl$_2$ (1.82 g, 2.48 mmol) was added. The reaction was then stirred at 100° C. for 16 h under nitrogen atmosphere. The cooled reaction mixture was filtered through a plug of celite, which was washed through with EtOAc until TLC indicated all the desired product had eluted from plug. The filtrate was concentrated in vacuo and the residue was purified by flash chromatography (0% to 20% EtOAc in hexane) to afford the title compound as a yellow solid (3.4 g, 85%). $^1$H NMR (400 MHz, CDCl$_3$): δ 7.35-7.28 (m, 1H), 7.24 (d, J=8.4 Hz, 1H), 7.13 (ddd, J=17.8, 11.4, 1.8 Hz, 1H), 6.82 (ddd, J=10.8, 7.6, 0.7 Hz, 1H), 6.26 (dt, J=17.8, 1.3 Hz, 1H), 5.53 (ddd, J=11.4, 2.6, 1.4 Hz, 1H).

Step 3: 4-fluoro-1-((2-(trimethylsilyl)ethoxy)methyl)-3-vinyl-1H-indazole (45)

To an ice-cold solution of 4-fluoro-3-vinyl-1H-indazole (3.4 g, 21.0 mmol) in THF (80 mL) was added NaH (60% w/w dispersion in mineral oil, 0.92 g, 23.1 mmol) and stirred cold for 15 min before 2-(trimethylsilyl)ethoxymethyl chloride (4.4 mL, 23.1 mmol) was added under nitrogen atmosphere. The reaction was stirred at 0° C. for 1 h and TLC indicated consumption of the starting material. The reaction mixture was quenched by dropwise addition of H$_2$O until effervescence ceased. The mixture was diluted with EtOAc (100 mL), the layers separated, and the organic layer was washed with H$_2$O (2×50 mL), and then brine (20 mL) before being dried over anhydrous MgSO$_4$ and concentrated in vacuo. The residue was purified by flash chromatography (0% to 20% EtOAc in hexane) to afford the title compound as a yellow oil (3.53 g, 58%). $^1$H NMR (300 MHz, CDCl$_3$): δ 7.37-7.28 (m, 2H), 7.08 (ddd, J=17.8, 11.4, 1.9 Hz, 1H), 6.84 (ddd, J=10.8, 5.8, 2.6 Hz, 1H), 6.24 (dt, J=17.8, 1.4 Hz, 1H), 5.69 (s, 2H), 5.50 (ddd, J=11.4, 2.7, 1.5 Hz, 1H), 3.61-3.53 (m, 2H), 0.97-0.81 (m, 2H), −0.06 (s, 9H).

Step 4: 2-(4-fluoro-1-((2-(trimethylsilyl)ethoxy)methyl)-1H-indazol-3-yl)ethan-1-ol (46)

An ice-cold solution of 4-fluoro-1-((2-(trimethylsilyl)ethoxy)methyl)-3-vinyl-1H-indazole (3.53 g, 12.1 mmol) in anhydrous THF (17 mL) was treated with 9-borabicyclo[3.3.1]nonane (0.5 M in THF, 60.4 mL, 30.2 mmol) and the mixture was stirred at RT for 16 h. The reaction was cooled to 0° C. and 4 M aq. NaOH (30.2 mL, 121 mmol) and $H_2O_2$ (30% w/w in $H_2O$, 13.7 mL, 121 mmol) were added in an alternating manner at a rate that maintained a gentle effervescence and a temperature below the boiling point of THF. The mixture was then stirred at RT for 2 h. The reaction was quenched by addition of saturated aq. $Na_2S_2O_3$ and then extracted with EtOAc (3×20 mL). The combined organic layer was washed with brine (20 mL), dried over anhydrous $Na_2SO_4$ and concentrated in vacuo. The residue was purified by flash chromatography (0% to 20% EtOAc in hexane) to afford the title compound as a colourless oil (3.2 g, 86%). $^1$H NMR (400 MHz, $CDCl_3$): δ 7.37-7.27 (m, 2H), 6.79 (ddd, J=10.4, 7.3, 1.0 Hz, 1H), 5.66 (s, 2H), 4.08 (t, J=6.2 Hz, 2H), 3.60-3.51 (m, 2H), 3.31 (t, J=5.9 Hz, 2H), 0.93-0.84 (m, 2H), −0.06 (s, 9H).

Step 5: 2-(4-fluoro-1-((2-(trimethylsilyl)ethoxy)methyl)-1H-indazol-3-yl)ethyl methanesulfonate (47)

2-(4-fluoro-1-((2-(trimethylsilyl)ethoxy)methyl)-1H-indazol-3-yl)ethyl methanesulfonate was synthesised according to General Procedure A with 2-(4-fluoro-1-((2-(trimethylsilyl)ethoxy)methyl)-1H-indazol-3-yl)ethan-1-ol (3.2 g, 10.3 mmol), $Et_3N$ (2.2 mL, 15.5 mmol) and methanesulfonyl chloride (0.96 mL, 12.4 mmol). The title compound was obtained as a colourless oil (3.96 g, quant.) which was used in the next step without further purification. $^1$H NMR (400 MHz, $CDCl_3$): δ 7.37-7.28 (m, 2H), 6.82 (ddd, J=10.4, 7.2, 1.1 Hz, 1H), 5.65 (s, 2H), 4.67 (t, J=7.0 Hz, 2H), 3.59-3.46 (m, 4H), 2.97 (s, 3H), 0.93-0.84 (m, 2H), −0.06 (s, 9H).

Step 6: 2-(4-fluoro-1-((2-(trimethylsilyl)ethoxy)methyl)-1H-indazol-3-yl)-N,N-dimethylethan-1-amine (48)

2-(4-fluoro-1-((2-(trimethylsilyl)ethoxy)methyl)-1H-indazol-3-yl)-N,N-dimethylethan-1-amine was synthesised according to General Procedure B with 2-(4-fluoro-1-((2-(trimethylsilyl)ethoxy)methyl)-1H-indazol-3-yl)ethyl methanesulfonate (222 mg, 0.57 mmol), $K_2CO_3$ (790 mg, 5.71 mmol) and N,N-dimethylamine (2 M in THF, 2.9 mL, 5.71 mmol). The title compound was obtained as a yellow oil (84.7 mg, 0.25 mmol) and used in the next step without further purification. $^1$H NMR (400 MHz, $CDCl_3$): δ 7.31-7.22 (m, 2H), 6.76 (ddd, J=10.4, 7.1, 1.2 Hz, 1H), 5.63 (s, 2H), 3.59-3.43 (m, 2H), 3.29-3.14 (m, 2H), 2.86-2.74 (m, 2H), 2.35 (s, 6H), 0.89-0.82 (m, 2H), −0.08 (s, 9H).

Step 7: 2-(4-fluoro-1H-indazol-3-yl)-N,N-dimethylethan-1-amine (A13)

To an ice-cold solution of 2-(4-fluoro-1-((2-(trimethylsilyl)ethoxy)methyl)-1H-indazol-3-yl)-N,N-dimethylethan-1-amine (80 mg, 0.24 mmol) in MeOH (3 mL) was added 37% aq. HCl (1.5 mL) and the reaction mixture was stirred at 80° C. 16 h. The cooled reaction was quenched by dropwise addition of 5 M aq. NaOH (3 mL) and then concentrated under a stream of nitrogen gas. The remaining aqueous mixture was extracted with EtOAc (3×10 mL) and the combined organic layer was washed with brine (10 mL), before being dried over anhydrous $MgSO_4$ and concentrated in vacuo to afford the title compound as a yellow solid (47 mg, 0.23 mmol). $^1$H NMR (400 MHz, $CDCl_3$): δ 7.10-7.00 (m, 1H), 6.90-6.82 (m, 1H), 6.62 (dd, J=10.6, 7.6 Hz, 1H), 3.26 (t, J=7.3 Hz, 2H), 2.88 (t, J=7.3 Hz, 2H), 2.40 (s, 6H).

Step 8: 2-(4-fluoro-1H-indazol-3-yl)-N,N-dimethylethan-1-amine fumarate (A13·fumarate)

2-(4-fluoro-1H-indazol-3-yl)-N,N-dimethylethan-1-amine (47 mg, 0.23 mmol) was formulated as the fumarate salt as per General Procedure F (41.5 mg, 69%) as a white crystalline solid. LCMS (Condition A): $t_R$ (3.901 min) m/z=208.15 [M+H]$^+$; $^1$H NMR (400 MHz, DMSO-$d_6$): δ 7.35-7.23 (m, 2H), 6.81 (ddd, J=11.0, 4.9, 3.3 Hz, 1H), 6.51 (s, 1H), 3.22-3.11 (m, 2H), 2.91-2.77 (m, 2H), 2.37 (s, 6H); $^{13}$C NMR (101 MHz, DMSO-$d_6$): δ 167.3, 155.7 (d, J=248.2 Hz), 144.0 (d, J=9.3 Hz), 140.7, 134.8, 127.3 (d, J=7.8 Hz), 111.2 (d, J=21.7 Hz), 106.8, 104.1 (d, J=18.8 Hz), 57.7, 44.1, 25.2; $^1$H qNMR Purity: 100% (ERETIC).

Example 17: Synthesis of 2-(5-fluoro-1H-indazol-3-yl)-N,N-dimethylethan-1-amine (A17)

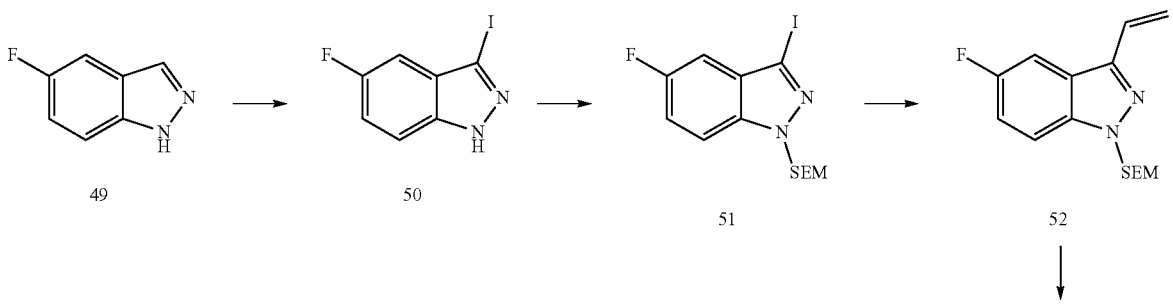

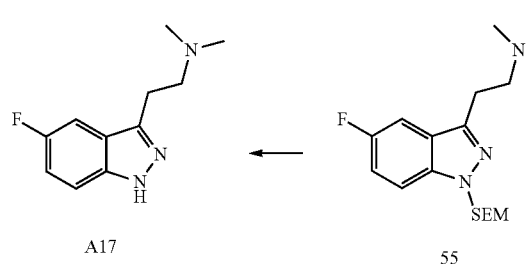
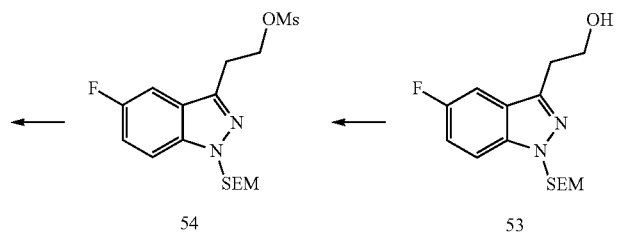

Step 1: 5-fluoro-3-iodo-1H-indazole (50)

To a mixture of 5-fluoro-1H-indazole (15 g, 110 mmol), KOH (30.9 g, 550 mmol), and 12 (83.9 g, 330 mmol) was stirred at RT for 6 h under nitrogen atmosphere. The reaction was diluted with $H_2O$ (500 mL) and then extracted with EtOAc (3×100 mL). The combined organic layer was dried over anhydrous $Na_2SO_4$ and concentrated in vacuo. The residue was purified by column chromatography (1% to 25% EtOAc in petroleum ether) to afford the title compound as a brown oil (20 g, 69%). LCMS: m/z=263.0 [M+H]+.

Step 2: 5-fluoro-3-iodo-1-((2-(trimethylsilyl)ethoxy)methyl)-1H-indazole (51)

To an ice-cold solution of 5-fluoro-3-iodo-1H-indazole (8.0 g, 30.5 mmol) in THF (80 mL) was added NaH (60% w/w dispersion in mineral oil, 1.22 g, 30.5 mmol) and 2-(trimethylsilyl)ethoxymethyl chloride (5.9 mL, 33.5 mmol) was added under nitrogen atmosphere. The reaction was stirred at RT for 3 h and TLC indicated consumption of the starting material. The reaction mixture was quenched by dropwise addition of $H_2O$ (300 mL) and then extracted with EtOAc (3×100 mL). The combined organic layer was dried over anhydrous $Na_2SO_4$ and concentrated in vacuo. The residue was purified by column chromatography (2% to 25% EtOAc in petroleum ether) to afford the title compound as a brown oil (10.0 g, 83%). $^1$H NMR (300 MHz, $CDCl_3$): δ 7.65-7.61 (m, 1H), 7.39-7.31 (m, 1H), 7.27-7.24 (m, 1H), 5.82 (s, 2H), 3.70-3.64 (m, 2H), 1.01-0.97 (m, 2H), 0.06 (s, 9H).

Step 3: 5-fluoro-1-((2-(trimethylsilyl)ethoxy)methyl)-3-vinyl-1H-indazole (52)

A mixture of 5-fluoro-3-iodo-1-((2-(trimethylsilyl)ethoxy)methyl)-1H-indazole (9.0 g, 22.9 mmol), $K_2CO_3$ (9.5 g, 68.8 mmol), 4,4,5,5-tetramethyl-2-vinyl-1,3,2-dioxaborolane (3.53 g, 22.9 mmol), and Pd(dppf)$Cl_2$ (840 mg, 1.15 mmol) was purged and backfilled with nitrogen gas three times and then stirred at 90° C. for 12 h under nitrogen atmosphere.

The cooled reaction mixture was concentrated in vacuo and then the residue was diluted with $H_2O$ (500 mL) and extracted with EtOAc (3×150 mL). The combined organic layer was dried over anhydrous $Na_2SO_4$ and concentrated in vacuo. The residue was purified by column chromatography (2% to 17% EtOAc in petroleum ether) to afford the title compound as a brown oil (5.0 g, 75%). $^1$H NMR (400 MHz, $CDCl_3$): δ 7.64-7.56 (m, 2H), 7.28-7.26 (m, 1H), 7.10-7.03 (m, 1H), 6.13-6.08 (m, 1H), 5.76 (s, 2H), 5.63-5.60 (m, 1H), 3.65-3.61 (m, 2H), 0.98-0.94 (m, 2H), 0.01 (s, 9H).

Step 4: 2-(5-fluoro-1-((2-(trimethylsilyl)ethoxy)methyl)-1H-indazol-3-yl)ethan-1-ol (53)

An ice-cold solution of 5-fluoro-1-((2-(trimethylsilyl)ethoxy)methyl)-3-vinyl-1H-indazole (2.0 g, 6.84 mmol) in anhydrous THF (20 mL) was treated with 9-borabicyclo[3.3.1]nonane (5.01 g, 41.0 mmol) and the mixture was stirred at RT for 2 h. The reaction was then cooled to 0° C. and 4 M aq. NaOH (10 mL, 40 mmol) and $H_2O_2$ (30% w/w in $H_2O$, 10 mL, 88 mmol) was added dropwise. The mixture was then stirred at RT for 12 h. The reaction was diluted with $H_2O$ (100 mL) and then extracted with EtOAc (3×50 mL). The combined organic layer was dried over anhydrous $Na_2SO_4$ and concentrated in vacuo. The residue was purified by column chromatography (2% to 17% EtOAc in petroleum ether) to afford the title compound as a brown oil (1.8 g, 85%). LCMS: m/z=311.3 [M+H]+. $^1$H NMR (400 MHz, $CDCl_3$): δ 7.56-7.53 (m, 1H), 7.40-7.37 (m, 1H), 7.28-7.23 (m, 1H), 5.73 (s, 2H), 4.20-4.12 (m, 2H), 3.64-3.59 (m, 2H), 3.25-3.21 (m, 2H), 1.36-1.31 (m, 1H), 0.98-0.93 (m, 2H), 0.01 (s, 9H).

Step 5: 2-(5-fluoro-1-((2-(trimethylsilyl)ethoxy)methyl)-1H-indazol-3-yl)ethyl methanesulfonate (54)

2-(5-fluoro-1-((2-(trimethylsilyl)ethoxy)methyl)-1H-indazol-3-yl)ethyl methanesulfonate was synthesised according to General Procedure A with 2-(5-fluoro-1-((2-(trimethylsilyl)ethoxy)methyl)-1H-indazol-3-yl)ethan-1-ol (1.8 g, 5.80 mmol), $Et_3N$ (1.6 mL, 11.6 mmol) and methanesulfonyl chloride (0.78 mL, 10.1 mmol). After column chromatography (2% to 17% EtOAc in petroleum ether) the title compound was obtained as a brown oil (2.0 g, 89%).

Step 6: 2-(5-fluoro-1-((2-(trimethylsilyl)ethoxy)methyl)-1H-indazol-3-yl)-N,N-dimethylethan-1-amine (55)

2-(5-fluoro-1-((2-(trimethylsilyl)ethoxy)methyl)-1H-indazol-3-yl)-N,N-dimethylethan-1-amine was synthesised according to General Procedure B with 2-(5-fluoro-1-((2-(trimethylsilyl)ethoxy)methyl)-1H-indazol-3-yl)ethyl methanesulfonate (1.0 g, 2.57 mmol), $K_2CO_3$ (3.6 g, 25.7 mmol) and N,N-dimethylamine (2 M in THF, 6.45 mL, 12.9 mmol). After column chromatography (2% to 17% EtOAc in petroleum ether) the title compound was obtained as a brown oil (800 mg) which was used in the next step without further purification.

Step 7: 2-(5-fluoro-1H-indazol-3-yl)-N,N-dimethylethan-1-amine (A17)

To a solution of crude 2-(5-fluoro-1-((2-(trimethylsilyl)ethoxy)methyl)-1H-indazol-3-yl)-N,N-dimethylethan-1- amine (400 mg) and tetrabutylammonium fluoride (1 M in THF, 5.93 mL, 5.93 mmol) in THF (4 mL) was added ethylenediamine (356 mg, 5.93 mmol). The reaction was stirred at 60° C. for 16 h and then the cooled reaction mixture was concentrated in vacuo. The residue was purified by prep-HPLC (column: Phenomenex Luna C18, 100×40 mm, 3 µm; mobile phase: [H$_2$O (0.2% formic acid)-MeCN]; gradient: 1%-30% B over 8.00 min) to afford the title compound as a brown oil (20.2 mg, 4% over 2 steps). LCMS (Condition B): t$_R$ (1.313 min) m/z=208.1 [M+H]$^+$; $^1$H NMR (400 MHz, MeOD-d$_4$): δ 8.52 (s, 1H), 7.53-7.46 (m, 2H), 7.24-7.20 (m, 1H), 3.53-3.48 (m, 2H), 3.40-3.35 (m, 2H), 2.89 (s, 6H).

Example 18: Synthesis of N-ethyl-2-(5-fluoro-1H-indazol-3-yl)-N-methylethan-1-amine (A18)

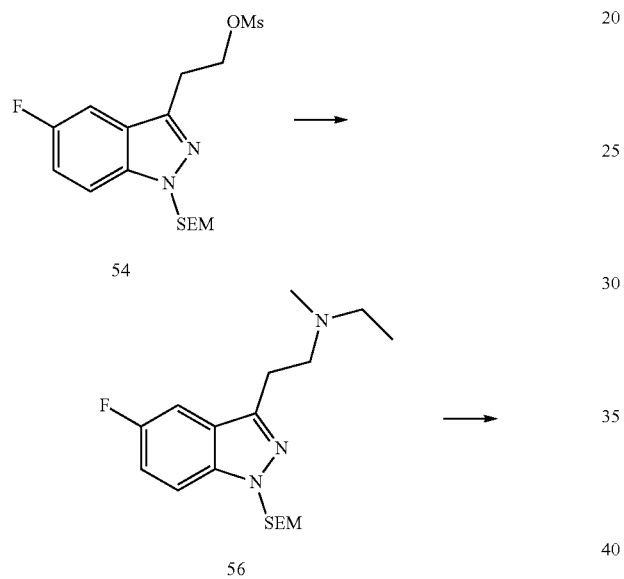

Step 1: N-ethyl-2-(5-fluoro-1-((2-(trimethylsilyl)ethoxy)methyl)-1H-indazol-3-yl)-N-methylethan-1-amine (56)

N-ethyl-2-(5-fluoro-1-((2-(trimethylsilyl)ethoxy)methyl)-1H-indazol-3-yl)-N-methylethan-1-amine was synthesised according to General Procedure B with 2-(5-fluoro-1-((2-(trimethylsilyl)ethoxy)methyl)-1H-indazol-3-yl)ethyl methanesulfonate (1.0 g, 2.57 mmol), K$_2$CO$_3$ (3.6 g, 25.7 mmol) and N-methylethanamine (1.11 mL, 12.9 mmol). After column chromatography (2% to 17% EtOAc in petroleum ether) the title compound was obtained as a brown oil (800 mg) which was used in the next step without further purification.

Step 2: N-ethyl-2-(5-fluoro-1H-indazol-3-yl)-N-methylethan-1-amine (A18)

To a solution of crude N-ethyl-2-(5-fluoro-1-((2-(trimethylsilyl)ethoxy)methyl)-1H-indazol-3-yl)-N-methylethan-1-amine (400 mg) and tetrabutylammonium fluoride (1 M in THF, 5.69 mL, 5.69 mmol) in THF (4 mL) was added ethylenediamine (341 mg, 5.69 mmol). The reaction was stirred at 60° C. for 16 h and then the cooled reaction mixture was concentrated in vacuo. The residue was purified by prep-HPLC (column: Phenomenex Luna C18, 100×40 mm, 3 µm; mobile phase: [H$_2$O (0.2% formic acid)-MeCN]; gradient: 1%-30% B over 8.00 min) to afford the title compound as a brown oil (20.2 mg, 4% over 2 steps). LCMS (Condition B): t$_R$ (1.498 min) m/z=222.1 [M+H]$^+$; $^1$H NMR (400 MHz, MeOD-d$_4$): δ 8.53 (s, 1H), 7.53-7.46 (m, 2H), 7.24-7.21 (m, 1H), 3.54-3.50 (m, 2H), 3.41-3.36 (m, 2H), 3.24 (q, J=7.2 Hz, 2H), 2.87 (s, 3H), 1.34 (t, J=7.2 Hz, 3H).

Example 19: Synthesis of N-(2-(5-fluoro-1H-indazol-3-yl)ethyl)-N-methylpropan-2-amine (A19)

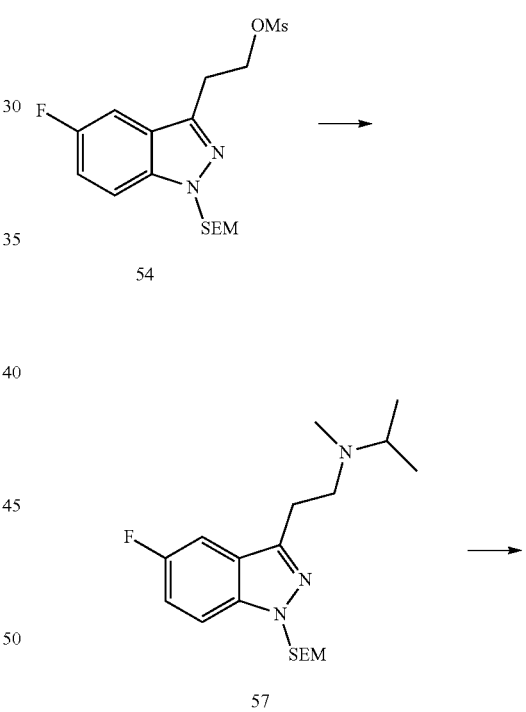

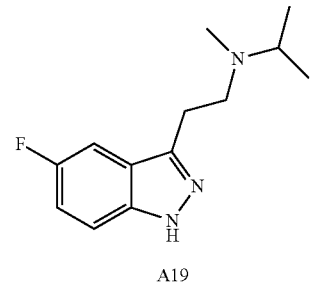

Step 1: N-(2-(5-fluoro-1-((2-(trimethylsilyl)ethoxy)methyl)-1H-indazol-3-yl)ethyl)-N-methylpropan-2-amine (57)

N-(2-(5-fluoro-1-((2-(trimethylsilyl)ethoxy)methyl)-1H-indazol-3-yl)ethyl)-N-methylpropan-2-amine was synthesised according to General Procedure B with 2-(5-fluoro-1-((2-(trimethylsilyl)ethoxy)methyl)-1H-indazol-3-yl)ethyl methanesulfonate (1.0 g, 2.57 mmol), K$_2$CO$_3$ (3.6 g, 25.7 mmol) and N-methylpropan-2-amine (2.7 mL, 25.7 mmol). After column chromatography (2% to 17% EtOAc in petroleum ether) the title compound was obtained as a brown oil (800 mg) which was used in the next step without further purification.

Step 2: N-(2-(5-fluoro-1H-indazol-3-yl)ethyl)-N-methylpropan-2-amine (A19)

To a solution of crude N-(2-(5-fluoro-1-((2-(trimethylsilyl)ethoxy)methyl)-1H-indazol-3-yl)ethyl)-N-methylpropan-2-amine (415 mg) and tetrabutylammonium fluoride (1 M in THF, 5.69 mL, 5.69 mmol) in THF (4 mL) was added ethylenediamine (341 mg, 5.69 mmol). The reaction was stirred at 60° C. for 16 h and then the cooled reaction mixture was concentrated in vacuo. The residue was purified by prep-HPLC (column: Phenomenex Luna C18, 100×40 mm, 3 µm; mobile phase: [H$_2$O (0.2% formic acid)-MeCN]; gradient: 1%-30% B over 8.00 min) to afford the title compound as a brown oil (20.2 mg, 3% over 2 steps). LCMS (Condition B): t$_R$ (1.615 min) m/z=236.1 [M+H]$^+$; $^1$H NMR (400 MHz, MeOD-d$_4$): δ 8.53 (s, 1H), 7.53-7.47 (m, 2H), 7.25-7.21 (m, 1H), 3.72 (sept, J=6.4 Hz, 1H), 3.58-3.54 (m, 2H), 3.43-3.39 (m, 2H), 2.86 (s, 3H), 1.37 (d, J=6.4 Hz, 6H).

Example 20: Synthesis of N-(2-(5-fluoro-1H-indazol-3-yl)ethyl)-N-methylcyclopropanamine (A20)

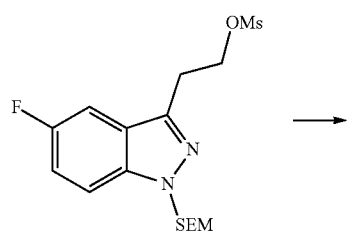

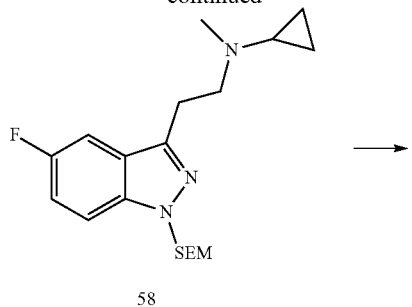

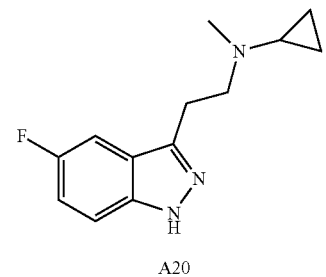

Step 1: N-(2-(5-fluoro-1-((2-(trimethylsilyl)ethoxy)methyl)-1H-indazol-3-yl)ethyl)-N-methylcyclopropanamine (58)

N-(2-(5-fluoro-1-((2-(trimethylsilyl)ethoxy)methyl)-1H-indazol-3-yl)ethyl)-N-methylcyclopropanamine was synthesised according to General Procedure B with 2-(5-fluoro-1-((2-(trimethylsilyl)ethoxy)methyl)-1H-indazol-3-yl)ethyl methanesulfonate (1.0 g, 2.57 mmol), K$_2$CO$_3$ (3.6 g, 25.7 mmol) and N-methylcyclopropanamine (1.83 g, 25.7 mmol). After column chromatography (2% to 17% EtOAc in petroleum ether) the title compound was obtained as a brown oil (800 mg) which was used in the next step without further purification.

Step 2: N-(2-(5-fluoro-1H-indazol-3-yl)ethyl)-N-methylcyclopropanamine (A20)

To a solution of crude N-(2-(5-fluoro-1-((2-(trimethylsilyl)ethoxy)methyl)-1H-indazol-3-yl)ethyl)-N-methylcyclopropanamine (400 mg) and tetrabutylammonium fluoride (1 M in THF, 5.50 mL, 5.50 mmol) in THF (4 mL) was added ethylenediamine (330 mg, 5.50 mmol). The reaction was stirred at 60° C. for 16 h and then the cooled reaction mixture was concentrated in vacuo. The residue was purified by prep-HPLC (column: Phenomenex Luna C18, 100×40 mm, 3 µm; mobile phase: [H$_2$O (0.2% formic acid)-MeCN]; gradient: 1%-30% B over 8.00 min) to afford the title compound as a brown oil (20.5 mg, 3% over 2 steps). LCMS (Condition B): t$_R$ (1.564 min) m/z=234.1 [M+H]$^+$; $^1$H NMR (400 MHz, MeOD-d$_4$): δ 8.36 (s, 1H), 7.51-7.43 (m, 2H), 7.21-7.18 (m, 1H), 3.47-3.41 (m, 2H), 3.40-3.30 (m, 2H), 2.49-2.43 (m, 1H), 0.82-0.79 (m, 4H).

Example 67: Synthesis of 2-(7-fluoro-1H-indazol-3-yl)-N,N-dimethylethan-1-amine (A67)

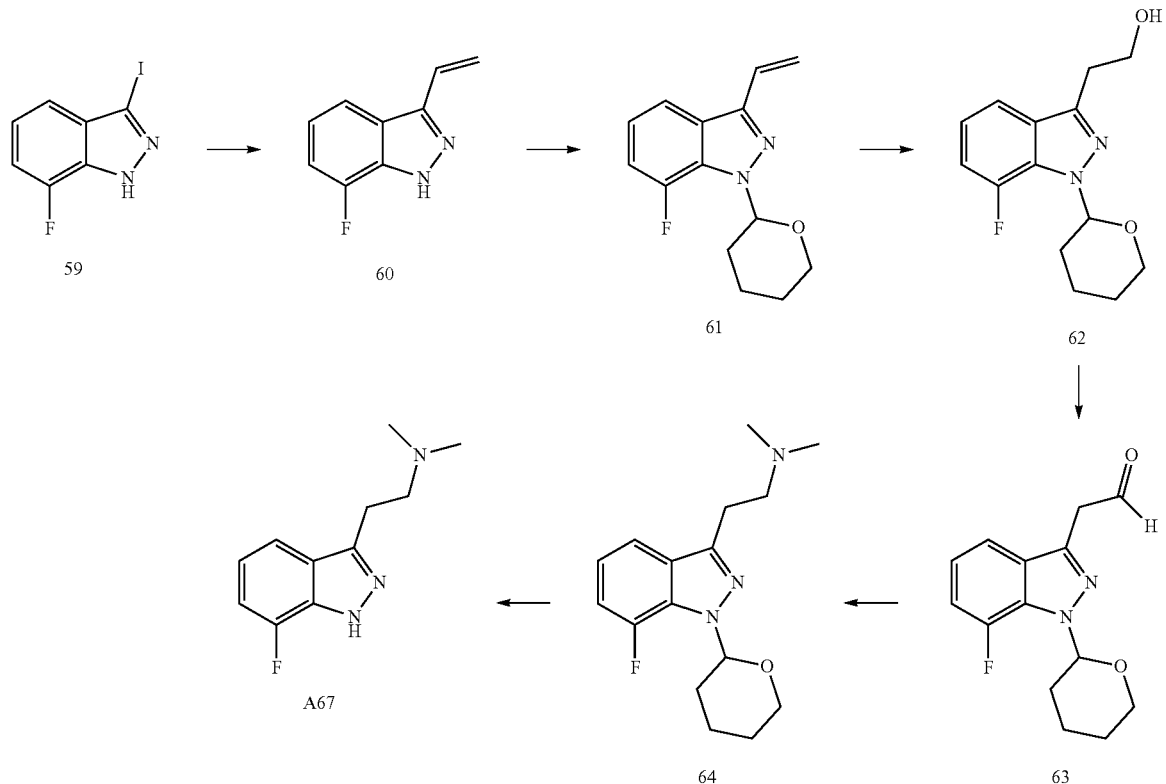

Step 1: 7-fluoro-3-vinyl-1H-indazole (60)

A solution of 7-fluoro-3-iodo-1H-indazole (5.0 g, 19.1 mmol) in 4:1 1,4-dioxane and H₂O (180 mL) was purged with nitrogen gas for 25 minutes. Pd(dppf)Cl₂ (1.40 g, 1.91 mmol), 4,4,5,5-tetramethyl-2-vinyl-1,3,2-dioxaborolane (3.23 g, 21.0 mmol) and K₂CO₃ (7.91 g, 57.2 mmol) were added and the mixture was stirred at 100° C. under nitrogen atmosphere 16 h. After cooling, the reaction mixture was passed through a plug of silica and celite, which was washed through with EtOAc. The filtrate was washed with H₂O (3×60 mL) and then brine (60 mL) before being dried over anhydrous MgSO₄ and concentrated under reduced pressure. The residue was purified by flash chromatography (SiO₂, 0-15% EtOAc/hexane) to provide 7-fluoro-3-vinyl-1H-indazole (2.49 g, 80%) as a white solid. ¹H NMR (400 MHz, DMSO-d₆): δ 13.66 (s, 1H), 7.82 (d, J=8.1 Hz, 1H), 7.22 (dd, J=11.3, 7.6 Hz, 1H), 7.13 (td, J=7.9, 4.6 Hz, 1H), 7.04 (dd, J=18.0, 11.5 Hz, 1H), 6.11 (dd, J=18.0, 1.2 Hz, 1H), 5.51 (dd, J=11.5, 1.2 Hz, 1H).

Step 2: 7-fluoro-1-(tetrahydro-2H-pyran-2-yl)-3-vinyl-1H-indazole (61)

A mixture of 7-fluoro-3-vinyl-1H-indazole (2.49 g, 15.4 mmol) in CH₂Cl₂ (200 mL), 3,4-dihydro-2H-pyran (3.87 g, 46.1 mmol) and 4-methylbenzenesulfonic acid monohydrate (292 mg, 1.54 mmol) was stirred at RT under nitrogen atmosphere 16 h. The mixture was washed with 1 M aq. Na₂CO₃ (2×100 mL) and then brine (50 mL) before being dried over anhydrous MgSO₄ and concentrated under reduced pressure. The residue was purified by flash chromatography (0-10% EtOAc/hexane) to provide 7-fluoro-1-(tetrahydro-2H-pyran-2-yl)-3-vinyl-1H-indazole (3.05 g, 81%) as a white solid. ¹H NMR (400 MHz, CDCl₃): δ 7.71-7.60 (m, 1H), 7.14-7.05 (m, 2H), 7.03 (ddd, J=18.0, 11.5, 0.5 Hz, 1H), 6.10 (dd, J=18.0, 1.1 Hz, 1H), 5.89 (dd, J=10.1, 2.5 Hz, 1H), 5.55 (dd, J=11.5, 1.1 Hz, 1H), 4.15-4.04 (m, 1H), 3.83-3.69 (m, 1H), 2.72-2.52 (m, 1H), 2.12-2.02 (m, 1H), 1.84-1.68 (m, 2H), 1.36-1.25 (m, 2H).

Step 3: 2-(7-fluoro-1-(tetrahydro-2H-pyran-2-yl)-1H-indazol-3-yl)ethan-1-ol (62)

A solution of 7-fluoro-1-(tetrahydro-2H-pyran-2-yl)-3-vinyl-1H-indazole (3.08 g, 12.5 mmol) in anhydrous THF (150 mL) at 0° C. was treated with 2 M BH₃-dimethyl sulfide complex in THF (18.8 mL, 37.5 mmol) dropwise and the mixture was stirred at RT for 3 h under nitrogen atmosphere. The reaction was cooled to 0° C. and 4 M aq. NaOH (25 mL, 0.10 mmol) was added dropwise followed by H₂O₂ (30% w/w in H₂O, 22.7 mL, 0.20 mmol) and the reaction was stirred at RT under nitrogen atmosphere 16 h. The reaction was quenched at 0° C. by addition of saturated aq. Na₂S₂O₃ and then extracted with EtOAc (3×50 mL). The combined organics were washed with brine (2×40 mL), dried over anhydrous MgSO₄ and concentrated under reduced pressure. The residue was purified by flash chromatography (10-50% EtOAc/hexane) to afford 2-(7-fluoro-1-(tetrahydro-2H-pyran-2-yl)-1H-indazol-3-yl)ethan-1-ol (1.60 g, 48%) as a white solid. $^{1}$H NMR (400 MHz, DMSO-$d_6$): δ 7.61 (dt, J=8.0, 0.7 Hz, 1H), 7.23 (ddd, J=12.3, 7.7, 0.8 Hz, 1H), 7.12 (td, J=7.8, 4.3 Hz, 1H), 5.75 (dd, J=10.1, 2.1 Hz, 1H), 4.76 (t, J=5.3 Hz, 1H), 3.95-3.85 (m, 1H), 3.76 (td, J=6.9, 5.1 Hz, 2H), 3.68-3.57 (m, 1H), 3.05 (t, J=7.0 Hz, 2H), 2.48-2.35 (m, 1H), 2.07-1.96 (m, 2H), 1.80-1.65 (m, 1H), 1.62-1.46 (m, 2H).

Step 4: 2-(7-fluoro-1-(tetrahydro-2H-pyran-2-yl)-1H-indazol-3-yl)acetaldehyde (63)

A mixture of 2-(7-fluoro-1-(tetrahydro-2H-pyran-2-yl)-1H-indazol-3-yl)ethan-1-ol (1.54 g, 5.83 mmol) and DMSO (911 mg, 11.7 mmol) in EtOAc (60 mL) was treated with IBX (3.26 g, 11.7 mmol) and the mixture was stirred at 80° C. for 1 h. A second portion of IBX (3.26 g, 11.7 mmol) and DMSO (911 mg, 11.7 mmol) were added and the mixture was stirred for 1 h at 80° C. After cooling, the reaction mixture was filtered through celite and washed with saturated aq. $Na_2S_2O_3$ (2×30 mL) and then brine (20 mL) before being dried over anhydrous $MgSO_4$ and concentrated under reduced pressure. The crude material was used directly in the next reaction without further purification.

Step 5: 2-(7-fluoro-1-(tetrahydro-2H-pyran-2-yl)-1H-indazol-3-yl)-N,N-dimethylethan-1-amine (64)

A solution of crude 2-(7-fluoro-1-(tetrahydro-2H-pyran-2-yl)-1H-indazol-3-yl)acetaldehyde (510 mg) in $CH_2Cl_2$ (30 mL) was treated with 2 M $Me_2NH$ in THF (1.94 mL, 3.89 mmol) and $NaBH(OAc)_3$ (824 mg, 3.89 mmol) and the mixture was stirred at RT 16 h. The reaction was quenched with 2 M aq. NaOH (10 mL) and then extracted with $CH_2Cl_2$ (3×20 mL). The combined organics were washed with brine (10 mL), dried over anhydrous $MgSO_4$ and concentrated under reduced pressure. The residue was purified by flash chromatography (0.1-10% MeOH/$NH_3$ in $CH_2Cl_2$) to provide 2-(7-fluoro-1-(tetrahydro-2H-pyran-2-yl)-1H-indazol-3-yl)-N,N-dimethylethan-1-amine (505 mg, 89%) as a light brown oil. $^{1}$H NMR (400 MHz, CDCl$_3$): δ 7.48-7.40 (m, 1H), 7.10-6.99 (m, 2H), 5.83 (dd, J=10.3, 2.5 Hz, 1H), 4.13-4.04 (m, 1H), 3.75 (td, J=11.5, 2.6 Hz, 1H), 3.21-3.08 (m, 2H), 2.84-2.72 (m, 2H), 2.67-2.52 (m, 1H), 2.35 (s, 6H), 2.20-1.99 (m, 2H), 1.84-1.67 (m, 2H), 1.59 (dt, J=9.4, 2.1 Hz, 1H).

Step 6: 2-(7-fluoro-1H-indazol-3-yl)-N,N-dimethylethan-1-amine (A67)

2-(7-fluoro-1-(tetrahydro-2H-pyran-2-yl)-1H-indazol-3-yl)-N,N-dimethylethan-1-amine (398 mg, 1.37 mmol) was dissolved in a mixture of 6 M aq. HCl (5 mL) and MeOH (5 mL) and the reaction was stirred at RT for 3 h. The reaction mixture was diluted with water (10 mL) and adjusted to pH 13 with 5 M aq. NaOH before being extracted with 3:1 CHCl$_3$:iPrOH (3×20 mL). The combined organics were washed with brine (15 mL), dried over anhydrous $MgSO_4$ and concentrated under reduced pressure. The residue was purified by flash chromatography (1-20% MeOH/$NH_3$ in $CH_2Cl_2$) to provide 2-(7-fluoro-1H-indazol-3-yl)-N,N-dimethylethan-1-amine (230 mg, 81%) as a light pink solid. $^{1}$H NMR (400 MHz, CDCl$_3$): δ 10.78 (br s, 1H), 7.44 (dt, J=8.0, 0.7 Hz, 1H), 6.98 (td, J=7.8, 4.4 Hz, 1H), 6.89 (ddd, J=11.0, 7.7, 0.8 Hz, 1H), 3.23-3.15 (m, 2H), 2.90-2.82 (m, 2H), 2.41 (s, 6H).

Step 7: 2-(7-fluoro-1H-indazol-3-yl)-N,N-dimethyl-ethan-1-amine fumarate (A67-fumarate)

2-(7-fluoro-1H-indazol-3-yl)-N,N-dimethylethan-1-amine (249 mg, 1.20 mmol) was formulated as the fumarate salt according to General Procedure F which was isolated as clear crystalline solid (324 mg, 83%). LCMS (Condition A): $t_R$ (3.889 min) m/z=208.10 [M+H]$^{+}$; $^{1}$H NMR (600 MHz, DMSO-$d_6$): δ 7.61 (d, J=8.1 Hz, 1H), 7.20-7.14 (m, 1H), 7.06 (m, 1H), 6.55 (s, 2H), 3.24-3.19 (m, 2H), 3.09-3.04 (m, 2H), 2.53 (s, 6H).

Example 68: Synthesis of N-ethyl-2-(7-fluoro-1H-indazol-3-yl)-N-methylethan-1-amine (A68)

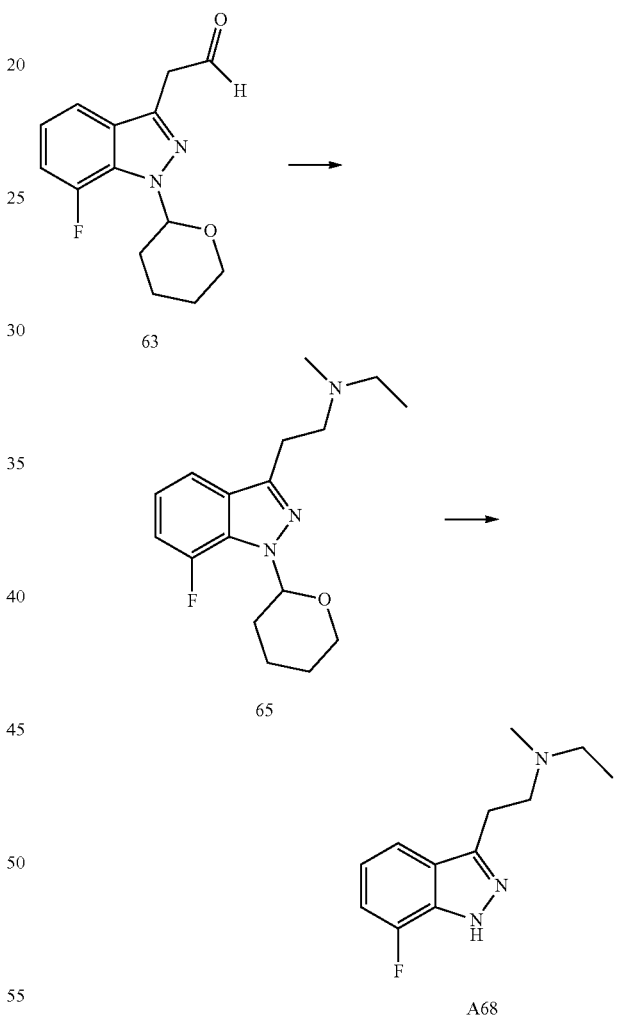

Step 1: N-ethyl-2-(7-fluoro-1-(tetrahydro-2H-pyran-2-yl)-1H-indazol-3-yl)-N-methylethan-1-amine (65)

A solution of crude 2-(7-fluoro-1-(tetrahydro-2H-pyran-2-yl)-1H-indazol-3-yl)acetaldehyde (510 mg) in $CH_2Cl_2$ (30 mL) was treated with MeNHEt (0.33 mL, 3.89 mmol) and $NaBH(OAc)_3$ (824 mg, 3.89 mmol) and the mixture was stirred at RT 16 h. The reaction was quenched with 2 M aq. NaOH (10 mL) and then extracted with $CH_2Cl_2$ (3×20 mL).

The combined organics were washed with brine (10 mL), dried over anhydrous MgSO₄ and concentrated under reduced pressure. The residue was purified by flash chromatography (0.1-10% MeOH/NH₃ in CH₂Cl₂) to provide N-ethyl-2-(7-fluoro-1-(tetrahydro-2H-pyran-2-yl)-1H-indazol-3-yl)-N-methylethan-1-amine (446 mg, 75%) as a light brown oil. $^1$H NMR (400 MHz, CDCl₃): δ 7.48-7.39 (m, 1H), 7.10-6.98 (m, 2H), 5.83 (dd, J=10.3, 2.4 Hz, 1H), 4.13-4.04 (m, 1H), 3.75 (td, J=11.5, 2.6 Hz, 1H), 3.21-3.09 (m, 2H), 2.89-2.81 (m, 2H), 2.66-2.50 (m, 3H), 2.36 (s, 3H), 2.19-1.99 (m, 2H), 1.84-1.66 (m, 2H), 1.63-1.54 (m, 1H), 1.10 (t, J=7.1 Hz, 3H).

Step 2: N-ethyl-2-(7-fluoro-1H-indazol-3-yl)-N-methylethan-1-amine (A68)

N-ethyl-2-(7-fluoro-1-(tetrahydro-2H-pyran-2-yl)-1H-indazol-3-yl)-N-methylethan-1-amine (439 mg, 1.44 mmol) was dissolved in a mixture of 6 M aq. HCl (5 mL) and MeOH (5 mL) and the reaction was stirred at RT for 3 h. The reaction mixture was diluted with water (10 mL) and adjusted to pH 13 with 5 M aq. NaOH before being extracted with 3:1 CHCl₃:iPrOH (3×20 mL). The combined organics were washed with brine (15 mL), dried over anhydrous MgSO₄ and concentrated under reduced pressure. The residue was purified by flash chromatography (1-20% MeOH/NH₃ in CH₂Cl₂) to provide N-ethyl-2-(7-fluoro-1H-indazol-3-yl)-N-methylethan-1-amine (242 mg, 76%) as an off-white solid. $^1$H NMR (400 MHz, CDCl₃): δ 10.50 (br s, 1H), 7.46 (dt, J=8.1, 0.8 Hz, 1H), 7.02 (td, J=7.3, 4.2 Hz, 1H), 7.00-6.95 (m, 1H), 3.24-3.15 (m, 2H), 2.95-2.86 (m, 2H), 2.60 (q, J=7.2 Hz, 2H), 2.40 (s, 3H), 1.12 (t, J=7.2 Hz, 3H).

Step 3: N-ethyl-2-(7-fluoro-1H-indazol-3-yl)-N-methylethan-1-amine fumarate (A68-fumarate)

N-ethyl-2-(7-fluoro-1H-indazol-3-yl)-N-methylethan-1-amine (238 mg, 1.08 mmol) was formulated as the fumarate salt according to General Procedure F which was isolated as a clear crystalline solid (178 mg, 49%). LCMS (Condition A): $t_R$ (4.001 min) m/z=222.15 [M+H]⁺; $^1$H NMR (600 MHz, DMSO-d₆): δ 7.62 (d, J=8.0 Hz, 1H), 7.18 (dd, J=11.4, 7.6 Hz, 1H), 7.07 (td, J=7.7, 4.2 Hz, 1H), 3.27-3.22 (m, 2H), 3.18-3.12 (m, 2H), 2.88 (q, J=7.2 Hz, 2H), 2.57 (s, 3H), 1.12 (t, J=7.1 Hz, 3H).

Example 69: Synthesis of 2-(4,5-difluoro-1H-indazol-3-yl)-N,N-dimethylethan-1-amine (A69)

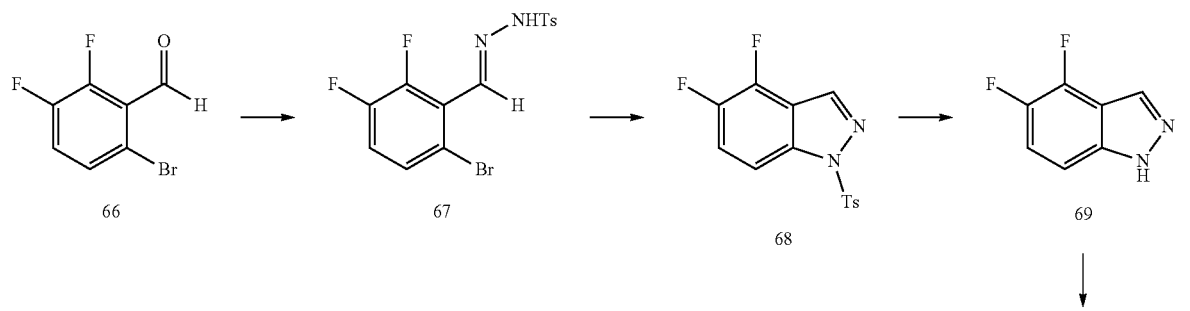

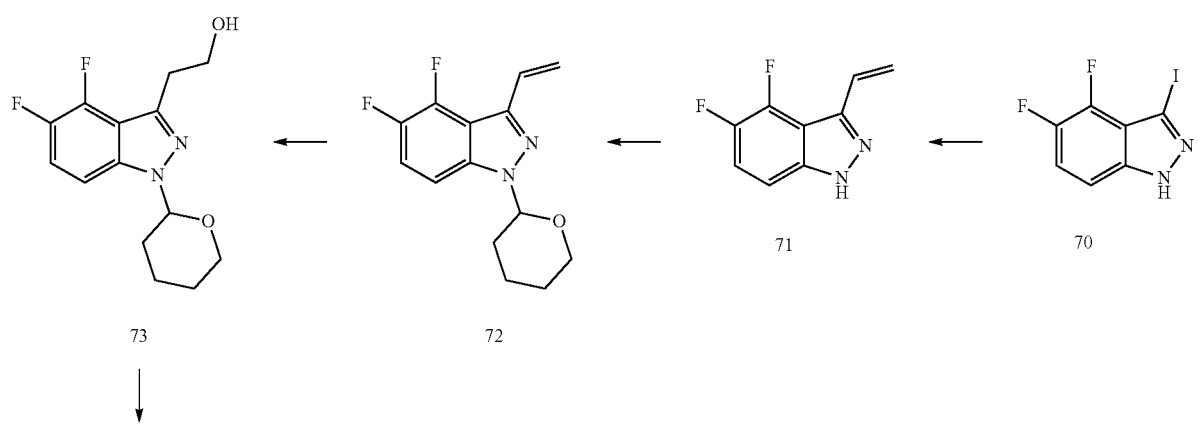

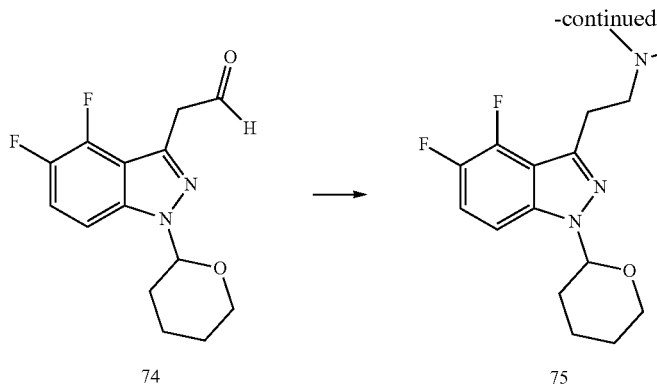

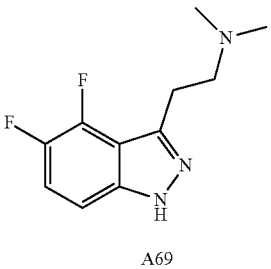

-continued

74

75

A69

Step 1: (E)-N'-(6-bromo-2,3-difluorobenzylidene)-4-methylbenzenesulfonohydrazide (67)

To a stirred solution of 6-bromo-2,3-difluorobenzaldehyde (20.0 g, 90.5 mmol) in MeOH (400 mL) was added 4-methylbenzenesulfonohydrazide (16.9 g, 90.5 mmol) and the mixture was stirred at RT until no further precipitation was observed. The mixture was filtered and the solid was washed with minimal MeOH to afford (E)-N'-(6-bromo-2,3-difluorobenzylidene)-4-methylbenzenesulfonohydrazide (33.5 g, 95%) as a white solid which was used in the next reaction without further purification.

Step 2: 4,5-difluoro-1-tosyl-1H-indazole (68)

To a solution of (E)-N'-(6-bromo-2,3-difluorobenzylidene)-4-methylbenzenesulfonohydrazide (33.0 g, 84.8 mmol) in isoamyl alcohol (250 mL) was added $Cu_2O$ (6.07 g, 42.4 mmol) and the mixture was stirred at reflux for 3 h. After cooling to RT, the mixture was diluted with EtOAc (250 mL) and then filtered. The filtrate was concentrated under a stream of nitrogen gas and the resulting solid was suspended in hexane and filtered. The filtered solid was washed with hexane and the remaining pale green powder was identified as 4,5-difluoro-1-tosyl-1H-indazole (25.5 g, 98%). $^1$H NMR (400 MHz, DMSO-$d_6$): δ 8.76 (d, J=0.9 Hz, 1H), 8.00-7.92 (m, 1H), 7.87-7.82 (m, 2H), 7.78 (ddd, J=10.9, 9.2, 7.5 Hz, 1H), 7.45-7.39 (m, 2H), 2.34 (s, 3H).

Step 3: 4,5-difluoro-1H-indazole (69)

To a stirred suspension of 4,5-difluoro-1-tosyl-1H-indazole (24.8 g, 80.4 mmol) in anhydrous MeOH (300 mL) at 0° C. was added magnesium (19.6 g, 804 mmol) portionwise and the mixture was stirred under nitrogen atmosphere for 30 minutes allowing to warm to RT. The reaction was quenched with ice cold 1 M aq. HCl and diluted with EtOAc before passing through a pad of celite. The filter cake was washed with hot THF several times. The filtrate was washed with saturated aq. $Na_2CO_3$ and then brine before being dried over anhydrous $MgSO_4$ and concentrated under reduced pressure. The crude material was passed through a silica plug, eluting with 40% EtOAc/hexane. After concentrating under reduced pressure, the material was redissolved in EtOAc and crystalised by addition of hexane. The off-white crystaline solid was collected by vacuum filtration and identified as 4,5-difluoro-1H-indazole (10.8 g, 87%). $^1$H NMR (400 MHz, DMSO-$d_6$): δ 13.44 (br s, 1H), 8.25 (d, J=0.9 Hz, 1H), 7.49-7.35 (m, 2H).

Step 4: 4,5-difluoro-3-iodo-1H-indazole (70)

To a stirred solution of 4,5-difluoro-1H-indazole (7.2 g, 46.8 mmol) in MeOH (120 mL) at 0° C. was added $I_2$ (23.8 g, 93.6 mmol) followed by 2 M aq. NaOH (117 mL) and the reaction was stirred at RT for 20 min. The reaction was cooled to 0° C., neutralised with concentrated aq. HCl and then treated with saturated aq. $Na_2S_2O_3$ until iodine colour disappeared. The mixture was diluted with water and the precipitate was filtered by suction filtration to afford 4,5-difluoro-3-iodo-1H-indazole (13.0 g, 99%) as an off-white solid. $^1$H NMR (400 MHz, DMSO-$d_6$): δ 13.77 (br s, 1H), 7.54-7.38 (m, 2H).

Step 5: 4,5-difluoro-3-vinyl-1H-indazole (71)

A solution of 4,5-difluoro-3-iodo-1H-indazole (13.0 g, 46.4 mmol) in 4:1 1,4-dioxane and water (170 mL) was purged with nitrogen gas for 25 minutes. Pd(dppf)$Cl_2$ (3.40 g, 4.64 mmol), 4,4,5,5-tetramethyl-2-vinyl-1,3,2-dioxaborolane (7.15 g, 46.4 mmol) and $K_2CO_3$ (19.2 g, 139 mmol) were added and the mixture was stirred at 100° C. under nitrogen atmosphere 16 h. After cooling, the reaction mixture was passed through a plug of silica and celite, which was washed through with EtOAc. The filtrate was washed with water (3×60 mL) and then brine (60 mL) before being dried over anhydrous $MgSO_4$ and concentrated under reduced pressure. The residue was purified by flash chromatography ($SiO_2$, 10% EtOAc/$CH_2Cl_2$) to provide 4,5-difluoro-3-vinyl-1H-indazole (6.21 g, 74%) as an off-white solid. $^1$H NMR (400 MHz, DMSO-$d_6$): δ 13.53 (br s, 1H), 7.50-7.33 (m, 2H), 6.99 (ddd, J=17.8, 11.4, 2.1 Hz, 1H), 6.06 (dt, J=17.8, 1.6 Hz, 1H), 5.46 (ddd, J=11.4, 2.8, 1.5 Hz, 1H).

Step 6: 4,5-difluoro-1-(tetrahydro-2H-pyran-2-yl)-3-vinyl-1H-indazole (72)

A mixture of 4,5-difluoro-3-vinyl-1H-indazole (6.21 g, 34.5 mmol) in $CH_2Cl_2$ (500 mL), 3,4-dihydro-2H-pyran (8.70 g, 103 mmol) and 4-methylbenzenesulfonic acid monohydrate (656 mg, 3.45 mmol) was stirred at RT under nitrogen atmosphere 16 h. The mixture was washed with 1 M aq. $Na_2CO_3$ (2×100 mL) and then brine (50 mL) before being dried over anhydrous $MgSO_4$ and concentrated under reduced pressure. The residue was purified by flash chromatography (10% EtOAc/hexane) to provide 4,5-difluoro-1-(tetrahydro-2H-pyran-2-yl)-3-vinyl-1H-indazole (6.60 g, 72%) as a white solid. $^1$H NMR (400 MHz, DMSO-$d_6$): δ 7.66-7.47 (m, 2H), 6.97 (ddd, J=17.8, 11.4, 2.0 Hz, 1H), 6.08 (dt, J=17.8, 1.5 Hz, 1H), 5.85 (dd, J=9.7, 2.5 Hz, 1H), 5.52

(ddd, J=11.4, 2.8, 1.4 Hz, 1H), 3.91-3.82 (m, 1H), 3.73 (m, 1H), 2.41-2.26 (m, 1H), 1.99 (m, 2H), 1.81-1.64 (m, 1H), 1.57 (m, 2H).

Step 7: 2-(4,5-difluoro-1-(tetrahydro-2H-pyran-2-yl)-1H-indazol-3-yl)ethan-1-ol (73)

To a solution of 4,5-difluoro-1-(tetrahydro-2H-pyran-2-yl)-3-vinyl-1H-indazole (6.60 g, 25.0 mmol) in anhydrous THF (70 mL) at 0° C. was added 0.5 M 9-borabicyclo[3.3.1]nonane in THF (125 mL, 62.4 mmol) dropwise and the mixture was stirred at RT under nitrogen atmosphere 16 h. After cooling to 0° C., 4 M aq. NaOH (50 mL) was added dropwise followed by $H_2O_2$ (30% w/w in $H_2O$, 45.3 mL) and the mixture was stirred at RT for 2 h. After cooling to 0° C. the reaction was quenched with saturated aq. $Na_2S_2O_3$ and then extracted with EtOAc (3×60 mL). The combined organics were washed with brine (40 mL), dried over anhydrous $MgSO_4$ and concentrated under reduced pressure. The residue was purified by flash chromatography (0-50% EtOAc/hexane) to provide 2-(4,5-difluoro-1-(tetrahydro-2H-pyran-2-yl)-1H-indazol-3-yl)ethan-1-ol (4.96 g, 70%) as a white solid. $^1$H NMR (400 MHz, DMSO-$d_6$): δ 7.56-7.42 (m, 2H), 5.78 (dd, J=9.8, 2.6 Hz, 1H), 4.76 (t, J=5.3 Hz, 1H), 3.92-3.82 (m, 1H), 3.81-3.67 (m, 3H), 3.08 (t, J=7.1 Hz, 2H), 2.40-2.27 (m, 1H), 2.06-1.97 (m, 1H), 1.97-1.90 (m, 1H), 1.80-1.65 (m, 1H), 1.57 (dq, J=8.6, 4.3 Hz, 2H).

Step 8: 2-(4,5-difluoro-1-(tetrahydro-2H-pyran-2-yl)-1H-indazol-3-yl)acetaldehyde (74)

To a solution of 2-(4,5-difluoro-1-(tetrahydro-2H-pyran-2-yl)-1H-indazol-3-yl)ethan-1-ol (3.40 g, 12.1 mmol) in EtOAc (100 mL) at 0° C. was added Dess-Martin periodinane (7.75 g, 95% purity, 17.4 mmol) and t-BuOH (1.29 g, 17.3 mmol) and the mixture was warmed to RT and stirred for 1 h. The reaction mixture was filtered through a pad of celite and then cooled on an ice bath. The cold organic phase was washed with 0.5 M aq. NaOH (2×30 mL), then brine (30 mL) before being dried over $MgSO_4$ and concentrated under reduced pressure. The off-white solid (3.36 g) was used in the next reaction without further purification.

Step 9: 2-(4,5-difluoro-1-(tetrahydro-2H-pyran-2-yl)-1H-indazol-3-yl)-N,N-dimethylethan-1-amine (75)

To a mixture of 2 M $Me_2NH$ in THF (2.01 mL, 4.02 mmol) in $CH_2Cl_2$ (30 mL) at 0° C. was added NaBH(OAc)$_3$ (851 mg, 4.02 mmol) followed by a solution of crude 2-(4,5-difluoro-1-(tetrahydro-2H-pyran-2-yl)-1H-indazol-3-yl)acetaldehyde (563 mg) in $CH_2Cl_2$ (7 mL) and the mixture was stirred at RT 16 h. The reaction mixture was quenched by addition of 2 M aq. NaOH (10 mL) and then extracted with $CH_2Cl_2$ (3×20 mL). The combined organics were washed with brine (10 mL), dried over anhydrous $MgSO_4$ and concentrated under reduced pressure. The residue was purified by flash chromatography (0.1-15% MeOH/$NH_3$ in $CH_2Cl_2$) to provide 2-(4,5-difluoro-1-(tetrahydro-2H-pyran-2-yl)-1H-indazol-3-yl)-N,N-dimethylethan-1-amine (340 mg, 55%) as an off-white solid. $^1$H NMR (400 MHz, DMSO-$d_6$): δ 7.56-7.43 (m, 2H), 5.77 (dd, J=9.7, 2.6 Hz, 1H), 3.91-3.81 (m, 1H), 3.79-3.64 (m, 1H), 3.11-3.03 (m, 2H), 2.69-2.59 (m, 2H), 2.39-2.26 (m, 1H), 2.21 (s, 6H), 2.06-1.97 (m, 1H), 1.97-1.89 (m, 1H), 1.79-1.65 (m, 1H), 1.61-1.51 (m, 2H).

Step 10: 2-(4,5-difluoro-1H-indazol-3-yl)-N,N-dimethylethan-1-amine (A69)

2-(4,5-difluoro-1-(tetrahydro-2H-pyran-2-yl)-1H-indazol-3-yl)-N,N-dimethylethan-1-amine (337 mg, 1.09 mmol) was deprotected according to General Procedure D. After flash chromatography (0.1-15% MeOH/$NH_3$ in $CH_2Cl_2$), the product was obtained as an off-white solid (130 mg, 35%). $^1$H NMR (400 MHz, CDCl$_3$): δ 11.1 (br s, 1H), 7.03 (ddd, J=10.4, 9.0, 7.2 Hz, 1H), 6.81 (ddd, J=8.9, 3.2, 1.0 Hz, 1H), 3.26 (t, J=7.2 Hz, 2H), 2.91 (t, J=7.2 Hz, 2H), 2.44 (s, 6H).

Step 11: 2-(4,5-difluoro-1H-indazol-3-yl)-N,N-dimethylethan-1-amine fumarate (A69-fumarate)

2-(4,5-difluoro-1H-indazol-3-yl)-N,N-dimethylethan-1-amine (124 mg, 0.55 mmol) was formulated as the fumaric acid salt according to General Procedure F as white crystals (150 mg, 80%). LCMS (Condition A): $t_R$ (4.080 min) m/z=226.10 [M+H]$^+$; $^1$H NMR (600 MHz, DMSO-$d_6$): δ 13.24 (br s, 1H), 7.44-7.37 (m, 1H), 7.32 (dd, J=9.0, 3.2 Hz, 1H), 6.53 (s, 2H), 3.26-3.20 (m, 2H), 3.03 (t, J=7.9 Hz, 2H), 2.50 (s, 6H).

Example 70: Synthesis of 2-(4,5-difluoro-1H-indazol-3-yl)-N-ethyl-N-methylethan-1-amine (A70)

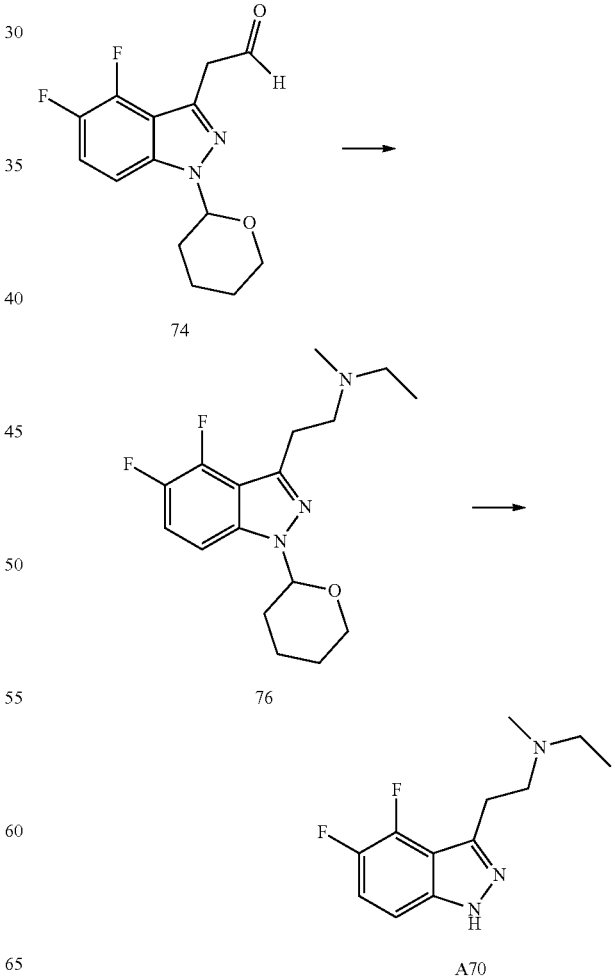

Step 1: 2-(4,5-difluoro-1-(tetrahydro-2H-pyran-2-yl)-1H-indazol-3-yl)-N-ethyl-N-methylethan-1-amine (76)

To a mixture of MeNHEt (0.35 mL, 4.02 mmol) in CH₂Cl₂ (30 mL) at 0° C. was added NaBH(OAc)₃ (851 mg, 4.02 mmol) followed by a solution of 2-(4,5-difluoro-1-(tetrahydro-2H-pyran-2-yl)-1H-indazol-3-yl)acetaldehyde (563 mg, 2.01 mmol) in CH₂Cl₂ (7 mL) and the mixture was stirred at RT 16 h. The reaction mixture was quenched by addition of 2 M aq. NaOH (10 mL) and then extracted with CH₂Cl₂ (3×20 mL). The combined organics were washed with brine (10 mL), dried over anhydrous MgSO₄ and concentrated under reduced pressure. The residue was purified by flash chromatography (0.1-10% MeOH/NH₃ in CH₂Cl₂) to provide 2-(4,5-difluoro-1-(tetrahydro-2H-pyran-2-yl)-1H-indazol-3-yl)-N-ethyl-N-methylethan-1-amine (362 mg, 56%) as an off-white solid. $^1$H NMR (400 MHz, DMSO-d₆): δ 7.56-7.42 (m, 2H), 5.77 (dd, J=9.7, 2.6 Hz, 1H), 3.91-3.81 (m, 1H), 3.79-3.64 (m, 1H), 3.11-3.02 (m, 2H), 2.75-2.66 (m, 2H), 2.43 (q, J=7.1 Hz, 2H), 2.39-2.28 (m, 1H), 2.22 (s, 3H), 2.06-1.97 (m, 1H), 1.97-1.89 (m, 1H), 1.79-1.65 (m, 1H), 1.61-1.51 (m, 2H), 0.96 (t, J=7.1 Hz, 3H).

Step 2: 2-(4,5-difluoro-1H-indazol-3-yl)-N-ethyl-N-methylethan-1-amine (A70)

2-(4,5-difluoro-1-(tetrahydro-2H-pyran-2-yl)-1H-indazol-3-yl)-N-ethyl-N-methylethan-1-amine (350 mg, 1.08 mmol) was deprotected according to General Procedure D. After flash chromatography (0.1-15% MeOH/NH₃ in CH₂Cl₂) 2-(4,5-difluoro-1H-indazol-3-yl)-N-ethyl-N-methylethan-1-amine (211 mg, 45%) was obtained as a clear brown oil. $^1$H NMR (400 MHz, CDCl₃): δ 10.9 (br s, 1H), 7.10 (ddd, J=10.4, 9.0, 7.2 Hz, 1H), 6.95 (ddd, J=9.0, 3.1, 1.0 Hz, 1H), 3.31-3.23 (m, 2H), 3.02-2.94 (m, 2H), 2.68 (q, J=7.2 Hz, 2H), 2.45 (s, 3H), 1.16 (t, J=7.2 Hz, 3H).

Step 3: 2-(4,5-difluoro-1H-indazol-3-yl)-N-ethyl-N-methylethan-1-amine fumarate (A70-fumarate)

2-(4,5-difluoro-1H-indazol-3-yl)-N-ethyl-N-methylethan-1-amine (200 mg, 0.84 mmol) was formulated as the fumaric acid salt according to General Procedure F as white crystals (258 mg, 71%). LCMS (Condition A): t_R (4.187 min) m/z=240.10 [M+H]⁺; $^1$H NMR (600 MHz, DMSO-d₆): δ 13.27 (s, 1H), 7.41 (m, 1H), 7.32 (dd, J=9.1, 3.2 Hz, 1H), 6.54 (s, 3H), 3.30-3.24 (m, 2H), 3.18-3.12 (m, 2H), 2.88 (q, J=7.2 Hz, 2H), 2.56 (s, 3H), 1.12 (t, J=7.2 Hz, 3H).

Example 28: Synthesis of N-(2-(4,5-difluoro-1-(tetrahydro-2H-pyran-2-yl)-1H-indazol-3-yl)ethyl)-N-methylpropan-2-amine (A71)

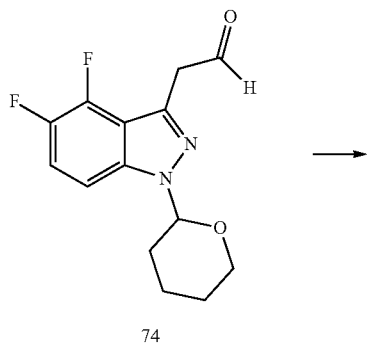

74

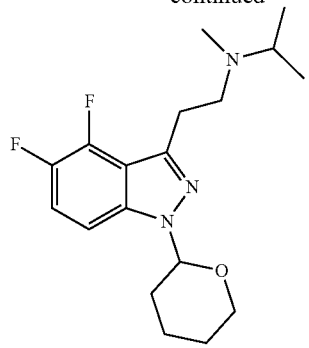

77

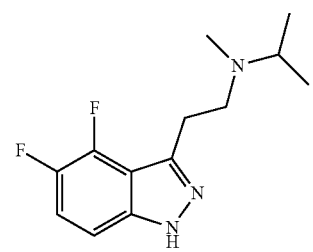

A71

Step 1: N-(2-(4,5-difluoro-1-(tetrahydro-2H-pyran-2-yl)-1H-indazol-3-yl)ethyl)-N-methylpropan-2-amine (77)

To a mixture of MeNHiPr (0.42 mL, 4.02 mmol) in CH₂Cl₂ (30 mL) at 0° C. was added NaBH(OAc)₃ (851 mg, 4.02 mmol) followed by a solution of crude 2-(4,5-difluoro-1-(tetrahydro-2H-pyran-2-yl)-1H-indazol-3-yl)acetaldehyde (563 mg) in CH₂Cl₂ (7 mL) and the mixture was stirred at RT 16 h. The reaction mixture was quenched by addition of 2 M aq. NaOH (10 mL) and then extracted with CH₂Cl₂ (3×20 mL). The combined organics were washed with brine (10 mL), dried over anhydrous MgSO₄ and concentrated under reduced pressure. The residue was purified by flash chromatography (0.1-10% MeOH/NH₃ in CH₂Cl₂) to provide N-(2-(4,5-difluoro-1-(tetrahydro-2H-pyran-2-yl)-1H-indazol-3-yl)ethyl)-N-methylpropan-2-amine (402 mg, 59%) as a brown oil. $^1$H NMR (400 MHz, DMSO-d₆): δ 7.56-7.42 (m, 2H), 5.78 (dd, J=9.8, 2.6 Hz, 1H), 3.91-3.81 (m, 1H), 3.79-3.64 (m, 1H), 3.09-3.01 (m, 2H), 2.83 (hept, J=6.6 Hz, 1H), 2.77-2.68 (m, 2H), 2.40-2.28 (m, 1H), 2.23 (s, 3H), 2.05-1.97 (m, 1H), 1.97-1.88 (m, 1H), 1.80-1.64 (m, 1H), 1.62-1.51 (m, 2H), 0.92 (d, J=6.5 Hz, 6H).

Step 2: N-(2-(4,5-difluoro-1-(tetrahydro-2H-pyran-2-yl)-1H-indazol-3-yl)ethyl)-N-methylpropan-2-amine (A71)

N-(2-(4,5-difluoro-1-(tetrahydro-2H-pyran-2-yl)-1H-indazol-3-yl)ethyl)-N-methylpropan-2-amine (395 mg, 1.17 mmol) was deprotected according to General Procedure D. After flash chromatography (0.1-15% MeOH/NH₃ in CH₂Cl₂)N-(2-(4,5-difluoro-1-(tetrahydro-2H-pyran-2-yl)-1H-indazol-3-yl)ethyl)-N-methylpropan-2-amine (162 mg, 55%) was obtained as a white crystalline solid. LCMS (Condition A): t_R (4.320 min) m/z=254.15 [M+H]⁺; $^1$H NMR (600 MHz, DMSO-d₆): δ 13.06 (s, 1H), 7.42-7.34 (m, 1H), 7.28 (dd, J=9.0, 3.2 Hz, 1H), 3.06-3.00 (m, 2H), 2.78 (hept, J=6.5 Hz, 1H), 2.72-2.66 (m, 2H), 2.43 (s, 3H), 0.90 (d, J=6.5 Hz, 6H).

Example 29: Synthesis of 3-(2-(azetidin-1-yl)ethyl)-4,5-difluoro-1H-indazole (A72)

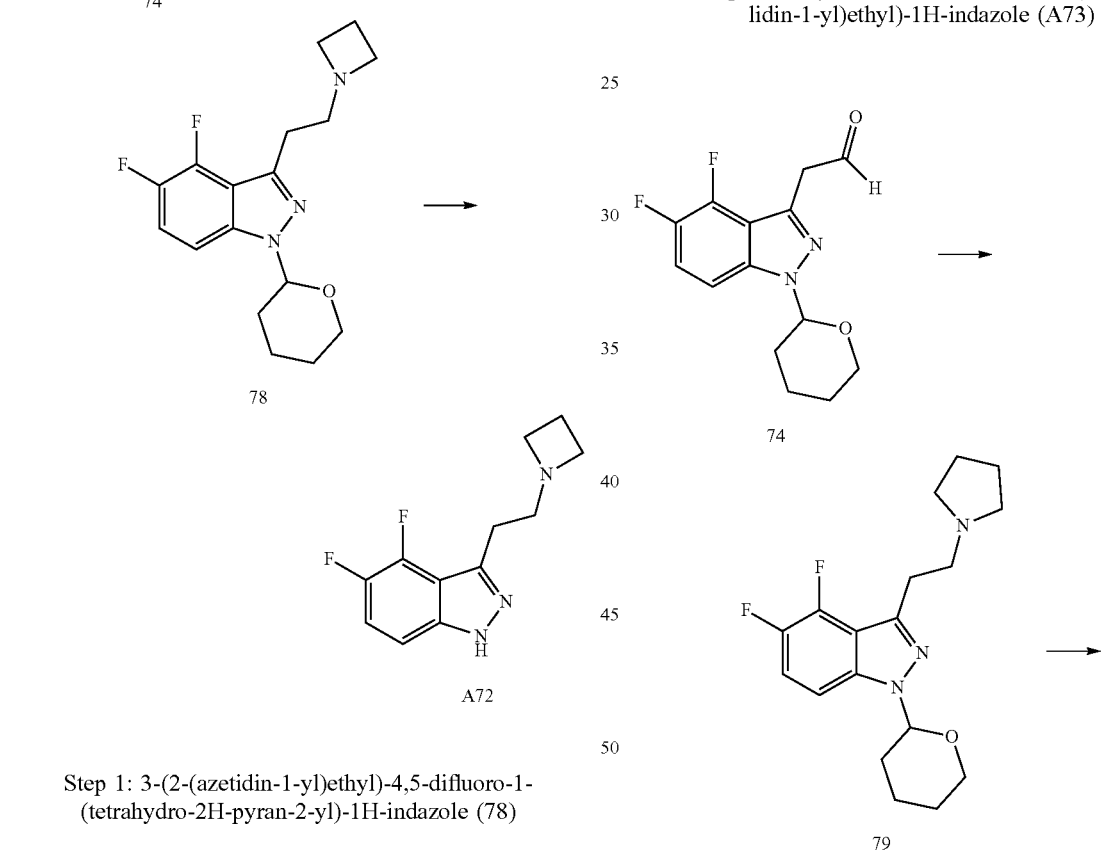

Step 1: 3-(2-(azetidin-1-yl)ethyl)-4,5-difluoro-1-(tetrahydro-2H-pyran-2-yl)-1H-indazole (78)

To a mixture of azetidine (0.42 mL, 4.02 mmol) in CH$_2$Cl$_2$ (30 mL) at 0° C. was added NaBH(OAc)$_3$ (851 mg, 4.02 mmol) followed by a solution of crude 2-(4,5-difluoro-1-(tetrahydro-2H-pyran-2-yl)-1H-indazol-3-yl)acetaldehyde (563 mg) in CH$_2$Cl$_2$ (7 mL) and the mixture was stirred at RT 16 h. The reaction mixture was quenched by addition of 2 M aq. NaOH (10 mL) and then extracted with CH$_2$Cl$_2$ (3×20 mL). The combined organics were washed with brine (10 mL), dried over anhydrous MgSO$_4$ and concentrated under reduced pressure. The residue was purified by flash chromatography (0.1-10% MeOH/NH$_3$ in CH$_2$Cl$_2$) to provide 3-(2-(azetidin-1-yl)ethyl)-4,5-difluoro-1-(tetrahydro-2H-pyran-2-yl)-1H-indazole (350 mg, 54%) as a light pink solid. $^1$H NMR (400 MHz, DMSO-d$_6$): δ 7.56-7.42 (m, 2H), 5.77 (dd, J=9.8, 2.6 Hz, 1H), 3.91-3.82 (m, 1H), 3.79-3.66 (m, 1H), 3.10 (t, J=7.0 Hz, 4H), 2.94-2.86 (m, 2H), 2.78-2.67 (m, 2H), 2.40-2.26 (m, 1H), 2.06-1.98 (m, 1H), 1.97-1.88 (m, 3H), 1.79-1.64 (m, 1H), 1.62-1.51 (m, 2H).

Step 2: 3-(2-(azetidin-1-yl)ethyl)-4,5-difluoro-1H-indazole (A72)

3-(2-(azetidin-1-yl)ethyl)-4,5-difluoro-1-(tetrahydro-2H-pyran-2-yl)-1H-indazole (350 mg, 1.09 mmol) was deprotected according to General Procedure D. After flash chromatography (0.1-15% MeOH/NH$_3$ in CH$_2$Cl$_2$), the purified material was dissolved in CH$_2$Cl$_2$ and crystalised by addition of hexane. The off-white crystals were collected by filtration and identified as 3-(2-(azetidin-1-yl)ethyl)-4,5-difluoro-1H-indazole (96 mg, 37%). LCMS (Condition A): t$_R$ (4.129 min) m/z=238.10 [M+H]$^+$; $^1$H NMR (600 MHz, DMSO-d$_6$): δ 13.07 (s, 1H), 7.42-7.34 (m, 1H), 7.28 (dd, J=9.1, 3.2 Hz, 1H), 3.07 (t, J=6.9 Hz, 4H), 2.89 (t, J=7.5 Hz, 2H), 2.68 (t, J=7.5 Hz, 2H), 1.91 (pent, J=7.0 Hz, 2H).

Example 30: Synthesis of 4,5-difluoro-3-(2-(pyrrolidin-1-yl)ethyl)-1H-indazole (A73)

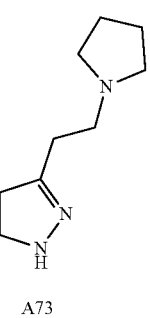

Step 1: 4,5-difluoro-3-(2-(pyrrolidin-1-yl)ethyl)-1-(tetrahydro-2H-pyran-2-yl)-1H-indazole (79)

To a mixture of pyrrolidine (0.33 mL, 4.02 mmol) in CH$_2$Cl$_2$ (30 mL) at 0° C. was added NaBH(OAc)$_3$ (851 mg, 4.02 mmol) followed by a solution of crude 2-(4,5-difluoro-1-(tetrahydro-2H-pyran-2-yl)-1H-indazol-3-yl)acetaldehyde (563 mg) in CH$_2$Cl$_2$ (7 mL) and the mixture was stirred at RT 16 h. The reaction mixture was quenched by addition of 2 M aq. NaOH (10 mL) and then extracted with CH$_2$Cl$_2$ (3×20 mL). The combined organics were washed with brine (10 mL), dried over anhydrous MgSO$_4$ and concentrated under reduced pressure. The residue was purified by flash chromatography (0.1-10% MeOH/NH$_3$ in CH$_2$Cl$_2$) to provide 4,5-difluoro-3-(2-(pyrrolidin-1-yl)ethyl)-1-(tetrahydro-2H-pyran-2-yl)-1H-indazole (339 mg, 50%) as a light pink solid. $^1$H NMR (400 MHz, DMSO-d$_6$): δ 7.56-7.43 (m, 2H), 5.78 (dd, J=9.7, 2.6 Hz, 1H), 3.91-3.81 (m, 1H), 3.79-3.64 (m, 1H), 3.15-3.07 (m, 2H), 2.81 (t, J=7.8 Hz, 2H), 2.57-2.51 (m, 4H), 2.40-2.26 (m, 1H), 2.06-1.98 (m, 1H), 1.97-1.89 (m, 1H), 1.80-1.63 (m, 5H), 1.61-1.51 (m, 2H).

Step 2: 4,5-difluoro-3-(2-(pyrrolidin-1-yl)ethyl)-1H-indazole (A73)

4,5-difluoro-3-(2-(pyrrolidin-1-yl)ethyl)-1-(tetrahydro-2H-pyran-2-yl)-1H-indazole (339 mg, 1.01 mmol) was deprotected according to General Procedure D. After flash chromatography (0.1-15% MeOH/NH$_3$ in CH$_2$Cl$_2$) 4,5-difluoro-3-(2-(pyrrolidin-1-yl)ethyl)-1H-indazole (175 mg, 45%) was obtained as a colourless crystalline solid. $^1$H NMR (400 MHz, CDCl$_3$): δ 11.2 (br s, 1H), 7.02 (ddd, J=10.5, 9.0, 7.2 Hz, 1H), 6.82 (dd, J=9.0, 3.1 Hz, 1H), 3.31 (t, J=7.3 Hz, 2H), 3.10 (t, J=7.3 Hz, 2H), 2.87-2.76 (m, 4H), 1.94-1.84 (m, 4H).

Step 3: 4,5-difluoro-3-(2-(pyrrolidin-1-yl)ethyl)-1H-indazole fumarate (A73-fumarate)

4,5-difluoro-3-(2-(pyrrolidin-1-yl)ethyl)-1H-indazole (200 mg, 0.84 mmol) was formulated as the fumaric acid salt according to General Procedure F as white crystals (165 mg, 71%). LCMS (Condition A): t$_R$ (4.232 min) m/z=252.15 [M+H]$^+$; $^1$H NMR (600 MHz, DMSO-d$_6$): δ 13.29 (s, 1H), 7.41 (ddd, J=10.9, 8.9, 7.1 Hz, 1H), 7.32 (dd, J=9.1, 3.1 Hz, 1H), 6.50 (s, 2H), 3.31-3.25 (m, 2H), 3.25-3.19 (m, 2H), 2.98 (t, J=6.3 Hz, 4H), 1.87-1.79 (m, 4H).

Example 31: Synthesis of 2-(4,5-difluoro-1H-indazol-3-yl)-N-(2-methoxybenzyl)ethan-1-amine (A74)

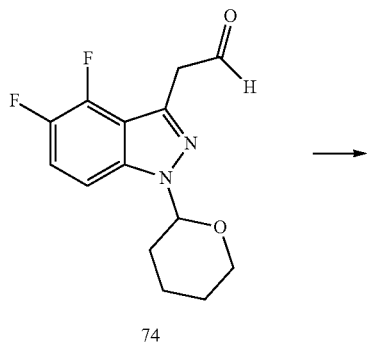

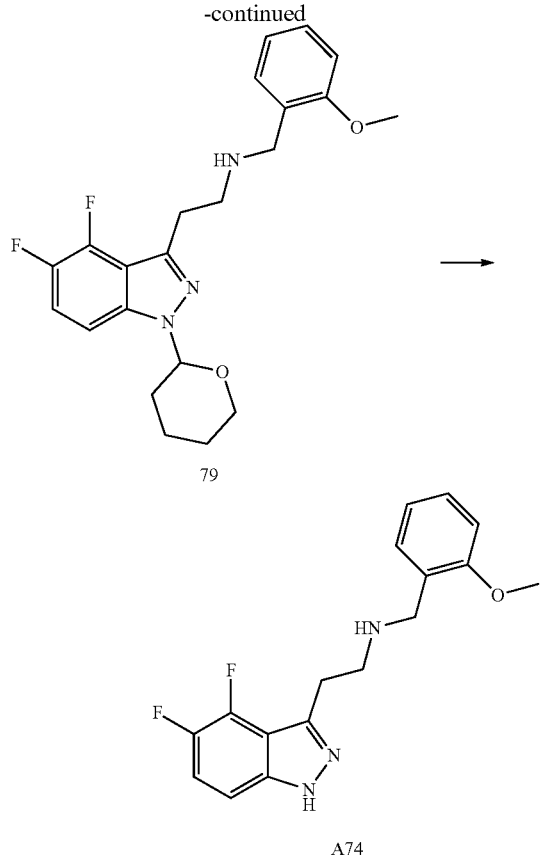

Step 1: 2-(4,5-difluoro-1-(tetrahydro-2H-pyran-2-yl)-1H-indazol-3-yl)-N-(2-methoxybenzyl)ethan-1-amine (79)

To a mixture of (2-methoxyphenyl)methanamine (0.52 mL, 4.02 mmol) in CH$_2$Cl$_2$ (30 mL) at 0° C. was added NaBH(OAc)$_3$ (851 mg, 4.02 mmol) followed by a solution of 2-(4,5-difluoro-1-(tetrahydro-2H-pyran-2-yl)-1H-indazol-3-yl)acetaldehyde (563 mg, 2.01 mmol) in CH$_2$Cl$_2$ (7 mL) and the mixture was stirred at RT 16 h. The reaction mixture was quenched by addition of 2 M aq. NaOH (10 mL) and then extracted with CH$_2$Cl$_2$ (3×20 mL). The combined organics were washed with brine (10 mL), dried over anhydrous MgSO$_4$ and concentrated under reduced pressure. The residue was purified by flash chromatography (0.1-10% MeOH/NH$_3$ in CH$_2$Cl$_2$) to provide 2-(4,5-difluoro-1-(tetrahydro-2H-pyran-2-yl)-1H-indazol-3-yl)-N-(2-methoxybenzyl)ethan-1-amine (359 mg, 45%) as an off-white solid. $^1$H NMR (400 MHz, DMSO-d$_6$): δ 7.56-7.42 (m, 2H), 7.29-7.16 (m, 2H), 7.29-7.16 (m, 2H), 5.78 (dd, J=9.7, 2.6 Hz, 1H), 3.89-3.81 (m, 1H), 3.79-3.64 (m, 6H), 3.12 (t, J=7.2 Hz, 2H), 2.92 (t, J=7.2 Hz, 2H), 2.39-2.25 (m, 1H), 2.06-1.97 (m, 1H), 1.97-1.89 (m, 1H), 1.79-1.64 (m, 1H), 1.59-1.51 (m, 2H).

Step 2: 2-(4,5-difluoro-1H-indazol-3-yl)-N-(2-methoxybenzyl)ethan-1-amine (A74)

2-(4,5-difluoro-1-(tetrahydro-2H-pyran-2-yl)-1H-indazol-3-yl)-N-(2-methoxybenzyl)ethan-1-amine (359 mg, 0.89 mmol) was deprotected according to General Procedure D. After flash chromatography (0.1-15% MeOH/NH$_3$ in CH$_2$Cl$_2$) 2-(4,5-difluoro-1H-indazol-3-yl)-N-(2-methoxybenzyl)ethan-1-amine (145 mg, 37%) was obtained as a brown oil. $^1$H NMR (400 MHz, CDCl$_3$): δ 7.22 (t, J=7.6 Hz, 2H), 7.09 (ddd, J=10.4, 9.0, 7.1 Hz, 1H), 6.96 (ddd, J=9.0, 3.2, 0.9 Hz, 1H), 6.87 (td, J=7.4, 1.1 Hz, 1H), 6.83-6.78 (m, 1H), 3.94 (s, 2H), 3.77 (s, 3H), 3.28 (t, J=6.7 Hz, 2H), 3.15 (t, J=6.5 Hz, 2H).

Step 3: 2-(4,5-difluoro-1H-indazol-3-yl)-N-(2-methoxybenzyl)ethan-1-amine fumarate (A74-fumarate)

2-(4,5-difluoro-1H-indazol-3-yl)-N-(2-methoxybenzyl)ethan-1-amine (145 mg, 0.46 mmol) was formulated as the fumaric acid salt according to General Procedure F as an off-white powder (168 mg, 85%). LCMS (Condition A): $t_R$ (4.920 min) m/z=318.15 [M+H]$^+$; $^1$H NMR (600 MHz, DMSO-d$_6$): δ 13.35 (s, 1H), 7.41 (m, 1H), 7.36 (dd, J=7.5, 1.7 Hz, 1H), 7.34-7.30 (m, 2H), 7.01 (d, J=8.3 Hz, 1H), 6.93 (t, J=7.4 Hz, 1H), 6.50 (s, 2H), 4.01 (s, 2H), 3.78 (s, 3H), 3.29 (t, J=7.5 Hz, 2H), 3.18 (t, J=7.5 Hz, 2H).

Example 32: Synthesis of 2-(4,6-difluoro-1H-indazol-3-yl)-N-ethyl-N-methylethan-1-amine (A29)

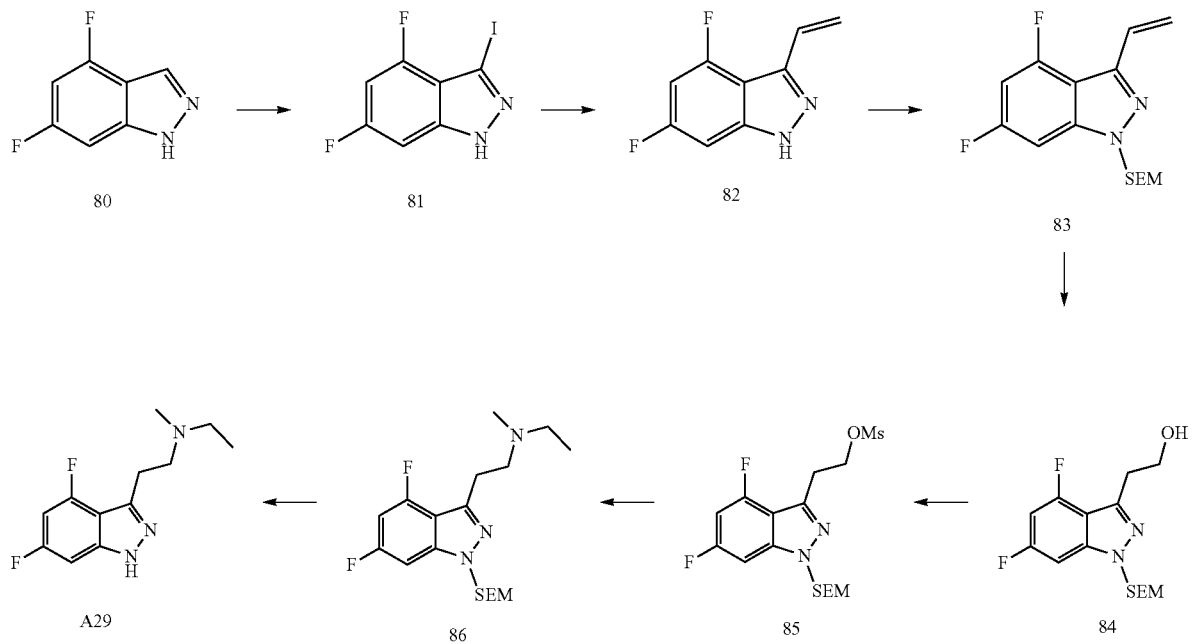

Step 1: 4,6-difluoro-3-iodo-1H-indazole (81)

To a stirred solution of 4,6-difluoro-1H-indazole (10 g, 65 mmol) in MeOH (120 mL) at 0° C. was added I2 (33 g, 130 mmol) followed by 2 M aq. NaOH (117 mL) and the reaction was stirred at RT for 20 min. The reaction was cooled to 0° C., neutralised with concentrated aq. HCl and then treated with saturated aq. Na$_2$S$_2$O$_3$ until iodine colour disappeared. The mixture was diluted with water and the precipitate was filtered by suction filtration to afford 4,6-difluoro-3-iodo-1H-indazole (11 g, 61% yield) as an off-white solid.

Step 2: 4,6-difluoro-3-vinyl-1H-indazole (82)

4,6-difluoro-3-vinyl-1H-indazole was synthesised analogously to step 2 of example A13.

Step 3: 4,6-difluoro-1-((2-(trimethylsilyl)ethoxy)methyl)-3-vinyl-1H-indazole (83)

4,6-difluoro-1-((2-(trimethylsilyl)ethoxy)methyl)-3-vinyl-1H-indazole was synthesised analogously to step 3 of example A13.

Step 4: 2-(4,6-difluoro-1-((2-(trimethylsilyl)ethoxy)methyl)-1H-indazol-3-yl)ethan-1-ol (84)

2-(4,6-difluoro-1-((2-(trimethylsilyl)ethoxy)methyl)-1H-indazol-3-yl)ethyl methanesulfonate was synthesised according to General Procedure A with 2-(4,6-difluoro-1-((2-(trimethylsilyl)ethoxy)methyl)-1H-indazol-3-yl)ethan-1-ol (496 mg, 1.51 mmol), Et$_3$N (0.32 mL, 2.27 mmol) and methanesulfonyl chloride (0.14 mL, 1.81 mmol). 2-(4,6-difluoro-1-((2-(trimethylsilyl)ethoxy)methyl)-1H-indazol-3-yl)ethyl methanesulfonate (305 mg, 50%) was obtained as clear yellow oil. $^1$H NMR (400 MHz, CDCl$_3$): δ 6.98 (dd, J=8.7, 1.9 Hz, 1H), 6.63 (ddd, J=10.1, 9.5, 1.9 Hz, 1H), 5.59 (s, 2H), 4.06 (q, J=5.6 Hz, 2H), 3.59-3.51 (m, 2H), 3.26 (t, J=5.9 Hz, 2H), 0.93-0.84 (m, 2H), −0.05 (s, 9H).

Step 5: 2-(4,6-difluoro-1-((2-(trimethylsilyl)ethoxy)methyl)-1H-indazol-3-yl)ethyl methanesulfonate (85)

To a solution of 2-(4,6-difluoro-1-((2-(trimethylsilyl)ethoxy)methyl)-1H-indazol-3-yl)ethan-1-ol (496 mg, 1.51 mmol) and Et$_3$N (0.32 mL, 2.27 mmol) in CH$_2$Cl$_2$ (6.6 mL) at 0° C. was added methanesulfonyl chloride (0.14 mL, 1.81 mmol) and the mixture was stirred at RT for 2 hours. The reaction was poured into saturated aq. NaHCO$_3$ (15 mL) and extracted with CH$_2$Cl$_2$ (3×50 mL). The pooled organics were washed with brine (50 mL), dried over Na$_2$SO$_4$, and concentrated under reduced pressure to provide 2-(4,6-difluoro-1-((2-(trimethylsilyl)ethoxy)methyl)-1H-indazol-3-yl)ethyl methanesulfonate (305 mg, 50%) as clear yellow oil. $^1$H NMR (400 MHz, CDCl$_3$): δ 7.00 (dd, J=8.6, 1.9 Hz, 1H), 6.65 (ddd, J=10.2, 9.5, 1.9 Hz, 1H), 5.59 (s, 2H), 4.65 (t, J=6.9 Hz, 2H), 3.58-3.51 (m, 2H), 3.46 (t, J=6.9 Hz, 2H), 2.98 (s, 3H), 0.93-0.85 (m, 2H), −0.05 (s, 9H).

Step 6: 2-(4,6-difluoro-1-((2-(trimethylsilyl)ethoxy)methyl)-1H-indazol-3-yl)-N-ethyl-N-methylethan-1-amine (86)

2-(4,6-difluoro-1-((2-(trimethylsilyl)ethoxy)methyl)-1H-indazol-3-yl)-N-ethyl-N-methylethan-1-amine was synthesised according to General Procedure B with 2-(4,6-difluoro-1-((2-(trimethylsilyl)ethoxy)methyl)-1H-indazol-3-yl)ethyl methanesulfonate (150 mg, 0.37 mmol), K$_2$CO$_3$ (510 mg, 3.69 mmol) and MeNHEt (0.32 mL, 3.69 mmol). The title compound was obtained as a yellow oil (135 mg, 99%) which was used in the next step without further purification. $^1$H NMR (400 MHz, CDCl$_3$): δ 6.96 (dd, J=8.7, 1.9 Hz, 1H), 6.61 (ddd, J=10.1, 9.5, 1.9 Hz, 1H), 5.58 (s, 2H), 3.58-3.49 (m, 2H), 3.21-3.12 (m, 2H), 2.86-2.77 (m, 2H), 2.53 (q, J=7.2 Hz, 2H), 2.35 (s, 3H), 1.08 (t, J=7.1 Hz, 3H), 0.92-0.84 (m, 2H), −0.06 (s, 9H).

Step 7: 2-(4,6-difluoro-1H-indazol-3-yl)-N-ethyl-N-methylethan-1-amine (A29)

To a stirred solution of 2-(4,6-difluoro-1-((2-(trimethylsilyl)ethoxy)methyl)-1H-indazol-3-yl)-N-ethyl-N-methylethan-1-amine (135 mg, 0.37 mmol) in MeOH (7.2 mL) was added conc. HCl (3.0 mL) dropwise and the mixture was stirred at 80° C. 16 h. The reaction mixture was quenched by addition of 5 M aq. NaOH (2.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure to afford 2-(4,6-difluoro-1H-indazol-3-yl)-N-ethyl-N-methylethan-1-amine (29 mg, 33%) as a yellow solid. LCMS (Condition A): t$_R$ (4.186 min) m/z=240.15 [M+H]$^+$; $^1$H NMR (600 MHz, DMSO-d$_6$): δ 13.06 (s, 1H), 7.15-7.09 (m, 1H), 6.91-6.85 (m, 1H), 3.07-3.01 (m, 2H), 2.72-2.66 (m, 2H), 2.42 (q, J=7.1 Hz, 2H), 2.21 (s, 3H), 0.96 (t, J=7.1 Hz, 3H).

Example 33: Synthesis of 2-(4,6-difluoro-1H-indazol-3-yl)-N-(2-methoxybenzyl)ethan-1-amine (A33)

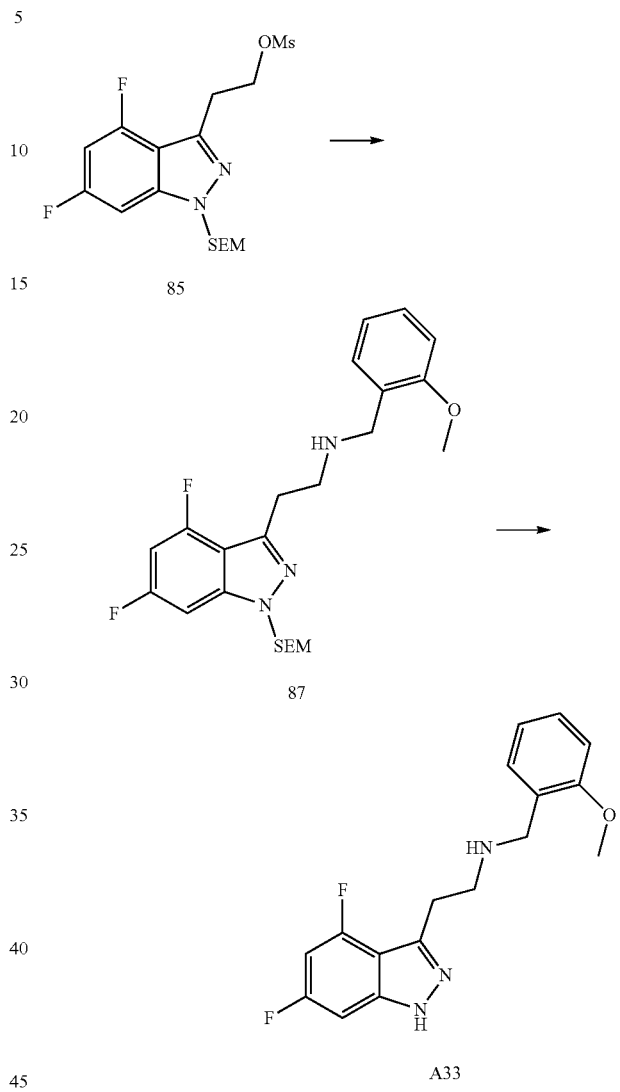

Step 1: 2-(4,6-difluoro-1-((2-(trimethylsilyl)ethoxy)methyl)-1H-indazol-3-yl)-N-(2-methoxybenzyl)ethan-1-amine (87)

2-(4,6-difluoro-1-((2-(trimethylsilyl)ethoxy)methyl)-1H-indazol-3-yl)-N-(2-methoxybenzyl)ethan-1-amine was synthesised according to General Procedure B with 2-(4,6-difluoro-1-((2-(trimethylsilyl)ethoxy)methyl)-1H-indazol-3-yl)ethyl methanesulfonate (150 mg, 0.37 mmol), K$_2$CO$_3$ (510 mg, 3.69 mmol) and (2-methoxyphenyl)methanamine (0.48 mL, 3.69 mmol). The title compound was obtained as a yellow oil (151 mg, 91%) which was used in the next step without further purification. $^1$H NMR (400 MHz, CDCl$_3$): δ 7.25-7.19 (m, 2H), 6.98-6.80 (m, 3H), 6.60 (ddd, J=10.1, 9.6, 1.9 Hz, 1H), 5.57 (s, 2H), 3.85 (s, 2H), 3.78 (s, 3H), 3.57-3.50 (m, 2H), 3.21 (t, J=7.1 Hz, 2H), 3.05 (t, J=7.2 Hz, 2H), 0.91-0.83 (m, 2H), −0.07 (s, 9H).

Step 2: 2-(4,6-difluoro-1H-indazol-3-yl)-N-(2-methoxybenzyl)ethan-1-amine (A33)

To a stirred solution of 2-(4,6-difluoro-1-((2-(trimethylsilyl)ethoxy)methyl)-1H-indazol-3-yl)-N-(2-methoxybenzyl)ethan-1-amine (150 mg, 0.34 mmol) in MeOH (7 mL) was added conc. HCl (1.5 mL) dropwise and the mixture was stirred at 80° C. for 3 hours. The reaction mixture was quenched by addition of 5 M NaOH (2.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure to afford 2-(4,6-difluoro-1H-indazol-3-yl)-N-(2-methoxybenzyl)ethan-1-amine (47 mg, 44%) as a pink oil. $^1$H NMR (400 MHz, CDCl$_3$): δ 7.22 (td, J=7.4, 1.7 Hz, 2H), 6.89-6.79 (m, 2H), 6.54-6.40 (m, 2H), 3.91 (s, 2H), 3.75 (s, 3H), 3.23 (t, J=5.9 Hz, 2H), 3.14 (t, J=6.4 Hz, 2H).

Step 3: 2-(4,6-difluoro-1H-indazol-3-yl)-N-(2-methoxybenzyl)ethan-1-amine fumarate (A33-fumarate)

2-(4,6-difluoro-1H-indazol-3-yl)-N-(2-methoxybenzyl)ethan-1-amine (47 mg, 0.15 mmol) was formulated as the fumaric acid salt according to General Procedure F as an orange solid (48 mg, 75%). LCMS (Condition A): t$_R$ (4.937 min) m/z=318.15 [M+H]$^+$; $^1$H NMR (600 MHz, DMSO-d$_6$): δ 13.3 (s, 1H), 7.41-7.34 (m, 2H), 7.19-7.15 (m, 1H), 7.05 (d, J=8.3 Hz, 1H), 6.96 (t, J=7.4 Hz, 1H), 6.90 (t, J=10.1 Hz, 1H), 6.44 (s, 2H), 4.12 (s, 2H), 3.79 (s, 3H), 3.35-3.26 (m, 4H).

Example 34: Synthesis of 2-(4-fluoro-1H-indazol-3-yl)-N-(2-methoxybenzyl)ethan-1-amine (A34)

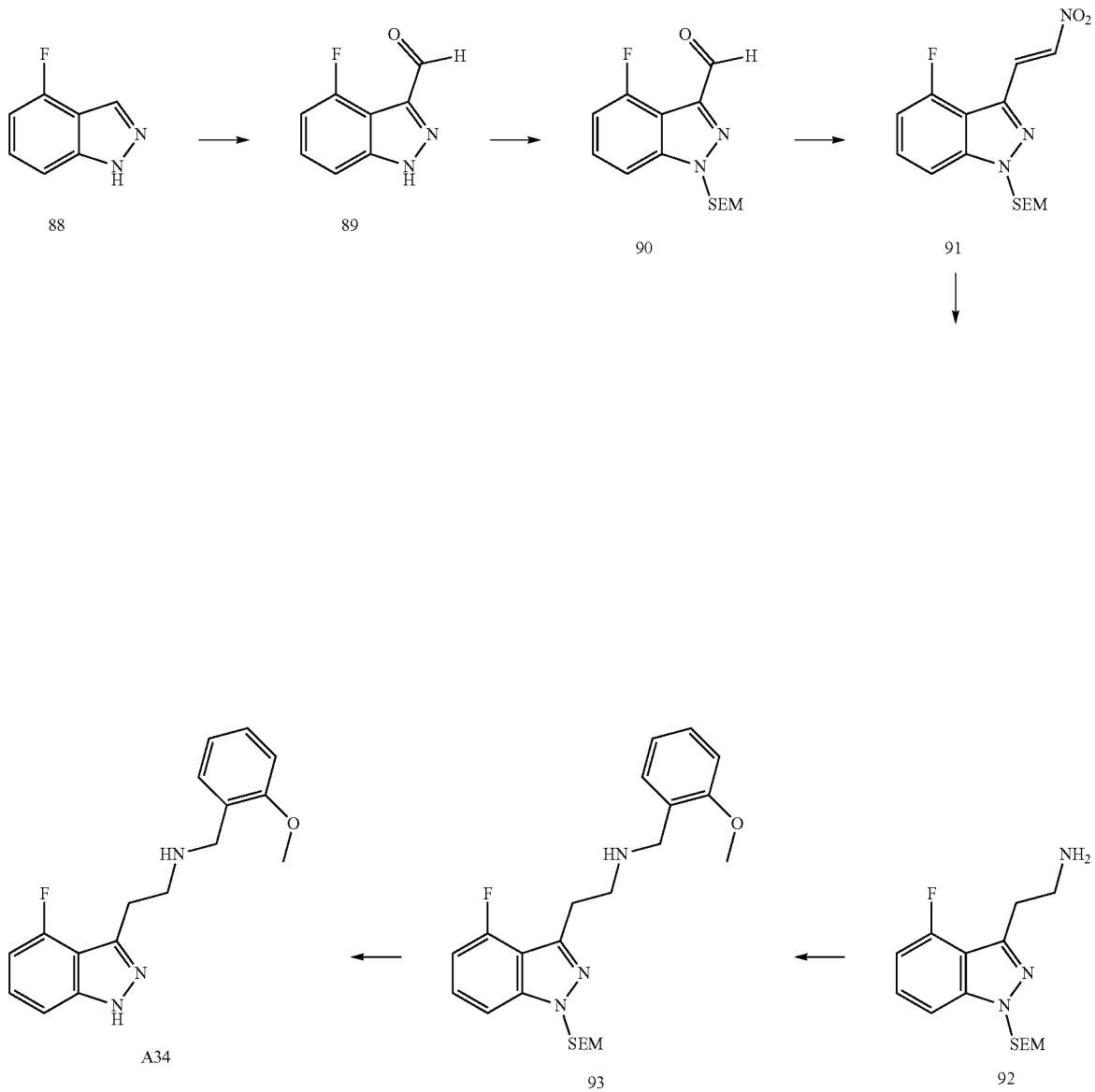

Step 1: 4-fluoro-1H-indazole-3-carbaldehyde (89)

To a solution of NaNO$_2$ (20.4 g, 296 mmol) in H$_2$O (100 mL) and DMF (70 mL) was slowly added 2 M aq. HCl (49.9 mL, 99.9 mmol) and the resulting mixture was stirred for 10 min under nitrogen atmosphere. The mixture was cooled to 0° C. and a solution of 4-fluoroindole (5.0 g, 37.0 mmol) in DMF (70 mL) was added dropwise over 2 h. After addition, the reaction mixture was stirred at RT for 2.5 h. Upon completion, the reaction mixture was neutralised with 2 M aq. NaOH and extracted with EtOAc (3×150 mL). The residue was purified by flash chromatography (0-60% EtOAc/hexane) to provide 4-fluoro-1H-indazole-3-carbaldehyde (865 mg, 14%) as a white solid. $^1$H NMR (400 MHz, MeOD-d$_4$): δ 10.19 (d, J=3.5 Hz, 1H), 7.48-7.41 (m, 1H), 7.33-7.26 (m, 1H), 7.07-6.95 (m, 1H).

Step 2: 4-fluoro-1-((2-(trimethylsilyl)ethoxy) methyl)-1H-indazole-3-carbaldehyde (90)

To a stirred solution of 4-fluoro-1H-indazole-3-carbaldehyde (865 mg, 5.27 mmol) in anhydrous THF (10 mL) at 0° C. was added 60% w/w NaH mineral oil dispersion (232 mg, 5.80 mmol) portionwise. A solution of (2-chloromethoxyethyl)tris(methyl)silane (93% purity, 1.04 g, 5.80 mmol) in anhydrous THF (10 mL) was added dropwise and the mixture was stirred at 0° C. for 1 h. The reaction was quenched by dropwise addition of H$_2$O until cessation of effervescence. EtOAc (30 mL) was added and the organic phase was washed with water (2×15 mL) and brine (15 mL) before being dried over anhydrous MgSO$_4$ and concentrated under reduced pressure. The residue was purified by flash chromatography (0-20% EtOAc/Hexane) to afford a 1:1 mixture of 4-fluoro-1-((2-(trimethylsilyl)ethoxy)methyl)-1H-indazole-3-carbaldehyde and 4-fluoro-2-((2-(trimethylsilyl)ethoxy)methyl)-2H-indazole-3-carbaldehyde (870 mg, 55%) as an orange oil which was used in the next step without further purification. $^1$H NMR (400 MHz, MeOD-d$_4$): δ 10.26-10.11 (m, 2H), 7.62 (d, J=8.5 Hz, 1H), 7.58-7.49 (m, 1H), 7.48-7.35 (m, 2H), 7.15-7.05 (m, 1H), 6.93-6.82 (m, 1H), 5.90 (s, 2H), 5.74 (s, 2H), 3.74-3.44 (m, 4H), 1.07-0.73 (m, 4H), −0.08 (s, 18H).

Step 3: (E)-4-fluoro-3-(2-nitrovinyl)-1-((2-(trimethylsilyl)ethoxy)methyl)-1H-indazole (91)

To a solution of 4-fluoro-1-((2-(trimethylsilyl)ethoxy)methyl)-1H-indazole-3-carbaldehyde (854 mg, 2.9 mmol) in MeNO$_2$ (15 mL) was added NH$_4$OAc (112 mg, 1.45 mmol) and the mixture was stirred at 65° C. 16 h under nitrogen atmosphere. After cooling, H$_2$O (30 mL) was added to reaction and the mixture was extracted with EtOAc (3×20 mL). The organic phase was washed with brine (20 mL) before being dried over anhydrous MgSO$_4$ and concentrated under reduced pressure. The residue was purified by flash chromatography (0-20% EtOAc/hexane) to afford (E)-4-fluoro-3-(2-nitrovinyl)-1-((2-(trimethylsilyl)ethoxy)methyl)-1H-indazole (591 mg, 60%) as a yellow solid. $^1$H NMR (400 MHz, MeOD-d$_4$): δ 8.29 (dd, J=13.7, 0.9 Hz, 1H), 8.05 (d, J=13.7 Hz, 1H), 7.61 (dt, J=8.5, 0.7 Hz, 1H), 7.53 (ddd, J=8.4, 7.6, 4.8 Hz, 1H), 7.09 (ddd, J=11.2, 7.7, 0.7 Hz, 1H), 5.85 (s, 2H), 3.66-3.60 (m, 2H), 0.92-0.83 (m, 2H), −0.08 (s, 9H).

Step 4: 2-(4-fluoro-1-((2-(trimethylsilyl)ethoxy) methyl)-1H-indazol-3-yl)ethan-1-amine (92)

A solution of (E)-4-fluoro-3-(2-nitrovinyl)-1-((2-(trimethylsilyl)ethoxy)methyl)-1H-indazole (584 mg, 1.73 mmol) in anhydrous THF (15 mL) was cooled to 0° C. and LiAlH$_4$ (263 mg, 6.92 mmol) was added portionwise under nitrogen. The mixture was refluxed for 1.5 h and then after cooling, was quenched with cold water (1 mL), then 4 M NaOH (1 mL) followed by more water (3 mL). The resulting mixture was filtered through a pad of celite and the filter cake washed through with THF. The filtrate was concentrated under reduced pressure to give a yellow oil, which was purified by column chromatography (1-15% MeOH/NH$_3$ in CH$_2$Cl$_2$) to provide 2-(4-fluoro-1-((2-(trimethylsilyl)ethoxy)methyl)-1H-indazol-3-yl)ethan-1-amine (183 mg, 34%) as a yellow oil. $^1$H NMR (400 MHz, MeOD): δ 7.46-7.35 (m, 2H), 6.85 (ddd, J=10.7, 6.6, 1.7 Hz, 1H), 5.70 (s, 2H), 3.62-3.54 (m, 2H), 3.26-3.18 (m, 2H), 3.15-3.09 (m, 2H), 0.89-0.81 (m, 2H), −0.09 (s, 9H).

Step 5: 2-(4-fluoro-1-((2-(trimethylsilyl)ethoxy) methyl)-1H-indazol-3-yl)-N-(2-methoxybenzyl) ethan-1-amine (93)

To a stirred solution of 2-(4-fluoro-1-((2-(trimethylsilyl) ethoxy)methyl)-1H-indazol-3-yl)ethan-1-amine (131 mg, 0.42 mmol) in CH$_2$Cl$_2$ (10 mL) at 0° C. was added NaBH(OAc)$_3$ (179 mg, 0.85 mmol) followed by a solution of 3-methoxybenzaldehyde (57 mg, 0.42 mmol) in CH$_2$Cl$_2$ (10 mL) dropwise and the mixture was stirred at RT for 3 h. The reaction was quenched by addition of 2 M NaOH (2.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure. The residue was purified by flash chromatography (1-15% MeOH/NH$_3$ in CH$_2$Cl$_2$) to provide 2-(4-fluoro-1-((2-(trimethylsilyl)ethoxy)methyl)-1H-indazol-3-yl)-N-(2-methoxybenzyl)ethan-1-amine (167 mg, 34%) as a yellow oil. $^1$H NMR (400 MHz, MeOD-d$_4$): δ 7.46-7.34 (m, 2H), 7.25-7.18 (m, 2H), 6.94-6.83 (m, 3H), 5.69 (s, 2H), 3.85 (s, 2H), 3.71 (s, 3H), 3.62-3.50 (m, 2H), 3.27 (t, J=7.0 Hz, 2H), 3.07 (t, J=7.0 Hz, 2H), 0.88-0.78 (m, 2H), −0.10 (s, 9H).

Step 6: 2-(4-fluoro-1H-indazol-3-yl)-N-(2-methoxybenzyl)ethan-1-amine (A34)

To a stirred solution of 2-(4-fluoro-1-((2-(trimethylsilyl) ethoxy)methyl)-1H-indazol-3-yl)-N-(2-methoxybenzyl) ethan-1-amine (0.10 g, 0.23 mmol) in MeOH (5 mL) was added conc. HCl (1.5 mL) dropwise and the mixture was stirred at 80° C. 16 h. The reaction mixture was quenched by addition of 5 M aq. NaOH (2.0 mL) and then volatiles were removed under a stream of nitrogen gas. The remaining aqueous phase was extracted with EtOAc (3×10 mL) and the combined organics were washed with brine, dried over MgSO$_4$ and concentrated under reduced pressure to afford 2-(4-fluoro-1H-indazol-3-yl)-N-(2-methoxybenzyl)ethan-1-amine (70 mg, 100%) as a yellow oil. $^1$H NMR (400 MHz, MeOD-d$_4$): δ 7.34-7.24 (m, 2H), 7.23-7.15 (m, 2H), 6.88-6.82 (m, 2H), 6.72 (ddd, J=10.9, 7.2, 1.1 Hz, 1H), 3.76 (s, 2H), 3.66 (s, 3H), 3.23 (t, J=7.0 Hz, 2H), 2.99 (t, J=7.0 Hz, 2H).

Step 6: 2-(4-fluoro-1H-indazol-3-yl)-N-(2-methoxybenzyl)ethan-1-amine dihydrochloride (A34.2HCl)

2-(4-fluoro-1H-indazol-3-yl)-N-(2-methoxybenzyl) ethan-1-amine (70 mg, 0.23 mmol) was formulated as the dihydrochloride salt according to General Procedure E which was collected as an off-white solid (14 mg, 21%). LCMS (Condition A): $t_R$ (4.804 min) m/z=300.15 [M+H]$^+$; $^1$H NMR (400 MHz, DMSO-d$_6$): δ 13.27 (d, J=2.0 Hz, 1H), 9.09 (s, 2H), 7.50-7.38 (m, 2H), 7.38-7.30 (m, 2H), 7.10 (dd, J=8.3, 1.0 Hz, 1H), 7.01 (td, J=7.5, 1.1 Hz, 1H), 6.90-6.81 (m, 1H), 4.21 (t, J=5.2 Hz, 2H), 3.85 (s, 3H), 3.46-3.32 (m, 4H).

Example 35: Synthesis of 2-(5,7-difluoro-1H-indazol-3-yl)-N,N-dimethylethan-1-amine (A35)

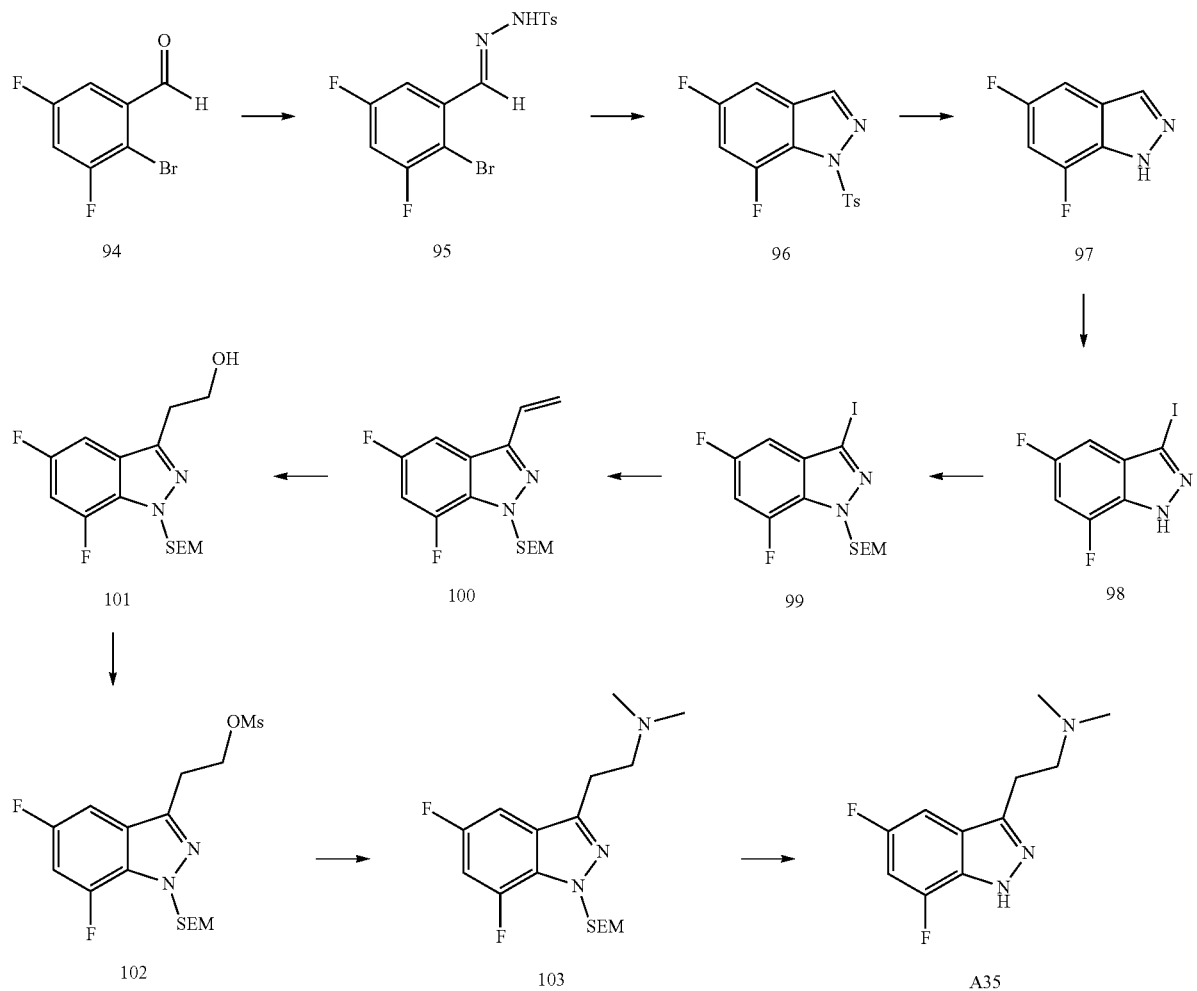

Step 1: (E)-N'-(2-bromo-3,5-difluorobenzylidene)-4-methylbenzenesulfonohydrazide (95)

To a stirred solution of 2-bromo-3,5-difluorobenzaldehyde (5.0 g, 22.6 mmol) in MeOH (50 mL) at 0° C. under nitrogen atmosphere was added 4-methylbenzenesulfonohydrazide (4.0 g, 21.5 mmol) and the mixture was stirred at RT for 2 h. The reaction mixture concentrated under reduced pressure to afford (E)-N'-(2-bromo-3,5-difluorobenzylidene)-4-methylbenzenesulfonohydrazide which was used in the next step without further purification.

Step 2: 5,7-difluoro-1-tosyl-1H-indazole (96)

To a stirred solution of (E)-N'-(2-bromo-3,5-difluorobenzylidene)-4-methylbenzenesulfonohydrazide in isoamyl alcohol (50 mL) was added Cu$_2$O (0.92 g, 6.43 mmol) at RT and the resulting reaction mixture was stirred at 120° C. for 3 h. The reaction mixture was diluted with ice-cold H$_2$O (300 mL) and extracted with EtOAc (3×100 mL). The combined organics were dried over Na$_2$SO$_4$, concentrated under reduced pressure and the crude material was purified by column chromatography (product eluted at 60% CH$_2$Cl$_2$ in hexane) to afford 5,7-difluoro-1-tosyl-1H-indazole (4.0 g, 57% yield) as a brown solid. LCMS (Condition C): $t_R$ (1.839 min) m/z=308.8 [M+H]$^+$; $^1$H NMR (400 MHz, DMSO-d$_6$): δ 8.62 (d, J=2.4 Hz, 1H), 7.78 (d, J=8.4 Hz, 2H), 7.68-7.58 (m, 2H), 7.43 (d, J=8.0 Hz, 2H), 2.34 (s, 3H).

Step 3: 5,7-difluoro-1H-indazole (97)

To a stirred solution of 5,7-difluoro-1-tosyl-1H-indazole (1.0 g, 3.24 mmol) in DMSO (10 mL) and water (10 mL)

was added K$_2$CO$_3$ (2.24 g, 16.2 mmol) and reaction mixture was stirred at 120° C. for 2 h. The reaction mixture was diluted with ice-cold H$_2$O (300 mL) and extracted with EtOAc (3×100 mL). The combined organics were washed with ice-cold H$_2$O to remove DMSO, dried over Na$_2$SO$_4$ and concentrated under reduced pressure to afford 5,7-difluoro-1H-indazole (350 mg, 70%) as a brown solid. LCMS (Condition C): t$_R$ (1.827 min) m/z=154.8 [M+H]$^+$; $^1$H NMR (400 MHz, DMSO-d$_6$): δ 13.77 (s, 1H), 8.18-8.17 (m, 1H), 7.45 (dd, J=8.4, 1.6 Hz, 1H), 7.35-7.29 (m, 1H).

Step 4: 5,7-difluoro-3-iodo-1H-indazole (98)

To a stirred solution of 5,7-difluoro-1H-indazole (1.0 g, 6.49 mmol) in DMF (10 mL) was added NIS (3.16 g, 14.0 mmol) at RT and the reaction mixture was stirred at RT for 2 h. The reaction mixture was diluted with ice cold H$_2$O (300 mL) and extracted with EtOAc (3×100 mL). The combined organics were washed with ice-cold H$_2$O, dried over Na$_2$SO$_4$ and concentrated under reduced pressure and the crude material was purified by flash column chromatography (product eluted at 20% EtOAc in hexane) to afford 5,7-difluoro-3-iodo-1H-indazole (854 mg, 47%) as a brown solid. LCMS (Condition C): t$_R$ (1.632 min) m/z=278.8 [M+H]$^+$; $^1$H NMR (400 MHz, DMSO-d$_6$): δ 14.22 (s, 1H), 7.49-7.43 (m, 1H), 7.13 (dd, J=8.4, 2.0 Hz, 1H).

Step 5: 5,7-difluoro-3-iodo-1-((2-(trimethylsilyl)ethoxy)methyl)-1H-indazole (99)

To a stirred solution of 5,7-difluoro-3-iodo-1H-indazole (0.5 g, 1.78 mmol) in DMF (5.0 mL) at 0° C. was added 60% w/w NaH mineral oil dispersion (0.11 g, 2.67 mmol). After 30 min, (2-(chloromethoxy)ethyl)trimethylsilane (0.59 g, 3.57 mmol) was added and the reaction mixture was stirred at RT for 1 h. The reaction mixture was poured into ice cold H$_2$O (300 mL) and extracted with EtOAc (2×300 mL). The combined organics were dried over Na$_2$SO$_4$, concentrated under reduced pressure and the crude material was purified by column chromatography (product eluted at 3% EtOAc in hexane) to afford 5,7-difluoro-3-iodo-1-((2-(trimethylsilyl)ethoxy)methyl)-1H-indazole (0.34 g, 46%) as a yellow liquid. $^1$H NMR (400 MHz, DMSO-d$_6$): δ 7.61-7.55 (m, 1H), 7.19 (dd, J=8.0, 1.6, Hz, 1H), 5.74 (s, 2H), 3.56-3.50 (m, 2H), 0.77 (t, J=5.2 Hz, 2H), 0.01 (s, 9H).

Step 6: 5,7-difluoro-1-((2-(trimethylsilyl)ethoxy)methyl)-3-vinyl-1H-indazole (100)

To a stirred solution of 5,7-difluoro-3-iodo-1-((2-(trimethylsilyl)ethoxy)methyl)-1H-indazole (0.5 g, 1.22 mmol) in THF (5 mL) was added 4,4,5,5-tetramethyl-2-vinyl-1,3,2-dioxaborolane (0.19 g, 1.22 mmol) and K$_2$CO$_3$ (0.5 g, 3.65 mmol) in water (1 mL) at RT and the reaction mixture was purged with nitrogen gas for 30 min. Pd(dppf)Cl$_2$ (0.04 g, 0.06 mmol) was added and the reaction mixture was stirred at 100° C. for 16 h. The reaction mixture was poured into H$_2$O (300 mL) and extracted with EtOAc (3×100 mL). The combined organics were dried over Na$_2$SO$_4$, concentrated under reduced pressure and the crude material was purified by column chromatography (product eluted at 1% EtOAc in hexane) to afford 5,7-difluoro-1-((2-(trimethylsilyl)ethoxy)methyl)-3-vinyl-1H-indazole (0.25 g, 66%) as a brown liquid. LCMS (Condition C): t$_R$ (2.579 min) m/z=311.0 [M+H]$^+$; $^1$H NMR (400 MHz, DMSO-d$_6$): δ 7.78 (dd, J=8.2, 1.4 Hz, 1H), 7.51-7.45 (m, 1H), 7.00 (dd, J=18.0, 11.2 Hz, 1H), 6.16 (d, 17.6 Hz, 1H), 5.72 (s, 2H), 5.56 (d, J=12.0 Hz, 1H), 3.59-3.51 (m, 2H), 0.80-0.76 (m, 2H), 0.14 (s, 9H).

Step 7: 2-(5,7-difluoro-1-((2-(trimethylsilyl)ethoxy)methyl)-1H-indazol-3-yl)ethan-1-ol (101)

To a stirred solution of 5,7-difluoro-1-((2-(trimethylsilyl)ethoxy)methyl)-3-vinyl-1H-indazole (0.5 g, 1.61 mmol) in THF (5.0 mL) at 0° C. was added 0.5 M 9-borabicyclo[3.3.1]nonane in THF (16 mL, 8.0 mmol) under nitrogen atmosphere and the reaction mixture was stirred at RT for 6 h. After cooling to 0° C., 30% w/w aq. H$_2$O$_2$ (8.5 mL) was added dropwise followed by 4 M aq. NaOH (1.8 mL). The resulting reaction mixture was stirred at RT for 16 h. The reaction mixture was poured into H$_2$O (300 mL) and extracted with EtOAc (3×100 mL). The combined organics were dried over Na$_2$SO$_4$, concentrated under reduced pressure and the crude material was purified by column chromatography (product eluted at 20% EtOAc in hexane) to afford 2-(5,7-difluoro-1-((2-(trimethylsilyl)ethoxy)methyl)-1H-indazol-3-yl)ethan-1-ol (0.32 g, 60%) as a yellow liquid. LCMS (Condition C): t$_R$ (2.019 min) m/z=328.9 [M+H]$^+$; $^1$H NMR (400 MHz, DMSO-d$_6$): δ 7.52 (dd, J=8.4, 2.0 Hz, 1H), 7.42-7.37 (m, 1H), 5.67 (s, 2H), 4.76 (t, J=5.2 Hz, 1H), 3.74 (q, J=6.8 Hz, 2H), 3.50 (t, J=8.0 Hz, 2H), 3.03 (t, J=6.8 Hz, 2H), 0.76 (t, J=4.8 Hz, 2H), 0.12 (s, 9H).

Step 8: 2-(5,7-difluoro-1-((2-(trimethylsilyl)ethoxy)methyl)-1H-indazol-3-yl)ethyl methanesulfonate (102)

To a stirred solution of 2-(5,7-difluoro-1-((2-(trimethylsilyl)ethoxy)methyl)-1H-indazol-3-yl)ethan-1-ol (0.32 g, 0.97 mmol) in CH$_2$Cl$_2$ (3 mL) at 0° C. was added methanesulfonyl chloride (0.5 mL) and Et$_3$N (2 mL) under nitrogen atmosphere and the reaction mixture was stirred at RT for 2 h. The reaction mixture was poured into H$_2$O (200 mL) and extracted with CH$_2$Cl$_2$ (2×100 mL). The combined organics were dried over Na$_2$SO$_4$, concentrated under reduced pressure and the crude material was purified by column chromatography (product eluted at 20% EtOAc in hexane) to afford 2-(5,7-difluoro-1-((2-(trimethylsilyl)ethoxy)methyl)-1H-indazol-3-yl)ethyl methanesulfonate (0.27 g, 68%) as a brown liquid. LCMS (Condition C): t$_R$ (2.645 min) m/z=406.8 [M+H]$^+$; $^1$H NMR (400 MHz, DMSO-d$_6$): δ 7.60 (dd, J=8.4, 2.0 Hz, 1H), 7.47-7.41 (m, 1H), 5.69 (s, 2H), 4.56 (t, J=6.8 Hz, 2H), 3.51 (t, J=8.0 Hz, 2H), 3.37-3.35 (m, 2H), 3.14 (s, 3H), 0.78 (t, J=8.0 Hz, 2H), 0.12 (s, 9H).

Step 9: 2-(5,7-difluoro-1-((2-(trimethylsilyl)ethoxy)methyl)-1H-indazol-3-yl)-N,N-dimethylethan-1-amine (103)

2-(5,7-difluoro-1-((2-(trimethylsilyl)ethoxy)methyl)-1H-indazol-3-yl)-N,N-dimethylethan-1-amine was synthesised according to General Procedure B with 2-(5,7-difluoro-1-((2-(trimethylsilyl)ethoxy)methyl)-1H-indazol-3-yl)ethyl methanesulfonate (0.27 g, 0.66 mmol), K$_2$CO$_3$ (0.92 g, 6.66 mmol) and dimethylamine hydrochloride (0.27 g, 3.32 mmol). The title compound was obtained as a brown liquid (0.25 g, quant.) which was used in the next reaction without further purification. LCMS (Condition C): t$_R$ (2.006 min) m/z=356.2 [M+H]$^+$; $^1$H NMR (400 MHz, DMSO-d$_6$): δ 7.56-7.53 (m, 1H), 7.42-7.34 (m, 1H), 5.67 (s, 2H), 3.51-3.47 (m, 2H), 3.04-3.00 (m, 2H), 2.63-2.51 (m, 2H), 2.19 (s, 6H), 0.80-0.75 (m, 2H), −0.13 (s, 9H).

Step 10: 2-(5,7-difluoro-1H-indazol-3-yl)-N,N-dimethylethan-1-amine (A35)

To a stirred solution of 2-(5,7-difluoro-1-((2-(trimethylsilyl)ethoxy)methyl)-1H-indazol-3-yl)-N,N-dimethylethan-1-amine (0.25 g, 0.70 mmol) in CH₂Cl₂ (5 mL) at 0° C. was added 4 M HCl in dioxane (15 mL) and the reaction mixture was stirred at RT for 16 h. The reaction mixture was quenched with 4 N aq. NaOH solution (10 mL), diluted with H₂O (50 mL) and extracted with CH₂Cl₂ (2×70 mL). The combined organics were dried over Na₂SO₄, concentrated under reduced pressure and the crude material was purified by reverse phase column chromatography (product eluted at 45% MeCN in H₂O) to afford 2-(5,7-difluoro-1H-indazol-3-yl)-N,N-dimethylethan-1-amine (0.045 g, 28%) as an off-white solid. LCMS (Condition C): $t_R$ (1.081 min) m/z=225.93 [M+H]⁺; ¹H NMR (400 MHz, DMSO-d₆): δ 13.37 (s, 1H), 7.46 (dd, J=8.0, 2.0 Hz, 1H), 7.27 (t, J=9.6 Hz, 1H), 3.02 (t, J=7.6 Hz, 2H), 2.61 (d, J=8.0 Hz, 2H), 2.19 (s, 6H).

Example 36: Synthesis of 2-(5,7-difluoro-1H-indazol-3-yl)-N-ethyl-N-methylethan-1-amine (A36)

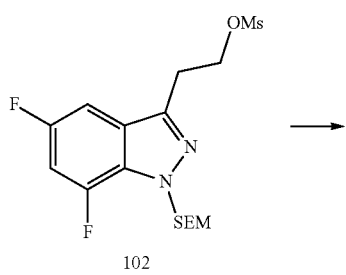

Step 1: 2-(5,7-difluoro-1-((2-(trimethylsilyl)ethoxy)methyl)-1H-indazol-3-yl)-N-ethyl-N-methylethan-1-amine (104)

2-(5,7-difluoro-1-((2-(trimethylsilyl)ethoxy)methyl)-1H-indazol-3-yl)-N-ethyl-N-methylethan-1-amine was synthesised according to General Procedure B with 2-(5,7-difluoro-1-((2-(trimethylsilyl)ethoxy)methyl)-1H-indazol-3-yl)ethyl methanesulfonate (0.23 g, 0.57 mmol), K₂CO₃ (0.78 g, 5.65 mmol) and N-methylethanamine (0.17 g, 2.88 mmol). The title compound was obtained as a yellow liquid (0.2 g, 96%) which was used in the next step without further purification. LCMS (Condition C): $t_R$ (1.588 min) m/z=370.2 [M+H]⁺; ¹H NMR (400 MHz, DMSO-d₆): δ 7.54 (dd, J=8.4, 2.0 Hz, 1H), 7.42-7.36 (m, 1H), 5.66 (s, 2H), 3.49 (t, J=8.0 Hz, 2H), 3.02 (t, J=7.2 Hz, 2H), 2.69 (t, J=8.0 Hz, 2H), 2.40 (q, J=7.2 Hz, 2H), 2.20 (s, 3H), 0.94 (t, J=6.8 Hz, 3H), 0.76 (t, J=7.6 Hz, 2H), 0.13 (s, 9H).

Step 2: 2-(5,7-difluoro-1H-indazol-3-yl)-N-ethyl-N-methylethan-1-amine (A36)

To a stirred solution of 2-(5,7-difluoro-1-((2-(trimethylsilyl)ethoxy)methyl)-1H-indazol-3-yl)-N-ethyl-N-methylethan-1-amine (0.2 g, 0.54 mmol) in CH₂Cl₂ (5 mL) at 0° C. was added 4 M HCl in dioxane (12 mL) and the reaction mixture was stirred at RT for 16 h. The reaction mixture was quenched with 4 N aq. NaOH (150 mL) and extracted with CH₂Cl₂ (3×100 mL). The combined organics were dried over Na₂SO₄, concentrated under reduced pressure and the crude material was purified by reverse phase column chromatography (product eluted at 39% MeCN in H₂O) to afford 2-(5,7-difluoro-1H-indazol-3-yl)-N-ethyl-N-methylethan-1-amine (0.052 g, 40%) as a white solid. LCMS (Condition C): $t_R$ (1.104 min) m/z=239.9 [M+H]⁺; ¹H NMR (400 MHz, DMSO-d₆): δ 13.40 (s, 1H), 7.47 (dd, J=8.8, 1.6 Hz, 1H), 7.28 (t, J=10.4 Hz, 1H), 3.06 (t, J=7.2 Hz, 2H), 2.83-2.73 (m, 2H), 2.52-2.49 (m, 2H), 2.28 (s, 3H), 0.98 (t, J=6.8 Hz, 3H).

Example 37: Synthesis of N-(2-(5,7-difluoro-1H-indazol-3-yl)ethyl)-N-methylpropan-2-amine (A37)

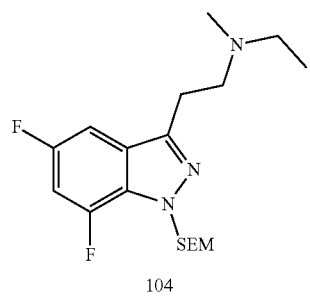

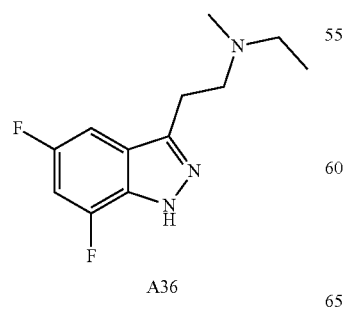

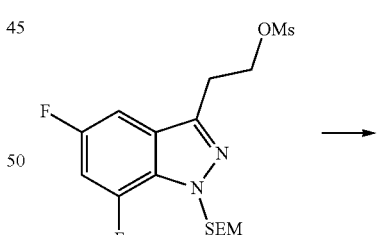

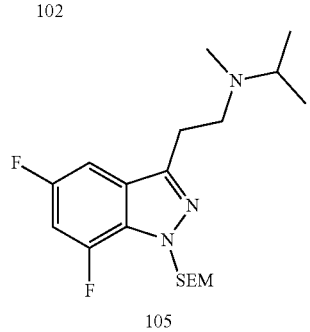

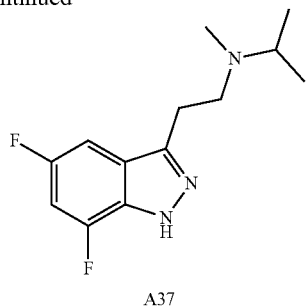

A37

Step 1: N-(2-(5,7-difluoro-1-((2-(trimethylsilyl)
ethoxy)methyl)-1H-indazol-3-yl)ethyl)-N-methyl-
propan-2-amine (105)

N-(2-(5,7-difluoro-1-((2-(trimethylsilyl)ethoxy)methyl)-1H-indazol-3-yl)ethyl)-N-methylpropan-2-amine was synthesised according to General Procedure B with 2-(5,7-difluoro-1-((2-(trimethylsilyl)ethoxy)methyl)-1H-indazol-3-yl)ethyl methanesulfonate (0.28 g, 0.69 mmol), $K_2CO_3$ (0.95 g, 6.87 mmol) and N-methylpropan-2-amine (0.25 g, 3.44 mmol). The title compound was obtained as a brown liquid (0.23 g, 87%) which was used in the next reaction without further purification. LCMS (Condition C): $t_R$ (1.703 min) m/z=384.21 [M+H]$^+$; $^1$H NMR (400 MHz, DMSO-$d_6$): δ 7.52 (d, J=8.4 Hz, 1H), 7.39 (t, J=9.6 Hz, 1H), 5.67 (s, 2H), 3.48 (t, J=8.0 Hz, 2H), 2.99 (t, J=7.2 Hz, 2H), 2.80-2.77 (m, 1H), 2.69 (t, J=7.6 Hz, 2H), 2.19 (s, 3H), 0.89 (d, J=6.8 Hz, 6H), 0.76 (t, J=8.0 Hz, 2H), 0.13 (s, 9H).

Step 2: N-(2-(5,7-difluoro-1-((2-(trimethylsilyl)
ethoxy)methyl)-1H-indazol-3-yl)ethyl)-N-methyl-
propan-2-amine (A37)

To a stirred solution of N-(2-(5,7-difluoro-1-((2-(trimethylsilyl)ethoxy)methyl)-1H-indazol-3-yl)ethyl)-N-methylpropan-2-amine (0.23 g, 0.59 mmoL) in $CH_2Cl_2$ (5 mL) at 0° C. was added 4 M HCl in 1,4-dioxane (8 mL) and the reaction mixture was stirred at RT for 16 h. The reaction mixture was quenched with 4 N aq. NaOH (100 mL) and extracted with EtOAc (3×100 mL). The combined organics were dried over $Na_2SO_4$, concentrated under reduced pressure and the crude material was purified by reverse phase column chromatography (product eluted at 40% MeCN in water) to afford N-(2-(5,7-difluoro-1-((2-(trimethylsilyl)ethoxy)methyl)-1H-indazol-3-yl)ethyl)-N-methylpropan-2-amine (0.059 g, 39%) as a white solid. LCMS (Condition C): $t_R$ (1.118 min) m/z=253.8 [M+H]$^+$; $^1$H NMR (400 MHz, DMSO-$d_6$): δ 13.36 (s, 1H), 7.44 (dd, J=8.8, 2.0 Hz, 1H), 7.26 (t, J=10.8 Hz, 1H), 2.99 (t, J=7.2 Hz, 2H), 2.83-2.77 (m, 1H), 2.69 (t, J=8.0 Hz, 2H), 2.20 (s, 3H), 0.90 (d, J=6.4 Hz, 6H).

Example 38: Synthesis of 2-(6-fluoro-4-methoxy-1H-indazol-3-yl)-N,N-dimethylethan-1-amine (A38)

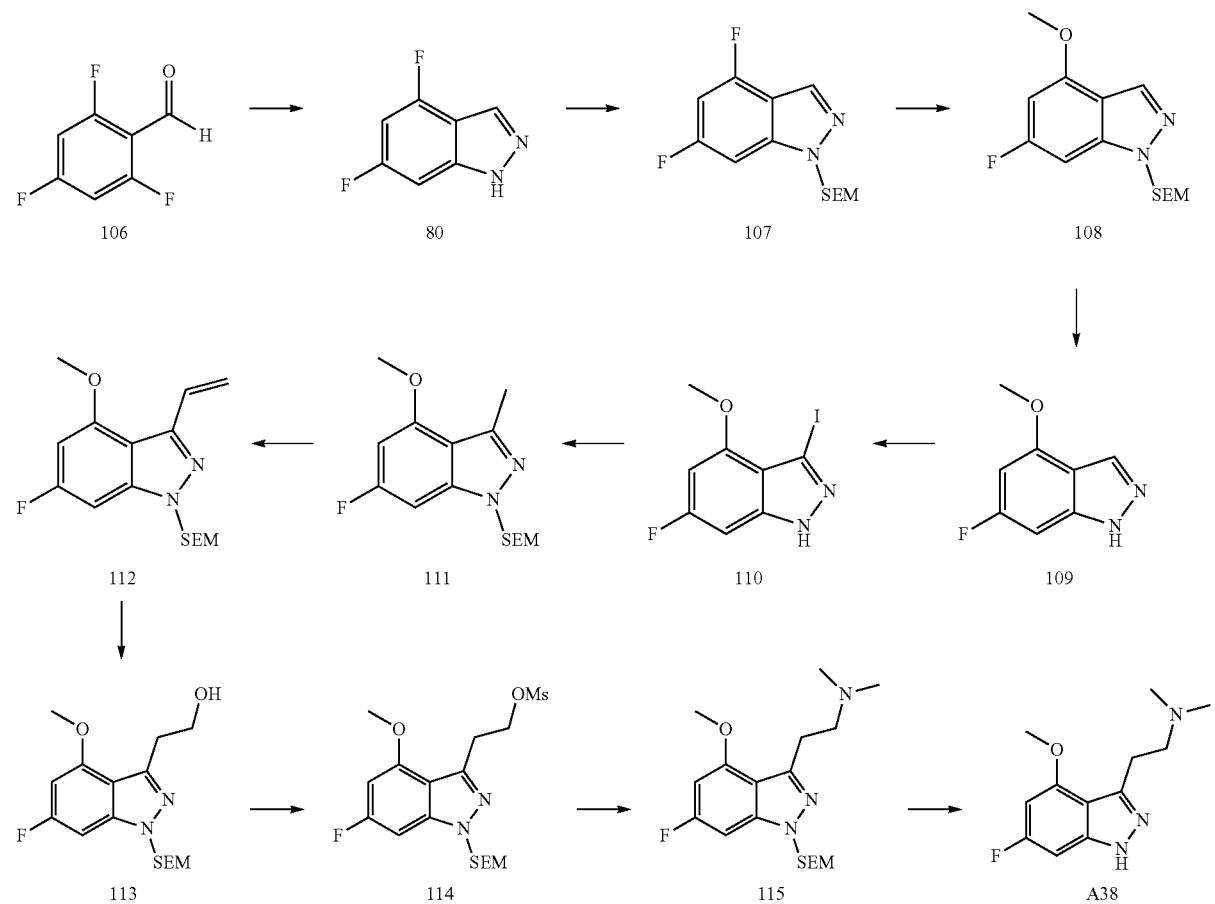

Step 1: 4,6-difluoro-1H-indazole (80)

A stirred solution of the 2,4,6-trifluorobenzaldehyde (10.0 g, 62.46 mmol) in hydrazine monohydrate (6.07 mL, 124.9 mmol) was heated at 100° C. for 48 h. After completion, the reaction mixture was diluted with water (1 L) and extracted with EtOAc (3×350 mL). The combined organic layers were dried over $Na_2SO_4$ and concentrated under vacuum to afford 4,6-difluoro-1H-indazole (9.9 g, quant.) as a brown solid. LCMS (Condition C): $t_R$ (1.728 min) m/z=155.0 [M+H]$^+$; $^1$H NMR (400 MHz, DMSO-$d_6$): δ13.32 (s, 1H), 8.21 (s, 1H), 7.26-7.23 (m, 1H), 7.01-6.95 (m, 1H).

Step 2: 4,6-difluoro-1-((2-(trimethylsilyl)ethoxy)methyl)-1H-indazole (107)

Two parallel reactions containing a solution of 4,6-difluoro-1H-indazole (5.0 g, 32.4 mmol) in DMF (50 mL) was added 60% w/w NaH mineral oil dispersion (1.94 g. 48.7 mmol) portion wise at 0° C. After 15 min, 2-(trimethylsilyl)ethoxymethyl chloride (5.75 mL, 32.4 mmol) was added dropwise and the resulting reaction mixture was stirred at RT for 6 h. After completion the reaction mixture was quenched with cold water (2×200 mL) and extracted with EtOAc (2×200 mL). The combined organic layers were dried over $Na_2SO_4$ and concentrated under reduced pressure. The resultant crude mass was purified by flash column chromatography (product eluted at 32% EtOAc in hexane) to afford 4,6-difluoro-1-((2-(trimethylsilyl)ethoxy)methyl)-1H-indazole (14.9 g, 81%) as a brown liquid. LCMS (Condition C): $t_R$ (2.332 min) m/z=284.8 [M+H]$^+$.

Step 3: 6-fluoro-4-methoxy-1-((2-(trimethylsilyl)ethoxy)methyl)-1H-indazole (108)

To a stirred solution of 4,6-difluoro-1-((2-(trimethylsilyl)ethoxy)methyl)-1H-indazole (1.0 g, 3.52 mmol) in 1,4-dioxane (7.0 mL) was added 60% w/w NaH mineral oil dispersion (0.14 g. 3.52 mmol) at 0° C. After 15 min, MeOH (3.5 mL) was added dropwise and the reaction mixture was stirred at RT for 3 h followed by 2 h at 50° C. and for 16 h at 90° C. The reaction mixture was concentrated to remove excess MeOH, then diluted with cold water (2×250 mL) and extracted with EtOAc (2×250 mL). The combined organics were dried over $Na_2SO_4$ and concentrated under reduced pressure. The resultant crude was purified by flash column chromatography (product eluted at 10% EtOAc in hexane) to afford 6-fluoro-4-methoxy-1-((2-(trimethylsilyl)ethoxy)methyl)-1H-indazole (0.67 g, 64%) as a pale yellow gum. LCMS (Condition C): $t_R$ (2.237 min) m/z=296.8 [M+H]$^+$; $^1$H NMR (400 MHz, DMSO-$d_6$): δ 8.09 (s, 1H), 7.16 (d, J=8.0 Hz, 1H), 6.59 (dd, J=11.6, 1.6 Hz, 1H), 5.67 (s, 2H), 3.93 (s, 3H), 3.50 (t, J=7.6 Hz, 2H), 0.79 (t, J=8.0 Hz, 2H), −0.11 (s, 9H).

Step 4: 6-fluoro-4-methoxy-1H-indazole (109)

A stirred solution of 6-fluoro-4-methoxy-1-((2-(trimethylsilyl)ethoxy)methyl)-1H-indazole (4.7 g, 15.9 mmol) in 4 M HCl in 1,4-dioxane (150 mL) was stirred at RT for 48 h. The reaction mixture was then quenched with saturated aq. $NaHCO_3$ solution (300 mL) and extracted with EtOAc (3×200 mL). The combined organic layers were dried over $Na_2SO_4$ and concentrated under reduced pressure, and the resultant crude was purified by reverse phase column chromatography (product eluted at 38% MeCN in water) to afford 6-fluoro-4-methoxy-1H-indazole (1.5 g, 57%) as an off-white solid. LCMS (Condition C): $t_R$ (1.324 min) m/z=166.8 [M+H]$^+$.

Step 5: 6-fluoro-3-iodo-4-methoxy-1H-indazole (110)

To a stirred solution of 6-fluoro-4-methoxy-1H-indazole (1.5 g, 9.02 mmol) in DMF (40 mL) was added KOH (2.0 g, 36.1 mmol) at 0° C. After 10 min, Iodine (4.58 g, 18.1 mmol) was added portionwise and the reaction mixture was stirred at RT for 24 h. The reaction was quenched with saturated aq. $Na_2S_2O_3$ solution (100 mL), and the precipitate was filtered and filtrate extracted with EtOAc (2×100 mL). The combined organic layers were dried over $Na_2SO_4$ and concentrated under reduced pressure to afford 6-fluoro-3-iodo-4-methoxy-1H-indazole (2.7 g, quant.) as an off-white solid. LCMS (Condition C): $t_R$ (1.529 min) m/z=292.6 [M+H]$^+$; $^1$H NMR (400 MHz, DMSO-$d_6$): δ13.44 (s, 1H), 6.89 (d, J=9.2 Hz, 1H), 6.52 (d, J=11.6 Hz, 1H), 3.91 (s, 3H).

Step 6: 6-fluoro-3-iodo-4-methoxy-1-((2-(trimethylsilyl)ethoxy)methyl)-1H-indazole (111)

To a stirred solution of 6-fluoro-3-iodo-4-methoxy-1H-indazole (2.7 g, 9.24 mmol) in DMF (40 mL) was added 60% w/w NaH mineral oil dispersion (0.55 g, 13.9 mmol) portionwise at 0° C. After 10 min, (2-(chloromethoxy)ethyl)trimethylsilane (1.63 mL, 9.24 mmol) was added dropwise at RT and the mixture was stirred at RT for 1 h. The reaction mixture was quenched with ice cold water (2×100 mL) and extracted with EtOAc (2×200 mL). The combined organic layers were dried over $Na_2SO_4$ and concentrated under reduced pressure. The crude material was purified by reverse phase column chromatography (product eluted at 99% MeCN in water) to afford 6-fluoro-3-iodo-4-methoxy-1-((2-(trimethylsilyl)ethoxy)methyl)-1H-indazole (1.6 g, 41%) as a pale yellow liquid. LCMS (Condition C): $t_R$ (2.438 min) m/z=422.8 [M+H]$^+$; $^1$H NMR (400 MHz, DMSO-$d_6$): δ7.20 (dd, J=9.2, 1.6 Hz, 1H), 6.61 (dd, J=12, 1.6 Hz, 1H), 5.63 (s, 2H), 3.92 (s, 3H), 3.50 (t, J=8.0 Hz, 2H), 0.86-0.76 (m, 2H), −0.10 (s, 9H).

Step 7: 6-fluoro-4-methoxy-1-((2-(trimethylsilyl)ethoxy)methyl)-3-vinyl-1H-indazole (112)

To a stirred solution of 6-fluoro-3-iodo-4-methoxy-1-((2-(trimethylsilyl)ethoxy)methyl)-1H-indazole (0.5 g, 1.18 mmol) and 4,4,5,5-tetramethyl-2-vinyl-1,3,2-dioxaborolane (0.18 g, 1.18 mmol) in THF (7.0 mL) was added solution of $K_2CO_3$ (0.49 g, 3.55 mmol) in $H_2O$ (1.75 mL) at RT and the reaction mixture was purged with nitrogen gas for 15 min. Then Pd(dppf)Cl$_2$ (0.04 g, 0.17 mmol) was added at RT and the reaction mixture was stirred at 100° C. for 16 h. The reaction mixture was diluted with ice-cold $H_2O$ (100 mL) and extracted with EtOAc (3×70 mL). The combined organic layers were dried over $Na_2SO_4$ and concentrated under reduced pressure. The crude material was purified by reverse phase column chromatography (product eluted at 100% MeCN in water) to afford 6-fluoro-4-methoxy-1-((2-(trimethylsilyl)ethoxy)methyl)-3-vinyl-1H-indazole (0.26 g, 68%) as a brown liquid. LCMS (Condition C): $t_R$ (2.712 min) m/z=323.2 [M+H]$^+$.

Step 8: 2-(6-fluoro-4-methoxy-1-((2-(trimethylsilyl)ethoxy)methyl)-1H-indazol-3-yl)ethan-1-ol (113)

To a stirred solution of 6-fluoro-4-methoxy-1-((2-(trimethylsilyl)ethoxy)methyl)-3-vinyl-1H-indazole (0.76 g, 2.35 mmol) in THF (5 mL) was added 0.5 M 9-borabicyclo[3.3.1]nonane in THF (30.6 mL, 15.3 mmol) at 0° C. and the reaction mixture was stirred at RT for 2 h. More 0.5 M 9-Borabicyclo[3.3.1]nonane in THF (15.3 mL, 7.65 mmol) was added at 0° C. and the reaction mixture was stirred at RT for 6 h. The reaction mixture was quenched with 30% w/w aq. $H_2O_2$ (19.1 mL) dropwise followed by 4 M aq. NaOH solution (3.82 mL, 15.3 mmol) at 0° C. and the reaction mixture was stirred at RT for 6 h. The reaction mixture was diluted with ice cold water (100 mL) and extracted with EtOAc (2×70 mL). The combined organic layers were dried over $Na_2SO_4$ and concentrated under reduced pressure. The crude material was purified by flash column chromatography (product eluted at 25% EtOAc in hexane) to afford 2-(6-fluoro-4-methoxy-1-((2-(trimethylsilyl)ethoxy)methyl)-1H-indazol-3-yl)ethan-1-ol (0.24 g, 30%) as a pale yellow liquid. LCMS (Condition C): $t_R$ (1.965 min) m/z=341.1 [M+H]$^+$; $^1$H NMR (400 MHz, DMSO-$d_6$): δ 7.06 (dd, J=9.2, 1.2 Hz, 1H), 6.54 (d, J=10.4 Hz, 1H), 5.57 (s, 2H), 4.65 (t, J=5.2 Hz, 1H), 3.92 (s, 3H), 3.71 (q, J=13.2, 7.2 Hz, 2H), 3.48 (t, J=8.0 Hz, 2H), 3.07 (t, J=8.0 Hz, 2H), 0.78 (t, J=8.0 Hz, 2H), −0.10 (s, 9H).

Step 9: 2-(6-fluoro-4-methoxy-1-((2-(trimethylsilyl)ethoxy)methyl)-1H-indazol-3-yl)ethyl methanesulfonate (114)

2-(6-fluoro-4-methoxy-1-((2-(trimethylsilyl)ethoxy)methyl)-1H-indazol-3-yl)ethyl methanesulfonate was synthesised according to General Procedure A with 2-(6-fluoro-4-methoxy-1-((2-(trimethylsilyl)ethoxy)methyl)-1H-indazol-3-yl)ethan-1-ol (0.24 g, 0.70 mmol), Et$_3$N (2.4 mL) and methanesulfonyl chloride (0.24 mL). After column chromatography (SiO$_2$, product eluted at 18% EtOAc in hexane) the title compound was obtained as a yellow gum (0.2 g, 68%). LCMS (Condition C): $t_R$ (2.181 min) m/z=419.1 [M+H]$^+$; $^1$H NMR (400 MHz, DMSO-$d_6$): δ 7.12 (d, J=8.0 Hz, 1H), 6.59 (d, J=11.6 Hz, 1H), 5.60 (s, 2H), 4.55 (t, J=6.8 Hz, 2H), 3.94 (s, 3H), 3.50 (t, J=8.0 Hz, 2H), 3.37-3.33 (m, 2H), 3.14 (s, 3H), 0.79 (t, J=8.0 Hz, 2H), −0.09 (s, 9H).

Step 10: 2-(6-fluoro-4-methoxy-1-((2-(trimethylsilyl)ethoxy)methyl)-1H-indazol-3-yl)-N,N-dimethylethan-1-amine (115)

2-(6-fluoro-4-methoxy-1-((2-(trimethylsilyl)ethoxy)methyl)-1H-indazol-3-yl)-N,N-dimethylethan-1-amine was synthesised according to General Procedure B with 2-(6-fluoro-4-methoxy-1-((2-(trimethylsilyl)ethoxy)methyl)-1H-indazol-3-yl)ethyl methanesulfonate (0.2 g, 0.47 mmol), K$_2$CO$_3$ (0.66 g, 4.77 mmol) and Me$_2$NH (0.11 g, 2.38 mmol). The title compound was obtained as a yellow gum (0.17 g, 97%) which was used in the next step without further purification. LCMS (Condition C): $t_R$ (2.042 min) m/z=367.8 [M+H]$^+$.

Step 11: 2-(6-fluoro-4-methoxy-1H-indazol-3-yl)-N,N-dimethylethan-1-amine (A38)

The title compound was synthesised according to General Procedure C utilising 2-(4-fluoro-5-methoxy-1-((2-(trimethylsilyl)ethoxy)methyl)-1H-indazol-3-yl)-N,N-dimethylethan-1-amine (130 mg, 0.35 mmol) which after reverse phase chromatography (product eluted at 38% MeCN in H$_2$O) was obtained as a white solid (49 mg, 45%). LCMS (Condition C): $t_R$ (1.085 min) m/z=237.7 [M+H]$^+$; $^1$H NMR (400 MHz, DMSO-$d_6$): δ12.66 (s, 1H), 6.75 (d, J=8.4 Hz, 1H), 6.44-6.41 (m, 1H), 3.91 (s, 3H), 3.02 (t, J=7.2 Hz, 2H), 2.56 (t, J=8.0 Hz, 2H), 2.19 (s, 6H).

Step 12: 2-(6-fluoro-4-methoxy-1H-indazol-3-yl)-N,N-dimethylethan-1-amine fumarate (A38-fumarate)

2-(6-fluoro-4-methoxy-1H-indazol-3-yl)-N,N-dimethylethan-1-amine (46 mg, 0.19 mmol) was formulated as the fumarate salt as per General Procedure F to produce the title compound as a white solid (52 mg, 76% yield). LCMS (Condition C): $t_R$ (1.115 min) m/z=237.8 [M+H]$^+$; $^1$H NMR (400 MHz, DMSO-$d_6$): δ 12.80 (s, 1H), 6.78 (dd, J=9.2, 1.6 Hz, 1H), 6.54 (s, 2H), 6.47-6.44 (m, 1H), 3.91 (s, 3H), 3.14 (t, J=7.2 Hz, 2H), 2.88 (t, J=8.0 Hz, 2H), 2.40 (s, 6H).

Example 39: Synthesis of N-ethyl-2-(6-fluoro-4-methoxy-1H-indazol-3-yl)-N-methylethan-1-amine (A39)

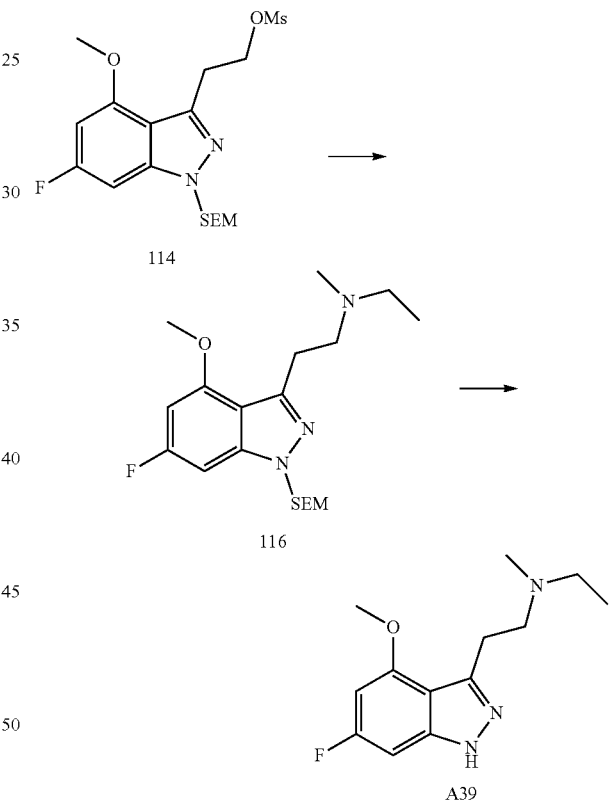

Step 1: N-ethyl-2-(6-fluoro-4-methoxy-1-((2-(trimethylsilyl)ethoxy)methyl)-1H-indazol-3-yl)-N-methylethan-1-amine (116)

N-ethyl-2-(6-fluoro-4-methoxy-1-((2-(trimethylsilyl)ethoxy)methyl)-1H-indazol-3-yl)-N-methylethan-1-amine was synthesised according to General Procedure B with 2-(6-fluoro-4-methoxy-1-((2-(trimethylsilyl)ethoxy)methyl)-1H-indazol-3-yl)ethyl methanesulfonate (0.27 g, 0.64 mmol), K$_2$CO$_3$ (0.89 g, 6.45 mmol) and N-methylethanamine (0.19 g, 3.22 mmol). The title compound was obtained as a yellow gum (0.24 g, 98%) which was used in the next step without further purification. LCMS (Condition C): $t_R$ (1.567 min) m/z=382.3 [M+H]$^+$; $^1$H NMR (400 MHz, DMSO-d$_6$): δ 7.06 (dd, J=9.6, 1.6 Hz, 1H), 6.54 (dd, J=11.6, 1.2 Hz, 1H), 5.57 (s, 2H), 3.92 (s, 3H), 3.48 (t, J=8.0 Hz, 2H), 3.02 (t, J=7.6 Hz, 2H), 2.65 (t, J=8.0 Hz, 2H), 2.41 (q, J=14.4, 7.2 Hz, 2H), 2.21 (s, 3H), 0.97 (t, J=7.2 Hz, 3H), 0.77 (t, J=8.0 Hz, 2H), −0.10 (s, 9H).

Step 2: N-ethyl-2-(6-fluoro-4-methoxy-1H-indazol-3-yl)-N-methylethan-1-amine (A39)

The title compound was synthesised according to General Procedure C utilising N-ethyl-2-(6-fluoro-4-methoxy-1H-indazol-3-yl)-N-methylethan-1-amine (240 mg, 0.62 mmol) which after purification by reverse phase chromatography (product eluted at 33% MeCN in H$_2$O) generated the title compound as a white solid (57 mg, 36%). LCMS (Condition C): $t_R$ (1.119 min) m/z=251.9 [M+H]$^+$; $^1$H NMR (400 MHz, DMSO-d$_6$): δ12.65 (s, 1H), 6.75 (d, J=8.0 Hz, 1H), 6.43 (d, J=11.6 Hz, 1H), 3.90 (s, 3H), 3.02 (t, J=7.6 Hz, 2H), 2.64 (t, J=8.4 Hz, 2H), 2.41 (q, J=14.4, 7.2 Hz, 2H), 2.21 (s, 3H), 0.98 (t, J=7.2 Hz, 3H).

Step 3: N-ethyl-2-(6-fluoro-4-methoxy-1H-indazol-3-yl)-N-methylethan-1-amine fumarate (A39-fumarate)

N-ethyl-2-(6-fluoro-4-methoxy-1H-indazol-3-yl)-N-methylethan-1-amine (51 mg, 0.2 mmol) was formulated as the fumarate salt as per General Procedure F to produce the title compound as a white solid (60 mg, 81% yield). LCMS (Condition C): $t_R$ (1.139 min) m/z=251.9 [M+H]$^+$; $^1$H NMR (400 MHz, DMSO-d$_6$): δ12.83 (s, 1H), 6.78 (dd, J=9.2, 1.6 Hz, 1H), 6.53 (s, 2H) 6.46 (d, J=11.6 Hz, 1H), 3.91 (s, 3H), 3.15 (t, J=6.8 Hz, 2H), 2.93 (t, J=8.4 Hz, 2H), 2.73-2.71 (m, 2H), 2.45 (s, 3H), 1.08 (t, J=7.2 Hz, 3H).

Example 40: Synthesis of 3-(2-(azetidin-1-yl)ethyl)-6-fluoro-4-methoxy-1H-indazole (A40)

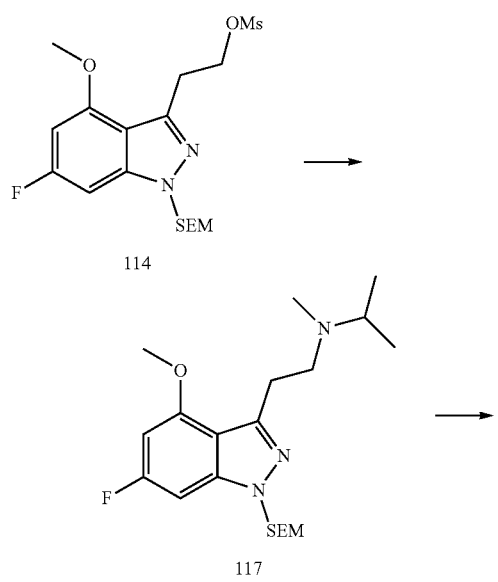

-continued

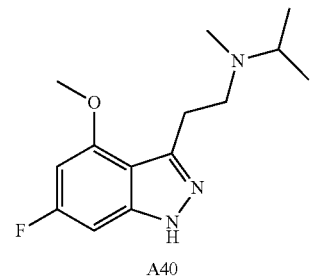

A40

Step 1: N-(2-(6-fluoro-4-methoxy-1-((2-(trimethylsilyl)ethoxy)methyl)-1H-indazol-3-yl)ethyl)-N-methylpropan-2-amine (117)

N-(2-(6-fluoro-4-methoxy-1-((2-(trimethylsilyl)ethoxy)methyl)-1H-indazol-3-yl)ethyl)-N-methylpropan-2-amine was synthesised according to General Procedure B with 2-(6-fluoro-4-methoxy-1-((2-(trimethylsilyl)ethoxy)methyl)-1H-indazol-3-yl)ethyl methanesulfonate (0.27 g, 0.64 mmol, 1.0 eq), K$_2$CO$_3$ (0.89 g, 6.45 mmol, 10.0 eq) and N-methylpropan-2-amine (0.23 g, 3.22 mmol, 5.0 eq). The title compound was obtained as a yellow gum (0.24 g, 94% yield) which was used in the next step without further purification. LCMS (Condition C): $t_R$ (1.633 min) m/z=396.2 [M+H]$^+$.

Step 2: N-(2-(6-fluoro-4-methoxy-1H-indazol-3-yl)ethyl)-N-methylpropan-2-amine (A40)

The title compound was synthesised according to General Procedure C utilising N-(2-(6-fluoro-4-methoxy-1-((2-(trimethylsilyl)ethoxy)methyl)-1H-indazol-3-yl)ethyl)-N-methylpropan-2-amine (240 mg, 0.61 mmol) which upon purification (C18 SiO$_2$, product eluted at 38% MeCN in H$_2$O) generated the title compound as a white solid (59 mg, 37%). LCMS (Condition C): $t_R$ (1.168 min) m/z=265.9 [M+H]$^+$; $^1$H NMR (400 MHz, DMSO-d$_6$): δ 12.64 (s, 1H), 6.75 (d, J=9.2 Hz, 1H), 6.43 (d, J=11.6 Hz, 1H), 3.90 (s, 3H), 2.99 (t, J=7.6 Hz, 2H), 2.81-2.78 (m, 1H), 2.64 (t, J=8.4 Hz, 2H), 2.21 (s, 3H), 0.93 (d, J=6.8 Hz, 6H).

Step 3: N-(2-(6-fluoro-4-methoxy-1H-indazol-3-yl)ethyl)-N-methylpropan-2-amine fumarate (A40-fumarate)

N-(2-(6-fluoro-4-methoxy-1H-indazol-3-yl)ethyl)-N-methylpropan-2-amine (22 mg, 0.08 mmol) was formulated as the fumarate salt as per General Procedure F to produce the title compound as a white solid (19 mg, 58%). LCMS (Condition C): $t_R$ (1.570 min) m/z=266.2 [M+H]$^+$; $^1$H NMR (400 MHz, DMSO-d$_6$): δ 12.76 (s, 1H), 6.79 (dd, J=9.2, 1.6 Hz, 1H), 6.54 (s, 2H), 6.46 (dd, J=11.6, 1.6 Hz, 1H), 3.91 (s, 3H), 3.20-3.16 (m, 3H), 3.02-2.98 (m, 2H), 2.50 (s, 3H), 1.10 (d, J=6.4 Hz, 6H).

Example 41: Synthesis of 3-(2-(azetidin-1-yl)ethyl)-6-fluoro-4-methoxy-1H-indazole (A41)

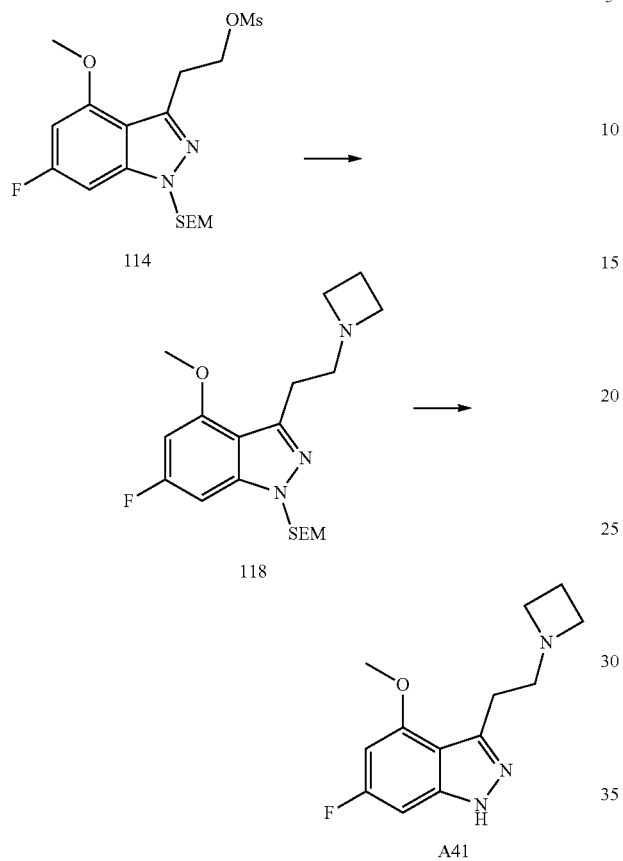

Step 1: 3-(2-(azetidin-1-yl)ethyl)-6-fluoro-4-methoxy-1-((2-(trimethylsilyl)ethoxy)methyl)-1H-indazole (118)

3-(2-(azetidin-1-yl)ethyl)-6-fluoro-4-methoxy-1-((2-(trimethylsilyl)ethoxy)methyl)-1H-indazole was synthesised according to General Method B with 2-(6-fluoro-4-methoxy-1-((2-(trimethylsilyl)ethoxy)methyl)-1H-indazol-3-yl)ethyl methanesulfonate (0.41 g, 0.97 mmol), $K_2CO_3$ (1.35 g 9.79 mmol) and azetidine (0.27 g, 4.89 mmol). The title compound was obtained as a yellow gum (0.4 g, quant.) which was used in the next step without further purification. LCMS (Condition C): $t_R$ (1.667 min) m/z=380.3 $[M+H]^+$; $^1$H NMR (400 MHz, DMSO-$d_6$): δ 7.06 (dd, J=9.6, 2.0 Hz, 1H), 6.54 (dd, J=11.6, 2.0 Hz, 1H), 5.56 (s, 2H), 3.92 (s, 3H), 3.50-3.46 (m, 2H), 3.07 (t, J=6.8 Hz, 4H), 2.87-2.83 (m, 2H), 2.65-2.62 (m, 2H), 1.95-1.88 (m, 2H), 0.80-0.76 (m, 2H), −0.09 (s, 9H).

Step 2: 3-(2-(azetidin-1-yl)ethyl)-6-fluoro-4-methoxy-1H-indazole (A41)

The title compound was synthesised according to General Procedure C utilising 3-(2-(azetidin-1-yl)ethyl)-6-fluoro-4-methoxy-1-((2-(trimethylsilyl)ethoxy)methyl)-1H-indazole (0.4 g, 1.05 mmol) which upon purification (reverse phase, 43% MeCN in $H_2O$) generated the title compound as a white solid (30 mg, 36%). LCMS (Condition C): $t_R$ (1.074) m/z=249.8 $[M+H]^+$; $^1$H NMR (400 MHz, DMSO-$d_6$): δ 12.66 (s, 1H), 6.77-6.74 (m, 1H), 6.45-6.41 (m, 1H), 3.92 (s, 3H), 3.11 (t, J=6.8 Hz, 4H), 2.86 (t, J=7.2 Hz, 2H), 2.66 (t, J=8.0 Hz, 2H), 1.97-1.90 (m, 2H).

Example 42: Synthesis of 6-fluoro-4-methoxy-3-(2-(pyrrolidin-1-yl)ethyl)-1H-indazole (A42)

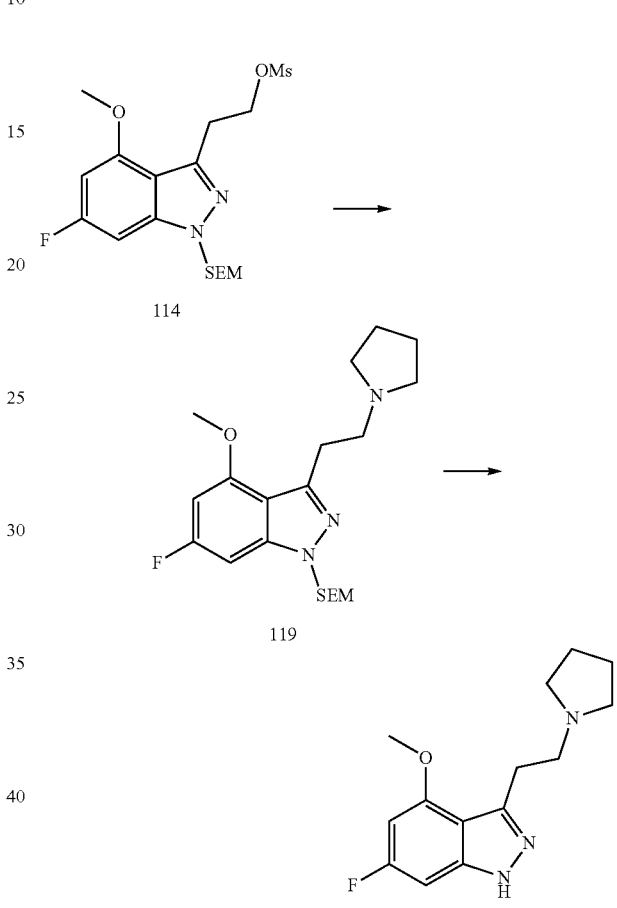

Step 1: 6-fluoro-4-methoxy-3-(2-(pyrrolidin-1-yl)ethyl)-1-((2-trimethylsilyl)ethoxy)methyl)-1H-indazole (119)

6-fluoro-4-methoxy-3-(2-(pyrrolidin-1-yl)ethyl)-1-((2-trimethylsilyl)ethoxy)methyl)-1H-indazole was synthesised according to General Method B with 2-(6-fluoro-4-methoxy-1-((2-(trimethylsilyl)ethoxy)methyl)-1H-indazol-3-yl)ethyl methanesulfonate (0.41 g, 0.97 mmol), $K_2CO_3$ (1.35 g 9.79 mmol) and pyrrolidine (0.34 g, 4.89 mmol). The title compound was obtained as a yellow gum (0.41 g, quant. yield) which was used in the next reaction without further purification. LCMS (Condition C): $t_R$ (1.937) m/z=394.3 $[M+H]^+$; $^1$H NMR (400 MHz, DMSO-$d_6$): δ 7.06 (dd, J=9.6, 2.0 Hz, 1H), 6.54 (dd, J=11.6, 1.6 Hz, 1H), 5.57 (s, 2H), 3.92 (s, 3H), 3.49 (t, J=3.2 Hz, 2H), 3.08-3.04 (m, 2H), 2.75-2.71 (m, 2H), 2.51-2.48 (m, 4H), 1.69-1.66 (m, 4H), 0.79-0.75 (m, 2H), −0.09 (s, 9H).

Step 2: 3-(2-(azetidin-1-yl)ethyl)-6-fluoro-4-methoxy-1H-indazole (A42)

The title compound was synthesised according to General Procedure C utilising 6-fluoro-4-methoxy-3-(2-(pyrrolidin-1-yl)ethyl)-1-((2-(trimethylsilyl)ethoxy)methyl)-1H-indazole (0.4 g, 1.05 mmol) which upon purification (reverse phase, 51% MeCN in H$_2$O) generated the title compound as a white solid (19 mg, 7%). LCMS (Condition C): $t_R$ (1.117) m/z=263.9 [M+H]$^+$; $^1$H NMR (400 MHz, DMSO-d$_6$): 12.66 (s, 1H), 6.75 (dd, J=9.2 Hz, 1.6 Hz, 1H), 6.42 (d, J=11.6 Hz, 1H), 3.90 (s, 3H), 3.06 (t, J=7.6 Hz, 2H), 2.71 (t, J=8.4 Hz, 2H), 2.50-2.48 (m, 4H), 1.71-1.67 (m, 4H).

Example 43: Synthesis of 3-(2-(2-azabicyclo[3.1.0]hexan-2-yl)ethyl)-6-fluoro-4-methoxy-1H-indazole (A43)

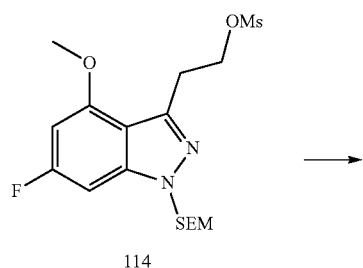

114

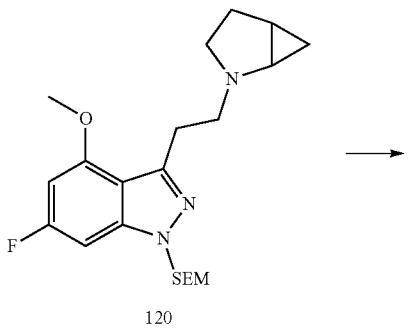

120

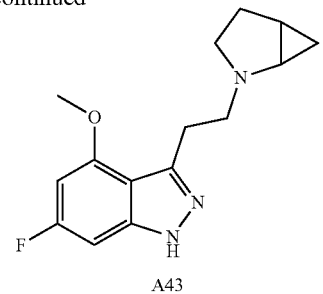

A43

Step 1: 3-(2-(2-azabicyclo[3.1.0]hexan-2-yl)ethyl)-6-fluoro-4-methoxy-1-((2-(trimethylsilyl)ethoxy)methyl)-1H-indazole (120)

3-(2-(2-azabicyclo[3.1.0]hexan-2-yl)ethyl)-6-fluoro-4-methoxy-1-((2-(trimethylsilyl)ethoxy)methyl)-1H-indazole was synthesised according to General Method B with 2-(6-fluoro-4-methoxy-1-((2-(trimethylsilyl)ethoxy)methyl)-1H-indazol-3-yl)ethyl methanesulfonate (0.37 g, 0.88 mmol), K$_2$CO$_3$ (1.22 g, 8.83 mmol) and 2-azabicyclo[3.1.0]hexane hydrochloride (0.52 g, 4.41 mmol). The title compound was obtained as a yellow gum (0.37 g, quant.) which was used in the next step without further purification. LCMS (Condition C): $t_R$ (1.817 min) m/z=406.2 [M+H]$^+$; $^1$H NMR (400 MHz, DMSO-d$_6$): δ 7.07 (dd, J=9.6, 1.6 Hz, 1H), 6.54 (dd, J=11.6, 2.0 Hz, 1H), 5.58 (s, 2H), 3.92 (s, 3H), 3.49 (t, J=8.0 Hz, 2H), 3.09-3.06 (m, 2H), 2.87-2.78 (m, 1H), 2.76-2.70 (m, 3H), 1.84-1.75 (m, 3H), 1.39-1.34 (m, 1H), 0.78 (t, J=8.0 Hz, 2H), 0.64-0.62 (m, 1H), 0.04-0.02 (m, 1H), −0.09 (s, 9H).

Step 3-(2-(2-azabicyclo[3.1.0]hexan-2-yl)ethyl)-6-fluoro-4-methoxy-1H-indazole (A43)

The title compound was synthesised according to General Procedure C utilising 3-(2-(2-azabicyclo[3.1.0]hexan-2-yl)ethyl)-6-fluoro-4-methoxy-1-((2-(trimethylsilyl)ethoxy)methyl)-1H-indazole (0.37 g, 0.91 mmol) which upon purification (reverse phase, 53% MeCN in H$_2$O) generated the title compound as a white solid (62 mg, 25%). LCMS: $t_R$ (1.103) m/z=175.9 [M+H]$^+$; $^1$H NMR (400 MHz, DMSO-d$_6$): δ 12.69 (s, 1H), 6.76 (dd, J=9.6, 2.0 Hz, 1H), 6.43 (dd, J=12.0 1.6 Hz, 1H), 3.90 (s, 3H), 3.11-3.07 (m, 2H), 2.91-2.86 (m, 1H), 2.87-2.68 (m, 3H), 1.86-1.74 (m, 3H), 1.35-1.32 (m, 1H), 0.65-0.62 (m, 1H), 0.06-0.01 (m, 1H).

Example 44: Synthesis of 2-(7-fluoro-4-methoxy-1H-indazol-3-yl)-N,N-dimethylethan-1-amine (A44)

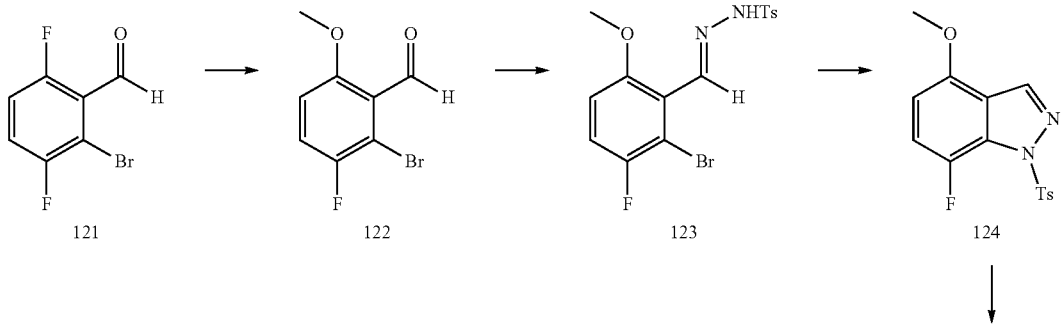

121  122  123  124

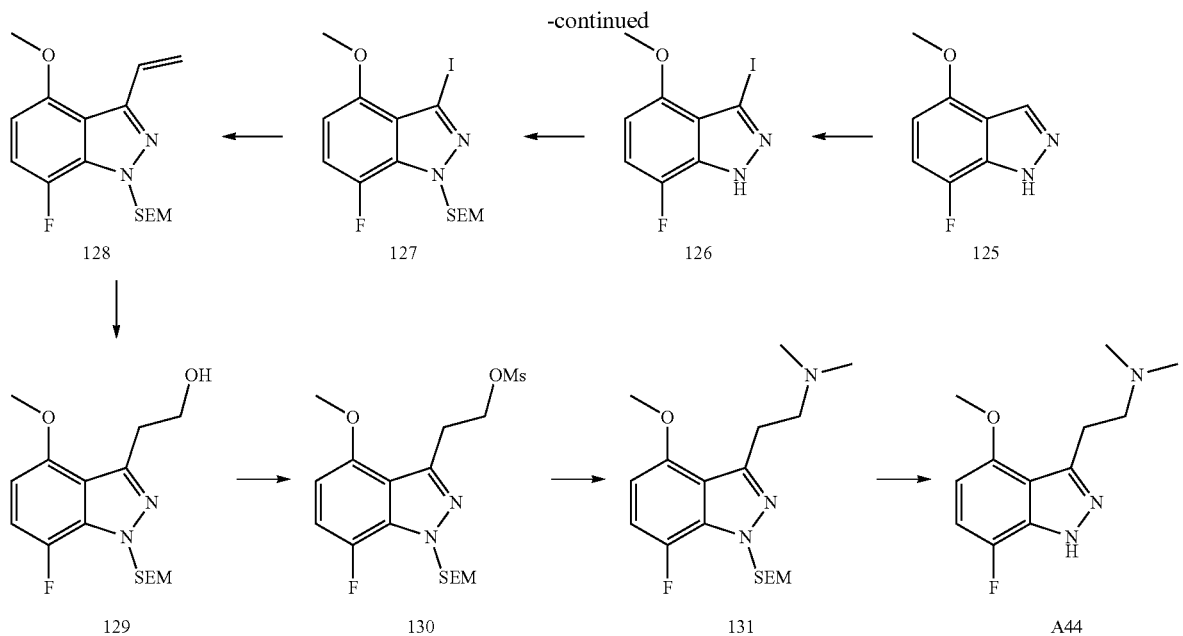

Step 1: 2-bromo-3-fluoro-6-methoxybenzaldehyde (122)

To a stirred solution of 2-bromo-3,6-difluorobenzaldehyde (10.0 g, 45.2 mmol) in THF (500 ml) and MeOH (100 ml) was added NaOMe (2.93 g, 52.3 mmol) and the mixture was stirred at 60° C. for 16 h. The reaction mixture was concentrated under reduced pressure and the crude material was purified by trituration using petroleum ether and n-pentane to afford 2-bromo-3-fluoro-6-methoxybenzaldehyde (10 g, 95%) as a white solid. 1H NMR (400 MHz, DMSO-d$_6$): δ 10.25 (s, 1H), 7.64 (t, J=9.2 Hz, 1H), 7.30-7.27 (m, 1H), 3.89 (s, 3H).

Step 2: (E)-N'-(2-bromo-3-fluoro-6-methoxybenzylidene)-4-methylbenzenesulfonohydrazide (123)

To a stirred solution of 2-bromo-3-fluoro-6-methoxybenzaldehyde (10.0 g, 42.9 mmol) in MeOH (100 mm) was added 4-methylbenzenesulfonohydrazide (8.3 g, 45.1 mmol) at 0° C. under nitrogen atmosphere and the resulting reaction mixture was stirred at RT for 1 h. The reaction mixture was concentrated under reduced pressure to afford (E)N'(2-bromo-3-fluoro-6-methoxybenzylidene)-4-methylbenzenesulfonohydrazide which was used in the next reaction without further purification.

Step 3: 7-fluoro-4-methoxy-1-tosyl-1H-indazole (124)

To a stirred solution of (E)-N'-(2-bromo-3-fluoro-6-methoxybenzylidene)-4-methylbenzenesulfonohydrazide (10.0 g) in isoamyl alcohol (100 mL) was added Cu$_2$O (3.06 g, 2.1 mmol) and the resulting reaction mixture was stirred at 100° C. for 2 h. The reaction mixture was diluted with water (600 mL) and extracted with EtOAc (2×400 mL). The combined organic layers were dried over Na$_2$SO$_4$ and concentrated under reduced pressure and the crude material was purified by column chromatography (product eluted at 40% EtOAc in hexane) to afford 7-fluoro-4-methoxy-1-tosyl-1H-indazole (3.0 g, 22%) as a yellow solid. LCMS (Condition C): t$_R$ (1.863 min) m/z=320.79 [M+H]$^+$.

Step 4: 7-fluoro-4-methoxy-1H-indazole (125)

To a stirred solution of 7-fluoro-4-methoxy-1-tosyl-1H-indazole (1.0 g, 3.12 mmol) in DMSO (5 mL) and water (5 mL) was added K$_2$CO$_3$ (1.2 g, 9.37 mmol) and the mixture was stirred at 120° C. for 2 h. The reaction mixture was poured into ice-cold H$_2$O (100 mL) and the solid material was collected by filtration and dried under reduced pressure to afford 7-fluoro-4-methoxy-1H-indazole (500 mg, 96%) as an off-white solid. LCMS (Condition C): t$_R$ (1.659 min) m/z=167.3 [M+H]$^+$.

Step 5: 7-fluoro-3-iodo-4-methoxy-1H-indazole (126)

To a stirred solution of 7-fluoro-4-methoxy-1H-indazole (3.0 g, 18.1 mmol) in DMF (8 mL) was added N-iodosuccinimide (6.0 g, 26.7 mmol) and the reaction mixture was stirred at RT for 1 h. The reaction mixture was poured into ice cold H$_2$O (100 mL) and the solid material was collected by filtration and dried under reduced pressure to afford 7-fluoro-3-iodo-4-methoxy-1H-indazole (5.5 g, Quantitative yield) as an off white solid which was used in the next reaction without further purification. LCMS (Condition C): t$_R$ (1.890 min) m/z=293.0 [M+H]$^+$.

Step 6: 7-fluoro-3-iodo-4-methoxy-1-((2-(trimethylsilyl)ethoxy)methyl)-1H-indazole (127)

To a stirred solution of 7-fluoro-3-iodo-4-methoxy-1H-indazole (5.5 g, 18.8 mmol) in DMF (50 mL) was added 60% w/w NaH mineral oil dispersion (0.67 g, 28.3 mmol) at 0° C. After 15 min, (2-(chloromethoxy)ethyl)trimethylsilane (3.1 g, 18.6 mmol) was added at 0° C. and the reaction mixture was stirred at RT for 1 h. The reaction mixture was poured into ice cold H$_2$O (20 mL), further diluted with water (400 mL) and extracted with EtOAc (2×250 mL). The combined organic layers were dried over Na$_2$SO$_4$ and concentrated under reduced pressure and the crude material was purified by reverse phase column chromatography (product eluted at 8:2 MeCN:H$_2$O) to afford 7-fluoro-3-iodo-4-methoxy-1-((2-(trimethylsilyl)ethoxy)methyl)-1H-indazole (0.9 g, 11%) as a yellow solid. $^1$H NMR (400 MHz, DMSO-d$_6$): δ 7.25-7.20 (m, 1H), 6.55 (dd, J=8.8, 1.8 Hz, 1H), 5.68 (s, 2H), 3.89 (s, 3H), 3.51 (t, J=7.6 Hz, 2H), 0.77 (t, J=7.6 Hz, 2H), −0.12 (s, 9H).

Step 7: 7-fluoro-4-methoxy-1-((2-(trimethylsilyl)ethoxy)methyl)-3-vinyl-1H-indazole (128)

To a stirred solution of 7-fluoro-3-iodo-4-methoxy-1-((2-(trimethylsilyl)ethoxy)methyl)-1H-indazole (0.25 g, 0.59 mmol) in THF (4 mL) was added 4,4,5,5-tetramethyl-2-vinyl-1,3,2-dioxaborolane (0.09 g, 0.59 mmol) and a solution of K$_2$CO$_3$ (0.24 g, 1.74 mmol) in H$_2$O (1 mL) and the reaction mixture was purged with nitrogen gas for 15 min. Pd(dppf)Cl$_2$ (0.02 g, 0.03 mmol) was added and the reaction mixture was stirred at 90° C. for 16 h. The reaction mixture was poured into H$_2$O (200 mL) and extracted with EtOAc (2×120 mL). The combined organics were dried over Na$_2$SO$_4$ and concentrated under reduced pressure and the crude material was purified by normal phase column chromatography (product eluted at 2% EtOAc in hexane) to afford 7-fluoro-4-methoxy-1-((2-(trimethylsilyl)ethoxy)methyl)-3-vinyl-1H-indazole (105 mg, 55%) as a yellow liquid. $^1$H NMR (400 MHz, DMSO-d$_6$): δ 7.22-7.14 (m, 2H), 6.56 (dd, J=8.4, 2.4 Hz, 1H), 6.12 (dd, J=17.6, 2.0 Hz, 1H), 5.70 (s, 2H), 5.42 (dd, J=11.2, 2.0 Hz, 1H), 3.91 (s, 3H), 3.54 (t, J=8.0 Hz, 2H), 0.79 (t, J=7.6 Hz, 2H), −0.12 (s, 9H).

Step 8: 2-(7-fluoro-4-methoxy-1-((2-(trimethylsilyl)ethoxy)methyl)-1H-indazol-3-yl)ethan-1-ol (129)

To a stirred solution of 7-fluoro-4-methoxy-1-((2-(trimethylsilyl)ethoxy)methyl)-3-vinyl-1H-indazole (0.44 g, 1.36 mmol) in THF (7 mL) was added 0.5 M 9-borabicyclo[3.3.1]nonane in THF (15 mL, 7.5 mmol) at 0° C. under nitrogen atmosphere and the reaction mixture was stirred at RT for 16 h. The reaction mixture was quenched with 30% w/w aq. H$_2$O$_2$ (19 mL) followed by 4 M aq. NaOH (2 mL) at 0° C. and the mixture was stirred at RT for 3 h. The reaction mixture was poured into H$_2$O (200 mL) and extracted with EtOAc (2×110 mL). The combined organic layers were dried over Na$_2$SO$_4$ and concentrated under reduced pressure and the crude material was purified by flash column chromatography (product eluted at 17% EtOAc in hexane) to afford 2-(7-fluoro-4-methoxy-1-((2-(trimethylsilyl)ethoxy)methyl)-1H-indazol-3-yl)ethan-1-ol (0.25 g, 54%) as a pale yellow liquid. LCMS (Condition C): t$_R$ (1.954 min) m/z=341.0 [M+H]$^+$; $^1$H NMR (400 MHz, DMSO-d$_6$): δ 7.21-7.14 (m, 1H), 6.48 (d, J=5.6 Hz, 1H), 5.63 (s, 2H), 4.67 (s, 1H), 3.89 (s, 3H), 3.72 (bs, 2H), 3.50 (bs, 2H), 3.16-3.11 (m, 2H), 0.77 (bs, 2H), −0.11 (s, 9H).

Step 9: 2-(7-fluoro-4-methoxy-1-((2-(trimethylsilyl)ethoxy)methyl)-1H-indazol-3-yl)ethyl methanesulfonate (130)

2-(7-fluoro-4-methoxy-1-((2-(trimethylsilyl)ethoxy)methyl)-1H-indazol-3-yl)ethyl methanesulfonate was synthesised according to General Procedure A with 2-(7-fluoro-4-methoxy-1-((2-(trimethylsilyl)ethoxy)methyl)-1H-indazol-3-yl)ethan-1-ol (0.25 g, 0.73 mmol), Et$_3$N (4.4 mL) and methanesulfonyl chloride (0.6 mL, 7.75 mmol). After flash column chromatography (SiO$_2$, product eluted at 30% EtOAc in hexane) the title compound was obtained as a white liquid (0.24 g, 78%). $^1$H NMR (400 MHz, DMSO-d$_6$): δ 7.19 (t, J=9.2 Hz, 1H), 6.53 (d, J=8.4 Hz, 1H), 5.65 (s, 2H), 4.57 (t, J=6.8 Hz, 2H) 3.91 (s, 3H), 3.51 (t, J=7.6 Hz, 2H), 3.39 (t, J=6.8 Hz, 2H), 3.17-3.14 (m, 3H), 0.78 (t, J=7.6 Hz, 2H), −0.11 (s, 9H).

Step 10: 2-(7-fluoro-4-methoxy-1-((2-(trimethylsilyl)ethoxy)methyl)-1H-indazol-3-yl)-N,N-dimethylethan-1-amine (131)

2-(7-fluoro-4-methoxy-1-((2-(trimethylsilyl)ethoxy)methyl)-1H-indazol-3-yl)-N,N-dimethylethan-1-amine was synthesised according to General Method B with 2-(7-fluoro-4-methoxy-1-((2-(trimethylsilyl)ethoxy)methyl)-1H-indazol-3-yl)ethyl methanesulfonate (0.24 g, 0.57 mmol), K$_2$CO$_3$ (0.79 g, 5.73 mmol) and dimethylamine hydrochloride (0.23 g, 2.86 mmol). The title compound was obtained as a light brown liquid (0.2 g, 95%) which was used in the next step without further purification. LCMS (Condition C): t$_R$ (1.535 min) m/z=368.25 [M+H]$^+$; $^1$H NMR (400 MHz, DMSO-d$_6$): δ 7.17-7.12 (m, 1H), 6.49 (dd, J=8.4, 2.4 Hz, 1H), 5.62 (s, 2H), 3.91 (s, 3H), 3.49 (t, J=8.0 Hz, 2H), 3.08 (t, J=7.2 Hz, 2H), 2.58 (t, J=8.0 Hz, 2H), 2.19 (s, 6H), 0.76 (t, J=7.6 Hz, 2H), −0.12 (s, 9H).

Step 11: 2-(7-fluoro-4-methoxy-1H-indazol-3-yl)-N,N-dimethylethan-1-amine (A44)

To a stirred solution of 2-(7-fluoro-4-methoxy-1-((2-(trimethylsilyl)ethoxy)methyl)-1H-indazol-3-yl)-N,N-dimethylethan-1-amine (0.2 g, 0.54 mmol) in CH$_2$Cl$_2$ (4 mL) was added 4 M HCl in 1,4-dioxane (10 mL) at 0° C. and the reaction mixture was stirred at RT for 16 h. The reaction mixture was quenched with 4 N aq. NaOH (100 mL) and extracted with CH$_2$Cl$_2$ (3×50 mL). The combined organic layers were dried over Na$_2$SO$_4$ and concentrated under reduced pressure and the crude material was purified by reverse phase column chromatography (product eluted at 36% MeCN in water) to afford 2-(7-fluoro-4-methoxy-1H-indazol-3-yl)-N,N-dimethylethan-1-amine (0.05 g, 39%) as a brown sticky solid. LCMS (Condition C): t$_R$ (1.094 min) m/z=238.0 [M+H]$^+$; $^1$H NMR (400 MHz, DMSO-d$_6$): δ 13.16 (s, 1H), 7.05-7.00 (m, 1H), 6.36 (dd, J=8.4, 2.4 Hz, 1H), 3.87 (s, 3H), 3.08 (t, J=7.2 Hz, 2H), 2.61 (t, J=8.0 Hz, 2H), 2.21 (s, 6H).

Step 11: 2-(7-fluoro-4-methoxy-1H-indazol-3-yl)-N,N-dimethylethan-1-amine fumarate (A44-fumarate)

To a stirred solution 2-(7-fluoro-4-methoxy-1H-indazol-3-yl)-N,N-dimethylethan-1-amine (0.05 g, 0.21 mmol) in acetone (1 mL) was added fumaric acid (0.02 g, 0.21 mmol) at RT and the reaction mixture was refluxed at 80° C. for 5 min, then cooled to RT and left to stand for 16 h. The material was dried under reduced pressure and then lyophilised from MeCN:H$_2$O (1:1) to afford 2-(7-fluoro-4-methoxy-1H-indazol-3-yl)-N,N-dimethylethan-1-amine fumarate salt (0.066 g, 92%) as an off-white solid. LCMS (Condition C): t$_R$ (1.081 min) m/z=237.73 [M+H]$^+$; $^1$H NMR (400 MHz, DMSO-d$_6$): δ 13.20 (s, 2H), 7.07-7.02 (m, 1H), 6.55 (s, 2H), 6.39 (dd, J=8.4, 2.8 Hz, 1H), 3.88 (s, 2H) 3.20 (t, J=7.2 Hz, 2H), 2.94 (t, J=8.4 Hz, 2H), 2.46 (s, 6H).

Example 45: Synthesis of N-ethyl-2-(7-fluoro-4-methoxy-1H-indazol-3-yl)-N-methylethan-1-amine (A45)

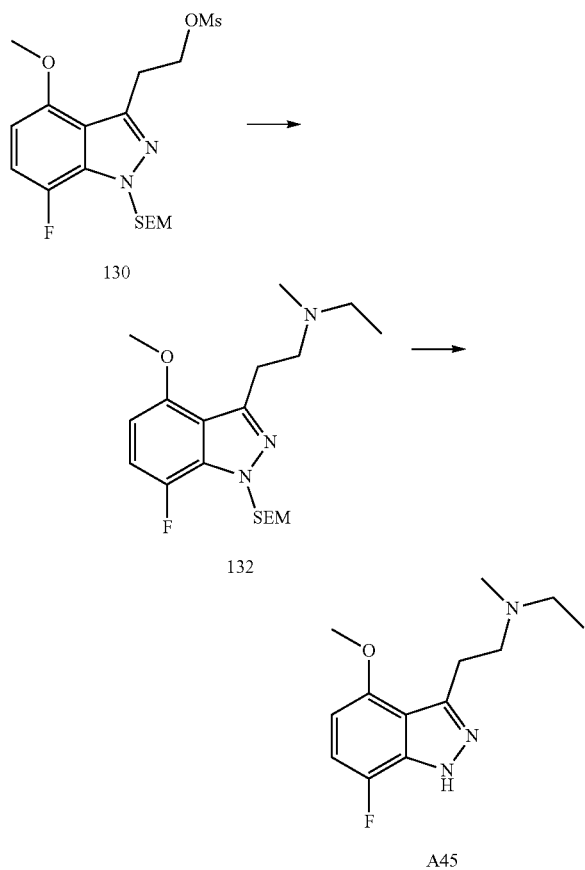

Step 1: N-ethyl-2-(7-fluoro-4-methoxy-1-((2-(trimethylsilyl)ethoxy)methyl)-1H-indazol-3-yl)-N-methylethan-1-amine (132)

N-ethyl-2-(7-fluoro-4-methoxy-1-((2-(trimethylsilyl)ethoxy)methyl)-1H-indazol-3-yl)-N-methylethan-1-amine was synthesised according to General Procedure B with 2-(7-fluoro-4-methoxy-1-((2-(trimethylsilyl)ethoxy)methyl)-1H-indazol-3-yl)ethyl methanesulfonate (0.28 g, 0.67 mmol), $K_2CO_3$ (0.92 g, 6.72 mmol) and N-methylethanamine (0.20 g, 3.36 mmol). The title compound was obtained as a yellow liquid (0.23 g, 90%) which was used in the following step without further purification. LCMS (Condition C): $t_R$ (1.627 min) m/z=382.0 [M+H]$^+$; $^1$H NMR (400 MHz, DMSO-d$_6$): δ 7.17-7.12 (m, 1H), 6.49 (dd, J=8.4, 2.4 Hz, 1H), 5.62 (s, 2H), 3.91 (s, 3H), 3.49 (t, J=8.0 Hz, 2H), 3.08-3.04 (m, 2H), 2.69-2.65 (m, 2H), 2.41 (q, J=14.4, 7.2 Hz, 2H), 2.22 (s, 3H), 0.97 (t, J=7.2 Hz, 3H), 0.755 (t, J=4.8 Hz, 2H), −0.12 (s, 9H).

Step 2: N-ethyl-2-(7-fluoro-4-methoxy-1H-indazol-3-yl)-N-methylethan-1-amine (A45)

To a stirred solution of N-ethyl-2-(7-fluoro-4-methoxy-1-((2-(trimethylsilyl)ethoxy)methyl)-1H-indazol-3-yl)-N-methylethan-1-amine (0.23 g, 0.59 mmol) in $CH_2Cl_2$ (5 mL) was added 4 M HCl in 1,4-dioxane (7 mL) at RT and the reaction mixture was stirred for 7 h. The reaction mixture was quenched with 4 N aq. NaOH (100 mL) and extracted with EtOAc (3×100 mL). The combined organic layers were dried over $Na_2SO_4$ and concentrated under reduced pressure, and the crude material was purified by reverse phase column chromatography (product eluted at 42% MeCN in $H_2O$) to afford N-ethyl-2-(7-fluoro-4-methoxy-1H-indazol-3-yl)-N-methylethan-1-amine (0.05 g, 33% yield) as a white liquid. LCMS (Condition C): $t_R$ (1.132 min) m/z=251.8 [M+H]$^+$; $^1$H NMR (400 MHz, DMSO-d$_6$): δ 13.15 (s, 1H), 7.02 (t, J=8.8 Hz, 1H), 6.36 (d, J=6.8 Hz, 1H), 3.87 (s, 3H) 3.06 (t, J=7.6 Hz, 2H), 2.66 (t, J=8.4 Hz, 2H), 2.43-2.41 (m, 2H), 2.22 (s, 3H), 0.98 (t, J=7.2 Hz, 3H).

Step 3: N-ethyl-2-(7-fluoro-4-methoxy-1H-indazol-3-yl)-N-methylethan-1-amine fumarate (A45-fumarate)

To a stirred solution N-ethyl-2-(7-fluoro-4-methoxy-1H-indazol-3-yl)-N-methylethan-1-amine (0.05 g, 0.20 mmol) in acetone (1 mL) was added fumaric acid (0.023 g, 0.20 mmol) at RT and the reaction mixture was refluxed at 80° C. for 5 min, then cooled to RT and left to stand for 16 h. The material was dried under reduced pressure and lyophilised from MeCN:$H_2O$ (1:1) to afford N-ethyl-2-(7-fluoro-4-methoxy-1H-indazol-3-yl)-N-methylethan-1-amine fumarate salt (0.054 g, 74%) as an off-white solid. LCMS (Condition C): $t_R$ (1.106 min) m/z=251.9 [M+H]$^+$; $^1$H NMR (400 MHz, DMSO-d$_6$): δ 13.26 (s, 1H), 7.07-7.02 (m, 1H), 6.55 (s, 2H), 6.39 (dd, J=8.4, 2.4 Hz, 1H), 3.88 (s, 3H) 3.19 (t, J=7.2 Hz, 2H), 2.95 (t, J=8.4 Hz, 2H), 2.72-2.70 (m, 2H), 2.44 (s, 3H), 1.08 (t, J=7.2 Hz, 3H).

Example 46: Synthesis of N-(2-(7-fluoro-4-methoxy-1H-indazol-3-yl)ethyl)-N-methylpropan-2-amine (A46)

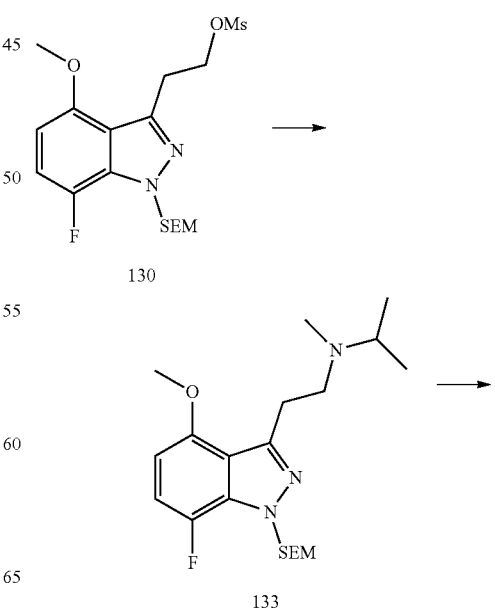

-continued

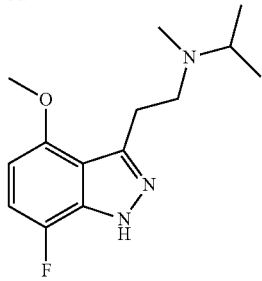

A46

Step 1: N-(2-(7-fluoro-4-methoxy-1-((2-(trimethylsilyl)ethoxy)methyl)-1H-indazol-3-yl)ethyl)-N-methylpropan-2-amine (133)

N-(2-(7-fluoro-4-methoxy-1-((2-(trimethylsilyl)ethoxy)methyl)-1H-indazol-3-yl)ethyl)-N-methylpropan-2-amine was synthesised according to General Procedure B with 2-(7-fluoro-4-methoxy-1-((2-(trimethylsilyl)ethoxy)methyl)-1H-indazol-3-yl)ethyl methanesulfonate (0.4 g, 0.95 mmol), $K_2CO_3$ (1.30 g, 9.41 mmol) and N-methylpropan-2-amine (0.35 g, 4.79 mmol). The title compound was obtained as a pale yellow liquid (0.35 g, 93%) which was used in the next step without further purification. LCMS (Condition C): $t_R$ (1.713 min) m/z=396.3 [M+H]$^+$; $^1$H NMR (400 MHz, DMSO-$d_6$): δ 7.16-7.11 (m, 1H), 6.48 (dd, J=8.4, 2.4 Hz, 1H), 5.62 (s, 2H), 3.89 (s, 3H), 3.49 (t, J=8.0 Hz, 2H), 3.03 (t, J=7.6 Hz, 2H), 2.80-2.77 (m, 1H), 2.66 (t, J=8.0 Hz, 2H), 2.21 (s, 3H), 0.92 (d, J=6.8 Hz, 6H), 0.76 (t, J=8.0 Hz, 1H), −0.12 (s, 9H).

Step 2: N-(2-(7-fluoro-4-methoxy-1H-indazol-3-yl)ethyl)-N-methylpropan-2-amine (A46)

To a stirred solution of N-(2-(7-fluoro-4-methoxy-1-((2-(trimethylsilyl)ethoxy)methyl)-1H-indazol-3-yl)ethyl)-N-methylpropan-2-amine (0.35 g, 0.88 mmol) in $CH_2Cl_2$ (5 mL) was added 4 M HCl in 1,4-dioxane (7 mL) at RT and the reaction mixture was stirred for 9 h. The reaction mixture was quenched with 4 N aq. NaOH (100 mL) and extracted with $CH_2Cl_2$ (3×60 mL). The combined organic layers were dried over $Na_2SO_4$ and concentrated under reduced pressure, and the crude material was purified by reverse phase column chromatography (product eluted at 35% MeCN in $H_2O$) to afford N-(2-(7-fluoro-4-methoxy-1H-indazol-3-yl)ethyl)-N-methylpropan-2-amine (0.045 g, 19%) as a white liquid. LCMS (Condition C): $t_R$ (1.118 min) m/z=265.99 [M+H]$^+$; $^1$H NMR (400 MHz, DMSO-$d_6$): δ 13.14 (s, 1H), 7.02 (t, J=8.8 Hz, 1H), 6.36 (d, J=6.8 Hz, 1H), 3.87 (s, 3H), 3.04 (t, J=7.6 Hz, 2H), 2.81-2.78 (m, 1H), 2.66 (t, J=8.0 Hz, 2H), 2.21 (s, 3H), 0.93 (d, J=6.8 Hz, 6H).

Step 3: N-(2-(7-fluoro-4-methoxy-1H-indazol-3-yl)ethyl)-N-methylpropan-2-amine fumarate (A46-fumarate)

To a stirred solution N-(2-(7-fluoro-4-methoxy-1H-indazol-3-yl)ethyl)-N-methylpropan-2-amine (0.045 g, 0.17 mmol) in acetone (2 mL) was added fumaric acid (0.02 g, 0.17 mmol) at RT and the reaction mixture was refluxed at 100° C. for 5 min, then cooled to RT and left to stand for 16 h. The material was dried under reduced pressure and lyophilised from MeCN:$H_2O$ (1:1) to afford N-(2-(7-fluoro-4-methoxy-1H-indazol-3-yl)ethyl)-N-methylpropan-2-amine fumarate salt (0.045 g, 70%) as an off-white solid. LCMS (Condition C): $t_R$ (1.148 min) m/z=265.9 [M+H]$^+$; $^1$H NMR (400 MHz, DMSO-$d_6$): δ 13.30 (s, 1H), 7.05 (t, J=9.2 Hz, 1H), 6.53 (s, 2H), 6.39 (d, J=6.4 Hz, 1H), 3.88 (s, 3H), 3.21-3.18 (m, 3H), 2.99-2.95 (m, 2H), 2.45 (s, 3H), 1.07 (d, J=6.4 Hz, 6H).

Example 47: Synthesis of 3-(2-(azetidin-1-yl)ethyl)-7-fluoro-4-methoxy-1H-indazole (A47)

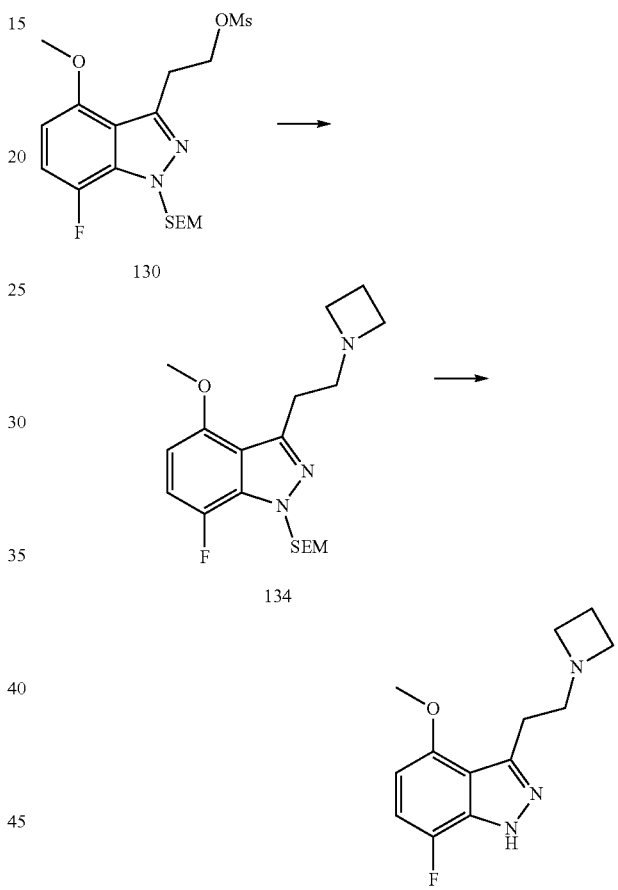

Step 1: 3-(2-(azetidin-1-yl)ethyl)-7-fluoro-4-methoxy-1-((2-(trimethylsilyl)ethoxy)methyl)-1H-indazole (134)

3-(2-(azetidin-1-yl)ethyl)-7-fluoro-4-methoxy-1-((2-(trimethylsilyl)ethoxy)methyl)-1H-indazole was synthesised according to General Procedure B with 2-(7-fluoro-4-methoxy-1-((2-(trimethylsilyl)ethoxy)methyl)-1H-indazol-3-yl) ethyl methanesulfonate (0.27 g, 0.64 mmoL), $K_2CO_3$ (0.89 g, 6.45 mmol) and azetidine (0.18 g, 3.23 mmol). The title compound as obtained as a light brown liquid (0.26 g, quant.) which was used in the next step without further purification. LCMS (Condition C): $t_R$ (1.986 min) m/z=380.3 [M+H]$^+$; $^1$H NMR (400 MHz, DMSO-$d_6$): δ 7.16-7.11 (m, 1H), 6.48 (dd, J=8.4, 2.0 Hz, 1H), 5.62 (s, 2H), 3.88 (s, 3H), 3.49 (t, J=7.6 Hz, 2H), 3.07 (t, J=6.8 Hz, 4H), 2.89 (t, J=7.2 Hz, 2H), 2.64 (t, J=7.6 Hz, 2H), 1.91 (t, J=6.8 Hz, 2H), 0.77 (t, J=7.6 Hz, 2H), −0.12 (s, 9H).

Step 2: 3-(2-(azetidin-1-yl)ethyl)-7-fluoro-4-methoxy-1H-indazole (A47)

To a stirred solution of 3-(2-(azetidin-1-yl)ethyl)-7-fluoro-4-methoxy-1-((2-(trimethylsilyl)ethoxy)methyl)-1H-indazole (0.26 g, 0.68 mmol) in $CH_2Cl_2$ (5 mL) was added 4 M HCl in 1,4-dioxane (13 mL) at 0° C. and the reaction mixture was stirred at RT for 9 h. The reaction mixture was quenched with 4 N aq. NaOH solution (100 mL) and extracted with $CH_2Cl_2$ (2×100 mL). The combined organics were dried over $Na_2SO_4$, concentrated under reduced pressure and the crude material was purified by reverse phase column chromatography (product eluted at 42% MeCN in $H_2O$) to afford 3-(2-(azetidin-1-yl)ethyl)-7-fluoro-4-methoxy-1H-indazole (0.072 g, 42%) as a brown sticky solid. LCMS (Condition C): $t_R$ (1.422 min) m/z=250.1 $[M+H]^+$; $^1H$ NMR (400 MHz, DMSO-$d_6$): δ 13.14 (s, 1H), 7.02 (t, J=8.4 Hz, 1H), 6.36 (d, J=7.2 Hz, 1H), 3.87 (s, 3H), 3.09 (t, J=6.8 Hz, 4H), 2.90 (t, J=7.2 Hz, 2H), 2.65 (t, J=7.6 Hz, 2H), 1.94-1.91 (m, 2H).

Step 3: 3-(2-(azetidin-1-yl)ethyl)-7-fluoro-4-methoxy-1H-indazole fumarate (A47-fumarate)

To a stirred solution 3-(2-(azetidin-1-yl)ethyl)-7-fluoro-4-methoxy-1H-indazole (0.072 g, 0.29 mmol) in acetone (2 mL) was added fumaric acid (0.03 g, 0.28 mmol) and the mixture was refluxed at 80° C. for 5 min, then cooled and left to stand at RT for 16 h. The solid was dried under reduce pressure and lyophilised from MeCN:$H_2O$ (1:1) to afford 3-(2-(azetidin-1-yl)ethyl)-7-fluoro-4-methoxy-1H-indazole Fumarate salt (0.091 g, 86% yield) as an off white solid. LCMS (Condition C): $t_R$ (1.487 min) m/z=250.1 $[M+H]^+$; $^1H$ NMR (400 MHz, DMSO-$d_6$): δ 13.26 (s, 2H), 7.05 (t, J=8.8 Hz, 1H), 6.53 (s, 2H), 6.38 (d, J=6.8 Hz, 1H), 3.88 (s, 3H), 3.53 (t, J=6.8 Hz, 4H), 3.0 (s, 4H), 2.13-2.08 (m, 2H).

Example 48: Synthesis of 7-fluoro-4-methoxy-3-(2-(pyrrolidin-1-yl)ethyl)-1H-indazole (A48)

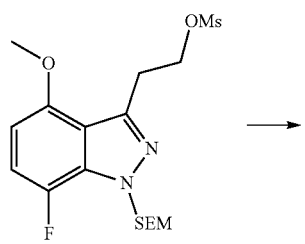

130

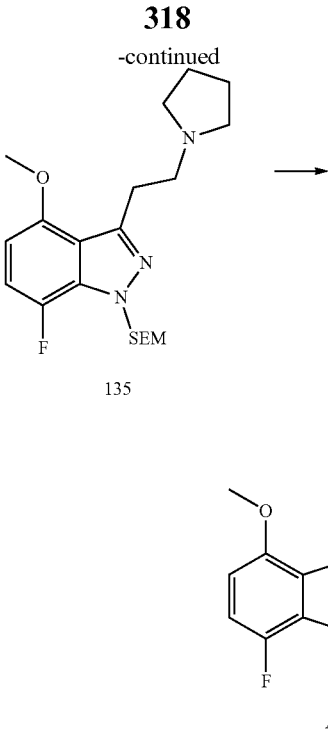

135

A48

Step 1: 7-fluoro-4-methoxy-3-(2-(pyrrolidin-1-yl)ethyl)-1-((2-(trimethylsilyl)ethoxy)methyl)-1H-indazole (135)

7-fluoro-4-methoxy-3-(2-(pyrrolidin-1-yl)ethyl)-1-((2-(trimethylsilyl)ethoxy)methyl)-1H-indazole was synthesised according to General Procedure B with 2-(7-fluoro-4-methoxy-1-((2-(trimethylsilyl)ethoxy)methyl)-1H-indazol-3-yl) ethyl methanesulfonate (0.48 g, 1.16 mmol), $K_2CO_3$ (1.6 g, 11.6 mmol) and pyrrolidine (0.41 g, 5.80 mmol). The title compound was obtained as a light brown liquid (0.48 g, quant.) which was used in the next step without further purification. LCMS (Condition C): $t_R$ (2.112 min) m/z=394.6 $[M+H]^+$; $^1H$ NMR (400 MHz, DMSO-$d_6$): δ 7.17-7.12 (m, 1H), 6.49 (dd, J=8.4, 2.4 Hz, 1H), 5.63 (s, 2H), 3.89 (s, 3H), 3.50 (t, J=7.6 Hz, 2H), 3.10 (t, J=7.2 Hz, 2H), 2.74 (t, J=8.4 Hz, 2H), 2.51-2.48 (m, 4H), 1.67 (br s, 4H), 0.76 (t, J=8.0 Hz, 2H), −0.12 (s, 9H).

Step 2: 7-fluoro-4-methoxy-3-(2-(pyrrolidin-1-yl)ethyl)-1H-indazole (A48)

To a stirred solution of 7-fluoro-4-methoxy-3-(2-(pyrrolidin-1-yl)ethyl)-1-((2-(trimethylsilyl)ethoxy)methyl)-1H-indazole (0.48 g, 1.22 mmol) in $CH_2Cl_2$ (10 mL) was added 4 M HCl in 1,4-dioxane (10 mL) at 0° C. and the reaction mixture was stirred at RT for 16 h. The reaction mixture was quenched with 4 N aq. NaOH solution (100 mL) and extracted with $CH_2Cl_2$ (3×50 mL). The combined organics were dried over $Na_2SO_4$, concentrated under reduced pressure and the crude material was purified by reverse phase column chromatography (product eluted at 43% MeCN in $H_2O$) to afford 7-fluoro-4-methoxy-3-(2-(pyrrolidin-1-yl)ethyl)-1H-indazole (159 mg, 50%) as a white solid. LCMS (Condition C): $t_R$ (1.467 min) m/z=264.14 $[M+H]^+$; $^1H$ NMR (400 MHz, DMSO-$d_6$): δ 13.16 (s, 1H), 7.04-6.99 (m, 1H), 6.36 (dd, J=8.0, 2.0 Hz, 1H), 3.87 (s, 3H), 3.11 (t, J=7.2 Hz, 2H), 2.73 (t, J=8.4 Hz, 2H), 2.50-2.48 (m, 4H), 1.67 (br s, 4H).

Example 49: Synthesis of 3-(2-(2-azabicyclo[3.1.0]hexan-2-yl)ethyl)-7-fluoro-4-methoxy-1H-indazole (A49)

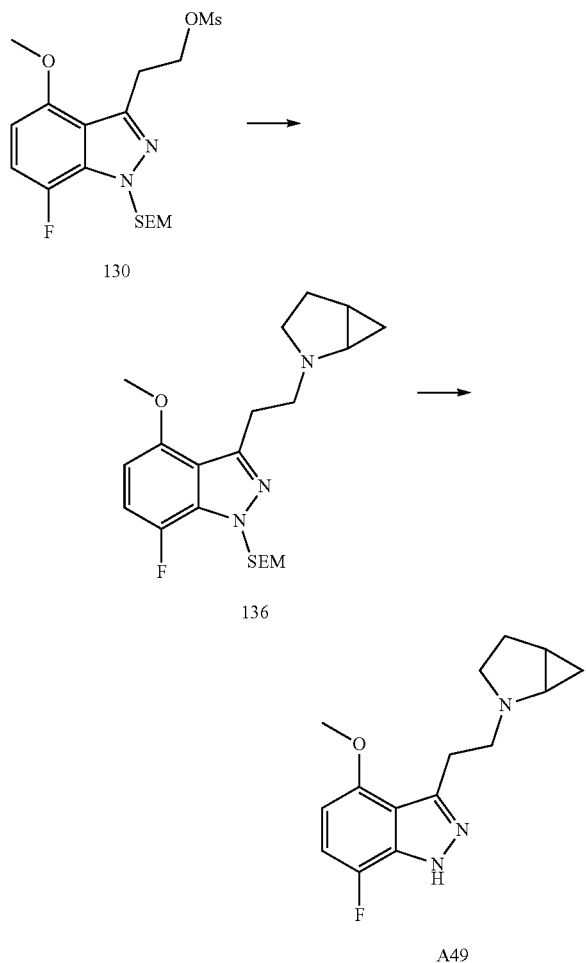

Step 1: 3-(2-(2-azabicyclo[3.1.0]hexan-2-yl)ethyl)-7-fluoro-4-methoxy-1-((2-(trimethylsilyl)ethoxy)methyl)-1H-indazole (136)

3-(2-(2-azabicyclo[3.1.0]hexan-2-yl)ethyl)-7-fluoro-4-methoxy-1-((2-(trimethylsilyl)ethoxy)methyl)-1H-indazole was synthesised according to General Procedure B with 2-(7-fluoro-4-methoxy-1-((2-(trimethylsilyl)ethoxy)methyl)-1H-indazol-3-yl) ethyl methanesulfonate (0.48 g, 1.16 mmol), $K_2CO_3$ (1.6 g, 11.6 mmol) and 2-azabicyclo[3.1.0]hexane hydrochloride (0.69 g, 5.77 mmol). The title compound was obtained as a light brown liquid (0.48 g, quant.) which was used in the next step without further purification. LCMS (Condition C): $t_R$ (2.151 min) m/z=406.7 $[M+H]^+$; $^1H$ NMR (400 MHz, DMSO-$d_6$): δ 7.17-7.12 (m, 1H), 6.49 (dd, J=8.8, 2.8 Hz, 1H), 5.63 (s, 2H), 3.89 (s, 3H), 3.50 (t, J=8.0 Hz, 2H), 3.17-3.10 (m, 2H), 2.87-2.80 (m, 1H), 2.78-2.70 (m, 3H), 1.84-1.75 (m, 3H), 1.33 (bs, 1H), 0.77 (t, J=8.0 Hz, 2H), 0.63 (bs, 1H), 0.12 (s, 9H).

Step 2: 3-(2-(2-azabicyclo[3.1.0]hexan-2-yl)ethyl)-7-fluoro-4-methoxy-1H-indazole (A49)

To a stirred solution of 3-(2-(2-azabicyclo[3.1.0]hexan-2-yl)ethyl)-7-fluoro-4-methoxy-1-((2-(trimethylsilyl)ethoxy)methyl)-1H-indazole (0.48 g, 1.18 mmol) in $CH_2Cl_2$ (10 mL) was added 4 M HCl in 1,4-dioxane (10 mL) at 0° C. and the reaction mixture was stirred at RT for 16 h. The reaction mixture was quenched with 4 N aq. NaOH solution (100 mL) and extracted with $CH_2Cl_2$ (3×50 mL). The combined organics were dried over $Na_2SO_4$, concentrated under reduced pressure and the crude material was purified by reverse phase column chromatography (product eluted at 43% MeCN in $H_2O$) to afford 3-(2-(2-azabicyclo[3.1.0]hexan-2-yl)ethyl)-7-fluoro-4-methoxy-1H-indazole (137 mg, 42%) as a white solid. LCMS (Condition C): $t_R$ (1.494 min) m/z=276.1 $[M+H]^+$; $^1H$ NMR (400 MHz, DMSO-$d_6$): δ 13.14 (s, 1H), 7.03 (t, J=8.4, 1H), 6.37 (d, J=8.0 Hz, 1H), 3.87 (s, 3H), 3.15-3.13 (m, 2H), 2.89-2.85 (m, 1H), 2.82-2.73 (m, 3H), 1.81-1.74 (m, 3H), 1.35-1.33 (m, 1H), 0.65-0.62 (m, 1H), 0.06-0.01 (m, 1H).

Example 50: Synthesis of 2-(4-fluoro-5-methoxy-1H-indazol-3-yl)-N,N-dimethylethan-1-amine (A50)

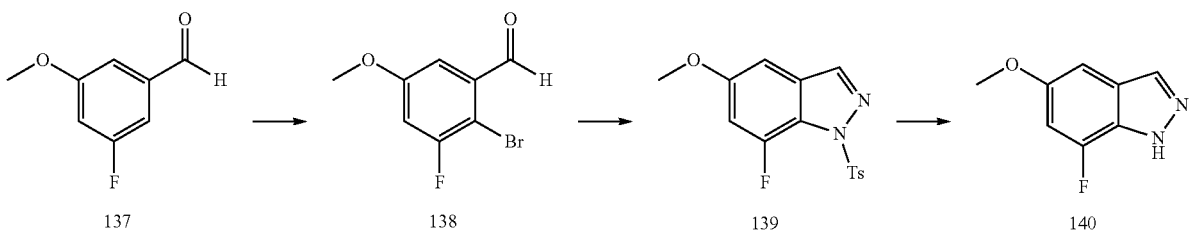

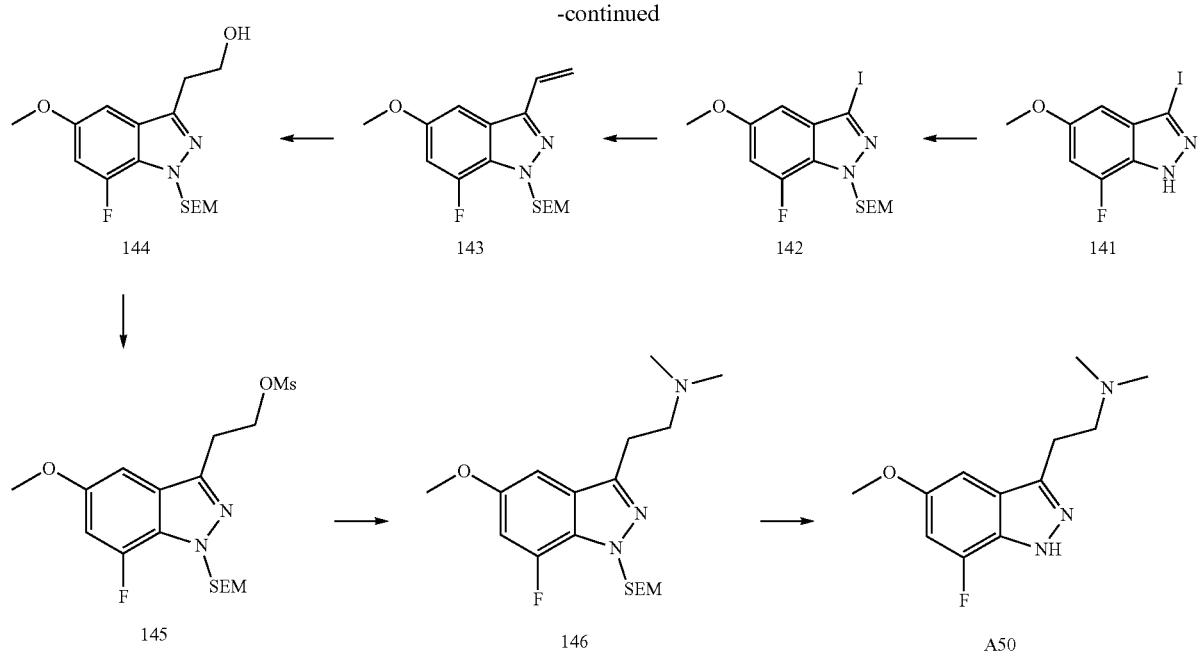

Step 1: 2-bromo-3-fluoro-5-methoxybenzaldehyde (138)

To an ice-cold solution of 3-fluoro-5-methoxybenzaldehyde (10 g, 64.9 mmol) in $H_2O$ (250 mL) was added KBr (19.3 g, 162.2 mmol) under a nitrogen atmosphere. After 15 min, $Br_2$ (3.3 mL, 64.9 mmol) was added dropwise and then the reaction mixture was allowed to warm to RT and stirred at RT for 16 h under a nitrogen atmosphere. The reaction mixture was diluted with water (70 mL) and the precipitate was collected by filtration under vacuum. The solid was dried under vacuum to afford the title compound as an orange solid (12.0 g, 79%). $^1$H NMR (400 MHz, DMSO-$d_6$): δ 10.17 (s, 1H), 7.44-7.40 (m, 1H), 7.23 (d, J=2.0 Hz, 1H), 3.85 (s, 3H).

Step 2: 7-fluoro-5-methoxy-1-tosyl-1H-indazole (139)

To a solution of 2-bromo-3-fluoro-5-methoxybenzaldehyde (6.0 g, 25.7 mmol) in methanol (60 mL) was added 4-methylbenzenesulfonohydrazide (5.0 g, 27.0 mmol) at RT and the resulting mixture was stirred at RT for 1 h. The mixture was concentrated in vacuo and the residue was taken up in isoamyl alcohol (60 mL) and treated with $Cu_2O$ (1.84 g, 12.9 mmol). The mixture was stirred at reflux for 16 h. The cooled reaction mixture was poured into ice-cold $H_2O$ (100 mL) and extracted with EtOAc (2×80 mL). The combined organic layer was dried over anhydrous $Na_2SO_4$ and concentrated in vacuo. The residue was purified by column chromatography (0% to 25% EtOAc in hexane) to afford the title compound as an off-white solid (4.0 g, 49%). $^1$H NMR (400 MHz, DMSO-$d_6$): δ 8.53 (d, J=2.0 Hz, 1H), 7.73 (d, J=8.0 Hz, 2H), 7.45 (d, J=8.0 Hz, 2H), 7.23-7.18 (m, 2H), 3.81 (s, 3H), 2.31 (s, 3H).

Step 3: 7-fluoro-5-methoxy-1H-indazole (140)

In eight batches: to an ice-cold solution of 7-fluoro-5-methoxy-1-tosyl-1H-indazole (1.0 g, 3.12 mmol) in DMSO (10 mL) and water (10 mL) was added $K_2CO_3$ (1.29 g, 9.36 mmol) and the resulting mixture was stirred at 100° C. for 5 h. The cooled reaction mixture was then diluted with ice-cold $H_2O$ (150 mL) and extracted with EtOAc (2×90 mL). The combined organic layer was dried over anhydrous $Na_2SO_4$ and concentrated in vacuo. The residue was purified by column chromatography (0% to 25% EtOAc in hexane) to afford an off-white solid. The solid from eight batches were combined and identified as the title compound (1.3 g, 31%). $^1$H NMR (400 MHz, DMSO-$d_6$): δ13.46 (s, 1H), 8.06-8.04 (m, 1H), 7.04 (d, J=1.2 Hz, 1H), 6.91 (dd, J=12.4, 1.6 Hz, 1H), 3.79 (s, 3H).

Step 4: 7-fluoro-3-iodo-5-methoxy-1H-indazole (141)

To a solution of 7-fluoro-5-methoxy-1H-indazole (1.3 g, 7.82 mmol) in DMF (13 mL) was added N-iodosuccinimide (2.64 g, 11.73 mmol). The reaction mixture was stirred at RT for 2 h until TLC indicated consumption of the starting material. The reaction was poured into ice-cold $H_2O$ (50 mL) and the off-white solid was collected, dried under vacuum to a constant weight, and was identified as the title compound (2.2 g, 96%). $^1$H NMR (400 MHz, DMSO-$d_6$): δ 13.94 (s, 1H), 7.04 (dd, J=12.0, 1.6 Hz, 1H), 6.64-6.61 (m, 1H), 3.83 (s, 3H).

Step 5: 7-fluoro-3-iodo-5-methoxy-1-((2-(trimethylsilyl)ethoxy)methyl)-1H-indazole (142)

To an ice-cold solution of 7-fluoro-3-iodo-5-methoxy-1H-indazole (2.2 g, 7.53 mmol) in DMF (30 mL) was added NaH (60% w/w dispersion in mineral oil, 0.27 g, 11.3 mmol) and stirred cold for 10 min before 2-(trimethylsilyl)ethoxymethyl chloride (2.50 g, 15.1 mmol) was added under a nitrogen atmosphere. The reaction was stirred at RT for 1 h and TLC indicated consumption of the starting material. The reaction mixture was poured into ice-cold $H_2O$ (100 mL) and then extracted with EtOAc (2×50 mL). The combined organic layer was dried over anhydrous $Na_2SO_4$ and concentrated in vacuo. The residue was purified by reverse phase column chromatography (product eluted at 96% MeCN in $H_2O$) to afford the title compound as a yellow oil (1.3 g, 41%). $^1$H NMR (400 MHz, DMSO-$d_6$): δ 7.14 (dd, J=12.8, 2.0 Hz, 1H), 6.68 (d, J=2.0 Hz, 1H), 5.69 (s, 2H), 3.85 (s, 3H), 3.57-3.48 (m, 2H), 0.78-0.74 (m, 2H), −0.11 (s, 9H).

Step 6: 7-fluoro-5-methoxy-1-((2-(trimethylsilyl) ethoxy)methyl)-3-vinyl-1H-indazole (143)

A solution of 7-fluoro-3-iodo-5-methoxy-1-((2-(trimethylsilyl)ethoxy)methyl)-1H-indazole (750 mg, 1.77 mmol) and 4,4,5,5-tetramethyl-2-vinyl-1,3,2-dioxaborolane (270 mg, 1.77 mmol) in THF (12 mL) was added $K_2CO_3$ (730 mg, 5.32 mmol), pre-dissolved in $H_2O$ (3 mL). The reaction mixture was sparged with nitrogen gas for 15 min before Pd(dppf)Cl$_2$ (60 mg, 0.09 mmol) was added under nitrogen atmosphere. The mixture was stirred at 100° C. for 16 h under a nitrogen atmosphere and then the cooled reaction mixture was poured into $H_2O$ (100 mL) before being extracted with EtOAc (2×60 mL). The combined organic layer was dried over anhydrous $Na_2SO_4$ and concentrated in vacuo. The residue was purified by column chromatography (0% to 2% EtOAc in hexane) to afford the title compound as a colourless oil (360 mg, 63%). $^1$H NMR (400 MHz, DMSO-$d_6$): δ 7.25 (d, J=1.6 Hz, 1H), 7.07-6.98 (m, 2H), 6.12 (d, J=18.0 Hz, 1H), 5.68 (s, 2H), 5.53 (d, J=11.6 Hz, 1H), 3.85 (s, 3H), 3.51 (t, J=8.0 Hz, 2H), 0.77 (t, J=7.6 Hz, 2H), −0.12 (s, 9H).

Step 7: 2-(7-fluoro-5-methoxy-1-((2-(trimethylsilyl)ethoxy)methyl)-1H-indazol-3-yl)ethan-1-ol (144)

To an ice-cold solution of 7-fluoro-5-methoxy-1-((2-(trimethylsilyl)ethoxy)methyl)-3-vinyl-1H-indazole (360 mg, 1.11 mmol) in THF (4.5 mL) was added 9-borabicyclo[3.3.1]nonane (0.5 M in THF, 14.5 mL, 7.25 mmol) under nitrogen atmosphere. The reaction was then stirred at RT for 5 h. The reaction was then cooled in an ice bath and treated dropwise with $H_2O_2$ (30% w/w in $H_2O$, 7.5 mL, 246 mmol) and 4 M aq. NaOH (1.5 mL) before being stirred at RT for 16 h. The reaction was then poured into $H_2O$ (70 mL) before being extracted with EtOAc (2×50 mL). The combined organic layer was dried over anhydrous $Na_2SO_4$ and concentrated in vacuo. The residue was purified by column chromatography (0% to 25% EtOAc in hexane) to afford the title compound as a colourless oil (375 mg, quant.). $^1$H NMR (400 MHz, DMSO-$d_6$): δ 7.08 (s, 1H), 6.98 (d, J=13.2 Hz, 1H), 5.62 (s, 2H), 4.74 (t, J=5.6 Hz, 1H), 3.81 (s, 3H), 3.75 (dt, J=6.8, 5.6 Hz, 2H), 3.48 (t, J=7.6 Hz, 2H), 3.03 (t, J=6.8 Hz, 2H), 0.76 (t, J=7.6 Hz, 2H), −0.12 (s, 9H).

Step 8: 2-(7-fluoro-5-methoxy-1-((2-(trimethylsilyl) ethoxy)methyl)-1H-indazol-3-yl)ethyl methanesulfonate (145)

2-(7-fluoro-5-methoxy-1-((2-(trimethylsilyl)ethoxy) methyl)-1H-indazol-3-yl)ethyl methanesulfonate was synthesised according to General Procedure A with 2-(7-fluoro-5-methoxy-1-((2-(trimethylsilyl)ethoxy)methyl)-1H-indazol-3-yl)ethan-1-ol (375 mg, 1.11 mmol), Et$_3$N (6.0 mL, 43.4 mmol) and methanesulfonyl chloride (0.6 mL, 7.68 mmol). After column chromatography (SiO$_2$, 0% to 20% EtOAc in hexane) the title compound was obtained as a colourless oil (200 mg, 43%). $^1$H NMR (400 MHz, DMSO-$d_6$): δ 7.16 (d, J=2.0 Hz, 1H), 7.02 (dd, J=13.2 Hz, 2.0 Hz, 1H), 5.65 (s, 2H), 4.57 (t, J=6.8 Hz, 2H), 3.82 (s, 3H), 3.49 (t, J=7.6 Hz, 2H), 3.35-3.28 (m, 2H), 3.13 (s, 3H), 0.77 (t, J=7.6 Hz, 2H), −0.11 (s, 9H).

Step 9: 2-(7-fluoro-5-methoxy-1-((2-(trimethylsilyl) ethoxy)methyl)-1H-indazol-3-yl)-N,N-dimethyl-ethan-1-amine (146)

2-(7-fluoro-5-methoxy-1-((2-(trimethylsilyl)ethoxy) methyl)-1H-indazol-3-yl)-N,N-dimethylethan-1-amine was synthesised according to General Procedure B with 2-(7-fluoro-5-methoxy-1-((2-(trimethylsilyl)ethoxy)methyl)-1H-indazol-3-yl)ethyl methanesulfonate (200 mg, 0.47 mmol), $K_2CO_3$ (650 mg, 4.77 mmol) and N,N-dimethylamine hydrochloride (110 mg, 2.38 mmol). After purification by reverse phase column chromatography (product eluted at 30% MeCN in $H_2O$) the title compound was obtained as a colourless oil (70 mg, 40%). $^1$H NMR (400 MHz, DMSO-$d_6$): δ 7.08 (s, 1H), 7.00-6.96 (m, 1H), 5.62 (s, 2H), 3.82 (s, 3H), 3.47 (t, J=6.4 Hz, 2H), 3.01 (t, J=6.4 Hz, 2H), 2.62 (t, J=6.8 Hz, 2H), 2.20 (s, 6H), 0.78-0.74 (m, 2H), −0.13 (s, 9H).

Step 10: 2-(7-fluoro-5-methoxy-1H-indazol-3-yl)-N,N-dimethylethan-1-amine formate (A50-formate)

The title compound was synthesised according to General Procedure C utilising 2-(7-fluoro-5-methoxy-1-((2-(trimethylsilyl)ethoxy)methyl)-1H-indazol-3-yl)-N,N-dimethyl-ethan-1-amine (70 mg, 0.19 mmol) which upon reverse phase purification (product eluted at 20% MeCN in 0.2% aq. formic acid) generated the title compound as an off-white solid (17 mg, 21%). LCMS: $t_R$ (1.082 min) m/z=237.93 [M+H]$^+$; 1H NMR (400 MHz, DMSO-$d_6$): δ 13.12 (br. s, 1H), 8.20 (s, 1H), 7.02 (d, J=1.6 Hz, 1H), 6.88 (dd, J=12.4, 1.2 Hz, 1H), 3.81 (s, 3H), 3.04 (t, J=7.2 Hz, 2H), 2.70 (t, J=7.6 Hz, 2H), 2.28 (s, 6H).

Example 51: Synthesis of N-ethyl-2-(7-fluoro-5-methoxy-1H-indazol-3-yl)-N-methylethan-1-amine (A51)

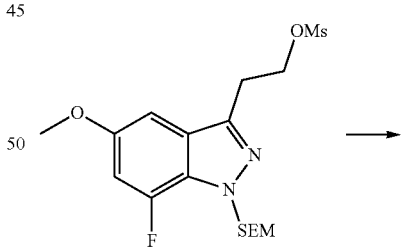

145

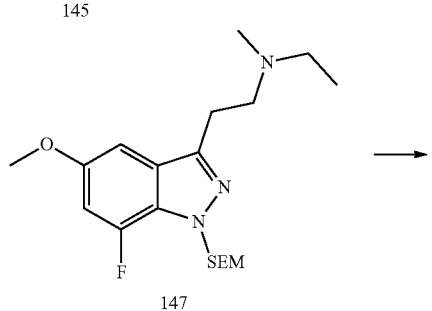

147

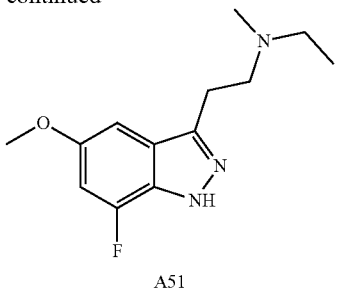

A51

Step 1: N-ethyl-2-(7-fluoro-5-methoxy-1-((2-(trimethylsilyl)ethoxy)methyl)-1H-indazol-3-yl)-N-methylethan-1-amine (147)

N-ethyl-2-(7-fluoro-5-methoxy-1-((2-(trimethylsilyl)ethoxy)methyl)-1H-indazol-3-yl)-N-methylethan-1-amine was synthesised according to General Procedure B with 2-(7-fluoro-5-methoxy-1-((2-(trimethylsilyl)ethoxy)methyl)-1H-indazol-3-yl)ethyl methanesulfonate (210 mg, 0.50 mmol), $K_2CO_3$ (690 mg, 5.01 mmol) and N-methylethanamine (0.22 mL, 2.50 mmol). The title compound was obtained as a brown resin (160 mg, 86%) which was used in the next step without further purification. LCMS (Condition C): m/z=382.38 [M+H]+.

Step 2: N-ethyl-2-(7-fluoro-5-methoxy-1H-indazol-3-yl)-N-methylethan-1-amine (A51)

The title compound was synthesised according to General Procedure C utilising N-ethyl-2-(7-fluoro-5-methoxy-1-((2-(trimethylsilyl)ethoxy)methyl)-1H-indazol-3-yl)-N-methylethan-1-amine (160 mg, 0.41 mmol) which upon reverse phase purification (product eluted at 40% MeCN in $H_2O$) afforded the title compound as an off-white solid (54 mg, 52%). LCMS (Condition C): $t_R$ (1.138 min) m/z=251.83 [M+H]+; 1H NMR (400 MHz, DMSO-$d_6$): δ 13.05 (s, 1H), 7.00 (s, 1H), 6.87 (d, J=12.0 Hz, 1H), 3.80 (s, 3H), 3.01 (t, J=7.6 Hz, 2H), 2.69 (t, J=7.6 Hz, 2H), 2.43 (q, J=7.2 Hz, 2H), 2.22 (s, 3H) 0.97 (t, J=7.2 Hz, 3H).

Example 52: Synthesis of N-(2-(7-fluoro-5-methoxy-1H-indazol-3-yl)ethyl)-N-methylpropan-2-amine (A52)

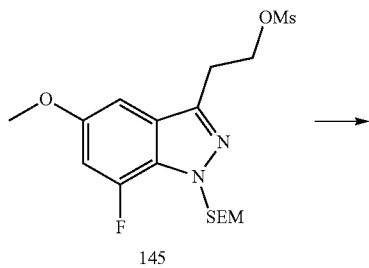

145

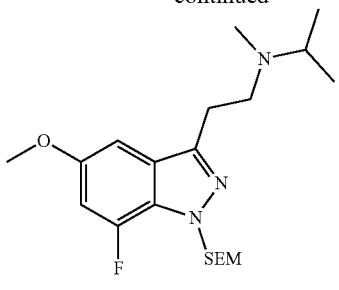

148

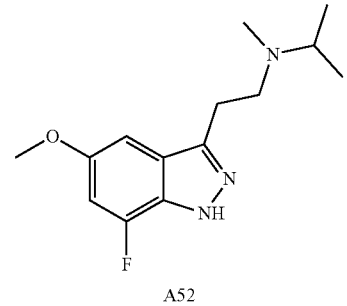

A52

Step 1: N-(2-(7-fluoro-5-methoxy-1-((2-(trimethylsilyl)ethoxy)methyl)-1H-indazol-3-yl)ethyl)-N-methylpropan-2-amine (148)

N-(2-(7-fluoro-5-methoxy-1-((2-(trimethylsilyl)ethoxy)methyl)-1H-indazol-3-yl)ethyl)-N-methylpropan-2-amine was synthesised according to General Procedure B with 2-(7-fluoro-5-methoxy-1-((2-(trimethylsilyl)ethoxy)methyl)-1H-indazol-3-yl)ethyl methanesulfonate (210 mg, 0.50 mmol), $K_2CO_3$ (690 mg, 5.01 mmol) and N-methylpropan-2-amine (0.21 mL, 2.50 mmol). The title compound was obtained as a brown resin (190 mg, 96%) which was used in the next step without further purification. 1H NMR (400 MHz, DMSO-$d_6$): δ 7.06 (d, J=2.0 Hz, 1H), 6.97 (dd, J=12.8, 2.0 Hz, 1H), 5.62 (s, 2H), 3.82 (s, 3H), 3.47 (t, J=8.0 Hz, 2H), 2.98 (t, J=7.2 Hz, 2H), 2.87-2.80 (m, 1H), 2.71 (t, J=8.0 Hz, 2H), 2.21 (s, 3H), 0.91 (d, J=6.8 Hz, 6H), 0.75 (t, J=8.0 Hz, 2H), −0.12 (s, 9H).

Step 2: N-(2-(7-fluoro-5-methoxy-1H-indazol-3-yl)ethyl)-N-methylpropan-2-amine (A52)

The title compound was synthesised according to General Procedure C utilising N-(2-(7-fluoro-5-methoxy-1-((2-(trimethylsilyl)ethoxy)methyl)-1H-indazol-3-yl)ethyl)-N-methylpropan-2-amine (190 mg, 0.48 mmol) which upon reverse phase purification (product eluted at 40% MeCN in $H_2O$) generated the title compound as a white solid (17 mg, 13%). LCMS (Condition C): $t_R$ (1.185 min) m/z=265.83 [M+H]+; 1H NMR (400 MHz, DMSO-$d_6$): δ 13.10 (s, 1H), 7.00 (s, 1H), 6.87 (d, J=12.8 Hz, 1H), 3.80 (s, 3H), 2.98 (t, J=7.6 Hz, 2H), 2.84-2.81 (m, 1H), 2.71 (t, J=7.6 Hz, 2H), 2.21 (s, 3H), 0.92 (d, J=6.4 Hz, 6H).

Example 53: Synthesis of 3-(2-(azetidin-1-yl)ethyl)-7-fluoro-5-methoxy-1H-indazole (A53)

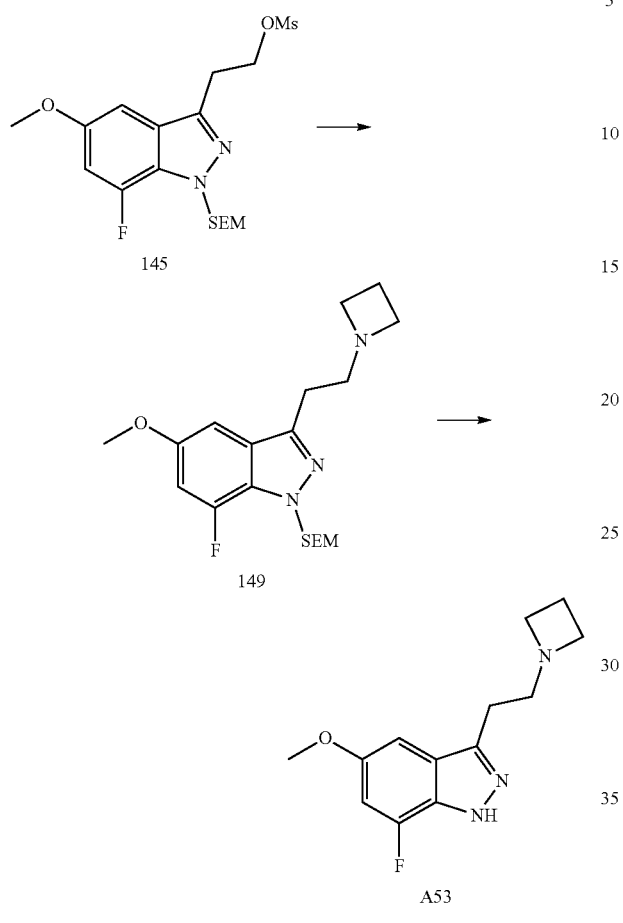

Step 1: 3-(2-(azetidin-1-yl)ethyl)-7-fluoro-5-methoxy-1-((2-(trimethylsilyl)ethoxy)methyl)-1H-indazole (149)

3-(2-(azetidin-1-yl)ethyl)-7-fluoro-5-methoxy-1-((2-(trimethylsilyl)ethoxy)methyl)-1H-indazole was synthesised according to General Method B with 2-(7-fluoro-5-methoxy-1-((2-(trimethylsilyl)ethoxy)methyl)-1H-indazol-3-yl)ethyl methanesulfonate (440 mg, 1.05 mmol), $K_2CO_3$ (1.45 g, 10.51 mmol) and azetidine (0.35 mL, 5.25 mmol). The title compound was obtained as a brown oil (370 mg, 93%) which was used in the next step without further purification. $^1$H NMR (400 MHz, DMSO-$d_6$): δ 7.05 (s, 1H), 6.98 (d, J=12.8 Hz, 1H), 5.61 (s, 2H), 3.82 (s, 3H), 3.48 (t, J=7.6 Hz, 2H), 3.08 (t, J=6.8 Hz, 4H), 2.86-2.82 (m, 2H), 2.70 (t, J=7.2 Hz, 2H), 1.95-1.88 (m, 2H), 0.76 (t, J=8.0 Hz, 2H), −0.12 (s, 9H).

Step 2: 3-(2-(azetidin-1-yl)ethyl)-7-fluoro-5-methoxy-1H-indazole (A53)

The title compound was synthesised according to General Procedure C utilising 3-(2-(azetidin-1-yl)ethyl)-7-fluoro-5-methoxy-1-((2-(trimethylsilyl)ethoxy)methyl)-1H-indazole (370 mg, 0.97 mmol) which upon reverse phase purification (product eluted at 42% MeCN in $H_2O$) generated the title compound as a white solid (100 mg, 41%). LCMS (Condition C): $t_R$ (1.625 min) m/z=250.35 [M+H]$^+$; $^1$H NMR (400 MHz, DMSO-$d_6$): δ 13.05 (s, 1H), 6.99 (s, 1H), 6.87 (d, J=12.4 Hz, 1H), 3.80 (s, 3H), 3.09 (t, J=6.8 Hz, 4H), 2.83 (t, J=7.6 Hz, 2H), 2.69 (t, J=7.6 Hz, 2H), 1.93 (sept, J=6.8 Hz, 2H).

Example 54: Synthesis of 7-fluoro-5-methoxy-3-(2-(pyrrolidin-1-yl)ethyl)-1H-indazole (A54)

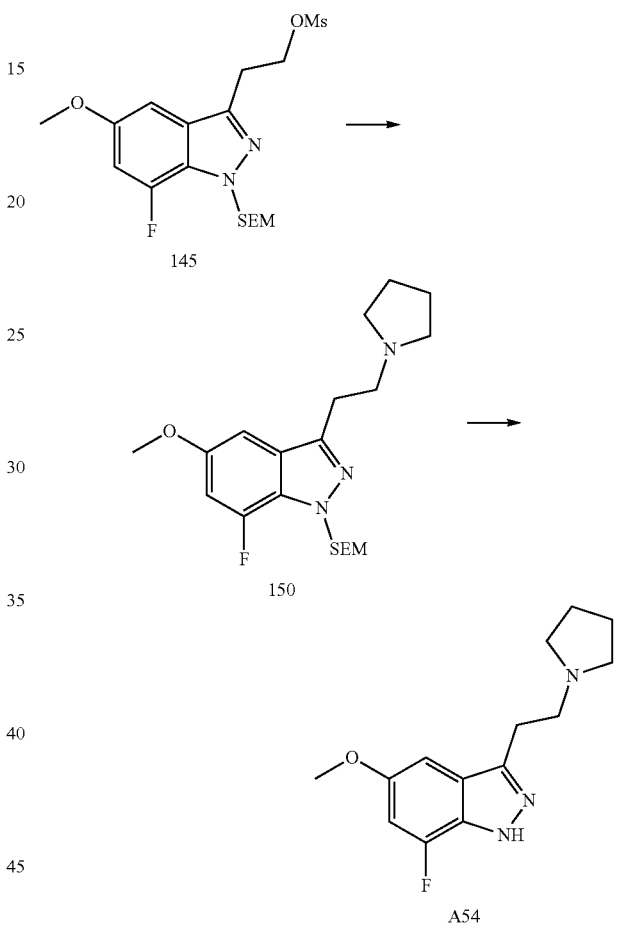

Step 1: 7-fluoro-5-methoxy-3-(2-(pyrrolidin-1-yl)ethyl)-1-((2-(trimethylsilyl)ethoxy)methyl)-1H-indazole (150)

7-fluoro-5-methoxy-3-(2-(pyrrolidin-1-yl)ethyl)-1-((2-(trimethylsilyl)ethoxy)methyl)-1H-indazole was synthesised according to General Procedure B with 2-(7-fluoro-5-methoxy-1-((2-(trimethylsilyl)ethoxy)methyl)-1H-indazol-3-yl)ethyl methanesulfonate (440 mg, 1.05 mmol), $K_2CO_3$ (1.45 g, 10.5 mmol) and pyrrolidine (0.43 mL, 5.25 mmol). The title compound as was obtained as a brown oil (400 mg, 97%) which was used in the next step without further purification. $^1$H NMR (400 MHz, DMSO-$d_6$): δ 7.07 (s, 1H), 6.98 (d, J=12.8 Hz, 1H), 5.62 (s, 2H), 3.82 (s, 3H), 3.47 (t, J=8.0 Hz, 2H), 3.04 (t, J=7.6 Hz, 2H), 2.78 (t, J=7.6 Hz, 2H), 2.52-2.48 (m, 4H), 1.70-1.60 (m, 4H), 0.75 (t, J=8.0 Hz, 2H), −0.13 (s, 9H).

Step 2: 7-fluoro-5-methoxy-3-(2-(pyrrolidin-1-yl) ethyl)-1H-indazole (A54)

The title compound was synthesised according to General Procedure C utilising 7-fluoro-5-methoxy-3-(2-(pyrrolidin-1-yl)ethyl)-1-((2-(trimethylsilyl)ethoxy)methyl)-1H-indazole (400 mg, 1.01 mmol) which upon reverse phase purification (product eluted at 40% MeCN in H$_2$O) generated the title compound as an off-white solid (150 mg, 56%). LCMS (Condition C): t$_R$ (1.643 min) m/z=264.36 [M+H]$^+$; $^1$H NMR (400 MHz, CDCl$_3$): δ 6.86 (s, 1H), 6.73 (d, J=12.0 Hz, 1H), 3.87 (s, 3H), 3.26 (t, J=7.6 Hz, 2H), 3.07 (t, J=7.6 Hz, 2H), 2.85-2.72 (m, 4H), 1.98-1.87 (m, 4H).

Example 55: Synthesis 3-(2-(2-azabicyclo[3.1.0] hexan-2-yl)ethyl)-7-fluoro-5-methoxy-1H-indazole (A55)

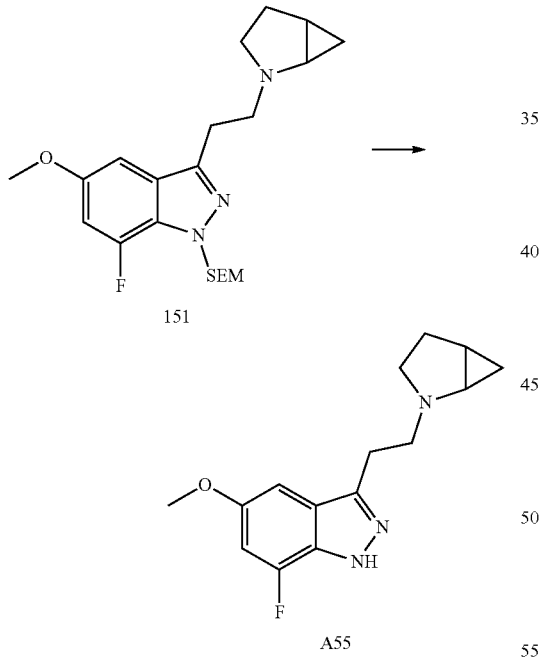

A55

Step 1: 3-(2-(2-azabicyclo[3.1.0]hexan-2-yl)ethyl)-7-fluoro-5-methoxy-1-((2-(trimethylsilyl)ethoxy) methyl)-1H-indazole (151)

3-(2-(2-azabicyclo[3.1.0]hexan-2-yl)ethyl)-7-fluoro-5-methoxy-1-((2-(trimethylsilyl)ethoxy)methyl)-1H-indazole was synthesised according to General Procedure B with 2-(7-fluoro-5-methoxy-1-((2-(trimethylsilyl)ethoxy) methyl)-1H-indazol-3-yl)ethyl methanesulfonate (440 mg, 1.05 mmol), K$_2$CO$_3$ (1.45 g, 10.51 mmol) and 2-azabicyclo [3.1.0]hexane hydrochloride (620 mg, 5.25 mmol). The title compound was obtained as a brown oil (400 mg, 94%) which was used in the next step without further purification. $^1$H NMR (400 MHz, DMSO-d$_6$): δ 7.09 (d, J=2.0 Hz, 1H), 6.98 (dd, J=13.2, 2.0 Hz, 1H), 5.62 (s, 2H), 3.82 (s, 3H), 3.48 (t, J=8.0 Hz, 2H), 3.09-3.05 (m, 2H), 2.89-2.87 (m, 2H), 2.81-2.73 (m, 2H), 1.85-1.73 (m, 3H), 1.21-1.09 (m, 1H), 0.76 (t, J=8.0 Hz, 2H), 0.65-0.64 (m, 1H), 0.03-0.01 (m, 1H), −0.12 (s, 9H).

Step 2: 3-(2-(2-azabicyclo[3.1.0]hexan-2-yl)ethyl)-7-fluoro-5-methoxy-1H-indazole (A55)

The title compound was synthesised according to General Procedure C utilising 3-(2-(2-azabicyclo[3.1.0]hexan-2-yl) ethyl)-7-fluoro-5-methoxy-1-((2-(trimethylsilyl)ethoxy) methyl)-1H-indazole (400 mg, 0.98 mmol) which upon reverse phase purification (product eluted at 46% MeCN in H$_2$O) generated the title compound as an off-white solid (100 mg, 37%). LCMS (Condition C): t$_R$ (1.647 min) m/z=276.41 [M+H]$^+$; $^1$H NMR (400 MHz, DMSO-d$_6$): δ13.05 (s, 1H), 7.02 (s, 1H), 6.88 (d, J=12.4 Hz, 1H), 3.80 (s, 3H), 3.10-3.05 (m, 2H), 2.89-2.87 (m, 1H), 2.83-2.74 (m, 3H), 1.88-1.75 (m, 3H), 1.36-1.33 (m, 1H), 0.68-0.65 (m, 1H), 0.06-0.00 (m, 1H).

Example 56: Synthesis of 3-(2-(azetidin-1-yl)ethyl)-6-fluoro-5-methoxy-1H-indazole (A56)

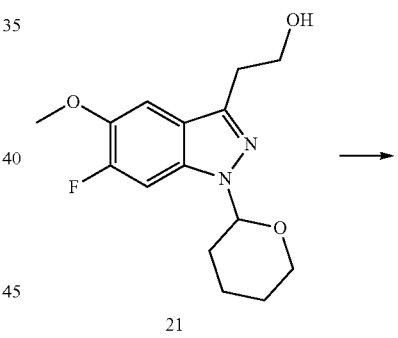

21

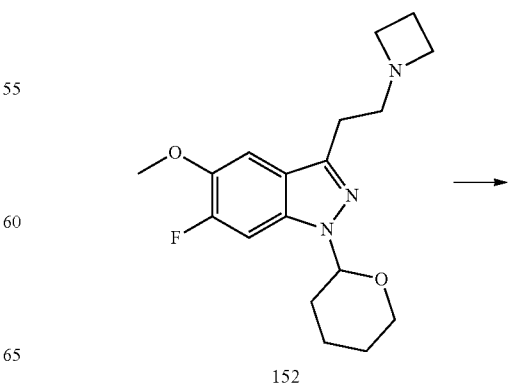

152

-continued

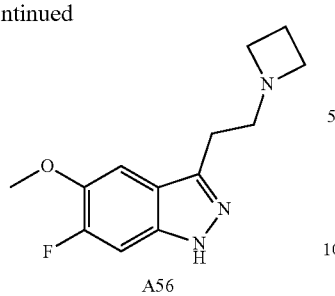

A56

Step 1: 3-(2-(azetidin-1-yl)ethyl)-6-fluoro-5-methoxy-1-(tetrahydro-2H-pyran-2-yl)-1H-indazole (152)

To an ice-cold solution of 2-(6-fluoro-5-methoxy-1-(tetrahydro-2H-pyran-2-yl)-1H-indazol-3-yl)ethan-1-ol (1.0 g, 3.40 mmol) in $CH_2Cl_2$ (15 mL) in a pressure tube, was added $Et_3N$ (0.71 mL, 5.10 mmol) and methanesulfonyl chloride (0.32 mL, 4.08 mmol) and the mixture was stirred at RT for 1 h. The reaction was concentrated under a stream of nitrogen gas. The residue was dissolved in DMF (5 mL) and then treated with azetidine (1.1 mL, 17.0 mmol) and the pressure tube was sealed and heated at 80° C. for 2 h. The reaction was diluted with EtOAc (100 mL) and washed with $H_2O$ (5×20 mL), saturated aq. $NH_4Cl$ (2×20 mL) and then brine (3×20 mL). The combined aqueous layer was extracted once with EtOAc (50 mL) and the combined organics were dried over anhydrous $Na_2SO_4$ and concentrated in vacuo. The residue was purified by flash chromatography (0.1% to 8% MeOH/$NH_3$ in $CH_2Cl_2$) to afford the title compound as a yellow oil (440 mg, 39%). $^1H$ NMR (400 MHz, $CDCl_3$): δ 7.49-7.13 (m, 1H), 7.09 (d, J=8.0 Hz, 1H), 5.51 (dd, J=9.8, 2.6 Hz, 1H), 4.10-4.01 (m, 1H), 3.92 (s, 3H), 3.76-3.64 (m, 1H), 3.25 (t, J=7.0 Hz, 4H), 2.99-2.90 (m, 2H), 2.89-2.77 (m, 2H), 2.58-2.35 (m, 1H), 2.18-1.95 (m, 4H), 1.84-1.48 (m, 3H). $^{13}C$ NMR (400 MHz, $CDCl_3$): δ 153.7 (d, J=248.4 Hz), 144.3 (d, J=13.6 Hz), 143.9 (d, J=4.2 Hz), 134.8 (d, J=11.3 Hz), 119.3, 102.0 (d, J=3.2 Hz), 97.6 (d, J=24.0 Hz), 86.0, 67.9, 58.8, 56.7, 55.4, 29.8, 25.9, 25.2, 22.9, 17.9.

Step 2: 3-(2-(azetidin-1-yl)ethyl)-6-fluoro-5-methoxy-1H-indazole fumarate (A56-fumarate)

The title compound was synthesised according to General Procedure D utilising 3-(2-(azetidin-1-yl)ethyl)-6-fluoro-5-methoxy-1-(tetrahydro-2H-pyran-2-yl)-1H-indazole (440 mg, 1.32 mmol) which upon purification generated the title compound as a colourless oil (225 mg) which was formulated as the fumarate salt as per General Procedure F (215 mg, 34%) as a white crystalline solid. LCMS (Condition A): $t_R$ (4.019 min) m/z=250.10 [M+H]$^+$; $^1H$ NMR (600 MHz, DMSO-$d_6$): δ 7.42 (d, J=8.2 Hz, 1H), 7.34 (d, J=11.1 Hz, 1H), 6.56 (s, 4H), 3.90 (t, J=7.9 Hz, 4H), 3.87 (s, 3H), 3.46-3.34 (m, 2H), 3.13-3.04 (m, 2H), 2.27 (p, J=7.9 Hz, 2H). $^{13}C$ NMR (151 MHz, DMSO-$d_6$): δ167.2, 152.7 (d, J=245.7 Hz), 143.2 (d, J=13.7 Hz), 140.7, 135.0 (d, J=11.6 Hz), 134.7, 117.2, 101.7, 97.0 (d, J=23.3 Hz), 56.2, 53.4, 53.3, 22.2, 16.2; $^1H$ qNMR Purity: 98.8% (ERETIC).

Example 57: Synthesis of 6-fluoro-5-methoxy-3-(2-(3-methylazetidin-1-yl)ethyl)-1H-indazole (A57)

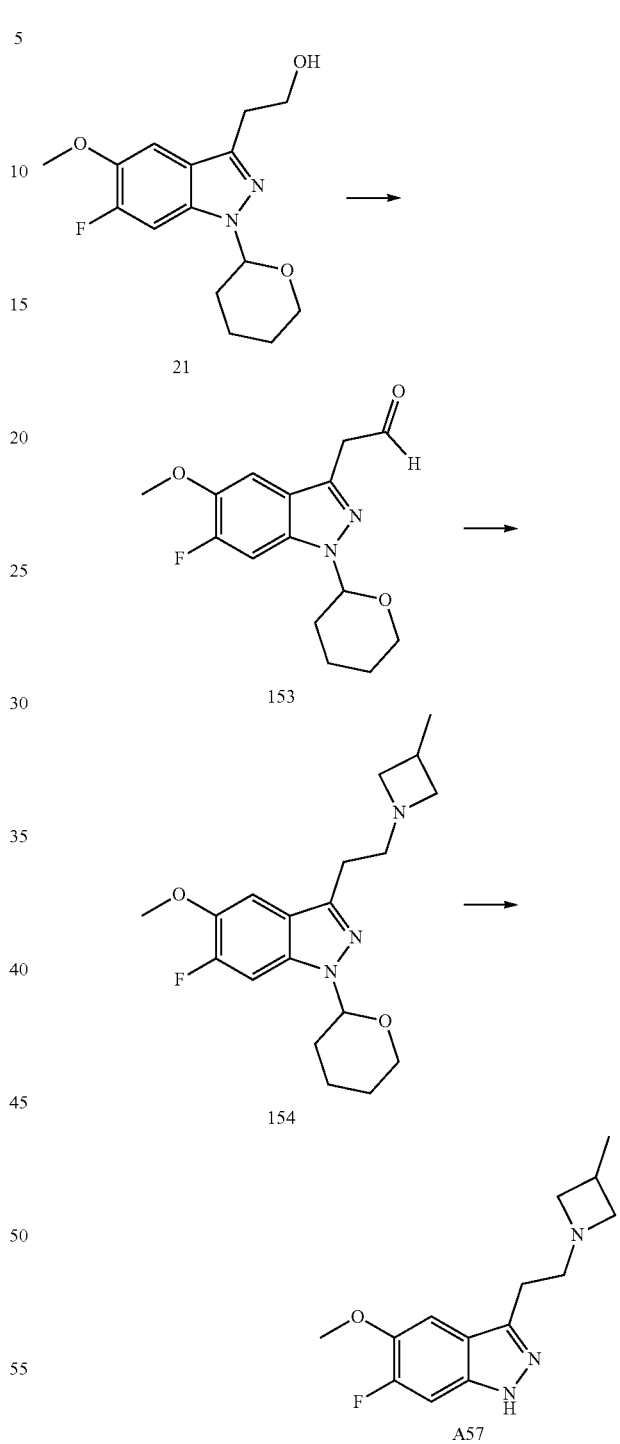

Step 1: 2-(6-fluoro-5-methoxy-1-(tetrahydro-2H-pyran-2-yl)-1H-indazol-3-yl)acetaldehyde (153)

A mixture of 2-(6-fluoro-5-methoxy-1-(tetrahydro-2H-pyran-2-yl)-1H-indazol-3-yl)ethan-1-ol (5 g, 17.0 mmol) and DMSO (2.4 mL, 34.0 mmol) in EtOAc (175 mL) was treated with IBX (9.5 g, 34.0 mmol) and the mixture was stirred at 80° C. for 1 h. TLC indicated starting material remained so additional DMSO (7.2 mL) was added and the mixture was heated at 100° C. for 1 h. The cooled reaction was filtered through a celite plug to remove the insoluble material and the plug was washed with EtOAc. The combined filtrate was washed with saturated aq. Na₂S₂O₃ (3×50 mL), brine (2×100 mL) and then dried over anhydrous Na₂SO₄ and concentrated in vacuo. The residue (4.5 g) was used in the next step without further purification.

Step 2: 6-fluoro-5-methoxy-3-(2-(3-methylazetidin-1-yl)ethyl)-1-(tetrahydro-2H-pyran-2-yl)-1H-indazole (154)

A solution of 3-methylazetidine hydrochloride (353 mg, 3.28 mmol) in methanol (10 mL) was treated with NaCNBH₃ (206 mg, 3.28 mmol) and then crude 2-(6-fluoro-5-methoxy-1-(tetrahydro-2H-pyran-2-yl)-1H-indazol-3-yl)acetaldehyde (800 mg) and the resulting mixture was stirred at RT for 16 h. The reaction was then quenched with water (20 mL) and extracted with CH₂Cl₂ (5×20 mL). The combined organic layer was washed with brine (20 mL), dried over anhydrous Na₂SO₄ and concentrated in vacuo. The residue was purified by flash chromatography (0.1% to 8% MeOH/NH₃ in CH₂Cl₂) to afford the title compound as a yellow oil (323 mg) which was used in next step without further purification.

Step 3: 6-fluoro-5-methoxy-3-(2-(3-methylazetidin-1-yl)ethyl)-1H-indazole fumarate (A57-fumarate)

The title compound was synthesised according to General Procedure D utilising crude 6-fluoro-5-methoxy-3-(2-(3-methylazetidin-1-yl)ethyl)-1-(tetrahydro-2H-pyran-2-yl)-1H-indazole (320 mg) which upon purification generated the title compound as a colourless oil (195 mg) which was formulated as the fumarate salt as per General Procedure F (297 mg, 18% over 2 steps) as a white solid. LCMS (Condition A): $t_R$ (4.168 min) m/z=264.10 [M+H]⁺; ¹H NMR (400 MHz, DMSO-d₆): δ 7.39-7.32 (m, 2H), 6.55 (s, 5H), 4.20-4.00 (m, 2H), 3.84 (s, 3H), 3.73-3.64 (m, 2H), 3.50 (t, J=7.4 Hz, 2H), 3.10 (t, J=7.4 Hz, 2H), 2.92-2.69 (m, 1H), 1.14 (d, J=6.8 Hz, 3H); ¹H qNMR Purity: 97.5% (ERETIC).

Example 58: Synthesis of 6-fluoro-5-methoxy-3-(2-(2-methylazetidin-1-yl)ethyl)-1H-indazole (A58)

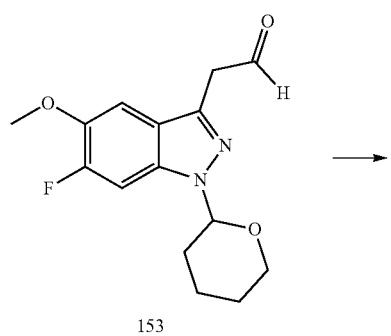

153

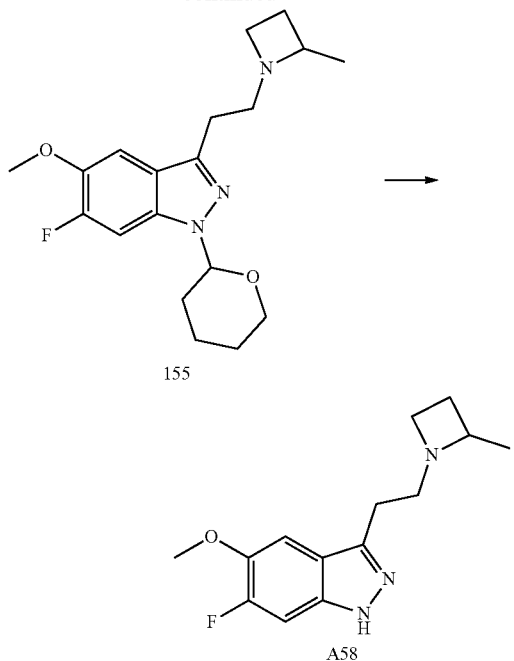

155

A58

Step 1: 6-fluoro-5-methoxy-3-(2-(2-methylazetidin-1-yl)ethyl)-1-(tetrahydro-2H-pyran-2-yl)-1H-indazole (155)

A solution of 2-methylazetidine hydrochloride (353 mg, 3.28 mmol) in methanol (10 mL) was treated with NaCNBH₃ (206 mg, 3.28 mmol) and then crude 2-(6-fluoro-5-methoxy-1-(tetrahydro-2H-pyran-2-yl)-1H-indazol-3-yl)acetaldehyde (800 mg) and the resulting mixture was stirred at RT for 16 h. The reaction was then quenched with water (20 mL) and extracted with CH₂Cl₂ (5×20 mL). The combined organic layer was washed with brine (20 mL), dried over anhydrous Na₂SO₄ and concentrated in vacuo. The residue was purified by flash chromatography (0.1% to 8% MeOH/NH₃ in CH₂Cl₂) to afford the title compound as a yellow oil (407 mg) which was used in next step without further purification.

Step 2: 6-fluoro-5-methoxy-3-(2-(2-methylazetidin-1-yl)ethyl)-1H-indazole fumarate (A58-fumarate)

The title compound was synthesised according to General Procedure D utilising crude 6-fluoro-5-methoxy-3-(2-(2-methylazetidin-1-yl)ethyl)-1-(tetrahydro-2H-pyran-2-yl)-1H-indazole (400 mg) which upon purification generated the title compound as a white solid (160 mg) which was formulated as the fumarate salt as per General Procedure F (238 mg, 18% over 2 steps) as a white solid. LCMS (Condition A): $t_R$ (4.135 min) m/z=264.10 [M+H]⁺; ¹H NMR (400 MHz, DMSO-d₆): δ 7.38-7.31 (m, 2H), 6.53 (s, 3.6H), 4.53-4.34 (m, 1H), 3.97-3.86 (m, 1H), 3.87-3.72 (m, 4H), 3.63-3.36 (m, 2H), 3.13 (t, J=7.4 Hz, 2H), 2.46-2.33 (m, 1H), 2.19-2.07 (m, 1H), 1.41 (d, J=6.7 Hz, 3H). ¹H qNMR Purity: 99.7% (ERETIC).

Example 59: Synthesis of 6-fluoro-5-methoxy-3-(2-(pyrrolidin-1-yl)ethyl)-1H-indazole (A59)

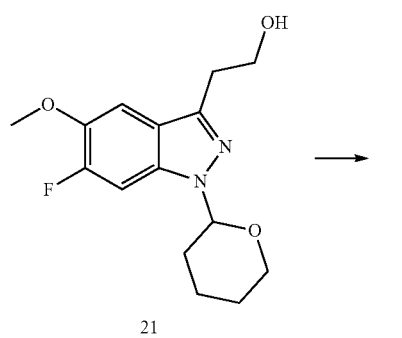

21

Step 1: 6-fluoro-5-methoxy-3-(2-(pyrrolidin-1-yl)ethyl)-1-(tetrahydro-2H-pyran-2-yl)-1H-indazole (156)

To an ice-cold solution of 2-(6-fluoro-5-methoxy-1-(tetrahydro-2H-pyran-2-yl)-1H-indazol-3-yl)ethan-1-ol (285 mg, 0.97 mmol) in CH$_2$Cl$_2$ (5 mL) in a pressure tube, was added Et$_3$N (0.20 mL, 1.45 mmol) and methanesulfonyl chloride (0.09 mL, 1.16 mmol) and the mixture was stirred at RT for 1 h. The reaction was concentrated under a stream of nitrogen gas. The residue was dissolved in DMF (2 mL) and then treated with pyrrolidine (0.80 mL, 9.67 mmol) and the pressure tube was sealed and heated at 80° C. for 2 h. The reaction was diluted with EtOAc (50 mL) and washed with H$_2$O (5×10 mL), saturated aq. NH$_4$Cl (2×15 mL) and then brine (3×15 mL). The combined aqueous layer was extracted once with EtOAc (20 mL) and then the combined EtOAc layers were dried over anhydrous Na$_2$SO$_4$ and concentrated in vacuo. The residue was purified by flash chromatography (0.1% to 5% MeOH/NH$_3$ in CH$_2$Cl$_2$) to afford the title compound as a yellow oil (283 mg, 84%). $^1$H NMR (400 MHz, CDCl$_3$): δ 7.29-7.23 (m, 1H), 7.15 (d, J=8.0 Hz, 1H), 5.51 (dd, J=9.8, 2.6 Hz, 1H), 4.14-4.01 (m, 1H), 3.92 (s, 3H), 3.77-3.64 (m, 1H), 3.27-3.16 (m, 2H), 3.04-2.90 (m, 2H), 2.83-2.64 (m, 4H), 2.56-2.36 (m, 1H), 2.15-1.96 (m, 2H), 1.94-1.79 (m, 4H), 1.79-1.53 (m, 3H).

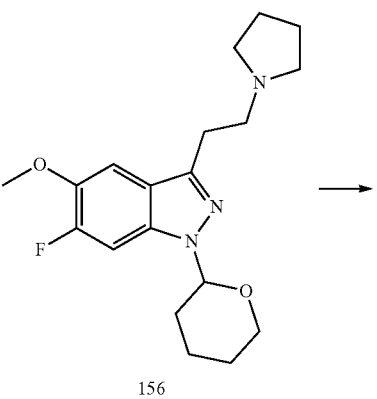

156

Step 2: 6-fluoro-5-methoxy-3-(2-(pyrrolidin-1-yl)ethyl)-1H-indazole fumarate (A59-fumarate)

The title compound was synthesised according to General Procedure D utilising 6-fluoro-5-methoxy-3-(2-(pyrrolidin-1-yl)ethyl)-1-(tetrahydro-2H-pyran-2-yl)-1H-indazole (280 mg, 0.81 mmol) which upon purification generated the title compound as a colourless oil (149 mg) which was formulated as the fumarate salt as per General Procedure F (191 mg, 50%) as a white solid. LCMS (Condition A): t$_R$ (4.114 min) m/z=264.15 [M+H]$^+$; $^1$H NMR (600 MHz, DMSO-d$_6$): δ 7.42 (d, J=8.1 Hz, 1H), 7.35 (d, J=11.1 Hz, 1H), 6.51 (s, 3H), 3.86 (s, 3H), 3.51-3.42 (m, 2H), 3.34-3.19 (m, 6H), 1.97-1.87 (m, 4H). $^{13}$C NMR (151 MHz, DMSO-d$_6$): δ 167.8, 153.0 (d, J=246.3 Hz), 143.5 (d, J=13.8 Hz), 140.9, 135.2, 135.1, 117.3, 101.8, 97.3 (d, J=23.5 Hz), 56.5, 53.3, 52.9, 23.4, 23.0; $^1$H qNMR Purity: 97.4% (ERETIC).

Example 60: Synthesis of 3-(2-(2-azabicyclo[3.1.0]hexan-2-yl)ethyl)-6-fluoro-5-methoxy-1H-indazole (A60)

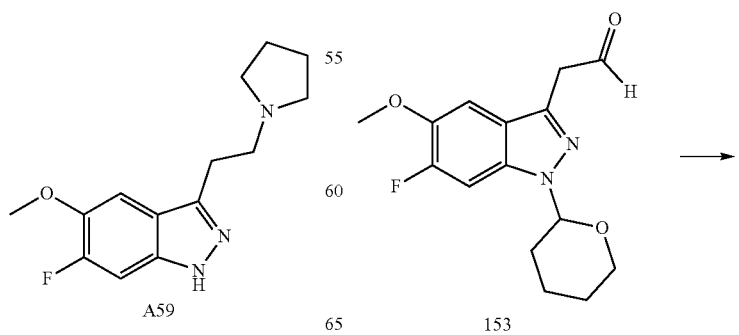

A59         153

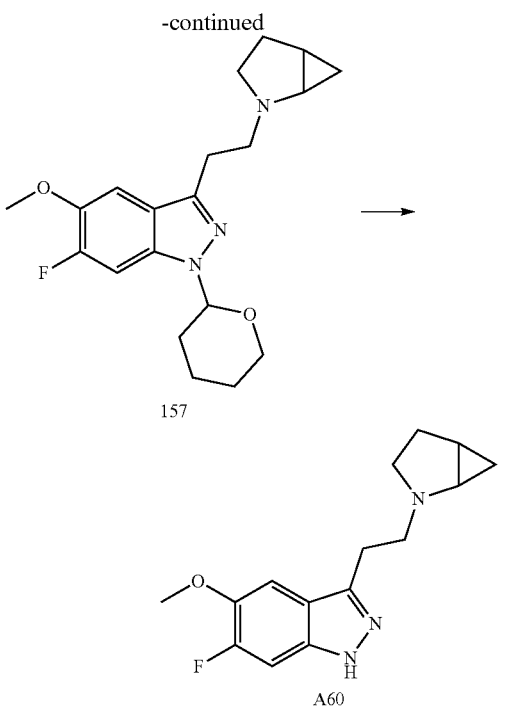

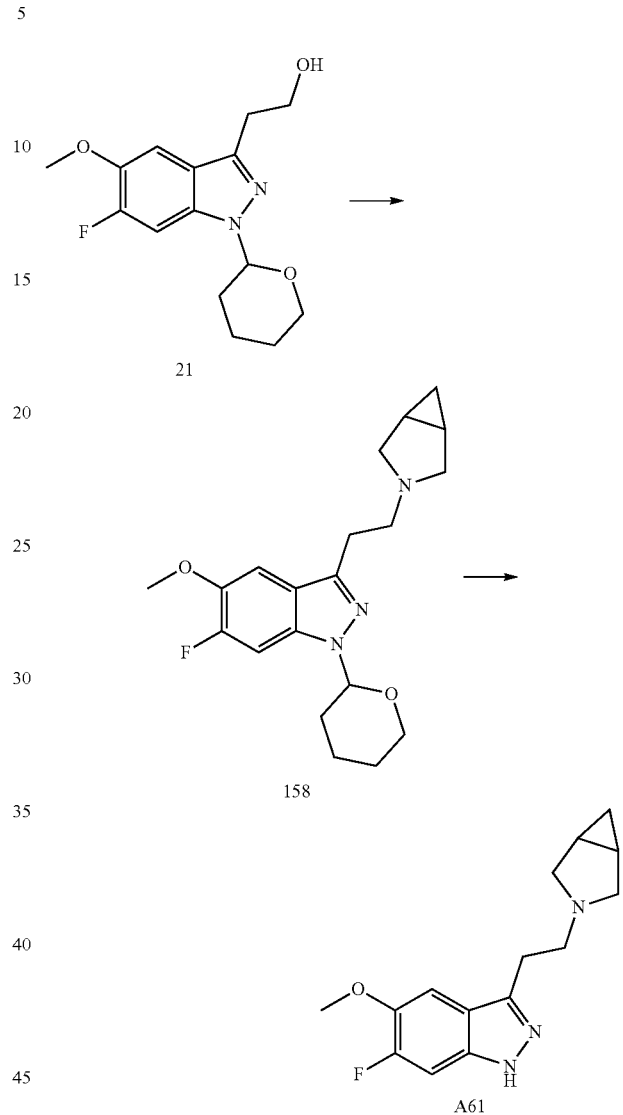

Example 61: Synthesis of 3-(2-(3-azabicyclo[3.1.0] hexan-3-yl)ethyl)-6-fluoro-5-methoxy-1H-indazole (A61)

Step 1: 3-(2-(2-azabicyclo[3.1.0]hexan-2-yl)ethyl)-6-fluoro-5-methoxy-1-(tetrahydro-2H-pyran-2-yl)-1H-indazole (157)

A solution of 2-azabicyclo[3.1.0]hexane hydrochloride (393 mg, 3.28 mmol) in methanol (10 mL) was treated with NaCNBH$_3$ (206 mg, 3.28 mmol) and then crude 2-(6-fluoro-5-methoxy-1-(tetrahydro-2H-pyran-2-yl)-1H-indazol-3-yl)acetaldehyde (800 mg) and the resulting mixture was stirred at RT for 16 h. The reaction was then quenched with H$_2$O (20 mL) and extracted with CH$_2$Cl$_2$ (5×20 mL). The combined organic layer was washed with brine (20 mL), dried over anhydrous Na$_2$SO$_4$ and concentrated in vacuo. The residue was purified by flash chromatography (0.1% to 8% MeOH/NH$_3$ in CH$_2$Cl$_2$) to afford the title compound as a yellow oil (484 mg) which was used in next step without further purification.

Step 2: 3-(2-(2-azabicyclo[3.1.0]hexan-2-yl)ethyl)-6-fluoro-5-methoxy-1H-indazole fumarate (A60-fumarate)

The title compound was synthesised according to General Procedure D utilising crude 3-(2-(2-azabicyclo[3.1.0]hexan-2-yl)ethyl)-6-fluoro-5-methoxy-1-(tetrahydro-2H-pyran-2-yl)-1H-indazole (480 mg) which upon purification generated the title compound as an off-white solid (225 mg) which was formulated as the fumarate salt as per General Procedure F (305 mg, 27% over 2 steps) as a white solid. LCMS (Condition A): $t_R$ (4.182 min) m/z=276.15 [M+H]$^+$; $^1$H NMR (600 MHz, DMSO-d$_6$): δ 7.42-7.28 (m, 2H), 6.47 (s, 2.3H), 3.84 (s, 3H), 3.56-3.38 (m, 4H), 3.38-3.21 (m, 2H), 2.77 (q, J=11.1 Hz, 1H), 2.13-1.92 (m, 2H), 1.80-1.68 (m, 1H), 1.14-0.98 (m, 1H), 0.71 (q, J=7.5 Hz, 1H); $^{13}$C NMR (151 MHz, DMSO-d$_6$): δ 169.1, 153.7 (d, J=246.4 Hz), 144.2 (d, J=13.8 Hz), 141.3, 135.8, 135.7, 117.8, 102.2, 97.9 (d, J=23.7 Hz), 57.0, 52.6, 49.8, 40.9, 31.5, 25.5, 23.7, 16.5; $^1$H qNMR Purity: 98.3% (ERETIC).

Step 1: 3-(2-(3-azabicyclo[3.1.0]hexan-3-yl)ethyl)-6-fluoro-5-methoxy-1-(tetrahydro-2H-pyran-2-yl)-1H-indazole (158)

In two batches: to an ice-cold solution of 2-(6-fluoro-5-methoxy-1-(tetrahydro-2H-pyran-2-yl)-1H-indazol-3-yl)ethan-1-ol (500 mg, 1.70 mmol) in CH$_2$Cl$_2$ (10 mL) in a pressure tube, was added Et$_3$N (0.36 mL, 2.55 mmol) and methanesulfonyl chloride (0.16 mL, 2.04 mmol) and the mixture was stirred at RT for 1 h. The reaction was concentrated under a stream of nitrogen gas. The residue was dissolved in DMF (3 mL) and then treated with 3-azabicyclo[3.1.0]hexane (282 mg, 3.40 mmol) and the pressure tube was sealed and heated at 80° C. for 2 h. The reaction was diluted with EtOAc (50 mL) and washed with H$_2$O (5×10 mL), saturated aq. NH$_4$Cl (2×15 mL) and then brine (3×15 mL). The combined aqueous layer was extracted once with EtOAc (20 mL) and then the combined EtOAc layers were dried over anhydrous $Na_2SO_4$ and concentrated in vacuo. The residue was purified by flash chromatography (0.1% to 5% $MeOH/NH_3$ in $CH_2Cl_2$) to afford a yellow oil and the product from both batches were combined and identified as the title compound (460 mg, 38%). $^1H$ NMR (400 MHz, $CDCl_3$): δ 7.24 (d, J=11.0 Hz, 1H), 7.15 (d, J=8.0 Hz, 1H), 5.50 (dd, J=9.8, 2.6 Hz, 1H), 4.12-3.99 (m, 1H), 3.93 (s, 3H), 3.79-3.62 (m, 1H), 3.29-3.05 (m, 4H), 3.02-2.88 (m, 2H), 2.61-2.32 (m, 3H), 2.13-1.91 (m, 2H), 1.80-1.55 (m, 3H), 1.50-1.33 (m, 2H), 0.93-0.70 (m, 1H), 0.55-0.33 (m, 1H). $^{13}C$ NMR (101 MHz, $CDCl_3$): δ 153.6 (d, J=248.4 Hz), 144.3 (d, J=13.7 Hz), 143.8, 134.7 (d, J=11.2 Hz), 119.2, 102.1 (d, J=3.0 Hz), 97.4 (d, J=24.1 Hz), 85.9, 77.4, 68.0, 56.8, 55.4, 54.8, 31.1, 29.8, 26.4, 25.2, 22.9, 15.5, 7.4.

Step 2: 3-(2-(3-azabicyclo[3.1.0]hexan-3-yl)ethyl)-6-fluoro-5-methoxy-1H-indazole fumarate (A61-fumarate)

The title compound was synthesised according to General Procedure D utilising 3-(2-(3-azabicyclo[3.1.0]hexan-3-yl)ethyl)-6-fluoro-5-methoxy-1-(tetrahydro-2H-pyran-2-yl)-1H-indazole (450 mg, 1.25 mmol) which upon purification generated the title compound as a colourless oil (230 mg) which was formulated as the fumarate salt as per General Procedure F (342 mg, 61%) as a white solid. LCMS (Condition A): $t_R$ (4.207 min) m/z=276.15 [M+H]$^+$; $^1H$ NMR (400 MHz, DMSO-$d_6$): δ 7.36 (d, J=8.2 Hz, 1H), 7.31 (d, J=11.2 Hz, 1H), 6.58 (s, 3H), 3.87 (s, 3H), 3.28 (d, J=9.6 Hz, 2H), 3.18-2.98 (m, 4H), 2.75 (d, J=9.2 Hz, 2H), 1.60-1.44 (m, 2H), 0.65 (q, J=4.1 Hz, 1H), 0.54-0.37 (m, 1H); $^{13}C$ NMR (101 MHz, DMSO-$d_6$): δ 166.7, 152.5 (d, J=245.5 Hz), 143.0 (d, J=13.6 Hz), 142.1, 134.9 (d, J=11.4 Hz), 134.4, 117.2, 101.8, 97.0, 56.2, 54.5, 53.4, 24.7, 14.9, 6.9; $^1H$ qNMR Purity: 99.5% (ERETIC).

Example 62: Synthesis of N-benzyl-2-(5-methoxy-1H-indazol-3-yl)ethan-1-amine (A62)

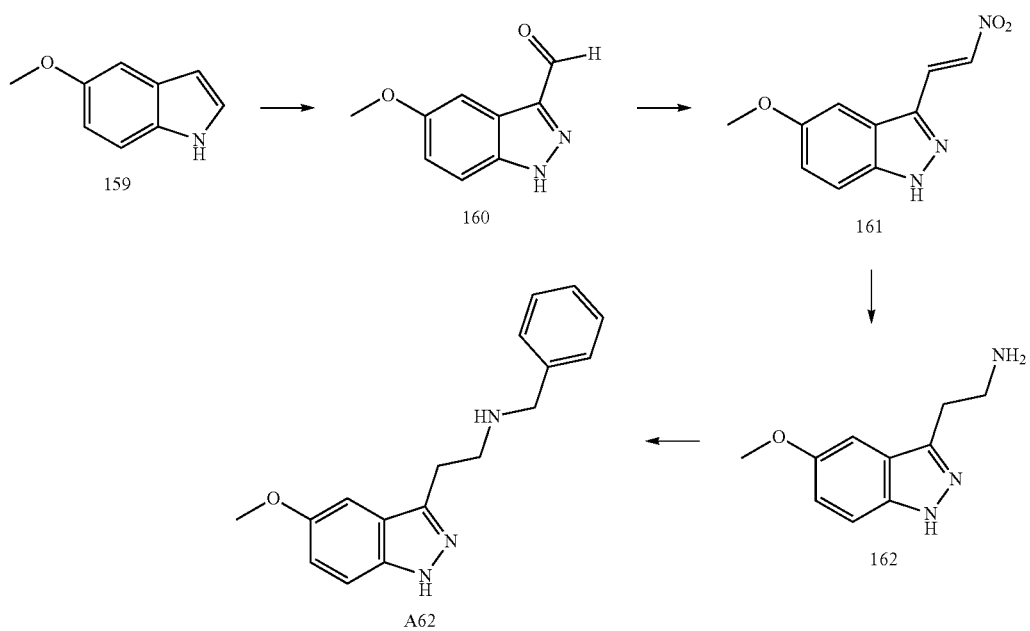

Step 1: 5-methoxy-1H-indazole-3-carbaldehyde (160)

A stirred solution of NaNO$_2$ (18.8 g, 272 mmol) in H$_2$O (130 mL) and DMF (90 mL) at 0° C. under nitrogen atmosphere was treated with 2 M aq. HCl (46 mL, 91.7 mmol) dropwise over 20 minutes. Maintaining 0° C., a solution of 5-methoxyindole (5.0 g, 34 mmol) in DMF (50 mL) was added dropwise over 1.5 h under nitrogen atmosphere. The mixture was kept in an ice bath and neutralised with aq. NaOH and then extracted with EtOAc (3×100 mL). The combined organics were dried over anhydrous MgSO$_4$ and concentrated under reduced pressure. The residue was purified by flash chromatography (EtOAc/hexane) to provide 5-methoxy-1H-indazole-3-carbaldehyde as a light brown solid (4.49 g, 75%). $^1$H NMR (400 MHz, DMSO-d$_6$): δ 14.03 (br s, 1H), 10.16 (s, 1H), 7.62 (dd, J=9.1, 0.7 Hz, 1H), 7.50 (d, J=2.3 Hz, 1H), 7.13 (dd, J=9.0, 2.4 Hz, 1H), 3.83 (s, 3H).

Step 2: (E)-5-methoxy-3-(2-nitrovinyl)-1H-indazole (161)

A solution of 5-methoxy-1H-indazole-3-carbaldehyde (3.23 g, 18.3 mmol) in MeNO$_2$ (60 mL) was treated with NH$_4$OAc (3.82 g, 49.5 mmol) and the mixture was stirred under nitrogen atmosphere at 60° C. for 3 h. After cooling, the mixture was diluted with EtOAc (140 mL) which was then washed with water (2×80 mL) and brine (2×80 mL). The organic phase was dried over anhydrous MgSO$_4$ and concentrated under reduced pressure. The residue was purified by flash chromatography (0-60% EtOAc/hexane) to provide (E)-5-methoxy-3-(2-nitrovinyl)-1H-indazole (2.18 g, 54%) as an orange solid. $^1$H NMR (400 MHz, DMSO-d$_6$): δ 13.97 (s, 1H), 8.38 (d, J=13.7 Hz, 1H), 8.27 (d, J=13.7 Hz, 1H), 7.61-7.54 (m, 2H), 7.11 (dd, J=9.0, 2.3 Hz, 1H), 3.88 (s, 3H).

Step 3: 2-(5-methoxy-1H-indazol-3-yl)ethan-1-amine (162)

A stirred solution of (E)-5-methoxy-3-(2-nitrovinyl)-1H-indazole (2.18 g, 9.96 mmol) in anhydrous THF (50 mL) at 0° C. was treated with LiAlH$_4$ (1.89 g, 21.0 mmol) which was then refluxed under nitrogen atmosphere for 3 h. The reaction was cooled to 0° C. and quenched by sequential addition of cold water (2 mL), 15% NaOH (2 mL) and then more water (6 mL). The mixture was filtered through a plug of celite which was washed through with warm THF. The combined filtrate was dried over anhydrous MgSO$_4$ and concentrated under reduced pressure. The residue was purified by flash chromatography (SiO$_2$, 1-20% MeOH/NH$_3$ in CH$_2$Cl$_2$) to provide 2-(5-methoxy-1H-indazol-3-yl)ethan-1-amine (943 mg, 50%) as a brown/yellow oil which slowly solidified. $^1$H NMR (400 MHz, DMSO-d$_6$): δ 12.51 (br s, 1H), 7.35 (dd, J=8.9, 0.7 Hz, 1H), 7.12 (dd, J=2.3, 0.7 Hz, 1H), 6.96 (dd, J=8.9, 2.3 Hz, 1H), 3.78 (s, 3H), 3.00-2.84 (m, 4H).

Step 4: N-benzyl-2-(5-methoxy-1H-indazol-3-yl)ethan-1-amine (A62)

A solution of 2-(5-methoxy-1H-indazol-3-yl)ethan-1-amine (178 mg, 0.93 mmol) in CH$_2$Cl$_2$ (20 mL) and MeOH (5 mL) at 0° C. was treated with NaBH(OAc)$_3$ (237 mg, 1.12 mmol) and stirred for 5 minutes. A solution of benzaldehyde (99 mg, 0.93 mmol) in CH$_2$Cl$_2$ (10 mL) was added dropwise and the mixture was stirred at RT 16 h. The reaction was quenched by addition of 2.5 M aq. NaOH (3 mL) and then volatiles were removed under reduced pressure. The aqueous phase was extracted with EtOAc (3×15 mL) and the combined organics were washed with brine (15 mL), dried over anhydrous MgSO$_4$ and concentrated under reduced pressure. The residue was purified by flash chromatography (0-20% MeOH/NH$_3$ in CH$_2$Cl$_2$) to provide N-benzyl-2-(5-methoxy-1H-indazol-3-yl)ethan-1-amine (67 mg, 26%) as an off-white solid. $^1$H NMR (400 MHz, DMSO-d$_6$): δ 12.50 (s, 1H), 7.41-7.15 (m, 6H), 7.09 (d, J=2.3 Hz, 1H), 6.96 (dd, J=8.9, 2.3 Hz, 1H), 3.77 (s, 2H), 3.76 (s, 3H), 3.09-2.98 (m, 2H), 2.94-2.83 (m, 2H).

Step 4: N-benzyl-2-(5-methoxy-1H-indazol-3-yl)ethan-1-amine fumarate (A62-fumarate)

N-benzyl-2-(5-methoxy-1H-indazol-3-yl)ethan-1-amine (64 mg, 0.23 mmol) was formulated as the fumarate salt according to General Procedure F which was isolated as an off-white solid (54 mg, 57%). LCMS (Condition A): t$_R$ (4.552 min) m/z=282.15 [M+H]$^+$; $^1$H NMR (600 MHz, DMSO-d$_6$): δ 12.62 (br s, 1H), 7.49-7.41 (m, 2H), 7.41-7.30 (m, 4H), 7.13 (dd, J=2.4, 0.7 Hz, 1H), 6.98 (dd, J=9.0, 2.3 Hz, 1H), 6.53 (s, 2H), 4.04 (s, 3H), 3.77 (s, 2H), 3.23-3.08 (m, 4H).

Example 63: Synthesis of 2-(5-methoxy-1H-indazol-3-yl)-N-(2-methoxybenzyl)ethan-1-amine (A63)

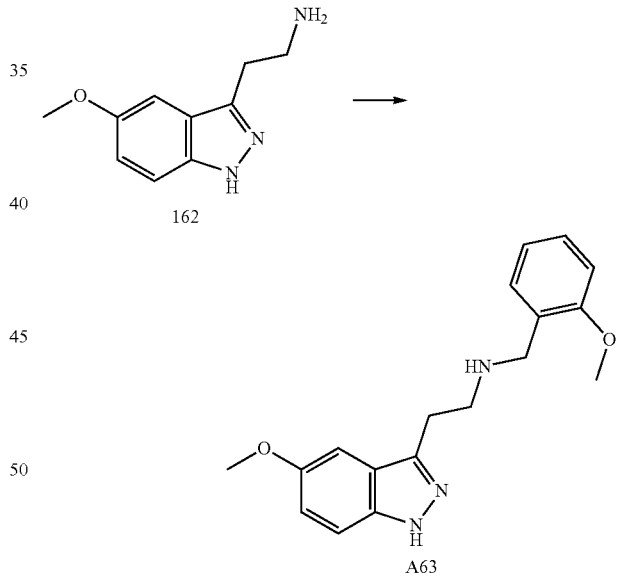

Step 1: 2-(5-methoxy-1H-indazol-3-yl)-N-(2-methoxybenzyl)ethan-1-amine (A63)

A solution of 2-(5-methoxy-1H-indazol-3-yl)ethan-1-amine (200 mg, 1.05 mmol) in CH$_2$Cl$_2$ (20 ml) and MeOH (5 mL) at 0° C. was treated with NaBH(OAc)$_3$ (266 mg, 1.26 mmol) portionwise and stirred for 5 minutes. A solution of 2-methoxybenzaldehyde (142 mg, 1.05 mmol) in CH$_2$Cl$_2$ (10 mL) was added dropwise and the mixture was allowed to stir at RT 16 h. The reaction was quenched by addition of 2.5 M aq. NaOH (3 mL) and then volatiles were removed under reduced pressure. The aqueous phase was extracted with EtOAc (3×15 mL) and the combined organics were washed with brine (15 mL), dried over anhydrous MgSO$_4$ and concentrated under reduced pressure. The residue was purified by flash chromatography (0-20% MeOH/NH$_3$ in CH$_2$Cl$_2$) to provide 2-(5-methoxy-1H-indazol-3-yl)-N-(2-methoxybenzyl)ethan-1-amine (214 mg, 66%) as an off-white solid. $^1$H NMR (400 MHz, DMSO-d$_6$): δ 12.50 (s, 1H), 7.35 (dd, J=8.9, 0.6 Hz, 1H), 7.28 (dd, J=7.4, 1.8 Hz, 1H), 7.24-7.14 (m, 1H), 7.09 (d, J=2.3 Hz, 1H), 6.96 (dd, J=9.0, 2.4 Hz, 1H), 6.92 (dd, J=8.4, 1.0 Hz, 1H), 6.87 (td, J=7.4, 1.1 Hz, 1H), 3.75 (s, 3H), 3.71 (s, 2H), 3.70 (s, 3H), 3.09-2.98 (m, 2H), 2.93-2.80 (m, 2H).

Step 2: 2-(5-methoxy-1H-indazol-3-yl)-N-(2-methoxybenzyl)ethan-1-amine fumarate (A63-fumarate)

2-(5-methoxy-1H-indazol-3-yl)-N-(2-methoxybenzyl)ethan-1-amine (224 mg, 0.72 mmol) was formulated as the fumarate salt according to General Procedure F which was isolated as light brown crystals (256 mg, 83%). LCMS (Condition A): t$_R$ (4.698 min) m/z=312.20 [M+H]$^+$; $^1$H NMR (600 MHz, DMSO-d$_6$): δ 12.67 (s, 1H), 7.41-7.35 (m, 2H), 7.32 (ddd, J=8.2, 7.4, 1.8 Hz, 1H), 7.13 (dd, J=2.3, 0.7 Hz, 1H), 7.02 (dd, J=8.3, 1.1 Hz, 1H), 6.99 (dd, J=9.0, 2.3 Hz, 1H), 6.94 (td, J=7.4, 1.1 Hz, 1H), 6.51 (s, 2H), 4.01 (s, 2H), 3.78 (s, 3H), 3.78 (s, 3H), 3.24-3.09 (m, 4H).

Example 64: Synthesis of N-(2-fluorobenzyl)-2-(5-methoxy-1H-indazol-3-yl)ethan-1-amine (A64)

Step 1: N-(2-fluorobenzyl)-2-(5-methoxy-1H-indazol-3-yl)ethan-1-amine (A64)

A solution of 2-(5-methoxy-1H-indazol-3-yl)ethan-1-amine (200 mg, 1.05 mmol) in CH$_2$Cl$_2$ (20 ml) and MeOH (5 mL) at 0° C. was treated with NaBH(OAc)$_3$ (266 mg, 1.26 mmol) portionwise and stirred for 5 minutes. A solution of 2-fluorobenzaldehyde (142 mg, 1.05 mmol) in CH$_2$Cl$_2$ (10 mL) was added dropwise and the mixture was allowed to stir at RT for 16 h. The reaction was quenched by addition of 2.5 M aq. NaOH (3 mL) and then volatiles were removed under reduced pressure. The aqueous phase was extracted with EtOAc (3×15 mL) and the combined organics were washed with brine (15 mL), dried over anhydrous MgSO$_4$ and concentrated under reduced pressure. The residue was purified by flash chromatography (0-20% MeOH/NH$_3$ in CH$_2$Cl$_2$) to provide 2-(5-methoxy-1H-indazol-3-yl)-N-(2-methoxybenzyl)ethan-1-amine (214 mg, 66%) as an off-white solid. $^1$H NMR (300 MHz, DMSO-d$_6$): δ 12.50 (s, 1H), 7.35 (dd, J=8.9, 0.6 Hz, 1H), 7.28 (dd, J=7.4, 1.8 Hz, 1H), 7.24-7.14 (m, 1H), 7.09 (d, J=2.3 Hz, 1H), 6.96 (dd, J=9.0, 2.4 Hz, 1H), 6.92 (dd, J=8.4, 1.0 Hz, 1H), 6.87 (td, J=7.4, 1.1 Hz, 1H), 3.75 (s, 3H), 3.71 (s, 2H), 3.70 (s, 3H), 3.09-2.98 (m, 2H), 2.93-2.80 (m, 2H).

Step 2: N-(2-fluorobenzyl)-2-(5-methoxy-1H-indazol-3-yl)ethan-1-amine dihydrochloride (A64·2HCl)

N-(2-fluorobenzyl)-2-(5-methoxy-1H-indazol-3-yl)ethan-1-amine (146 mg, 0.49 mmol) was formulated as the dihydrochloride salt according to General Procedure E which was isolated as an off-white solid (107 mg, 65%). LCMS (Condition A): t$_R$ (4.554 min) m/z=300.15 [M+H]$^+$; $^1$H NMR (600 MHz, DMSO-d$_6$): δ 9.61 (s, 2H), 7.75 (td, J=7.6, 1.7 Hz, 1H), 7.54-7.44 (m, 1H), 7.40 (dd, J=9.0, 0.7 Hz, 1H), 7.34-7.30 (m, 1H), 7.28 (dt, J=7.5, 1.3 Hz, 1H), 7.22 (d, J=2.3 Hz, 1H), 7.01 (dd, J=9.0, 2.3 Hz, 1H), 4.29 (t, J=5.8 Hz, 2H), 3.80 (s, 3H), 3.39-3.32 (m, 4H).

Example 65: Synthesis of N-(3-fluorobenzyl)-2-(5-methoxy-1H-indazol-3-yl)ethan-1-amine (A65)

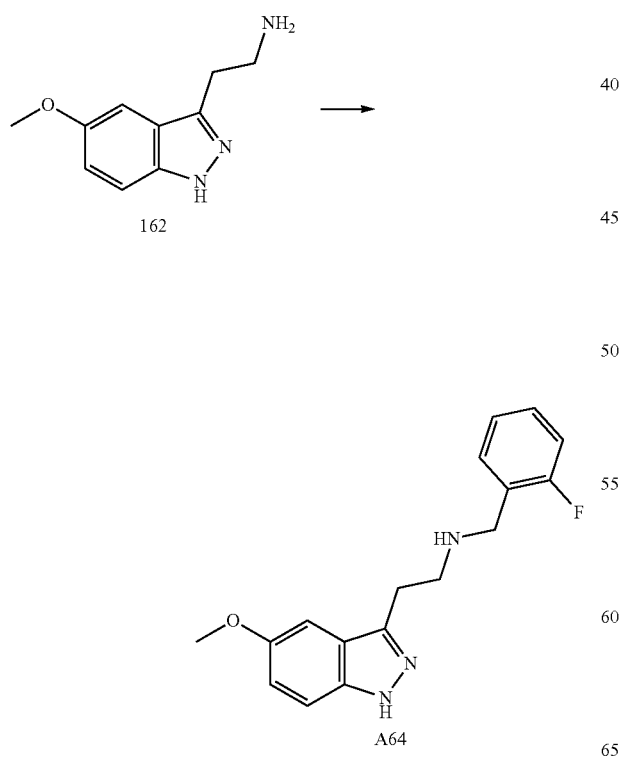

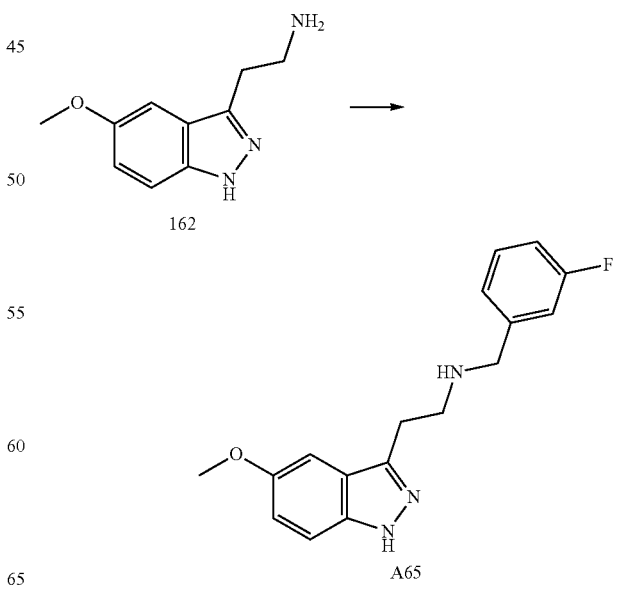

Step 1: N-(3-fluorobenzyl)-2-(5-methoxy-1H-indazol-3-yl)ethan-1-amine (A65)

A stirred solution of 2-(5-methoxy-1H-indazol-3-yl)ethan-1-amine (207 mg, 1.08 mmol) in CH$_2$Cl$_2$ (10 mL) at 0° C. was treated with NaBH(OAc)$_3$ (275 mg, 1.3 mmol) followed by a solution of 3-fluorobenzaldehyde (134 mg, 1.08 mmol) in CH$_2$Cl$_2$ (5 mL) dropwise and the mixture was stirred at RT for 3 h. The reaction was quenched by addition of 1 M NaOH (5 mL) and volatiles were removed under reduced pressure. The aqueous phase was extracted with EtOAc (3×15 mL) and the combined organics washed with brine (15 mL), dried over anhydrous MgSO$_4$ and concentrated under reduced pressure. The residue was purified by flash chromatography (0-20% MeOH/NH$_3$ in CH$_2$Cl$_2$) to provide N-(3-fluorobenzyl)-2-(5-methoxy-1H-indazol-3-yl)ethan-1-amine (70 mg, 48%) as a yellow oil which slowly crystalised. $^1$H NMR (400 MHz, CDCl$_3$) δ 7.33 (dd, J=9.0, 0.7 Hz, 1H), 7.29-7.22 (m, 1H), 7.12-7.09 (m, 1H), 7.09-7.03 (m, 2H), 6.98 (dd, J=2.4, 0.7 Hz, 1H), 6.92 (tdd, J=8.5, 2.7, 1.0 Hz, 1H), 3.90 (s, 2H), 3.84 (s, 3H), 3.25-3.10 (m, 4H).

Step 2: N-(3-fluorobenzyl)-2-(5-methoxy-1H-indazol-3-yl)ethan-1-amine dihydrochloride (A65.2HCl)

N-(3-fluorobenzyl)-2-(5-methoxy-1H-indazol-3-yl)ethan-1-amine (64 mg, 0.21 mmol) was formulated as the dihydrochloride salt according to General Procedure E which was isolated as an off-white solid (33 mg, 46%). LCMS (Condition A): t$_R$ (4.642 min) m/z=300.15 [M+H]$^+$; $^1$H NMR (400 MHz, DMSO-d$_6$): δ 12.75 (br s, 1H), 9.50 (br s, 1H), 7.53-7.46 (m, 2H), 7.44-7.38 (m, 2H), 7.30-7.23 (m, 1H), 7.20 (d, J=2.3 Hz, 1H), 7.01 (dd, J=9.0, 2.4 Hz, 1H), 4.26 (t, J=5.9 Hz, 2H), 3.80 (s, 3H), 3.35-3.28 (m, 4H); $^{13}$C NMR (101 MHz, DMSO-d$_6$): δ 153.7, 140.1, 136.7, 134.7 (d, J=7.9 Hz), 130.8 (d, J=8.5 Hz), 128.4, 126.2 (d, J=3.1 Hz), 121.6, 118.3, 116.9 (d, J=22.3 Hz), 115.9 (d, J=20.5 Hz), 111.3, 99.1, 55.5, 49.2, 45.4, 23.1.

Example 66: Synthesis of 2-(5-methoxy-1H-indazol-3-yl)-N-(3-methoxybenzyl)ethan-1-amine (A66)

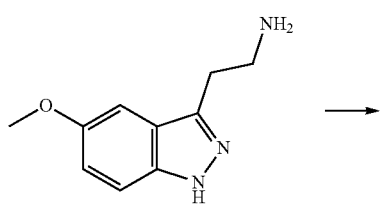

162

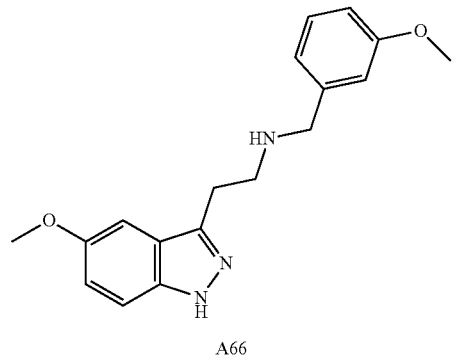

A66

Step 1: 2-(5-methoxy-1H-indazol-3-yl)-N-(3-methoxybenzyl)ethan-1-amine (A66)

A stirred solution of 2-(5-methoxy-1H-indazol-3-yl)-N-(3-methoxybenzyl)ethan-1-amine (207 mg, 1.08 mmol) in CH$_2$Cl$_2$ (10 mL) at 0° C. was treated with NaBH(OAc)$_3$ (275 mg, 1.30 mmol) followed by a solution of 3-methoxybenzaldehyde (147 mg, 1.08 mmol) in CH$_2$Cl$_2$ (5 mL) dropwise and the mixture was stirred at RT for 3 h. The reaction was quenched by addition of 1 M NaOH (5 mL) and volatiles were removed under reduced pressure. The aqueous phase was extracted with EtOAc (3×15 mL) and the combined organics washed with brine (15 mL), dried over anhydrous MgSO$_4$ and concentrated under reduced pressure. The residue was purified by flash chromatography (0-20% MeOH/NH$_3$ in CH$_2$Cl$_2$) to provide 2-(5-methoxy-1H-indazol-3-yl)-N-(3-methoxybenzyl)ethan-1-amine (163 mg, 48%) as a yellow oil which slowly solidified. $^1$H NMR (400 MHz, CDCl$_3$) δ 7.31 (dd, J=9.0, 0.7 Hz, 1H), 7.21 (t, J=8.1 Hz, 1H), 7.03 (dd, J=9.0, 2.3 Hz, 1H), 6.97 (d, J=2.3 Hz, 1H), 6.93-6.88 (m, 2H), 6.80-6.76 (m, 1H), 3.89 (s, 2H), 3.83 (s, 3H), 3.77 (s, 3H), 3.24-3.10 (m, 4H).

Step 2: 2-(5-methoxy-1H-indazol-3-yl)-N-(3-methoxybenzyl)ethan-1-amine dihydrochloride (A66.2HCl)

2-(5-methoxy-1H-indazol-3-yl)-N-(3-methoxybenzyl)ethan-1-amine (131 mg, 0.42 mmol) was formulated as the dihydrochloride salt according to General Procedure E which was isolated as a pale brown powder (76 mg, 45%). LCMS (Condition A): t$_R$ (4.653 min) m/z=312.15 [M+H]$^+$; $^1$H NMR (400 MHz, DMSO-d$_6$): δ 12.74 (br s, 1H), 9.60 (br s, 2H), 7.40 (dd, J=9.0, 0.7 Hz, 1H), 7.34 (dd, J=8.3, 7.5 Hz, 1H), 7.27 (dd, J=2.6, 1.5 Hz, 1H), 7.22 (d, J=2.2 Hz, 1H), 7.14 (dt, J=7.7, 1.2 Hz, 1H), 7.00 (dd, J=9.0, 2.4 Hz, 1H), 6.97 (ddd, J=8.4, 2.6, 0.9 Hz, 1H), 4.19 (t, J=5.8 Hz, 2H), 3.79 (s, 3H), 3.78 (s, 3H), 3.37-3.23 (m, 4H).

Example 67: Synthesis of 3-(2-(2-azabicyclo[3.1.0]hexan-2-yl)ethyl)-6-fluoro-5-methoxy-1-methyl-1H-indazole (A67)

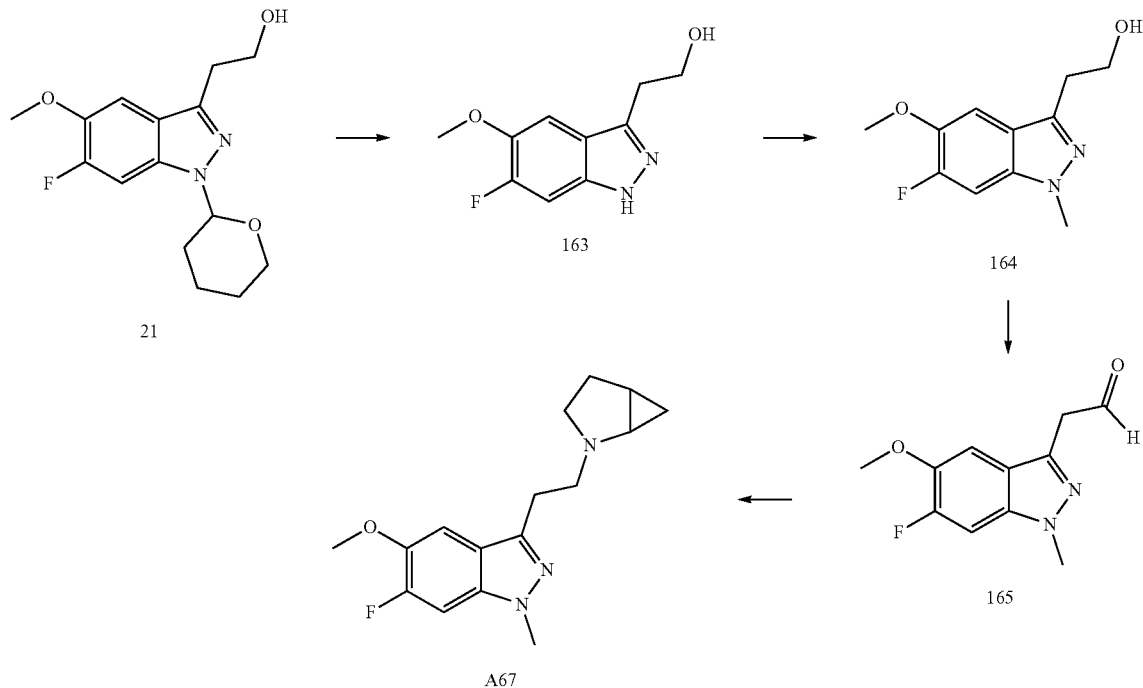

Step 1: 2-(6-fluoro-5-methoxy-1H-indazol-3-yl)ethan-1-ol (163)

An ice-cold solution of 2-(6-fluoro-5-methoxy-1-(tetrahydro-2H-pyran-2-yl)-1H-indazol-3-yl)ethan-1-ol (3.3 g, 11.2 mmol) in MeOH (33 mL) was treated with dropwise 37% aq. HCl (3.3 mL) and the reaction was stirred at reflux for 3 h. The reaction mixture was concentrated under a stream of nitrogen gas and the residue was diluted with saturated aq. $Na_2CO_3$ (50 mL) before being extracted with $CHCl_3$:IPA (3:1, 3×50 mL). The combined organic layer was dried over anhydrous $Na_2SO_4$, filtered, and the filtrate concentrated in vacuo. The residue was triturated in hot diethyl ether with a few drops of methanol and once cooled, the solid was collected by filtration under vacuum to afford the title compound as a white solid (1.05 g, 45%). $^1$H NMR (400 MHz, DMSO-$d_6$): δ 12.59 (s, 1H), 7.35 (d, J=8.2 Hz, 1H), 7.29 (d, J=11.2 Hz, 1H), 4.70 (t, J=5.3 Hz, 1H), 3.86 (s, 3H), 3.75 (td, J=7.2, 5.4 Hz, 2H), 3.03 (t, J=7.2 Hz, 2H). $^{13}$C NMR (101 MHz, DMSO-$d_6$): δ 152.5 (d, J=245.2 Hz), 142.8, 142.8 (d, J=13.9 Hz), 134.75 (d, J=11.0 Hz), 117.7, 102.1, 96.6 (d, J=23.0 Hz), 60.5, 56.2, 30.5.

Step 2: 2-(6-fluoro-5-methoxy-1-methyl-1H-indazol-3-yl)ethan-1-ol (164)

To an ice-cold solution of 2-(6-fluoro-5-methoxy-1H-indazol-3-yl)ethan-1-ol (1 g, 4.76 mmol) in anhydrous DMF (10 mL) was added sodium hydride (60% w/w, 190 mg, 4.76 mmol) and the resulting solution was stirred cold for 30 min before iodomethane (0.33 mL, 5.23 mmol) was added dropwise. The resulting solution was stirred cold for 30 min and then quenched with half saturated aq. $NH_4Cl$ (10 mL). The mixture was then extracted with EtOAc (5×30 mL) and the combined organic layer was washed with brine (3×50 mL). The combined brine layer was extracted once with EtOAc (20 mL) and then the EtOAc layers were combined and concentrated in vacuo. The residue was purified by flash chromatography (0.1% to 5% MeOH/$NH_3$ in DCM) to afford the title compound as a white solid (680 mg, 64%). $^1$H NMR (400 MHz, DMSO-$d_6$): δ 7.50 (d, J=11.5 Hz, 1H), 7.35 (d, J=8.3 Hz, 1H), 4.70 (t, J=5.4 Hz, 1H), 3.89 (s, 3H), 3.86 (s, 3H), 3.74 (td, J=7.1, 5.4 Hz, 2H), 3.01 (t, J=7.1 Hz, 2H). $^{13}$C NMR (101 MHz, DMSO-$d_6$): δ 152.5 (d, J=245.5 Hz), 142.9 (d, J=13.7 Hz), 141.7, 134.8 (d, J=11.5 Hz), 118.1, 102.2 (d, J=3.0 Hz), 96.4 (d, J=23.6 Hz), 60.5, 56.2, 35.2, 30.3. $^{19}$F NMR (376 MHz, DMSO-$d_6$): δ −132.9.

Step 3: 2-(6-fluoro-5-methoxy-1-methyl-1H-indazol-3-yl)acetaldehyde (165)

To a suspension of 2-(6-fluoro-5-methoxy-1-methyl-1H-indazol-3-yl)ethan-1-ol (215 mg, 0.96 mmol) in EtOAc (20 mL) was added Dess-Martin periodinane (488 mg, 1.15 mmol) and tBuOH (85 mg, 1.15 mmol) and the mixture was stirred at RT for 3 h. The reaction mixture was filtered through a pad of celite and the filtrate was washed with 0.5 M aq. $Na_2S_2O_3$ (2×40 mL), brine (20 mL) and then concentrated under reduced pressure to afford crude 2-(6-fluoro-5-methoxy-1-methyl-1H-indazol-3-yl)acetaldehyde (215 mg) as a yellow oil, which was used in the next step without further purification.

Step 4: 3-(2-(2-azabicyclo[3.1.0]hexan-2-yl)ethyl)-6-fluoro-5-methoxy-1-methyl-1H-indazole (A67)

A solution of crude 2-(6-fluoro-5-methoxy-1-methyl-1H-indazol-3-yl)acetaldehyde (215 mg) in MeOH (30 mL) at 0° C. was treated with 2-azabicyclo[3.1.0]hexane hydrochloride (138 mg, 1.15 mmol) and NaCNBH$_3$ (121 mg, 1.92 mmol) and the mixture was stirred at rt overnight. The reaction was quenched with 2 M aq. NaOH (5 mL) and then volatiles were removed under a stream of nitrogen gas. The remaining aqueous phase was extracted with CH$_2$Cl$_2$ (3×15 mL) and the combined organics were washed with brine (15 mL), dried over Na$_2$SO$_4$ and concentrated under reduced pressure. The residue was purified by flash chromatography (SiO$_2$, 0-6% MeOH/NH$_3$ in CH$_2$Cl$_2$) to afford 3-(2-(2-azabicyclo[3.1.0]hexan-2-yl)ethyl)-6-fluoro-5-methoxy-1-methyl-1H-indazole (99 mg, 36% over two steps) as an off-white solid. $^1$H NMR (400 MHz, CDCl$_3$): δ 7.12 (d, J=7.9 Hz, 1H), 7.04 (d, J=10.7 Hz, 1H), 3.95 (s, 3H), 3.93 (s, 3H), 3.29-3.05 (m, 3H), 3.03-2.86 (m, 3H), 1.57-1.44 (m, 1H), 0.76-0.70 (m, 1H), 0.24-0.15 (m, 1H).

Step 5: 3-(2-(2-azabicyclo[3.1.0]hexan-2-yl)ethyl)-6-fluoro-5-methoxy-1-methyl-1H-indazole fumarate (A67-fumarate)

3-(2-(2-azabicyclo[3.1.0]hexan-2-yl)ethyl)-6-fluoro-5-methoxy-1-methyl-1H-indazole (98 mg, 0.34 mmol) was formulated as the fumarate salt according to General Procedure F which was isolated as white crystals (99 mg, 63%). $^1$H NMR (400 MHz, DMSO-d$_6$): δ 7.53 (d, J=11.4 Hz, 1H), 7.38 (d, J=8.2 Hz, 1H), 6.59 (s, 2H), 3.90 (s, 3H), 3.87 (s, 3H), 3.15-3.01 (m, 3H), 2.99-2.87 (m, 3H), 2.15-2.03 (m, 1H), 1.95-1.77 (m, 2H), 1.50-1.40 (m, 1H), 0.82-0.74 (m, 1H), 0.23-0.14 (m, 1H); $^{13}$C NMR (101 MHz, DMSO-d$_6$): δ 166.5, 152.5 (d, J=246 Hz), 143.0 (d, J=14 Hz), 141.5, 134.9 (d, J=12 Hz), 134.3, 117.7, 101.9 (d, J=3 Hz), 96.6 (d, J=24 Hz), 56.2, 52.8, 47.8, 40.1, 35.3, 26.0, 25.2, 14.8, 1.9; $^1$H qNMR Purity: 97.9% (ERETIC).

Example 36a: 2-(1H-indazol-3-yl)-N,N-dimethyl-ethan-1-amine (P-56)

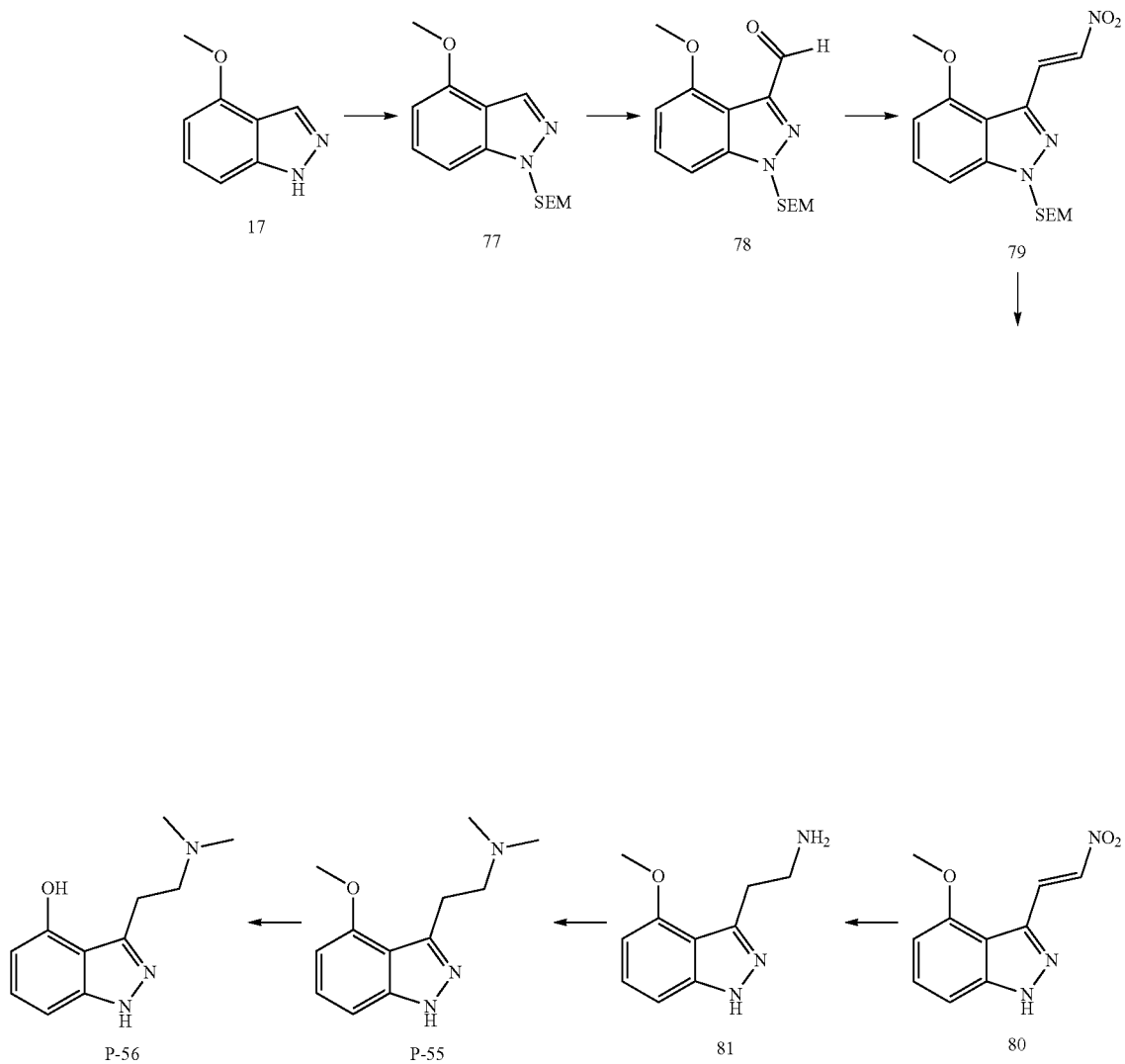

Step 1: 4-methoxy-1-((2-(trimethylsilyl)ethoxy) methyl)-1H-indazole (77)

To a solution of N-cyclohexyl-N-methylcyclohexanamine (17.2 g, 88.0 mmol) in THF (105 mL) was added [2-(chloromethoxy)ethyl]trimethylsilane (13.5 g, 81.0 mmol) and 4-methoxy-1H-indazole (10.0 g, 67.5 mmol). The mixture was stirred at 25° C. for 12 h, at which point the reaction mixture was combined with 0.5 M NaOH (120 mL) and the product was extracted with EtOAc (20 mL×2). The combined organic layers were washed with $H_2O$ (20 mL), then brine (20 mL), and then dried over $Na_2SO_4$, filtered, and the filtrate concentrated in vacuo. The residue was purified by column chromatography ($SiO_2$, Petroleum ether/EtOAc, v/v, 50/1 to 20/1) to afford 4-methoxy-1-((2-(trimethylsilyl) ethoxy)methyl)-1H-indazole (12.0 g, 64%) as a yellow oil. $^1$H NMR (400 MHz, $CDCl_3$): δ 8.16 (s, 1H), 7.30-7.33 (m, 1H), 7.20-7.24 (m, 1H), 6.35 (d, J=7.2 Hz, 1H), 5.70 (s, 2H), 3.95 (s, 3H), 3.60-3.64 (m, 2H), 0.92-0.96 (m, 2H), −0.02 (s, 9H).

Step 2: 4-methoxy-1-((2-(trimethylsilyl)ethoxy) methyl)-1H-indazole-3-carbaldehyde (78)

To a solution of 4-methoxy-1-((2-(trimethylsilyl)ethoxy) methyl)-1H-indazole (10.0 g, 35.9 mmol) in THF (60 mL), cooled to −65° C., was added 2.5 M n-BuLi in hexanes (35.9 mL, 89.8 mmol) and DMF (5.25 g, 71.8 mmol). The mixture was stirred at −65° C. for 2 h. The reaction was quenched by dropwise addition of $H_2O$ (10 mL) at 0° C. and was then further diluted with $H_2O$ (30 mL) before the product was extracted with $CH_2Cl_2$ (40 mL×3). The combined organics were washed with brine (30 mL), dried over anhydrous $Na_2SO_4$, filtered, and the filtrate concentrated in vacuo. The residue was purified by column chromatography ($SiO_2$, Petroleum ether/EtOAc, v/v, 50/1 to 5/1) to afford 4-methoxy-1-((2-(trimethylsilyl)ethoxy)methyl)-1H-indazole-3-carbaldehyde (8.00 g, 73%) as a yellow oil. $^1$H NMR (400 MHz, $CDCl_3$): δ 10.54 (s, 1H), 7.34-7.47 (m, 1H), 7.30-7.32 (m, 1H), 6.65 (d, J=7.2 Hz, 1H), 6.14 (s, 2H), 4.0 (s, 3H), 3.65-3.69 (m, 2H), 0.91-0.95 (m, 2H), −0.03 (s, 9H).

Step 3: (E)-4-methoxy-3-(2-nitrovinyl)-1-((2-(trimethylsilyl)ethoxy)methyl)-1H-indazole (79)

To a solution of 4-methoxy-1-((2-(trimethylsilyl)ethoxy) methyl)-1H-indazole-3-carbaldehyde (3.00 g, 9.79 mmol) in $MeNO_2$ (6.91 mL, 129 mmol) was added $NH_4OAc$ (377 mg, 4.89 mmol) and the mixture was stirred at 100° C. for 2 h. The reaction mixture was cooled to 0° C. and diluted with $H_2O$ (20 mL) then extracted with EtOAc (20 mL×2). The combined organic layers were washed with brine (10 mL), dried over $Na_2SO_4$ and concentrated in vacuo. The residue was subjected to column chromatography (Petroleum ether/EtOAc, v/v, 50/1 to 5/1) to yield crude (E)-4-methoxy-3-(2-nitrovinyl)-1-((2-(trimethylsilyl)ethoxy)methyl)-1H-indazole (7.00 g) as a yellow solid which was used in the subsequent step without purification.

Step 4: (E)-4-methoxy-3-(2-nitrovinyl)-1H-indazole (80)

Crude (E)-4-methoxy-3-(2-nitrovinyl)-1-((2-(trimethylsilyl)ethoxy)methyl)-1H-indazole (6.00 g) was dissolved in 4 M HCl in MeOH (5 mL) and stirred at 25° C. for 12 h. The reaction mixture was concentrated in vacuo to give (E)-4-methoxy-3-(2-nitrovinyl)-1H-indazole (3.70 g) as a yellow solid. $^1$H NMR (400 MHz, $CDCl_3$): δ 8.44 (d, J=13.6 Hz, 1H), 8.08 (d, J=13.6 Hz, 1H), 7.29-31 (m, 1H), 7.05 (d, J=8.4 Hz, 1H), 6.57 (d, J=7.6 Hz, 1H), 3.97 (s, 3H).

Step 5: 2-(4-methoxy-1H-indazol-3-yl)ethan-1-amine (81)

To an ice-cold solution of (E)-4-methoxy-3-(2-nitrovinyl)-1H-indazole (3.70 g, 16.9 mmol) in THF (37 mL) was added $LiAlH_4$ (7.05 g, 186 mmol) portionwise. The mixture was then heated to 50° C. and stirred for 3 h. The mixture was then cooled to 0° C. and quenched by portionwise addition of $Na_2SO_4 \cdot 10H_2O$ (7.00 g). The mixture was stirred at 20° C. for 10 min and then filtered. The filtrate was concentrated in vacuo to give 2-(4-methoxy-1H-indazol-3-yl)ethan-1-amine (2.60 g) as a brown solid. LCMS (ESI+): m/z 192.2 $[M+H]^+$.

Step 6: 2-(4-methoxy-1H-indazol-3-yl)-N,N-dimethylethan-1-amine (P-55)

To a solution of 2-(4-methoxy-1H-indazol-3-yl)ethan-1-amine (0.30 g, 1.57 mmol) in MeOH (3 mL) was added 37% w/w aqueous formaldehyde (431 mg, 5.31 mmol), AcOH (376 mg, 6.26 mmol) and $NaBH_3CN$ (197 mg, 3.13 mmol). The mixture was stirred at 20° C. for 3 h. The reaction mixture was then concentrated in vacuo and the residue was purified by preparative HPLC (column: Waters Xbridge BEH C18 (100*30 mm*10 μm); mobile phase: [water ($NH_4HCO_3$)-ACN]; B %: 10-35%, 8 min) to give 2-(4-methoxy-1H-indazol-3-yl)-N,N-dimethylethan-1-amine (20.0 mg, 4% over 2 steps) as a white solid. $^1$H NMR (400 MHz, $CDCl_3$): δ 7.24-7.26 (m, 1H), 6.99 (d, J=8.4 Hz, 1H), 6.44 (d, J=7.6 Hz, 1H), 3.96 (s, 1H), 3.28 (t, J=8.0 Hz, 2H), 2.79 (t, J=8.0 Hz, 2H), 2.38 (s, 6H). LCMS (ESI+): m/z 220.1 $[M+H]^+$. HPLC Purity (220 nm): 98.5%.

Step 7: 3-(2-(dimethylamino)ethyl)-1H-indazol-4-ol (P-56)

To a solution of 2-(4-methoxy-1H-indazol-3-yl)-N,N-dimethylethan-1-amine (70.0 mg, 0.32 mmol) in $CS_2$ (1 mL) was added $AlCl_3$ (297 mg, 2.23 mmol) and the mixture was stirred at 50° C. for 4 h. The reaction mixture was concentrated in vacuo then quenched with MeOH (30 mL) and concentrated again. The residue was purified by preparative HPLC (column: Phenomenex C18 (75*30 mm*3 μm); mobile phase: [water ($NH_4HCO_3$)-ACN]; B: 1-40%, 8 min) to afford 3-(2-(dimethylamino)ethyl)-1H-indazol-4-ol (9.4 mg, 14%) as a colourless oil. $^1$H NMR (400 MHz, $D_2O$): δ 7.21 (t, J=8.0 Hz, 1H), 6.79 (d, J=8.4 Hz, 1H), 6.27 (d, J=7.6 Hz, 1H), 3.29-3.34 (m, 4H), 2.72 (s, 6H). LCMS (ESI+): m/z 206.1 $[M+H]^+$. HPLC Purity (220 nm): 96.0%.

Example 37a: 2-(1H-indazol-3-yl)-N,N-diethylethan-1-amine (P-43)

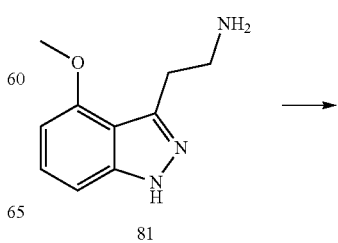

81

353
-continued

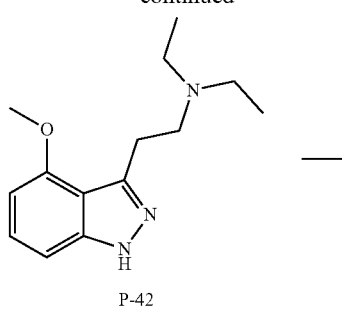

P-42

↓

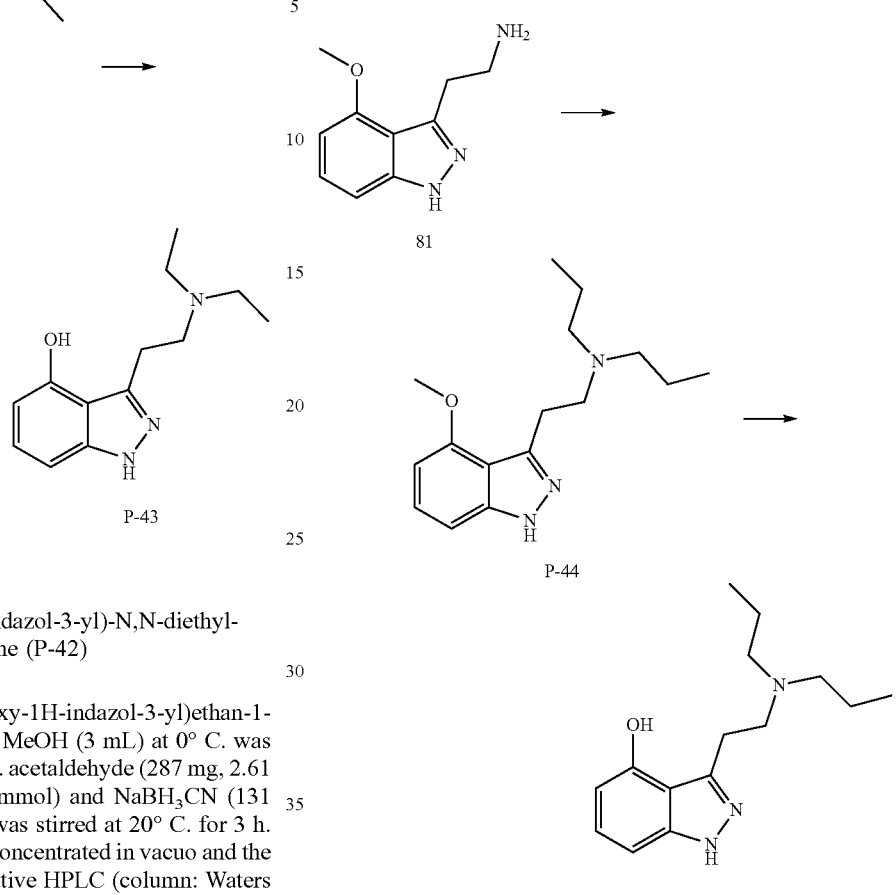

Step 1: 2-(4-methoxy-1H-indazol-3-yl)-N,N-diethyl-ethan-1-amine (P-42)

To a solution of 2-(4-methoxy-1H-indazol-3-yl)ethan-1-amine (200 mg, 1.05 mmol) in MeOH (3 mL) at 0° C. was added a 40% w/w solution of aq. acetaldehyde (287 mg, 2.61 mmol), AcOH (251 mg, 4.18 mmol) and NaBH$_3$CN (131 mg, 2.08 mmol). The mixture was stirred at 20° C. for 3 h. The reaction mixture was then concentrated in vacuo and the residue was purified by preparative HPLC (column: Waters Xbridge Prep OBD C18 (150*40 mm*10 μm); mobile phase: [water (NH$_4$HCO$_3$)-ACN]; B %: 10-55%, 8 min) to give 2-(4-methoxy-1H-indazol-3-yl)-N,N-diethylethan-1-amine (26 mg, 8% over 2 steps) as a colourless oil. $^1$H NMR (400 MHz, CDCl$_3$): δ 7.25-7.27 (m, 1H), 7.01 (d, J=8.4 Hz, 1H), 6.45 (d, J=7.6 Hz, 1H), 3.96 (s, 3H), 3.25-3.29 (m, 2H), 2.74 (q, J=7.2 Hz, 4H), 2.97-3.01 (m, 2H), 1.15 (t, J=6.8 Hz, 6H). LCMS (ESI+): m/z 248.1 [M+H]$^+$.

Step 2: 3-(2-(diethylamino)ethyl)-1H-indazol-4-ol (P-43)

To a solution of 2-(4-methoxy-1H-indazol-3-yl)-N,N-diethylethan-1-amine (78.9 mg, 0.32 mmol) in CS$_2$ (1 mL) was added AlCl$_3$ (297 mg, 2.23 mmol). The mixture was stirred at 50° C. for 4 h at which point the reaction mixture was concentrated in vacuo then quenched with MeOH (30 mL) and concentrated again. The residue was purified by preparative HPLC (column: Phenomenex Luna C18 (75*30 mm*3 μm); mobile phase: [water (formic acid)-ACN]; B: 1-30%, 8 min) to afford 3-(2-(diethylamino)ethyl)-1H-indazol-4-ol as a formate salt (12.2 mg, 16%) which was a colourless oil. $^1$H NMR (400 MHz, MeOD-d$_4$): δ). 8.55 (br s, 1H), 7.18 (t, J=7.6 Hz, 1H), 6.93 (d, J=8.4 Hz, 1H), 6.43 (d, J=7.6 Hz, 1H), 3.56-3.58 (m, 2H), 3.48-3.50 (m, 2H), 3.27-3.32 (m, 4H), 1.36 (t, J=7.2 Hz, 6H). LCMS (ESI+): m/z 234.1 [M+H]$^+$. HPLC Purity (220 nm): 95.6%.

354
Example 38a: 2-(1H-indazol-3-yl)-N,N-dipropyl-ethan-1-amine (P-45)

Step 1: 2-(4-methoxy-1H-indazol-3-yl)-N,N-dipropylethan-1-amine (P-44)

To a solution of 2-(4-methoxy-1H-indazol-3-yl)ethan-1-amine (200 mg, 1.05 mmol) and propanal (151 mg, 2.60 mmol) in MeOH (2 mL) at 0° C. was added AcOH (251 mg, 4.18 mmol) and NaBH$_3$CN (164 mg, 2.61 mmol) and the mixture was stirred at 20° C. for 3 h. The reaction mixture was then concentrated in vacuo and the residue was purified by preparative HPLC (column: Phenomenex Luna C18 (75*30 mm*3 μm); mobile phase: [water (formic acid)-ACN]; B: 1-30%, 8 min) to give the formate salt of 2-(4-methoxy-1H-indazol-3-yl)-N,N-dipropylethan-1-amine (20.0 mg, 5% over 2 steps) as a colourless oil. $^1$H NMR (400 MHz, CDCl$_3$): δ 8.62 (s, 1H), 7.26 (t, J=8.0 Hz, 1H), 7.03 (d, J=8.4 Hz, 1H), 6.43 (d, J=7.6 Hz, 1H), 3.94 (s, 3H), 3.34-3.40 (m, 4H), 2.93-2.97 (m, 4H), 1.72-1.80 (m, 4H), 0.96 (t, J=7.2 Hz, 6H). LCMS (ESI+): m/z 276.2 [M+H]$^+$. HPLC Purity (220 nm): 96.4%.

Step 2: 3-(2-(dipropylamino)ethyl)-1H-indazol-4-ol (P-45)

To a solution of 2-(4-methoxy-1H-indazol-3-yl)-N,N-dipropylethan-1-amine (110 mg, 0.40 mmol) in CS$_2$ (22 mL) was added AlCl$_3$ (799 mg, 5.99 mmol) and the mixture was stirred at 50° C. under N2 for 2 h. The reaction mixture was concentrated in vacuo and then quenched with MeOH (30 mL) and concentrated again. The residue was purified by preparative HPLC (column: Phenomenex Luna C18 (75*30 mm*3 μm); mobile phase: [water (formic acid)-ACN]; B: 1-30%, 8 min) to afford the formate salt of 3-(2-(dipropylamino)ethyl)-1H-indazol-4-ol (21.3 mg, 20%) which was a white solid. $^1$H NMR (400 MHz, CDCl$_3$): δ 7.23 (t, J=7.6 Hz, 1H), 6.87 (d, J=8.4 Hz, 1H), 6.52 (d, J=7.6 Hz, 1H), 3.22-3.24 (m, 2H), 2.90-2.93 (m, 2H), 2.55-2.59 (m, 4H), 1.51-1.57 (m, 4H), 0.86 (t, J=7.2 Hz, 6H). LCMS (ESI+): m/z 262.2 [M+H]$^+$. HPLC Purity (220 nm): 97.0%.

Example 39a: 3-(2-(diisopropylamino)ethyl)-1H-indazol-4-ol (P-47)

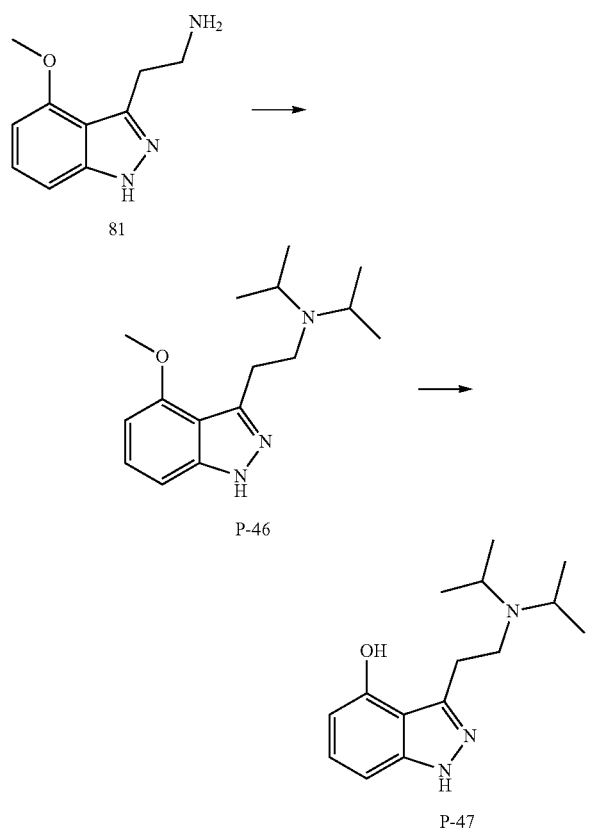

Step 1: N-isopropyl-N-(2-(4-methoxy-1H-indazol-3-yl)ethyl)propan-2-amine (P-46)

To a solution of 2-(4-methoxy-1H-indazol-3-yl)ethan-1-amine (300 mg, 1.57 mmol) in DCE (2 mL) was added NaBH(OAc)$_3$ (1.20 g, 5.66 mmol) and acetone (227 mg, 3.91 mmol) and the mixture was stirred at 25° C. for 48 h. and the reaction mixture was concentrated in vacuo, then diluted with H$_2$O (15 mL) and extracted with CH$_2$Cl$_2$ (30 mL×3). The combined organic layers were washed with brine (20 mL), dried over anhydrous Na$_2$SO$_4$ and concentrated in vacuo. The residue was purified by preparative HPLC (column: Phenomenex C18 (75*30 mm*3 μm); mobile phase: [water (formic acid)-ACN]; B: 1-5%, 8 min) to give the formate salt of N-isopropyl-N-(2-(4-methoxy-1H-indazol-3-yl)ethyl)propan-2-amine (17.6 mg, 3% over 2 steps) which was a white solid. $^1$H NMR (400 MHz, CDCl$_3$): δ 8.70 (s, 1H), 7.24-7.26 (m, 1H), 7.30 (d, J=8.4 Hz, 1H), 6.43 (d, J=7.6 Hz, 1H), 3.94 (s, 3H), 3.62-3.67 (m, 2H), 3.50-3.54 (m, 2H), 3.21-3.26 (m, 2H), 1.40 (d, J=6.4 Hz, 12H). LCMS (ESI+): m/z 276.2 [M+H]$^+$. HPLC Purity (220 nm): 96.0%.

Step 2: 3-(2-(diisopropylamino)ethyl)-1H-indazol-4-ol (P-47)

To a solution of N-isopropyl-N-(2-(4-methoxy-1H-indazol-3-yl)ethyl)propan-2-amine (50.0 mg, 0.18 mmol) in CS$_2$ (1 mL) was added AlCl$_3$ (169 mg, 1.27 mmol) and the mixture was stirred at 50° C. for 4 h The reaction mixture was concentrated in vacuo and then quenched with MeOH (30 mL) and concentrated again. The residue was purified by preparative HPLC (column: Waters Xbridge Prep OBD C18 (150*40 mm*10 μm); mobile phase: [water (NH$_4$HCO$_3$)-ACN]; B: 10-55%, 8 min) to afford 3-(2-(diisopropylamino)ethyl)-1H-indazol-4-ol (14 mg, 34%) as a brown solid. $^1$H NMR (400 MHz, D$_2$O): δ 7.23-7.27 (m, 1H), 6.89 (d, J=8.4 Hz, 1H), 6.38 (d, J=7.6 Hz, 1H), 3.65-3.72 (m, 2H), 3.42 (s, 4H), 1.26 (d, J=6.8 Hz, 6H). LCMS (ESI+): m/z 262.2 [M+H]$^+$. HPLC Purity (220 nm): 96.6%.

Scheme 13: Compounds of general formula (I) can be synthesised from the appropriately substituted indazole following the outlined sequence of steps in Scheme 13 or similar as one skilled in the art may consider. Under nitrosation conditions, indoles readily convert to indazoles such as intermediate 24, subsequent Henry reaction with nitromethane provides access to nitroalkene 25. Reduction of the nitroalkene gives rise to the alkylamine 26, subsequent reductive alkylation provides compounds of general structure (1), exemplified by P-8. It is not outside the scope of this application that one skilled in the art could protect the amine with a suitable protecting group such as a benzyl or carbamate, subject the protected amine to alkylation with an electrophile followed by subsequent deprotection to give rise to a secondary amine, which then can be subjected to a second alkylation with a different electrophile to give rise to compounds of general structure (1), by which the alkylamine contains alkyl groups that are dissimilar (general structure (1)). Suitable protecting groups are described in Wuts, P. G. M. and Greene, T. W. 'Greene's Protective Groups in Organic Synthesis' (4$^{th}$ Ed.) 2006, John Wiley & Sons, Inc., Hoboken, new Jersey, USA.

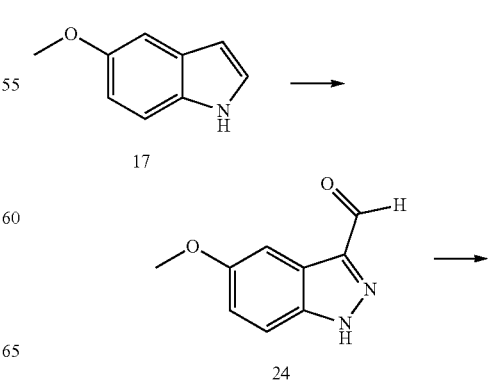

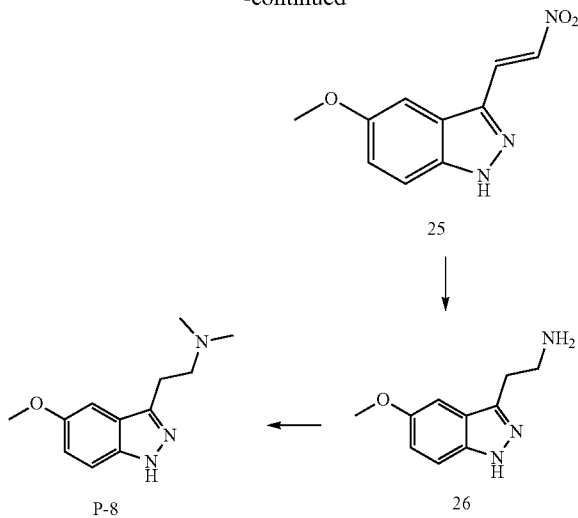

Example 41a: 2-(5-methoxy-1H-indazol-3-yl)-N,N-dimethylethan-1-amine (P-8)

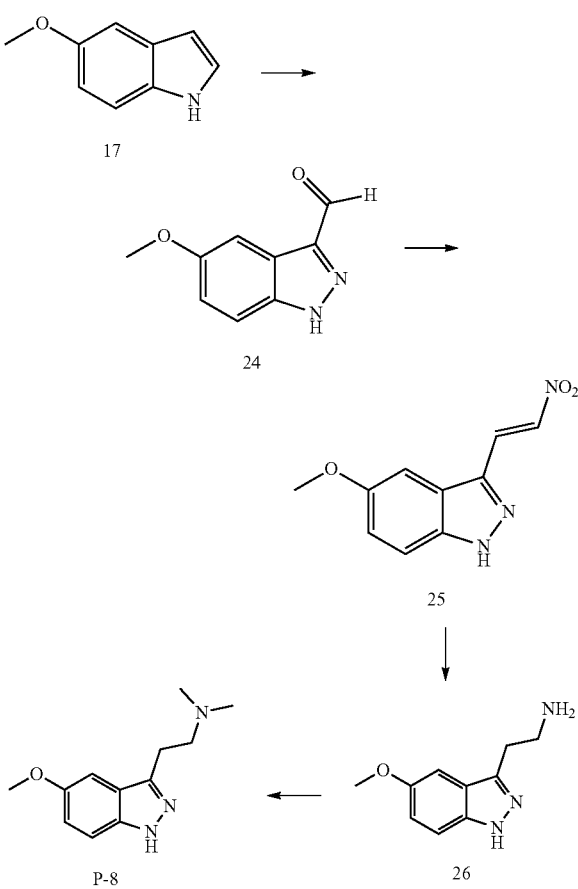

Step 1: 5-methoxy-1H-indazole-3-carbaldehyde (24)

To a solution of starting 5-methoxy-1H-indole (4.00 g, 27.1 mmol) in H$_2$O (20 mL) and THF (7 mL) was added NaNO$_2$ (9.38 g, 135 mmol) and 1 M aqueous HCl (135 mL). The mixture was stirred at 25° C. for 12 h. The reaction mixture was extracted with EtOAc (20 mL×3). The combined organic layers were dried over Na$_2$SO$_4$, filtered, and the filtrate concentrated in vacuo. The residue was triturated with CH$_2$Cl$_2$:petroleum ether (v/v 5:1) at 20° C. for 20 min to give 5-methoxy-1H-indazole-3-carbaldehyde (5.70 g) as an off-white solid that was used immediately in the next step. LCMS (ESI+): m/z 177.1 [M+H]$^+$.

Step 2: (E)-5-methoxy-3-(2-nitrovinyl)-1H-indazole (25)

To a solution of 5-methoxy-1H-indazole-3-carbaldehyde (4.50 g, 25.5 mmol) was added NH$_4$OAc (393 mg, 5.11 mmol) and nitromethane (71 mL). The mixture was stirred at 60° C. for 16 h. The reaction mixture was concentrated in vacuo, the residue was diluted with H$_2$O (20 mL), and then extracted with EtOAc (20 mL×3). The combined organic layers were dried over Na$_2$SO$_4$, filtered, and the filtrate concentrated in vacuo to give (E)-5-methoxy-3-(2-nitrovinyl)-1H-indazole (4.00 g) as a brown solid which was used immediately in the next step.

Step 3: 2-(5-methoxy-1H-indazol-3-yl)ethan-1-amine (26)

To a suspension of LiAlH$_4$ (2.08 g, 54.7 mmol) in THF (20 mL) was added (E)-5-methoxy-3-(2-nitrovinyl)-1H-indazole (2.00 g, 9.12 mmol) in THF (10 mL) at 0° C. The mixture was then stirred at 25° C. for 20 h before being cooled to 0° C. and quenched by dropwise addition H$_2$O (20 mL). The mixture was then extracted with EtOAc (20 mL×3) and the combined organics washed with brine (1×50 mL) before being dried Na$_2$SO$_4$, filtered, and the filtrate concentrated in vacuo to give 2-(5-methoxy-1H-indazol-3-yl)ethan-1-amine (1.40 g, crude) as a white solid that was subjected to alkylation conditions below. LCMS (ESI+): m/z 192.0 [M+H]$^+$.

Step 4: 2-(5-methoxy-1H-indazol-3-yl)-N,N-dimethylethan-1-amine (P-8)

To an ice cold solution of crude 2-(5-methoxy-1H-indazol-3-yl)ethan-1-amine (2.00 g) in MeOH (10 mL) was added AcOH (2.51 g, 41.8 mmol) to adjust the pH to 4, followed by the addition of NaBH$_3$CN (1.31 g, 20.9 mmol) and 37% w/w aqueous formaldehyde (2.12 g, 26.1 mmol). The mixture was stirred at 20° C. for 1 h before being concentrated in vacuo and the residue generated was purified by preparative HPLC (column: Phenomenex C18 80*40 mm*3 µm; mobile phase: [water (formic acid)-ACN]; B: 5-35%, 8 min). The collected material was further purified by preparative HPLC (column: Phenomenex Luna C18 200*40 mm*10 µm; mobile phase: [water (formic acid)-ACN]; B: 1-20%, 8 min) to give the formate salt of 2-(5-methoxy-1H-indazol-3-yl)-N,N-dimethylethan-1-amine as a white solid (134 mg). $^1$H NMR (400 MHz, DMSO-d$_6$): δ 8.24 (s, 1H), 7.36 (d, J=8.8 Hz, 1H), 7.14 (d, J=2.4 Hz, 1H), 6.97 (dd, J=8.8, 2.4 Hz, 1H), 3.80 (s, 3H), 3.00-3.09 (m, 2H), 2.74-2.83 (m, 2H), 2.32 (s, 6H). LCMS (ESI+): m/z 220.1 [M+H]$^+$. HPLC Purity (220 nm): 97.9%.

Step 4a: 2-(5-methoxy-1H-indazol-3-yl)-N,N-dimethylethan-1-amine bis-hydrochloride (P-8.2HCl)

To an ice cold (0° C.) solution of 2-(5-methoxy-1H-indazol-3-yl)-N,N-dimethylethan-1-amine (100 mg, 0.45 mmol) in anhydrous Et$_2$O (5 mL) and abs. EtOH (1 mL) was added 2 M HCl in Et$_2$O dropwise over 10 min until the pH of the reaction solution was acidic. The resulting precipitate was collected by filtration and dried overnight in a vacuum desiccator to afford 2-(5-methoxy-1H-indazol-3-yl)-N,N-dimethylethan-1-amine as the dihydrochloride salt (78 mg, 59%) which was a white solid. $^1$H NMR (400 MHz, DMSO-d$_6$): δ 10.83 (s, 1H), 7.44-7.36 (m, 1H), 7.28 (d, J=2.0 Hz, 1H), 7.01 (dd, J=9.0, 2.4 Hz, 1H), 3.81 (s, 3H), 3.55-3.28 (m, 4H), 2.84 (d, J=4.8 Hz, 6H). qNMR Purity (ERETIC): 98.8%.

Scheme 14: Compounds of general formula (I) can be synthesised from the appropriately substituted formyl-aza-indole following the outlined sequence of steps in Scheme 14 or similar as one skilled in the art may consider. Addition of SEM protecting group to formyl-aza-indole starting material 24 allows access to intermediate 82. Reaction of intermediate 82 with nitromethane yields intermediate 83 which can be converted to the nitrostyrene 84. Chemoselective reduction with LiAlH$_4$ allows access to the primary amine 85 which permits tertiary amine synthesis using an appropriate aldehyde and reducing agent affording intermediate 86. Final removal of the SEM protecting group provides compounds of general formula (I) (exemplified by P-48). One skilled in the art will recognise that utilising different aldehydes would allow access to compounds of general formula (I) disclosed herein.

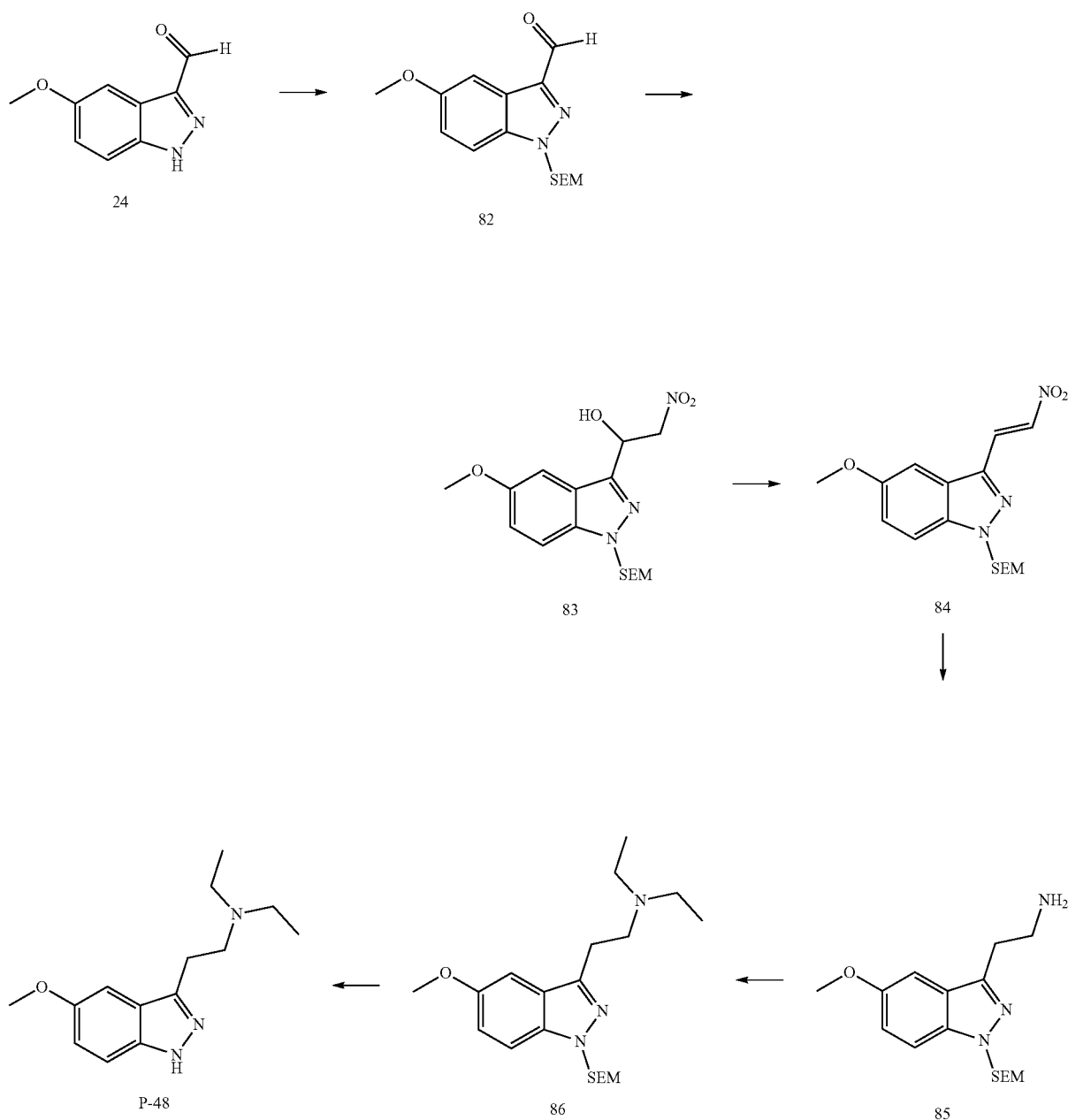

Example 42a: N,N-diethyl-2-(5-methoxy-1H-indazol-3-yl)ethan-1-amine (P-48)

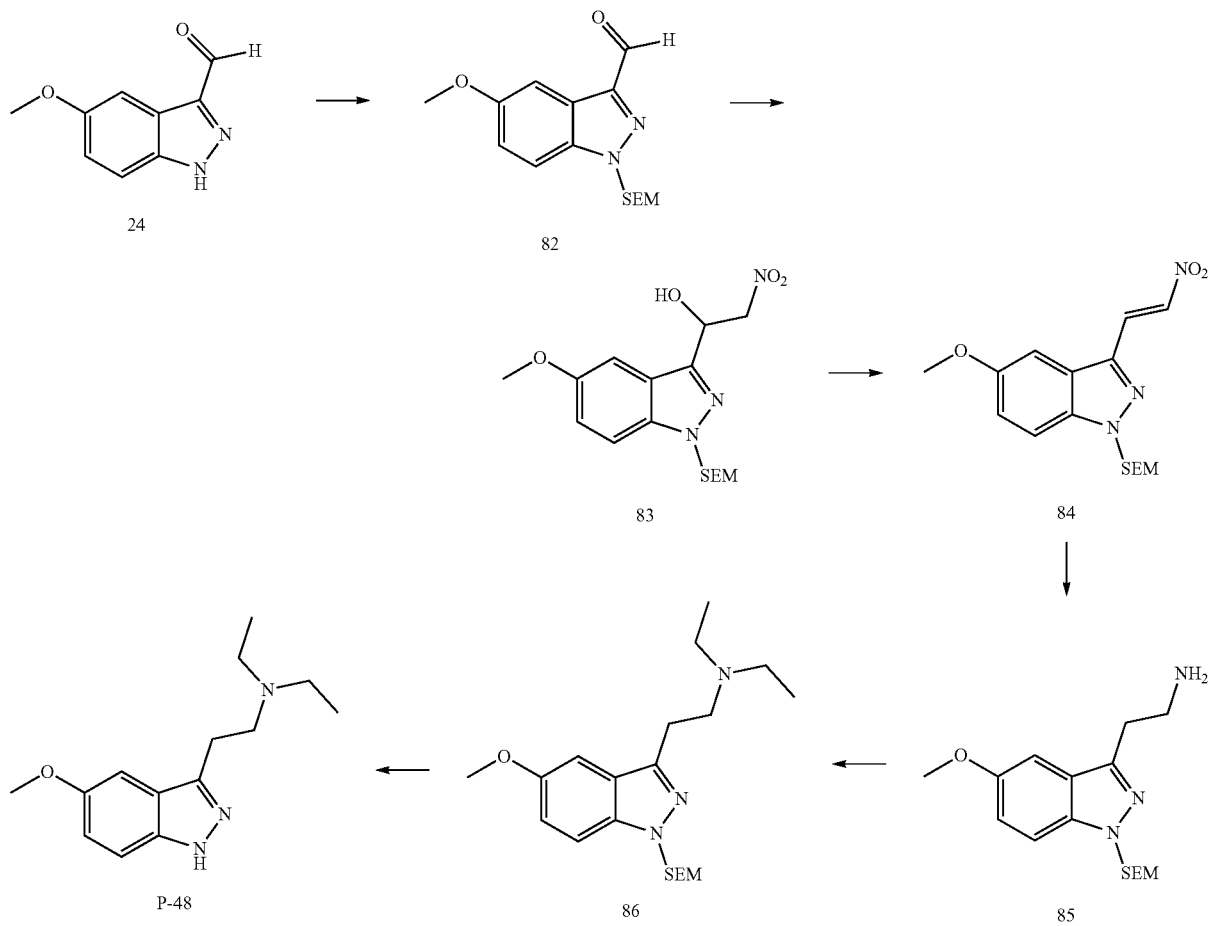

Step 1: 5-methoxy-1-((2-(trimethylsilyl)ethoxy)methyl)-1H-indazole-3-carbaldehyde (82)

To a solution of 5-methoxy-1H-indazole-3-carbaldehyde (15.0 g, 85.2 mmol) and DIPEA (17.6 g, 136.2 mmol) in DMF (150 mL) was added (2-(chloromethoxy)ethyl)trimethylsilane (17.0 g, 102.0 mmol) and the mixture was stirred at ambient temperature for 2 h. The reaction mixture was quenched with $H_2O$ (300 mL) and then extracted with EtOAc (150×3 mL). The combined organics were filtered, dried over $Na_2SO_4$, filtered, and the filtrate concentrated in vacuo. The residue was purified by column chromatography (EtOAc in Petroleum ether, 2-5% v/v) to provide 5-methoxy-1-((2-(trimethylsilyl)ethoxy)methyl)-1H-indazole-3-carbaldehyde (11.4 g, 44%) as a yellow solid. $^1$H NMR (300 MHz, $CDCl_3$): δ $^1$H NMR (300 MHz, $CDCl_3$) δ 10.23 (s, 1H), 7.65 (d, J=2.4 Hz, 1H), 7.53 (d, J=9.3 Hz, 1H), 7.15 (dd, J=9.1, 2.4 Hz, 1H), 5.78 (s, 2H), 3.90 (s, 3H), 3.56 (t, J=8.2 Hz, 2H), 0.89 (t, J=8.2 Hz, 2H), −0.07 (s, 9H).

Step 2: 1-(5-methoxy-1-((2-(trimethylsilyl)ethoxy)methyl)-1H-indazol-3-yl)-2-nitroethan-1-ol (83)

To a solution of 5-methoxy-1-((2-(trimethylsilyl)ethoxy)methyl)-1H-indazole-3-carbaldehyde (8.60 g, 28.1 mmol) and KOtBu (915 mg, 8.15 mmol) in tBuOH (50 mL) and 1,4-dioxane (50 mL) was added nitromethane (4.98 g, 81.6 mmol) and the mixture was stirred at ambient temperature for 5 h. The reaction was quenched with $H_2O$ (200 mL) and then extracted with EtOAc (100 mL×3). The combined organic layers were washed with brine (150 mL×2), dried over $Na_2SO_4$, filtered, and the filtrate concentrated in vacuo to provide crude 1-(5-methoxy-1-((2-(trimethylsilyl)ethoxy)methyl)-1H-indazol-3-yl)-2-nitroethan-1-ol (11.4 g) as a yellow oil which was used in the subsequent step without further purification.

Step 3: (E)-5-methoxy-3-(2-nitrovinyl)-1-((2-(trimethylsilyl)ethoxy)methyl)-1H-indazole (84)

To a solution of crude 1-(5-methoxy-1-((2-(trimethylsilyl)ethoxy)methyl)-1H-indazol-3-yl)-2-nitroethan-1-ol (6.69 g) in $CH_2Cl_2$ (80 mL) was added N,N-dimethylpyridin-4-amine (100 mg, 0.82 mmol) followed by acetic anhydride (2.22 g, 21.7 mmol) and the mixture was stirred at ambient temperature for 1 h. The reaction was quenched with $H_2O$ (200 mL) and then extracted with $CH_2Cl_2$ (100 mL×3). The combined organics were washed with brine (100 mL×2), dried over $Na_2SO_4$, filtered, and the filtrate concentrated in vacuo. The residue was partially purified by flash chromatography (Petroleum ether/EtOAc, v/v, 50/1 to 20/1) to afford crude (E)-5-methoxy-3-(2-nitrovinyl)-1-((2-(trimethylsilyl)ethoxy)methyl)-1H-indazole (4.00 g) as a yellow solid which was used in the subsequent step without further purification.

Step 4: 2-(5-methoxy-1-((2-(trimethylsilyl)ethoxy)methyl)-1H-indazol-3-yl)ethan-1-amine (85)

To an ice cold solution of crude (E)-5-methoxy-3-(2-nitrovinyl)-1-((2-(trimethylsilyl)ethoxy)methyl)-1H-indazole (4.00 g) in anhydrous THF (150 mL) was added LiAlH$_4$ (1.76 g, 46.4 mmol) portionwise and stirring continued at this temperature for 1 h. The reaction was quenched by sequential addition of H$_2$O (1.76 mL), NaOH (1.76 mL, 15% aq. soln.), H$_2$O (5.28 mL) and filtered through a pad of celite. The filtrate was concentrated in vacuo and the residue was partially purified by flash chromatography (MeOH in EtOAc, 0% to 10% v/v) to provide 2-(5-methoxy-1-((2-(trimethylsilyl)ethoxy)methyl)-1H-indazol-3-yl)ethan-1-amine (1.32 g, 15% over 3 steps) as a yellow oil. $^1$H NMR (300 MHz, CDCl$_3$) δ 7.37 (d, J=9.0 Hz, 2H), 7.06 (dd, J=9.0, 2.2 Hz, 2H), 6.99 (d, J=2.3 Hz, 2H), 5.59 (s, 2H), 3.83 (s, 3H), 3.51 (m, 4H), 3.37 (t, J=6.4 Hz, 2H), 0.81-0.92 (m, 2H), −0.08 (s, 9H). LCMS (ESI+): m/z 322.2 [M+H]$^+$.

Step 5: N,N-diethyl-2-(5-methoxy-1-((2-(trimethylsilyl)ethoxy)methyl)-1H-indazol-3-yl)ethan-1-amine (86)

To a solution of 2-(5-methoxy-1-((2-(trimethylsilyl)ethoxy)methyl)-1H-indazol-3-yl)ethan-1-amine (150 mg, 0.47 mmol), DIPEA (242 mg, 1.87 mmol) and acetaldehyde (62.0 mg, 1.41 mmol) in CH$_2$Cl$_2$ (10 mL) was added NaBH(OAc)$_3$ (549 mg, 2.59 mmol) in portions which was then stirred at ambient temperature for 16 h. The reaction was quenched with H$_2$O (50 mL) and then extracted with CH$_2$Cl$_2$ (20 mL×3). The combined organics were washed with brine (20 mL×2), dried over Na$_2$SO$_4$, filtered, and the filtrate concentrated in vacuo. The residue was partially purified by preparative thin layer chromatography (CH$_2$Cl$_2$: MeOH, 10:1, v/v) to afford crude N,N-diethyl-2-(5-methoxy-1-((2-(trimethylsilyl)ethoxy)methyl)-1H-indazol-3-yl)ethan-1-amine (137 mg) as a colourless oil which was used in the subsequent step without further purification. LCMS (ESI+): m/z 378.3 [M+H]$^+$.

Step 6: N,N-diethyl-2-(5-methoxy-1H-indazol-3-yl)ethan-1-amine (P-48)

To a solution of crude N,N-diethyl-2-(5-methoxy-1-((2-(trimethylsilyl)ethoxy)methyl)-1H-indazol-3-yl)ethan-1-amine (160 mg) in CH$_2$Cl$_2$ (5 mL) was added TFA (10 mL) which was then stirred at ambient temperature for 1 h. The reaction was then quenched with saturated aqueous Na$_2$CO$_3$ solution (30 mL) and then extracted with CH$_2$Cl$_2$ (15 mL×3). The combined organic layers were washed with brine (20 mL×2), dried over Na$_2$SO$_4$, filtered, and the filtrate concentrated in vacuo. The residue was dissolved in MeOH (5 mL) before addition of aqueous NH$_3$ (10 mL) and was then stirred at 50° C. for 1 h. The reaction was concentrated in vacuo and the residue was purified by preparative thin layer chromatography (CH$_2$Cl$_2$:MeOH, 10:1, v/v) to obtain crude N,N-diethyl-2-(5-methoxy-1H-indazol-3-yl)ethan-1-amine (21.0 mg) as a colourless oil which was used in the subsequent step without further purification. LCMS (ESI+): m/z 248.3 [M+H]$^+$.

Step 7: N,N-diethyl-2-(5-methoxy-1H-indazol-3-yl)ethan-1-amine bis-hydrochloride (P-48.2HCl)

To a solution of crude N,N-diethyl-2-(5-methoxy-1H-indazol-3-yl)ethan-1-amine (21 mg) in MeOH (0.5 mL) was added HCl (4 M in Et$_2$O) until the reaction solution was acidic. Stirring was continued at ambient temperature for 30 min. The reaction was concentrated in vacuo and the solid residue was triturated with Et$_2$O to afford N,N-diethyl-2-(5-methoxy-1H-indazol-3-yl)ethan-1-amine as the dihydrochloride salt (18.4 mg, 12% over 3 steps) which was an off-white solid. $^1$H NMR (300 MHz, MeOD-d$_4$): δ 7.44 (d, J=9.0 Hz, 1H), 7.21 (s, 1H), 7.12 (d, J=9.0 Hz, 1H), 3.87 (s, 3H), 3.64 (t, J=7.2 Hz, 2H), 3.33-3.48 (m, 6H), 1.37 (t, J=7.2 Hz, 6H). LCMS (ESI+): m/z 248.2 [M+H]$^+$. HPLC Purity (254 nm): 97.5%.

Example 43a: N,N-dipropyl-2-(5-methoxy-1H-indazol-3-yl)ethan-1-amine (P-49)

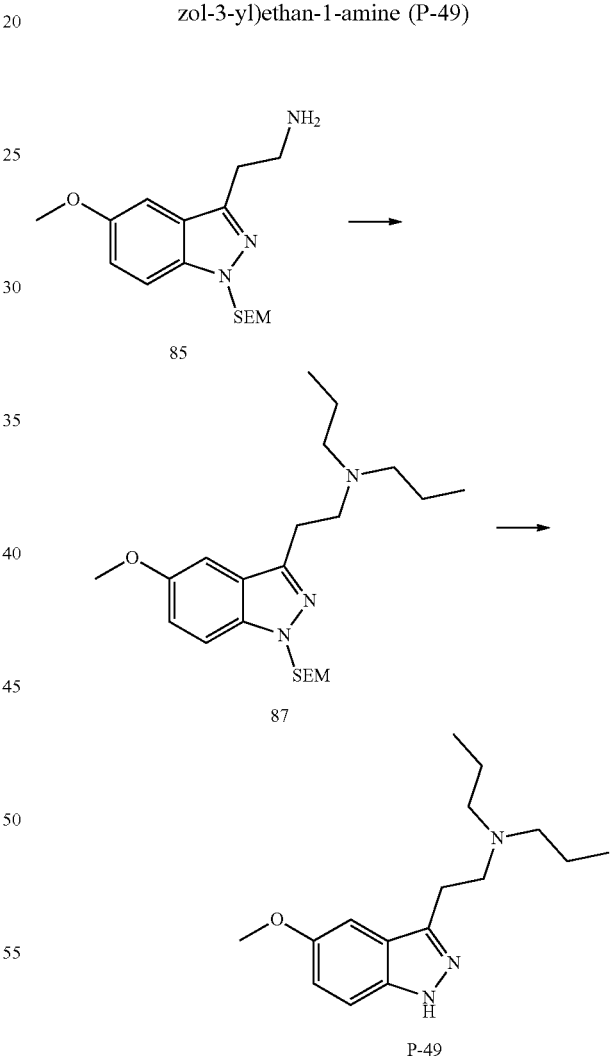

Step 1: N-(2-(5-methoxy-1-((2-(trimethylsilyl)ethoxy)methyl)-1H-indazol-3-yl)ethyl)-N-propylpropan-1-amine (87)

To a solution of 2-(5-methoxy-1-((2-(trimethylsilyl)ethoxy)methyl)-1H-indazol-3-yl)ethan-1-amine (150 mg, 0.47 mmol), DIPEA (242 mg, 1.87 mmol) and propanal (68.0 mg, 1.17 mmol) in $CH_2Cl_2$ (10 mL) was added $NaBH(OAc)_3$ (594 mg, 2.80 mmol) in portions and the reaction mixture was stirred at ambient temperature for 16 h. The reaction was quenched with $H_2O$ (50 mL) and then extracted with $CH_2Cl_2$ (20 mL×3). The combined organic layers were washed with brine (20 mL×2), dried over $Na_2SO_4$, filtered, and the filtrate concentrated under reduced pressure. The residue was purified by preparative thin layer chromatography ($CH_2Cl_2$:MeOH, 20:1, v/v) to afford crude N-(2-(5-methoxy-1-((2-(trimethylsilyl)ethoxy)methyl)-1H-indazol-3-yl)ethyl)-N-propylpropan-1-amine (120 mg) as a light yellow oil which was used in the subsequent step without further purification. LCMS (ESI+): m/z 406.3 $[M+H]^+$.

Step 2: N,N-dipropyl-2-(5-methoxy-1H-indazol-3-yl)ethan-1-amine (P-49)

To a solution of crude N-(2-(5-methoxy-1-((2-(trimethylsilyl)ethoxy)methyl)-1H-indazol-3-yl)ethyl)-N-propylpropan-1-amine (120 mg) in $CH_2Cl_2$ (5 mL) was added TFA (10 mL) and the reaction mixture was stirred at ambient temperature for 1 h. The reaction mixture was quenched with saturated aqueous $Na_2CO_3$ solution (30 mL) and extracted with $CH_2Cl_2$ (15 mL×3). The combined organic layer was washed with brine (20 mL×2), dried over $Na_2SO_4$, filtered, and the filtrate concentrated under reduced pressure. The residue obtained was dissolved in MeOH (5 mL) stirred at 50° C. for 1 h after addition of aqueous $NH_3$ solution (10 mL). The mixture was concentrated under reduced pressure and the residue was purified by preparative thin layer chromatography ($CH_2Cl_2$:MeOH, 10:1, v/v) to afford crude N,N-dipropyl-2-(5-methoxy-1H-indazol-3-yl)ethan-1-amine (24.0 mg) as a colourless oil which was used in the subsequent step without further purification. LCMS (ESI+): m/z 276.2 $[M+H]^+$.

Step 3: N,N-dipropyl-2-(5-methoxy-1H-indazol-3-yl)ethan-1-amine bis-hydrochloride (P-49.2HCl)

Crude N,N-dipropyl-2-(5-methoxy-1H-indazol-3-yl)ethan-1-amine (24.0 mg) was dissolved in MeOH (0.5 mL) and then added to solution of 2 M HCl in $Et_2O$ (2 mL) at ambient temperature. The mixture was stirred at ambient temperature for 30 min and then concentrated under reduced pressure. The solid residue was washed with $Et_2O$ to provide N,N-dipropyl-2-(5-methoxy-1H-indazol-3-yl)ethan-1-amine as the dihydrochloride salt (27.0 mg, 17% over 3 steps) as an off-white solid. $^1$H NMR (300 MHz, MeOD-$d_4$): δ 7.42 (d, J=9.1 Hz, 1H), 7.19 (d, J=2.2 Hz, 1H), 7.10 (dd, J=9.0, 2.2 Hz, 1H), 3.85 (s, 3H), 3.64 (t, J=7.3 Hz, 2H), 3.43 (t, J=7.4f Hz, 2H), 3.19-3.25 (m, 4H), 1.78 (sext, J=8.0 Hz, 4H), 1.01 (t, J=7.3 Hz, 6H). LCMS (ESI+): m/z 276.4 $[M+H]^+$. HPLC Purity (254 nm): 95.4%.

Example 45a: N-ethyl-2-(5-methoxy-1H-indazol-3-yl)-N-methylethan-1-amine (P-51)

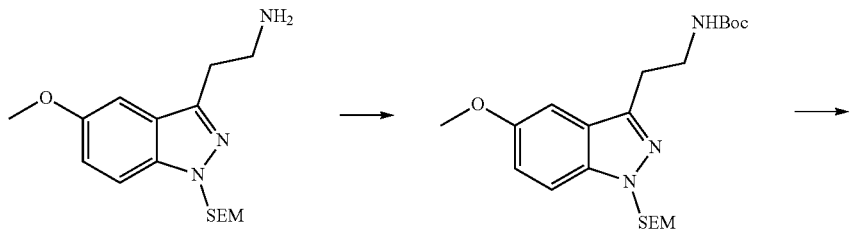

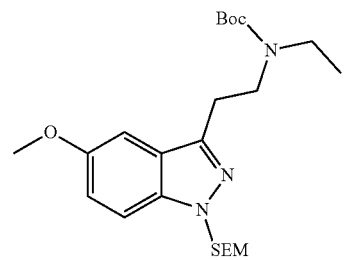

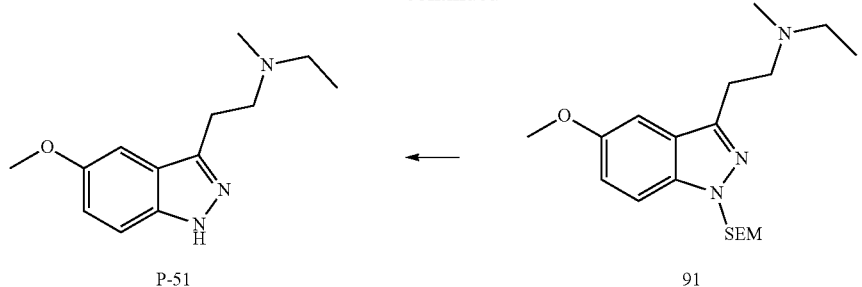

P-51 ← 91

Step 1: tert-butyl (2-(5-methoxy-1-((2-(trimethylsilyl)ethoxy)methyl)-1H-indazol-3-yl)ethyl)carbamate (89)

To a solution of 2-(5-methoxy-1-((2-(trimethylsilyl)ethoxy)methyl)-1H-indazol-3-yl)ethan-1-amine (200 mg, 0.62 mmol) and Et$_3$N (126 mg, 1.25 mmol) in THF (20 mL) was added di-tert-butyl dicarbonate (204 mg, 0.94 mmol) and the mixture was stirred at ambient temperature for 2 h. The reaction was quenched with H$_2$O (50 mL) and then extracted with EtOAc (20 mL×3). The combined organics were washed with brine (30 mL×2), dried over anhydrous Na$_2$SO$_4$, filtered, and the filtrate concentrated under reduced pressure. The crude product was purified by flash chromatography (SiO$_2$, petroleum ether:EtOAc, v/v, 10:1 to 4:1) to obtain crude tert-butyl (2-(5-methoxy-1-((2-(trimethylsilyl)ethoxy)methyl)-1H-indazol-3-yl)ethyl)carbamate (197 mg) as a light yellow oil which was used in the subsequent step without further purification. LCMS (ESI+): m/z 422.2 [M+H]$^+$.

Step 2: tert-butyl ethyl(2-(5-methoxy-1-((2-(trimethylsilyl)ethoxy)methyl)-1H-indazol-3-yl)ethyl)carbamate (90)

To a solution of crude tert-butyl (2-(5-methoxy-1-((2-(trimethylsilyl)ethoxy)methyl)-1H-indazol-3-yl)ethyl)carbamate (197 mg) dissolved in DMF (8 mL), was added sodium hydride (23.0 mg, 0.96 mmol) at 0° C. The reaction mixture was stirred at 0° C. for 30 min and then iodoethane (88.0 mg, 0.56 mmol) was added and the mixture was stirred for another 2 h. The reaction mixture was quenched with saturated aq. NH$_4$Cl (20 mL) solution and then extracted with EtOAc (20 mL×3). The combined organic layers were washed with brine (20 mL×2), dried over Na$_2$SO$_4$, filtered, and the filtrate concentrated under reduced pressure. The crude product was purified by flash chromatography (SiO$_2$, petroleum ether:EtOAc, v/v, 10:1 to 4:1) to provide tert-butyl ethyl(2-(5-methoxy-1-((2-(trimethylsilyl)ethoxy)methyl)-1H-indazol-3-yl)ethyl)carbamate (160 mg) as a light yellow oil which was used in the subsequent step without further purification. LCMS (ESI+): m/z 450.4 [M+H]$^+$.

Step 3: N-ethyl-2-(5-methoxy-1-((2-(trimethylsilyl)ethoxy)methyl)-1H-indazol-3-yl)-N-methylethan-1-amine (91)

To a solution of crude tert-butyl ethyl(2-(5-methoxy-1-((2-(trimethylsilyl)ethoxy)methyl)-1H-indazol-3-yl)ethyl)carbamate (160 mg) in THF (10 mL) was added LiAlH$_4$ (41.0 mg, 1.08 mmol) at ambient temperature and the mixture was stirred at 50° C. for 3 h. The reaction was quenched with saturated NH$_4$Cl solution (20 mL) and extracted with EtOAc (20 mL×3). The combined organics were washed with brine (20 mL), dried over Na$_2$SO$_4$, filtered, and the filtrate concentrated under reduced pressure. The crude product was purified by flash chromatography (SiO$_2$, CH$_2$Cl$_2$:MeOH, v/v, 50:1 to 20:1) to give N-ethyl-2-(5-methoxy-1-((2-(trimethylsilyl)ethoxy)methyl)-1H-indazol-3-yl)-N-methylethan-1-amine (102 mg) as a light yellow oil which was used in the subsequent step without further purification. LCMS (ESI+): m/z 364.3 [M+H]$^+$.

Step 4: N-ethyl-2-(5-methoxy-1H-indazol-3-yl)-N-methylethan-1-amine (P-51)

To a solution of crude N-ethyl-2-(5-methoxy-1-((2-(trimethylsilyl)ethoxy)methyl)-1H-indazol-3-yl)-N-methylethan-1-amine (155 mg, 426 μmol) in THF (6 mL) at 0° C. was added 37% aqeuous HCl (3 mL) and the reaction mixture was stirred at ambient temperature overnight. The reaction was quenched with saturated NaHCO$_3$ (30 mL) and then extracted with EtOAc (20 mL×3). The combined organics were washed with brine (20 mL×2), dried over Na$_2$SO$_4$, filtered, and the filtrate concentrated under reduced pressure. The residue was then purified by preparative thin layer chromatography (CH$_2$Cl$_2$:MeOH:NH$_3$(aq.), 100:10:1) to provide N-ethyl-2-(5-methoxy-1H-indazol-3-yl)-N-methylethan-1-amine (40.6 mg, 28% over 4 steps) as a white solid. $^1$H NMR (300 MHz, MeOD-d$_4$): δ 7.35 (d, J=9.1 Hz, 1H), 7.10 (d, J=2.0 Hz, 1H), 7.02 (dd, J=9.0, 2.2 Hz, 1H), 3.83 (s, 3H), 3.10-3.16 (m, 2H), 2.82-2.88 (m, 2H), 2.61 (q, J=7.3 Hz, 2H), 2.38 (s, 3H), 1.12 (t, J=7.2 Hz, 3H). LCMS (ESI+): m/z 234.3 [M+H]$^+$. HPLC Purity (254 nm): 99.8%.

Example 46a: N-(2-(5-methoxy-1H-indazol-3-yl)ethyl)-N-methylpropan-2-amine (P-52)

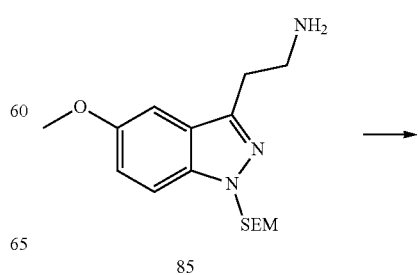

85

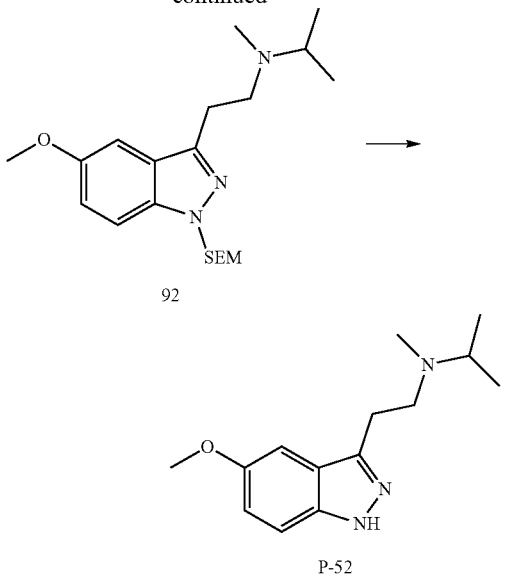

Step 1: N-(2-(5-methoxy-1-((2-(trimethylsilyl)ethoxy)methyl)-1H-indazol-3-yl)ethyl)-N-methylpropan-2-amine (92)

To a solution of 2-(5-methoxy-1-((2-(trimethylsilyl)ethoxy)methyl)-1H-indazol-3-yl)ethan-1-amine (100 mg, 0.31 mmol), acetone (36.1 mg, 0.62 mmol) and DIPEA (121 mg, 0.94 mmol) in CH$_2$Cl$_2$ (5 mL) was added NaBH(OAc)$_3$ (132 mg, 0.62 mmol) in portions and the mixture was stirred at ambient temperature for 16 h. To this was added formaldehyde (37% w/w aq. solution, 51.4 mg, 0.63 mmol) and NaBH(OAc)$_3$ (132 mg, 0.62 mmol) and the mixture was stirred for another 4 h at ambient temperature. The reaction was quenched with H$_2$O (30 mL) and extracted with CH$_2$Cl$_2$ (15 mL×3). The combined organics were dried over anhydrous Na$_2$SO$_4$ and concentrated under reduced pressure. The crude product was purified by preparative thin layer chromatography (CH$_2$Cl$_2$:MeOH, 10:1, v/v) to afford N-(2-(5-methoxy-1-((2-(trimethylsilyl)ethoxy)methyl)-1H-indazol-3-yl)ethyl)-N-methylpropan-2-amine (105 mg) as a yellow oil which was used in the subsequent step without further purification.

Step 2: N-(2-(5-methoxy-1H-indazol-3-yl)ethyl)-N-methylpropan-2-amine bis-hydrochloride (P-52.2HCl)

To a stirred solution of crude N-(2-(5-methoxy-1-((2-(trimethylsilyl)ethoxy)methyl)-1H-indazol-3-yl)ethyl)-N-methylpropan-2-amine (170 mg) in THF (6 mL) was added HCl (37% v/v aq. solution, 1.5 mL) and the reaction mixture was stirred at ambient temperature for 1 h. The reaction was concentrated under reduced pressure and the resulting residue was dissolved in MeOH (5 mL). To this was added aqueous NH$_3$ solution (10 mL) which was then stirred at ambient temperature for 2 h. The mixture was concentrated under reduced pressure and the residue subjected to preparative thin layer chromatography (CH$_2$Cl$_2$:MeOH, 10:1, v/v) to provide crude N-(2-(5-methoxy-1H-indazol-3-yl)ethyl)-N-methylpropan-2-amine (65.0 mg) as a white solid. The impure free base was dissolved in MeOH (1 mL) and added to a solution of 2 M HCl in Et$_2$O (1 mL) which was then stirred at ambient temperature for 30 min. After concentrating the mixture, the residue was purified by preparative HPLC (column: YMC-Pack ODS-A C18 (250*20 mm*5 μm); mobile phase: [water-MeOH]; B: 20-90% 40 min) to afford N-(2-(5-methoxy-1H-indazol-3-yl)ethyl)-N-methylpropan-2-amine as the dihydrochloride salt (20.0 mg, 20% over 2 steps). $^1$H NMR (300 MHz, MeOD-d$_4$): δ 7.41 (d, J=6.9 Hz, 1H), 7.21 (s, 1H), 7.07 (d, J=6.9 Hz, 1H), 3.86 (s, 3H), 3.75-3.85 (m, 1H), 3.38-3.50 (m, 3H), 2.89 (s, 3H), 1.39 (d, J=6.3 Hz, 6H). LCMS (ESI+): m/z 248.3 [M+H]$^+$. HPLC Purity (254 nm): 99.9%.

Example 75: Synthesis of 3-(2-(2-azabicyclo[3.1.0]hexan-2-yl)ethyl)-6-fluoro-5-methoxy-1-methyl-1H-indazole (A75)

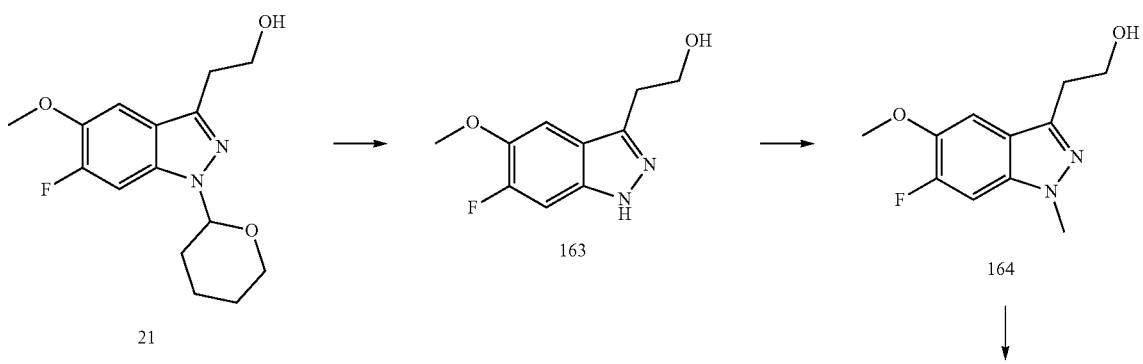

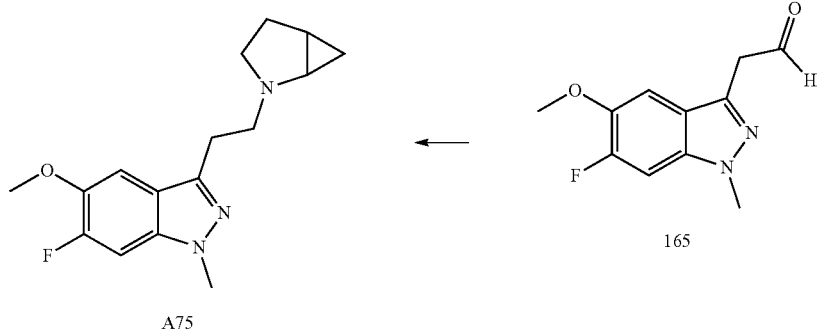

Step 1: 2-(6-fluoro-5-methoxy-1H-indazol-3-yl)ethan-1-ol (163)

An ice-cold solution of 2-(6-fluoro-5-methoxy-1-(tetrahydro-2H-pyran-2-yl)-1H-indazol-3-yl)ethan-1-ol (3.3 g, 11.2 mmol) in MeOH (33 mL) was treated with dropwise 37% aq. HCl (3.3 mL) and the reaction was stirred at reflux for 3 h. The reaction mixture was concentrated under a stream of nitrogen gas and the residue was diluted with saturated aq. $Na_2CO_3$ (50 mL) before being extracted with $CHCl_3$:IPA (3:1, 3×50 mL). The combined organic layer was dried over anhydrous $Na_2SO_4$, filtered, and the filtrate concentrated in vacuo. The residue was triturated in hot diethyl ether with a few drops of methanol and once cooled, the solid was collected by filtration under vacuum to afford the title compound as a white solid (1.05 g, 45%). $^1$H NMR (400 MHz, DMSO-$d_6$): δ 12.59 (s, 1H), 7.35 (d, J=8.2 Hz, 1H), 7.29 (d, J=11.2 Hz, 1H), 4.70 (t, J=5.3 Hz, 1H), 3.86 (s, 3H), 3.75 (td, J=7.2, 5.4 Hz, 2H), 3.03 (t, J=7.2 Hz, 2H). $^{13}$C NMR (101 MHz, DMSO-$d_6$): δ 152.5 (d, J=245.2 Hz), 142.8, 142.8 (d, J=13.9 Hz), 134.75 (d, J=11.0 Hz), 117.7, 102.1, 96.6 (d, J=23.0 Hz), 60.5, 56.2, 30.5.

Step 2: 2-(6-fluoro-5-methoxy-1-methyl-1H-indazol-3-yl)ethan-1-ol (164)

To an ice-cold solution of 2-(6-fluoro-5-methoxy-1H-indazol-3-yl)ethan-1-ol (1 g, 4.76 mmol) in anhydrous DMF (10 mL) was added sodium hydride (60% w/w, 190 mg, 4.76 mmol) and the resulting solution was stirred cold for 30 min before iodomethane (0.33 mL, 5.23 mmol) was added dropwise. The resulting solution was stirred cold for 30 min and then quenched with half saturated aq. $NH_4Cl$ (10 mL). The mixture was then extracted with EtOAc (5×30 mL) and the combined organic layer was washed with brine (3×50 mL). The combined brine layer was extracted once with EtOAc (20 mL) and then the EtOAc layers were combined and concentrated in vacuo. The residue was purified by flash chromatography (0.1% to 5% MeOH/$NH_3$ in DCM) to afford the title compound as a white solid (680 mg, 64%). $^1$H NMR (400 MHz, DMSO-$d_6$): δ 7.50 (d, J=11.5 Hz, 1H), 7.35 (d, J=8.3 Hz, 1H), 4.70 (t, J=5.4 Hz, 1H), 3.89 (s, 3H), 3.86 (s, 3H), 3.74 (td, J=7.1, 5.4 Hz, 2H), 3.01 (t, J=7.1 Hz, 2H). $^{13}$C NMR (101 MHz, DMSO-$d_6$): δ 152.5 (d, J=245.5 Hz), 142.9 (d, J=13.7 Hz), 141.7, 134.8 (d, J=11.5 Hz), 118.1, 102.2 (d, J=3.0 Hz), 96.4 (d, J=23.6 Hz), 60.5, 56.2, 35.2, 30.3. $^{19}$F NMR (376 MHz, DMSO-$d_6$): δ −132.9.

Step 3: 2-(6-fluoro-5-methoxy-1-methyl-1H-indazol-3-yl)acetaldehyde (165)

To a suspension of 2-(6-fluoro-5-methoxy-1-methyl-1H-indazol-3-yl)ethan-1-ol (215 mg, 0.96 mmol) in EtOAc (20 mL) was added Dess-Martin periodinane (488 mg, 1.15 mmol) and tBuOH (85 mg, 1.15 mmol) and the mixture was stirred at RT for 3 h. The reaction mixture was filtered through a pad of celite and the filtrate was washed with 0.5 M aq. $Na_2S_2O_3$ (2×40 mL), brine (20 mL) and then concentrated under reduced pressure to afford crude 2-(6-fluoro-5-methoxy-1-methyl-1H-indazol-3-yl)acetaldehyde (215 mg) as a yellow oil, which was used in the next step without further purification.

Step 4: 3-(2-(2-azabicyclo[3.1.0]hexan-2-yl)ethyl)-6-fluoro-5-methoxy-1-methyl-1H-indazole (A75)

A solution of crude 2-(6-fluoro-5-methoxy-1-methyl-1H-indazol-3-yl)acetaldehyde (215 mg) in MeOH (30 mL) at 0° C. was treated with 2-azabicyclo[3.1.0]hexane hydrochloride (138 mg, 1.15 mmol) and $NaCNBH_3$ (121 mg, 1.92 mmol) and the mixture was stirred at rt overnight. The reaction was quenched with 2 M aq. NaOH (5 mL) and then volatiles were removed under a stream of nitrogen gas. The remaining aqueous phase was extracted with $CH_2Cl_2$ (3×15 mL) and the combined organics were washed with brine (15 mL), dried over $Na_2SO_4$ and concentrated under reduced pressure. The residue was purified by flash chromatography ($SiO_2$, 0-6% MeOH/$NH_3$ in $CH_2Cl_2$) to afford 3-(2-(2-azabicyclo[3.1.0]hexan-2-yl)ethyl)-6-fluoro-5-methoxy-1-methyl-1H-indazole (99 mg, 36% over two steps) as an off-white solid. $^1$H NMR (400 MHz, $CDCl_3$): δ 7.12 (d, J=7.9 Hz, 1H), 7.04 (d, J=10.7 Hz, 1H), 3.95 (s, 3H), 3.93 (s, 3H), 3.29-3.05 (m, 3H), 3.03-2.86 (m, 3H), 1.57-1.44 (m, 1H), 0.76-0.70 (m, 1H), 0.24-0.15 (m, 1H).

Step 5: 3-(2-(2-azabicyclo[3.1.0]hexan-2-yl)ethyl)-6-fluoro-5-methoxy-1-methyl-1H-indazole fumarate (A75-fumarate)

3-(2-(2-azabicyclo[3.1.0]hexan-2-yl)ethyl)-6-fluoro-5-methoxy-1-methyl-1H-indazole (98 mg, 0.34 mmol) was formulated as the fumarate salt according to General Procedure F which was isolated as white crystals (99 mg, 63%). $^1$H NMR (400 MHz, DMSO-$d_6$): δ 7.53 (d, J=11.4 Hz, 1H), 7.38 (d, J=8.2 Hz, 1H), 6.59 (s, 2H), 3.90 (s, 3H), 3.87 (s, 3H), 3.15-3.01 (m, 3H), 2.99-2.87 (m, 3H), 2.15-2.03 (m, 1H), 1.95-1.77 (m, 2H), 1.50-1.40 (m, 1H), 0.82-0.74 (m, 1H), 0.23-0.14 (m, 1H); $^{13}$C NMR (101 MHz, DMSO-$d_6$): δ 166.5, 152.5 (d, J=246 Hz), 143.0 (d, J=14 Hz), 141.5, 134.9 (d, J=12 Hz), 134.3, 117.7, 101.9 (d, J=3 Hz), 96.6 (d, J=24 Hz), 56.2, 52.8, 47.8, 40.1, 35.3, 26.0, 25.2, 14.8, 1.9; $^1$H qNMR Purity: 97.9% (ERETIC).

Functional Assays 5-$HT_{2A}$, 5-$HT_{2B}$ AND 5-$HT_{2C}$ Receptors

Activity at 5-HT2A, 5-HT2B and 5-HT2C receptors was determined using a FLIPR Ca2+ flux assay at WuXi AppTec Co. Ltd. (Hong Kong) Discovery Biology Unit according to their standard protocols. Briefly, stably transfected cells expressing the receptor of interest (HEK293 for 5-HT2A and 5-HT2C; CHO-K1 for 5-HT2B) were grown and plated in a 384 well plate and incubated at 37° C. and 5% $CO_2$ overnight. A 250 mM stock solution of probenecid in FLIPR calcium assay buffer (10 mL) was freshly prepared and combined with a fluorescent dye (Fluo-4 Direct) to give a final assay concentration of 2.5 mM. Reference compounds were 4-fold serially diluted and the screening compounds were 3-fold serially diluted in 100% DMSO for 10 points using Agilent Bravo, and 750 nL was added to a 384 well compound plate using Echo along with 30 μL assay buffer. The fluorescent dye was then added to the assay plate along with assay buffer to a final volume of 40 μL. The cell plate was incubated for 50 min at 37° C. and 5% $CO_2$ and placed into the FLIPR Tetra along with the compound plate. 10 μL of references and compounds were then transferred from the compound plate into the cell plate and the fluorescent signal was read.

Activation data are provided in a similar assay tested at a single 10 μM concentration.

TABLE 1

Agonist activity of exemplified compounds at selected serotonin (5-HT) receptors in $Ca^{2+}$ flux functional assays.

| Code[1] | 5-HT2A $EC_{50}$ (nM) | 5-HT2A $E_{max}$ (%) | 5-HT2B $EC_{50}$ (nM) | 5-HT2B $E_{max}$ (%) | 5-HT2C $EC_{50}$ (nM) | 5-HT2C $E_{max}$ (%) | 5-HT2B % Activation @ 10 mM |
|---|---|---|---|---|---|---|---|
| P-1 | 34.88 | 47.69 | >10000 | −1.07 | 18.79 | 74.29 | |
| P-2 | >10000 | 15.85 | >10000 | −0.67 | 2072 | 20.57 | |
| P-3 | 49.72 | 41.38 | >10000 | −0.67 | 121.1 | 41.19 | |
| P-4 | 1228 | 34.95 | >10000 | −0.27 | 240.9 | 17.91 | |
| P-5 | 24.42 | 56.19 | >10000 | −0.87 | 38.37 | 79.08 | |
| P-6 | 43.13 | 66.41 | >10000 | 0.34 | >10000 | −0.79 | |
| P-7 | >10000 | −0.3 | >10000 | 0.17 | 2343 | 40.16 | |
| P-8 | 202.9 | 69.97 | >10000 | 17.9 | 532.3 | 72.39 | |
| P-9 | 1023 | 37.3 | >10000 | 2.53 | >10000 | −30.53 | |
| P-10 | 6.110 | 82.81 | 283.6 | 47.12 | 68.63 | 99.11 | |
| P-11 | 4.165 | 99.06 | 52.18 | 92.13 | 91.13 | 96.32 | |
| P-12 | 6.956 | 85.65 | 22.23 | 101.87 | 199.6 | 110.09 | |
| P-13 | 10.08 | 79.64 | >10000 | 2.25 | 31.92 | 95.83 | |
| P-14 | 20.97 | 78.91 | >10000 | 1.06 | 139.0 | 98.26 | |
| P-17 | 279.5 | 84.66 | >10000 | 0.37 | >10000 | −0.53 | |
| P-18 | 85.53 | 89.44 | >10000 | 9.35 | >10000 | −0.33 | |
| P-19 | 72.86 | 112.37 | >10000 | 13.27 | >10000 | 0.16 | |
| P-20 | 93.26 | 76.74 | >10000 | 1.38 | >10000 | −0.08 | |
| P-21 | 108.6 | 79.80 | >10000 | 4.56 | >10000 | −0.15 | |
| P-22 | 690.9 | 55.49 | >10000 | 1.91 | >10000 | 0.27 | |
| P-23 | 1238 | 54.98 | >10000 | 0.88 | >10000 | −0.04 | |
| P-24 | 80.76 | 56.55 | >10000 | 6.16 | >10000 | 24.74 | |
| P-25 | 108.8 | 70.30 | >10000 | 8.23 | >10000 | 20.98 | |
| P-26 | 1619 | 58.34 | >10000 | 3.08 | >10000 | 0.90 | |
| P-27 | 856.9 | 80.23 | >10000 | 35.63 | >10000 | 0.54 | |
| P-28 | 781.7 | 70.54 | >10000 | 0.69 | >10000 | −0.06 | |
| P-29 | 555.4 | 71.56 | >10000 | 0.59 | >10000 | 0.48 | |
| P-30 | 387.3 | 56.61 | >10000 | 0.03 | >10000 | 1.04 | |
| P-31 | 1016 | 54.48 | >10000 | 1.01 | >10000 | 0.01 | |
| P-32 | 413.8 | 57.78 | >10000 | 0.14 | >10000 | 0.61 | |
| P-33 | 640.8 | 54.73 | >10000 | 0.01 | >10000 | 0.33 | |
| P-34 | 149.6 | 82.59 | >10000 | 14.70 | 681.6 | 91.66 | |
| P-35 | 78.99 | 82.20 | 78.45 | 74.65 | 7178 | 55.58 | |
| P-36 | 77.06 | 113.99 | 96.44 | 48.92 | >10000 | 38.38 | |
| P-37 | 86.83 | 82.79 | >10000 | 2.60 | 532.8 | 105.33 | |
| P-38 | 77.69 | 83.13 | 610.3 | 19.57 | 1922 | 70.16 | |
| P-42 | 2979 | 68.77 | >10000 | 0.24 | 3488 | 70.51 | |
| P-43 | 2183 | 38.93 | >10000 | 8.01 | >10000 | 28.82 | |
| P-44 | 259.3 | 97.62 | 490.3 | 39.36 | 1704 | 77.24 | |
| P-45 | 159.8 | 100.25 | >10000 | 8.93 | >10000 | 40.22 | |
| P-48 | 6986 | 58.60 | >10000 | 16.12 | >10000 | 4.22 | |
| P-49 | 1395 | 67.61 | >10000 | 30.67 | >10000 | −0.46 | |
| P-51 | 525.7 | 79.08 | >10000 | 30.87 | >10000 | 24.61 | |
| P-52 | 1840 | 77.29 | >10000 | 0.22 | >10000 | 0.09 | |
| P-55 | 255.8 | 58.72 | >10000 | 1.35 | 366.5 | 83.62 | |
| P-56 | 794.2 | 50.53 | >10000 | −0.39 | 1256 | 63.60 | |
| A1 | 28.3 | 82 | NT | NT | 8.21 | 84 | 21 |
| A2 | 31.5 | 87 | NT | NT | 15.5 | 86 | 57 |
| A3 | 96.5 | 76 | NT | NT | 170 | 80 | 17 |
| A4 | 62.7 | 67 | NT | NT | 17.1 | 91 | 2 |
| A5 | 44.1 | 87 | NT | NT | 281 | 105 | 44 |
| A6 | 110 | 86 | NT | NT | 786 | 101 | 40 |
| A7 | 318 | 63 | NT | NT | 4176 | 67 | 7 |
| A8 | 208 | 71 | NT | NT | 507 | 102 | 6 |

TABLE 1-continued

Agonist activity of exemplified compounds at selected serotonin (5-HT) receptors in $Ca^{2+}$ flux functional assays.

| | 5-HT2A | | 5-HT2B | | 5-HT2C | | 5-HT2B |
|---|---|---|---|---|---|---|---|
| Code[1] | $EC_{50}$ (nM) | $E_{max}$ (%) | $EC_{50}$ (nM) | $E_{max}$ (%) | $EC_{50}$ (nM) | $E_{max}$ (%) | % Activation @ 10 mM |
| A9 | 809 | 75 | NT | NT | 1102 | 73 | 0 |
| A10 | 831 | 69 | NT | NT | 2856 | 68 | 1 |
| A11 | 1377 | 64 | NT | NT | >10000 | 22 | 0 |
| A13 | 2046 | 55 | NT | NT | 944 | 48 | 0 |
| A17 | 167 | 82 | NT | NT | 34 | 80 | 25 |
| A18 | 264 | 55 | NT | NT | 128 | 79 | 16 |
| A19 | >10000 | 25 | NT | NT | 1525 | 69 | 1 |
| A20 | 419 | 45 | NT | NT | 206 | 83 | 1 |
| A67 | 422 | 63 | NT | NT | 1667 | 37 | 0 |
| A68 | 469 | 40 | NT | NT | 1917 | 32 | 0 |
| A69 | 276 | 79 | NT | NT | 132 | 62 | 5 |
| A70 | 383 | 78 | NT | NT | 226 | 76 | 0 |
| A71 | 850 | 57 | NT | NT | 1944 | 52 | 0 |
| A72 | 1348 | 78 | NT | NT | 973 | 37 | NT |
| A73 | 768 | 87 | NT | NT | 1785 | 70 | 18 |
| A74 | 59.5 | 89 | NT | NT | 133 | 95 | 0 |
| A29 | 687 | 33 | NT | NT | 1480 | 70 | 0 |
| A33 | 14.4 | 91 | NT | NT | 159 | 90 | 23 |
| A34 | 55.2 | 86 | NT | NT | 167 | 84 | 0 |
| A35 | 213 | 72 | NT | NT | 495 | 54 | 1 |
| A36 | 361 | 70 | NT | NT | 732 | 55 | 0 |
| A37 | 810 | 57 | NT | NT | >10000 | 11 | 0 |
| A38 | 75 | 77 | NT | NT | 203 | 75 | 0 |
| A39 | 116 | 75 | NT | NT | 375 | 78 | 0 |
| A40 | 322 | 72 | NT | NT | >10000 | 68 | 0 |
| A41 | 1075 | 78 | NT | NT | 1418 | 65 | NT |
| A42 | 697 | 81 | NT | NT | 944 | 89 | NT |
| A43 | 29.7 | 89 | NT | NT | 39.9 | 99 | 102 |
| A44 | 93.0 | 52 | NT | NT | 222 | 44 | 0 |
| A45 | 163 | 67 | NT | NT | 614 | 61 | 0 |
| A46 | 133 | 74 | NT | NT | >10000 | 0 | 0 |
| A47 | 105 | 88 | NT | NT | 64 | 72 | 17 |
| A48 | 533 | 70 | NT | NT | 556 | 67 | NT |
| A49 | 216 | 69 | NT | NT | 166 | 59 | 7 |
| A50 | 242 | 79 | NT | NT | >10000 | 11 | 2 |
| A51 | 88 | 85 | NT | NT | 1367 | 43 | 1 |
| A52 | 650 | 42 | NT | NT | >10000 | 0 | 0 |
| A53 | 318 | 94 | NT | NT | 1180 | 48 | 0 |
| A54 | 1376 | 75 | NT | NT | 3259 | 38 | NT |
| A55 | 39.8 | 86.2 | NT | NT | 206.53 | 86.99 | 48 |
| A56 | 105 | 90 | NT | NT | 3067 | 50 | 11 |
| A57 | 610 | 70 | NT | NT | >10000 | 3 | 0 |
| A58 | 1130 | 57 | NT | NT | >10000 | 19 | 0 |
| A59 | 202 | 79 | NT | NT | 3872 | 66 | 5 |
| A60 | 8.12 | 92 | NT | NT | 255 | 90 | 89 |
| A61 | 1577 | 67 | NT | NT | >10000 | 21 | NT |
| A62 | 29.1 | 81 | NT | NT | 179 | 85 | 0 |
| A63 | 2.24 | 92 | NT | NT | 32.5 | 88 | 11 |
| A64 | 68.7 | 79 | NT | NT | 602 | 82 | 0 |
| A65 | 91.6 | 70 | NT | NT | 891 | 81 | 1 |
| A66 | 50.0 | 63 | NT | NT | 1261 | 53 | 0 |
| A75 | 63.4 | 77 | NT | NT | NT | NT | NT |

Note:
Compounds denoted with "P-#" are described in WO 2023/115165, the entire contents of which is incorporated herein by reference.

Example 49a: In Vivo Pharmacokinetics Experiments

The study was conducted using established procedures in accordance with the Australian Code of Practice for the Care and Use of Animals for Scientific Purposes, and the study protocols were reviewed and approved by the Monash Institute of Pharmaceutical Sciences Animal Ethics Committee.

The systemic exposure of selected examples was studied in non-fasted male C57BL/6 mice weighing between 18.9-25.5 g. Mice had access to food and water ad libitum throughout the pre- and post-dose sampling period.

On the day of dosing, the formulation of each compound was prepared by dissolving solid compound in phosphate buffer saline (50 mM) using vortexing, creating colourless solutions (pH 6.4-6.5) for each compound.

Compounds were dosed to mice by IP injection (10 mL/kg dose volume via a 27G needle; n=9 mice per compound) and blood samples were collected at 5 and 30 min; 1, 2 and 4 h post-dose (n=3 mice per time point for each compound). A maximum of three blood samples were obtained from each mouse, with plasma samples being taken via submandibular bleed (approximately 120 µL). Once collected, blood samples were centrifuged immediately, supernatant plasma was removed, and stored at −80° C. until analysis by LCMS.

In addition, at the 5 and 30 min and 4 h post-dose time points, the whole brain was rapidly removed from the carcass soon after the blood collection. The whole brains were blotted to remove excess blood, placed into pre-weighed polypropylene vials, and weighed. The brains were snap frozen in dry ice and subsequently stored frozen (−80° C.) until analysis.

Bioanalytical Method Summary:

Concentrations of test compound in plasma and tissue samples were determined using an LCMS/MS method validated for linearity, accuracy, precision, matrix factor and recovery (Table 2). Test compound standard solutions were diluted from a concentrated stock solution (32 mM in $H_2O$) using 50% can in $H_2O$ (v/v) and a calibration curve was prepared in a matched matrix to the test samples.

Plasma: The plasma calibration curve was prepared by spiking aliquots of blank mouse plasma (25 µL) with test compound standard solutions (5 µL) and internal standard solution (5 µL of diazepam, 5 µg/mL in 50% acetonitrile in water). Test plasma samples (25 µL) were thawed, mixed, and then spiked with internal standard solution (5 µL). Plasma protein precipitation was performed by addition of acetonitrile (3-fold volume ratio) and thorough vortex mixing. Samples were centrifuged (RCF=9391× g) for 3 minutes and the supernatant (90 µL) was collected for analysis.

Tissue: Pre-weighed tissue samples (brain) were homogenised using a glass rod in buffer containing an EDTA/potassium fluoride solution (0.1 M/4 mg/mL) as a stabilisation cocktail to minimise the potential for ex vivo degradation (3 mL cocktail/g tissue). The tissue homogenate was briefly centrifuged (RCF=79× g) for 10 seconds to separate the foam layer before transferring an aliquot of the tissue homogenate (200 µL) to a fresh Eppendorf tube for sample extraction. Calibration standards were prepared by spiking blank brain homogenate (200 µL) with the solution standards (10 µL) and the internal standard (10 µL). Study samples were similarly prepared, except that acetonitrile (10 µL) was added instead of solution standards to maintain the same volume. Protein precipitation was carried out by the addition of a 3-fold volume of acetonitrile, followed by vortex mixing and centrifugation (RCF=9391×g) for 3 min to recover the supernatant for analysis.

Replicate analysis: Triplicate analytical replicate (ARs) samples were prepared similarly to the standards for each sample type at three concentrations (50, 500 and 2,000 ng/mL) and repeat injections of these ARs were included throughout the analytical run to assess assay performance. The extraction of the test compound from the standards and ARs were conducted as described above.

All test samples were quantified within the calibration range of the assay and the assay performance for ARs were deemed acceptable. The stability of each test compound was confirmed in homogenate during the period of sample processing (15 min; <15% loss).

TABLE 2

Summary of bioanalytical method for a subset of exemplar compounds

| Instrument | Waters Xevo TQS Micro coupled to a Waters Acquity UPLC |
| --- | --- |
| Detection | Positive electrospray ionisation multiple-reaction monitoring mode |
| Column | Kinetex 2.6 u PFP 100 A column (50 × 2.1 mm, 2.6 µm) |
| LC Conditions | Gradient cycle time: 4 min; Injection vol: 1 µL; Flow rate: 0.4 mL/min |
| Mobile Phase | (A) 0.005M ammonium formate in water; (B) 0.05% ammonium formate in methanol |
| Sample Preparation | Plasma: Protein precipitation using acetonitrile (3-fold volume ratio) Tissue: Protein precipitation using acetonitrile (3-fold volume ratio) |

| Analyte | $t_R$* (min) | Transition (m/z) | Cone Voltage (V) | CID# (V) |
| --- | --- | --- | --- | --- |
| P-8 | 2.31 | 220.17 > 175.03 | 20 | 20 |
| P-5 | 2.18 | 220.11 > 58.00 | 20 | 15 |
| P-3 | 2.18 | 220.11 > 175.10 | 20 | 15 |
| P-1 | 1.91 | 220.11 > 175.03 | 20 | 15 |
| Diazepam (IS) | 1.87/2.41 | 285.15 > 193.10 | 40 | 25 |

The highest abundance product ion with minimum interference with the matrix were selected for quantification. Data acquisition was performed using MassLynx software (V4.2).

IS: Internal standard

*Retention time

Collision-Induced Dissociation

Maximal plasma concentrations of compounds P-8, P-5, P-3, and P-1 following IP administration at 10 mg/kg are shown in Table 3. Comprehensive pharmacokinetic data including brain penetration information is displayed in FIG. 1 and/or Table 4.

TABLE 3

Exposure parameters for a subset of exemplar compounds: P-8, P-5, P-3, and P-1 in male C57BL/6 mice following IP administration at 10 mg/kg.

| Parameter | P-8 | P-5 | P-3 | P-1 |
|---|---|---|---|---|
| Plasma $C_{max}$ (μM) | 7.66 | 5.38 | 5.80 | 6.53 |
| $T_{max}$ (min) | 5 | 5 | 5 | 5 |
| Plasma $AUC_{0-last}$ (h*μM) | 1.94 | 1.63 | 1.70 | 1.37 |

TABLE 4

Individual and mean ± SD (n = 3) plasma and brain concentrations, and brain-to-plasma (B:P) ratios, of a subset of exemplar compounds P-8, P-5, P-3, and P-1 in male C57BL/6 mice following IP administration at 10 mg/kg.

| | | Plasma Concentration (μM) | | Brain Parenchyma Concentration (μM) | | B:P Ratio | |
|---|---|---|---|---|---|---|---|
| Time (h) | Mouse ID | Individual | Mean ± SD | Individual | Mean ± SD | Individual | Mean ± SD |
| P-8 | | | | | | | |
| 0.083 | 1 | 5.42 | 7.66 ± 3.25 | 3.60 | 5.41 ± 2.01 | 0.66 | 0.72 ± 0.089 |
| | 2 | 6.18 | | 5.06 | | 0.82 | |
| | 3 | 11.4 | | 7.57 | | 0.66 | |
| 0.5 | 4 | 0.846 | 0.744 ± 0.139 | 5.77 | 6.12 ± 1.32 | 6.8 | 8.3 ± 1.4 |
| | 5 | 0.800 | | 7.58 | | 9.5 | |
| | 6 | 0.586 | | 5.01 | | 8.6 | |
| 4 | 7 | ND | 0.0030 | 0.0263 | 0.0326 ± 0.0174 | — | 6.4 |
| | 8 | 0.0030$^a$ | | 0.0192 | | 6.4 | |
| | 9 | ND | | 0.0522 | | — | |
| P-5 | | | | | | | |
| 0.083 | 10 | 5.88 | 5.38 ± 3.18 | 0.23 | 0.984 ± 0.540 | 0.21 | 0.19 ± 0.022 |
| | 11 | 1.97 | | 0.365 | | 0.19 | |
| | 12 | 8.28 | | 1.36 | | 0.16 | |
| 0.5 | 13 | 0.815 | 0.859 ± 0.111 | 1.61 | 1.97 ± 0.414 | 2.0 | 2.3 ± 0.26 |
| | 14 | 0.985 | | 2.42 | | 2.5 | |
| | 15 | 0.776 | | 1.86 | | 2.4 | |
| 4 | 16 | <LLQ | — | <LLQ | — | — | — |
| | 17 | <LLQ | | <LLQ | | — | |
| | 18 | <LLQ | | <LLQ | | — | |
| P-3 | | | | | | | |
| 0.083 | 1A | 6.70 | 5.80 ± 0.793 | 9.02 | 6.46 ± 2.26 | 1.3 | 1.1 ± 0.24 |
| | 2A | 5.48 | | 4.78 | | 0.87 | |
| | 3A | 5.21 | | 5.57 | | 1.1 | |
| 0.5 | 4A | 0.865 | 0.791 ± 0.0641 | 8.62 | 7.80 ± 0.745 | 10 | 9.9 ± 0.36 |
| | 5A | 0.752 | | 7.64 | | 10 | |
| | 6A | 0.756 | | 7.15 | | 9.5 | |
| 4 | 7A | 0.0071 | 0.0057 ± 0.0012 | 0.0465 | 0.0554 ± 0.0324 | 6.6 | 9.9 ± 6.2 |
| | 8A | 0.0053 | | 0.0913 | | 17 | |
| | 9A | 0.0047 | | 0.0283 | | 6.1 | |
| P-1 | | | | | | | |
| 0.083 | 10A | 7.66 | 6.53 ± 1.93 | 2.06 | 1.89 ± 0.776 | 0.27 | 0.28 ± 0.048 |
| | 11A | 4.30 | | 1.04 | | 0.24 | |
| | 12A | 7.63 | | 2.56 | | 0.34 | |
| 0.5 | 13A | 1.03 | 0.585 ± 0.387 | 0.307 | 0.482 ± 0.201 | 0.30 | 1.2 ± 1.0 |
| | 14A | 0.307 | | 0.701 | | 2.3 | |
| | 15A | 0.420 | | 0.437 | | 1.0 | |
| 4 | 16A | <LLQ | — | <LLQ | — | — | — |
| | 17A | <LLQ | | ND | | — | |
| | 18A | <LLQ | | <LLQ | | — | |

ND-Not Detected; < LLQ-Below the analytical lower limit of quantitation

Example 50a: Biotelemetry and Head-Twitch Response (HTR) Experiments

Mice (C57BL/6J males) were purchased from the Jackson Laboratory (Bar Harbor, ME, USA) at 5-6 weeks of age and allowed at least 1-2 weeks to acclimate to the NIDA, Intramural Research Program (IRP), animal research facility in Baltimore, MD, USA. The animal facility is fully accredited by the Association for the Assessment and Accreditation of Laboratory Animal Care, and all procedures were approved by the NIDA IRP Animal Care and Use Committee. Mice were initially group housed 3-5 per cage during acclimation and housed in a 12 h light-dark cycle throughout the study, with lights on at 0700 h. Food and water were available ad libitum except during testing. Cohorts of 20-24 mice were used for each test drug. The mice were subjected to experimental testing once every 1-2 weeks for 2-3 months to complete dose-effect curves and antagonist experiments. A minimum of 7 days between treatments was utilized to avoid any tolerance to effects of repeated drug administration. All drug doses represent the weight of the salt dissolved in 0.9% saline vehicle. Mice were tested first in dose-response studies to assess the effects of each compound at doses from 0.03 to 30 mg/kg s.c. and were subsequently tested in antagonist reversal studies utilizing pretreatment with M100907 and WAY100635. All experiments were conducted from 0900 to 1700 local time during the light phase, as sensitivity of rodents to other tryptamine psychedelics is diurnal, with maximal HTR observed in the middle of the light phase. Experiments were run during the light phase also to avoid any potential influence of melatonin receptor activity on HTR as melatonin and related agonists are known to reduce HTR induced by DOI in rats. For each experiment, mice were acclimated to the testing room in their home cage for at least 1 h prior to experimental sessions. Behavioral test sessions were carried out in Tru Scan mouse locomotor arenas equipped with photobeam arrays (Coulbourn Instruments, Holliston, MA, USA), which were modified with cylindrical inserts and transparent floors useful in detecting mouse HTR.

Subcutaneous Temperature Transponder Implants. At least 1 week prior to the start of the experiments, mice received s.c. implanted temperature transponders (14×2 mm, model IPTT-300, Bio Medic Data Systems, Inc., Seaford, DE, USA) under brief isoflurane anesthesia. Mice were single housed post implant for the remainder of the study to protect the transponder from removal by cage mates. Temperature was determined noninvasively using a handheld receiver that is sensitive to signals emitted from the implanted transponders.

Prior to each experiment, mouse body weight and temperature were recorded. Mice were then placed into testing chambers for acclimation. In dose-response studies, after a brief 5 min acclimation, mouse body temperature was recorded for baseline measurement, mice received s.c. injection of test substance or vehicle, and animals were returned to the testing arena for 30 min. During the session, locomotor activity was monitored via photobeam tracking of movements in the horizontal plane to yield distance traveled in centimeter. HTR was monitored by the analysis of GoPro Hero Black 7 video recordings (120 frames per sec and 960p resolution) using a commercially available software package from Clever Sys Inc. (Reston, VA, USA).82 Post-treatment body temperature values were also recorded, and temperature data are represented as change from pretreatment baseline.

In antagonist reversal experiments, mice received a s.c. injection of either receptor antagonists or vehicle and were returned to the testing chamber for 30 min. During this period, locomotor activity was monitored to examine the potential effects of antagonist treatment on general behavior or movement. At 30 min after antagonist administration, mice were given test drug or vehicle and returned to the chambers for an additional 30 min of video recording used for analyses.

All statistical analyses were conducted using GraphPad Prism 9 (La Jolla, CA, USA). Dose-response data from mouse experiments were analyzed using nonlinear regression, and potency values were determined from the rising phase of the curves for HTR measures. For mouse studies, one-way ANOVA with Dunnett's post hoc test was used to compare all conditions to vehicle controls (0 or 0, 0) in dose-response and antagonist experiments. Time-course drug effects for all parameters in mouse studies are shown for reference. Mean HTR count, distance traveled, and temperature change for each condition were used for statistical comparisons. Alpha was set at 0.05 for all analyses.

Results of these experiments for P-4, P-3 and P-1 are shown in FIGS. 2, 3, 4 and 5. These data show that compounds of the invention are well-tolerated. These data also show that the compounds are not promoting increased head-twitch response, suggesting they are likely not hallucinogenic.

Example 51a: Tail Suspension Test Experiments

Male ICR mice (23±3 g) were purchased from Bio-LASCO (Taipei, Taiwan) at 4-5 weeks of age and allowed 5-7 days to acclimate to the animal research facility at Pharmacology Discovery Services (Taipei, Taiwan). Mice were housed in groups of 10 in a large cage (47×25×15 cm) on a 12-hour light cycle (lights on: 0700) and provided ad libitum food and water except during acute restraint stress and tail-suspension testing. Temperature was maintained at 20-24° C., and all rooms (colony and testing rooms) had similar lighting intensity. All aspects of this work including housing, experimentation, and animal disposal were performed in accordance with the "Guide for the Care and Use of Laboratory Animals: Eighth Edition" (The National Academies Press, Washington, DC, 2011) in a facility accredited by the Association for Assessment and Accreditation of Laboratory Animal Care. All experiments were conducted between 0900 to 1700 local time, during the light phase. Each mouse underwent a single behavioural experiment in which they were randomly allocated to receive a single treatment with vehicle (50 mM phosphate buffered saline, pH=6.5), Ketamine as a positive control (10 mg/kg, diluted in 0.9% saline from 50 mg/ml stock), or one dose of a test drug (n=10 per dose of test drug, n=12 for vehicle, n=12 for ketamine). All drug doses represent the freebase dose in salt form dissolved in vehicle. All solutions were delivered at 5 ml/kg via intraperitoneal injection.

Acute Restraint Stress (ARS) Procedure: Mice were moved from the colony room to the procedure room in which ARS was to be performed. Mice received oral gavage of water (10 ml/kg) to avoid dehydration, and then were individually restrained for 5 hours in a clear plastic cylinder (50 mL centrifuge tube with air holes drilled for ventilation), positioned horizontally on a bench with bench towel to absorb urine. This restraint prevented physical movement, without causing pain. Restrainers were washed with veterinary disinfectant between mice.

Drug Administration: Immediately after the 5-hour ARS procedure, mice were removed from the restrainers, placed in their home cage, and transported to the room in which Tail Suspension Test was to be conducted. Mice then received intraperitoneal injection with vehicle, ketamine (10 mg/kg), P-3·HCl (3, 10 mg/kg) or P-8·2HCl (3, 10, 30 mg/kg), and were then placed back in their home cage. 10 minutes after treatment, animals then underwent the Tail Suspension Test.

Tail Suspension Test (TST) Procedure: Mice were individually suspended on the edge of a shelf, 58 cm above a tabletop, using adhesive tape placed approximately 1 cm from the tip of the tail, for a total duration of 7 minutes. Using a stopwatch, the experimenters blinded to treatment groups recorded the duration of immobility (defined as hanging passively and motionless) during the 5 minutes spanning from 2-7 minutes. The data from 0-2 minutes was not recorded. Mice undergoing TST were never in view of other mice. Following TST, mice were euthanized via carbon dioxide inhalation.

Figure 6:
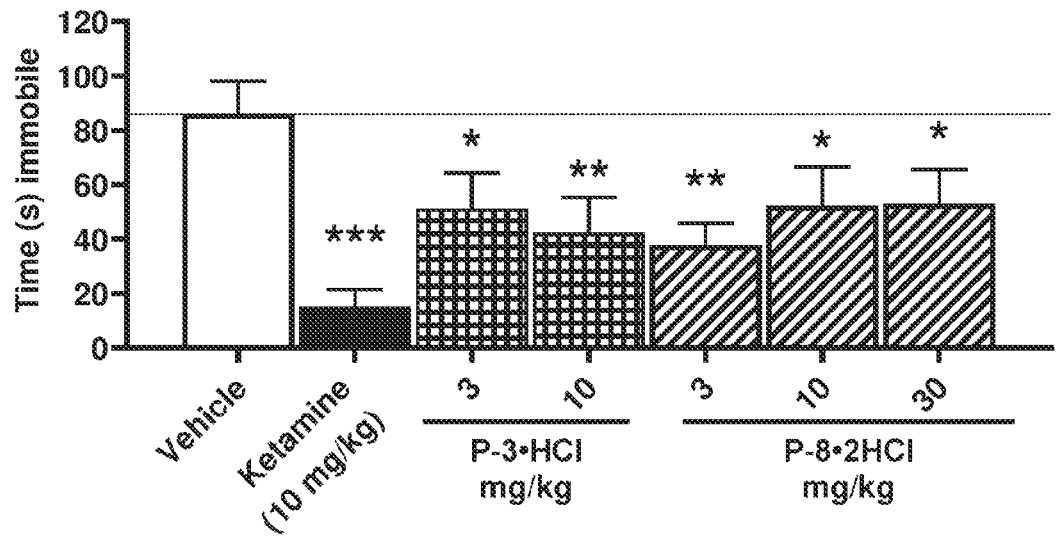
FIG. 6: Time immobilisation results from tail suspension test (TST) experiments described in Example 51a for compounds P-3.2HCl (3 mg/kg; 10 mg/kg) and P-8.2HCl (3 mg/kg; 10 mg/kg; 30 mg/kg) compared with ketamine (10 mg/kg) and vehicle.

Statistical Analysis: Statistical analyses were conducted using GraphPad Prism 9 (La Jolla, CA, USA), using a priori simple effect comparisons within a one-way ANOVA to compare the test compounds to the Vehicle condition, on time spent immobile (in seconds). The datapoints shown in FIG. 6 represent the mean±the standard error of the mean. Significance was set at $\alpha=0.05$. * Signifies $p<0.05$; $p<0.01$. *$p<0.001$.

Figure 7:
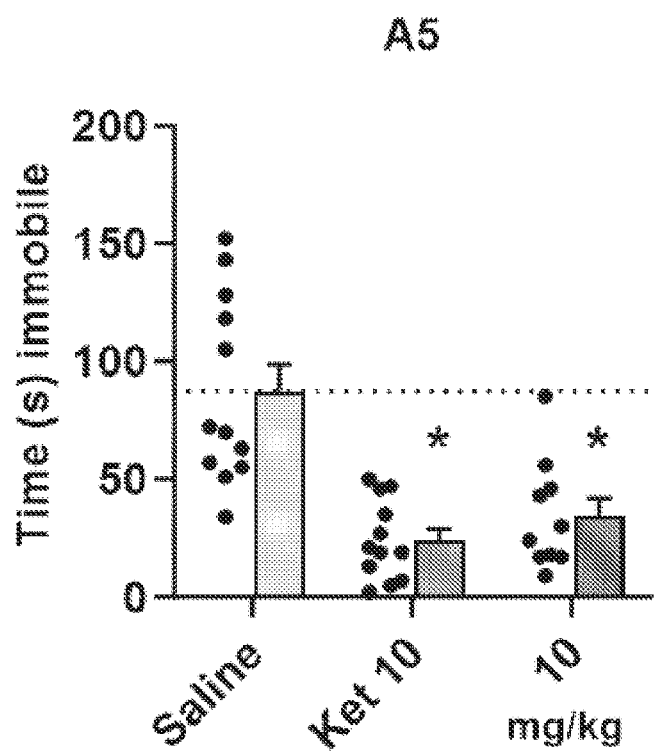
FIG. 7: Time immobilisation results from tail suspension test (TST) experiments described in Example 51a for compound A5 (10 mg/kg) compared with ketamine (10 mg/kg) and vehicle.

Results of this experiment for compounds P-3 and P-8 are shown in FIG. 6 and for compound A5 in FIG. 7. This data indicates the compounds of the invention decrease the immobility time of mice in an Acute Restraing Stressor—Tail Suspension Test mouse model of depression. This indicates that compounds of the invention are likely to be anti-depressant.

Example 53a: IPOne for Receptor Profiling

Briefly, stably transfected cells expressing the receptor of interest (CHO-K1 for human 5-HT2A, mouse 5-HT2A and rat 5-HT2A) grown to mid-log phase in culture media without antibiotics are detached with PBS-EDTA, centrifuged and resuspended in the HTRF IP-One Gq Detection Kit (Revvity, 62IPAPEJ) stimulation buffer.

Test compounds are dissolved in 100% DMSO at a concentration of 10 mM (master solution). Serial dilutions are prepared from master solution in 100% DMSO to obtain intermediate concentrations 200-fold higher than the concentrations to be tested. Each sample is diluted 100-fold in stimulation buffer and dispensed in test plate (5 μl per well) For agonist testing (384-well, suspension), 5 μl of cell suspension are dispensed in the wells of the 384-well assay plate containing 5 μl of test compound or reference agonist diluted in stimulation buffer. The plate is incubated for 60 min. at 37° C. with 5% $CO_2$. After addition of the lysis buffer containing IP1-d2 and anti-IP1 cryptate detection reagents, plates are incubated 1-hour at room temperature, and fluorescence ratios are measured according to the manufacturer specification, with the HTRF kit.

Example 54a: Tissue Binding

Method:
Mouse Brain Homogenate Binding:
Stock solutions of test compound(s) and control compound propranolol in DMSO at the concentration of 10 mM are prepared. 2 μL of stock solution (10 mM) is diluted with 98 μL DMSO to obtain working solution (200 μM). 3.5 μL of working solution is removed and is mixed with 697 μL of brain tissue homogenate to achieve final concentration of 1 μM (0.5% DMSO). The resulting mixture is vortexed thoroughly.

Procedure for Equilibrium Dialysis
The assay is run avoiding lights and oxygen after assembling the dialysis set up following the manufacturer's instructions. Cells are loaded with 150 μL of brain tissue homogenate sample and are dialyzed against equal volume of dialysis buffer (PBS). The assay is performed in duplicate. The dialysis plate is sealed and placed in an incubator at 37° C. at approximately 150 rpm for 6 hours. At the end of dialysis, the seal is removed and 50 μL of each post-dialysis samples is pipetted from both buffer and brain tissue homogenate chambers into separate tubes in plate.

Procedure for Sample Analysis
50 μL of blank brain tissue homogenate is added to the buffer samples, and an equal volume of PBS is added to the collected brain tissue homogenate samples. 400 μL of room temperature quench solution (acetonitrile containing internal standards (IS, 200 nM Labetalol, 100 nM Alprazolam and 2 μM Ketoprofen)) is added to precipitate protein. The composition is vortexed for 5 minutes. Samples in plate are centrifuged at 3,220 g for 30 minutes at room temperature. 100 μL of the supernatant is transferred to a new plate. The supernatant may be diluted with 100 μL or 200 μL water according to the LC/MS signal response and peak shape. The composition is mixed well and samples are analysed using LC/MS/MS.

Mouse Plasma Protein Binding:
Preparation of Stock Solutions and Working Solutions
Stock solutions of test compound(s) and control compound warfarin in DMSO are prepared at a concentration of 10 mM. 2 μL of stock solution (10 mM) is diluted with 98 μL DMSO to obtain working solution (200 μM). 3.5 μL of working solution is removed to mix with 697 μL of human, monkey, dog, rat or mouse plasma to achieve final concentration of 1 μM (0.1% DMSO). The composition is vortexed thoroughly.

Procedure for Equilibrium Dialysis
The assay is run avoiding lights and oxygen. The dialysis is assembled and set up following the manufacturer's instructions. Cells are loaded with 150 μL of plasma sample and are dialyzed against equal volume of dialysis buffer (PBS). The assay is performed in duplicate. The dialysis plate is sealed and is placed the plate in an incubator at 37° C. at approximately 150 rpm for 6 hours. At the end of dialysis, the seal removed and 50 μL each of post-dialysis samples from both buffer and plasma chambers are pipetted into separate tubes in plate.

Procedure for Sample Analysis
50 μL of blank plasma is added to the buffer samples, and an equal volume of PBS is added to the collected plasma samples. 400 μL of room temperature quench solution (acetonitrile containing internal standards (IS, 100 nM alprazolam, 200 nM labetalol, 200 nM imipramine and 2 μM ketoprofen)) is added to precipitate protein. The composition is vortexed for 5 minutes. Samples in plate are centrifuged at 3,220 g for 30 minutes at room temperature. 100 μL of the supernatant is transferred to a new plate. The supernatant may be diluted with 100 μL or 200 μL water according to the LC/MS signal response and peak shape. The composition is mixed well and samples are analysed using LC/MS-MS.

Stability Determination in Plasma
50 μL of spiked plasma sample is transferred to a new plate. Samples are incubated at 37° C., 5% $CO_2$ for 0 and 6 hrs. At designated time points, 50 µL of PBS is added to the wells. The compositions are mixed thoroughly and then 400 µL of room temperature quench solution (acetonitrile containing internal standards (IS, 100 nM alprazolam, 200 nM labetalol, 200 nM imipramine and 2 µM ketoprofen)) is added to precipitate protein.

Samples are vortexed for 2 minutes and centrifuged for 30 minutes at 3,220 g. The aliquot of 100 µL of the supernatant is diluted by ultra-pure water (100 µL or 200 µL according to the LC/MS signal response and peak shape) and the mixture is used for LC-MS/MS analysis.

Example 55a: Pharmacokinetics+Brain Penetration

Method:
The study is conducted using established procedures by Pharmaron in vivo pharmacology services and are briefly outlined below.
Dosing Information
The study groups are shown in the following table.

| Group | Treatment | Dose Level (mg/kg) | Dose Volume (mL/kg) | Conc. (mg/mL) | Administration Route | No. of Animals |
|---|---|---|---|---|---|---|
| 1 | Test Article | 3 | 5 | 0.6 | IV | 3 males |
| 2 | | 5 | 5 | 1 | IPA | 3 males |
| 3 | | 5 | 5 | 1 | IPB | 2 males/time point 6 in total |
| 4 | | 10 | 10 | 1 | PO | 3 males |

All animals have free access to food and water.

| Pharmacokinetics (PK) Schedule: | |
|---|---|
| Group | PK time points |
| IV | Plasma: 0.083, 0.25, 0.5, 1, 2, 4, 6, 8 h post dose |
| IP | IPA: Plasma: 0.25, 0.5, 1, 2, 4, 6, 8 h post dose Brain: 8 h post dose |
| | IPB: Brain and plasma: 0.25, 1, 4 h post dose |
| PO | Plasma: 0.25, 0.5, 1, 2, 4, 6, 8 h post dose |

| Blood Sample Collection and Processing | |
|---|---|
| Collection Site: | Dorsal metatarsal vein |
| Volume Collected: | ~0.03 mL per time point |
| Anticoagulant: | EDTA-K2 |
| Samples Processing and Storage: | 1) Approximately 0.03 mL blood is collected at each time point. Blood of each sample is transferred into plastic micro centrifuge tubes containing anticoagulant and is mixed well with anticoagulant. Blood samples is centrifuged at 4,000 g for 5 minutes at 4° C. to obtain plasma. |
| | 2) The samples are stored in a freezer at −75 ± 15° C. prior to analysis. |
| Tissue Sample Processing and Storage | 1) The mouse is fully exsanguinated prior to tissue collection. Procedure: open chest cavity, cut ventricle and perform a gentle iv saline flush (saline flush volume ~20 ml) with the animal placed head down at a 45 degree angle to facilitate blood removal. |
| | 2) Tissue samples are collected at adopted time point, quick frozen in ice box and kept at −75 ± 15° C. |
| | 3) All tissue samples are weighted and homogenized with water by tissue weight (g) to water volume (mL) at ratio 1:3 before analysis. The actual concentration is the detected value multiplied by the dilution factor. |

Dose Formulation

Samples are freshly prepared in PBS solution to a maximum concentration of 1 mg/mL.

Bioanalytical Method Qualification

Internal Standard

Verapamil and dexamethasone are normally used as internal standards.

Bioanalytical Criteria

The standard curve is run in duplicate with a minimum of six standards, and a minimum of five standards and the LLOQ should fall within ±20% of the nominal value. The lower limit of quantitation (LLOQ) should have a minimum signal to noise ratio of 5. A minimum of duplicate QC's at three concentrations (low, mid, and high QC) should be incorporated into each run with the low QC no more than 3×LLOQ, the mid QC around the middle of the curve, and the high QC should be near the ULOQ (minimally 80% but less than 100% of the value of the highest standard) for the run and the mean value should be within ±20% of the theoretical value. The results of the QC's provide the basis for accepting or rejecting the run. At least 67% or four of six QC's should be within 20% of their respective nominal values; 33% of the QC's (not replicates of the same concentration) can fall outside 20% of nominal value. The simplest model that adequately describes the concentration-response relationship should be used. Linear or quadratic regression can be used. Weighting should be 1/x, or 1/x2.

PK Samples Analyses

Concentrations of compound in the plasma and brain samples are analyzed using a LC-MS/MS method.

WinNonlin (Phoenix™, version 8.3) or other similar software are used for pharmacokinetic calculations. The following pharmacokinetic parameters are calculated, whenever possible from the plasma and brain concentration versus time data: IV administration: $T_{1/2}$, C0, $AUC_{last}$, $AUC_{inf}$, $MRT_{inf}$, Cl, $V_{ss}$, $V_z$, Number of Points for Regression.

IP and PO administration: $T_{1/2}$, $C_{max}$, $T_{max}$, $MRT_{inf}$, $AUC_{inf}$, $AUC_{last}$, $AUC_{0-24hr}$, Vz/f, CL/f, Number of Points for Regression.

Brain NCA parameter values post IP doing are analysed using the sparse sample analysis. Brain Kp values are reported at all sampled time points and also based on the Cmax and AUC values.

Additional pharmacokinetic or statistical analysis may be performed at the discretion of the contributing scientist, and will be documented in the data summary.

Also described herein are the following embodiments 1 to 71:

1. A compound of formula (I):

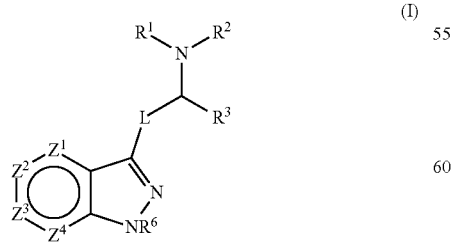

(I)

or a pharmaceutically acceptable salt, solvate, tautomer, N-oxide, stereoisomer, metabolite, polymorph or prodrug thereof, wherein $R^1$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ are combined with the atoms to which they are attached to form a $C_{3-8}$ heterocycloalkyl including 0, 1 or 2 additional ring heteromoieties selected from O, S, S(O), $SO_2$, N and $NR^4$, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), $SO_2$ and $NR^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl, said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), $SO_2$, N and $NR^5$, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, $CO_2R^5$, $C(O)N(R^5)_2$, $OR^5$, $N(R^5)_2$, $NO_2$, $SR^5$ and $SO_2R^5$, said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N and $NR^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-11}$ heterocycloalkyl, $C_{6-12}$ aryl and $C_{5-11}$ heteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-11}$ heteroaryl each being optionally substituted with one or more substituents independently selected from halogen, CN, $C_{1-8}$ alkoxy, $C_{1-8}$ alkylamino, $C_{1-8}$alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

L is selected from $C_{1-4}$ alkylene, $C_2$-$C_4$ alkenylene and $C_2$-$C_4$ alkynylene;

$Z^1$ is $CR^8$ or N;

$Z^2$ is $CR^9$ or N;

$Z^3$ is $CR^{10}$ or N;

$Z^4$ is $CR^{11}$ or N;

$R^6$ is selected from hydrogen, $C_{1-6}$ alkyl, $C_{2-6}$ alkenyl, $C_{2-6}$ alkynyl, $C_{1-6}$ alkyleneP(O)(OR^{12})_2$, $C(O)R^{12}$, $CO_2R^{12}$, $C(O)N(R^{12})_2$, $S(O)R^{12}$ and $SO_2R^{12}$, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, $CO_2R^{12}$, $C(O)N(R^{12})_2$, $OR^{12}$, $N(R^{12})_2$, $NO_2$, $SR^{12}$ and $SO_2R^{12}$, said $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-11}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{12}$;

each $R^{12}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

$R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively, when $Z^1$ is $CR^8$ and $Z^2$ is $CR^9$, or when $Z^2$ is $CR^9$ and $Z^3$ is $CR^{10}$, or when $Z^3$ is $CR^{10}$ and $Z^4$ is $CR^{11}$, then $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-11}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl;

said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-11}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$; and wherein the compound of formula (I) is not one of the following:

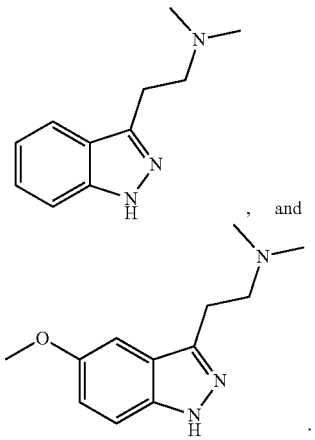

, and

2. The compound of embodiment 1, wherein $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

3. The compound of embodiment 2, wherein $R^1$ and $R^2$ are each independently selected from $C_{1-4}$ alkyl.

4. The compound of embodiment 3, wherein $R^1$ and $R^2$, together with the nitrogen to which they are attached, form any one of the following:

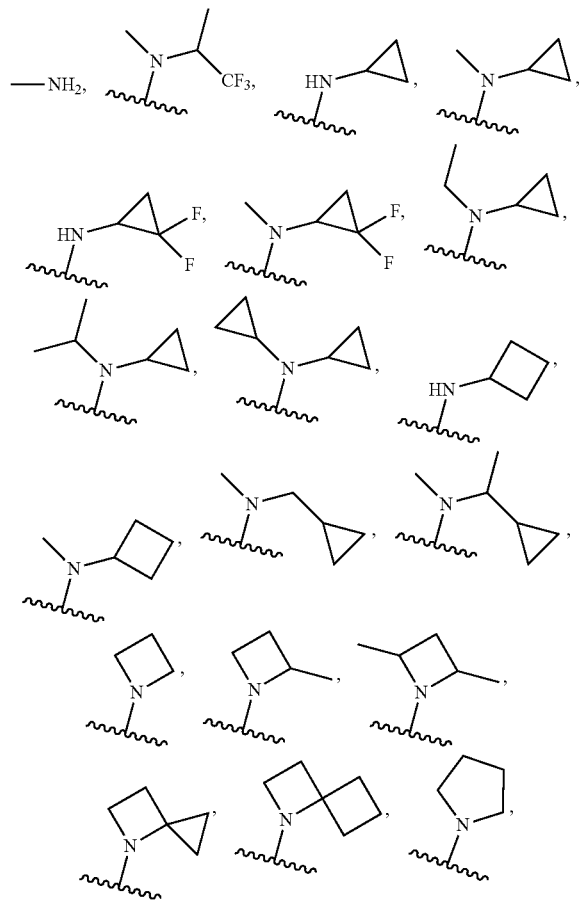

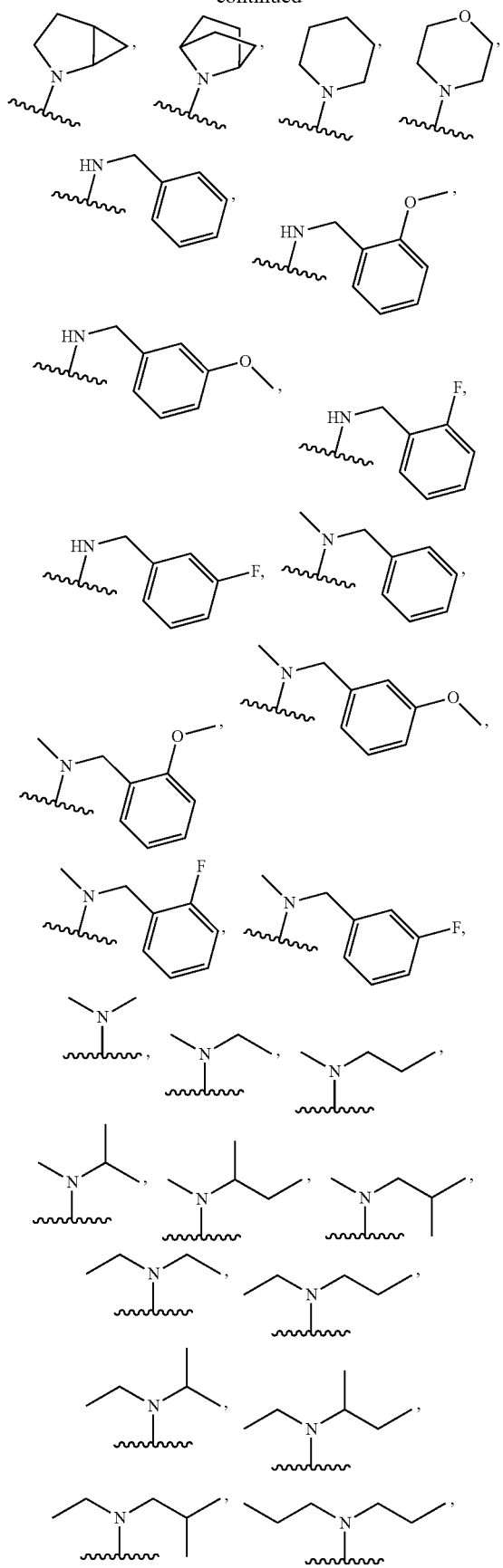
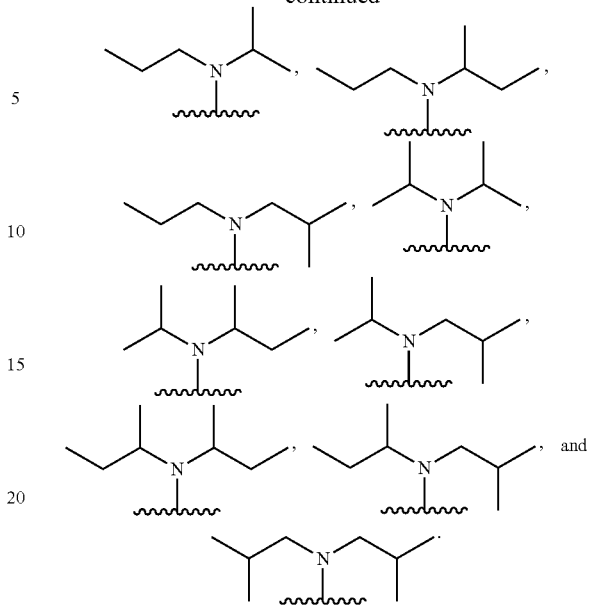

5. The compound of embodiment 1, wherein $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is as defined in embodiment 1.

6. The compound of any one of embodiments 1 to 5, wherein $R^3$ is hydrogen.

7. The compound of embodiment 1, wherein $R^3$ and one of $R^1$ and $R^2$ are combined with the atoms to which they are attached to form a $C_{3-8}$ heterocycloalkyl, said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is as defined in embodiment 1.

8. The compound of any one of embodiments 1 to 7, wherein $R^8$ $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined in embodiment 1.

9. The compound of embodiment 8, wherein $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined in embodiment 1.

10. The compound of embodiment 9, wherein 1 or 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$ $R^9$, $R^{10}$ and $R^{11}$ are each hydrogen.

11. The compound of any one of embodiments 1 to 7, wherein $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

12. The compound of embodiment 11, wherein $R^8$ and $R^9$ are combined to form a $C_{5-8}$ heterocycloalkyl or $C_{5-10}$ heteroaryl selected from the following:

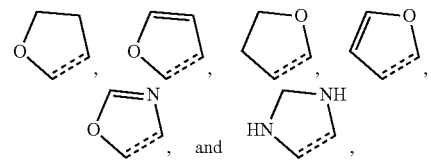

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

13. The compound of embodiment 12, wherein $R^8$ and $R^9$ are combined to form a $C_{5-8}$ heterocycloalkyl or $C_{5-10}$ heteroaryl selected from the following:

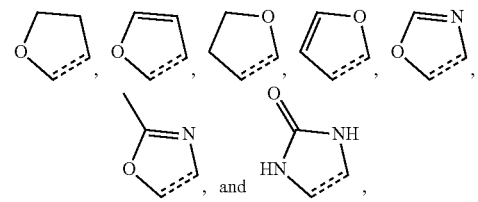

wherein the dashed bond denotes the bond shared with the aromatic ring to which $R^8$ and $R^9$ are attached.

14. The compound of any one of embodiments 1 to 13, wherein L is $C_{1-4}$ alkylene.

15. The compound of embodiment 14, wherein L is methylene.

16. The compound of any one of embodiments 1 to 15, wherein $R^6$ is selected from hydrogen and $C_{1-6}$ alkyl.

17. The compound of embodiment 16, wherein $R^6$ is hydrogen.

18. The compound of any one of embodiments 1 to 17, wherein one or more of $Z^1$, $Z^2$, $Z^3$ and $Z^4$ are heteroatoms.

19. The compound of any one of embodiments 1-18 having the formula (II):

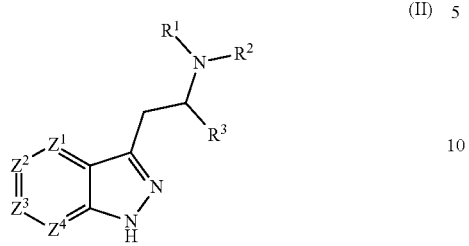

wherein $R^1$, $R^2$, $R^3$, $Z^1$, $Z^2$, $Z^3$ and $Z^4$ are as defined in any one of embodiments 1 to 18.

20. The compound of embodiment 19 having the formula (IIa):

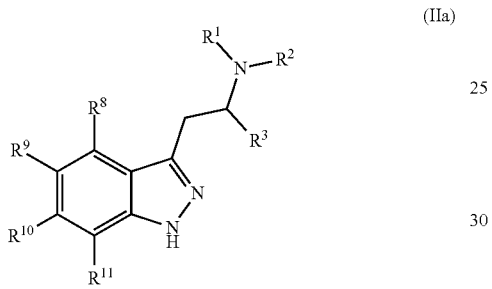

wherein $R^1$, $R^2$, $R^3$, $R^8$, $R^9$, $R^{10}$ and $R^{11}$ are as defined in any one of embodiments 1 to 18.

21. The compound of embodiment 1 selected from any one of the following:

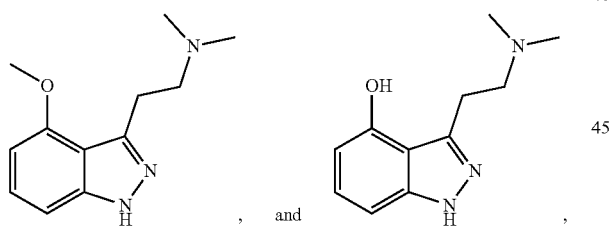

or a pharmaceutically acceptable salt, solvate, tautomer, N-oxide, stereoisomer, metabolite, polymorph or prodrug thereof.

32. A medicament comprising a compound of any one of embodiments 1 to 21, or a pharmaceutically acceptable salt, solvate, tautomer, N-oxide, stereoisomer, metabolite, polymorph or prodrug thereof.

33. A pharmaceutical composition comprising a compound of any one of embodiments 1 to 21, or a pharmaceutically acceptable salt, solvate, tautomer, N-oxide, stereoisomer, metabolite, polymorph or prodrug thereof, and a pharmaceutically acceptable excipient.

34. A method of treating a disease, disorder or condition by activation of a serotonin receptor, the method comprising administering to a subject in need thereof a compound of formula (I):

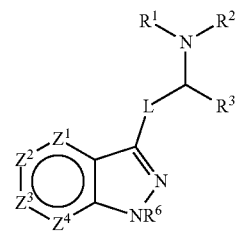

or a pharmaceutically acceptable salt, solvate, tautomer, N-oxide, stereoisomer, metabolite, polymorph or prodrug thereof, wherein $R^1$ and $R^2$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl, said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_4$-$C_{14}$ alkyleneheterocycloalkyl, $C_3$-$C_8$ heterocycloalkyl, $C_{6-12}$ aryl, $C_{7-18}$ alkylenearyl, $C_{5-11}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

$R^2$ is independently selected from hydrogen, $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$haloalkyl, $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, $CO_2R^4$, $C(O)N(R^4)_2$, $OR^4$, $N(R^4)_2$, $NO_2$, $SR^4$ and $SO_2R^4$, said $C_{3-8}$ cycloalkyl, $C_{4-14}$ alkylenecycloalkyl, $C_3$-$C_8$ heterocycloalkyl, $C_4$-$C_{14}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$;

alternatively $R^1$ and $R^2$ are combined with the atoms to which they are attached to form a $C_{3-8}$ heterocycloalkyl including 0, 1 or 2 additional ring heteromoieties selected from O, S, S(O), SO$_2$, N and NR$^4$,
  said $C_{3-8}$ heterocycloalkyl being further optionally substituted with one or more substituents independently selected from halogen, (O), CN, $C_{1-8}$ alkoxy, $C_{1-8}$ alkylamino, $C_{1-8}$alkylsulfonyl, CO$_2$R$^4$, C(O)N(R$^4$)$_2$, OR$^4$, N(R$^4$)$_2$, NO$_2$, SR$^4$, SO$_2$R$^4$, $C_{1-6}$ alkyl, $C_{1-6}$ haloalkyl, $C_{2-6}$alkenyl, $C_{2-6}$ haloalkenyl, $C_{2-6}$ alkynyl, $C_{2-6}$ haloalkynyl, $C_{1-8}$ alkylamino, $C_{1-8}$ alkylsulfonyl, $C_{3-6}$ cycloalkyl and $C_{3-6}$ heterocycloalkyl including 1 or 2 ring heteromoieties selected from O, S, N, S(O), SO$_2$ and NR$^4$;

$R^3$ is selected from hydrogen, $C_{1-6}$ alkyl, $C_{3-8}$ cycloalkyl, or $C_{4-14}$ alkylenecycloalkyl;

alternatively $R^3$ and one of $R^1$ and $R^2$ are combined with the atoms to which they are attached to form a $C_{3-12}$ heterocycloalkyl,
  said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$alkylsulfonyl, CO$_2$R$^4$, C(O)N (R$^4$)$_2$, OR$^4$, N(R$^4$)$_2$, NO$_2$, SR$^4$, SO$_2$R$^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), SO$_2$ and NR$^4$;

each $R^4$ is independently selected from hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl, and $C_{3-7}$ heterocycloalkyl including 1 or 2 ring heteromoieties selected from O, S, S(O), SO$_2$, N and NR$^5$,
  said $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-7}$ cycloalkyl and $C_{3-7}$ heterocycloalkyl each being optionally substituted with one or more substituents independently selected from halogen, CN, $C_{1-8}$ alkoxy, $C_{1-8}$ alkylamino, $C_{1-8}$ alkylsulfonyl, CO$_2$R$^5$, C(O)N(R$^5$)$_2$, OR$^5$, N(R$^5$)$_2$, NO$_2$, SR$^5$ and SO$_2$R$^5$,
  said $C_3$-$C_7$ cycloalkyl and $C_{3-7}$ heterocycloalkyl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO$_2$, N and NR$^5$;

each $R^5$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{5-11}$ heterocycloalkyl, $C_{6-12}$ aryl and $C_{5-11}$ heteroaryl,
  said $C_{1-6}$ alkyl, $C_{2-6}$ alkenyl, $C_{2-6}$ alkynyl, $C_{1-6}$ haloalkyl, $C_{3-8}$ cycloalkyl, $C_{5-10}$ heterocycloalkyl, $C_{6-12}$ aryl and $C_{5-11}$ heteroaryl each being optionally substituted with one or more substituents selected from halogen, CN, $C_{1-8}$ alkoxy, $C_{1-8}$ alkylamino, $C_{1-8}$ alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NHCH$_3$, NO$_2$, SH, SCH$_3$, SO$_2$CH$_3$, SOCH$_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO$_2$, N, NH and NCH$_3$;

L is selected from $C_{1-4}$ alkylene, $C_2$-$C_4$ alkenylene and $C_2$-$C_4$ alkynylene;

$Z^1$ is CR$^8$ or N;
$Z^2$ is CR$^9$ or N;
$Z^3$ is CR$^{10}$ or N;
$Z^4$ is CR$^{11}$ or N;

$R^6$ is selected from hydrogen, $C_{1-6}$ alkyl, $C_{2-6}$ alkenyl, $C_{2-6}$ alkynyl, $C_{1-6}$ alkyleneP(O)(OR$^{12}$)$_2$, C(O)R$^{12}$, CO$_2$R$^{12}$, C(O)N(R$^{12}$)$_2$, S(O)R$^{12}$ and SO$_2$R$^{12}$, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl,
  said $C_{1-6}$ alkyl, $C_{2-6}$ alkenyl, $C_{2-6}$ alkynyl, $C_{3-6}$ cycloalkyl, $C_{6-9}$ alkylenecycloalkyl, $C_{3-6}$ heterocyclyl, $C_{6-9}$ alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, CO$_2$R$^{12}$, C(O)N(R$^{12}$)$_2$, OR$^{12}$, N(R$^{12}$)$_2$, NO$_2$, SR$^{12}$ and SO$_2$R$^{12}$,
  said $C_{3-6}$ cycloalkyl, $C_{6-9}$ alkylenecycloalkyl, $C_{3-6}$ heterocyclyl, $C_6$-s alkyleneheterocycloalkyl, $C_{4-7}$ heterocyclyl, $C_{7-10}$ alkyneneheterocycloalkyl, $C_{6-12}$ aryl, $C_{7-18}$ alkylenearyl, $C_{5-11}$ heteroaryl, and $C_{6-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), SO$_2$ and NR$^{12}$;

each $R^{12}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl,
  said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, CO$_2$H, CO$_2$CH$_3$, C(O)NH$_2$, C(O)N(CH$_3$)$_2$, C(O)NHCH$_3$, OH, NH$_2$, N(CH$_3$)$_2$, NHCH$_3$, NO$_2$, SH, SCH$_3$, SO$_2$CH$_3$, SOCH$_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), SO$_2$, N, NH and NCH$_3$;

$R^8$, $R^9$, $R^{10}$ and $R^{11}$ are each independently selected from hydrogen, halogen, CN, OR$^{13}$, N(R$^{13}$)$_2$, SR$^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, CO$_2$R$^{13}$, C(O)R$^{13}$, C(O)N(R$^{13}$)$_2$, C(O)C(O)N(R$^{13}$)$_2$, OC(O)R$^{13}$, OC(O)OR$^{13}$, OC(O)N(R$^{13}$)$_2$, OS(O)R$^{13}$, OS(O)N(R$^{13}$)$_2$, OSO$_2$R$^{13}$, OP(O)(OR$^{13}$)$_2$, OC$_{1-6}$alkyleneP(O)(OR$^{13}$)$_2$, S(O)R$^{13}$'S(O)N(R$^{13}$)$_2$, SO$_2$R$^{13}$, N(R$^{13}$)$_2$, N(R$^{13}$)C(O)R$^{13}$, N(R$^{13}$)C(O)OR$^{13}$, N(R$^{13}$)C(O)N(R$^{13}$)$_2$, NO$_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

each $R^{13}$ is independently selected from hydrogen, $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{6-16}$ alkyleneheteroaryl, said $C_{1-6}$ alkyl, $C_{2-6}$ alkenyl, $C_{2-6}$ alkynyl, $C_{1-6}$ haloalkyl, $C_{3-8}$ cycloalkyl, $C_{4-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{6-16}$ alkyleneheteroaryl each being optionally substituted with one or more substituents independently selected from halogen, CN, $C_{1-8}$ alkoxy, $C_{1-8}$ alkylamino, $C_{1-8}$alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$;

alternatively, when $Z^1$ is $CR^8$ and $Z^2$ is $CR^9$, or when $Z^2$ is $CR^9$ and $Z^3$ is $CR^{10}$, or when $Z^3$ is $CR^{10}$ and $Z^4$ is $CR^{11}$, then $R^8$ and $R^9$, or $R^9$ and $R^{10}$, or $R^{10}$ and $R^{11}$ are combined with the atoms to which they are each attached to form a $C_{4-8}$ cycloalkyl, $C_{5-8}$ heterocycloalkyl, $C_{6-12}$ aryl, or $C_{5-10}$ heteroaryl, said $C_{4-8}$ cycloalkyl, $C_{5-8}$ heterocycloalkyl, $C_{6-12}$ aryl, and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2R^{14}$, $C(O)N(R^{14})_2$, $OR^{14}$, $N(R^{14})_2$, $NO_2$, $SR^{14}$, $SO_2R^{14}$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^{14}$;

each $R^{14}$ is independently selected from hydrogen, $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-10}$ heteroaryl;

said $C_{1-6}$ alkyl, $C_2$-$C_6$ alkenyl, $C_2$-$C_6$ alkynyl, $C_1$-$C_6$ haloalkyl, $C_3$-$C_7$ cycloalkyl, $C_{3-10}$ heterocycloalkyl, $C_{6-12}$ aryl and $C_{5-11}$ heteroaryl each being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

35. The method of embodiment 34, wherein $R^1$ and $R^2$ are each independently selected from $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-8}$ cycloalkyl and $C_{4-14}$ alkylenecycloalkyl.

36. The method of embodiment 35, wherein $R^1$ and $R^2$ are each independently selected from $C_{1-4}$ alkyl.

37. The method of embodiment 36, wherein $R^1$ and $R^2$, together with the nitrogen to which they are attached, form any one of the following:

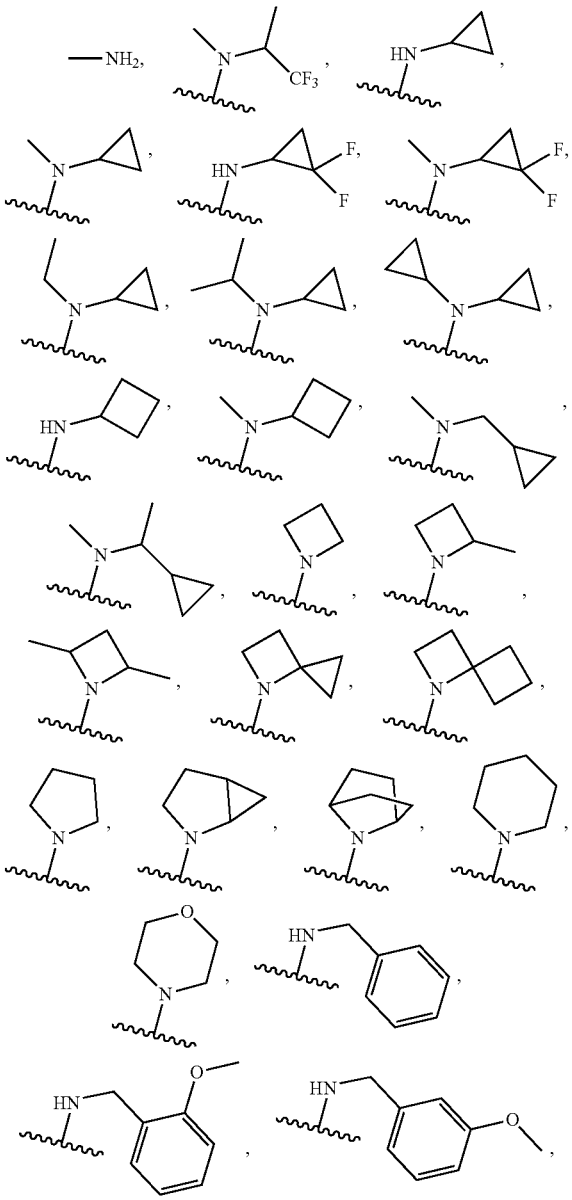

-continued

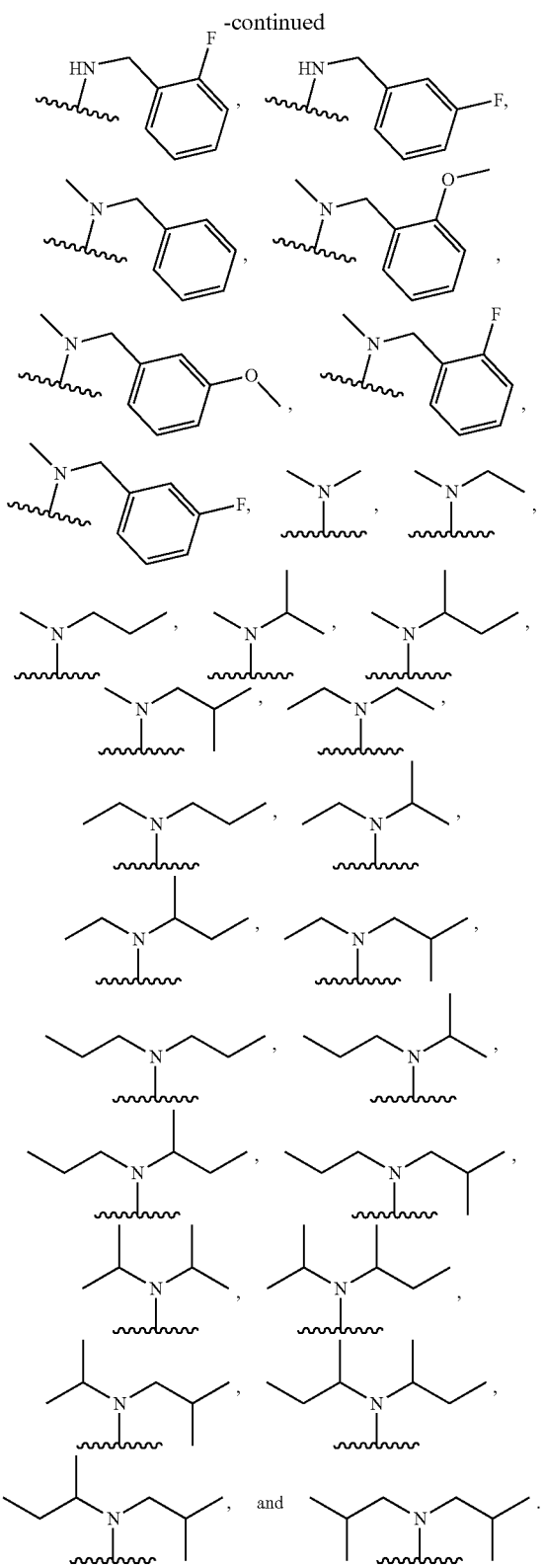

38. The method of embodiment 34, wherein $R^1$ and $R^2$ are combined with the atoms to which they are attached to form $C_{3-6}$ heterocycloalkyl, said $C_{3-6}$ heterocycloalkyl being optionally substituted with one or more substituents independently selected from halogen, CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$ and $SO_2R^4$, (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is as defined in embodiment 1.

39. The method of any one of embodiments 34 to 38, wherein $R^3$ is hydrogen.

40. The method of embodiment 34, wherein $R^3$ and one of $R^1$ and $R^2$ are combined with the atoms to which they are attached to form a $C_{3-8}$ heterocycloalkyl, said $C_{3-12}$ heterocycloalkyl being further optionally substituted with one or more substituents independently selected from halogen, (O), CN, $C_{1-8}$ alkoxy, $C_{1-8}$ alkylamino, $C_{1-8}$ alkylsulfonyl, $CO_2R^4$, $C(O)N(R^4)_2$, $OR^4$, $N(R^4)_2$, $NO_2$, $SR^4$, $SO_2R^4$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, N, S(O), $SO_2$ and $NR^4$, wherein $R^4$ is as defined in embodiment 1.

41. The method of any one of embodiments 34 to 40, wherein $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)R^{13}$, $C(O)N(R^{13})_2$, $C(O)C(O)N(R^{13})_2$, $OC(O)R^{13}$, $OC(O)OR^{13}$, $OC(O)N(R^{13})_2$, $OS(O)R^{13}$, $OS(O)N(R^{13})_2$, $OSO_2R^{13}$, $OP(O)(OR^{13})_2$, $OC_{1-6}$alkyleneP(O)(OR^{13})_2$, $S(O)R^{13}$, $S(O)N(R^{13})_2$, $SO_2R^{13}$, $N(R^{13})_2$, $N(R^{13})C(O)R^{13}$, $N(R^{13})C(O)OR^{13}$, $N(R^{13})C(O)N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2R^{13}$, $C(O)N(R^{13})_2$, $OR^{13}$, $N(R^{13})_2$, $NO_2$, $SR^{13}$ and $SO_2R^{13}$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, and $NR^{13}$;

wherein $R^{13}$ is as defined in embodiment 34.

42. The method of embodiment 41, wherein $R^8$, $R^9$, $R^{10}$ and $R^{11}$ are each independently selected from hydrogen, halogen, CN, $OR^{13}$, $N(R^{13})_2$, $SR^{13}$, $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $CO_2R^{13}$, $C(O)N(R^{13})_2$, $OC(O)R^{13}$, $OSO_2R^{13}$, $OP(O)(OR^{13})_2$, $OC_{1-6}$alkyleneP(O)(OR^{13})_2$, $S(O)R^{13}$, $SO_2R^{13}$, $N(R^{13})_2$, $NO_2$, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, $C_{4-16}$ alkyleneheteroaryl, said $C_{1-6}$ alkyl, $C_{1-6}$ haloalkyl, $C_{2-6}$ alkenyl, $C_2$-$C_6$ haloalkenyl, $C_{2-6}$ alkynyl, $C_{2-6}$ haloalkynyl, $C_{1-6}$ alkylamine, $C_{1-6}$ alkoxy, $C_{1-6}$ haloalkoxy, $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-10}$ heteroaryl, and $C_{4-16}$ alkyleneheteroaryl being optionally substituted with one or more substituents independently selected from halogen, CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NO_2$, $NHCH_3$, SH, $SCH_3$, $SO_2CH_3$, and $SOCH_3$, said $C_{3-8}$ cycloalkyl, $C_{3-14}$ alkylenecycloalkyl, $C_{3-10}$ heterocycloalkyl, $C_{4-16}$ alkyleneheterocycloalkyl, $C_{6-12}$ aryl, $C_{7-18}$ alkylenearyl, $C_{5-11}$ heteroaryl, and $C_{4-16}$ alkyleneheteroaryl each being further optionally substituted with one or more substituents independently selected from (O), $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$cycloalkyl and $C_{3-6}$ heterocycloalkyl including 1 or 2 ring heteromoieties selected from O, S, S(O), $SO_2$, N, NH and $NCH_3$;

wherein $R^{13}$ is as defined in embodiment 34.

43. The method of any one of embodiments 34 to 42, wherein 1 or 2 of $R^8$, $R^9$, $R^{10}$ and $R^{11}$ when present are each independently selected from halogen, $C_{1-6}$ alkyl, $C_{1-6}$ haloalkyl and $OR^{13}$ wherein $R^{13}$ is selected from $C_{1-6}$ alkyl and $C_{1-6}$ haloalkyl, and the other of $R^8$, $R^9$, $R^{10}$ and $R^{11}$ are each hydrogen.

44. The method of any one of embodiments 34 to 42, wherein $R^8$ and $R^9$ when present are combined with the atoms to which they are each attached to form a $C_{5-8}$ heterocycloalkyl or $C_{5-10}$ heteroaryl, said $C_{5-8}$ heterocycloalkyl and $C_{5-10}$ heteroaryl each being further optionally substituted with one or more substituents independently selected from halogen, (O), CN, $C_{1-8}$ alkoxy, $C_{1-8}$ alkylamino, $C_{1-8}$ alkylsulfonyl, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, $C_{3-6}$ cycloalkyl and $C_{3-6}$ heterocycloalkyl including 1 or 2 ring heteromoieties selected from O, S, S(O), $SO_2$, N, NH and $NCH_3$.

45. The method of embodiment 44, wherein $R^8$ and $R^9$ are combined to form a $C_{5-8}$ heterocycloalkyl or $C_{5-10}$ heteroaryl selected from the following:

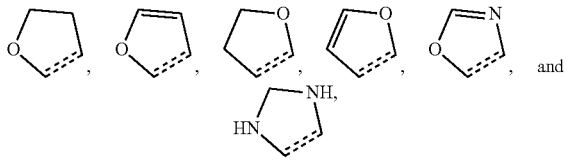

wherein the dashed bond denotes the bond shared with the aromatic ring to which $R^8$ and $R^9$ are attached;

said $C_{5-8}$ heterocycloalkyl and $C_{5-10}$ heteroaryl each being further optionally substituted with one or more substituents independently selected from halogen, (O), CN, $CO_2H$, $CO_2CH_3$, $C(O)NH_2$, $C(O)N(CH_3)_2$, $C(O)NHCH_3$, OH, $NH_2$, $N(CH_3)_2$, $NHCH_3$, $NO_2$, SH, $SCH_3$, $SO_2CH_3$, $SOCH_3$, $C_{1-6}$ alkyl and $C_{1-6}$ haloalkyl.

46. The method of embodiment 45, wherein $R^8$ and $R^9$ are combined to form a $C_{5-8}$ heterocycloalkyl or $C_{5-10}$ heteroaryl selected from the following:

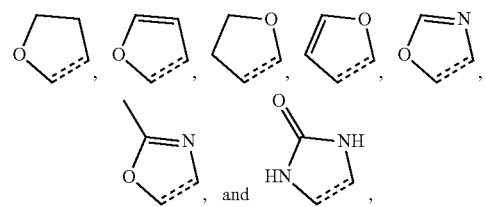

where the dashed bond denotes the bond shared with the aromatic ring to which $R^8$ and $R^9$ are attached.

47. The method of any one of embodiments 34 to 46, wherein L is $C_{1-4}$ alkylene.

48. The method of embodiment 47, wherein L is $C_1$ alkylene.

49. The method of embodiment 48, wherein L is methylene.

50. The method of any one of embodiments 34 to 49, wherein $R^6$ is selected from hydrogen and $C_{1-6}$ alkyl.

51. The method of embodiment 50, wherein $R^6$ is hydrogen.

52. The method of any one of embodiments 34 to 51, wherein one or more of $Z^1$, $Z^2$, $Z^3$ and $Z^4$ are heteroatoms.

58. The method of any one of embodiments 34 to 52 having the formula (II):

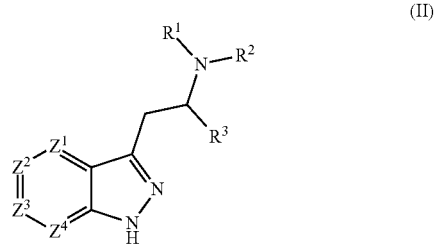

wherein $R^1$, $R^2$, $R^3$, $Z^1$, $Z^2$, $Z^3$ and $Z^4$ are as defined in any one of embodiments 34 to 52.

59. The method of embodiment 58 having the formula (IIa):

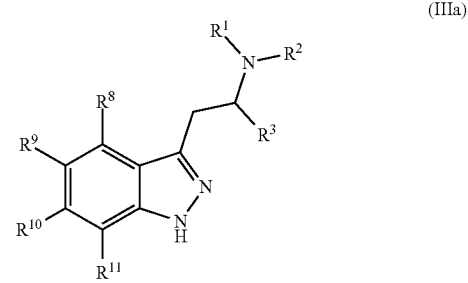

wherein $R^1$, $R^2$, $R^3$, $R^8$, $R^9$, $R^{10}$ and $R^{11}$ are as defined in any one of embodiments 34 to 52.

65. The method of embodiment 34, wherein the compound of formula (I) is selected from any one of the following:

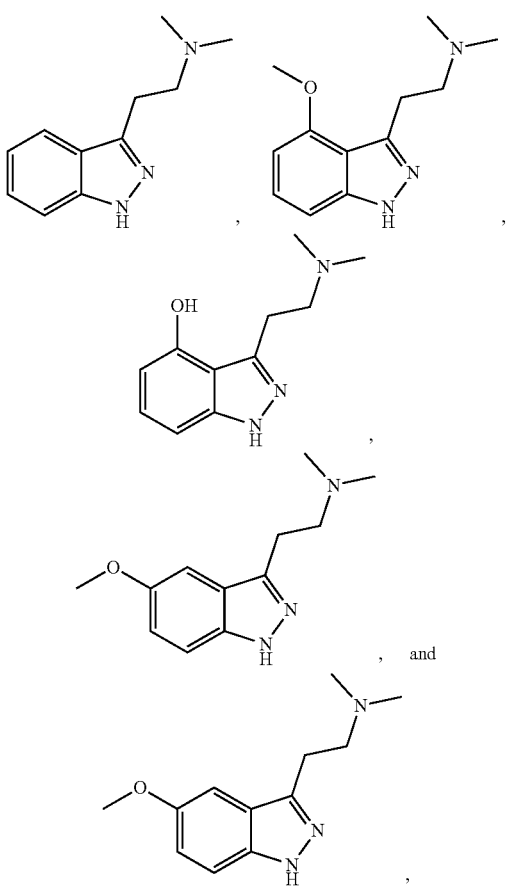

or a pharmaceutically acceptable salt, solvate, tautomer, N-oxide, stereoisomer, metabolite, polymorph or prodrug thereof.

66. A method of treating a disease, disorder or condition by activation of a serotonin receptor, the method comprising administering to a subject in need thereof a compound of formula (I) as defined in any one of embodiments 34 to 65, or a pharmaceutically acceptable salt, solvate, tautomer, N-oxide, stereoisomer, metabolite, polymorph or prodrug thereof, in combination with another known agent useful for treatment of a disease, disorder or condition by activation of a serotonin receptor.

67. A method of treating a mental illness, the method comprising administering to a subject in need thereof a compound of formula (I) as defined in any one of embodiments 34 to 65, or a pharmaceutically acceptable salt, solvate, tautomer, N-oxide, stereoisomer, metabolite, polymorph or prodrug thereof.

68. The method of embodiment 67, wherein the mental illness is selected from anxiety disorders; depression; mood disorders; psychotic disorders; impulse control and addiction disorders; drug addiction; obsessive-compulsive disorder (OCD); post-traumatic stress disorder (PTSD); stress response syndromes; dissociative disorders; depersonalization disorder; factitious disorders; sexual and gender disorders; somatic symptom disorders; hallucinations; delusions; psychosis; and combinations thereof.

69. A method for treating a central nervous system (CNS) disease, disorder or condition and/or a neurological disease, disorder or condition, the method comprising administering to a subject in need thereof a compound of formula (I) as defined in any one of embodiments 34 to 65, or a pharmaceutically acceptable salt, solvate, tautomer, N-oxide, stereoisomer, metabolite, polymorph or prodrug thereof.

70. The method of embodiment 69, wherein the CNS disease, disorder or condition and/or neurological disease, disorder or condition is selected from neurological diseases including neurodevelopmental diseases and neurodegenerative diseases such as Alzheimer's disease; presenile dementia; senile dementia; vascular dementia; Lewy body dementia; cognitive impairment, Parkinson's disease and Parkinsonian related disorders such as Parkinson dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neuro-otological and eye movement disorders; neurodegenerative diseases of the retina amyotrophic lateral sclerosis; tardive dyskinesias; hyperkinetic disorders; attention deficit hyperactivity disorder and attention deficit disorders; restless leg syndrome; Tourette's syndrome; schizophrenia; autism spectrum disorders; tuberous sclerosis; Rett syndrome; cerebral palsy; disorders of the reward system including eating disorders such as anorexia nervosa and bulimia nervosa; binge eating disorder, trichotillomania, dermotillomania, nail biting; migraine; fibromyalgia; and peripheral neuropathy of any etiology, and combinations thereof.

71. A method for increasing neuronal plasticity and/or increasing dendritic spine density, the method comprising contacting a neuronal cell with a compound of formula (I) as defined in any one of embodiments 34 to 65, or a pharmaceutically acceptable salt, solvate, tautomer, N-oxide, stereoisomer, metabolite, polymorph or prodrug thereof, in an amount sufficient to increase neuronal plasticity and/or increase dendritic spine density of the neuronal cell.

The invention claimed is:
1. A compound, selected from:

| Code | Structure |
|------|-----------|
| A-1 | 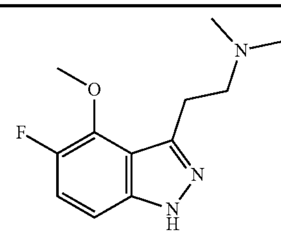 |
| A-2 | 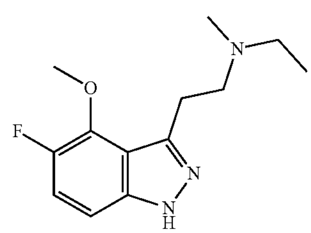 [SMILES: CCN(C)CCc1n[nH]c2ccc(F)c(OC)c12] |
| A-3 | 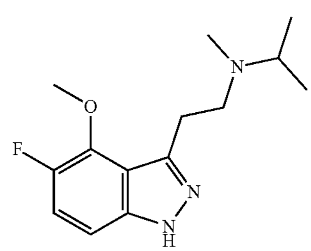 [SMILES: COc1c(F)ccc2[nH]nc(CCN(C)C(C)C)c12] |

| Code | Structure |
|---|---|
| A-4 | 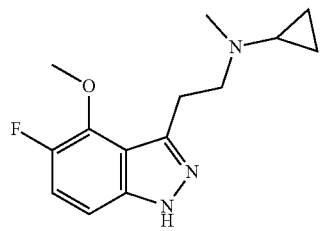 [SMILES: COc1c(F)ccc2[nH]nc(CCN(C)C3CC3)c12] |
| A-5 | 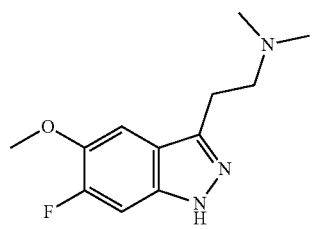 |
| A-6 | 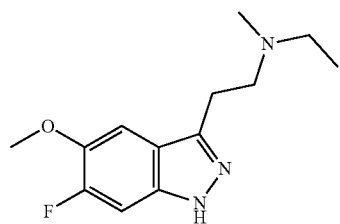 [SMILES: CCN(C)CCc1n[nH]c2cc(F)c(OC)cc12] |
| A-7 | 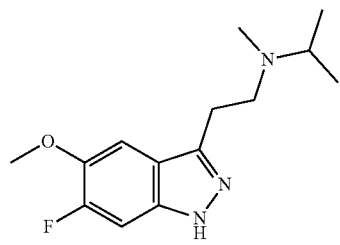 [SMILES: COc1cc2c(CCN(C)C(C)C)n[nH]c2cc1F] |
| A-8 | 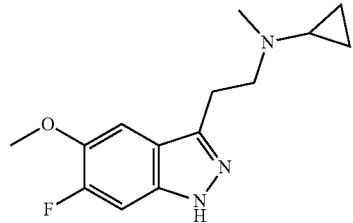 [SMILES: COc1cc2c(CCN(C)C3CC3)n[nH]c2cc1F] |
| A-9 | 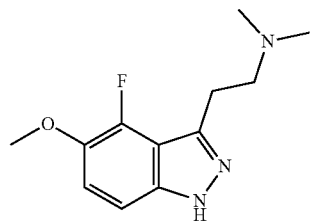 |
| Code | Structure |
|---|---|
| A-10 | 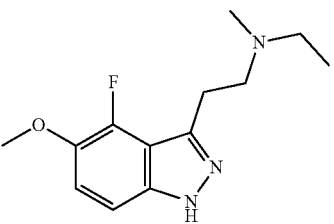 [SMILES: CCN(C)CCc1n[nH]c2ccc(OC)c(F)c12] |
| A-11 | 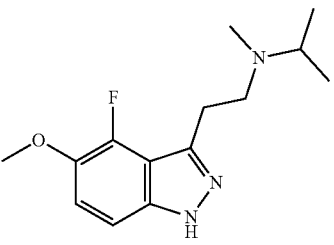 [SMILES: COc1ccc2[nH]nc(CCN(C)C(C)C)c2c1F] |
| A-12 | 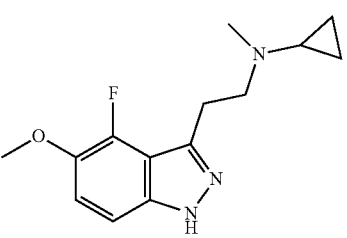 [SMILES: COc1ccc2[nH]nc(CCN(C)C3CC3)c2c1F] |
| A-13 | 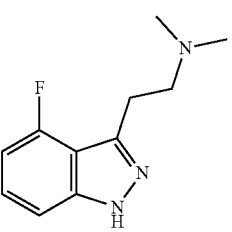 |
| A-14 | 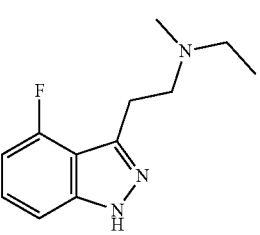 [SMILES: CCN(C)CCc1n[nH]c2cccc(F)c12] |
| A-15 | 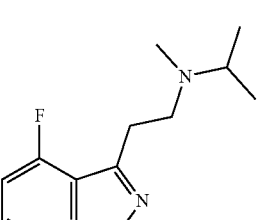 |

411
-continued
| Code | Structure |
|---|---|
| A-16 | 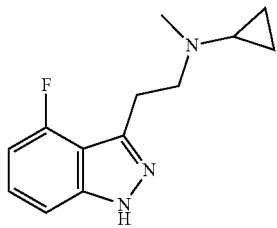 [SMILES: CN(CCc1n[nH]c2cccc(F)c12)C1CC1] |
| A-17 | 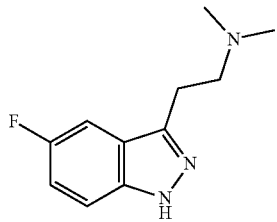 |
| A-18 | 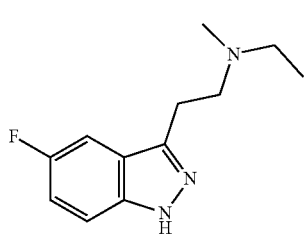 |
| A-19 | 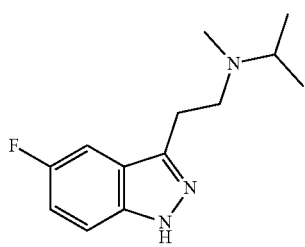 [SMILES: CC(C)N(C)CCc1n[nH]c2ccc(F)cc12] |
| A-20 | 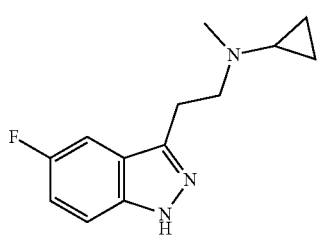 [SMILES: CN(CCc1n[nH]c2ccc(F)cc12)C1CC1] |
| A-21 | 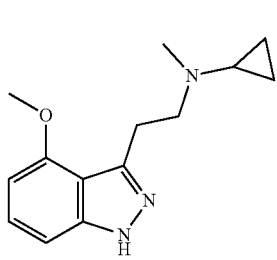 [SMILES: COc1cccc2[nH]nc(CCN(C)C3CC3)c12] |
412
-continued
| Code | Structure |
|---|---|
| A-22 | 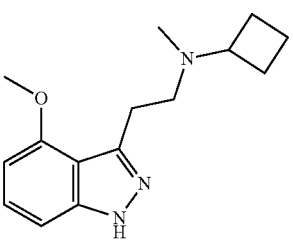 [SMILES: COc1cccc2[nH]nc(CCN(C)C3CCC3)c12] |
| A-23 | 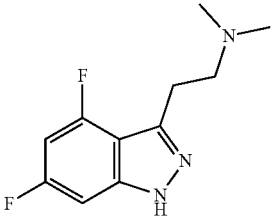 [SMILES: CN(C)CCc1n[nH]c2cc(F)cc(F)c12] |
| A-24 | 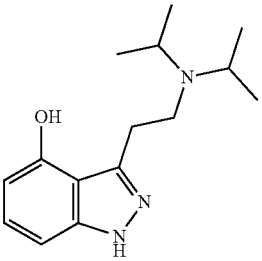 [SMILES: CC(C)N(CCc1n[nH]c2cccc(O)c12)C(C)C] |
| A-25 | 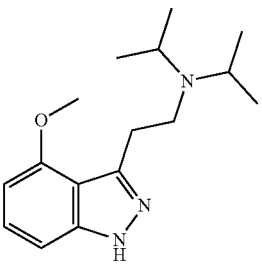 [SMILES: COc1cccc2[nH]nc(CCN(C(C)C)C(C)C)c12] |
| A-26 | 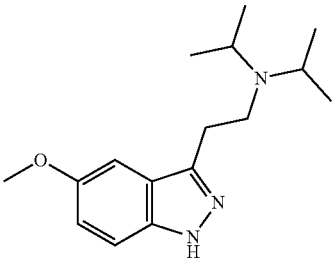 [SMILES: COc1ccc2[nH]nc(CCN(C(C)C)C(C)C)c2c1] |

| Code | Structure |
|---|---|
| A-27 | 3-(2-((3-methoxybenzyl)amino)ethyl)-5-methoxy-1H-indazole |
| A-28 | 3-(2-((3-fluorobenzyl)amino)ethyl)-5-methoxy-1H-indazole |
| A-29 | 2-(4,6-difluoro-1H-indazol-3-yl)-N-ethyl-N-methylethan-1-amine |
| A-30 | 2-(4,6-difluoro-1H-indazol-3-yl)-N-isopropyl-N-methylethan-1-amine |
| A-31 | 2-(4,6-difluoro-1H-indazol-3-yl)-N-cyclopropyl-N-methylethan-1-amine |

| Code | Structure |
|---|---|
| A-32 | 2-(4,6-difluoro-1-methyl-1H-indazol-3-yl)-N,N-dimethylethan-1-amine |
| A-33 | 3-(2-((2-methoxybenzyl)amino)ethyl)-4,6-difluoro-1H-indazole |
| A-34 | 3-(2-((2-methoxybenzyl)amino)ethyl)-4-fluoro-1H-indazole |
| A-35 | 2-(5,7-difluoro-1H-indazol-3-yl)-N,N-dimethylethan-1-amine |
| A-36 | 2-(5,7-difluoro-1H-indazol-3-yl)-N-ethyl-N-methylethan-1-amine |
| A-37 | 2-(5,7-difluoro-1H-indazol-3-yl)-N-isopropyl-N-methylethan-1-amine |

415
-continued
| Code | Structure |
|---|---|
| A-38 | 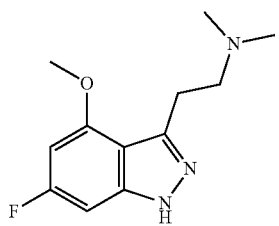 [SMILES: COc1cc(F)cc2[nH]nc(CCN(C)C)c12] |
| A-39 | 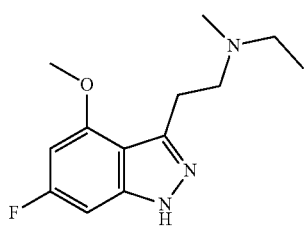 [SMILES: CCN(C)CCc1n[nH]c2cc(F)cc(OC)c12] |
| A-40 | 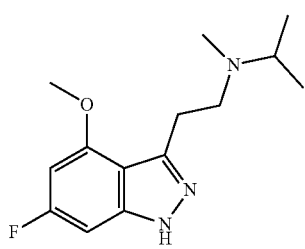 [SMILES: COc1cc(F)cc2[nH]nc(CCN(C)C(C)C)c12] |
| A-41 | 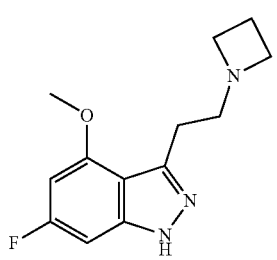 [SMILES: COc1cc(F)cc2[nH]nc(CCN3CCC3)c12] |
| A-42 | 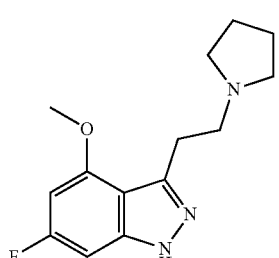 |
| A-43 | 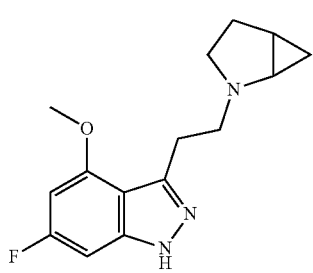 [SMILES: COc1cc(F)cc2[nH]nc(CCN3CCC4CC43)c12] |
416
-continued
| Code | Structure |
|---|---|
| A-44 | 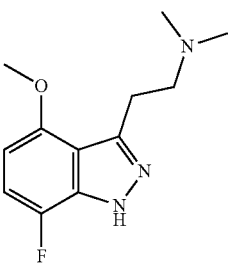 [SMILES: COc1ccc(F)c2[nH]nc(CCN(C)C)c12] |
| A-45 | 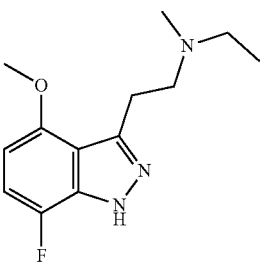 [SMILES: CCN(C)CCc1n[nH]c2c(F)ccc(OC)c12] |
| A-46 | 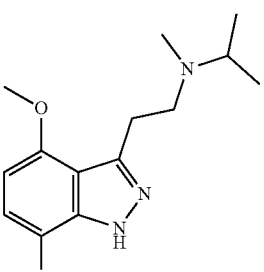 |
| A-47 | 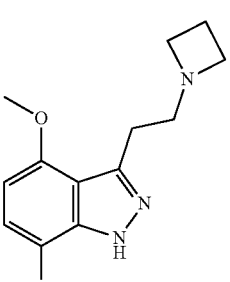 |
| A-48 | 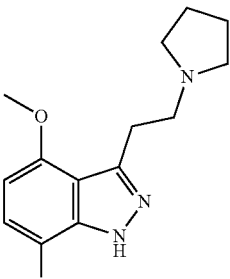 |

-continued
| Code | Structure |
|---|---|
| A-49 | 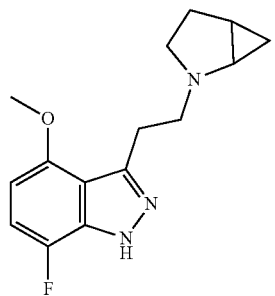 [SMILES: COc1ccc(F)c2[nH]nc(CCN3CCC4CC43)c12] |
| A-50 | 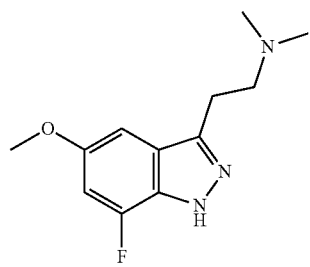 |
| A-51 | 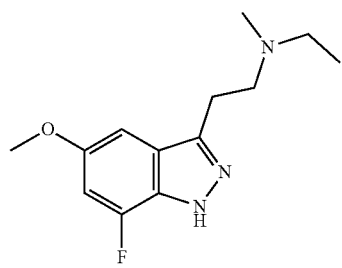 [SMILES: CCN(C)CCc1n[nH]c2c(F)cc(OC)cc12] |
| A-52 | 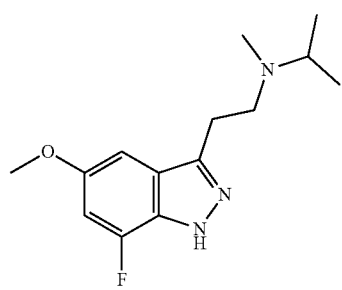 [SMILES: COc1cc(F)c2[nH]nc(CCN(C)C(C)C)c2c1] |
| A-53 | 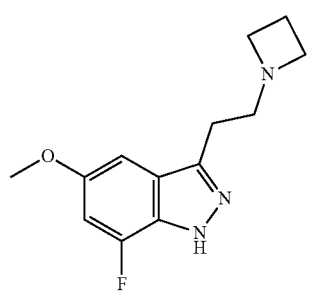 [SMILES: COc1cc(F)c2[nH]nc(CCN3CCC3)c2c1] |
-continued
| Code | Structure |
|---|---|
| A-54 | 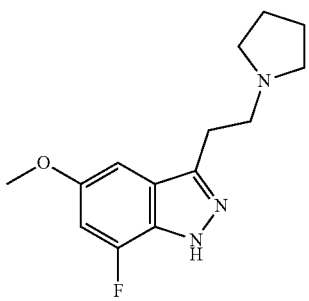 [SMILES: COc1cc(F)c2[nH]nc(CCN3CCCC3)c2c1] |
| A-55 | 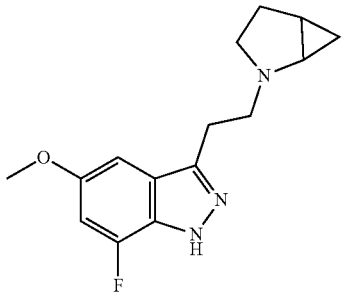 [SMILES: COc1cc(F)c2[nH]nc(CCN3CCC4CC43)c2c1] |
| A-56 | 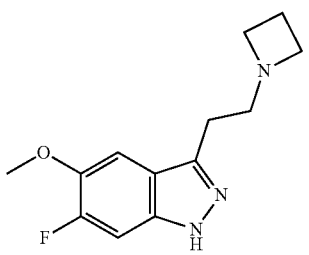 [SMILES: COc1cc2c(CCN3CCC3)n[nH]c2cc1F] |
| A-57 | 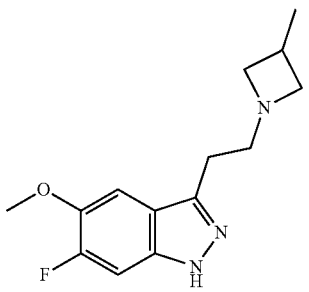 [SMILES: COc1cc2c(CCN3CC(C)C3)n[nH]c2cc1F] |
| A-58 | 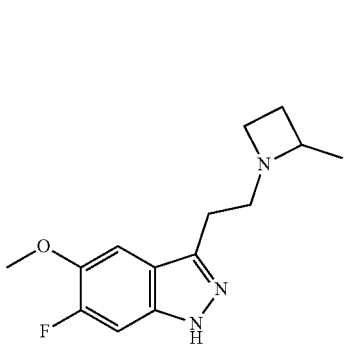 |

| Code | Structure |
|---|---|
| A-59 | 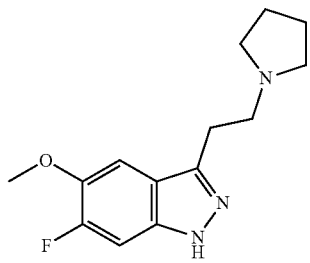 [SMILES: COc1cc2c(CCN3CCCC3)n[nH]c2cc1F] |
| A-60 | 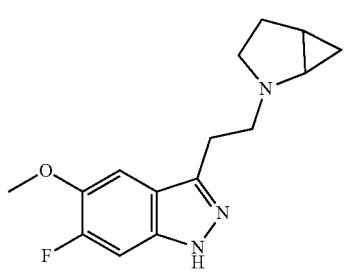 [SMILES: COc1cc2c(CCN3CCC4CC43)n[nH]c2cc1F] |
| A-61 | 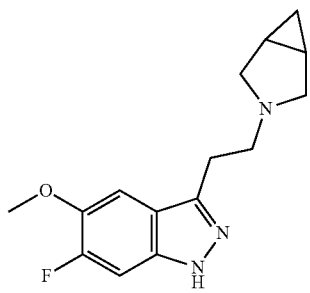 [SMILES: COc1cc2c(CCN3CC4CC4C3)n[nH]c2cc1F] |
| A-62 | 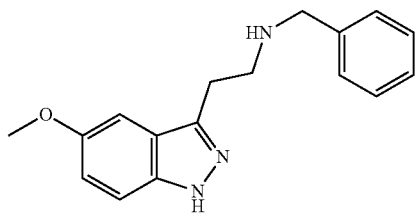 [SMILES: COc1ccc2[nH]nc(CCNCc3ccccc3)c2c1] |
| A-63 | 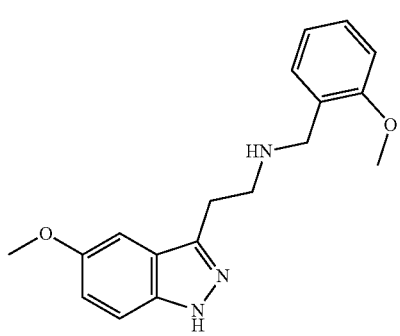 [SMILES: COc1ccc2[nH]nc(CCNCc3ccccc3OC)c2c1] |
| Code | Structure |
|---|---|
| A-64 | 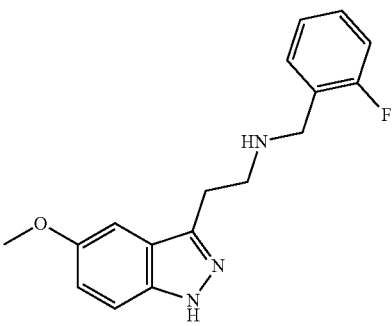 [SMILES: COc1ccc2[nH]nc(CCNCc3ccccc3F)c2c1] |
| A-65 | 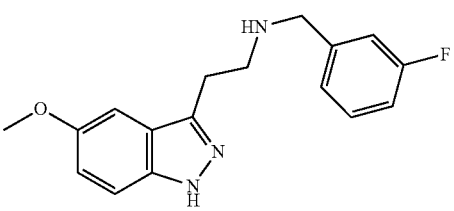 [SMILES: COc1ccc2[nH]nc(CCNCc3cccc(F)c3)c2c1] |
| A-66 | 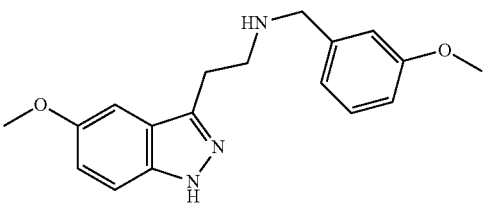 |
| A-67 | 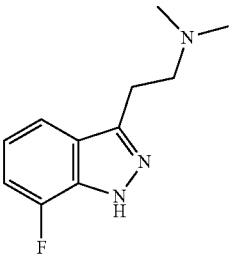 |
| A-68 | 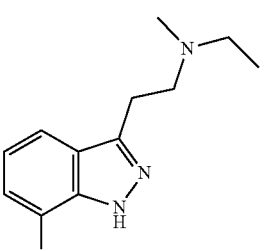 |
| A-69 | 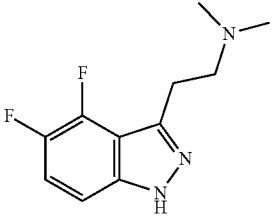 |

| Code | Structure |
|---|---|
| A-70 | 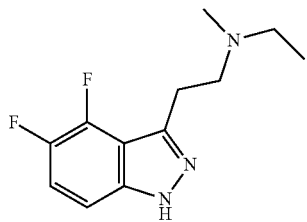 [SMILES: CCN(C)CCc1n[nH]c2ccc(F)c(F)c12] |
| A-71 | 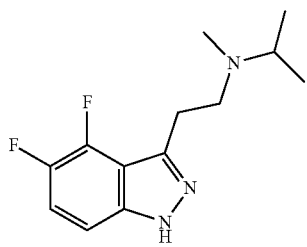 [SMILES: CC(C)N(C)CCc1n[nH]c2ccc(F)c(F)c12] |
| A-72 | 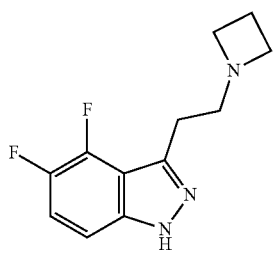 [SMILES: Fc1ccc2[nH]nc(CCN3CCC3)c2c1F] |
| Code | Structure |
|---|---|
| A-73 | 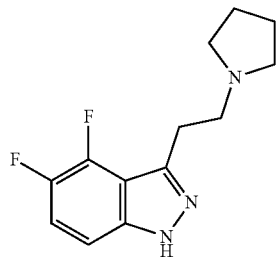 |
| A-74 | 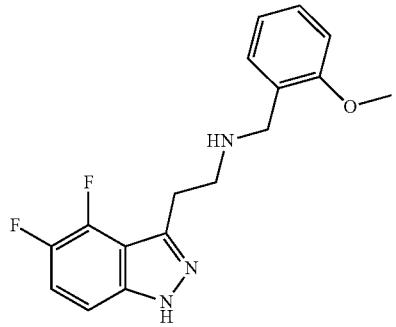 [SMILES: COc1ccccc1CNCCc1n[nH]c2ccc(F)c(F)c12] |
| A-75 | 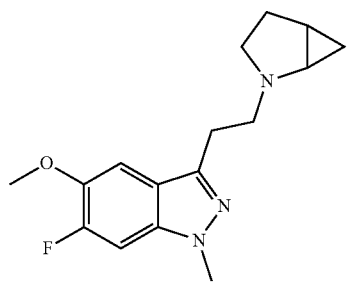 [SMILES: COc1cc2c(CCN3CCC4CC43)nn(C)c2cc1F] |
or a pharmaceutically acceptable salt, solvate, tautomer, N-oxide, or stereoisomer, thereof.
* * * * *